United States Patent
DeGoey et al.

(10) Patent No.: US 7,834,043 B2
(45) Date of Patent: Nov. 16, 2010

(54) HIV PROTEASE INHIBITING COMPOUNDS

(75) Inventors: David A. DeGoey, Salem, WI (US);
Charles A. Flentge, Salem, WI (US);
William J. Flosi, Evanston, IL (US);
David J. Grampovnik, Waukegan, IL (US); Dale J. Kempf, Libertyville, IL (US); Larry L. Klein, Lake Forest, IL (US); Ming C. Yeung, Grayslake, IL (US); John T. Randolph, Libertyville, IL (US); Xiu C. Wang, Libertyville, IL (US); Su Yu, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 1465 days.

(21) Appl. No.: 11/008,713

(22) Filed: Dec. 9, 2004

(65) Prior Publication Data

US 2005/0148623 A1 Jul. 7, 2005

Related U.S. Application Data

(60) Provisional application No. 60/528,974, filed on Dec. 11, 2003.

(51) Int. Cl.
*A01N 43/50* (2006.01)
(52) U.S. Cl. .................. 514/392; 548/322.5; 548/324.1
(58) Field of Classification Search .............. 546/274.4; 548/324.1, 324.5, 326.1, 322.5; 544/301; 514/392
See application file for complete search history.

(56) References Cited

U.S. PATENT DOCUMENTS

| 4,221,789 A | 9/1980 | Rodriguez et al. |
| 5,142,056 A | 8/1992 | Kempf et al. |
| 5,294,720 A | 3/1994 | Jadhav et al. |
| 5,354,866 A | 10/1994 | Kempf et al. |
| 5,541,206 A | 7/1996 | Kempf et al. |
| 5,712,417 A | 1/1998 | Budt et al. |
| 5,914,332 A | 6/1999 | Sham et al. |
| 6,204,257 B1 | 3/2001 | Stella et al. |
| 6,559,137 B1 | 5/2003 | Tung et al. |

FOREIGN PATENT DOCUMENTS

| EP | 0 005 689 | 11/1979 |
| EP | 0 342 541 | 11/1989 |
| EP | 0 365 992 | 5/1990 |
| EP | 0 428 849 | 5/1991 |
| EP | 0 580 402 | 1/1994 |
| EP | 0 346 847 | 5/1994 |
| EP | 0 604 910 | 7/1994 |
| WO | 89/10752 | 11/1989 |
| WO | 93/07128 | 4/1993 |
| WO | 94/14436 | 7/1994 |
| WO | 97/19061 | 5/1997 |
| WO | 00/40558 | 7/2000 |

OTHER PUBLICATIONS

Spina et al, Curr Opin Oncol, Sep. 2005, 17(5), abstract.*
Y. Becker, et al.,Asymmetric Hydroformylation and Hydrocarboxylation of Enamides. Synthesis of Alanine and Proline, J. Org. Chem., vol. 45, pp. 2145-2151 (1980).
Ghosh, et al., "Asymmetric dihydroxylation route to a dipeptide isostere of a protease inhibitor: enantioselective synthesis of the core unit of ritonavir", Chem. Commun., pp. 1025-1026 (1999).
J. Golik, "Synthesis and Antitumor Evaluation of Paclitaxel Phosphonooxymethyl Ethers: A Novel Class of Water Soluble Paclitaxel Pro-Drugs", Bioorg. Med. Chem. Lett, vol. 6, pp. 1837-1842 (1996).
Jindrich, J., et al., Synthesis of N-(3-Fluoro-2-Phosphonomethoxypropyl) (FPMP) Derivates of Heterocyclic Bases, Collect Czech. Chem. Commun., vol. 58 (7), pp. 1645-1667 (1993).
R. Randad, et al., "De Novo Design of NonPeptidic HIV-1 Protease Inhibotors: Incorporation of Structural Water", Bioorg. Med. Chem. Lett., vol. 4, No. 10, pp. 1247-1252 (1994).
Scholz, D. et al., "Inhibitors of HIV-1 Proteinase Containing 2-Heterosubstituted 4-Amino-3-hydroxy-5-phenylpentanoic Acid: Synthesis, Enzyme Inhibition, and Antiviral Activity", J. of Med. Chem., vol. 37, pp. 3079-3089 (1994).
A. Smith, et al., "Pyrrolinone-Based HIV Protesase Inhibotrs. Design, Synthesis, and Antiviral Activity: Evidence for Improved Transport", J. Am. Chem. Soc., vol. 117, pp. 11113-11123 (1995).
H. Takechi, et al., Photoreactions of Succinimides with an N-Acyl Group in the Side Chain. Synthesis and Stereochemistry of Tricyclic Pyrrolo [1,2-a]pyrazine Ring Systems$^1$)Chem. Pharm. Bull., vol. 34, No. 8, pp. 3142-3152 (1986).
J. Vacca, et al., "Conformationally Constrained HIV-1 Protease Inhibitors", Bioorg. Med. Chem. Letts., vol. 4, No. 3, pp. 499-504 (1994).
Ettmayer, P., et al., "Novel, Extended Transition State Mimic in HIV-I Protease Inhibitors with Peripheral $C_2$-Symmetry", *Biorganic & Med. Chem. Ltrs.*, 4(24):2851-2856 (1994).
Kempf, D.J., et al., "Antiviral and Pharmacokinetic Properties of $C_2$ Symmetric Inhibitors of the Human Immunodeficiency Virus Type 1 Protease", *Antimicrobial Agents and Chemotherapy*, 2209-2214 (1991).
Nillroth, U., et al., "Human Immunodeficiency Virus Type 1 Proteinase Resistance to Symmetric Cyclic urea Inhibitor Analogs", *Antimicrobial Agents & Chemotherapy*, 2383-2388 (1997).
Tossi, A., et al., "Aspartic protease inhibitors", *Eur. J. Biochem.*, 267:1715-1722 (2000).

* cited by examiner

*Primary Examiner*—Janet L Andres
*Assistant Examiner*—David E Gallis
(74) *Attorney, Agent, or Firm*—Xu Zhang

(57) ABSTRACT

A compound of the formula

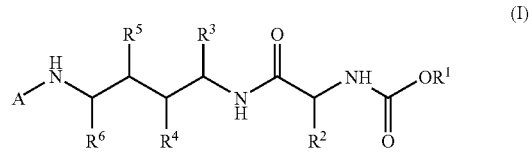

is disclosed as an HIV protease inhibitor. Methods and compositions for inhibiting an HIV infection are also disclosed.

9 Claims, No Drawings

HIV PROTEASE INHIBITING COMPOUNDS

This application claims priority to U.S. patent application Ser. No. 60/528,974, filed Dec. 11, 2003 and is incorporated herein by reference.

TECHNICAL FIELD

The present invention relates to novel compounds and a composition and a method for inhibiting human immunodeficiency virus (HIV) protease, a composition and method for inhibiting or treating an HIV infection, processes for making the compounds and synthetic intermediates employed in the processes.

BACKGROUND OF THE INVENTION

The genome of the human immunodeficiency virus (HIV) encodes a protease that is responsible for the proteolytic processing of one or more polyprotein precursors such as the pol and gag gene products. HIV protease processes the gag precursor into core proteins and also processes the pol precursor into reverse transcriptase and protease.

The correct processing of the precursor polyproteins by HIV protease is necessary for the assembly of infectious virions. Therefore, inhibition of HIV protease provides a useful target for development of therapeutic agents for treatment of HIV infection.

In recent years, inhibitors of HIV protease have become an important class of therapeutic agents for inhibition and treatment of HIV infection in humans. HIV protease inhibitors are especially effective when administered in combination with other classes of HIV therapeutic agents, especially inhibitors of HIV reverse transcriptase, in "cocktails" of HIV therapeutic agents.

At the present time, the HIV protease inhibitors saquinavir, ritonavir, indinavir, nelfinavir, amprenavir, lopinavir/ritonavir, fosamprenavir, and atazanavir have been approved in the U.S. for treatment of HIV infection. There is a continuing need for improved HIV protease inhibitors that are very potent, that have reduced side-effects and that are effective against resistant strains of HIV.

SUMMARY OF THE INVENTION

The present invention provides a compound of formula (I)

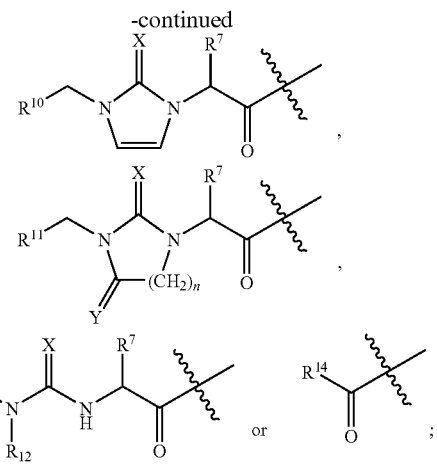

or a pharmaceutically acceptable salt form, prodrug or stereoisomer thereof, wherein:

A is

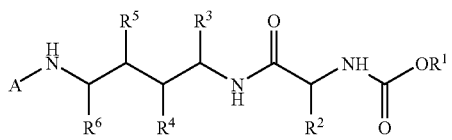

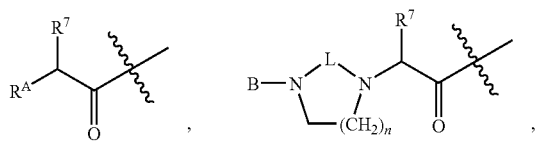

X is O, S or NH;
Y is O, S or NH;
B is H or —$CH_2R^9$;
L is —C(=O), —C(=S), —C(=NH) or —$S(O)_2$;
$R^A$ is —N(H)C(O)$R^8$, —O($R_a$), —OC(O)O$R_a$, —N$R_aR_b$, —N($R_b$)S(O)$_2R_a$, —N($R_b$)alkylN($R_b$)S(O)$_2R_a$, —N($R_b$)alkylN($R_b$)C(O)O$R_a$, —N($R_b$)alkylN($R_b$)C(O)NR$_aR_b$, -alkylS$R_a$, -alkylS(O)$R_a$ or -alkylS(O)$_a$ or -alkylS(O)$_2R_a$;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —O$R_a$, —S$R_a$, —SO$R_a$, —$SO_2R_a$, —NR$_aR_b$, —NR$_b$C(O)$R_a$, —N($R_b$)C(O)O$R_a$, —N($R_a$)C(=N)NR$_aR_b$, —N($R_a$)C(O)NR$_aR_b$, —C(O)NR$_aR_b$, —C(O)O$R_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^4$ is H and R$^5$ is OR$^{16}$; or

R$^5$ is H and R$^4$ is OR$^{16}$; or

R$^4$ and R$^5$ are —OR$^{16}$;

R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^8$ is —OR$_a$, —NR$_a$R$_b$, —N(R$_b$)C(O)OR$_a$, -alkylOR$_a$, -alkylOC(O)R$_a$, or —O-alkylC(O)R$_a$;

R$^9$ is alkyl, alkenyl, alkynyl, cycloalkyl, cycloalkenyl, aryl, heteroaryl or heterocycle; wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cyanoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$;

R$^{9a}$ is cycloalkyl, cycloalkenyl, heterocycle, aryl or heteroaryl; wherein each R$^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)C(O)OR$_a$, C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkyl-C(O)NR$_a$R$_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{14}$ is —OR$_a$, -alkylOR$_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —S(O)$_2$NR$_a$R$_b$, —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{16}$ is hydrogen or $R^{15}$;

$R^{15}$ is

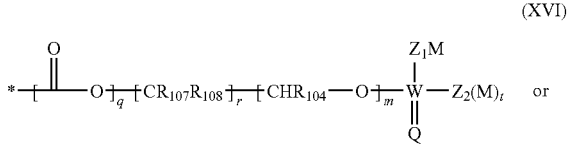

(XVI)

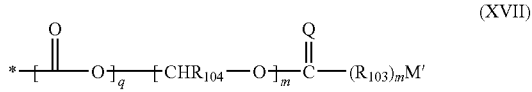

(XVII)

$R_{103}$ is C(R$_{105}$)$_2$, O or —N(R$_{105}$);

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —N(R$_{105}$)$_2$, alkyl, alkenyl, and $R_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R$ $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$, $NO_2$ and phenyl; provided that when M is $-N(R_{105})_2$, $Z_1$ and $Z_2$ are $CH_2$;

$Z_1$ is $CH_2$, O, S, $-N(R_{105})$, or, when M is absent, H;

$Z_2$ is $CH_2$, O, S or $-N(R_{105})$;

Q is O or S;

W is P or S; wherein when W is S, $Z_1$ and $Z_2$ are not S;

M' is H, alkyl, alkenyl or $R_{106}$; wherein 1 to 4 $-CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $-OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $-OR_{105}$, $-R_{105}$, $-N(R_{105})_2$, $-N(R_{105})C(O)R_{105}$, $-CN$, $-C(O)OR_{105}$, $-C(O)N(R_{105})_2$, halo and $-CF_3$;

each $R_{107}$ and $R_{108}$ are independently selected from the group consisting of hydrogen and alkyl;

q is 0 or 1;

m is 0 or 1;

m' is 0 or 1;

m'' is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, alkyl, alkenyl, alkynyl, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_a$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

The present invention also provides the processes of making a compound of the present invention and intermediates employed in the processes.

The present invention further provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, and a pharmaceutically acceptable carrier.

The present invention yet further provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, and one, two, three, four, five or six agents selected from the group consisting of a second HIV protease inhibitor, a HIV reverse transcriptase inhibitor, an HIV entry/fusion inhibitor, an HIV integrase inhibitor and an HIV budding/maturation inhibitor, and a pharmaceutically acceptable carrier.

The present invention also provides a pharmaceutical composition comprising a therapeutically effective amount of a compound or combination of compounds of the present invention, or a pharmaceutically acceptable salt form, stereoisomer, ester, salt of an ester, prodrug, salt of a prodrug, or combination thereof, ritonavir or a pharmaceutically acceptable salt form or prodrug thereof, and a pharmaceutically acceptable carrier.

The present invention still further provides a method of inhibiting the replication of an HIV virus comprising contacting said virus with a therapeutically effective amount of a compound or combination of compounds of the present invention, or a pharmaceutically acceptable salt form, stereoisomer, ester, salt of an ester, prodrug, salt of a prodrug, or combination thereof, and a pharmaceutically acceptable carrier.

The present invention still further provides a method of inhibiting the replication of an HIV virus comprising contacting said virus with the pharmaceutical composition of the present invention.

The present invention further provides a method of inhibiting HIV protease comprising contacting said HIV protease with a therapeutically effective amount of a compound or combination of compounds of the present invention, or a pharmaceutically acceptable salt form, stereoisomer, ester, salt of an ester, prodrug, salt of a prodrug, or combination thereof, and a pharmaceutically acceptable carrier.

The present invention further provides a method of inhibiting HIV protease comprising contacting said HIV protease with the pharmaceutical composition of the present invention.

The present invention also provides a method of treating or preventing an HIV infection comprising administering to a patient in need of such treatment a therapeutically effective amount of a compound or combination of compounds of the present invention, or a pharmaceutically acceptable salt form, stereoisomer, ester, salt of an ester, prodrug, salt of a prodrug, or combination thereof, and a pharmaceutically acceptable carrier.

The present invention also provides a method of treating or preventing an HIV infection comprising administering to a patient in need of such treatment the pharmaceutical composition of the present invention.

DETAILED DESCRIPTION OF THE INVENTION

As used in the present specification the following terms have the meanings indicated:

As used herein, the singular forms "a", "an", and "the" may include plural reference unless the context clearly dictates otherwise.

The term "activated carboxylic acid group" as used herein refers to acid halides such as acid chlorides and also refers to activated ester derivatives including, but not limited to, formic and acetic acid derived anhydrides, anhydrides derived from alkoxycarbonyl halides such as isobutyloxycarbonyl-chloride and the like, anhydrides derived from reaction of the carboxylic acid with N,N'-carbonyldiimidazole and the like, N-hydroxysuccinimide derived esters, N-hydroxyphthalimide derived esters, N-hydroxybenzotriazole derived esters, N-hydroxy-5-norbornene-2,3-dicarboximide derived esters, 2,4,5-trichlorophenol derived esters, p-nitrophenol derived esters, phenol derived esters, pentachlorophenol derived esters, 8-hydroxyquinoline derived esters and the like.

The term "alkanoyl" as used herein refers to an alkyl group attached to the parent molecular moiety through a carbonyl group. Representative examples of alkanoyl include, but not limited to, methylcarbonyl, ethylcarbonyl and tert-butylcarbonyl.

The term "alkyl," as used herein, refers to a group derived from a straight or branched chain saturated hydrocarbon containing 1, 2, 3, 4, 5, 6, 7, 8, 9 or 10 carbon atoms. Representative examples of alkyl groups include, but not limited to, r-propyl, butyl, methyl, 1-methylpropyl, 2-methylbutyl, 3-methylpropyl, tert-butyl, 1,1-dimethylethyl, 1-methylethyl and isopropyl (1-methylethyl).

The term "alkylamino" as used herein refers to —N(H)R$^{90}$ wherein R$^{90}$ is alkyl.

The term "alkylaminocarbonyl" as used herein refers to an alkylamino group attached to the parent molecular moiety through a carbonyl group.

The term "alkenyl," as used herein, refers to a straight or branched chain group of 2, 3, 4, 5, 6, 7, 8, 9 or 10 carbon atoms containing at least one carbon-carbon double bond. Representative examples of alkenyl groups include, but not limited to, allyl, propenyl and 3-methyl-2-butenyl.

The term "alkynyl," as used herein, refers to a straight or branched chain hydrocarbon of 2, 3, 4, 5, 6, 7, 8, 9 or 10 carbon atoms containing at least one carbon-carbon triple bond. Representative examples of alkynyl groups include, but not limited to, ethynyl, 2-methyl-3-butynyl and 3-pentynyl.

The term "alkoxy," as used herein, refers to an alkyl group attached to the parent molecular moiety through an oxygen atom. Representative examples of alkoxy groups include, but not limited to, tert-butoxy, methoxy, 2-methoxy-1,1-dimethylethyl, 2-ethoxy-1,1-dimethylethyl and isopropoxy.

The term "alkoxyalkyl," as used herein, refers to an alkyl group substituted by at least one alkoxy group.

The term "alkoxycarbonyl," as used herein, refers to an alkoxy group attached to the parent molecular moiety through a carbonyl group. Representative examples of alkoxycarbonyl groups include, but not limited to, tert-butoxycarbonyl, ethoxycarbonyl and methoxycarbonyl.

The term "aryl" as used herein, refers to a phenyl group, or a bicyclic or tricyclic hydrocarbon fused ring systems wherein one or more of the rings is a phenyl group. Bicyclic fused ring systems have a phenyl group fused to a monocyclic cycloalkenyl group, as defined herein, a monocyclic cycloalkyl group, as defined herein, or another phenyl group. Tricyclic fused ring systems are exemplified by a bicyclic fused ring system fused to a monocyclic cycloalkenyl group, as defined herein, a monocyclic cycloalkyl group, as defined herein, or another phenyl group. Representative examples of aryl groups include, but not limited to, anthracenyl, azulenyl, fluorenyl, indanyl, indenyl, naphthyl, phenyl and tetrahydronaphthyl. The aryl groups of the present invention can be substituted or unsubstituted, and are connected to the parent molecular moiety through any substitutable carbon atom of the group.

The term "arylalkyl", as used herein, refers to an aryl group, as defined herein, attached to the parent molecular moiety through an alkyl group. Representative examples of arylalkyl groups include, but are not limited to, phenylmethyl (benzyl), naphthylmethyl, phenylethyl, tetrahydronaphthyl-methyl and naphthylethyl.

The term "carbonyl" as used herein, refers to —C(=O).

The term "cyano," as used herein, refers to —CN.

The term "cyanoalkyl," as used herein, refers to a cyano group attached to the parent molecular moiety through an alkyl group.

The term "cycloalkenyl," as used herein, refers to a non-aromatic, partially unsaturated, monocyclic, bicyclic or tricyclic hydrocarbon ring system, having three to fourteen carbon atoms, zero heteroatom and one, two, three or four double bonds. Representative examples of cycloalkenyl groups include, but not limited to, cyclopropyl, cyclobutyl, cyclopentyl, cyclohexenyl, octahydronaphthalenyl and norbornylenyl. The cycloalkenyl groups of the present invention can be unsubstituted or substituted, and are attached to the parent molecular moiety through any substitutable carbon atom of the group.

The term "cycloalkenylalkyl", as used herein, refers to a cycloalkenyl group attached to the parent molecular moiety through an alkyl group.

The term "cycloalkyl," as used herein, refers to a saturated monocyclic, bicyclic, or tricyclic hydrocarbon ring system having three to fourteen carbon atoms and zero heteroatom. Representative examples of cycloalkyl groups include, but not limited to, cyclopropyl, cyclobutyl, cyclopentyl, cyclohexyl, cycloheptyl, bicyclo[3.1.1]heptyl, 6,6-dimethylbcyclo[3.1.1]heptyl and adamantyl like. The cycloalkyl groups of the present invention can be unsubstituted or substituted, and are connected to the parent molecula moiety through any substitutable carbon atom of the group.

The term "cycloalkylalkyl", as used herein, refers to a cycloalkyl group attached to the parent molecular moiety through an alkyl group.

The term "dialkylamino" as used herein refers to —NR$^{90}$R$^{91}$, wherein R$^{90}$ and R$^{91}$ are alkyls.

The term "dialkylamninocarbonyl" as used herein refers to a dialkylamino group as defined herein, appended to the parent molecular moiety through a carbonyl group.

The terms "halo," and "halogen" as used herein, refer to F, Cl, Br, and I.

The term "haloalkoxy," as used herein, refers to a haloalkyl group attached to the parent molecular moiety through an oxygen atom.

The term "haloalkenyl" as used herein, refers to an alkenyl group substituted by one, two, three or four halogen atoms.

The term "haloalkyl" as used herein, refers to an alkyl group substituted by one, two, three, or four halogen atoms. Examples of haloalkyl include, but are not limited to, trifluoromethyl, fluoromethyl, difluoromethyl, 1-fluoroethyl, 1,2-difluoroethyl, and 1,2,3-trifluoroethyl.

The term "heteroaryl" as used herein, refers to an aromatic five- or six-membered ring where at least one atom is selected from the group consisting of N, O, and S, and the remaining atoms are carbon. The term "heteroaryl" also includes bicyclic systems where a heteroaryl ring is fused to a phenyl group, a monocyclic cycloalkyl group, as defined herein, a monocyclic cycloalkenyl group, as defined herein, a monocyclic heterocycle group, as defined herein, or an additional monocyclic heteroaryl group. The term "heteroaryl" also includes tricyclic systems where a bicyclic system is fused to a phenyl group, a monocyclic cycloalkyl group, as defined herein, a monocyclic cycloalkenyl group, as defined herein, a monocyclic heterocycle group, as defined herein, or an additional monocyclic heteroaryl group. Representative examples of heteroaryl groups include, but not limited to, benzothienyl, benzoxazolyl, benzimidazolyl, benzoxadiazolyl, dibenzofuranyl, dihydrobenzothiazolyl, furanyl, imidazolyl, imidazopyridyl, indazolyl, indolyl, isoindolyl, isoxazolyl, isoquinolinyl, isothiazolyl, oxadiazolyl, oxazolyl, thiazolyl, thienopyridinyl, thienyl, triazolyl, thiadiazolyl, tetrazolyl, pyridyl, pyridazinyl, pyrimidinyl, pyrazinyl, pyrazolyl, pyrrolyl, quinolinyl, tetrahydroquinolinyl and triazinyl. The heteroaryl groups of the present invention can be substituted or unsubstituted, and are connected to the parent molecular moiety through any substitutable carbon or nitrogen atom in the groups. In addition, the nitrogen heteroatoms may or may not be quaternized or oxidized to the N-oxide. Also, the nitrogen containing rings may or may not be N-protected.

The term "heteroarylalkyl" as used herein, refers to an heteroaryl group as defined herein, appended to the parent molecular moiety through an alkyl group as defined herein.

The term "heterocycle" as used herein, refers to cyclic, non-aromatic, saturated or partially unsaturated, three, four, five-, six-, or seven-membered rings containing at least one atom selected from the group consisting of oxygen, nitrogen, and sulfur. The term "heterocycle" also includes bicyclic systems where a heterocycle ring is fused to a phenyl group, a monocyclic cycloalkenyl group, as defined herein, a monocyclic cycloalkyl group, as defined herein, or an additional monocyclic heterocycle group. The term "heterocycle" also includes tricyclic systems where a bicyclic system is fused to a phenyl group, a monocyclic cycloalkenyl group, as defined herein, a monocyclic cycloalkyl group, as defined herein, or an additional monocyclic heterocycle group. The heterocycle groups of the invention are substituted or unsubstituted, and are connected to the parent molecular moiety through any substitutable carbon or nitrogen atom in the groups. Representative examples of heterocycle groups include, but not limited to, benzoxazinyl, dihydroindolyl, dihydropyridinyl, 1,3-dioxanyl, 1,4-dioxanyl, 1,3-dioxolanyl, hexahydrofurofuranyl, isoindolinyl, morpholinyl, piperazinyl, pyrrolidinyl, tetrahydropyridinyl, piperidinyl, thiomorpholinyl and tetrahydropyranyl. The nitrogen heteroatoms may or may not be quaternized or oxidized to the N-oxide. In addition, the nitrogen containing heterocyclic rings may or may not be N-protected.

The term "heterocyclealkyl" as used herein, refers to an heterocycle group as defined herein, appended to the parent molecular moiety through an alkyl group as defined herein.

The term "hydroxy," as used herein, refers to —OH.

The term "hydroxyalkyl" as used herein, refers to an alkyl group substituted by at least one hydroxy group. Representative examples of hydroxyalkyl include, but are not limited to 1-hydroxy-1-methylethyl and 2-hydroxy-1,1-dimethylethyl.

The term "nitro," as used herein, refers to —NO$_2$.

The term "nitroalkyl" as used herein, refers to an alkyl group substituted by at least one nitro group.

The term "oxo," as used herein, refers to =O.

It is understood that each of the terms as defined hereinabove: alkanoyl, alkenyl, alkoxy, alkoxyalkyl, alkoxycarbonyl, alkyl, alkylamino, alkylaminocarbonyl, alkynyl, aryl, arylalkyl, cyanoalkyl, cycloalkenyl, cycloalkenylalkyl, cycloalkyl, cycloalkylalkyl, dialkylamino, dialkylaminocarbonyl, haloalkoxy, haloalkenyl, haloalkyl, heteroaryl, heteroarylalkyl, heterocycle, heterocyclealkyl, hydroxyalkyl, nitroalkyl, may be unsubstituted or substituted.

The term "treating" as used herein, refers to reversing, alleviating, inhibiting the progress of, or preventing the disorder or condition, or one or more symptoms of such disorder or condition to which such term applies. The term "treatment", as used herein, refers to the act of treating, as "treating" is defined immediately above.

A "patient" is any individual treated with a compound or combination of compounds of the present invention, or a therapeutically acceptable salt, solvate, prodrug, or salt of a prodrug, as defined herein. Patients include humans, as well as other animals such as companion animals (e.g. dogs and cats) and livestock. Patients may be experiencing one or more symptoms of a condition responsive to HIV modulation, or may be free of such symptom(s) (i.e. treatment may be prophylactic).

In a first embodiment the present invention provides a compound of formula (I)

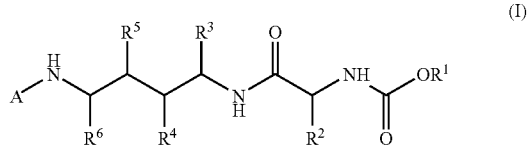

or a pharmaceutically acceptable salt form, prodrug or stereoisomer thereof, wherein:

A is

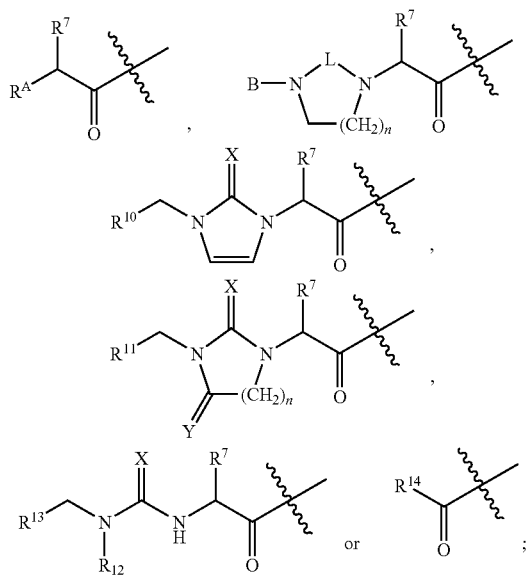

X is O, S or NH;
Y is O, S or NH;
B is H or —CH$_2$R$_9$;
L is —C(=O), —C(=S), —C(=NH) or —S(O)$_2$;
RA is —N(H)C(O)R$^8$, —O(a), —OC(O)OR$_a$, —NR$_a$R$_b$, —N(R$_b$)S(O)$_2$R$_a$, —N(R$_b$)alkylN(R$_b$)S(O)$_2$R$_a$, —N(R$_b$)alkylN(R$_b$)C(O)OR$_a$, —N(R$_b$)alkylN(R$_b$)C(O)NR$_a$R$_b$, -alkylSR$_a$, -alkylS(O)R$_a$ or -alkylS(O)$_2$R$_a$;
R$^1$ is alkyl, alkenyl, alkynyl, cycloalkyl, cycloalkenyl, heterocycle, aryl or heteroaryl; wherein each R$^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and R$^{1a}$;
R$^{1a}$ is cycloalkyl, cycloalkenyl, heterocycle, aryl or heteroaryl; wherein each R$^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;
R$^2$ is alkyl, alkenyl, alkynyl, cycloalkyl, cycloalkenyl, heterocycle, aryl or heteroaryl; wherein each R$^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^2$a;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(allyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;
R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;
R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;
R$^4$ is H and R$^5$ is OR$^{16}$; or
R$^5$ is H and R$^4$ is OR$^{16}$; or
R$^4$ and R$^5$ are —OR$^{16}$;
R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl;

wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), and -alkylC(O)N(alkyl)$_2$;

$R^7$ is —N($R_b$)C(O)O$R_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —O$R_a$, —OC(O)$R_a$, —S$R_a$, —SO$R_a$, —$SO_2R_a$, —N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkyl-C(O)N(alkyl)$_2$;

$R^8$ is —O$R_a$, —N$R_aR_b$, —N($R_b$)C(O)O$R_a$, -alkylO$R_a$, -alkylOC(O)$R_a$, or -alkylC(O)$R_a$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —O$R_a$, —S$R_a$, —SO$R_a$, —$SO_2R_a$, —$SO_2$N$R_a$, —$SO_2$O$R_a$, —N$R_aR_b$, —N($R_b$)C(O)$R_a$, —N($R_b$)$SO_2R_a$, —N($R_b$)$SO_2$N$R_aR_b$, —N($R_b$)C(O)N$R_aR_b$, —N($R_b$)C(O)O$R_a$, —C(O)$R_a$, —C(O)N$R_aR_b$, —C(O)O$R_a$, haloalkyl, nitroalkyl, cynaoalkyl, formylalkyl, -alkylO$R_a$, -alkyl-O—P(O)(O$R_a$)(O$R_a$), -alkylN$R_aR_b$, -alkylN($R_b$)C(O)O$R_a$, -alkylN($R_b$)$SO_2$N$R_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkylC(O)$R_a$, -alkylC(O)N$R_aR_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —O$R_a$, —S$R_a$, —SO$R_a$, —$SO_2R_a$, —$SO_2$N$R_a$, —$SO_2$O$R_a$, —N$R_aR_b$, —N($R_b$)C(O)$R_a$, —N($R_b$)$SO_2R_a$, —N($R_b$)$SO_2$N$R_aR_b$, —N($R_b$)C(O)N$R_aR_b$, —N($R_b$)C(O)O$R_a$, —C(O)$R_a$, —C(O)N$R_aR_b$, —C(O)O$R_a$, haloalkyl, nitroalkyl, cynaoalkyl, formylalkyl, -alkylO$R_a$, -alkyl-O—P(O)(O$R_a$)(O$R_a$), -alkylN$R_aR_b$, -alkylN($R_b$)C(O)O$R_a$, -alkylN($R_b$)$SO_2$N$R_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkylC(O)$R_a$, -alkylC(O)N$R_aR_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —O$R_a$, —S$R_a$, —SO$R_a$, —$SO_2R_a$, —$SO_2$N$R_a$, —$SO_2$O$R_a$, —N$R_aR_b$, —N($R_b$)C(O)$R_a$, —N($R_b$)$SO_2R_a$, —N($R_b$)$SO_2$N$R_aR_b$, —N($R_b$)C(O)N$R_aR_b$, —N($R_b$)C(O)O$R_a$, —C(O)$R_a$, —C(O)N$R_aR_b$, —C(O)O$R_a$, haloalkyl, nitroalkyl, cynaoalkyl, formylalkyl, -alkylO$R_a$, -alkyl-O—P(O)(O$R_a$)(O$R_b$), -alkylN$R_aR_b$, -alkylN($R_b$)C(O)O$R_a$, -alkylN($R_b$)$SO_2$N$R_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkylC(O)$R_a$, -alkylC(O)N$R_aR_b$ and $R^{11a}$;

$R^{11a}$ is cycloalkyl, cycloalkenyl, heterocycle, aryl or heteroaryl; wherein each $R^{11}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N (H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, SO$_2$OR$_a$, —NR$_a$R$_b$, —N(R$_b$)C(O)R$_a$, —N(R$_b$)C(O)OR$_a$, —C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkyl-C(O)NR$_a$R$_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{14}$ is —OR$_a$, -alkylOR$_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —S(O)$_2$NR$_a$R$_b$, —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)2, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{16}$ is hydrogen or $R^{15}$;

$R^{15}$ is

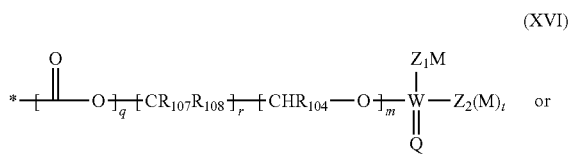

(XVI)

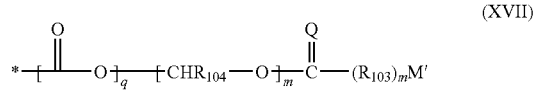

(XVII)

$R_{103}$ is C(R$_{105}$)$_2$, O or —N(R$_{105}$);

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —N(R$_{105}$)$_2$, alkyl, alkenyl, and $R_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N(R$_{105}$); and wherein any hydrogen in said alkyl, alkenyl or $R_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, $Z_1$ and $Z_2$ are —CH$_2$;

$Z_1$ is CH$_2$, O, S, —N(R$_{105}$), or, when M is absent, H;

$Z_2$ is CH$_2$, O, S or —N(R$_{105}$);

Q is O or S;

W is P or S; wherein when W is S, $Z_1$ and $Z_2$ are not S;

M' is H, alkyl, alkenyl or $R_{106}$; wherein 1 to 4 —CH$_2$ radicals of the alkyl or alkenyl is optionally replaced by a heteroatom group selected from O, S, S(O), SO$_2$, or N(R$_{105}$); and wherein any, hydrogen in said alkyl, alkenyl or $R_{106}$ is optionally replaced with a substituent selected from the group consisting of oxo, —OR$_{105}$, —R$_{106}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

each R$_{107}$ and R$_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl$_2$, —SH, —S(alkyl), —SO$_2$(alkyl), —N(H)C(O)alkyl, —N(alkyl)C(O)alkyl, —N(H)C(O)NH$_2$, —N(H)C (O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_a$; alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_a$;

R$_a$ is aryl, heteroaryl or heterocycle; wherein each R$_a$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention of the first embodiment provides a compound of formula (I) wherein W is P; Q is O; $Z_1$ and $Z_2$ are O; and X, Y, B, L, R$^A$, R$^1$, R$^{1a}$, R$^2$, R$^{2a}$, R$^3$, R$^{3a}$, R$^4$, R$^5$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, M', R$_{106}$, R$_{107}$, R$_{108}$q, m, m', m'', r, t, R$_a$, R$_b$, R$_c$, and n are as defined in formula (I).

For example, the present invention of the first embodiment provides a compound of formula (I) wherein R$^4$ is H; R$^5$ is OR$^{16}$ and X, Y, B, L, R$^A$, R$^1$, R$^{1a}$, R$^2$, R$^{2a}$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein R$^4$ is OR$^{16}$, R$^5$ is H; and X, Y, B, L, R$^A$, R$^1$, R$^{1a}$, R$^2$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or —C(=S); X is O; Y is O; and B, R$^A$, R$^1$, R$^{1a}$, R$^2$, R$^{2a}$, R$^3$, R$^{3a}$, R$^4$, R$^5$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or —C(=S); X is O; Y is O; R$^4$ is H; R$^5$ is OR$^{16}$; and B, R$^A$, R$^1$, R$^{1a}$, R$^2$, R$^{2a}$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or —C(=S); X is O; Y is O; R$^4$ is OR$^1$; R$^5$ is H; and B, R$^A$, R$^1$, R$^{1a}$, R$^2$, R$^{2a}$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or —C(=S); X is O; Y is O; R$^4$ is H, R$^5$ is OR$^{16}$; R$^2$ is alkyl; and B, R$^A$, R$^1$, R$^{1a}$, R$^3$, R$^3$a, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or —C(=S); X is O; Y is O; R$^4$ is OR$^{16}$, R$^5$ is H; R$^2$ is alkyl; and B, R$^A$, R$^1$, R$^{1a}$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or C(=S); X is O; Y is O; R$^4$ is H; R$^5$ is OR$^{16}$; R$^2$ is alkyl; R$^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$; and B, R$^A$, R$^1$, R$^{1a}$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, R$^{15}$, R$^{16}$, R$_{103}$, R$_{104}$, R$_{105}$, M, $Z_1$, $Z_2$, Q, W, M', R$_{106}$, R$_{107}$, R$_{108}$q, m, m', m'', r, t, R$_a$, R$_b$, R$_c$, and n are as defined in formula (I).

For example, the present invention provides a compound of formula (I) wherein L is —C(=O) or —C(=S); X is O; Y is O; R$^4$ is OR$^{16}$; R$^5$ is H; R$^2$ is alkyl; R$^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$; and B, R$^A$, R$^1$, R$^{1a}$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{13}$, R$^{13a}$, R$^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m''', r, t, $R_a$, $R_b$, $R_c$, and n are as defined in formula (I).

For example, the present invention provides a compound of formula (I) wherein L is —C(=O) or —C(=S); X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; and B, $R^A$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, m, m', m''', r, t, $R_a$, $R_b$, $R_c$, n and the substituents of $R^{3a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; and B, $R^A$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m''', r, t, $R_a$, $R_b$, $R_c$, n and the substituents of $R^{3a}$ are as defined in formula (I).

For example, the present invention provides a compound of formula (I) wherein L is —C(=) or —C(=S); X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^6$ is arylalkyl substituted with 0 or one $R^{6a}$; and B, $R^A$, $R^1$, $R^{1a}$, $R^{3a}$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$ $R_{103}$, $R_{104}$, $R_{105}$, M, $Z_1$, $Z_2$, Q, W, M', $R_{107}$, $R_{108}$, q, m, m', m'''m, r, t, $R_a$, $R_b$, $R_c$, n and the substituents of $R^{3a}$ and $R^{6a}$ are as defined in formula (I).

For example, the present invention provides a compound of formula (I) wherein L is —C(=) or —C(=S); X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^6$ is arylalkyl substituted with 0 or one $R^{6a}$; and B, $R^A$, $R^1$, $R^{1a}$, $R^{3a}$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$ $R_{103}$, $R_{104}$, $R_{105}$, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^{6a}$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^6$ is arylalkyl substituted with 0 or one $R^{6a}$; $R_{104}$ is hydrogen or alkyl, each M is hydrogen or alkyl, $Z_1$ is O, $Z_2$ is O, Q is O, W is P, M' is hydrogen or alkyl, and B, $R^A$, $R^1$, $R^{1a}$, $R^{3a}$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{105}$, $R_{106}$, $R_{107}$, $R_{108}$, q, m, m', m''', r, t, $R_a$, $R_b$, $R_c$, n and substituents of $R^{3a}$, M, M' and $R^{6a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^6$ is arylalkyl substituted with 0 or one $R^{6a}$; $R_{104}$ is hydrogen or alkyl, $R_{105}$ is hydrogen or alkyl, each M is hydrogen or alkyl, $Z_1$ is O, $Z_2$ is O, Q is O, W is P, M' is hydrogen or alkyl, and B, $R^A$, $R^1$, $R^{1a}$, $R^{3a}$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{106}$, $R_{107}$, $R_{108}$, q, m, m', m''', r, t, $R_a$, $R_b$, $R_c$, n and the substituents of $R^{3a}$, M, M' and $R^{6a}$ are as defined in formula (I).

For example, the present invention provides a compound of formula (I) wherein L is —C(=) or —C(=S); X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^{3a}$ is aryl or heteroaryl; wherein each $R^{3a}$ is unsubstituted or substituted, and B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3}a$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^{3a}$ is aryl or heteroaryl;

wherein each $R^{3a}$ is wherein each $R^{3a}$ is unsubstituted or substituted; and B, $R^A$, $R^1$, $R^{1a}$, $R^6$, $R^{6a}$, $R^7$, $R^{7a}$, $R^8$, $R^9$, $R^{9a}$, $R^{10}$, $R_{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is C1, C2, C3, C4 or C5, alkyl, $R^3$ is phenylmethyl wherein the phenyl moiety of phenylmethyl is unsubstituted or substituted with one $R^{3a}$, $R^{3a}$ is aryl or heteroaryl wherein each $R^{3a}$ is unsubstituted or substituted; and B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$ M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is C1, C2, C3, C4 or C5 alkyl, $R^3$ is phenylmethyl wherein the phenyl moiety of phenylmethyl is unsubstituted or substituted with one $R^{3a}$, $R^{3a}$ is aryl or heteroaryl; wherein each $R^{3a}$ is unsubstituted or substituted; and B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^6$, $R_{103}$, $R_{104}$, $R_{105}$ M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is C1, C2, C3, C4 or C5 alkyl, $R^3$ is phenylmethyl wherein the phenyl moiety of the phenylmethyl is unsubstituted or substituted with one $R^{3a}$, $R^{3a}$ is unsubstituted or substituted pyridyl and B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ are as defined in formula (I).

For example, the present invention provides a compound of formula (I) wherein L is —C(=) or —C(=S); X is O; Y is O; $R^4$ is $OR^{16}$; $R^5$ is H; $R^2$ is C1, C2, C3, C4 or C5 alkyl, $R^3$ is phenylmethyl wherein the phenyl moiety of the phenylmethyl is unsubstituted or substituted with one $R^{3a}$, $R^{3a}$ is unsubstituted or substituted pyridyl; and B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is C1, C2, C3, C4 or C5 alkyl, $R^3$ is phenylmethyl wherein the phenyl moiety of the phenylmethyl is unsubstituted or substituted with one $R^{3a}$ wherein $R^{3a}$ is unsubstituted or substituted pyridyl; $R^6$ is phenylmethyl substituted with 0 or one $R^{6a}$ wherein $R^{6a}$ is unsubstituted or substituted aryl or unsubstituted or substituted heteroaryl;

and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^{6a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is C1, C2, C3, C4 or C5 alkyl, $R^3$ is phenylmethyl wherein the phenyl moiety of the phenylmethyl is unsubstituted or substituted with one $R^{3a}$, $R^{3a}$ is unsubstituted or substituted pyridyl; $R^6$ is phenylmethyl substituted with 0 or one $R^{6a}$ wherein $R^{6a}$ is unsubstituted or substituted aryl or unsubstituted or substituted heteroaryl; and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R^{3a}$ and $R^6$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is C1, C2, C3, C4 or C5 alkyl, $R^3$ is phenylmethyl wherein the phenyl moiety of the phenylmethyl is unsubstituted or substituted with one $R^{3a}$ wherein $R^{3a}$ is unsubstituted or substituted pyridyl; $R^6$ is phenylmethyl substituted with 0 or one $R^{6a}$ wherein $R^{6a}$ is unsubstituted or substituted pyridyl; and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{R107}$, $R_{108}$, q, m, m', m''', r, t, $R_a$, $R_b$, $R_c$, n and the substituents of $R^{3a}$ and $R^{6a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is C1, C2, C3, C4 or C5 alkyl, $R^3$ is phenylmethyl wherein the phenyl moiety of the phenylmethyl is unsubstituted or substituted with one $R^{3a}$, $R^{3a}$ is unsubstituted or substituted pyridyl; $R^6$ is phenylmethyl substituted with 0 or one $R^{6a}$ wherein $R^{6a}$ is unsubstituted or substituted pyridyl; and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^6$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is 1-methylpropyl, tert-butyl or isopropyl, $R^3$ is phenylmethyl wherein the phenyl moiety of the phenylmethyl is unsubstituted or substituted with one $R^{3a}$, $R^{3a}$ is unsubstituted or substituted pyridyl; $R^6$ is phenylmethyl substituted with 0 or one $R^{6a}$, wherein $R^{6a}$ is unsubstituted or substituted pyridyl; and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^{6a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is 1-methylpropyl, tert-butyl or isopropyl, $R^3$ is phenylmethyl wherein the phenyl moiety of the phenylmethyl is unsubstituted or substituted with one $R^{3a}$ wherein $R^{3a}$ is unsubstituted or substituted pyridyl; $R^6$ is phenylmethyl substituted with 0 or one $R^{6a}$, wherein $R^{6a}$ is unsubstituted or substituted pyridyl; and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^{6a}$ are as defined in formula (I).

For example, the present invention provides a compound of formula (I) wherein L is —C(=O) or —C(=S); X is O; Y is O; $R^4$ is H; $R^5$ is $OR^{16}$; $R^2$ is 1-methylpropyl, tert-butyl or isopropyl, $R^3$ is phenylmethyl wherein the phenyl moiety of the phenylmethyl is unsubstituted or substituted with one $R^{3a}$, $R^{3a}$ is unsubstituted or substituted pyridyl; $R^6$ is phenylmethyl substituted with 0 or one $R^{6a}$, wherein $R^{6a}$ is unsubstituted or substituted pyridyl; W is P; Q is O; $Z_1$ and $Z_2$ are O; and B, $R^{A,R1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, M', $R_{106}$, $R_{107}$, $R_{108}$, q, m, m', m''', r, t, $R_a$, $R_b$, $R_c$, n and the substituents of $R^{3a}$ and $R^{6a}$ are as defined in formula (I).

For example, the present invention provides a compound of formula (I) wherein L is —C(=O) or —C(=S); X is O; Y is O; $R^4$ is $OR^{16}$; $R^5$ is H; $R^2$ is 1-methylpropyl, tert-butyl or isopropyl, $R^3$ is phenylmethyl wherein the phenyl moiety of the phenylmethyl is unsubstituted or substituted with one $R^{3a}$ wherein $R^{3a}$ is unsubstituted or substituted pyridyl; $R^6$ is phenylmethyl substituted with 0 or one $R^{6a}$, wherein $R^{6a}$ is unsubstituted or substituted pyridyl; W is P; Q is O; $Z_1$ and $Z_2$ are O; and B, $R^A$, $R^1$, $R^{1a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, M', $R_{106}$, $R_{107}$, $R_{108}$, m, m', m''', r, t, $R_a$, $R_b$, $R_c$, n and the substituents of $R^{3a}$ and $R^{6a}$ are as defined in formula (I).

Exemplary compounds of the present invention of formula (I) include, but not limited to, the following:

methyl 7-benzyl-1,10-ditert-butyl-6-hydroxy-2,9,12-trioxo-4-[4-(2-pyridinyl)benzyl]-13-oxa-3,8,11-triazatetradec-1-ylcarbamate;

methyl 4-benzyl-1,10-ditert-butyl-5-hydroxy-2,9,12-trioxo-7-[4-(2-pyridinyl)benzyl]-13-oxa-3,8,11-triazatetradec-1-ylcarbamate;

methyl 1-{[(1-benzyl-3-hydroxy-4-{[3-methyl-2-(2-oxo-3-{[2-(2-pyrindinyl)-1,3-thiazol-4-yl]methyl}-1-imidazolidinyl)pentanoyl])amino}-5-phenylpentyl)amino]carbonyl}-2,2-dimethylpropylcarbamate;

methyl 1-({[1-benzyl-3-hydroxy-4-({3-methyl-2-[2-oxo-3-(4-quinolinylmethyl)-1-imidazolidinyl]pentanoyl}amino)-5-phenylpentyl]amino}carbonyl)-2,2-dimethylpropylcarbamate;

methyl 1-({[1-benzyl-3-hydroxy-4-({3-methyl-2-[2-oxo-3-(4-quinolinylmethyl)-1-imidazolidinyl]pentanoyl}amino)-5-phenylpentyl]amino}carbonyl)-2-methylbutylcarbamate;

methyl 1-{[(1-benzyl-3-hydroxy-4-{[2-(3-{[2-(methoxymethyl)-1,3-thiazol-4-yl]methyl}-2-oxo-1-imidazolidinyl)-3,3-dimethylbutanoyl]amino}-5-phenylpentyl)amino]carbonyl}-2,2-dimethylpropylcarbamate;

methyl 1-[({1-benzyl-3-hydroxy-4-[(3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate;

methyl 1-[({1-benzyl-2-hydroxy-4-[(3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate;

methyl 1-[({1-benzyl-2-hydroxy-4-[(3-methyl-2-{3-[(6-methyl-2-pyridinyl)methyl]-2-oxo-1-imidazolidinyl}pentanoyl)amino]-5-phenylpentyl}amino)carbonyl]-2-methylbutylcarbamate;

methyl 1-[({1-benzyl-4-[(3,3-dimethyl-2-{3-[(6-methyl-2-pyridinyl)methyl]-2-oxo-1-imidazolidinyl}butanoyl)amino]-2-hydroxy-5-phenylpentyl}amino)carbonyl]-2,2-dimethylpropylcarbamate;

methyl 1-[({1-benzyl-2-hydroxy-4-[(3-methyl-2-{3-[(2-methyl-1,3-thiazol-5-yl)methyl]-2-oxo-1-imidazolidinyl}pentanoyl)amino]-5-phenylpentyl}amino)carbonyl]-2,2-dimethylpropylcarbamate;

methyl 1-{[(1-benzyl-2-hydroxy-4-{[3-methyl-2-(2-oxo-3-{[2-(3-pyridinyl)-1,3-thiazol-4-yl]methyl}-1-imidazolidinyl)pentanoyl]amino}-5-phenylpentyl)amino]carbonyl}-2,2-dimethylpropylcarbamate;

methyl 1-[({1-benzyl-2-hydroxy-4-[(3-methyl-2-{3-[(6-methyl-3-pyridinyl)methyl]-2-oxo-1-imidazolidinyl}pentanoyl)amino]-5-phenylpentyl}amino)carbonyl]-2,2-dimethylpropylcarbamate;

methyl 1-[({1-benzyl-4-[(3,3-dimethyl-2-{3-[(2-methyl-1,3-thiazol-4-yl)methyl]-2-oxo-1-imidazolidinyl}butanoyl)amino]-2-hydroxy-5-phenylpentyl}amino)carbonyl]-2,2-dimethylpropylcarbamate;

methyl 1-[({1-benzyl-2-hydroxy-4-[(3-methyl-2-{3-[(2-methyl-3-pyridinyl)methyl]-2-oxo-1-imidazolidinyl}pentanoyl)amino]-5-phenylpentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-{[(1-benzyl-2-hydroxy-4-{[2-(3-{[6-(1-hydroxy-1-methylethyl)-2-pyridinyl]methyl}-2-oxo-1-imidazolidinyl)-3,3-dimethylbutanoyl]amino}-5-phenylpentyl)amino]carbonyl}-2,2-dimethylpropylcarbamate;

methyl 1-[({3-hydroxy-4-[(3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-{[(1-benzyl-4-{[3,3-dimethyl-2-(2-oxo-3-{[2-(3-pyridinyl)-1,3-thiazol-4-yl]methyl}-1-imidazolidinyl)butanoyl]amino}-2-hydroxy-5-phenylpentyl)amino]carbonyl}-2,2-dimethylpropylcarbamate;

methyl 1-({[1-benzyl-4-({3,3-dimethyl-2-[2-oxo-3-(3-pyridinylmethyl)-1-imidazolidinyl]butanoyl}amino)-2-hydroxy-5-phenylpentyl]amino}carbonyl)-2,2-dimethylpropylcarbamate;

methyl 1-[({3-hydroxy-4-[(3-methyl-2-{3-[(2-methyl-3-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-[({1-benzyl-4-[(3,3-dimethyl-2-{3-[(6-methyl-2-pyridinyl)methyl]-2-oxo-1-imidazolidinyl}butanoyl)amino]-3-hydroxy-5-phenylpentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate;

methyl 1-[({1-benzyl-4-[(3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate;

methyl 7-benzyl-1,10-ditert-butyl-5-hydroxy-2,9,12-trioxo-4-[4-(2-pyridinyl)benzyl]-13-oxa-3,8,11-triazatetradec-1-ylcarbamate;

(3R,3aS,6aR)-hexahydrofuro[2,3-b]furan-3-yl 1-benzyl-3-hydroxy-4-({2-[(methoxycarbonyl)amino]-3,3-dimethylbutanoyl}amino)-5-[4-(2-pyridinyl)phenyl]pentylcarbamate;

(3R,3aR,6aS)-hexahydrofuro[2,3-b]furan-3-yl 1-benzyl-3-hydroxy-4-({2-[(methoxycarbonyl)amino]-3,3-dimethylbutanoyl}amino)-5-[4-(2-pyridinyl)phenyl]pentylcarbamate;

(3R,3aS,6aR)-hexahydrofuro[2,3-b]furan-3-yl 1-benzyl-2-hydroxy-4-({2-[(methoxycarbonyl)amino]-3,3-dimethylbutanoyl}amino)-5-[4-(2-pyridinyl)phenyl]pentylcarbamate;

(3R,3aR,6aS)-hexahydrofuro[2,3-b]furan-3-yl 1-benzyl-2-hydroxy-4-({2-[(methoxycarbonyl)amino]-3,3-dimethylbutanoyl}amino)-5-[4-(2-pyridinyl)phenyl]pentylcarbamate;

methyl 1-[({2-hydroxy-4-[(3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 4-benzyl-10-tert-butyl-5-hydroxy-1-[1-methyl-i-(methylsulfanyl)ethyl]-2,9,12-trioxo-7-[4-(2-pyridinyl)benzyl]-13-oxa-3,8,11-triazatetradec-1-ylcarbamate;

methyl 4-benzyl-10-tert-butyl-5-hydroxy-1-[1-methyl-i-(methylsulfonyl)ethyl]-2,9,12-trioxo-7-[4-(2-pyridinyl)benzyl]-13-oxa-3,8,11-triazatetradec-1-ylcarbamate;

methyl 4-benzyl-10-tert-butyl-6-hydroxy-1-[1-methyl-i-(methylsulfanyl)ethyl]-2,9,12-trioxo-7-[4-(2-pyridinyl)benzyl]-1 3-oxa-3,8,11-triazatetradec-1-ylcarbamate;

methyl 4-benzyl-10-tert-butyl-6-hydroxy-1-[1-methyl-i-(methylsulfonyl)ethyl]-2,9,12-trioxo-7-[4-(2-pyridinyl)benzyl]-1 3-oxa-3,8,11-triazatetradec-1-ylcarbamate;

methyl 1-[({4-{[(2S)-3,3-dimethyl-2-(2-oxo-3-{[2-(3-pyridinyl)-1,3-thiazol-4-yl]methyl}-1-imidazolidinyl)butanoyl]amino}-3-hydroxy-5-phenyl-1-[4-(2-pyridinyl)benzyl]pentyl}amino)carbonyl]-2,2-dimethylpropylcarbamate;

methyl 1-[({4-{[3,3-dimethyl-2-(2-oxo-3-{[2-(3-pyridinyl)-1,3-thiazol-4-yl]methyl}-1-imidazolidinyl)butanoyl]amino}-2-hydroxy-5-phenyl-1-[4-(2-pyridinyl)benzyl]pentyl}amino)carbonyl]-2,2-dimethylpropylcarbamate;

methyl 1-[({3-hydroxy-4-[(3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-[({2-hydroxy-4-[(3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-[({4-{[(2,6-dimethylphenoxy)acetyl]amino}-3-hydroxy-5-phenyl-1-[4-(2-pyridinyl)benzyl]pentyl}amino)carbonyl]-2,2-dimethylpropylcarbamate;

methyl 1-[({4-{[(2,6-dimethylphenoxy)acetyl]amino}-2-hydroxy-5-phenyl-1-[4-(2-pyridinyl)benzyl]pentyl}amino)carbonyl]-2,2-dimethylpropylcarbamate;

methyl 1-[({3-hydroxy-4-({(2S)-2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl 1-[({2-hydroxy-4-({2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl 1-[({4-({3,3-dimethyl-2-[2-oxo-3-(4-quinolinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-({(2S)-3,3-dimethyl-2-[2-oxo-3-(4-quinolinylmethyl)-1-imidazolidinyl]butanoyl}amino)-2-hydroxy-5-phenyl-1-[4-(2-pyridinyl)benzyl]pentyl}amino)carbonyl]-2,2-dimethylpropylcarbamate;

methyl 1-[({2-hydroxy-4-{[2-(3-{[6-(1-hydroxy-1-methylethyl)-2-pyrindinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate;

methyl 1-[({3-hydroxy-4-{[2-(3-{[6-(1-hydroxy-1-methylethyl)-2-pyrindinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

(3R,3aS,6aR)-hexahydrofuro[2,3-b]furan-3-yl 1-benzyl-2-hydroxy-4-({2-[(methoxycarbonyl)amino]-3,3-dimethylbutanoyl}amino)-5-[4-(2-pyridinyl)phenyl]pentylcarbamate;

(3R,3aR,6aS)-hexahydrofuro[2,3-b]furan-3-yl 1-benzyl-2-hydroxy-4-({2-[(methoxycarbonyl)amino]-3,3-dimethylbutanoyl}amino)-5-[4-(2-pyridinyl)phenyl]pentylcarbamate;

methyl 1-[({4-{[3,3-dimethyl-2-(2-oxo-3-{[2-(3-pyridinyl)-1,3-thiazol-4-yl]methyl}-1-imidazolidinyl)butanoyl]amino}-3-hydroxy-5-phenyl-1-[4-(2-pyridinyl)benzyl]pentyl}amino)carbonyl]-2,2-dimethylpropylcarbamate;

methyl 1-[({4-{[(2,6-dimethylphenoxy)acetyl]amino}-3-hydroxy-5-phenyl-1-[4-(2-pyridinyl)benzyl]pentyl}amino)carbonyl]-2,2-dimethylpropylcarbamate;

methyl 1-[({3-hydroxy-4-{[2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2,4-dioxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[2-oxo-3-(4-quinolinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[(phenoxyacetyl)amino]butanoyl}amino)-3-hydroxy-5-phenyl-1-[4-(2-pyridinyl)benzyl]pentyl}amino)carbonyl]-2,2-dimethylpropylcarbamate;

methyl 7-benzyl-1,10-ditert-butyl-6-hydroxy-2,9,12-trioxo-4-[4-(2-pyridinyl)benzyl]-14-oxa-3,8,11-triazapentadec-1-ylcarbamate;

methyl 1-[({3-hydroxy-4-[(2-{3-[(2-isopropyl-1,3-thiazol-4-yl)methyl]-2,4-dioxo-1-imidazolidinyl}-3-methylpentanoyl)amino]-5-phenyl-1-[4-(2-pyridinyl)benzyl]pentyl}amino)carbonyl]-2,2-dimethylpropylcarbamate;

methyl 1-[({4-{[2-(2,4-dioxo-3-{[2-(3-pyridinyl)-1,3-thiazol-4-yl]methyl}-1-imidazolidinyl)-3-methylpentanoyl]amino}-3-hydroxy-5-phenyl-1-[4-(2-pyridinyl)benzyl]pentyl}amino)carbonyl]-2,2-dimethylpropylcarbamate;

methyl 1-[({4-{[3,3-dimethyl-2-({[(6-methyl-3-pyridinyl)oxy]acetyl}amino)butanoyl]amino}-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(1-methyl-1H-benzimidazol-2-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(2-methyl-1,3-thiazol-4-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

3-pyridinylmethyl 4-benzyl-1,10-ditert-butyl-5-hydroxy-2,9,12-trioxo-7-[4-(2-pyridinyl)benzyl]-13-oxa-3,8,11-triazatetradec-1-ylcarbamate;

benzyl 4-benzyl-1,10-ditert-butyl-5-hydroxy-2,9,12-trioxo-7-[4-(2-pyridinyl)benzyl]-13-oxa-3,8,11-triazatetradec-1-ylcarbamate;

methyl 7-benzyl-1,10-ditert-butyl-6-hydroxy-13-methyl-2,9,12-trioxo-14-phenyl-4-[4-(2-pyridinyl)benzyl]-3,8,11,13-tetraazatetradec-1-ylcarbamate;

methyl 7-benzyl-1,10-ditert-butyl-6-hydroxy-13-methyl-2,9,12-trioxo-14-phenyl-4-[4-)2-pyridinyl)benzyl]-3,8,11,13-tetraazatetradec-1-ylcarbamate;

methyl 1-[({4-({3,3-dimethyl-2-[3-(2-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[3-(3-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(2-methyl-1,3-thiazol-4-yl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-1-[4-(6-methyl-2-pyridinyl)benzyl]-5-phenylpentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate;

methyl 1-[({4-{[2-(3-benzyl-2-oxo-1-imidazolidinyl)-3,3-dimethylbutanoyl]amino}-2-hydroxy-5-phenyl-1-[4-(3-pyridinyl)benzyl]pentyl}amino)carbonyl]-2,2-dimethylpropylcarbamate;

methyl 1-[({3-hydroxy-4-({2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl 1-[({4-{[2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-5-phenyl-1-[4-(4-pyridinyl)benzyl]pentyl}amino)carbonyl]-2,2-dimethylpropylcarbamate;

methyl 1-[({4-[((2S)-3,3-dimethyl-2-{3-[(6-methyl-2-pyridinyl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate;

methyl 1-[({3-hydroxy-4-({2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl 1-[({4-({3,3-dimethyl-2-[3-(2-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[3-(3-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({3-hydroxy-4-({2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl 1-[({3-hydroxy-4-({2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-1-[4-(4-methyl-2-pyridinyl)benzyl]-5-phenylpentyl}amino)carbonyl]-2,2-dimethylpropylcarbamate;

methyl 1-[({4-{[2-(3-benzyl-2-oxo-1-imidazolidinyl)-3,3-dimethylbutanoyl]amino}-2-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(2-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[2-oxo-3-(3-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[2-oxo-3-(4-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 1-[({4-({3,3-dimethyl-2-[2-oxo-3-(2-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl 7-benzyl-1,10-ditert-butyl-5-hydroxy-4-[4-(6-methyl-3-pyridinyl)benzyl]-2,9,12-trioxo-13-oxa-3,8,11-triazatetradec-1-ylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-1-[4-(6-methyl-3-pyridinyl)benzyl]-5-phenylpentyl}amino)carbonyl]-2,2-dimethylpropylcarbamate;

methyl 1-[({4-[(3,3-dimethyl-2-{3-[(2-methyl-1,3-thiazol-4-yl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate;

methyl 7-benzyl-1,10-ditert-butyl-5-hydroxy-4-[4-(5-methyl-2-pyridinyl)benzyl]-2,9,12-trioxo-13-oxa-3,8,11-triazatetradec-1-ylcarbamate;

methyl 1-[({4-[(3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2-methylbutylcarbamate;

methyl 4-benzyl-1,10-ditert-butyl-5-hydroxy-7-[4-(5-methyl-2-pyridinyl)benzyl]-2,9,12-trioxo-13-oxa-3,8,11-triazatetradec-1-ylcarbamate;

methyl 1-[({4-{[2-(3-benzyl-2-oxo-1-imidazolidinyl)-3,3-dimethylbutanoyl]amino}-3-hydroxy-1-[4-(5-methyl-2-pyridinyl)benzyl]-5-phenylpentyl}amino)carbonyl]-2,2-dimethylpropylcarbamate;

methyl 1-[({1-benzyl-4-[(3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate;

methyl 4-benzyl-10-tert-butyl-5-hydroxy-1-[1-methyl-1-((R)-methylsulfinyl)ethyl]-2,9,12-trioxo-7-[4-(2-pyridinyl)benzyl]-13-oxa-3,8,11-triazatetradec-1-ylcarbamate;

methyl 1-[({2-hydroxy-4-[(3-methyl-2-{3-[(1-methyl-1H-benzimidazol-2-yl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-[({2-hydroxy-4-[(2-{3-[(2-isopropyl-1,3-thiazol-4-yl)methyl]-2-oxo-1-imidazolidinyl}-3-methylpentanoyl)amino]-5-phenyl-1-[4-(2-pyridinyl)benzyl]pentyl}amino)carbonyl]-2,2-dimethylpropylcarbamate;

methyl 1-[({3-hydroxy-4-[(3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(1-methyl-1H-benzimidazol-2-yl)methyl]-2-oxo-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(1-methyl-1H-benzimidazol-2-yl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate;

methyl 1-[({3-hydroxy-4-[(2-{3-[(2-isopropyl-1,3-thiazol-4-yl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate;

methyl 1-[({2-hydroxy-4-[(2-{3-[(2-isopropyl-1,3-thiazol-4-yl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate;

methyl 7-benzyl-1,10-ditert-butyl-5-hydroxy-2,9,12-trioxo-4-[4-(3-pyridinyl)benzyl]-13-oxa-3,8,11-triazatetradec-1-ylcarbamate;

methyl 7-benzyl-1,10-ditert-butyl-5-hydroxy-2,9,12-trioxo-4-[4-(4-pyridinyl)benzyl]-13-oxa-3,8,11-triazatetradec-1-ylcarbamate;

methyl 1-[({4-[(3,3-dimethyl-2-{3-[(2-methyl-1,3-thiazol-4-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(2-methyl-1,3-thiazol-4-yl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate;

methyl 1-[({4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl 7-benzyl-10-sec-butyl-1-tert-butyl-6-hydroxy-13-methyl-14-(2-methyl-1,3-thiazol-4-yl)-2,9,12-trioxo-4-[4-(2-pyridinyl)benzyl]-3,8,11,13-tetraazatetradec-1-ylcarbamate;

methyl 7-benzyl-10-sec-butyl-1-tert-butyl-5-hydroxy-13-methyl-14-(2-methyl-1,3-thiazol-4-yl)-2,9,12-trioxo-4-[4-(2-pyridinyl)benzyl]-3,8,11,13-tetraazatetradec-1-ylcarbamate;

methyl 1-[({4-{[2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate;

1,2,5,6-tetradeoxy-2,5-bis({2-[(methoxycarbonyl)amino]-3,3-dimethylbutanoyl}amino)-1,6-bis[4-(2-pyridinyl)phenyl]-D-iditol;

methyl 1-[({4-[(3,3-dimethyl-2-{3-[(6-methyl-2-pyridinyl)methyl]-2-oxo-1-imidazolidinyl}butanoyl)amino]-3-hydroxy-1-[4-(6-methoxy-2-pyridinyl)benzyl]-5-phenylpentyl}amino)carbonyl]-2,2-dimethylpropylcarbamate;

methyl 1-[({4-{[2-(3-benzyl-2-oxo-1-imidazolidinyl)-3,3-dimethylbutanoyl]amino}-3-hydroxy-1-[4-(6-methoxy-2-pyridinyl)benzyl]-5-phenylpentyl}amino)carbonyl]-2,2-dimethylpropylcarbamate;

methyl 1-[({4-[(2-{3-[(6-tert-butyl-2-pyridinyl)methyl]-2-oxo-1-imidazolidinyl}-3,3-dimethylbutanoyl)amino]-3-hydroxy-5-phenyl-1-[4-(2-pyridinyl)benzyl]pentyl}amino)carbonyl]-2,2-dimethylpropylcarbamate;

methyl 1,10-ditert-butyl-5-hydroxy-2,9,12-trioxo-4,7-bis[4-(2-pyridinyl)benzyl]-13-oxa-3,8,11-triazatetradec-1-ylcarbamate;

methyl 1-[({3-hydroxy-4-[(2-{3-[(6-isopropyl-2-pyridinyl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate;

methyl 1-[({4-[(2-{3-[(6-tert-butyl-2-pyridinyl)methyl]-2-oxo-1-imidazolidinyl}-3,3-dimethylbutanoyl)amino]-3-hydroxy-5-phenyl-1-[4-(2-pyridinyl)benzyl]pentyl}amino)carbonyl]-2,2-dimethylpropylcarbamate;

methyl 1-[({-4-{[2-(3-benzyl-2-oxo-1-imidazolidinyl)-3,3-dimethylbutanoyl]amino}-2-hydroxy-1-[4-(6-methoxy-2-pyridinyl)benzyl]-5-phenylpentyl}amino)carbonyl]-2,2-dimethylpropylcarbamate;

methyl 7-benzyl-1,10-ditert-butyl-5-hydroxy-4-[4-(6-methoxy-2-pyridinyl)benzyl]-2,9,12-trioxo-13-oxa-3,8,11-triazatetradec-1-ylcarbamate;

methyl 4-benzyl-1,10-ditert-butyl-5-hydroxy-7-[4-(6-methoxy-2-pyridinyl)benzyl]-2,9,12-trioxo-13-oxa-3,8,11-triazatetradec-1-ylcarbamate;

methyl 1-[({4-[(3,3-dimethyl-2-{3-[(6-methyl-2-pyridinyl)methyl]-2-oxo-1-imidazolidinyl}butanoyl)amino]-2-hydroxy-1-[4-(6-methoxy-2-pyridinyl)benzyl]-5-phenylpentyl}amino)carbonyl]-2,2-dimethylpropylcarbamate;

methyl 1-[({4-({2-[3-(2-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate;

methyl 1-[({4-({2-[3-(4-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate;

methyl 1-[({4-({2-[3-(3-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-3-hydroxy-1-[4-(5-methyl-2-pyridinyl)benzyl]-5-phenylpentyl}amino)carbonyl]-2,2-dimethylpropylcarbamate;

methyl 1-[({4-[(3,3-dimethyl-2-{3-[(6-methyl-2-pyridinyl)methyl]-2-oxo-1-imidazolidinyl}butanoyl)amino]-3-hydroxy-1-[4-(5-methyl-2-pyridinyl)benzyl]-5-phenylpentyl}amino)carbonyl]-2,2-dimethylpropylcarbamate;

methyl 1-[({3-hydroxy-4-[(2-{3-[(6-isopropyl-2-pyridinyl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate;

methyl 1-[({1-benzyl-4-[(3,3-dimethyl-2-{3-[(6-methyl-2-pyridinyl)methyl]-2-oxo-1-imidazolidinyl}butanoyl)amino]-3-hydroxy-5-[4-(2-pyridinyl)phenyl]pentyl}amino)carbonyl]-2,2-dimethylpropylcarbamate;

methyl 4-benzyl-1,10-disec-butyl-5-hydroxy-2,9,12-trioxo-7-[4-(2-pyridinyl)benzyl]-13-oxa-3,8,11-triazatetradec-1-ylcarbamate;

methyl 1-({[1-benzyl-2-hydroxy-4-({3-methyl-2-[2-oxo-3-(4-quinolinylmethyl)-1-imidazolidinyl]pentanoyl}amino)-5-phenylpentyl]amino}carbonyl)-2,2-dimethylpropylcarbamate;

methyl(1S)-1-({[(1S,3S,4S)-4-({(2S)-2-[3-(2-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate;

methyl(1S)-1-({[[(1S,3S,4S)-4-({(2S)-2-[3-(4-fluorobenzyl)-2-oxoimidazolidin-1-yl]-3,3-dimethylbutanoyl}amino)-3-hydroxy-5-phenyl-1-(4-pyridin-2-ylbenzyl)pentyl])amino}carbonyl)-2,2-dimethylpropylcarbamate;

methyl(1S)-1-({[[(1S,3S,4S)-4-({(2S)-2-[3-(3-fluorobenzyl)-2-oxoimidazolidin-1-yl]-3,3-dimethylbutanoyl}amino)-3-hydroxy5-phenyl-1-(4-pyridin-2-ylbenzyl)pentyl]amino}carbonyl)-2,2-dimethylpropylcarbamate;

methyl(1S)-1-({[[(1S,3S,4S)-4-[((2S)-3,3-dimethyl-2-{2-oxo-3-[2-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-4-[((2S)-3,3-dimethyl-2-{2-oxo-3-[4-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate;

methyl(1S)-1-({[[(1S,3S,4S)-4-[((2S)-3,3-dimethyl-2-{2-oxo-3-[3-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate;

methyl(1S)-1-({[[(1S,3S,4S)-4-({(2S)-2-[3-(2-amino-3-methylbenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate;

methyl(1S,4S,5S,7S,10S)-4benzyl-1 0-tert-butyl-5-hydroxy-2,9, 1 2-trioxo-7-(4-pyridin-2-ylbenzyl)-1-[(3R)-tetrahydrofuran-3-yl]-13-oxa-3,8,11-triazatetradec-1-ylcarbamate;

methyl(1S)-1-({[[(1S,3S,4S)-3-hydroxy-4-({(2S)-2-[3-(3-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate;

methyl(1S)-1-({[[(1S,3S,4S)-3-hydroxy-4-({(2S)-2-[3-(4-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate;

methyl(1 S)-1-({[[(1S,3S,4S)-3-hydroxy-4-({(2S)-2-[3-(2-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate;

methyl(1S,4S,5S,7S,10S)-4benzyl-1,10-di-tert-butyl-5-hydroxy-2,9,12-trioxo-7-[7-(1,3-thiazol-2-yl)benzyl]-13-oxa-3,8,11-triazatetradec-1-ylcarbamate;

methyl(1S,4S,5S,7S,10S)-4benzyl-10-tert-butyl-5-hydroxy-1-[(1S)-1-methylpropyl]-2,9,12-trioxo-7-(4-pyridin-2-ylbenzyl)-13-oxa-3,8,11-triazatetradec-1-ylcarbamate;

methyl(1S,4S,5S,7S,10S)-4benzyl-1,10-di-tert-butyl-5-hydroxy-2,9,12-trioxo-7-(4-pyridin-3-ylbenzyl)-13-oxa-3,8,11-triazatetradec-1-ylcarbamate;

methyl(1S)-1-({[(1 S,3S,4S)-3-hydroxy-4-{[(2S)-2-methyl-3-(methylsulfonyl)propanoyl]amino}-5-phenyl-1-(4-pyridin-2-ylbenzyl)pentyl]amino}carbonyl)-2,2-dimethylpropylcarbamate;

methyl(1S,4S,5S,7S,10S)-4benzyl-1,10-di-tert-butyl-5-hydroxy-2,9,12-trioxo-7-4-pyridin-4-ylbenzyl)-13-oxa-3,8,11-triazatetradec-1-ylcarbamate;

methyl(1S)-1-({[(1S,3S,4S)-3-hydroxy-4-{[(2S)-2-hydroxy-3,3-dimethylbutanoyl]amino}-5-phenyl-1-(4-pyridin-2-ylbenzyl)pentyl]amino}carbonyl)-2,2-dimethylpropylcarbamate;

methyl(1S,4S,6S,7S,10S)-7-benzyl-1,10-di-tert-butyl-6-hydroxy-12,12-dioxido-2,9-dioxo-4-(4-pyridin-2-ylbenzyl)-12-thia-3,8,11-triazatridec-1-ylcarbamate;

methyl(1R,4S,5S,7S,10S)-4-benzyl-10-tert-butyl-5-hydroxy-1-[(methylthio)methyl]-2,9,12-trioxo-7-(4-pyridin-2-ylbenzyl)-13-oxa-3,8,11-triazatetradec-1-ylcarbamate;

methyl(1R,4S,5S,7S,10S)-4-benzyl-10-tert-butyl-5-hydroxy-1-[(methylsulfonyl)methyl]-2,9,12-trioxo-7-(4-pyridin-2-ylbenzyl)-13-oxa-3,8,11-triazatetradec-1-ylcarbamate;

methyl(1R)-1-{[((1S,2S,4S)-4-{[4(aminosulfonyl)benzoyl]amino}-1-benzyl-2-hydroxy-5-phenylpentyl)amino]carbonyl}-2,2-dimethylpropylcarbamate;

methyl(1S)-1-({[(1S,3 S,4S)-3-hydroxy-4-{[(2R)-2-hydroxy-3-methyl-3-(methylsulfonyl)butanoyl]amino}-5-phenyl-1-(4pyridin-2-ylbenzyl)pentyl]amino}carbonyl)-2,2-dimethylpropylcarbamate;

methyl(1S)-1-({[(1R,3S,4S)-4-[(4-chloro-2-methylbenzoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1R,3S,4S)-3-hydroxy-4-[(4-methoxy-2-methylbenzoyl)amino]-5-phenyl-1-(4-pyridin-2-ylbenzyl)pentyl]amino}carbonyl)-2,2-dimethylpropylcarbamate;

methyl(1S)-1-({[(1R,3S,4S)-3-hydroxy-4-[(2-methylbenzoyl)amino]-5-phenyl-1-(4-pyridin-2-ylbenzyl)pentyl]amino}carbonyl)-2,2-dimethylpropylcarbamate;

methyl(1 S)-1-({[(1R,3S,4S)-4-{[(2S)-3,3-dimethyl-2-(2-oxoimidazolidin-1-yl)butanoyl]amino}-3-hydroxy-5-phenyl-1-(4-pyridin-2-ylbenzyl)pentyl]amino}carbonyl)-2,2-dimethylpropylcarbamate;

methyl(1S)-1-({[(1R,3 S,4S)-3-hydroxy-4-{[(2S,3 S)-3-methyl-2-(2-oxoimidazolidin-1-yl)pentanoyl]amino}-5-phenyl-1-(4-pyridin-2-ylbenzyl)pentyl]amino}carbonyl)-2,2-dimethylpropylcarbamate;

methyl(1S)-1-{[((1S,2S,4S)-4-{[3-(aminosulfonyl)benzoyl]amino}-1-benzyl-2-hydroxy-5-phenylpentyl)amino]carbonyl}-2,2-dimethylpropylcarbamate;

methyl(1S)-1-({[(1S,3S,4S)-4-[(3-chloro-2-methylbenzoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-[(3-hydroxy-2-methylbenzoyl)amino]-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-{[(3-methylisoxazol-4-yl)carbonyl]amino}-5-phenyl-1-(4-pyridin-2-ylbenzyl)pentyl]amino}carbonyl)-2,2-dimethylpropylcarbamate;

methyl(1S)-1-({[(1S,3S,4S)-4-{[(3,5-dimethylisoxazol-4-yl)carbonyl]amino}-3-hydroxy-5-phenyl-1-(4-pyridin-2-ylbenzyl)pentyl]amino}carbonyl)-2,2-dimethylpropylcarbamate;

methyl(1S,4S,5S,7S,10S)-4benzyl-10-tert-butyl-5-hydroxy-1-isobutyl-2,9,12-trioxo-7-(4-pyridin-2-ylbenzyl)-13-oxa-3,8,11-triazatetradec-1-ylcarbamate;

methyl(1S,4S,5S,7S,10S)-1-(2-amino-2-oxoethyl)-4-benzyl-10-tert-butyl-5-hydroxy-2,9,12-trioxo-7-(4-pyridin-2-ylbenzyl)-13-oxa-3,8,11-triazatetradec-1-ylcarbamate;

methyl 2-{[((1S,2S,4S)-1-benzyl-2-hydroxy-4-{[N-(methoxycarbonyl)-3-methyl-L-valyl]amino}-5-(4-pyridin-2-ylphenyl)pentyl]amino}-1-[(methoxycarbonyl)amino]-2-oxoethylcarbamate;

methyl(1S,4S,6S,7S,10S)-7-benzyl-1,10-di-tert-butyl-6-hydroxy-2,9,12,14-tetraoxo-4-(-4-pyridin-2-ylbenzyl)-15-oxa-3,8,11,13-tetraazahexadec-1-ylcarbamate;

methyl(1S,4S,6S,7S,10S)-7-benzyl-1,10-di-tert-butyl-6-hydroxy-14,14-dimethyl-2,9,12,15-tetraoxo-4-(4-pyridin-2-ylbenzyl)-13-oxa-3,8,11-triazahexadec-1-ylcarbamate;

(4S,7S,8S,10S,13S)-7-benzyl-4,13-di-tert-butyl-8-hydroxy-2,5,12,15-tetraoxo-10-(4-pyridin-2-ylbenzyl)-16-oxa-3,6,11,14-tetraazaheptadec-1-yl acetate;

methyl(1S)-1-({[(1S,3S,4S)-4-{[(2S)-2-(glycoloylamino)-3,3-dimethylbutanoyl]amino}-3-hydroxy-5-phenyl-1-(4-pyridin-2-ylbenzyl)pentyl]amino}carbonyl)-2,2-dimethylpropylcarbamate;

(3S,6S,7S,9S,12S)-6-benzyl3-[(tert-butoxycarbonyl)amino]-12-tert-butyl-7-hydroxy-2,2-dimethyl-4,11,14-trioxo-9-(4-pyridin-2-ylbenzyl)-15-oxa-5,10,13-triazahexadec-1-yl acetate;

methyl(1S,4S,5S,7S,10S)-4benzyl-10-tert-butyl-5-hydroxy-1-(2-hydroxy-1,1-dimethylethyl)-2,9,12-trioxo-7-(4-pyridin-2-ylbenzyl)-13-oxa-3,8,11-triazatetradec-1-ylcarbamate;

methyl(1S,4S,5S,7S,10S)-1-{[(aminocarbonyl)amino]methyl}-4-benzyl-10-tert-butyl-5-hydroxy-2,9,12-trioxo-7-(4-pyridin-2-ylbenzyl)-13-oxa-3,8,11-triazatetradec-1-ylcarbamate;

methyl(1S,4S,5S,7S,10S)-4benzyl-10-tert-butyl-5-hydroxy-2,9,12-trioxo-7-(4-pyridin-2-ylbenzyl)-1-(pyridin-2-ylmethyl)-13-oxa-3,8,11-triazatetradec-1-ylcarbamate;

methyl(1S,4S,5S,7S,10S)-4benzyl-10-tert-butyl-5-hydroxy-2,9,12-trioxo-7-(4-pyridin-2-ylbenzyl)-1-(1,3-thiazol-4-ylmethyl)-13-oxa-3,8,11-triazatetradec-1-ylcarbamate;

(3S,6S,7S,9S,12S)-6-benzyl-12-tert-butyl-7-hydroxy-3-[(methoxycarbonyl)amino]-2,2-dimethyl-4,11,14-trioxo-9-(4-pyridin-2-ylbenzyl)-15-oxa-5,10,13-triazahexadec-1-yl acetate;

methyl(1S,4R,6S,7S,10S)-7-benzyl 1,10-di-tert-butyl-6-hydroxy-15,15-dioxido-2,9-dioxo-4-(4-pyridin-2-ylbenzyl)-15-thia-3,8,11,14tetraazahexadec-1-ylcarbamate;

methyl(1S,4R,6S,7S,10S)-7-benzyl 1,1 0-di-tert-butyl-6-hydroxy-2,9,15-trioxo-4-(4-pyridin-2-ylbenzyl)-16-oxa-3,8,11,14-tetraazaheptadec-1-ylcarbamate;

methyl(1S)-1-({[(1R,3S,4S)-4-{[(2S)-2-(1,1-dioxido-1,2,5-thiadiazolidin-2-yl)-3,3-dimethylbutanoyl]amino}-3-hydroxy-5-phenyl-1-(4-pyridin-2-ylbenzyl)pentyl]amino}carbonyl)-2,2-dimethylpropylcarbamate;

methyl(5S,8S,10S,11S,14S)-11-benzyl-5-tert-butyl-10-hydroxy-14-[(methoxycarbonyl)amino]-15-methyl-3,6,13-trioxo-8-(4-pyridin-2-ylbenzyl)-2-oxa-4,7,12-triazahexadecan-16-oate;

methyl(5S,8S,10S,11S,14S)-11-benzyl-5-tert-butyl-10-hydroxy-14-[(methoxycarbonyl)amino]-15,15-dimethyl-3,6,13-trioxo-8-(4-pyridin-2-ylbenzyl)-2-oxa-4,7,12-triazahexadecan-16-oate;

methyl(1S)-1-[({((1S,2S,4S)-1-benzyl-2-hydroxy-5-phenyl-4-[(thien-2-ylcarbonyl)amino]pentyl}amino)carbonyl]-2,2-dimethylpropylcarbamate;

methyl(1S)-1-[({(1S,2S,4S)-1-benzyl-2-hydroxy-5-phenyl-4-[(thien-3-ylcarbonyl)amino]pentyl}amino)carbonyl]-2,2-dimethylpropylcarbamate;

methyl(1S)-1-{[((1S,2S,4S)-1-benzyl-2-hydroxy-4-{[(3-methylthien-2-yl)carbonyl]amino}-5-phenylpentyl)amino]carbonyl}-2,2-dimethylpropylcarbamate;

methyl(1S)-1-{[((1S,2S,4S)-1-benzyl-2-hydroxy-4-{[(5-methylthien-2-yl)carbonyl]amino}-5-phenylpentyl)amino]carbonyl}-2,2-dimethylpropylcarbamate;

methyl(1S)-1-{[((1S,2S,4S)-1-benzyl-2-hydroxy-4-{[(1-methyl-1H-pyrrol-2-yl)carbonyl]amino}-5-phenylpentyl)amino]carbonyl}-2,2-dimethylpropylcarbamate;

methyl(1S)-1-{[((1S,2S,4S)-1-benzyl-4-{[(3,5-dimethylisoxazol-4-yl)carbonyl]amino}-2-hydroxy-5-phenylpentyl)amino]carbonyl}-2,2-dimethylpropylcarbamate;

methyl(1S)-1-({[(1S,3S,4S)-4-{[(2S)2-(3-benzyl-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate;

methyl(1S)-1-({[(1R,3S,4S)-4-{[(2S)2-(3-{[6-(1-hydroxy-1-methylethyl)pyridin-2-yl]methyl}-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate;

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl (2S)-2-aminopropanoate;

methyl(1S)-1-({[(1R,3S,4S)4{(2S)-3,3-dimethyl-2-[3-({6-[1-methyl-1-(phosphonooxy)ethyl]pyridin-2-yl}methyl)-2-oxoimidazolidin-1-yl]butanoyl}amino)-3-hydroxy-5-phenyl-1-(4-pyridin-2-ylbenzyl)pentyl]amino}carbonyl)-2,2-dimethylpropylcarbamate;

(3S,5S,8S)-34(1S)-1-{[(2S)-2-(3-benzyl-2-oxoimidazolidin-1-yl)-3,3-dimethylbutanoyl]amino}-2-phenylethyl)-8-tert-butyl-7,10-dioxo-5-(4-pyridin-2-ylbenzyl)-2,11-dioxa-6,9-diazadodec-1-yl (dimethylamino)acetate;

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl (phosphonooxy)methyl carbonate;

(5S,7S,10S)-5(1S)-1-{[(2S)-2-(3-benzyl-2-oxoimidazolidin-1-yl)-3,3-dimethylbutanoyl]amino}-2-phenylethyl)-10-tert-butyl-3,9,12-trioxo-7-(4-pyridin-2-ylbenzyl)-2,4,13-trioxa-8,11-diazatetradec-1-yl (dimethylamino)acetate;

(5S,8S,10S)-10-((1S)-1-{[(2S)-2-(3-benzyl-2-oxoimidazolidin-1-yl)-3,3-dimethylbutanoyl]amino}-2-phenylethyl)-5-tert-butyl-3,6, 1 2-trioxo-8-(4-pyridin-2-ylbenzyl)-2,11-dioxa-4,7-diazapentadecan-15-oic acid;

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl {[ethoxy(hydroxy)phosphoryl]oxy}methyl carbonate;

methyl(1S,4S,6S)-64(1S)-1-{[(2S)-2-(3-benzyl-2-oxoimidazolidin-1-yl)-3,3-dimethylbutanoyl]amino}-2-phenylethyl)-1-tert-butyl-10-hydroxy-10-oxido-2-oxo-4-(4-pyridin-2-ylbenzyl)-7,9,11-trioxa-3-aza-10-phosphatridec-1-ylcarbamate;

methyl(1S,4S,6S)-64(1S)-1-{[(2S)-2-(3-benzyl-2-oxoimidazolidin-1-3,3-dimethylbutanoyl]amino}-2-phenylethyl)-1-tert-butyl-10,10-dihydroxy-10-oxido-2-oxo-4-(4-pyridin-2-ylbenzyl)-7,9-dioxa-3-aza-10-phosphadec-1-ylcarbamate;

methyl(1S,4S,5S,7S,10S)-4benzyl-1,10-bis(tert-butyl)-2,9,12-trioxo-5-(phosphonooxy)-7-(4-pyridin-2-ylbenzyl)-13-oxa-3,8,11-triazatetradec-1-ylcarbamate;

methyl(1S,4S,5S,7S,10S)-7-benzyl-1,10-bis(tert-butyl)-2,9,12-trioxo-5-[(phosphonooxy)methoxy]-4-(4-pyridin-2-ylbenzyl)-1 3-oxa-3,8,11-triazatetradec-1-ylcarbamate;

methyl(1S,4S,5S,7S,10S)-4benzyl-1,1 0-bis(tert-butyl)-2,9,12-trioxo-5-[(phosphonooxy)methoxy]-7-(4-pyridin-2-ylbenzyl)-1 3-oxa-3,8,1-triazatetradec-1-ylcarbamate;

methyl(1S,4S,6S)-64(1S)-1-{[(2S)-2-(3-benzyl-2-oxoimidazolidin-1-ylcarbamate; dimethylbutanoyl]amino}-2-phenylethyl)-1-tert-butyl-10,10-dihydroxy-8-methyl-10-oxido-2-oxo-4-(4-pyridin-2-ylbenzyl)-7,9-dioxa-3-aza-10-phosphadec-1-ylcarbamate;

methyl(1S,4S,5S)-4-benzyl-1-tert-butyl-5-{(2S)-2-[((2S)-3,3-dimethyl-2-{3-[(6-methylpyridin-2-yl)methyl]-2-oxoimidazolidin-1-yl}butanoyl)amino]-3-phenylpropyl}-9,9-dihydroxy-9-oxido-2-oxo-6,8-dioxa-3-aza-9-phosphanon-1-ylcarbamate;

methyl(1S,4S,5S,7S,10S)-4benzyl-1,10-bis(tert-butyl)-2,9,12-trioxo-5-[1-(phosphonooxy)ethoxy]-7-(4-pyridin-2-ylbenzyl)-13-oxa-3,8,11-triazatetradec-1-ylcarbamate; and methyl(1S)-3-amino-1-({[(1S,2S,4S)-1-benzyl-2-hydroxy-4-{[N-(methoxycarbonyl)-3-methyl-L-valyl]amino}-5-(4-pyridin-2-ylphenyl)pentyl]amino}carbonyl)-2,2-dimethyl-3-oxopropylcarbamate; or a pharmaceutical acceptable salt form, prodrug or stereoisomer thereof.

In a second embodiment, the present invention provides a compound of formula (II)

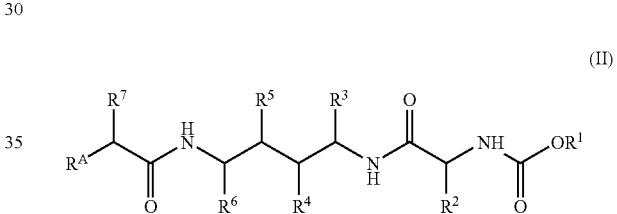

or a pharmaceutically acceptable salt form, prodrug, or stereoisomer thereof, wherein:

$R^A$ is —N(H)C(O)R$^8$, —O(R$_a$), —OC(O)OR$_a$, —NR$_a$R$_b$, —N(R$_b$)S(O)$_2$R$_a$, —N(R$_b$)alkylN(R$_b$)S(O)$_2$R$_a$, —N(R$_b$)alkylN(R$_b$)C(O)OR$_a$, —N(R$_b$)alkylN(R$_b$)C(O)NR$_a$R$_b$, -alkylSR$_a$, -alkylS(O)R$_a$ or -alkylS(O)$_2$R$_a$;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N (H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^2$ is alkyl, alkenyl, alkynyl, cycloalkyl, cycloalkenyl, heterocycle, aryl or heteroaryl; wherein each R$^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{2a}$;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^4$ is H and R$^5$ is OR$^{16}$; or
R$^5$ is H and R$^4$ is OR$^{16}$; or
R$^4$ and R$^5$ are —OR$^{16}$;

R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^8$ is —OR$_a$, —NR$_a$R$_b$, —N(R$_b$)C(O)OR$_a$, -alkylOR$_a$, -alkylOC(O)R$_a$, or —O-alkylC(O)R$_a$;

$R^{16}$ is hydrogen or $R^{15}$;

$R^{15}$ is

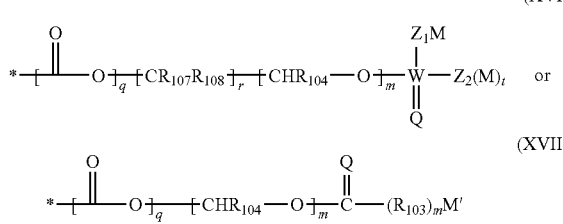

(XVI)

or (XVII)

$R_{103}$ is $C(R_{105})_2$, O or $-N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, $-N(R_{105})_2$, alkyl, alkenyl, and $R_{106}$; wherein 1 to 4 $-CH_2$ radicals of the alkyl or alkenyl, other than the $-CH_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$, $NO_2$ and phenyl; provided that when M is $-N(R_{105})_2$, Z, and $Z_2$ are $-CH_2$;

$Z_1$ is $CH_2$, O, S, $-N(R_{105})$, or, when M is absent, H;

$Z_2$ is $CH_2$, O, S or $-N(R_{105})$;

Q is O or S;

W is P or S; wherein when W is S, $Z_1$ and $Z_2$ are not S;

M' is H, alkyl, alkenyl or $R_{106}$; wherein 1 to 4—$CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $SO_2R_{106}$, $-N(R_{105})SO_2R_{105}$, halo, $-CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $-OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $-OR_{105}$, $-R_{105}$, $-N(R_{105})_2$, $-N(R_{105})C(O)R_{105}$, $-CN$, $-C(O)OR_{105}$, $-C(O)N(R_{105})_2$, halo and $-CF_3$;

each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, hydroxy, alkoxy, alkyl, alkenyl, alkynyl, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, cyanoalkyl, formylalkyl, nitroalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R_c$; and $R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, haloalkyl, hydroxyalkyl, alkoxyalkyl, -alkyl-$NH_2$, -alkyl-N(H)(alkyl), -alkyl-N(alkyl)$_2$, -alkyl-N(H)C(O)$NH_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)$NH_2$, -alkyl-C(O)N(H)(alkyl) and -alkyl-C(O)N(alkyl)$_2$.

For example, the present invention provides a compound of formula (II) wherein $R^4$ is H; $R^5$ is $OR^{16}$; and $R^A$, $R^1$, $R^{1a}$, $R^2$, $R^{2a}$, $R^3$, $R^{3a}$, $R^6$, $R^{6a}$, $R^7$, $R^{7a}$, $R^8$, $Z_2$, Q, W, M', $R_{106}$, $R_{107}$, $R_{108}$, q, m, m', m", r, t, $R_a$, $R_b$, and $R_c$ are as defined in formula (II).

For example, the present invention provides a compound of formula (II) wherein $R^4$ is $OR^{16}$ and $R^5$ is H; and $R^A$, $R^1$, $R^{1a}$, $R^2$, $R^{2a}$, $R^3$, $R^{3a}$, $R^6$, $R^{6a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t $R_a$, $R_b$ and $R_c$ are as defined in formula (II).

For example, the present invention provides a compound of formula (II) wherein $R^4$ is H; $R^5$ is $OR^{16}$; $R^2$ is alkyl; and $R^A$, $R^1$, $R^{1a}$, $R^3$, $R^{3a}$, $R^6$, $R^{1a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, and $R_c$ are as defined in formula (II).

For example, the present invention provides a compound of formula (II) wherein $R^4$ is $OR^{16}$; $R^5$ is H; $R^2$ is alkyl; and $R^A$, $R^1$, $R^{1a}$, $R^{2a}$, $R^3$, $R^{3a}$, $R^6$, $R^{6a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, and $R_c$ are as defined in formula (II).

For example, the present invention provides a compound of formula (II) wherein $R^4$ is H; $R^5$ is $OR^{15}$; $R^2$ is alkyl; $R^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R^{3a}$; and $R^A$, $R^1$, $R^{1a}$, $R^{3a}$, $R^6$, $R^{6a}$, $R^7$, $R^{7a}$, $R^8$, $R^{15}$, $R^{16}$, $R_{103}$, $R_{104}$, $R_{105}$, M, Z, Q, W, M, $Z_1$, $Z_2$, Q, W, M', $R_{106}$, $R_{107}$, $R_{108}$, q, m, m', m'', r, t, $R_a$, $R_b$, and $R_c$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R^{3a}$; and $R^A$, $R^1$, $R^{1a}$, $R^{3a}$, $R^6$, $R^{6a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, and $R_c$ are as defined in formula (II).

For example, the present invention provides a compound of formula (II) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; and $R^A$, $R^1$, $R^{1a}$, $R^{3a}$, $R^6$, $R^{6a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, and $R_a$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; and $R^A$, $R^1$, $R^{1a}$, $R^{3a}$, $R^6$, $R^{6a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, and $R_c$ are as defined in formula (II).

For example, the present invention provides a compound of formula (II) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^{3a}$ is unsubstituted or substituted aryl or unsubstituted or substituted heteroaryl; and $R^A$, $R^1$, $R^{1a}$, $R^6$, $R^{6a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and the substituents of $R^{3a}$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^{3a}$ is unsubstituted or substituted aryl or unsubstituted or substituted heteroaryl; and $R^A$, $R^1$, $R^{1a}$, $R^6$, $R^{6a}$, $R^7$, $R^{7a}$, $R^8$, $R^{15}$, $R^{16}$, $R_{103}$, $R_{104}$, $R^{105}$, M, $Z_1$, $Z_2$, Q, W, M', $R_{106}$, $R_{107}$, $R_{108}$, q, m, m', m'', r, t, $R_a$, $R_b$, $R_c$ and the substituents of $R^{3a}$ are as defined in formula (II).

For example, the present invention provides a compound of formula (II) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; and $R^A$, $R^1$, $R^{1a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, substituents of $R^{3a}$ and $R^6$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; and $R^A$, $R^1$, $R^{1a}$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and the substituents of $R^{3a}$ and $R^6$ are as defined in formula (II).

For example, the present invention provides a compound of formula (II) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —N($R_b$)C(O)O$R_a$, alkyl or heterocycle wherein the alky and heterocycle are independently substituted with 0, 1 or 2 substituents independently selected from the group consisting of halo, —O$R_a$, —OC(O)$R_a$, —S$R_a$, —SO$R_a$, —$SO_2R_a$, —N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$; and $R^A$, $R^1$, $R^7$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_a$ and the substituents of $R^{3a}$ and $R^6$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —N($R_b$)C(O)O$R_a$, alkyl or heterocycle wherein the alky and heterocycle are independently substituted with 0, 1 or 2 substituents independently selected from the group consisting of halo, —O$R_a$, —OC(O)$R_a$, —S$R_a$, —SO$R_a$, —$SO_2R_a$, —N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$; and $R^A$, $R^1$, $R^{1a}$, $R^{7a}$, $R^8$, $R^{15}$, $R^{16}$, $R_{103}$, $R_{104}$, $R_{105}$, M, Z, Q, W, M, $Z_1$, $Z_2$, Q, W, M', $R_{106}$, $R_{107}$, $R_{108}$, q, m, m', m'', r, t, $R_a$, $R_b$, $R_c$ and the substituents of $R^{3a}$ and $R^6$ are as defined in formula (II).

For example, the present invention provides a compound of formula (II) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —N($R_b$)C(O)

$OR_a$, alkyl or heterocycle wherein the alky and heterocycle are independently substituted with 0, 1 or 2 substituents independently selected from the group consisting of halo, —$OR_a$, —$OC(O)R_a$, —$SR_a$, —$SOR_a$, —$SO_2R_a$, —$NR_aR_b$, —$N(R_b)C(O)R_a$, —$N(R_b)C(O)OR_a$, —$N(R_a)C(=N)NR_aR_b$, —$N(R_a)C(O)NR_aR_b$, —$C(O)NR_aR_b$, —$C(O)OR_a$ and $R^{7a}$; $R^1$ is alkyl; and $R^4$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and the substituents of $R^{3a}$ and $R^6$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —$N(R_b)C(O)OR_a$, alkyl or heterocycle wherein the alky and heterocycle are independently substituted with 0, 1 or 2 substituents independently selected from the group consisting of halo, —$OR_a$, —$OC(O)R_a$, —$SR_a$, $SOR_a$, —$SO_2R_a$, $NR_aR_b$, —$N(R_b)C(O)R_a$, —$N(R_b)C(O)OR_a$, —$N(R_a)C(=N)NR_aR_b$, —$N(R_a)C(O)NR_aR_b$, —$C(O)NR_aR_b$, —$C(O)OR_a$, and $R^{7a}$; $R^1$ is alkyl; and $R^4$, $R^{7a}$, $R^8$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and the substituents of $R^{3a}$ and $R^6$ are as defined in formula (II).

For example, the present invention provides a compound of formula (II) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —$N(R_b)C(O)OR_a$, alkyl or heterocycle wherein the alky and heterocycle are independently substituted with 0, 1 or 2 substituents independently selected from the group consisting of halo, —$OR_a$, —$OC(O)R_a$, —$SR_a$, $\geq SOR_a$, —$SO_2R_a$, —$NR_aR_b$, —$N(R_b)C(O)R_a$, —$N(R_b)C(O)OR_a$, —$N(R_a)C(=N)NR_aR_b$, —$N(R_a)C(O)NR_aR_b$, —$C(O)NR_aR_b$, —$C(O)OR_a$ and $R^{7a}$; $R^1$ is alkyl; $Z_1$ and $Z_2$ are O; Q is O; W is P; and $R^4$, $R^{7a}$, $R^8$, $R^{15}$, $R^{16}$, $R_{103}$, $R_{104}$, $R_{105}$, M, M', $R_{106}$, $R_{107}$, $R_{108}$, q, m, m', m", r, t, $R_a$, $R_b$, $R_c$ and the substituents of $R^{3a}$ and $R^6$ are as defined in formula (II).

For example, the present invention provides a compound of formula (II) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —$N(R_b)C(O)OR_a$, alkyl or heterocycle wherein the alky and heterocycle are independently substituted with 0, 1 or 2 substituents independently selected from the group consisting of halo, —$OR_a$, —$OC(O)R_a$, -$SR_a$, —$SOR_a$, —$SO_2R_a$, —$NR_aR_b$, —$N(R_b)C(O)R_a$, —$N(R_b)C(O)OR_a$, $N(R_a)C(=N)NR_aR_b$, —$N(R_a)C(O)NR_aR_b$, —$C(O)NR_aR_b$, —$C(O)OR_a$ and $R^{7a}$; $R^1$ is alkyl; $Z_1$ and $Z_2$ are O; Q is O; W is P; and $R^4$, $R^{7a}$, $R^8$, $R^{15}$, $R^{16}$, $R_{103}$, $R_{104}$, $R_{105}$, M, M', $R_{106}$, $R_{107}$, $R_{108}$, q, m, m', m", r, t, $R_a$, $R_b$, $R_c$ and the substituents of $R^{3a}$ and $R^6$ are as defined in formula (II).

For example, the present invention provides a compound of formula (II) wherein $R^4$ is H; $R^5$ is $OR^{16}$; $R^2$ is C1, C2, C3, C4 or C5 alkyl; $R^3$ is phenylmethyl wherein the phenyl moiety the phenylmethyl is unsubstituted or substituted with one $R^{3a}$; $R^{3a}$ is unsubstituted or substituted aryl, or unsubstituted or substituted heteroaryl; $R^6$ is unsubstituted or substituted phenylmethyl; $R^7$ is —$N(R_b)C(O)OR_a$, C1-C5 alkyl or heterocycle wherein each of the C1-C5 alky and heterocycle are independently substituted with 0, 1 or 2 substituents independently selected from the group consisting of halo, —$OR_a$, —$OC(O)R_a$, —$SR_a$, —$SOR_a$, —$SO_2R_a$, —$NR_aR_b$, —$N(R_b)C(O)R_a$, —$N(R_b)C(O)OR_a$, —$N(R_a)C(=N)NR_aR_b$, —$N(R_a)C(O)NR_aR_b$, —$C(O)NR_aR_b$, —$C(O)OR_a$ and $R^{7a}$, wherein $R_a$ and $R_b$ are independently selected from the group consisting of hydrogen and C1-C5 alkyl; $R^1$ is C1, C2, C3, C4 or C5 alkyl; Z, and $Z_2$ are O; Q is O; W is P; and $R^4$, $R^{7a}$, $R^8$, $R^{15}$, $R^{16}$, $R_{103}$, $R_{104}$, $R_{105}$, M, M', $R_{106}$, $R_{107}$, $R_{105}$, q, m, m', m", r, t, $R_c$ and the substituents of $R^{3a}$ and $R^6$ are as defined in formula (II).

For example, the present invention provides a compound of formula (II) wherein $R^4$ is $OR^{16}$; $R^5$ is H; $R^2$ is C1, C2, C3, C4 or C5 alkyl; $R^3$ is phenylmethyl wherein the phenyl moiety of the phenylmethyl is unsubstituted or substituted with one $R^{3a}$; $R^{3a}$ is unsubstituted or substituted aryl, or unsubstituted or substituted heteroaryl; $R^6$ is unsubstituted or substituted arylalkyl; $R^7$ is —$N(R_b)C(O)OR_a$, C1-C5 alkyl or heterocycle wherein the each of the C1-C5 alky and heterocycle are independently substituted with 0, 1 or 2 substituents independently selected from the group consisting of halo, —$OR_a$, —$OC(O)R_a$, —$SR_a$, —$SOR_a$, —$SO_2R_a$, —$NR_aR_b$, —$N(R_b)C(O)R_a$, —$N(R_b)C(O)OR_a$, —$N(R_a)C(=N)NR_aR_b$, —$N(R_a)C(O)NR_aR_b$, —$C(O)NR_aR_b$, —$C(O)OR_a$ and $R^{7a}$, wherein $R_a$ and $R_b$ are independently selected from the group consisting of hydrogen and C1-C5 alkyl; $R^1$ is C1, C2, C3, C4 or C5 alkyl; $Z_1$ and $Z_2$ are O; Q is O; W is P; and $R^4$, $R^{7a}$, $R^8$, $R^{15}$, $R^{16}$, $R_{103}$, $R_{104}$, $R_{105}$, M, M', $R_{106}$, q, m, m', m", r, t, $R_c$ and the substituents of $R^{3a}$ and $R^{6a}$ are as defined in formula (II).

For example, the present invention provides a compound of formula (II) wherein $R^4$ is H; $R^5$ is $OR^{16}$; $R^2$ is C1, C2, C3, C4 or C5 alkyl; $R^3$ is phenylmethyl wherein the phenyl moiety of the phenylmethyl is unsubstituted or substituted with one $R^{13a}$; $R^{3a}$ is unsubstituted or substituted pyridyl; $R^6$ is unsubstituted or substituted phenylmethyl; $R^7$ is —$N(R_b)C(O)OR_a$, C1-C5 alkyl or tetrahydrofuranyl wherein each of the C1-C5 alky is independently substituted with 0, 1 or 2 substituent selected from the group consisting of halo, —$OR_a$, —$OC(O)R_a$, —$SR_a$, —$SOR_a$, —$SO_2R_a$, —$NR_aR_b$, —$N(R_b)C(O)R_a$, —$N(R_b)C(O)OR_a$, —$N(R_a)C(=N)NR_aR_b$, —$N(R_a)C(O)NR_aR_b$, $C(O)NR_aR_b$, —$C(O)OR_a$ and $R^{7a}$, wherein $R_a$ and $R_b$ are independently selected from the group consisting of hydrogen and C1-C5 alkyl and $R^{7a}$ is unsubstituted or substituted pyridyl or unsubstituted or substituted thiazolyl; $R^1$ is C1-C5 alkyl; $Z_1$ and $Z_2$ are O; Q is O; W is P; and $R^4$, $R^8$, $R^{15}$, $R^{16}$, $R_{103}$, $R_{104}$, $R_{105}$, M, W, M', $R_{106}$, $R_{107}$, $R_{108}$, q, m, m', m", r, t, $R_c$, and the substituents of $R^{3a}$, $R^{7a}$ and $R^6$ are as defined in formula (II).

For example, the present invention provides a compound of formula (II) wherein $R^4$ is $OR^{16}$; $R^5$ is H; $R^2$ is C1, C2, C3, C4 or C5 alkyl; $R^3$ is phenylmethyl wherein the phenyl moiety of the phenylmethyl is unsubstituted or substituted with one $R^{3a}$; $R^{3a}$ is unsubstituted or substituted pyridyl; $R^6$ is unsubstituted or substituted phenylmethyl; $R^7$ is —$N(R_b)C(O)OR_a$, C1-C5 alkyl or tetrahydrofuranyl wherein the C1-C5 alky is substituted with 0, 1 or 2 substituents selected from the group consisting of halo, —$OR_a$, —$OC(O)R_a$, —$SR_a$, —$SOR_a$, —$SO_2R_a$, —$NR_aR_b$, —$N(R_b)C(O)R_a$, —$N(R_b)C(O)OR_a$, —$N(R_a)C(=N)NR_aR_b$, —$N(R_a)C(O)NR_aR_b$, —$C(O)NR_aR_b$, —$C(O)OR_a$ and $R^{7a}$, wherein $R_a$ and $R_b$ are independently selected from the group consisting of hydrogen and C1-C5 alkyl and $R^{7a}$ is unsubstituted or substituted pyridyl or unsubstituted or substituted thiazolyl; $R^1$ is C1-C5 alkyl; $Z_1$ and $Z_2$ are O; Q is O; W is P; and $R^4$, $R^8$, $R^{15}$, $R^{16}$, $R_{103}$, $R_{104}$, $R_{105}$, M, M', $R_{106}$, $R_{107}$, $R_{108}$, q, m, m', m", r, t, $R_c$ and the substituents of $R^{3a}$, $R^6$ are as defined in formula (II).

For example, the present invention provides a compound of formula (II) wherein $R^4$ is H; $R^5$ is $OR^{16}$; $R^2$ is C1, C2, C3, C4 or C5 alkyl; $R^3$ is phenylmethyl wherein the phenyl moiety of the phenylmethyl is unsubstituted or substituted with one $R^{3a}$; $R^{3a}$ is unsubstituted or substituted pyridyl; $R^6$ is unsubstituted or substituted phenylmethyl; $R^7$ is —N($R_b$)C(O)O$R_a$, C1-C5 alkyl or tetrahydrofuranyl wherein each of the C1-C5 alky is independently substituted with 0, 1 or 2 substituent selected from the group consisting of halo, —O$R_a$, —OC(O)$R_a$, —S$R_a$, —SO$R_a$, —SO$_2R_a$, —N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$, wherein $R_a$ and $R_b$ are independently selected from the group consisting of hydrogen and C1-C5 alkyl and $R^{7a}$ is unsubstituted or substituted pyridyl or unsubstituted or substituted thiazolyl; $R^1$ is C1-C5 alkyl; $Z_1$ and $Z_2$ are O; Q is O; W is P; $R_{104}$ is hydrogen or C1-C5 alkyl; each M is independently selected from the group consisting of hydrogen and C1-C5 alkyl; and $R^4$, $R^8$, $R^{15}$, $R^{16}$, $R_{103}$, $R_{105}$, M', $R_{106}$, $R_{107}$, $R_{108}$, q, m, m', m", r, t, $R_c$ and the substituents of $R^{3a}$, $R^{7a}$, M and $R^6$ are as defined in formula (II).

For example, the present invention provides a compound of formula (II) wherein $R^4$ is O$R^{16}$; $R^5$ is H; $R^2$ is C1, C2, C3, C4 or C5 alkyl; $R^3$ is phenylmethyl wherein the phenyl moiety of the phenylmethyl is unsubstituted or substituted with one $R^{3a}$; $R^{3a}$ is unsubstituted or substituted pyridyl; $R^6$ is unsubstituted or substituted phenylmethyl; $R^7$ is —N($R_b$)C(O)O$R_a$, C1-C5 alkyl or tetrahydrofuranyl wherein each of the C1-C5 alky is independently substituted with 0, 1 or 2 substituents selected from the group consisting of halo, —O$R_a$, —OC(O)$R_a$, —S$R_a$, —SO$R_a$, —SO$_2R_a$, —N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$, wherein $R_a$ and $R_b$ are independently selected from the group consisting of hydrogen and C1-C5 alkyl and $R^{7a}$ is unsubstituted or substituted pyridyl or unsubstituted or substituted thiazolyl; $R^1$ is C1-C5 alkyl; $Z_1$ and $Z_2$ are O; Q is O; W is P; $R_{104}$ is hydrogen or C1-C5 alkyl; each M is independently selected from the group consisting of hydrogen, and C1-C5 alkyl; and $R^4$, $R^8$, $R^{15}$, $R^{16}$, $R_{103}$, $R_{105}$, $R_{107}$, $R_{108}$, M', $R_{106}$, q, m, m', m", r, t, $R_c$ and the substituents of $R^{3a}$, M, $R^{7a}$ and $R^6$ are as defined in formula (II).

For example, the present invention provides a compound of formula (II) wherein $R^4$ is H; $R^5$ is O$R^{16}$; $R^2$ is 1-methylpropyl, tert-butyl or isopropyl; $R^3$ is phenylmethyl wherein the phenyl moiety of the phenylmethyl is unsubstituted or substituted with one $R^{3a}$; $R^{3a}$ is unsubstituted or substituted pyridyl; $R^6$ is unsubstituted or substituted phenylmethyl; $R^7$ is —N(H)C(O)OCH$_3$, methyl, ethyl, propyl, r-butyl, 1-methylpropyl, 2-methylpropyl, 3-methylpropyl, tert-butyl, isopropyl, or tetrahydrofuranyl wherein each of the methyl, ethyl, propyl, r-butyl, 1-methylpropyl, 2-methylpropyl, 3-methylpropyl, tert-butyl, isopropyl is independently substituted with 0, 1 or 2 substituents selected from the group consisting of halo, —O$R_a$, —OC(O)$R_a$, —S$R_a$, —SO$R_A$, —SO$_2R_a$, –N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$, wherein $R_a$ and $R_b$ are independently selected from the group consisting of hydrogen and C1-C5 alkyl and $R^{7a}$ is unsubstituted or substituted pyridyl or unsubstituted or substituted thiazolyl; $R^1$ is C1-C5 alkyl; $Z_1$ and $Z_2$ are O; Q is O; W is P; $R_{104}$ is hydrogen or C1-C5 alkyl; each M is independently selected from the group consisting of hydrogen and C1-C5 alkyl; and $R^4$, $R^8$, $R^{15}$, $R^{16}$, $R_{103}$, $R_{105}$, M', $R_{106}$, $R_{107}$, $R_{108}$, q, m, m', m", r, t, $R_c$ and the substituents of $R^{3a}$, $R^{7a}$, M and $R^6$ are as defined in formula (II).

For example, the present invention provides a compound of formula (II) wherein $R^4$ is O$R^{16}$; $R^5$ is H; $R^2$ is 1-methylpropyl, tert-butyl or isopropyl; $R^3$ is phenylmethyl wherein the phenyl moiety of the phenylmethyl is unsubstituted or substituted with one $R^{3a}$; $R^{3a}$ is unsubstituted or substituted pyridyl; $R^6$ is unsubstituted or substituted phenylmethyl; $R^7$ is —N(H)C(O)OCH$_3$, methyl, ethyl, propyl, n-butyl, 1-methylpropyl, 2-methylpropyl, 3-methylpropyl, tert-butyl, isopropyl, or tetrahydrofuranyl wherein each of the methyl, ethyl, propyl, n-butyl, 1-methylpropyl, 2-methylpropyl, 3-methylpropyl, tert-butyl and isopropyl is substituted with 0, 1 or 2 substituents selected from the group consisting of halo, —O$R_a$, —OC(O)$R_a$, —S$R_a$, —SO$R_a$, —SO$_2R_a$, —N$R_aR_b$, —N($R_b$)C(O)$R_a$, —N($R_b$)C(O)O$R_a$, —N($R_a$)C(=N)N$R_aR_b$, —N($R_a$)C(O)N$R_aR_b$, —C(O)N$R_aR_b$, —C(O)O$R_a$ and $R^{7a}$, wherein $R_a$ and $R_b$ are independently selected from the group consisting of hydrogen and C1-C5 alkyl and $R^{7a}$ is unsubstituted or substituted pyridyl or unsubstituted or substituted thiazolyl; $R^1$ is C1-C5 alkyl; $Z_1$ and $Z_2$ are O; Q is O; W is P; $R_{104}$ is hydrogen or C1-C5 alkyl; each M is independently selected from the group consisting of hydrogen, and C1-C5 alkyl; and $R^4$, $R^8$, $R^{15}$, $R^{16}$, $R_{103}$, $R_{105}$, M', $R_{106}$, $R_{107}$, $R_{108}$, q, m, m', ml, r, t, $R_c$ and the substituents of $R^{3a}$, $R^{7a}$, M and $R^6$ are as defined in formula (II).

Exemplary compounds of the present invention of formula (II) include, but not limited, to the following:

methyl(1S,4R,6S,7S,10S)-7-benzyl-1,10-ditert-butyl-6-hydroxy-2,9,12-trioxo-4-[4-(2-pyridinyl)benzyl]-13-oxa-3,8,11-triazatetradec-1-ylcarbamate;

methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate;

methyl(1S,4S,5S,7S,10S)-7-benzyl-1,10-ditert-butyl-5-hydroxy-2,9,12-trioxo-4-[4-(2-pyridinyl)benzyl]-13-oxa-3,8,11-triazatetradec-1-ylcarbamate;

methyl(1R,4S,5S,7S,10S)-4-benzyl-10-tert-butyl-5-hydroxy-1-[1-methyl-1-(methylsulfanyl)ethyl]-2,9,12-trioxo-7-[4-(2-pyridinyl)benzyl]-13-oxa-3,8,11-triazatetradec-1-ylcarbamate;

methyl(1R,4S,5S,7S,10S)-4-benzyl-10-tert-butyl-5-hydroxy-1-[1-methyl-1-(methylsulfanyl)ethyl]-2,9,12-trioxo-7-[4-(2-pyridinyl)benzyl]-13-oxa-3,8,11-triazatetradec-1-ylcarbamate;

methyl(1R,4S,6S,7S,10S)-4-benzyl-10-tert-butyl-6-hydroxy-1-[1-methyl-1-(methylsulfanyl)ethyl]-2,9,12-trioxo-7-[4-(2-pyridinyl)benzyl]-13-oxa-3,8,11-triazatetradec-1-ylcarbamate;

methyl(1R,4S,6S,7S,10S)-4-benzyl-10-tert-butyl-6-hydroxy-1-[1-methyl-1-(methylsulfonyl)ethyl]-2,9,12-trioxo-7-[4-(2-pyridinyl)benzyl]-13-oxa-3,8,11-triazatetradec-1-ylcarbamate;

methyl(1S)-1-[({(1S,3S,4S)-4-({(2S)-3,3-dimethyl-2-[(phenoxyacetyl) amino]butanoyl}amino)-3-hydroxy-5-phenyl-1-[4-(2-pyridinyl)benzyl]pentyl}amino)carbonyl]-2,2-dimethylpropylcarbamate;

methyl(1S,4S,6S,7S,10S)-7-benzyl-1,10-ditert-butyl-6-hydroxy-2,9,12-trioxo-4-[4-(2-pyridinyl)benzyl]-14-oxa-3,8,11-triazapentadec-1-ylcarbamate;

methyl(1S)-1-[({(1S,3S,4S)-4-{[(2S)-3,3-dimethyl-2-({[(6-methyl-3pyridinyl)oxy]acetyl}amino)butanoyl]amino}-3-hydroxy-5-phenyl-1-[4-(2-pyridinyl)benzyl]pentyl}amino)carbonyl]-2,2-dimethylpropylcarbamate;

3-pyridinylmethyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate;

benzyl (1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate;

methyl(1S,4S,5S,7S,10S)-7-benzyl-1,10-ditert-butyl-5-hydroxy-4-[4-(6-methyl-3-pyridinyl)benzyl]-2,9,12-trioxo-13-oxa-3,8,11-triazatetradec-1-ylcarbamate;

methyl(1S,4S,5S,7S,10S)-7-benzyl-1,10-ditert-butyl-5-hydroxy-4-[4-(5-methylpyridinyl)benzyl]-2,9,12-trioxo-13-oxa-3,8,11-triazatetradec-1-ylcarbamate;

methyl(1S,4S,5S,7S,10S)-4-benzyl-1,10-ditert-butyl-5-hydroxy-7-[4-(5-methyl-2-pyridinyl)benzyl]-2,9,12-trioxo-13-oxa-3,8,11-triazatetradec-1-ylcarbamate;

methyl(1R,4S,5S,7S,10S)-4-benzyl-10-tert-butyl-5-hydroxy-1-[1-methyl-1-((R)-methylsulfonyl)ethyl]-2,9,12-trioxo-7-[4-(2-pyridinyl)benzyl]-13-oxa-3,8,11-triazatetradec-1-ylcarbamate;

methyl(1R,4S,5S,7S,10S)-4-benzyl-10-tert-butyl-5-hydroxy-1-[1-methyl-1-((S)-methylsulfinyl)ethyl]-2,9,12-trioxo-7-[4-(2-pyridinyl)benzyl]-13-oxa-3,8,11-triazatetradec-1-ylcarbamate;

methyl(1S,4S,5S,7S,10S)-7-benzyl-1,10-ditert-butyl-5-hydroxy-2,9,12-trioxo-4-[4-(3-pyridinyl)benzyl]-13-oxa-3,8,11-triazatetradec-1-ylcarbamate;

methyl(1S,4S,5S,7S,10S)-7-benzyl-1,10-ditert-butyl-5-hydroxy-2,9,12-trioxo-4-[4-(3-pyridinyl)benzyl]-13-oxa-3,8,11-triazatetradec-1-ylcarbamate;

1,2,5,6-tetradeoxy-2,5-bis({(2S)-2-[(methoxycarbonyl)amino]-3,3-dimethylbutanoyl}amino)-1,6-bis[4-(2-pyridinyl)phenyl]-D-iditol;

methyl(1S,4R,5R,7R,10S)-1,10-ditert-butyl-5-hydroxy-2,9,12-trioxo-4,7-bis[4-(2-pyridinyl)benzyl]-13-oxa-3,8,11-triazatetradec-1-ylcarbamate;

methyl(1S,4S,5S,7S,10S)-7-benzyl-1,10-ditert-butyl-5-hydroxy-4-[4-(6-methoxy-2-pyridinyl)benzyl]-2,9,12-trioxo-13-oxa-3,8,11-triazatetradec-1-ylcarbamate;

methyl(1S,4S,5S,7S,10S)-4-benzyl-1,10-ditert-butyl-5-hydroxy-7-[4-(6-methoxy-2-pyridinyl)benzyl]-2,9,12-trioxo-13-oxa-3,8,11-triazatetradec-1-ylcarbamate;

methyl(1S,4S,5S,7S,10S)-4-benzyl-1,10-disec-butyl-5-hydroxy-2,9,12-trioxo-7-[4-(2-pyridinyl)benzyl]-13-oxa-3,8,11-triazatetradec-1-ylcarbamate;

methyl(1S,4S,5S,7S,10S)-4-benzyl-10-tert-butyl-5-hydroxy-2,9,12-trioxo-7-(4-pyridin-2-ylbenzyl)-1-[(3R)-tetrahydrofuran-3-yl]-13-oxa-3,8,11-triazatetradec-1-ylcarbamate;

methyl(1S,4S,5S,7S,10S)-4-benzyl-1,10-di-tert-butyl-5-hydroxy-2,9,12-trioxo-7-[4-(1,3-thiazol-2-yl)benzyl]-13-oxa-3,8,11-triazatetradec-1-ylcarbamate;

methyl(1S,4S,5S,7S,10S)-4-benzyl-10-tert-butyl-5-hydroxy-1-[(1S)-1-methylpropyl]-2,9,12-trioxo-7-(4-pyridin-2-ylbenzyl)-13-oxa-3,8,11-triazatetradec-1-ylcarbamate;

methyl(1S,4S,5S,7S,10S)-4-benzyl-1,10-di-tert-butyl-5-hydroxy-2,9,12-trioxo-7-(4-pyridin-3-ylbenzyl)-13-oxa-3,8,11-triazatetradec-1-ylcarbamate;

methyl(1S)-1-({[(1S,3S,4S)-3-hydroxy-4-{[(2S)-2-methyl-3-(methylsulfonyl)propanoyl]amino}-5-phenyl-1-(4-pyridin-2-ylbenzyl)pentyl]amino}carbonyl)-2,2-dimethylpropylcarbamate;

methyl(1S,4S,5S,7S,10S)-4benzyl-1,10-di-tert-butyl-5-hydroxy-2,9,12-trioxo-7-(4-pyridin-4-ylbenzyl)-13-oxa-3,8,11-triazatetradec-1-ylcarbamate;

methyl(1S)-1-({[(1S,3S,4S)-3-hydroxy-4-{[(2S)-2-hydroxy-3,3-dimethylbutanoyl]amino}-5-phenyl-1-(4-pyridin-2-ylbenzyl)pentyl]amino}carbonyl)-2,2-dimethylpropylcarbamate;

methyl(1S,4S,6S,7S,10S)-7-benzyl-1,10-di-tert-butyl-6-hydroxy-12,12-dioxido-2,9-dioxo-4-(4-pyridin-2-ylbenzyl)-12-thia-3,8,11-triazatridec-1-ylcarbamate;

methyl(1R,4S,5S,7S,10S)-4-benzyl 10-tert-butyl-5-hydroxy-1-[(methylthio)methyl]-2,9,12-trioxo-7-(4-pyridin-2-ylbenzyl)-1 3-oxa-3,8, 11-triazatetradec-1-ylcarbamate;

methyl(1R,4S,5S,7S,10S)-4-benzyl 10-tert-butyl-5-hydroxy-1-[(methylsulfonyl)methyl]-2,9,12-trioxo-7-(4-pyridin-2-ylbenzyl)-1 3-oxa-3,8, 11-triazatetradec-1-ylcarbamate;

methyl(1S)-1-({[(1S,3S,4S)-3-hydroxy-4-{[(2R)-2-hydroxy-3-methyl-3-(methylsulfonyl)butanoyl]amino}-5-phenyl-1-(4-pyridin-2-ylbenzyl)pentyl]amino}carbonyl)-2,2-dimethylpropylcarbamate;

methyl(1S,4S,5S,7S,10S)-4benzyl-10-tert-butyl-5-hydroxy-1-isobutyl-2,9,12-trioxo-7-(4-pyridin-2-ylbenzyl)-13-oxa-3,8,11-triazatetradec-1-ylcarbamate;

methyl(1S,4S,5S,7S,10S)-1-(2-amino-2-oxoethyl)-4-benzyl-10-tert-butyl-5-hydroxy-2,9,12-trioxo-7-(4-pyridin-2-ylbenzyl)-13-oxa-3,8,11-triazatetradec-1-ylcarbamate;

methyl 2-{[(1S,2S,4S)-1-benzyl-2-hydroxy-4-{[N-(methoxycarbonyl)-3-methyl-L-valyl]amino}-5-(4-pyridin-2-ylphenyl)pentyl]amino}-1-[(methoxycarbonyl)amino]-2-oxoethylcarbamate;

methyl(1S,4S,6S,7S,10S)-7-benzyl-1,10-di-tert-butyl-6-hydroxy-2,9,12,14tetraoxo-4-(4-pyridin-2-ylbenzyl)-15-oxa-3,8,11,13-tetraazahexadec-1-ylcarbamate;

methyl(1S,4S,6S,7S,10S)-7-benzyl-1,10-di-tert-butyl-6-hydroxy-14,14 dimethyl-2,9,12,15-tetraoxo-4-(4-pyridin-2-ylbenzyl)-13-oxa-3,8,11-triazahexadec-1-ylcarbamate;

(4S,7S,8S,10S,13S)-7-benzyl-4,13-di-tert-butyl-8-hydroxy-2,5,12,15-tetraoxo-10-(4-pyridin-2-ylbenzyl)-16-oxa-3,6,11,14-tetraazaheptadec-1-yl acetate;

methyl(1S)-1-({[(1S,3S,4S)-4-{[(2S)-2-(glycoloylamino)-3,3-dimethylbutanoyl]amino}-3-hydroxy-5-phenyl-1-(4-pyridin-2-ylbenzyl)pentyl]amino}carbonyl)-2,2-dimethylpropylcarbamate;

(3S,6S,7S,9S,12S)-6-benzyl-3-[(tert-butoxycarbonyl)amino]-12-tert-butyl-7-hydroxy-2,2-dimethyl-4,11,14-trioxo-9-(4-pyridin-2-ylbenzyl)-15-oxa-5,10,13-triazahexadec-1-yl acetate;

methyl(1S,4S,5S,7S,10S)-4benzyl-10-tert-butyl-5-hydroxy-1-(2-hydroxy-1,1-dimethylethyl)-2,9,12-trioxo-7-(4-pyridin-2-ylbenzyl)-13-oxa-3,8,11-triazatetradec-1-ylcarbamate;

methyl(1S,4S,5S,7S,10S)-1-{[(aminocarbonyl)amino]methyl}-4-benzyl-10-tert-butyl-5-hydroxy-2,9,12-trioxo-7-(4-pyridin-2-ylbenzyl)-1 3-oxa-3,8,11-triazatetradec-1-ylcarbamate;

methyl(1S,4S,5S,7S,10S)-4benzyl-10-tert-butyl-5-hydroxy-2,9,12-trioxo-7-(4-pyridin-2-ylbenzyl)-1-(pyridin-2-ylmethyl)-13-oxa-3,8,11-triazatetradec-1-ylcarbamate;

methyl(1S,4S,5S,7S,10S)-4benzyl-10-tert-butyl-5-hydroxy-2,9,12-trioxo-7-(4-pyridin-2-ylbenzyl)-1-(1,3-thiazol-4-ylmethyl)-13-oxa-3,8,11-triazatetradec-1-ylcarbamate;

(3S,6S,7S,9S,12S)-6-benzyl 12-tert-butyl-7-hydroxy-3-[(methoxycarbonyl)amino]-2,2-dimethyl-4,11,14-trioxo-9-(4-pyridin-2-ylbenzyl)-15-oxa-5,10,13-triazahexadec-1-yl acetate;

methyl(1S,4R,6S,7S,10S)-7-benzyl 1,10-di-tert-butyl-6-hydroxy-15,15-dioxido-2,9-dioxo-4-(4-pyridin-2-ylbenzyl)-15-thia-3,8,11,14tetraazahexadec-1-ylcarbamate;

methyl(1S,4R,6S,7S,10S)-7-benzyl 1,10-di-tert-butyl-6-hydroxy-2,9,15-trioxo-4-(4-pyridin-2-ylbenzyl)-16-oxa-3,8,11,14-tetraazaheptadec-1-ylcarbamate;

methyl(5S,8S,10S,11S,14S)-10-benzyl-5-tert-butyl-1 0-hydroxy-14-[(methoxycarbonyl)amino]-15-methyl-3,6,13-trioxo-8-(4-pyridin-2-ylbenzyl)-2-oxa-4,7,12-triazahexadecan-16-oate;

methyl(5S,8S,10S,11S,14S)-11-benzyl-5-tert-butyl-10-hydroxy-14-[(methoxycarbonyl)amino]-15,15-dimethyl-3,6,13-trioxo-8-(4-pyridin-2-ylbenzyl)-2-oxa-4,7,12-triazahexadecan-16-oate;

methyl(1S,4S,5S,7S,10S)-4benzyl-1,10-bis(tert-butyl)-2,9,12-trioxo-5-(phosphonooxy)-7-(4-pyridin-2-ylbenzyl)-13-oxa-3,8,11-triazatetradec-1-ylcarbamate;

methyl(1S,4S,5S,7S,10S)-7-benzyl-1,10-bis(tert-butyl)-2,9,12-trioxo-5-[(phosphonooxy)methoxy]-4-(4-pyridin-2-ylbenzyl)-13-oxa-3,8,11-triazatetradec-1-ylcarbamate;

methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate;

methyl(1S,4S,5S,7S,10S)-4-benzyl-1,10-bis(tert-butyl)-2,9,12-trioxo-5-[1-(phosphonooxy)ethoxy]-7-(4-pyridin-2-ylbenzyl)-13-oxa-3,8,11-triazatetradec-1-ylcarbamate; and methyl(1S)-3-amino-1-({[(1S,2S,4S)-1-benzyl-2-hydroxy-4-{[N-methoxycarbonyl)-3-methyl-L-valyl]amino}-5-(4-pyridin-2-ylphenyl)pentyl]amino}carbonyl)-2,2-dimethyl-3-oxopropylcarbamate; or a pharmaceutical acceptable salt form, prodrug, or stereoisomer thereof.

In a third embodiment, the present invention provides a compound of formula (III)

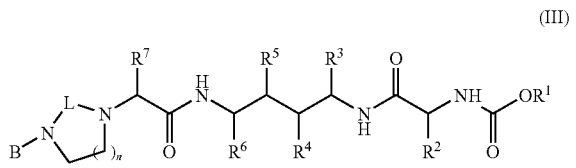

(III)

or a pharmaceutically acceptable salt form, prodrug or stereoisomer thereof, wherein:

B is H or —CH$_2$R$^9$;

L is —C(=O), —C(=S), —C(=NH) or —S(O)$_2$;

R$^1$ is alkyl, alkenyl, alkynyl, cycloalkyl, cycloalkenyl, heterocycle, aryl or heteroaryl; wherein each R$^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and R$^{1a}$;

R$^{1a}$ is cycloalkyl, cycloalkenyl, heterocycle, aryl or heteroaryl; wherein each R$^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^2$ is alkyl, alkenyl, alkynyl, cycloalkyl, cycloalkenyl, heterocycle, aryl or heteroaryl; wherein each R$^2$ is substituted with 0, 1 or 2 substituents independently selected from the group consisting of halo, —OR$_a$, —SR$_a$, —SOR$_a$, —SO$_2$R$_a$, NR$_a$R$_b$, NR$_b$C(O)R$_a$ —N(R$_a$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{2a}$;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^4$ is H and R$^5$ is OR$^{16}$; or

R$^5$ is H and R$^4$ is OR$^{16}$; or

R$^4$ and R$^5$ are —OR$^{16}$;

R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)

NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^9$ is alkyl, alkenyl, alkynyl, cycloalkyl, cycloalkenyl, aryl, heteroaryl or heterocycle; wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cyanoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$;

R$^{9a}$ is cycloalkyl, cycloalkenyl, heterocycle, aryl or heteroaryl; wherein each R$^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{16}$ is hydrogen or R$^{15}$;

R$^{15}$ is

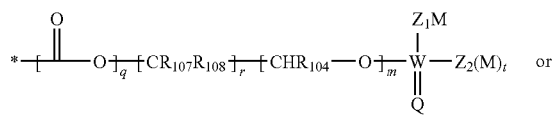

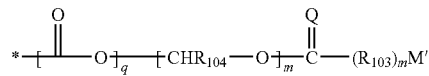

R$_{103}$ is C(R$_{105}$)$_2$, O or —N(R$_{105}$);

R$_{104}$ is hydrogen, alkyl, haloalkyl, alkoxycarbonyl, aminocarbonyl, alkylaminocarbonyl or dialkylaminocarbonyl, each M is independently selected from the group consisting of H, —N(R$_{105}$)$_2$, alkyl, alkenyl, and R$_{106}$; wherein 1 to 4 —C$_2$ radicals of the alkyl or alkenyl, other than the —CH$_2$ radical that is bound to Z, is optionally replaced by a heteroatom group selected from the group consisting of O, S, S(O), SO$_2$ and N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, Z$_1$ and Z$_2$ are —CH$_2$;

Z$_1$ is CH$_2$, O, S, N(R$_{105}$), or, when M is absent, H;

Z$_2$ is CH$_2$, O, S or —N(R$_{105}$);

Q is O or S;

W is P or S; wherein when W is S, Z$_1$ and Z$_2$ are not S;

M' is H, alkyl, alkenyl or R$_{106}$; wherein 1 to 4 —CH$_2$ radicals of the alkyl or alkenyl is optionally replaced by a heteroatom group selected from O, S, S(O), SO$_2$ or N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and —OC(O)alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $—OR_{105}$, $—R_{105}$, $—N(R_{105})_2$, $—N(R_{105})C(O)R_{105}$, —CN, $—C(O)OR_{105}$, $—C(O)N(R_{105})_2$, halo and $—CF_3$;

each $R_{107}$ and $R_{108}$ are independently selected from the group consisting of hydrogen and alkyl;

q is 0 or 1;
m is 0 or 1;
m' is 0 or 1;
m'' is 0 or 1;
r is 0, 1, 2, 3 or 4;
t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, hydroxy, alkoxy, alkyl, alkenyl, alkynyl, $—NH_2$, —N(H)(alkyl), $—N(alkyl)_2$, —SH, —S(alkyl), $—SO_2(alkyl)$, —N(H)C(O)alkyl, —N(alkyl)C(O)alkyl, $—N(H)C(O)NH_2$, —N(H)C(O)N(H)(alkyl), $—N(H)C(O)N(alkyl)_2$, —C(O)OH, —C(O)Oalkyl, $—C(O)NH_2$, —C(O)N(H)(alkyl), $—C(O)N(alkyl)_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$; alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, $—NH_2$, —N(H)(alkyl), $—N(alkyl)_2$, —SH, —S(alkyl), $—SO_2(alkyl)$, —N(H)C(O)alkyl, —N(alkyl)C(O)alkyl, $—N(H)C(O)NH_2$, —N(H)C(O)N(H)(alkyl), $—N(H)C(O)N(alkyl)_2$, —C(O)OH, —C(O)Oalkyl, $—C(O)NH_2$, —C(O)N(H)(alkyl), $—C(O)N(alkyl)_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, $—NH_2$, —N(H)(alkyl), $—N(alkyl)_2$, —SH, —S(alkyl), $—SO_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O) N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (III) wherein $R^4$ is H; $R^5$ is $OR^{16}$; and L, B, $R^1$, $R^{1a}$, $R^2$, $R_{2a}$, $R^3$, $R^{3a}$, $R^6$, $R^{6a}$, $R^7$, $R^{7a}$, $R^9$, $R^{9a}$, $R^{15}$, $R^{16}$, $R^{15}$, $R_{103}$, $R_{104}$, $R_{105}$, M, $Z_1$, $Z_2$, Q, W, M', $R_{106}$, $R_{107}$, $R_{108}$, q, m', m', m'', r, t, $R_a$, $R_b$, $R_c$ and n are as defined in formula (III).

For example, the present invention provides a compound of formula (III) wherein $R^4$ is $OR^{16}$; $R^5$ is H; and L, B, $R^1$, $R^{1a}$, $R^2$, $R^{2a}$, $R^3$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^1$ is a l; and L, B, $R^2$, $R^{2a}$, $R^3$, $R^{3a}$, $R^4$, $R^5$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^1$ is methyl; and L, B, $R^2$, $R^{2a}$, $R^3$, $R^{3a}$, $R^4$, $R^5$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^2$ is alkyl; and L, B, $R^1$, $R^{1a}$, $R^3$, $R^{3a}$, $R^4$, $R^5$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^2$ is tert-butyl, 1-methylpropyl or isopropyl; and L, B, $R^1$, $R_{1a}$, $R^3$, $R^{3a}$, $R^4$, $R^5$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, $—NH_2$, —N(H)(alkyl), $—N(alkyl)_2$, —SH, —S(alkyl), $—SO_2(alkyl)$, —N(H)C(O)alkyl, —N(alkyl)C(O)alkyl, $—N(H)C(O)NH_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$; and L, B, $R^1$, $R^{1a}$, $R^2$, $R^{2a}$, $R^{3a}$, $R^4$, $R^5$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^3$ is phenylmethyl, wherein the phenyl moiety of the phenylmethyl is unsubstituted or substituted with 0, 1, 2, 3 or 4 substituents selected from the group consisting of cyano, halo, nitro, oxo, alkyl, alkenyl, alkynyl, hydroxy, alkoxy, $—NH_2$, —N(H)(alkyl), $—N(alkyl)_2$, —SH, —S(alkyl), $—SO_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, alkylN(H)(alkyl), -alkylN(alkyl)$_2$, -alkylN(H)C(O)NH$_2$, -alkylN(H)C(O)N(H)

(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$; and L, B, R$^1$, R$^{1a}$, R$^2$, R$^{2a}$, R$^{3a}$, R$^4$, R$^5$, R$^6$, R$^{6a}$, R$^7$, R$^{7a}$, R$^9$, R$^{9a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ and n are as defined in formula (III).

For example, the present invention provides a compound of formula (III) wherein R$^6$ is unsubstituted or substituted arylalkyl; and L, B, R$^1$, R$^{1a}$, R$^2$, R$^{2a}$, R$^3$, R$^{3a}$, R$_4$, R$^5$, R$^7$, R$^{7a}$, R$^9$, R$^{9a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$, n and the substituents of R$^6$ are as defined in formula (III).

For example, the present invention provides a compound of formula (III) wherein R$^6$ is unsubstituted or substituted phenylmethyl; and L, B, R$^1$, R$^{1a}$, R$^2$, R$^{2a}$, R$^3$, R$^3$, R$^4$, R$^5$, R$^7$, R$^{7a}$, R$_9$, R$^{9a}$, R$^5$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$, n and the substituents of R$^6$ are as defined in formula (III).

For example, the present invention provides a compound of formula (III) wherein R$^7$ is —N(R$_b$)C(O)OR$_a$, alkyl or heterocycle wherein the alkyl and heterocycle are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;; and L, B, R$^1$, R$^{1a}$, R$^2$, R$^{2a}$, R$^3$, R$^{3a}$, R$^4$, R$^5$, R$^6$, R$^{6a}$, R$^{7a}$, R$^9$, R$^{9a}$, R$^{15}$, R$^6$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ and n are as defined in formula (III).

For example, the present invention provides a compound of formula (III) wherein R$^7$ is —N(H)C(O)OCH$_3$, methyl, ethyl, n-propyl, n-butyl, n-pentyl, tert-butyl, isopropyl, 1-methypropyl, 2-methylpropyl, 3-methylpropyl or tetrahydrofuranyl, wherein each of the methyl, ethyl, n-propyl, n-butyl, n-pentyl, tert-butyl, isopropyl, 1-methypropyl, 2-methylpropyl, 3-methylpropyl is independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$, wherein R$_a$ and R$_b$ are each independently selected from the group consisting of hydrogen, C1 alkyl, C2 alkyl, C3 alkyl, C4 alkyl and C5 alkyl and R$^{7a}$ is substituted or unsubstituted aryl or substituted or unsubstituted heteroaryl; and L, B, R$^1$, R$^{1a}$, R$^2$, R$^{2a}$, R$^3$, R$^{3a}$, R$^4$, R$^5$, R$^6$, R$^{6a}$, R$^9$, R$^{9a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ n and the substituents of R$^{7a}$ are as defined in formula (III).

For example, the present invention provides a compound of formula (III) wherein R$^9$ is aryl or heteroaryl, wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$, wherein R$_a$ and R$_b$ are each independently selected from the group consisting of hydrogen, C1alkyl, C2 alkyl, C3 alkyl, C4 alkyl and C5 alkyl; and L, B, R$^1$, R$^{1a}$, R$^2$, R$^{2a}$, R$^3$, R$^{3a}$, R$^4$, R$^5$, R$^6$, R$^{6a}$, R$^7$, R$^{7a}$, R$^{9a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ and n are as defined in formula (III).

For example, the present invention provides a compound of formula (III) wherein R$^9$ is phenyl substituted with 0, 1, 2 or 3 substituents independently selected from the group consisting of C1 alkyl, C2 alky, C3 alkyl, C4 alkyl, C5 alkyl, halo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, -alkylOR$_a$, -alkyl-O—P(O)(OR$_a$)(OR$_a$) and R$^{9a}$, wherein R$_a$ and R$_b$ are each selected from the group consisting of hydrogen, methyl, C1 alkyl, C2 alky, C3 alkyl, C4 alkyl, and C5 alkyl and R$^{9a}$ is pyridyl; and L, B, R$^1$, R$^{1a}$, R$^2$, W, R$^1$, R$^{1a}$, R$^4$, R$^5$, R$^6$, R$^{6a}$, R$^7$, R$^{7a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ and n are as defined in formula (III).

For example, the present invention provides a compound of formula (III) wherein R$^9$ is heteroaryl; wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R, —N(Rb)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$, wherein R$_a$ and R$_b$ are each independently selected from the group consisting of hydrogen, C1 alkyl, C2 alkyl, C3 alkyl, C4 alkyl and C5 alkyl, and R$^{9a}$ is substituted or substituted heteroaryl; and L, B, R$^1$, R$^{1a}$, R$^2$, R$^{2a}$, R$^3$, R$^{3a}$, R$^4$, R$^5$, R$^6$, R$^7$, R$^{7a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ n and the substituents of R$^{9a}$ are as defined in formula (III).

For example, the present invention provides a compound of formula (III) wherein R$^9$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, imidazo[1,5,a]pyridyl, benzimiazolyl, benzothienyl, benzthiazolyl or indazolyl, wherein each R$^9$ is independently substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$, wherein R$_a$ and R$_b$ are each independently selected from the group consisting of hydrogen, C1 alkyl, C2 alkyl, C3 alkyl, C4 alkyl and C5 alkyl, and R$^{9a}$ is unsubstituted or substituted pyridyl; and L, B, R$^1$, R$^{1a}$, R$^2$, R$^{2a}$, R$^3$, R$^{3a}$, R$^4$, R$^5$, R$^6$, R$^{6a}$, R$^7$, R$^{7a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m", r, t, R$_a$, R$_b$, R$_c$ n and the substituents of R$^{9a}$ are as defined in formula (III).

For example, the present invention provides a compound of formula (III) wherein R$^4$ is H; R$^5$ is OR$^{16}$; L is —C(=O) or —C(=S); R$^2$ is alkyl; and B, R$^1$, R$^{1a}$, R$^3$, R$^{3a}$, R$^6$, R$^{6a}$, R$^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m', m'', r, t, $R_a$, $R_b$, $R_c$ and n are as defined in formula (III).

For example, the present invention provides a compound of formula (III) wherein $R^4$ is $OR^{16}$; $R^5$ is H; L is —C(=O) or —C(=S); $R^2$ is alkyl; and B, $R^1$, $R^{1a}$, $R^3$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m', m'', r, t, $R_a$, $R_b$, $R_c$ and n are as defined in formula (III).

For example, the present invention provides a compound of formula (III) wherein $R^4$ is H; $R^5$ is $OR^{16}$; L is —C(=O) or —C(=S); $R^1$ is alkyl; and B, $R^2$, $R^{2a}$, $R^3$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M', $Z_1$, $Z_2$, Q, W, M', $R_a$, $R_b$, $R_c$ and n are as defined in formula (III).

For example, the present invention provides a compound of formula (III) wherein $R^4$ is $OR^{16}$; $R^5$ is H; L is —C(=O) or —C(=S); $R^1$ is alkyl; and B, $R^2$, $R^{2a}$, $R^3$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^4$ is H; $R^5$ is $OR^{16}$; L is —C(=O) or —C(=S); $R^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$; and B, $R^1$, $R^{1a}$, $R^2$, $R^{2a}$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^4$ is $OR^{16}$; $R^5$ is H; L is —C(γO) or —C(=S); $R^3$ is arylalkyl wherein the aryl moiety of the arylalkyl is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$; and B, $R^1$, $R^{1a}$, $R^2$, $R^{2a}$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^4$ is H; $R^5$ is $OR^{16}$; L is —C(=O) or —C(=S); $R^6$ is unsubstituted or substituted arylalkyl; and B, $R^1$, $R^{1a}$, $R^2$, $R^{2a}$, $R^3$, $R^{3a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_a$ n and the substituents of $R^6$ are as defined in formula (III).

For example, the present invention provides a compound of formula (III) wherein $R^4$ is $OR^{16}$; $R^5$ is H; L is —C(=O) or —C(=S); $R^6$ is unsubstituted or substituted arylalkyl; and B, $R^1$, $R^{1a}$, $R^2$, $R^{2a}$, $R^3$, $R^{3a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ c and the substituents of $R^6$ are as defined in formula (III).

For example, the present invention provides a compound of formula (III) wherein $R^4$ is H; $R^5$ is $OR^{16}$; L is —C(=O) or —C(=S); $R^7$ is —N(R$_b$)C(O)OR$_a$, C1 alkyl, C2 alkyl, C3 alkyl, C4 alkyl, C5 alkyl or tetrahydrofuranyl wherein the C1 alkyl, C2 alkyl, C3 alkyl, C4 alkyl and C5 alkyl are independently substituted with 0, 1 or 2 substituents selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{7a}$, wherein R$_a$ and R$_b$ are independently selected from the group consisting of hydrogen, C1 alkyl, C2 alkyl, C3 alkyl, C4 alkyl, and C5 alkyl; and B, $R^1$, $R^{1a}$, $R^2$, $R^{2a}$, $R^3$, $R^{3a}$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^4$ is $OR^{16}$; $R^5$ is H; L is —C(=O) or —C(=S); $R^7$ is —N(R$_b$)C(O)OR$_a$, C1 alkyl, C2 alkyl, C3 alkyl, C4 alkyl, C5 alkyl or tetrahydrofuranyl wherein the C1 alkyl, C2 alkyl, C3 alkyl, C4 alkyl and C5 alkyl are independently substituted with 0, 1 or 2 substituents selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{7a}$, wherein R$_a$ and R$_b$ are independently selected from the group consisting of hydrogen, C1 alkyl, C2 alkyl, C3 alkyl, C4 alkyl, and C5 alkyl; and B, R, $R^1$, $R^{1a}$, $R^2$, $R^{2a}$, $R^3$, $R^{3a}$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and n are as defined in formula (III).

For example, the present invention provides a compound of formula (III) wherein $R^4$ is H; $R^5$ is $OR^{16}$; L is —C(=O) or —C(=S); $R^9$ is unsubstituted or substituted aryl and B, $R^1$, $R^{1a}$, $R^2$, $R^{2a}$, $R^3$, $R^{3a}$, $R^6$, $R^{6a}$, $R^7$, $R^{7a}$, $R^{9a}$, $R^{15}$, $R^{16}$, $R^{103}$, $R^{104}$, $R_{105}$, M, $Z_1$, $R_2$, M, $Z_1$, $Z_2$, Q, W, M', $R_{106}$, $R_{107}$, $R_{108}$, q, m, m', m'', r, t, $R_a$, $R_b$, $R_c$ n and the substituents of $R^9$ are as defined in formula (III).

For example, the present invention provides a compound of formula (III) wherein $R^4$ is $OR^{16}$; $R^5$ is H; L is —C(=O) or —C(=S); $R^9$ is unsubstituted or substituted aryl; and B, $R^1$, $R^{1a}$, $R^{2a}$, $R^3$, $R^{3a}$, $R^6$, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ n and the substituents of $R^9$ are as defined in formula (III).

For example, the present invention provides a compound of formula (III) wherein $R^4$ is H; $R^5$ is $OR^{16}$; L is —C(=O) or —C(=S); $R^9$ is unsubstituted or substituted heteroaryl; and B, $R^1$, $R^{1a}$, $R^2$, $R^{2a}$, $R^3$, $R^{3a}$, $R^6$, $R^{6a}$, $R^7$, $R^{7a}$, $R^{9a}$, $R^{15}$, $R^{16}$, $R_{103}$, $R_{104}$, $R_{105}$, M, $Z_1$, $R_2$, Q, W, M', $R_{106, 107}$, $R_{108}$, q, m, m', m'', r, t, $R_a$, $R_b$, $R_c$ n and the substituents of $R^9$ are as defined in formula (III).

For example, the present invention provides a compound of formula (III) wherein $R^4$ is $OR^{16}$; $R^5$ is H; L is —C(=O) or —C(=S); $R^9$ is unsubstituted or substituted heteroaryl; and B, $R^1$, $R^{1a}$, $R^2$, $R^{2a}$, $R^3$, $R^{3a}$, $R^6$, $R^{6a}$, $R^7$, $R^{7a}$, $R^{9a}$, $R^{15}$, $R^{16}$, $R_{103}$, $R_{104}$, $R_{105}$, M', $R_{106}$, $R_{107}$, $R_{108}$, q, m, m', m'', r, t, $R_a$, $R_b$, $R_c$ n and the substituents of $R^9$ are as defined in formula (III).

For example, the present invention provides a compound of formula (III) wherein $R^4$ is H; $R^5$ is $OR^{16}$; L is —C(=O) or —C(=S); $R^2$ is alkyl; $R^3$ is arylalkyl wherein the aryl moiety of the arylalkyl is substituted with 0 or one $R^{3a}$; and B, $R^1$, $R^{1a}$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$ and n are as defined in formula (III).

For example, the present invention provides a compound of formula (III) wherein $R^4$ is $OR^{16}$; $R^5$ is H; L is —C(=O) or —C(=S); $R^2$ is alkyl; $R^3$ is arylalkyl wherein the aryl moiety of the arylalkyl is substituted with 0 or one $R^{3a}$; and B, $R^1$, $R^{1a}$, $R^{3a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m''', r, t, $R_a$, $R_b$, $R_a$ and n are as defined in formula (III).

For example, the present invention provides a compound of formula (III) wherein $R^4$ is H; $R^5$ is $OR^{16}$; L is —C(=O) or C(=S); $R^2$ is alkyl; $R^3$ is arylalkyl wherein the aryl moiety of the arylalkyl is substituted with 0 or one $R^{3a}$, $R^{3a}$ is aryl or heteroaryl wherein each $R^{3a}$ is substituted with 0, 1, 2, 3 or 4 substituents independently selected from the group consisting of cyano, halo, oxo, alkyl, alkenyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), and -alkylC(O)N(alkyl)$_2$; and B, $R^1$, $R^{1a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_a$ and n are as defined in formula (III).

For example, the present invention provides a compound of formula (III) wherein $R^4$ is $OR^{16}$; $R^5$ is H; L is —C(=O) or —C(=S); $R^2$ is alkyl; $R^3$ is arylalkyl wherein the aryl moiety of the arylalkyl is substituted with 0 or one $R^{3a}$, $R^{3a}$ is aryl or heteroaryl wherein each $R^{3a}$ is substituted with 0, 1, 2, 3 or 4 substituents independently selected from the group consisting of cyano, halo, oxo, alkyl, alkenyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), and -alkylC(O)N(alkyl)$_2$; and B, $R^1$, $R^{1a}$, $R^6$, $R^{6a}$, $R^7$, $R^{7a}$, $R^9$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$ and n are as defined in formula (III).

For example, the present invention provides a compound of formula (III) wherein $R^4$ is H; $R^5$ is $OR^{16}$; L is —C(=O) or —C(=S); $R^2$ is alkyl; $R^3$ is arylalkyl wherein the aryl moiety of the arylalkyl is substituted with 0 or one $R^{3a}$ wherein $R^{3a}$ is unsubstituted or substituted aryl or unsubstituted or substituted heteroaryl; $R^9$ is unsubstituted or substituted aryl or unsubstituted or substituted heteroaryl; and B, $R^1$, $R^{1a}$, $R^6$, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^9$ are as defined in formula (III).

For example, the present invention provides a compound of formula (III) wherein $R^4$ is $OR^{16}$; $R^5$ is H; L is —C(=O) or —C(=S); $R^2$ is alkyl; $R^3$ is arylalkyl wherein the aryl moiety of the arylalkyl is substituted with 0 or one $R^{3a}$ wherein $R^{3a}$ is unsubstituted or substituted aryl or unsubstituted or substituted heteroaryl; $R^9$ is unsubstituted or substituted aryl or unsubstituted or substituted heteroaryl; and B, $R^1$, $R^{1a}$, $R^6$, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^9$ are as defined in formula (III).

For example, the present invention provides a compound of formula (III) wherein L is —C(=O) or —C(=S); $R^1$ is alkyl; $R^2$ is alkyl; $R^3$ is unsubstituted or substituted arylalkyl; $R^4$ is H; $R^5$ is $OR^{16}$; $R^6$ is unsubstituted or substituted arylalkyl; $R^7$ is —N($R_b$)C(O)$OR_a$, alkyl or heterocycle wherein each $R^7$ is unsubstituted or substituted; $R^9$ is unsubstituted or substituted aryl; and B, $R^{3a}$, $R^6$, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^3$, $R^6$, $R^7$ and $R^9$ are as defined in formula (III).

For example, the present invention provides a compound of formula (III) wherein $R^1$ is alkyl; $R^2$ is alkyl; $R^3$ is unsubstituted or substituted arylalkyl; $R^4$ is $OR^{16}$; $R^5$ is H; L is —C(=O) or —C(=S); $R^6$ is unsubstituted or substituted arylalkyl; $R^7$ is —N($R_b$)C(O)$OR_a$, alkyl or heterocycle wherein each $R^7$ is unsubstituted or substituted; $R^9$ is unsubstituted or substituted aryl; and B, $R^{3a}$, $R^6$, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m''', r, t, $R_a$, $R_b$, $R_c$, n and the substituents of $R^3$, $R^6$, $R^7$ and $R^9$ are as defined in formula (III).

For example, the present invention provides a compound of formula (III) wherein $R^1$ is methyl, $R^2$ is 1-methylpropyl, isopropyl or tert-butyl, $R^3$ is phenylmethyl wherein the phenyl moiety of the phenylmethyl is unsubstituted or substituted with one $R^{3a}$, wherein $R^{3a}$ is unsubstituted or substituted pyridyl; $R^4$ is H; $R^5$ is $OR^{16}$; L is —C(=O) or —C(=S); $R^6$ is unsubstituted or substituted phenylmethyl; $R^9$ is unsubstituted or substituted phenyl; and B, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$, $R^6$ and $R^9$ are as defined in formula (III).

For example, the present invention provides a compound of formula (III) wherein $R^1$ is methyl, $R^2$ is 1-methylpropyl, isopropyl or tert-butyl, $R^3$ is phenylmethyl wherein the phenyl moiety of the phenylmethyl is unsubstituted or substituted with one $R^{3a}$, wherein $R^{3a}$ is unsubstituted or substituted pyridyl; $R^4$ is $OR^{16}$; $R^5$ is H; L is —C(=O) or —C(=S); $R^6$ is unsubstituted or substituted phenylmethyl; $R^9$ is unsubstituted or substituted phenyl; and B, $R^{6a}$, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$, $R^6$ and $R^9$ are as defined in formula (III).

For example, the present invention provides a compound of formula (III) wherein $R^1$ is alkyl; $R^2$ is alkyl; $R^3$ is unsubstituted or substituted arylalkyl; L is 'C(=O) or —C(=S); $R^4$ is H; $R^5$ is $OR^{16}$; $R^6$ is unsubstituted or substituted arylalkyl; $R^7$ is —N($R_b$)C(O)$OR_a$, alkyl or heterocycle wherein each $R^7$ is unsubstituted or substituted; $R^9$ is unsubstituted or substituted heteroaryl; and B, $R^{3a}$, $R^{6a}$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m''', r, t, $R_a$, $R_b$, $R_c$, n and the substituents of $R^3$, $R^6$, $R^7$ and $R^9$ are as defined in formula (III).

For example, the present invention provides a compound of formula (III) wherein $R^1$ is alkyl; $R^2$ is alkyl; $R^3$ is unsubstituted or substituted arylalkyl; L is —C(=O) or —C(=S); $R^4$ is $OR^{16}$; $R^5$ is H; $R^6$ is unsubstituted or substituted arylalkyl; $R^7$ is —N($R_b$)C(O)$OR_a$, alkyl or heterocycle wherein each $R^7$ is unsubstituted or substituted; $R^9$ is unsubstituted or substituted heteroaryl; and B, $R^{3a}$, $R^{6a}$, $R^{7a}$, $R^{9a}$, $R^{15}$, $R^6$, $R_{103}$, $R_{104}$, $R_{105}$, M, $Z_1$, $Z_2$, Q, W, M', $R_{106}$, $R_{107}$, $R_{108}$ q, m, m', m''', r, t, $R_a$, $R_b$, $R_c$, n and the substituents of $R^3$, $R^6$, $R^7$ and $R^9$ are as defined in formula (III).

For example, the present invention provides a compound of formula (III) wherein $R^1$ is methyl, $R^2$ is 1-methylpropyl, isopropyl or tert-butyl, $R^3$ is phenylmethyl wherein the phenyl moiety of the phenylmethyl is unsubstituted or substituted with one $R^{3a}$, wherein $R^{3a}$ is unsubstituted or substituted pyridyl; L is —C(=O) or —C(=S); $R^4$ is H; $R^5$ is $OR^{16}$, $R^6$ is unsubstituted or substituted phenylmethyl; $R^9$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, imidazo[1,5,b]pyridyl, benzimiazolyl, benzothienyl, benzthiazolyl or indazolyl wherein each $R^9$ is unsubstituted or substituted; and B, $R^7$, $R^{7a}$, $R^{9a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, n and the substituents of $R^{3a}$, $R^6$, and $R^9$ are as defined in formula (III).

For example, the present invention provides a compound of formula (III) wherein $R^1$ is methyl, $R^2$ is 1-methylpropyl, isopropyl or tert-butyl, $R^3$ is phenylmethyl wherein the phenyl moiety of the phenylmethyl is unsubstituted or substituted with one $R^{3a}$, wherein $R^{3a}$ is unsubstituted or substituted pyridyl; L is —C(=O) or —C(=S); $R^4$ is $OR^{16}$; $R^5$ is H, $R^6$ is unsubstituted or substituted phenylmethyl; $R^9$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, imidazo[1,5,b]pyridyl, benzimiazolyl, benzothienyl, benzthiazolyl or indazolyl wherein each $R^9$ is unsubstituted or substituted; and B, $R^7$, $R^{7a}$, $R^{9a}$, $R^{15}$, $R^{16}$, $R_{103}$, $R_{104}$, $R_{105}$, M, $Z_1$, $Z_2$, $R_{106}$, $R_{107}$, $R_{108}$, q, m, m', m", r, t, $R_a$, $R_b$, $R_c$, n and the substituents of $R^{3a}$, $R^6$, and $R^9$ are as defined in formula (III).

For example, the present invention provides a compound of formula (III) wherein $R^1$ is alkyl; $R^2$ is alkyl; $R^3$ is unsubstituted or substituted arylalkyl; L is —C(=O) or —C(=S); $R^4$ is H; $R^5$ is $OR^{16}$; $R^6$ is unsubstituted or substituted arylalkyl; $R^7$ is —N($R_b$)C(O)$OR_a$, alkyl or heterocycle wherein each $R^7$ is unsubstituted or substituted; $R^9$ is unsubstituted or substituted heteroaryl; each $R_{104}$ is independently hydrogen or alkyl; $Z_1$ and $Z_2$ are O, Q is O, W is P; and B, $R^{3a}$, $R^{6a}$, $R^{7a}$, $R^{9a}$, $R^{15}$, $R^{16}$, $R_{103}$, $R_{105}$, M, M', $R_{106}$, $R_{107}$, $R_{108}$, q, m, m', m", r, t, $R_a$, $R_b$, $R_c$, n and the substituents of $R^3$, $R^6$, $R^7$ and $R^9$ are as defined in formula (III).

For example, the present invention provides a compound of formula (III) wherein $R^1$ is alkyl; $R^2$ is alkyl; $R^3$ is unsubstituted or substituted arylalkyl; L is —C(=O) or —C(=S); $R^4$ is $OR^{16}$; $R^5$ is H; $R^6$ is unsubstituted or substituted arylalkyl; $R^7$ is —N($R_b$)C(O)$OR_a$, alkyl or heterocycle wherein each $R^7$ is unsubstituted or substituted; $R^9$ is unsubstituted or substituted heteroaryl; each $R_{104}$ is independently hydrogen or alkyl; $Z_1$ and $Z_2$ are O, Q is O, W is P; and B, $R^{3a}$, $R^{6a}$, $R^{7a}$, $R^{9a}$, $R^{15}$, $R^{16}$, $R_{103}$, $R_{105}$, M, M', $R_{106}$, $R_{107}$, $R_{108}$, q, m, m', m", r, t, $R_a$, $R_b$, $R_c$, n and the substituents of $R^3$, $R^6$, $R^7$ and $R^9$ are as defined in formula (III).

For example, the present invention provides a compound of formula (III) wherein $R^1$ is methyl, $R^2$ is I-methylpropyl, isopropyl or tert-butyl, $R^3$ is phenylmethyl wherein the phenyl moiety of the phenylmethyl is unsubstituted or substituted with one $R^{3a}$, wherein $R^{3a}$ is unsubstituted or substituted pyridyl; L is —C(=O) or —C(=S); $R^4$ is H; $R^5$ is $OR^{16}$, $R^6$ is phenylmethyl substituted with 0 or one $R^{6a}$; $R^9$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, imidazo[1,5,b]pyridyl, benzimiazolyl, benzothienyl, benzthiazolyl or indazolyl wherein each $R^9$ is unsubstituted or substituted; each $R_{104}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_i$ and $Z_2$ are O, Q is O, W is P; and B, $R^7$, $R^{7a}$, $R^{9a}$, $R^{15}$, $R^{16}$, $R_{103}$, M', $R_{106}$, $R_{107}$, $R_{108}$, q, m, m', m", r, t, $R_a$, $R_b$, $R_c$, n and the substituents of $R^{3a}$, $R^{6a}$, M, $R^7$ and $R^9$ are as defined in formula (III).

For example, the present invention provides a compound of formula (III) wherein $R^1$ is methyl, $R^2$ is 1-methylpropyl, isopropyl or tert-butyl, $R^3$ is phenylmethyl wherein the phenyl moiety of the phenylmethyl is unsubstituted or substituted with one $R^{3a}$, wherein $R^{3a}$ is unsubstituted or substituted pyridyl; L is —C(=O) or —C(=S); $R^4$ is $OR^{16}$, $R^5$ is H; $R^6$ is phenylmethyl substituted with 0 or one $R^{6a}$; $R^9$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, imidazo[1,5,b]pyridyl, benzimiazolyl, benzothienyl, benzthiazolyl or indazolyl wherein each $R^9$ is unsubstituted or substituted; each $R_{104}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_i$ and $Z_2$ are O, Q is O, W is P; and B, $R^7$, $R^{7a}$, $R^{9a}$, $R^{15}$, $R^{16}$, $R_{107}$, $R_{108}$, q, m, m', m", r, t, $R_a$, $R_b$, $R_c$, n and the substituents of $R^3$, $R^{6a}$, M, $R^7$ and $R^9$ are as defined in formula (III).

Exemplary compounds of the present invention of formula (III) include, but not limited to, the following:

methyl(1S)-1-{[(((1S,3S,4S)-1-benzyl-3-hydroxy-4-{[(2S)-3-methyl-2-(2-oxo-3-{[2-(2-pyridinyl)-1,3-thiazol-4-yl]methyl}-1-imidazolidinyl)pentanoyl]amino}-5-phenylpentyl)amino]carbonyl}-2,2-dimethylpropylcarbamate;

methyl(1S)-1-({[(1S,3S,4S)-1-benzyl-3-hydroxy-4-({(2S)-3-methyl-2-[2-oxo-3-)4-quinolinylmethyl)-1-imidazolidinyl]pentanoyl}amino)-5-phenylpentyl]amino}carbonyl)-2,2-dimethylpropylcarbamate;

methyl(1S)-1-({[(1S,3S,4S)-1-benzyl-3-hydroxy-4-({(2S )-3-methyl-2-[2-oxo-3-(4-quinolinylmethyl)-1-imidazolidinyl]pentanoyl}amino)-5-phenylpentyl]amino}carbonyl)-2-methylbutylcarbamate;

methyl(1S)-1-{[((1S,3S,4S)-1-benzyl-3-hydroxy-4-{[(2S)-2-(3-{[2-(methoxymethyl)-1,3-thiazol-4-yl]methyl}-2-oxo-1-imidazolidinyl)-3,3-dimethylbutanoyl]amino}-5-phenylpentyl)amino]carbonyl}-2,2-dimethylpropylcarbamate;

methyl(1S)-1-[({(1S,3S,4S)-1-benzyl-3-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate;

methyl(1S)-1-[({(1S,2S,4S)-1-benzyl-2-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate;

methyl(1S)-1-[({(1S,2S,4S)-1-benzyl-2-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2-methylbutylcarbamate;

methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-phenylpentyl}amino)carbonyl]-2,2-dimethylpropylcarbamate;

methyl(1S)-1-[({(1S,2S,4S)-1-benzyl-2-hydroxy-4-[((2S)-3-methyl-2-{3-[(2-methyl-1,3-thiazol-5-yl)methyl]-2-oxo-1-imidazolidinyl}pentanoyl)amino]-5-phenylpentyl}amino)carbonyl]-2,2-dimethylpropylcarbamate;

methyl(1S)-1-{[((1S,2S,4S)-1-benzyl-2-hydroxy-4-{[(2S)-3-methyl-2-(2-oxo-3-{[2-(3-pyridinyl)-1,3-thiazol-4-yl]methyl}-1-imidazolidinyl)pentanoyl]amino}-5-phenylpentyl)amino]carbonyl}-2,2-dimethylpropylcarbamate;

methyl(1S)-1-[({(1S,2S,4S)-1-benzyl-2-hydroxy-4-[((2S)-3-methyl-2-{3-[(6-methyl-3-pyrindinyl)methyl]-2- oxo-1-imidazolidinyl}pentanoyl)amino]-5-phenylpentyl}amino)carbonyl]-2,2-dimethylpropylcarbamate;

methyl(1S)-1-[({(1S,2S,4S)-1-benzyl-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenylpentyl}amino)carbonyl]-2,2-dimethylpropylcarbamate;

methyl(1S)-1-[({(1S,2S,4S)-1-benzyl-2-hydroxy-4-[((2S)-3-methyl-2-{3-[(2-methyl-3-pyridinyl)methyl]-2-oxo-1-imidazolidinyl}pentanoyl)amino]-5-phenylpentyl}amino)carbonyl]-2,2-dimethylpropylcarbamate;

methyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-{[((1S,2S,4S)-1-benzyl-2-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenylpentyl)amino]carbonyl}-2,2-dimethylpropylcarbamate;

methyl(1S)-1-[({(1S,3S,4S)-3-hydroxy-4-[((2S)-3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl(1S)-1-{[((1S,2S,4S)-1-benzyl-4-{[(2S)-3,3-dimethyl-2-(2-oxo-3-{[2-(3-pyridinyl)-1,3-thiazol-4-yl]methyl}-1-imidazolidinyl)butanoyl]amino}-2-hydroxy-5-phenylpentyl)amino]carbonyl}-2,2-dimethylpropylcarbamate;

methyl(1S)-1-({[(1S,2S,4S)-1-benzyl-4-({(2S)-3,3-dimethyl-2-[2-oxo-3-(3-pyridinylmethyl)-1-imidazolidinyl]butanoyl}amino)-2-hydroxy-5-phenylpentyl]amino}carbonyl)-2,2-dimethylpropylcarbamate;

methyl(1S)-1-[({(1S,3S,4S)-3-hydroxy-4-[((2S)-3-methyl-2-{3-[(2-methyl-3-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-phenylpentyl}amino)carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate;

methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate;

methyl(1S)-1-[({(1S,2S,4S)-2-hydroxy-4-[((2S)-3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl(1S)-1-[({(1R,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-4-{[(2S)-3,3-dimethyl-2-(2-oxo-3-{[2-(3-pyridinyl)-1,3-thiazol-4-yl]methyl}-1-imidazolidinyl)butanoyl]amino}-3-hydroxy-5-phenyl-1-[4-(2-pyridinyl)benzyl]pentyl}amino)carbonyl]-2,2-dimethylpropylcarbamate;

methyl(1S)-1-[({(1S,2S,4S)-4-{[(2S)-3,3-dimethyl-2-(2-oxo-3-{[2-(3-pyridinyl)-1,3-thiazol-4-yl]methyl}-1-imidazolidinyl)butanoyl]amino}-2-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-3-hydroxy-4-({(2S)-2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl(1S)-1-[({(1S,2S,4S)-2-hydroxy-4-({(2S)-2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl(1S)-1-[({(1S,3S,4S)-4-({(2S)-3,3-dimethyl-2-[2-oxo-3-(4-quinolinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl(1S)-1-[({(1S,2S,4S)-4-({(2S)-3,3-dimethyl-2-[2-oxo-3-(4-quinolinylmethyl)-1-imidazolidinyl]butanoyl}amino)-2-hydroxy-5-phenyl-1-[4-(2-pyridinyl)benzyl]pentyl}amino)carbonyl]-2,2-dimethylpropylcarbamate;

methyl(1S)-1-[({(1S,2S,4S)-2-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate;

methyl(1S)-1-[({(1S,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-2-pyridinyl)benzyl]pentyl}amino)carbonyl]-2,2-dimethylpropylcarbamate;

methyl(1S)-1-[({(1R,3S,4S)-4-{[(2S)-3,3-dimethyl-2-(2-oxo-3-{[2-(3-pyridinyl)-1,3-thiazol-4-yl]methyl}-1-imidazolidinyl)butanoyl]amino}-3-hydroxy-5-phenyl-1-[4-(2-pyridinyl)benzyl]pentyl}amino)carbonyl]-2,2-dimethylpropylcarbamate;

methyl(1S)-1-[({(1R,3S,4S)-3-hydroxy-4-{[(2S)-2-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate;

methyl(1S)-1-[({(1R,3S,4S)-4-({(2S)-3,3-dimethyl-2-[2-oxo-3-(4-quinolinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate;

methyl(1S)-1-[({(1R,3S,4S)-4-[((2S)-3,3-dimethyl-2-{3-[(1-methyl-1H-benzimidazol-2-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1R,3S,4S)-4-[((2S)-3,3-dimethyl-2-{3-[(2-methyl-1,3-thiazol-4-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-4-({(2S)-3,3-dimethyl-2-[3-(2-methylbenzyl)-2-oxo-1-imidazolidinyl]

butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1S,3S,4S)-4-({(2S)-3,3-dimethyl-2-[3-(3-methylbenzyl)-2-oxo-1-imidazolidinyl] butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1S,2S,4S)-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-2-pyridinyl)benzyl]-5-phenylpentyl}amino)carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate;

methyl(1S)-1-[({(1S,2S,4S)-4-{[(2S)-2-(3-benzyl-2-oxo-1-imidazolidinyl)-3,3-dimethylbutanoyl]amino}-2-hydroxy-5-phenyl-1-[4-(3-pyridinyl)benzyl]pentyl}amino) carbonyl]-2,2-dimethylpropylcarbamate;

methyl(1S)-1-[({(1S,3S,4S)-3-hydroxy-4-({(2S)-2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl(1S)-1-[({(1R,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino) carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(4-pyridinyl)benzyl]pentyl}amino)carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate;

methyl(1S)-1-[({(1S,3S,4S)-3-hydroxy-4-({(2S)-2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl(1S)-1-[({(1R,3S,4S)-4-({(2S)-3,3-dimethyl-2-[3-(2-methylbenzyl)-2-oxo-1-imidazolidinyl] butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1R,3S,4S)-4-({(2S)-3,3-dimethyl-2-[3-(3-methylbenzyl)-2-oxo-1-imidazolidinyl] butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1R,3S,4S)-3-hydroxy-4-({(2S)-2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl(1S)-1-[({(1R,3S,4S)-3-hydroxy-4-({(2S)-2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate;

methyl(1S)-1-[({(1S,2S,4S)-4-[((2S)-3,3-dimethyl-2-{3-[(6-methyl)-2-oxo-1-imidazolidinyl}butanoyl)amino]-2-hydroxy-1-[4-(4-methyl-2-pyridinyl)benzyl]-5-phenylpentyl}amino)carbonyl]-2,2-dimethylpropylcarbamate;

methyl(1S)-1-[({(1S,2S,4S)-4-{[(2S)-2-(3-benzyl-2-oxo-1-imidazolidinyl)-3,3-dimethylbutanoyl]amino}-2-hydroxy-5-phenyl-i-[4-(2-pyridinyl)benzyl]pentyl}amino)carbonyl]-2,2-dimethylpropylcarbamate;

methyl(1S)-1-[({(1S,3S,4S)-4-[((2S)-3,3-dimethyl-2-{3-[(2-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-4-[((2S)-3,3-dimethyl-2-{3-[(6-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-4-({(2S)-3,3-dimethyl-2-[2-oxo-3-(3-pyridinylmethyl)-1-imidazolidinyl] butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1S,3S,4S)-4-({(2S)-3,3-dimethyl-2-[2-oxo-3-(4-pyridinylmethyl)-1-imidazolidinyl] butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1S,3S,4S)-4-({(2S)-3,3-dimethyl-2-[2-oxo-3-(2-pyridinylmethyl)-1-imidazolidinyl] butanoyl}amino)-3-hydroxy-5-phenyl-1-[4-(2-pyridinyl) benzyl]pentyl}amino)carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-3-pyridinyl)benzyl]-5-phenylpentyl}amino)carbonyl]-2,2-dimethylpropylcarbamate;

methyl(1S)-1-[({(1S,2S,4S)-4-[((2S)-3,3-dimethyl-2-{3-[(2-methyl-1,3-thiazol-4-yl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate;

methyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2-methylbutylcarbamate;

methyl(1S)-1-[({(1S,3S,4S)-4-{[(2S)-2-(3-benzyl-2-oxo-1-imidazolidinyl)-3,3-dimethylbutanoyl]amino}-3-hydroxy-1-[4-(5-methyl-2-pyridinyl)benzyl]-5-phenylpentyl}amino)carbonyl]-2,2-dimethylpropylcarbamate;

methyl(1S)-1-[({(1S,2S,4R)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate;

methyl(1S)-1-[({(1S,2S,4S)-2-hydroxy-4-[((2S)-3-methyl-2-{3-[(1-methyl-1H-benzimidazol-2-yl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate;

methyl(1S)-1-[({(1S,2S,4S)-2-hydroxy-4-[((2S)-2-{3-[(2-isopropyl-1,3-thiazol-4-yl)methyl]-2-oxo-1-imidazolidinyl}-3-methylpentanoyl)amino]-5-phenyl-1-[4-(2-py-
ridinyl)benzyl]pentyl}amino)carbonyl]-2,2-
dimethylpropylcarbamate;

methyl(1S)-1-[({(1R,3S,4S)-3-hydroxy-4-[((2S)-3-me-
thyl-2-{3-[(6-methyl-2-pyridinyl)methyl]-2-oxo-1-
imidazolidinyl}pentanoyl)amino]-5-phenyl-1-[4-(2-pyridi-
nyl)benzyl]pentyl}amino)carbonyl]-2,2-
dimethylpropylcarbamate;

methyl(1S)-1-[({(1S,3S,4S)-4-[((2S)-3,3-dimethyl-2-{3-
[(1-methyl-1H-benzimidazol-2-yl)methyl]-2-oxo-1-
imidazolidinyl}butanoyl)amino]-3-hydroxy-5-phenyl-1-[4-
(2-pyridinyl)benzyl]pentyl}amino)carbonyl]-2,2-
dimethylpropylcarbamate;

methyl(1S)-1-[({(1S,2S,4S)-4-[((2S)-3,3-dimethyl-2-{3-
[(1-methyl-1H-benzimidazol-2-yl)methyl]-2-oxo-1-
imidazolidinyl}butanoyl)amino]-2-hydroxy-5-phenyl-1-[4-
(2-pyridinyl)benzyl]pentyl}amino)carbonyl]-2,2-
dimethylpropylcarbamate;

methyl(1S)-1-[({(1S,3S,4S)-3-hydroxy-4-[((2S)-2-{3-
[(2-isopropyl-1,3-thiazol-4-yl)methyl]-2-oxo-1-imidazo-
lidinyl}-3,3-dimethylbutanoyl)amino]-5-phenyl-1-[4-(2-py-
ridinyl)benzyl]pentyl}amino)carbonyl]-2,2-
dimethylpropylcarbamate;

methyl(1S)-1-[({(1S,2S,4S)-2-hydroxy-4-[((2S)-2-{3-
[(2-isopropyl-1,3-thiazol-4-yl)methyl]-2-oxo-1-imidazo-
lidinyl}-3,3-dimethylbutanoyl)amino]-5-phenyl-1-[4-(2-py-
ridinyl)benzyl]pentyl}amino)carbonyl]-2,2-
dimethylpropylcarbamate;

methyl(1S)-1-[({(1S,3S,4S)-4-[((2S)-3,3-dimethyl-2-{3-
[(2-methyl-1,3-thiazol-4-yl)methyl]-2-oxo-1-
imidazolidinyl}butanoyl)amino]-3-hydroxy-5-phenyl-1-[4-
(2-pyridinyl)benzyl]pentyl}amino)carbonyl]-2,2-
dimethylpropylcarbamate;

methyl(1S)-1-[({(1S,2S,4S)-4-[((2S)-3,3-dimethyl-2-{3-
[(2-methyl-1,3-thiazol-4-yl)methyl]-2-oxo-1-
imidazolidinyl}butanoyl)amino]-2-hydroxy-5-phenyl-1-[4-
(2-pyridinyl)benzyl]pentyl}amino)carbonyl]-2,2-
dimethylpropylcarbamate;

methyl(1S)-1-[({(1S,3R,4S)-4-[((2S)-3,3-dimethyl-2-{3-
[(6-methyl-2-pyridinyl)methyl]-2-oxo-1-
imidazolidinyl}butanoyl)amino]-3-hydroxy-5-phenyl-1-[4-
(2-pyridinyl)benzyl]pentyl}amino)carbonyl]-2,2-
dimethylpropylcarbamate;

methyl(1S)-1-[({(1R,3R,4S)-4-[((2S)-3,3-dimethyl-2-{3-
[(6-methyl-2-pyridinyl)methyl]-2-oxo-1-
imidazolidinyl}butanoyl)amino]-3-hydroxy-5-phenyl-1-[4-
(2-pyridinyl)benzyl]pentyl}amino)carbonyl]-2,2-
dimethylpropylcarbamate;

methyl(1S)-1-[({(1S,3S,4S)-4-{[(2S)-2-(3-benzyl-2-oxo-
1-imidazolidinyl)-3,3-dimethylbutanoyl]amino}-3-hy-
droxy-5-phenyl-1-[4-(2-pyridinyl)benzyl]pentyl}amino)
carbonyl]-2,2-dimethylpropylcarbamate; pyridinyl)methyl]-
2-oxo-1-imidazolidinyl}butanoyl)amino]-3-hydroxy-1-[4-
(6-methoxy-2-pyridinyl)benzyl]-5-phenylpentyl}amino)
carbonyl]-2,2-dimethylpropylcarbamate;

methyl(1S)-1-[({(1S,3S,4S)-4-{[(2S)-2-(3-benzyl-2-oxo-
1-imidazolidinyl)-3,3-dimethylbutanoyl]amino}-3-hy-
droxy-1-[4-(6-methoxy-2-pyridinyl)benzyl]-5-
phenylpentyl}amino)carbonyl]-2,2-
dimethylpropylcarbamate;

methyl(1S)-1-[({(1S,3S,4S)-4-[((2S)-2-{3-[(6-tert-butyl-
2-pyridinyl)methyl]-2-oxo-1-imidazolidinyl}-3,3-dimeth-
ylbutanoyl)amino]-3-hydroxy-5-phenyl-1-[4-(2-pyridinyl)
benzyl]pentyl}amino)carbonyl]-2,2-
dimethylpropylcarbamate;

methyl(1S)-1-[({(1R,3S,4S)-3-hydroxy-4-[((2S)-2-{3-
[(6-isopropyl-2-pyridinyl)methyl]-2-oxo-1-imidazolidinyl}-
3,3-dimethylbutanoyl)amino]-5-phenyl-1-[4-(2-pyridinyl)
benzyl]pentyl}amino)carbonyl]-2,2-
dimethylpropylcarbamate;

methyl(1S)-1-[({(1R,3S,4S)-4-[((2S)-2-{3-[(6-tert-butyl-
2-pyridinyl)methyl]-2-oxo-1-imidazolidinyl}-3,3-dimeth-
ylbutanoyl)amino]-3-hydroxy-5-phenyl-1-[4-(2-pyridinyl)
benzyl]pentyl}amino)carbonyl]-2,2-
dimethylpropylcarbamate;

methyl(1S)-1-[({(1S,2S,4S)-4-{[(2S)-2-(3-benzyl-2-oxo-
1-imidazolidinyl)-3,3-dimethylbutanoyl]amino}-2-hy-
droxy-1-[4-(6-methoxy-2-pyridinyl)benzyl]-5-
phenylpentyl}amino)carbonyl]-2,2-
dimethylpropylcarbamate;

methyl(1S)-1-[({(1S,2S,4S)-4-[((2S)-3,3-dimethyl-2-{3-
[(6-methyl]-2-oxo-1-imidazolidinyl}butanoyl)amino]-2-hy-
droxy-1-[4-(6-methoxy-2-pyridinyl)benzyl]-5-
phenylpentyl}amino)carbonyl]-2,2-
dimethylpropylcarbamate;

methyl(1S)-1-[({(1S,3S,4S)-4-({(2S)-2-[3-(2-aminoben-
zyl)-2-oxo-1-imidazolidinyl]-3,3-
dimethylbutanoyl}amino)-3-hydroxy-5-phenyl-1-[4-(2-py-
ridinyl)benzyl]pentyl}amino)carbonyl]-2,2-
dimethylpropylcarbamate;

methyl(1S)-1-[({(1S,3S,4S)-4-({(2S)-2-[3-(4-aminoben-
zyl)-2-oxo-1-imidazolidinyl]-3,3-
dimethylbutanoyl}amino)-3-hydroxy-5-phenyl-1-[4-(2-py-
ridinyl)benzyl]pentyl}amino)carbonyl]-2,2-
dimethylpropylcarbamate;

methyl(1S)-1-[({(1S,3S,4S)-4-({(2S)-2-[3-(3-aminoben-
zyl)-2oxo-1-imidazolidinyl}-3,3-dimethylbutanoyl}amino)-
3-hydroxy-5-phenyl-1-[4-(2-pyridinyl)benzyl]
pentyl}amino)carbonyl]-2,2-dimethylpropylcarbamate;

methyl(1S)-1-[({(1S,3S,4S)-4-[((2S)-3,3-dimethyl-2-{3-
[(6-methyl-2-pyridinyl)methyl]-2-oxo-1-
imidazolidinyl}butanoyl)amino]-3-hydroxy-1-[4-(5-me-
thyl-2-pyridinyl)benzyl]-5-phenylpentyl}amino)carbonyl]-
2,2-dimethylpropylcarbamate;

methyl(1S)-1-[({(1R,3S,4S)-4-[((2S)-3,3-dimethyl-2-{3-
[(6-methyl-2-pyridinyl)methyl]-2-oxo-1-
imidazolidinyl}butanoyl)amino]-3-hydroxy-1-[4-(5-me-
thyl-2-pyridinyl)benzyl]-5-phenylpentyl}amino)carbonyl]-
2,2-dimethylpropylcarbamate;

methyl(1S)-1-[({(1S,3S,4S)-3-hydroxy-4-[((2S)-2-{3-
[(6-isopropyl-2-pyridinyl)methyl]-2-oxo-1-imidazolidinyl}-
3,3-dimethylbutanoyl)amino]-5-phenyl-1-[4-(2-pyridinyl)
benzyl]pentyl}amino)carbonyl]-2,2-
dimethylpropylcarbamate;

methyl(1S)-1-[({(1S,3S,4S)-1-benzyl-4-[((2S)-3,3-dim-
ethyl-2-{3-[(6-methyl-2-pyridinyl)methyl]-2-oxo-1-
imidazolidinyl}butanoyl)amino]-3-hydroxy-5-[4-(2-pyridi-
nyl)phenyl]pentyl}amino)carbonyl]-2,2-
dimethylpropylcarbamate;

methyl(1S)-1-({[(1 S,2S,4S)-1-benzyl-2-hydroxy-4-
({(2S)-3-methyl-2-[2-oxo-3-(4-quinolinylmethyl)-1-imida-
zolidinyl]pentanoyl}amino)-5-phenylpentyl]
amino}carbonyl)-2,2-dimethylpropylcarbamate;

methyl(1S)-1-({[(1S,3S,4S)-4({(2S)-2-[3-(2-fluoroben-
zyl)-2-oxoimidazolidin-1-yl]-3,3-
dimethylbutanoyl}amino)-3-hydroxy-5-phenyl-1-(4-pyri-
din-2-ylbenzyl)pentyl]amino}carbonyl)-2,2-
dimethylpropylcarbamate;

methyl(1S)-1-({[(1S,3S,4S)-4({(2S)-2-[3-(4-fluoroben-
zyl)-2-oxoimidazolidin-1-yl]-3,3-
dimethylbutanoyl}amino)-3-hydroxy-5-phenyl-1-(4-pyri-
din-2-ylbenzyl)pentyl]amino}carbonyl)-2,2-
dimethylpropylcarbamate;

methyl(1S)-1-({[(1S,3S,4S)-4-({(2S)-2-[3-(3-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-4-[((2S)-3,3-dimethyl-2-{2-oxo-3-[2-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-4-[((2S)-3,3-dimethyl-2-{2-oxo-3-[4-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-4-[((2S)-3,3-dimethyl-2-{2-oxo-3-[2-oxo-3-[3-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-4-({(2S)-2-[3-(2-amino-3-methylbenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-({(2S)-2-[3-(3-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-({(2S)-2-[3-(4-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-({(2S)-2-[3-(2-hydroxybenzyl oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate;

methyl(1S)-1-({[(1R,3S,4S)-4-{[(2S)-3,3-dimethyl-2-(2-oxoimidazolidin-1-yl)butanoyl]amino}-3-hydroxy-5-phenyl-1-(4-pyridin-2-ylbenzyl)pentyl]amino}carbonyl)-2,2-dimethylpropylcarbamate;

methyl(1S)-1-({[(1R,3S,4S)-3-hydroxy-4-{[(2S,3S)-3-methyl-2-(2-oxoimidazolidin-1-yl)pentanoyl]amino}-5-phenyl-1-(4-pyridin-2-ylbenzyl)pentyl]amino}carbonyl)-2,2-dimethylpropylcarbamate;

methyl(1S)-1-({[(1R,3S,4S)-4-{[(2S)-2-(1,1-dioxido-1,2,5-thiadiazolidin-2-yl)-3,3-dimethylbutanoyl]amino}-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-4-{[(2S)-2-(3-benzyl-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate;

methyl(1S)-1-({[(1R,3S,4S)-4-{[(2S)-2-(3-{[6-(1-hydroxy-1-methylethyl)pyridin-2-yl]methyl}-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate;

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl (2S)-2-aminopropanoate;

methyl(1S)-1-({[(1R,3S,4S)-4{(2S)-3,3-dimethyl-2-[3-({6-[1-methyl-1-(phosphonooxy)ethyl]pyridin-2-yl}methyl)-2-oxoimidazolidin-1-yl]butanoyl}amino)-3-hydroxy-5-phenyl-1-(4-pyridin-2-ylbenzyl)pentyl]amino}carbonyl)-2,2-dimethylpropylcarbamate;

(3S,5S,8S)-3(1S)-1-{[(2S)-2-(3-benzyl-2-oxoimidazolidin-1-yl)-3,3-dimethylbutanoyl]amino}-2-phenylethyl)-8-tert-butyl-7,10-dioxo-5-(4-pyridin-2-ylbenzyl)-2,11-dioxa-6,9-diazadodec-1-yl (dimethylamino)acetate;

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl (phosphonooxy)methyl carbonate;

(5S,7S,10S)-54(1S)-1-{[(2S)-2-(3-benzyl-2-oxoimidazolidin-1-yl)-3,3-dimethylbutanoyl]amino}-2-phenylethyl)-10-tert-butyl-3,9,12-trioxo-7-(4-pyridin-2-ylbenzyl)-2,4,13-trioxa-8,11-diazatetradec-1-yl (dimethylamino)acetate;

(5S,8S,10S)-10-((1S)-1-{[(2S)-2-(3-benzyl-2-oxoimidazolidin-1-yl)-3,3-dimethylbutanoyl]amino}-2-phenylethyl)-5-tert-butyl-3,6,1 2-trioxo-8-(4-pyridin-2-ylbenzyl)-2,11-dioxa-4,7-diazapentadecan-15-oic acid;

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl {[ethoxy(hydroxy)phosphoryl]oxy}methyl carbonate;

methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10-hydroxy-10-oxido-2-oxo-4-(4-pyridin-2-ylbenzyl)-7,9,11-trioxa-3-aza-10-phosphatridec-1-ylcarbamate;

methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10,10-dihydroxy-10-oxido-2-oxo-4-(4-pyridin-2-ylbenzyl)-7,9-dioxa-3-aza-10-phosphadec-1-ylcarbamate;

methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10,10-dihydroxy-8-methyl-10-oxido-2-oxo-4-(4-pyridin-2-ylbenzyl)-7,9-dioxa-3-aza-10-phosphadec-1-ylcarbamate; and methyl(1S,4S,5S)-4-benzyl-1-tert-butyl-5-{(2S)-2-[((2S)-3,3-dimethyl-2-{3-[(6-methylpyridin-2-yl)methyl]-2-oxoimidazolidin-1-yl}butanoyl)amino]-3-phenylpropyl}-9,9-dihydroxy-9-oxido-2-oxo-6,8-dioxa-3-aza-9-phosphanon-1-ylcarbamate;

or a pharmaceutically acceptable salt form, prodrug, or stereoisomer thereof.

In a fourth embodiment, the present invention provides a compound of formula (IV)

(IV)

or a pharmaceutically acceptable salt form, prodrug or a stereoisomer thereof, wherein:

X is O, S or NH;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C (O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and R$^{1a}$;

R$^{1a}$ is cycloalkyl, cycloalkenyl, heterocycle, aryl or heteroaryl; wherein each R$^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^2$ is alkyl, alkenyl, alkynyl, cycloalkyl, cycloalkenyl, heterocycle, aryl or heteroaryl wherein each R$^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$—N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{2a}$;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^4$ is H and R$^5$ is OR$^{16}$; or
R$^5$ is H and R$^4$ is OR$^{16}$; or
R$^4$ and R$^5$ are —OR$^{16}$;

R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{16}$ is hydrogen or $R^{15}$;

$R^{15}$ is

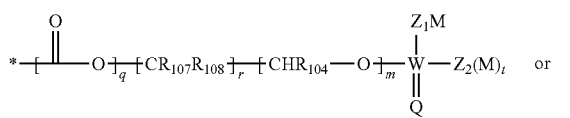

(XVI)

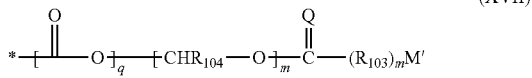

(XVII)

$R_{103}$ is C(R$_{105}$)$_2$, O or —N(R$_{105}$);

$R_{104}$ is hydrogen, alkyl, haloalkyl, alkoxycarbonyl, aminocarbonyl, alkylaminocarbonyl or dialkylaminocarbonyl;

each M is independently selected from the group consisting of H, —N(R$_{105}$)$_2$, alkyl, alkenyl, and R$_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, Z, and Z$_2$ are —CH$_2$;

Z$_1$ is CH$_2$, O, S, —N(R$_{105}$), or, when M is absent, H;

Z$_2$ is CH$_2$, O, S or —N(R$_{105}$);

Q is O or S;

W is P or S; wherein when W is S, Z$_1$ and Z$_2$ are not S;

M' is H, alkyl, alkenyl or R$_{106}$; wherein 1 to 4 —CH$_2$ radicals of the alkyl or alkenyl is optionally replaced by a heteroatom group selected from O, S, S(O), SO$_2$, or N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

each R$_{107}$ and R$_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

R$_a$ and R$_b$ at each occurrence are independently selected from the group consisting of hydrogen, alkyl, alkenyl, alkynyl, cycloalkyl, aryl, heteroaryl and heterocycle; wherein each R$_a$ and R$_b$, at each occurrence, is independently substituted with 0, 1, 2 or 3 substituents independently selected from the group consisting of cyano, nitro, halo, oxo, hydroxy, alkoxy, alkyl, alkenyl, alkynyl, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$; and R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$.

For example, the present invention provides a compound of formula (IV) wherein X is O; R$^4$ is H; R$^5$ is OR$^{16}$; and R$^1$, R$^{1a}$, R$^2$, R$^{2a}$, R$^3$, R$^{3a}$, R$^6$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, and R$_c$ are as defined in formula (IV).

For example, the present invention provides a compound of formula (IV) wherein X is O; R$^4$ is OR$^{16}$; R$^5$ is H; and R$^1$, R$^{1a}$, R$^2$, R$^{2a}$, R$^3$, R$^{3a}$, R$^6$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, and R$_c$ are as defined in formula (IV).

For example, the present invention provides a compound of formula (TV) wherein X is O; R$^4$ is H; R$^5$ is OR$^{16}$; R$^2$ is alkyl; and R$^1$, R$^{1a}$, R$^3$, R$^{3a}$, R$^6$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, and R$_c$ are as defined in formula (IV).

For example, the present invention provides a compound of formula (IV) wherein X is O; R$^4$ is OR$^{16}$; R$^5$ is H; R$^2$ is alkyl; and R$^1$, R$^{1a}$, R$^3$, R$^{3a}$, R$^6$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, and R$_c$ are as defined in formula (IV).

For example, the present invention provides a compound of formula (IV) wherein X is O; R$^4$ is H; R$^5$ is OR$^{16}$; R$^2$ is alkyl and R$^3$ is arylalkyl wherein the aryl moiety of the arylalkyl is unsubstituted or substituted; and R$^1$, R$^{1a}$, R$^{3a}$, R$^6$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of the aryl moiety of the arylalkyl of R$^3$ are as defined in formula (IV).

For example, the present invention provides a compound of formula (IV) wherein X is O; R$^4$ is OR$^{16}$; R$^5$ is H; R$^2$ is alkyl and R$^3$ is arylalkyl wherein the aryl moiety of the arylalkyl is unsubstituted or substituted; and R$^1$, R$^{1a}$, R$^{3a}$, R$^6$, R$^{6a}$, R$^7$, R$^{7a}$, R$^{10}$, R$^{10a}$, R$^{15}$, R$^{16}$, R$_{103}$, R$_{104}$, M, Z$_1$, Z$_2$, Q, W, M', R$_{106}$, R$_{107}$, R$_{108}$, q, m, m', m'', r, t, R$_a$, R$_b$, R$_c$ and the substituents of the aryl moiety of the arylalkyl of R$^3$ are as defined in formula (IV).

For example, the present invention provides a compound of formula (IV) wherein X is O; R$^4$ is H; R$^5$ is OR$^{16}$; R$^2$ is alkyl, R$^3$ is arylalkyl wherein the aryl moiety of the arylalkyl is unsubstituted or substituted with one R$^{3a}$, and R$^{3a}$ is aryl which is unsubstituted or substituted or heteroaryl which is unsubstituted or substituted; and R$^1$, R$^{1a}$, R$^6$, R$^{6a}$, R$^7$, R$_{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^{3a}$ are as defined in formula (IV).

For example, the present invention provides a compound of formula (IV) wherein X is O; R$^4$ is OR$^{16}$; R$^5$ is H; R$^2$ is alkyl, R$^3$ is arylalkyl wherein the aryl moiety of the arylalkyl is unsubstituted or substituted with one R$^{3a}$, and R$^{3a}$ is unsubstituted or substituted aryl or unsubstituted or substituted heteroaryl; and R$^1$, R$^{1a}$, R$^6$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^{3a}$ are as defined in formula (IV).

For example, the present invention provides a compound of formula (IV) wherein X is O; R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, and R$^{3a}$ is aryl or heteroaryl wherein each R$^{3a}$ is unsubstituted or substituted; R$^6$ is unsubstituted or substituted arylalkyl; and R$^1$, R$^{1a}$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^6$ and R$^{3a}$ are as defined in formula (IV).

For example, the present invention provides a compound of formula (I) wherein X is O; R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, and R$^{3a}$ is aryl or heteroaryl wherein each R$^{3a}$ is unsubstituted or substituted; R$^6$ is unsubstituted or substituted arylalkyl; and R$^1$, R$^{1a}$, R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^6$ and R$^{3a}$ are as defined in formula (IV).

For example, the present invention provides a compound of formula (IV) wherein X is O; R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, and R$^{3a}$ is aryl or heteroaryl wherein each R$^{3a}$ is independently unsubstituted or substituted; R$^6$ is unsubstituted or substituted arylalkyl, R$^1$ is alkyl; and R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^6$ and R$^{3a}$ are as defined in formula (IV).

For example, the present invention provides a compound of formula (IV) wherein X is O; R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, and R$^{3a}$ is aryl or heteroaryl wherein each R$_{3a}$ is unsubstituted or substituted; R$^6$ is unsubstituted or substituted arylalkyl, R$^1$ is alkyl; and R$^{6a}$, R$^7$, R$^{7a}$, R$^{10}$, R$^{10a}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^6$ and R$^{3a}$ are as defined in formula (IV).

For example, the present invention provides a compound of formula (IV) wherein X is O; R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, and R$^{3a}$ is aryl or heteroaryl wherein each R$^{3a}$ is independently unsubstituted or substituted; R$^6$ is unsubstituted or substituted arylalkyl, R$^1$ is alkyl; R$^7$ is —N(R$_b$)C(O)OR$_a$, alkyl or heterocycle wherein each R$^7$ is independently unsubstituted or substituted; and R$^{6a}$, R$^{7a}$, R$^{10}$, R$^{10a}$, R$^{15}$, R$^{16}$, R$_{103}$, R$_{104}$,R$_{105}$, M, Z$_1$, Z$_2$, Q, W, M', R$_{106}$, R$_{107}$, R$_{108}$, q, m, m', m'', r, t, R$_a$, R$_b$, R$_c$ and the substituents of R$^6$, R$^7$ and R$^{3a}$ are as defined in formula (IV).

For example, the present invention provides a compound of formula (IV) wherein X is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, and $R^{3a}$ is aryl or heteroaryl wherein each $R^{3a}$ is independently unsubstituted or substituted; $R^6$ is unsubstituted or substituted arylalkyl; $R^1$ is alkyl; $R^7$ is —$N(R_b)C(O)OR_a$, alkyl or heterocycle wherein each $R^7$ is independently unsubstituted or substituted; and $R^{6a}$, $R^{7a}$, $R^{10}$, $R^{10a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and the substituents of $R^6$, $R^7$ and $R^{3a}$ are as defined in formula (IV).

For example, the present invention provides a compound of formula (IV) wherein X is O; $R^4$ is H; $R^5$ is $OR^{16}$; $R^3$ is alkyl; $R^3$ is arylalkyl wherein the aryl moiety of the arylalkyl is unsubstituted or substituted with one $R^{3a}$, and $R^{3a}$ is aryl or heteroaryl wherein each $R^{3a}$ is independently unsubstituted or substituted; $R^6$ is unsubstituted or substituted arylalkyl, $R^1$ is alkyl; $R^7$ is —$N(R_b)C(O)OR_a$, alkyl or heterocycle wherein each $R^7$ is independently unsubstituted or substituted; $R^{10}$ is aryl or heteroaryl wherein each $R^{10}$ is independently unsubstituted or substituted; and $R^{6a}$, $R^{7a}$, $R^{10a}$, $R^{15}$, $R^{16}$, $R_{103}$, $R_{104}$, $R_{105}$, M, $Z_1$, $Z_2$, Q, W, M', $R_{106}$, m, m', m'', r, t, $R_a$, $R_b$, $R_c$ and the substituents of $R^6$, $R^7$, $R^{10}$ and $R^{3a}$ are as defined in formula (IV).

For example, the present invention provides a compound of formula (IV) wherein X is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, and $R^{3a}$ is aryl or heteroaryl wherein each $R^{3a}$ is independently unsubstituted or substituted; $R^6$ is unsubstituted or substituted arylalkyl; $R^1$ is alkyl; $R^7$ is —$N(R_b)C(O)OR_a$, alkyl or heterocycle wherein each $R^7$ is independently unsubstituted or substituted; $R^{10}$ is aryl or heteroaryl wherein each $R^{10}$ is independently unsubstituted or substituted; and $R^{6a}$, $R^{7a}$, $R^{10a}$, $R^5$, $R^6$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$ and the substituents of $R^6$, $R^7$, $R^{10}$, $R^{3a}$ are as defined in formula (IV).

For example, the present invention provides a compound of formula (IV) wherein X is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, and $R^{3a}$ is aryl or heteroaryl wherein each $R^{3a}$ is independently unsubstituted or substituted; $R^6$ is unsubstituted or substituted arylalkyl, $R^1$ is alkyl; $R^7$ is —$N(R_b)C(O)OR_a$, alkyl or heterocycle wherein each $R^7$ is independently unsubstituted or substituted; $R^{10}$ is aryl or heteroaryl wherein each $R^{10}$ is independently unsubstituted or substituted; each $R_{104}$ is independently hydrogen or alkyl; each M is independently hydrogen or alkyl; $Z_1$ and $Z_2$ are O, Q is O, W is P; each $R_{105}$ is independently hydrogen or alkyl; and $R^{6a}$, $R^{7a}$, $R^{10a}$, $R^{15}$, $R^{16}$, $R_{103}$, M', $R_{106}$, $R_{107}$, $R_{108}$, q, m, m', m'', r, t, $R_a$, $R_b$, $R_c$ and the substituents of $R^6$, $R^7$, $R^{10}$, $R^{3a}$, and M are as defined in formula (IV).

For example, the present invention provides a compound of formula (IV) wherein X is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, and $R^{3a}$ is aryl or heteroaryl wherein each $R^{3a}$ is independently unsubstituted or substituted; $R^6$ is unsubstituted or substituted arylalkyl; $R^1$ is alkyl; $R^7$ is —$N(R_b)C(O)OR_a$, alkyl or heterocycle wherein each $R^7$ is independently unsubstituted or substituted; $R^{10}$ is aryl or heteroaryl wherein each $R^{10}$ is independently unsubstituted or substituted; each $R_{104}$ is independently hydrogen or alkyl; each M is independently hydrogen, or alkyl; $Z_1$ and $Z_2$ are O, Q is O, W is P; each $R_{105}$ is independently hydrogen or alkyl; and $R^{6a}$, $R^{7a}$, $R^{10a}$, $R^{15}$, $R^{16}$, $R_{103}$, M', $R_{106}$, $R_{107}$, $R_{108}$, q, m, m', m'', r, t, $R_a$, $R_b$, $R_c$ and the substituents of $R^6$, $R^7$, $R^{10}$, M and $R^{3a}$ are as defined in formula (IV).

In a fifth embodiment the present invention provides a compound of formula (V)

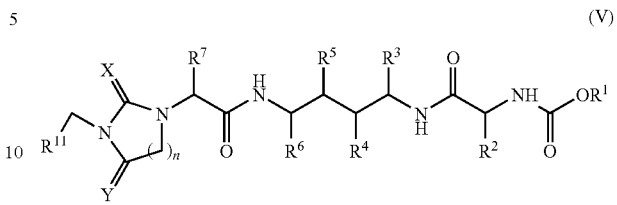

(V)

or a pharmaceutically acceptable salt form, prodrug or a stereoisomer thereof, wherein:

X is O, S or NH;

Y is O, S or NH;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —$OR_a$, —$SR_a$, —$SOR_a$, —$SO_2R_a$, —$NR_aR_b$, —$NR_bC(O)R_a$—$N(R_b)C(O)OR_a$, —$N(R_a)C(=N)NR_aR_b$, —$N(R_a)C(O)NR_aR_b$, —C(O)$NR_aR_b$, —C(O)$OR_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

$R^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^4$ is H and $R^5$ is OR$^{16}$; or
$R^5$ is H and $R^4$ is OR$^{16}$; or
$R^4$ and $R^5$ are —OR$^{16}$;

$R^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

$R^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

$R^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{11}$ is alkyl, alkenyl, alkynyl, cycloalkyl, cycloalkenyl, aryl, heteroaryl or heterocycle; wherein each R$^{11}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{11a}$;

$R^{11a}$ is cycloalkyl, cycloalkenyl, heterocycle, aryl or heteroaryl; wherein each R$^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{16}$ is hydrogen or $R^{15}$;
$R^{15}$ is $$*-\overset{O}{\underset{}{\overset{\|}{C}}}-O\!\!\!-\!\!\!\underset{q}{\overline{\phantom{|}}}\!\!\!-\!\!\!CR_{107}R_{108}\!\!\!-\!\!\!\underset{r}{\overline{\phantom{|}}}\!\!\!-\!\!\!CHR_{104}\!\!-\!\!O\!\!\!-\!\!\!\underset{m}{\overline{\phantom{|}}}\!\!\!-\!\!\!\underset{\underset{Q}{\|}}{W}\!\!\!-\!\!\!Z_2(M)_t \quad \text{or} \quad \text{(XVI)}$$

$$*-\overset{O}{\underset{}{\overset{\|}{C}}}-O\!\!\!-\!\!\!\underset{q}{\overline{\phantom{|}}}\!\!\!-\!\!\!CHR_{104}\!\!-\!\!O\!\!\!-\!\!\!\underset{m}{\overline{\phantom{|}}}\!\!\!-\!\!\!\overset{Q}{\underset{}{\overset{\|}{C}}}\!\!\!-\!\!\!(R_{103})_m M' \quad \text{(XVII)}$$

$R_{103}$ is $C(R_{105})_2$, O or $-N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, $-N(R_{105})_2$, alkyl, alkenyl, and $R_{106}$; wherein 1 to 4 $-CH_2$ radicals of the alkyl or alkenyl, other than the $-CH_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$, $NO_2$, $NO_2$ and phenyl; provided that when M is $-N(R_{105})_2$, $Z_1$ and $Z_2$ are $-CH_2$;

$Z_1$ is $CH_2$, O, S, $-N(R_{105})$, or, when M is absent, H;
$Z_2$ is $CH_2$, O, S or $-N(R_{105})$;
Q is O or S;
W is P or S; wherein when W is S, $Z_1$ and $Z_2$ are not S;

M' is H, alkyl, alkenyl or $R_{106}$; wherein 1 to 4 $-CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $-OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $-OR_{105}$, $-R_{105}$, $-N(R_{105})_2$, $-N(R_{105})C(O)R_{105}$, $-CN$, $-C(O)OR_{105}$, $-C(O)N(R_{105})_2$, halo and $-CF_3$;

each $R_{107}$ and $R_{108}$ are independently selected from the group consisting of hydrogen and alkyl;

q is 0 or 1;
m is 0 or 1;
m' is 0 or 1;
m" is 0 or 1;
r is 0, 1, 2, 3 or 4;
t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, hydroxy, alkoxy, alkyl, alkenyl, alkynyl, $-NH_2$, $-N(H)$(alkyl), $-N$(alkyl)$_2$, $-SH$, $-S$(alkyl), $-SO_2$(alkyl), $-N(H)C(O)$alkyl, $-N$(alkyl)$C(O)$alkyl, $-N(H)C(O)NH_2$, $-N(H)C(O)N(H)$(alkyl), $-N(H)C(O)N$(alkyl)$_2$, $-C(O)OH$, $-C(O)O$alkyl, $-C(O)NH_2$, $-C(O)N(H)$(alkyl), $-C(O)N$(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, $-NH_2$, $-N(H)$(alkyl), $-N$(alkyl)$_2$, $-SH$, $-S$(alkyl), $-SO_2$(alkyl), $-N(H)C(O)$alkyl, $-N$(alkyl)$C(O)$alkyl, $-N(H)C(O)NH_2$, $-N(H)C(O)N(H)$(alkyl), $-N(H)C(O)N$(alkyl)$_2$, $-C(O)OH$, $-C(O)O$alkyl, $-C(O)NH_2$, $-C(O)N(H)$(alkyl), $-C(O)N$(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, $-NH_2$, $-N(H)$(alkyl), $-N$(alkyl)$_2$, $-SH$, $-S$(alkyl), $-SO_2$(alkyl), $-N(H)C(O)$alkyl, $-N$(alkyl)$C(O)$alkyl, $-N(H)C(O)NH_2$, $-N(H)C(O)N(H)$(alkyl), $-N(H)C(O)N$(alkyl)$_2$, $-C(O)OH$, $-C(O)O$alkyl, $-C(O)NH_2$, $-C(O)N(H)$(alkyl), $-C(O)N$(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (V) wherein X is O; Y is O; and $R^1$, $R^{1a}$, $R^2$, $R^{2a}$, $R^3$, $R^{3a}$, $R^4$, $R^5$, $R^6$, $R^{6a}$, $R^7$, $R^{7a}$, $R^{11}$, $R^{11a}$, $R^{15}$, $R^{16}$, $R_{103}$, $R_{104}$, $R_{104}$, $R_{105}$, M, $Z_1$, $Z_2$, Q, W, M', $R_{106}$, $R_{107}$, $R_{108}$, q, m, m', m", r, t $R_a$, $R_b$, $R_c$ and n are as defined in formula (V).

For example, the present invention provides a compound of formula (V) wherein X is O; Y is O; $R^4$ is H; $R^5$ is $OR^{16}$;; and $R^1$, $R^{1a}$, $R^2$, $R^{2a}$, $R^3$, $R^{3a}$, $R^6$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and n are as defined in formula (V).

For example, the present invention provides a compound of formula (V) wherein X is O; Y is O; $R^4$ is $OR^{16}$; $R^5$ is H; and $R^{1a}$, $R^2$, $R^{2a}$, $R^3$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$ and n are as defined in formula (V).

For example, the present invention provides a compound of formula (V) wherein X is O; Y is O; $R^4$ is H; $R^5$ is $OR^{16}$; $R^2$ is alkyl; and $R^1$, $R^{1a}$, $R^3$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{105}$, q, m, m', m''', r, t, $R_a$, $R_b$, $R_c$ and n are as defined in formula (V).

For example, the present invention provides a compound of formula (V) X is O; Y is O; $R^4$ is $OR^{16}$; $R^5$ is H; $R^2$ is alkyl; and $R^1$, $R^{1a}$, $R^3$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$ and n are as defined in formula (V).

For example, the present invention provides a compound of formula (V) wherein X is O; Y is O; $R^4$ is H; $R^5$ is $OR^{16}$; $R^2$ is alkyl; and $R^3$ is arylalkyl wherein the aryl moiety of the arylalkyl is unsubstituted or substituted; and $R^1$, $R^{1a}$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of the aryl moiety of the arylalkyl of $R^3$ are as defined in formula (V).

For example, the present invention provides a compound of formula (V) wherein X is O; Y is O; $R^4$ is $OR^{16}$; $R^5$ is H; $R^2$ is alkyl; and $R^3$ is arylalkyl wherein the aryl moiety of the arylalkyl is unsubstituted or substituted; and $R^1$, $R^{1a}$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of the aryl moiety of the arylalkyl of $R^3$ are as defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$; and $R^1$, $R^{1a}$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, and n are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$; and $R^1$, $R^{1a}$, $R^{3a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, wherein $R^{3a}$ is aryl or heteroaryl and wherein each $R^{3a}$ is independently unsubstituted or substituted; and $R^1$, $R^{1a}$, $R^6$, $R^{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and substituents of $R^{3a}$ are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is aryl or heteroaryl and wherein each $R^{3a}$ is independently unsubstituted or substituted; and $R^1$, $R^{1a}$, $R^6$, $R_{6a}$, $R^7$, $R^{7a}$, $R^{11}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ are as defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl unsubstituted or substituted with one $R^{3a}$, wherein $R^{3a}$ is aryl or heteroaryl and wherein each $R^{3a}$ is independently unsubstituted or substituted; $R^{11}$ is aryl or heteroaryl and wherein each $R^{11}$ is independently unsubstituted or substituted; and $R^1$, $R^{1a}$, $R^6$, $R^{6a}$, $R^7$, $R^{7a}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^{11}$ are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is aryl or heteroaryl and wherein each $R^{3a}$ is independently unsubstituted or substituted; $R^{11}$ is aryl or heteroaryl and wherein each $R^{11}$ is independently unsubstituted or substituted; and $R^1$, $R^{1a}$, $R^6$, $R^{6a}$, $R^7$, $R^{7a}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$ and $R^{11}$, are as defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, wherein $R^{3a}$ is aryl or heteroaryl and wherein each $R^{3a}$ is independently unsubstituted or substituted; $R^{11}$ is aryl or heteroaryl and wherein each $R^{11}$ is independently unsubstituted or substituted; $R^7$ is —$N(R_b)C(O)OR_a$, alkyl, or heterocycle and wherein the alkyl or heterocycle is independently unsubstituted or substituted; and $R^1$, $R^{1a}$, $R^6$, $R^{6a}$, $R^{7a}$, $R^{11a}$, $R^{15}$, $R_{16}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$, $R^7$ and $R^{11}$, are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is aryl or heteroaryl and wherein each $R^{3a}$ is independently unsubstituted or substituted; $R^1$ is aryl or heteroaryl and wherein each $R^{11}$ is independently unsubstituted or substituted; $R^7$ is —$N(R_b)C(O)OR_a$, alkyl, or heterocycle and wherein the alkyl or heterocycle is independently unsubstituted or substituted; and $R^1$, $R^{1a}$, $R^6$, $R^{6a}$, $R^{7a}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, t, $R_a$, $R_b$, $R_c$, n and the substituents of $R^{3a}$, $R^7$ and $R^{11}$, are as defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{11}$ is unsubstituted or substituted aryl or unsubstituted or substituted heteroaryl; $R^7$ is —$N(R_b)C(O)OR_a$, unsubstituted or substituted alkyl, or unsubstituted or substituted heterocycle; $R^6$ is unsubstituted or substituted arylalkyl; and $R^1$, $R^{1a}$, $R^{6a}$, $R^{7a}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m''', r, r, $R_a$, $R_b$, $R_c$, n and the substituents of $R^{3a}$, $R^6$, $R^7$ and $R^{11}$, are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{11}$ is unsubstituted or substituted aryl or unsubstituted or substituted heteroaryl; $R^7$ is —$N(R_b)C(O)OR_a$, unsubstituted or substituted alkyl, or unsubstituted or substituted heterocycle; $R^6$ is unsubstituted or substituted arylalkyl; and $R^1$, $R^{1a}$, $R^{6a}$, $R^{7a}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, n and the substituents of $R^{3a}$, $R^6$, $R^7$ and $R^{11}$, are as defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{11}$ is unsubstituted or substituted aryl or unsubstituted or substituted heteroaryl; $R^7$ is —N($R_b$)C(O)O$R_a$, unsubstituted or substituted alkyl or unsubstituted or substituted heterocycle; $R^6$ is unsubstituted or substituted arylalkyl; $R^1$ is alkyl; and $R^{6a}$, $R^{7a}$, $R^{11a}$, $R^{15}$, $R^{16}$, $R_{103}$, $R_{104}$, $R_{105}$ M, $Z_1$, $Z_2$, Q, W, M', $R_{106}$, $R_{107}$, $R_{108}$, q, m, m', m", r, t, $R_a$, $R_b$, $R_c$, n and the substituents of $R^{3a}$, $R^6$, $R^7$ and $R^{11}$, are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{11}$ is unsubstituted or substituted aryl or unsubstituted or substituted heteroaryl; $R^7$ is —N($R_b$)C(O)O$R_a$, unsubstituted or substituted alkyl or unsubstituted or substituted heterocycle; $R^6$ is unsubstituted or substituted arylalkyl; $R^1$ is alkyl; and $R^{6a}$, $R^{7a}$, $R^{11a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, n and the substituents of $R^{3a}$, $R^6$, $R^7$ and $R^{11}$ are as defined in formula (V).

For example, the present invention provides a compound of formula (V) wherein X is O; Y is O; $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{11}$ is unsubstituted or substituted aryl or unsubstituted or substituted heteroaryl; $R^7$ is —N($R_b$)C(O)O$R_a$, unsubstituted or substituted alkyl or unsubstituted or substituted heterocycle; $R^6$ is unsubstituted or substituted arylalkyl; $R^1$ is alkyl; each $R_{104}$ is independently hydrogen or alkyl; each M is independently hydrogen or alkyl; $Z_1$ and $Z_2$ are O, Q is O, W is P; each $R_{105}$ is independently hydrogen or alkyl; and $R^{6a}$, $R^{7a}$, $R^{11a}$, $R^{15}$, $R^{16}$, $R_{103}$, M', $R_{106}$, $R_{107}$, $R_{108}$, q, m, m', m", r, t, $R_a$, $R_b$, $R_c$, n and the substituents of $R^{3a}$, $R^6$, $R^7$, M and $R^{11}$, are as defined in formula (V).

For example, the present invention provides a compound of formula (V) wherein X is O; Y is O; $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{11}$ is unsubstituted or substituted aryl or unsubstituted or substituted heteroaryl; $R^7$ is —N($R_b$)C(O)O$R_a$, unsubstituted or substituted alkyl or unsubstituted or substituted heterocycle; $R^6$ is unsubstituted or substituted arylalkyl; $R^1$ is alkyl; each $R_{104}$ is independently hydrogen or alkyl; each M is independently hydrogen or alkyl; $Z_1$ and $Z_2$ are O, Q is O, W is P; each $R_{105}$ is independently hydrogen or alkyl; and $R^{6a}$, $R^{7a}$, $R^{11a}$, $R^{15}$, $R^{16}$, $R_{103}$, M', $R_{106}$, $R_{107}$, $R_{108}$, q, m, m', m", r, t, $R_a$, $R_b$, $R_c$, n and the substituents of $R^{3a}$, $R^6$, $R^7$, M and $R^{11}$ are as defined in formula (V).

For example, the present invention provides a compound of formula (V) wherein X is O; Y is O; $R^4$ is H; $R^5$ is $OR^{16}$; $R^2$ is C1, C2, C3, C4 or C5 alkyl; $R^3$ is phenylmethyl wherein $R^{3a}$ is phenyl moiety of the phenylmethyl is unsubstituted or substituted with one $R^{3a}$, wherein $R^{3a}$ is unsubstituted or substituted pyridyl; $R^{11}$ is phenyl, thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each $R^{11}$ is independently unsubstituted or substituted; $R^7$ is —N($R_b$)C(O)O$R_a$, unsubstituted or substituted heterocycle or unsubstituted or substituted C1-C5 alkyl; $R^6$ is unsubstituted or substituted phenylmethyl; $R^1$ is C1, C2, C3, C4 or C5 alkyl; each $R_{104}$ is independently hydrogen or alkyl; each M is independently hydrogen, or alkyl; $Z_1$ and $Z_2$ are O, Q is O, W is P; each $R_{105}$ is independently hydrogen or alkyl; and $R^{6a}$, $R^{7a}$, $R^{11a}$, $R^{15}$, $R^{16}$, $R_{103}$, M', $R_{106}$, $R_{107}$, $R_{108}$, q, m, m', m", r, t, $R_a$, $R_b$, $R_a$, n and the substituents of $R^{3a}$, $R^6$, $R^7$, M and $R^{11}$ are as defined in formula (V).

For example, the present invention provides a compound of formula (V) wherein X is O; Y is O; $R^4$ is $OR^{16}$; $R^5$ is H; $R^2$ is C1, C2, C3, C4 or C5 alkyl; $R^3$ is phenylmethyl wherein the phenyl moiety of the phenylmethyl is unsubstituted or substituted with one $R^{3a}$, wherein $R^{3a}$ is unsubstituted or substituted pyridyl; $R^{11}$ is phenyl, thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each $R^{11}$ is independently unsubstituted or substituted; $R^7$ is —N($R_b$)C(O)O$R_a$, unsubstituted or substituted heterocycle or unsubstituted or substituted C1-C5 alkyl; $R^6$ is unsubstituted or substituted phenylmethyl; $R^1$ is C1, C2, C3, C4 or C5 alkyl; each $R_{104}$ is independently hydrogen or alkyl; each M is independently hydrogen, or alkyl; $Z_1$ and $Z_2$ are O, Q is O, W is P; each $R_{105}$ is independently hydrogen or alkyl; and $R^{6a}$, $R^{7a}$, $R^{11a}$, $R^{15}$, $R^{16}$, $R_{103}$, M', $R_{106}$, $R_{107}$, $R_{108}$, q, m, m', m", r, t, $R_a$, $R_b$, $R_a$, n and the substituents of $R^{3a}$, $R^6$, $R^7$, M and $R^{11}$ are as defined in formula (V).

Exemplary compounds of the present invention of formula (V) include, but not limited to, the following:

methyl(1S)-1-[({(1S,3S,4S)-3-hydroxy-4-[((2S)-3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate;

methyl(1S)-1-[({(1S,2S,4S)-2-hydroxy-4-[((2S)-3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate;

methyl(1S)-1-[({(1R,3S,4S)-4-[((2S)-3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-4-[((2S)-3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate;

methyl(1S)-1-[({(1S,2S,4S)-4-[((2S)-3,3-dimethyl-2-{3-[(6-methyl-2-pyridinyl)methyl]-2,4-dioxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate;

methyl(1S)-1-[({(1S,3S,4S)-3-hydroxy-4-[((2S)-2-{3-[(2-isopropyl-1,3-thiazol-4-yl)methyl]-2,4-dioxo-1-imidazolidinyl}-3-methylpentanoyl)amino]-5-phenyl-1-[4-(2-pyridinyl)benzyl]pentyl}amino)carbonyl]-2,2-dimethylpropylcarbamate; and methyl(1S)-1-[({(1S,3S,4S)-4-{[(2S)-2-(2,4-dioxo-3-{[2-(3-pyridinyl)-1,3-thiazol-4-yl]methyl}-1-imidazolidinyl)-3-methylpentanoyl]amino}-3-hydroxy-5-phenyl-1-[4-(2-pyridinyl)benzyl]pentyl}amino)carbonyl]-2,2-dimethylpropylcarbamate;

or a pharmaceutically acceptable salt form, prodrug or stereoisomer thereof.

In a sixth embodiment the present invention provides a compound of formula (VI)

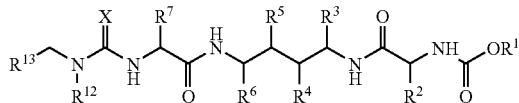

(VI)

or a pharmaceutically acceptable salt form, prodrug or a stereoisomer thereof, wherein:

X is O, S or NH;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —$OR_a$, —$SR_a$, —$SOR_a$, —$SO_2R_a$, —$NR_aR_b$, —$NR_bC(O)R_a$—N($R_b$)C(O)$OR_a$, —N($R_a$)C(=N)$NR_aR_b$, —N($R_a$)C(O)$NR_aR_b$, —C(O)$NR_aR_b$, —C(O)$OR_a$ and $R^{2a}$;

$R^{1a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkyl-C(O)N(alkyl)$_2$;

$R^3$ is alkyl, alkenyl, alkynyl, haloalkyl, haloalkenyl, -alkyl$OR_a$, -alkyl$SR_a$, -alkyl$SOR_a$, -alkyl$SO_2R_a$, -alkyl$NR_aR_b$, -alkylN($R_b$)C(O)$R_a$, -alkylN($R_b$)C(O)$OR_a$, -alkylN($R_a$)C(=N)$NR_aR_b$, -alkylN($R_a$)C(O)$NR_aR_b$, -alkylC(O)$NR_aR_b$, -alkylC(O)$OR_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), and -alkylC(O)N(alkyl)$_2$;

$R^4$ is H and $R^5$ is $OR^{16}$; or
$R^5$ is H and $R^4$ is $OR^{16}$; or
$R^4$ and $R^5$ are —$OR^{16}$;

$R^6$ is alkyl, alkenyl, alkynyl, haloalkyl, haloalkenyl, -alkyl$OR_a$, -alkyl$SR_a$, -alkyl$SOR_a$, -alkyl$SO_2R_a$, -alkyl$NR_aR_b$, -alkylN($R_b$)C(O)$R_a$, -alkylN($R_b$)C(O)$OR_a$, -alkylN($R_a$)C(=N)$NR_aR_b$, -alkylN($R_a$)C(O)$NR_aR_b$, -alkylC(O)$NR_aR_b$, -alkylC(O)$OR_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^{12}$ is alkyl, alkenyl, cycloalkyl, cycloalkenyl, cycloalkylalkyl or cycloalkenylalkyl; wherein each R$^{12}$ is substituted with 0, 1 or 2 substituents independently selected from the group consisting of hydroxy, alkoxy and halo;

R$^{13}$ is alkyl, alkenyl, alkynyl, cycloalkyl, cycloalkenyl, aryl, heteroaryl or heterocycle; wherein each R$^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)C(O)OR$_a$, —C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkyl-C(O)NR$_a$R$_b$ and R$^{13a}$;

R$^{13a}$ is cycloalkyl, cycloalkenyl, heterocycle, aryl or heteroaryl; wherein each R$^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{16}$ is hydrogen or R$^{15}$;

R$^{15}$ is

(XVI)

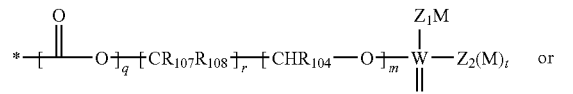

or (XVII)

R$_{103}$ is C(R$_{105}$)$_2$, O or —N(R$_{105}$);

R$_{104}$ is hydrogen, alkyl, haloalkyl, alkoxycarbonyl, aminocarbonyl, alkylaminocarbonyl or dialkylaminocarbonyl, each M is independently selected from the group consisting of H, N(R$_{105}$)$_2$, alkyl, alkenyl, and R$_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, Z$_1$ and Z$_2$ are —CH$_2$;

Z$_1$ is CH$_2$, O, S, —N(R$_{105}$), or, when M is absent, H;

Z$_2$ is CH$_2$, O, S or —N(R$_{105}$);

Q is O or S;

W is P or S; wherein when W is S, Z$_1$ and Z$_2$ are not S;

M' is H, alkyl, alkenyl or R$_{106}$; wherein 1 to 4 —CH$_2$ radicals of the alkyl or alkenyl is optionally replaced by a heteroatom group selected from O, S, S(O), SO$_2$, or N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$; each R$_{107}$ and R$_{108}$ are independently selected from the group consisting of hydrogen and alkyl;

q is 0 or 1;
m is 0 or 1;
m' is 0 or 1;
m" is 0 or 1;
r is 0, 1, 2, 3 or 4;
t is 0 or 1;
$R_a$ and $R_b$ at each occurrence are independently selected from the group consisting of hydrogen, alkyl, alkenyl, alkynyl, cycloalkyl, aryl, heteroaryl and heterocycle; wherein each $R_a$, and $R_b$, at each occurrence, is independently substituted with 0, 1, 2 or 3 substituents independently selected from the group consisting of cyano, nitro, halo, oxo, hydroxy, alkoxy, alkyl, alkenyl, alkynyl, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R_c$;
alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl), -alkylC(O)N(alkyl)$_2$ and $R_c$; and
$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl-$NH_2$, -alkyl-N(H)(alkyl), -alkyl-N(alkyl)$_2$, -alkyl-N(H)C(O)$NH_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)$NH_2$, -alkyl-C(O)N(H)(alkyl) and -alkyl-C(O)N(alkyl)$_2$.

For example, the present invention provides a compound of formula (VI) wherein $R^4$ is H; $R^{15}$ is $OR^{16}$; and X, $R^1$, $R^{1a}$, $R^2$, $R^{1a}$, $R^3$, $R^{3a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, Z, Q, W, M', $R_{106}$, q, m, m', m", r, t, $R_a$, $R_b$, and $R_c$ are as defined in formula (VI).

For example, the present invention provides a compound of formula (VI) wherein $R^4$ is $OR^{16}$; $R^5$ is H; and X, $R^1$, $R^{1a}$, $R^2$, $R^{2a}$, $R_3$, $R^{3a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, Z, Q, W, M', $R_{106}$, q, m, m', m", t, $R_a$, $R_b$, and $R_c$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted; and X, $R^1$, $R^{1a}$, $R^2$, $R^{2a}$, $R^{3a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and the substituents of the aryl moiety of arylalkyl of $R^3$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted; and X, $R^1$, $R^{1a}$, $R^2$, $R^{2a}$, $R^{3a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and the substituents of the aryl moiety of arylalkyl of $R^3$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$; and X, $R^1$, $R^{1a}$, $R^2$, $R^{2a}$, $R^{3a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, and $R_c$ are defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$ and X, $R^1$, $R^{1a}$, $R^2$, $R^{2a}$, $R^{3a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m", r, t, $R_a$, $R_b$, and $R_c$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; and X, $R^1$, $R^{1a}$, $R^2$, $R^{2a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; and X, $R^1$, $R^{1a}$, $R^2$, $R^{2a}$, $R^6$, $R^{6a}$, $R^7$, $R^{7a}$, $R^{12}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and the substituents of $R^{3a}$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; and X, $R^1$, $R^{1a}$, $R^2$, $R^{2a}$, $R^6$, $R^{6a}$, $R^7$, $R^{7a}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m", r, t, $R_a$, $R_b$, $R_c$ and substituents of $R^{3a}$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; and X, $R^1$, $R^{1a}$, $R^2$, $R^{2a}$, $R^6$, $R^{6a}$, $R^7$, $R^{7a}$, $R^{13}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m", r, t, $R_1$, $R_b$, $R_c$ and substituents of $R^{3a}$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; and X, $R^1$, $R^{1a}$, $R^2$, $R^{2a}$, $R^6$, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m", r, t, $R_a$, $R_b$, $R_c$ and substituents of $R^{3a}$ and $R^{13}$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; and X, $R^1$, $R^{1a}$, $R^2$, $R^{2a}$, $R^6$, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m", r, t, $R_a$, $R_b$, $R_c$ and the substituents of $R^{3a}$ and $R^{13}$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; and X, $R^1$, $R^{1a}$, $R^6$, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_a$ and the substituents of $R^{3a}$ and $R^{13}$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; and X, $R^1$, $R^{1a}$, $R^6$, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$ and $R^{13}$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ s alkyl; and X, $R^6$, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$ and $R^{13}$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; and X, $R^6$, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m', m", r, t, $R_a$, $R_b$, $R_c$ and substituents of $R^{3a}$, and $R^{13}$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; $R^6$ is unsubstituted or substituted arylalkyl; and X, $R^{6a}$, $R^7$, $R^{7a}$, $R^{13a}$, $R^{15}$, $R_{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$, $R^{13}$, and $R^6$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; $R^6$ is unsubstituted or substituted arylalkyl; and X, $R^{6a}$, $R^7$, $R^{7a}$, $R^{13a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$, $R^{13}$, and $R^6$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; $R^6$ is unsubstituted or substituted arylalkyl; $R^7$ is —N($R_b$)C(O)$OR_a$, unsubstituted or substituted alkyl, or unsubstituted or substituted heterocycle; and X, $R^{6a}$, $R^{7a}$, $R^{13a, R15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$, $R^{13}$, $R^6$ and $R^7$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; $R^6$ is unsubstituted or substituted arylalkyl; $R^7$ is —N($R_b$)C(O)$OR_a$, unsubstituted or substituted alkyl, or unsubstituted or substituted heterocycle; and X, $R^{6a}$, $R^{7a}$, $R^{3a}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$ and substituents of $R^{3a}$, $R^{13}$, $R^6$ and $R^7$ are as defined in formula (VI).

For example, the present invention provides a compound of formula (VI) wherein $R^4$ is H; $R^5$ is $OR^{16}$; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; $R^6$ is unsubstituted or substituted arylalkyl; $R^7$ is —N(&)C(O)$OR_a$, unsubstituted or substituted alkyl, or unsubstituted or substituted heterocycle; X is O; each $R_{104}$ is independently hydrogen or alkyl; each M is independently hydrogen, or alkyl; $Z_1$ and $Z_2$ are O; Q is O; W is P; each $R_{105}$ is independently hydrogen or alkyl; and $R^{6a}$, $R^{7a}$, $R^{13a}$, $R^{15}$, $R^{16}$, $R_{103}$, M', $R_{106}$, q, $R_{107}$, $R_{108}$, q, m, m', m", r, t, $R_a$, $R_b$, $R_c$ and substituents of $R^{3a}$, $R^{13}$, $R^6$, M and $R^7$ are as defined in formula (VI).

For example, the present invention provides a compound of formula (VI) wherein $R^4$ is $OR^{16}$; $R^5$ is H; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^{12}$ is alkyl; $R^{13}$ is unsubstituted or substituted aryl or unsubstituted or substituted heteroaryl; $R^2$ is alkyl; $R^1$ is alkyl; $R^6$ is unsubstituted or substituted arylalkyl; $R^7$ is —N($R_b$)C(O)$OR_a$, unsubstituted or substituted alkyl, or unsubstituted or substituted heterocycle; X is O; each $R_{104}$ is independently hydrogen or alkyl; each M is independently hydrogen, or alkyl; $Z_1$ and $Z_2$ are O; Q is O; W is P; each $R_{105}$ is independently hydrogen or alkyl; and $R^{6a}$, $R^{7a}$, $R^{13a}$, $R^{15}$, $R^{16}$, $R_{103}$, M', $R_{106}$, q, $R_{107}$, $R_{108}$, q, m, m', m''', r, t, $R_a$, $R_b$, $R_c$ and substituents of $R^{3a}$, $R^{13}$, $R^6$, M and $R^7$ are as defined in formula (VI).

For example, the present invention provides a compound of formula (VI) wherein $R^4$ is H; $R^5$ is $OR^{16}$; $R^3$ is phenylmethyl wherein the phenyl moiety of the phenylmethyl is unsubstituted or substituted with one $R^{3a}$, wherein $R^{3a}$ is unsubstituted or substituted pyridyl; $R^{12}$ is C1 alkyl, C2 alkyl or C3 alkyl; $R^{13}$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each $R^{13}$ is independently unsubstituted or substituted, $R^2$ is C1 alkyl, C2 alkyl, C3 alkyl, C4 alkyl or C5 alkyl; $R^1$ is C1 alkyl, C2 alkyl, C3 alkyl, C4 alkyl or C5 alkyl; $R^6$ is unsubstituted or substituted phenylmethyl; $R^7$ is —N(H)C(O)$OR_a$, tetrahydrofuranyl, or unsubstituted or substituted C1-C5 alkyl, wherein $R_a$ is C1-C5 alkyl; X is O; each $R_{104}$ is independently hydrogen, C1 alkyl, C2 alkyl, C3 alkyl, C4 alkyl or C5 alkyl; each M is independently hydrogen C1 alkyl, C2 alkyl, C3 alkyl, C4 alkyl or C5 alkyl; $Z_1$ and $Z_2$ are O; Q is O; W is P; each $R_{105}$ is independently hydrogen, C1 alkyl, C2 alkyl, C3 alkyl, C4 alkyl or C5 alkyl; and $R^{6a}$, $R^{7a}$, $R^{13a}$, $R^{15}$, $R_{16}$, $R_{103}$, M', $R_{106}$, $R_{107}$, $R_{108}$, q, m', m''', r, t, $R_a$, $R_b$, $R_c$ and substituents of $R^{3a}$, $R^{13}$, $R^6$, M and $R^7$ are as defined in formula (VI).

For example, the present invention provides a compound of formula (VI) wherein $R^4$ is $OR^{16}$; $R^5$ is H; $R^3$ is phenylmethyl wherein the phenyl moiety of the phenylmethyl is unsubstituted or substituted with one $R^{3a}$, wherein $R^{3a}$ is unsubstituted or substituted pyridyl; $R^{12}$ is C1 alkyl, C2 alkyl or C3 alkyl; $R^{13}$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each $R^{13}$ is independently unsubstituted or substituted; $R^2$ is C1 alkyl, C2 alkyl, C3 alkyl, C4 alkyl or C5 alkyl; $R^1$ is C1 alkyl, C2 alkyl, C3 alkyl, C4 alkyl or C5 alkyl; $R^6$ is unsubstituted or substituted phenylmethyl; $R^7$ is —N(H)C(O)$OR_a$, tetrahydrofuranyl, or unsubstituted or substituted C1-C5 alkyl, wherein $R_a$ is C1-C5 alkyl; X is O; each $R_{104}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_1$ and $Z_2$ are O; Q is O; W is P; each $R_{104}$ is independently hydrogen, C1 alkyl, C2 alkyl, C3 alkyl, C4 alkyl or C5 alkyl; and $R^{6a}$, $R^{7a}$, $R^{13a}$, $R^{15}$, $R^{16}$, $R_{103}$, M', $R_{106}$, $R_{107}$, $R_{108}$, q, m, m', m''', r, t, $R_a$, $R_b$, $R_a$ and substituents of $R^{3a}$, $R^{13}$, $R^6$, M and $R^7$ are as defined in formula (VI).

For example, the present invention provides a compound of formula (VI) wherein $R^4$ is H; $R^5$ is $OR^{16}$; $R^3$ is phenylmethyl wherein the phenyl moiety of the phenylmethyl is unsubstituted or substituted with one $R^{3a}$, wherein $R^{3a}$ is pyridyl substituted with 0 or one substituent selected from the group consisting of methyl and methoxide; $R^{12}$ is methyl, ethyl or n-propyl; $R^{13}$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each $R^{13}$ is independently unsubstituted or substituted; $R^2$ is 1-methylpropyl, tert-butyl, 2-methylpropyl, 3-methylpropyl or isopropyl; $R^1$ is methyl, ethyl, 1-methylpropyl, tert-butyl, 2-methylpropyl, 3-methylpropyl or isopropyl; $R^6$ is unsubstituted or substituted phenylmethyl; $R^7$ is —N(H)C(O)$OCH_3$, tetrahydrofuranyl, methyl, ethyl, propyl, n-butyl, isopropyl, 1-methylpropyl, 2-methylpropyl, 3-methylpropyl, or tert-butyl; wherein each of the methyl, ethyl, propyl, n-butyl, isopropyl, 1-methylpropyl, 2-methylpropyl, 3-methylpropyl, and tert-butyl are independently unsubstituted or substituted; X is O; each $R_{104}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_1$ and $Z_2$ are O; Q is O; W is P; each $R_{105}$ is independently hydrogen, C1 alkyl, C2 alkyl, C3 alkyl, C4 alkyl or C5 alkyl; and $R^{6a}$, $R^{7a}$, $R^{13a}$, $R^{15}$, $R^{16}$, $R_{103}$, M', $R_{106}$, $R_{107}$, $R_{108}$, q, m, m', m''', r, t, $R_a$, $R_b$, $R_c$ and substituents of $R^{13}$, $R^6$, M and $R^7$ are as defined in formula (VI).

For example, the present invention provides a compound of formula (VI) wherein $R^4$ is $OR^{16}$; $R^5$ is H; $R^3$ is phenylmethyl wherein the phenyl moiety of the phenylmethyl is unsubstituted or substituted with one $R^{3a}$, wherein $R^{3a}$ is pyridyl substituted with 0 or one substituent selected from the group consisting of methyl and methoxide; $R^{12}$ is methyl, ethyl or n-propyl; $R^{13}$ is thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each $R^{13}$ is independently unsubstituted or substituted; $R^2$ is 1-methylpropyl, tert-butyl, 2-methylpropyl, 3-methylpropyl or isopropyl; $R^1$ is methyl, ethyl, 1-methylpropyl, tert-butyl, 2-methylpropyl, 3-methylpropyl or isopropyl; $R^6$ is unsubstituted or substituted phenylmethyl; $R^7$ is —N(H)C(O)$OCH_3$, tetrahydrofuranyl, methyl, ethyl, propyl, n-butyl, isopropyl, 1-methylpropyl, 2-methylpropyl, 3-methylpropyl, or tert-butyl; wherein each of the methyl, ethyl, propyl, n-butyl, isopropyl, 1-methylpropyl, 2-methylpropyl, 3-methylpropyl, and tert-butyl are independently unsubstituted or substituted; X is O; each $R_{104}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_1$ and $Z_2$ are O; Q is O; W is P; each $R_{105}$ is independently hydrogen, C1 alkyl, C2 alkyl, C3 alkyl, C4 alkyl or C5 alkyl; and $R^{6a}$, $R^{7a}$, $R^{13a}$, $R^{15}$, $R^{16}$, $R_{103}$, M', $R_{106}$, $R_{107}$, $R_{108}$, q, m, m', m''', r, t, $R_a$, $R_b$, $R_c$ and substituents of $R^{13}$, $R^6$, M and $R^7$ are as defined in formula (VI).

Exemplary compounds of the present invention of formula (VI) include, but not limited, to the following:

methyl(1S,4S,6S,7S,10S)-7-benzyl-1,10-ditert-butyl-6-hydroxy-13-methyl-2,9,12-trioxo-14-phenyl-4-[4-(2-pyridinyl)benzyl]-3,8,11,13-tetraazatetradec-1-ylcarbamate;

methyl(1S,4R,6S,7S,10S)-7-benzyl-1,10-ditert-butyl-6-hydroxy-13-methyl-2,9,12-trioxo-14-phenyl-4-[4-(2-pyridinyl)benzyl]-3,8,11,13-tetraazatetradec-1-ylcarbamate;

methyl(1S,4S,6S,7S,10S)-7-benzyl-10-sec-butyl-1-tert-butyl-6-hydroxy-13-methyl-14-(2-methyl-1,3-thiazol-4-yl)-2,9,12-trioxo-4-[4-(2-pyridinyl)benzyl]-3,8,11,13-tetraazatetradec-1-ylcarbamate; and methyl(1S,4S,5S,7S,10S)-7-benzyl-10-sec-butyl-1-tert-butyl-5-hydroxy-13-methyl-14-(2-methyl-1,3-thiazol-4-yl)-2,9,12-trioxo-4-[4-(2-pyridinyl)benzyl]-3,8,11,13-tetraazatetradec-1-ylcarbamate; or a pharmaceutically acceptable salt form, prodrug or stereoisomer thereof.

In a seventh embodiment, the present invention provides a compound of formula (VII)

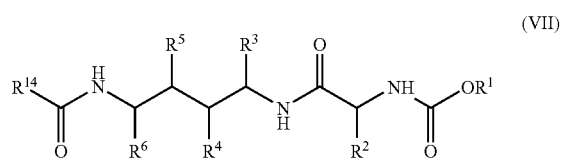

or a pharmaceutically acceptable salt form, prodrug or stereoisomer thereof, wherein:

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —OR$_a$, —SR$_a$, —SOR$_a$, —SO$_2$R$_a$, NR$_a$R$_b$, —NR$_b$C(O)R$_a$—N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^4$ is H and $R^5$ is OR$^{16}$; or $R^5$ is H and $R^4$ is OR$^{16}$; or $R^4$ and $R^5$ are —OR$^{16}$;

$R^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^{14}$ is —$OR_a$, -alkyl$OR_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —S(O)$_2$NR$_a$R$_b$, —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{16}$ is hydrogen or $R^{15}$;

$R^{15}$ is

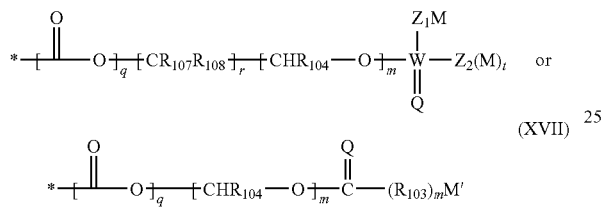

(XVI)

(XVII)

$R_{103}$ is C($R_{105}$)$_2$, O or —N($R_{105}$);

$R_{104}$ is hydrogen, alkyl, haloalkyl, alkoxycarbonyl, aminocarbonyl, alkylaminocarbonyl or dialkylaminocarbonyl;

each M is independently selected from the group consisting of H, —N($R_{105}$)$_2$, alkyl, alkenyl, and $R_{106}$; wherein 1 to 4 —$CH_2$ radicals of the alkyl or alkenyl, other than the —$CH_2$ radical that is bound to Z, is optionally replaced by a heteroatom group selected from the group consisting of O, S, S(O), $SO_2$ and N($R_{105}$); and wherein any hydrogen in said alkyl, alkenyl or $R_{106}$ is optionally replaced with a substituent selected from the group consisting of oxo, —$OR_{105}$, —$R_{105}$, —N($R_{105}$)$_2$, —CN, —C(O)$OR_{105}$, —C(O)N($R_{105}$)$_2$, —$SO_2$N($R_{105}$), —N($R_{105}$)C(O)$R_{105}$, —C(O)$R_{105}$, —$SR_{105}$, —S(O)$R_{105}$, —$SO_2R_{105}$, —$OCF_3$, —$SR_{106}$, —$SOR_{106}$, —$SO_2R_{106}$, —N($R_{105}$)$SO_2R_{105}$, halo, —$CF_3$, $NO_2$ and phenyl; provided that when M is —N($R_{105}$)$_2$, $Z_1$ and $Z_2$ are —$CH_2$;

$Z_1$ is $CH_2$, O, S, —N($R_{105}$), or, when M is absent, H;

$Z_2$ is $CH_2$, O, S or —N($R_{105}$);

Q is O or S;

W is P or S; wherein when W is S, $Z_1$ and $Z_2$ are not S;

M' is H, alkyl, alkenyl or $R_{106}$; wherein 1 to 4 —$CH_2$ radicals of the alkyl or alkenyl is optionally replaced by a heteroatom group selected from O, S, S(O), $SO_2$, or N($R_{105}$); and wherein any hydrogen in said alkyl, alkenyl or $R_{106}$ is optionally replaced with a substituent selected from the group consisting of oxo, —$OR_{105}$, —$R_{105}$, —N($R_{105}$)$_2$, —CN, —C(O)$OR_{105}$, —C(O)N($R_{105}$)$_2$, —$SO_2$N($R_{105}$), —N($R_{105}$)C(O)$R_{105}$, —C(O)$R_{105}$, —$SR_{105}$, —S(O)$R_{105}$, —$SO_2R_{105}$, —$OCF_3$, —$SR_{106}$, —$SOR_{106}$, —$SO_2R_{106}$, —N($R_{105}$)$SO_2R_{105}$, halo, —$CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and N($R_{105}$); and wherein any of said ring system is substituted with 0, 1, 2, 3, 4, 5 or 6 substituents selected from the group consisting of hydroxy, alkyl, alkoxy, and —OC(O)alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and N($R_{105}$); and wherein any one of said ring systems is substituted with 0, 1, 2, 3 or 4 substituents selected from the group consisting of oxo, —$OR_{105}$, —$R_{105}$, —N($R_{105}$)$_2$, —N($R_{105}$)C(O)$R_{105}$, —CN, —C(O)$OR_{105}$, —C(O)N($R_{105}$)$_2$, halo and —$CF_3$; each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, hydroxy, alkoxy, alkyl, alkenyl, alkynyl, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$; and $R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$.

For example, the present invention provides a compound of formula (VII) wherein W is P; Q is O; Z$_1$ and Z$_2$ are O; and R$^1$, R$^{1a}$, R$^3$, R$^{3a}$, R$^4$, R$^5$, R$^6$, R$^{6a}$, R$^{14}$, R$^{15}$, R$^{16}$, R$_{103}$, R$_{104}$, R$_{105}$, M, M', R$_{106}$, R$_{107}$, R$_{108}$, q, m, m', m'", r, t, R$_a$, R$_b$, and R$_c$, are as defined in formula (VII). For example, the present invention provides a compound of formula (VII) wherein R$^4$ is H, R$^5$ is OR$^{16}$; R$^2$ is alkyl; and R$^1$, R$^{1a}$, R$^3$, R$^{3a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, and R$_c$, are as defined in formula (VII).

For example, the present invention provides a compound of formula (VII) wherein R$^4$ is OR$^{16}$; R$^5$ is H; R$^2$ is alkyl; and R$^1$, R$^{1a}$, R$^3$, R$^{3a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, and R$_c$, are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted; and R$^1$, R$^{1a}$, R$^{3a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, R$_c$ and the substituents of the aryl moiety of the arylalkyl of R$^3$ are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted; and R$^1$, R$^{1a}$, R$^{3a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, R$_c$ and the substituents of the aryl moiety of the arylalkyl of R$^3$ are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted with one R$^{3a}$; and R$^1$, R$^{1a}$, R$^{3a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, and R$_c$ are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted with one R$^{3a}$; and R$^1$, R$^{1a}$, R$^{3a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, and R$_c$ are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, wherein R$^3$, is unsubstituted or substituted aryl or unsubstituted or substituted heteroaryl; and R$^1$, R$^{1a}$, R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, R$_c$, and the substituents of R$^{3a}$ are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; and R$^1$, R$^{1a}$, R$^6$, R$^{6a}$, R$^{14}$, R$^{15}$, R$^6$, R$_{103}$, R$_{104}$, R$_{105}$, M, Z$_1$, Z$_2$, Q, W, M', R$_{106}$, R$_{107}$, R$_{108}$, q, m, m', m'", r, t, R$_a$, R$_b$, R$_c$, and the substituents of R$^{3a}$ are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; and R$^6$, R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$ q, m, m', m'", r, t, R$_a$, R$_b$, R$_c$, and the substituents of R$^{3a}$ are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; and R$^6$, R$^{6a}$, R$^{14}$, R$^1$, R$^{16}$, R$_{103}$, R$_{104}$, R$_{105}$, M, Z$_1$, Z$_2$, Q, W, M', R$_{106}$, R$_{107}$, R$_{108}$ q, m, m', m'", r, t, R$_a$, R$_b$, R$_c$, and the substituents of R$^{3a}$ are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; R$^6$ is unsubstituted or substituted arylalkyl; and R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$ q, m, m', m'", r, t, R$_a$, R$_b$, R$_c$, and the substituents of R$^{3a}$ and R$^6$ are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; R$^6$ is unsubstituted or substituted arylalkyl; and R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$ q, m, m', m'", r, t, R$_a$, R$_b$, R$_c$, and the substituents of R$^{3a}$ and R$^6$ are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; R$^6$ is arylalkyl substituted with 0 or one R$^{6a}$; and R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$ q, m, m', m'", r, t, R$_a$, R$_b$, R$_c$, and the substituents of R$^{3a}$ are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; R$^6$ is arylalkyl substituted with 0 or one R$^{6a}$; and R$^{6a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$ q, m, m', m'", r, t, R$_a$, R$_b$, R$_c$, and the substituents of R$^{3a}$ are as defined in formula (VII).

For example, the present invention provides a compound of formula (VII) wherein R$^4$ is H; R$^5$ is OR$^{16}$; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; R$^6$ is arylalkyl substituted with 0 or one R$^{6a}$; each R$_{104}$ is independently hydrogen or alkyl; each R$_{105}$ is independently hydrogen or alkyl; each M is independently hydrogen or alkyl; Z$_1$ and Z$_2$ are O; Q is O; W is P; and R$^{6a}$, R$^{14}$, R$^{15}$, R$^{16}$, R$_{103}$, M', R$_{106}$, R$_{107}$, R$_{108}$, q, m, m', m'", r, t, R$_a$, R$_b$, R$_c$, and the substituents of R$^{3a}$ and M are as defined in formula (VII).

For example, the present invention provides a compound of formula (VII) wherein R$^4$ is OR$^{16}$; R$^5$ is H; R$^2$ is alkyl; R$^3$ is arylalkyl wherein the aryl moiety of the arylalkyl is unsubstituted or substituted with one R$^{3a}$, wherein R$^{3a}$ is unsubstituted or substituted aryl or unsubstituted or substituted heteroaryl; R$^1$ is alkyl; R$^6$ is arylalkyl substituted with 0 or one R$^{6a}$; each R$_{104}$ is independently hydrogen or alkyl; each R$_{105}$ is independently hydrogen or alkyl; each M is independently hydrogen or alkyl; $Z_1$ and $Z_2$ are O; Q is O; W is P; and $R^{6a}$, $R^{14}$, $R^{15}$, $R^{16}$, $R_{103}$, M', $R_{106}$, $R_{107}$, $R_{108}$, q, m, m', m'', r, t, $R_a$, $R_b$, $R_c$, and the substituents of $R^{3a}$ and M are as defined in formula (VII).

For example, the present invention provides a compound of formula (VII) wherein $R^4$ is H; $R^5$ is $OR^{16}$; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^1$ is alkyl; $R^6$ is arylalkyl substituted with 0 or one $R^{6a}$; each $R_{104}$ is independently hydrogen or alkyl; each $R_{105}$ is independently hydrogen or alkyl; each M is independently hydrogen or alkyl; $Z_1$ and $Z_2$ are O; Q is O; W is P; $R^{14}$ is —$OR_a$, -alkyl$OR_a$, unsubstituted or substituted aryl or unsubstituted or substituted heteroaryl; and $R^{6a}$, $R^{15}$, $R^{16}$, $R_{103}$, M', $R_{106}$, $R_{107}$, $R_{108}$, q, m, m', m'', r, t, $R_a$, $R_b$, $R_c$, and the substituents of $R^{3a}$, M and $R^{14}$ are as defined in formula (VII).

For example, the present invention provides a compound of formula (VII) wherein $R^4$ is $OR^{16}$; $R^5$ is H; $R^2$ is alkyl; $R^3$ is arylalkyl wherein the aryl moiety of the arylalkyl is unsubstituted or substituted with one $R^{3a}$, wherein $R^{3a}$ is unsubstituted or substituted aryl or unsubstituted or substituted heteroaryl; $R^1$ is alkyl; $R^6$ is arylalkyl substituted with 0 or one $R^{6a}$; each $R_{104}$ is independently hydrogen or alkyl; each $R_{105}$ is independently hydrogen or alkyl; each M is independently hydrogen or alkyl; $Z_1$ and $Z_2$ are O; Q is O; W is P; $R^{14}$ is —$OR_a$, -alkyl$OR_a$, unsubstituted or substituted aryl or unsubstituted or substituted heteroaryl; and $R^{6a}$, $R^{15}$, $R^{16}$, $R_{103}$, M', $R_{106}$, $R_{107}$, $R_{108}$, q, m, m', m'', r, t, $R_a$, $R_b$, $R_c$, and the substituents of $R^{3a}$, M and $R^{14}$ are as defined in formula (VII).

For example, the present invention provides a compound of formula (VII) wherein $R^4$ is H; $R^5$ is $OR^{16}$; $R^2$ is C1 alkyl, C2 alkyl, C3 alkyl, C4 alkyl or C5 alkyl; $R^3$ is phenylmethyl wherein the phenyl moiety of the phenylmethyl is unsubstituted or substituted with one $R^{3a}$, wherein $R^{3a}$ is unsubstituted or substituted pyridyl; $R^1$ is C1 alkyl, C2 alkyl, C3 alkyl, C4 alkyl or C5 alkyl; $R^6$ is phenylmethyl substituted with 0 or one $R^{6a}$ wherein $R^{6a}$ is unsubstituted or substituted pyridyl; each $R_{104}$ is independently hydrogen, C1 alkyl, C2 alkyl, C3 alkyl, C4 alkyl or C5 alkyl; each $R_{105}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_1$ and $Z_2$ are O; Q is O; W is P; $R^{14}$ is —$OR_a$, -alkyl$OR_a$, thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each of the thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl and indazolyl are independently unsubstituted or substituted; and $R^{15}$, $R^{16}$, $R_{103}$, M', $R_{106}$, $R_{107}$, $R_{108}$, q, m, m', m'', r, t, $R_a$, $R_b$, $R_c$, and the substituents of $R^{3a}$, $R^{6a}$, M and $R^{14}$ are as defined in formula (VII).

For example, the present invention provides a compound of formula (VII) wherein $R^4$ is $OR^{16}$; $R^5$ is H; $R^2$ is C1 alkyl, C2 alkyl, C3 alkyl, C4 alkyl or C5 alkyl; $R^3$ is phenylmethyl wherein the phenyl moiety of the phenylmethyl is unsubstituted or substituted with one $R^{3a}$ wherein $R^{3a}$ is unsubstituted or substituted pyridyl; $R^1$ is C1 alkyl, C2 alkyl, C3 alkyl, C4 alkyl or C5 alkyl; $R^6$ is phenylmethyl substituted with 0 or one $R^{6a}$ wherein $R^{6a}$ is unsubstituted or substituted pyridyl; each $R_{104}$ is independently hydrogen, C1 alkyl, C2 alkyl, C3 alkyl, C4 alkyl or C5 alkyl; each $R_{105}$ is independently hydrogen, C1 alkyl, C2 alkyl, C3 alkyl, C4 alkyl or C5 alkyl; each M is independently hydrogen, C1 alkyl, C2 alkyl, C3 alkyl, C4 alkyl or C5 alkyl; $Z_1$ and $Z_2$ are O; Q is O; W is P; $R^{14}$ is —$OR_a$, -alkyl$OR_a$, thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl or indazolyl wherein each of the thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl and indazolyl are independently unsubstituted or substituted; and $R^{15}$, $R^{16}$, $R_{103}$, M', $R_{106}$, $R_{107}$, $R_{108}$, q, m, m', m'', r, t, $R_a$, $R_b$, $R_a$, and the substituents of $R^{3a}$, $R^{6a}$, M and $R^{14}$ are as defined in formula (VII).

For example, the present invention provides a compound of formula (VII) wherein $R^4$ is H, $R^5$ is $OR^{16}$, $R^2$ is C1, C2, C3, C4 or C5 alkyl, $R^3$ is phenylmethyl substituted with wherein $R^{3a}$ is substituted or unsubstituted pyridyl, $R^{14}$ is $OR_a$, -alkyl$OR_a$, phenyl, oxazolyl, thienyl, or pyridyl, wherein $R_a$ is phenyl or hexahydro[2,3,b]furanyl and wherein each of the phenyl, oxazolyl, thienyl and pyridyl is independently unsubstituted or substituted; $R^6$ is phenylmethyl substituted with 0 or one $R^{6a}$ wherein $R^{6a}$ is substituted or unsubstituted pyridyl, $R^1$ is C1, C2, C3, C4 or C5 alkyl; and $R^{15}$, $R^{16}$, $R_{103}$, M', M, $R_{104}$, $R_{105}$, $R_{106}$, $R_{107}$, $R_{108}$, $Z_1$, $Z_2$, q, m, m', m'', r, t, $R_a$, $R_b$, $R_c$ and the substituents of M and $R^{14}$ are as defined in formula (VII).

For example, the present invention provides a compound of formula (VII) wherein $R^4$ is $OR^{16}$, $R^5$ is H, $R^2$ is C1, C2, C3, C4 or C5 alkyl, $R^3$ is phenylmethyl substituted with 0 or one $R^{3a}$ wherein $R^{3a}$ is substituted or unsubstituted pyridyl, $R^{14}$ is $OR_a$, -alkyl$OR_a$, phenyl, oxazolyl, thienyl, or pyridyl, wherein $R_a$ is phenyl or hexahydro[2,3,b]furanyl and wherein each of the phenyl, oxazolyl, thienyl and pyridyl is independently unsubstituted or substituted; $R^6$ is phenylmethyl substituted with 0 or one $R^{6a}$ wherein $R^{6a}$ is substituted or unsubstituted pyridyl, $R^1$ is C1, C2, C3, C4 or C5 alkyl; and $R^{15}$, $R^{16}$, $R_{103}$, M', M, $R_{104}$, $R_{105}$, $R_{106}$, $R_{107}$, $R_{108}$, $Z_1$, $Z_2$, q, m, m', m'', r, t, $R_a$, $R_b$, $R_c$ and the substituents of M and $R^{14}$ are as defined in formula (VII).

For example, the present invention provides a compound of formula (VII) wherein $R^4$ is H, $R^5$ is $OR^{16}$, $R^2$ is isopropyl, 1-methylpropyl or tert-butyl, $R^3$ is phenylmethyl substituted with 0 or one $R^{3a}$ wherein $R^{3a}$ is pyridyl substituted with 0 or one substituent selected from the group consisting of methyl and methoxide, $R^{14}$ is $OR_a$, -alkyl$OR_a$, phenyl, oxazolyl, thienyl, or pyridyl, wherein $R_a$ is phenyl or hexahydro[2,3,b]furanyl and wherein each of the phenyl, oxazolyl, thienyl and pyridyl is independently unsubstituted or substituted; 6 is phenylmethyl substituted with 0 or one $R^{6a}$, wherein $R^{6a}$ is pyridyl substituted with 0 or one substituent selected from the group consisting of methyl and methoxide; $R^1$ is methyl; and $R^{15}$, $R^{16}$, $R_{103}$, M', M, $R_{104}$, $R_{105}$, $R_{106}$, $R_{107}$, $R_{108}$, $Z_1$, $Z_2$, q, m, m', m'', r, t, $R_a$, $R_b$, $R_c$, and the substituents of M and $R^{14}$ are as defined in formula (VII).

For example, the present invention provides a compound of formula (VII) wherein $R^4$ is $OR^{16}$, $R^5$ is H, $R^2$ is isopropyl, 1-methylpropyl or tert-butyl, $R^3$ is phenylmethyl substituted with 0 or one $R^{3a}$ wherein $R^{3a}$ is pyridyl substituted with 0 or one substituent selected from the group consisting of methyl and methoxide, $R^{14}$ is $OR_a$, -alkyl$OR_a$, phenyl, oxazolyl, thienyl, or pyridyl, wherein $R_a$ is phenyl or hexahydro[2,3,b]furanyl and wherein each of the phenyl, oxazolyl, thienyl and pyridyl is independently unsubstituted or substituted; $R^6$ is phenylmethyl substituted with 0 or one $R^{6a}$, wherein $R^{6a}$ is pyridyl substituted with 0 or one substituent selected from the group consisting of methyl and methoxide; $R^1$ is methyl; and $R^{15}$, $R^{16}$, $R_{103}$, M', M, $R_{104}$, $R_{105}$, $R_{106}$, $R_{107}$, $R_{108}$, $Z_1$, $Z_2$, q, m, m', m'', r, t, $R_a$, $R_b$, $R_c$, and the substituents of M and $R^{14}$ are as defined in formula (VII).

Exemplary compounds of the present invention of formula (VII) include, but not limited to, the following:

(3R,3aS,6aR)-hexahydrofuro[2,3-b]furan-3-yl(1S,3S,4S)-1-benzyl-3-hydroxy-4-({(2S)-2-[(methoxycarbonyl)amino]-3,3-dimethylbutanoyl}amino)-5-[4-(2-pyridinyl)phenyl]pentylcarbamate;

(3R,3aR,6aS)-hexahydrofuro[2,3-b]furan-3-yl(1S,3S,4S)-1-benzyl-3-hydroxy-4-({(2S)-2-[(methoxycarbonyl)amino]-3,3-dimethylbutanoyl}amino)-5-[4-(2-pyridinyl)phenyl]pentylcarbamate;

(3R,3aS,6aR)-hexahydrofuro[2,3-b]furan-3-yl(1S,2S,4S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate;

(3R,3aR,6aS)-hexahydrofuro[2,3-b]furan-3-yl(1S,2S,4S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate;

methyl(1S)-1-[({(1S,3S,4S)-4-{[(2,6-dimethylphenoxy)acetyl]amino}-3-hydroxy-5-phenyl-1-[4-(2-pyridinyl)benzyl]pentyl}amino)carbonyl]-2,2-dimethylpropylcarbamate;

methyl(1S)-1-[({(1S,2S,4S)-4-{[(2,6-dimethylphenoxy)acetyl]amino}-2-hydroxy-5-phenyl-1-[4-(2-pyridinyl)benzyl]pentyl}amino)carbonyl]-2,2-dimethylpropylcarbamate;

(3R,3aS,6aR)-hexahydrofuro[2,3-b]furan-3-yl(1S,2S,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate;

(3R,3aR,6aS)-hexahydrofuro[2,3-b]furan-3-yl(1S,2S,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate;

methyl(1S)-1-[({(1R,3S,4S)-4-{[(2,6-dimethylphenoxy)acetyl]amino}-3-hydroxy-5-phenyl-1-[4-(2-pyridinyl)benzyl]pentyl}amino)carbonyl]-2,2-dimethylpropylcarbamate;

methyl(1R)-1-{[((1S,2S,4S)-4-{[4-(aminosulfonyl)benzoyl]amino}-1-benzyl-2-hydroxy-5-phenylpentyl)amino]carbonyl}-2,2-dimethylpropylcarbamate;

methyl(1S)-1-({[(1R,3S,4S)-4-[(4-chloro-2-methylbenzoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1R,3S,4S)-3-hydroxy-4-[(4-methoxy-2-methylbenzoyl)amino]-5-phenyl-1-(4-pyridin-2-ylbenzyl)pentyl]amino}carbonyl)-2,2-dimethylpropylcarbamate;

methyl(1S)-1-({[(1R,3S,4S)-3-hydroxy-4-[(2-methylbenzoyl)amino]-5-phenyl-1-(4-pyridin-2-ylbenzyl)pentyl]amino}carbonyl)-2,2-dimethylpropylcarbamate;

methyl(1S)-1-{[((1S,2S,4S)-4-{[3-(aminosulfonyl)benzoyl]amino}-1-benzyl-2-hydroxy-5-phenylpentyl)amino]carbonyl}-2,2-dimethylpropylcarbamate;

methyl(1S)-1-({[(1S,3S,4S)-4-[(3-chloro-2-methylbenzoyl)amino]-3-hydroxy-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-[(3-hydroxy-2-methylbenzoyl)amino]-5-phenyl-1-(4-pyridin-2-ylbenzyl)pentyl]amino}carbonyl)-2,2-dimethylpropylcarbamate;

methyl(1S)-1-({[(1S,3S,4S)-3-hydroxy-4-{[(3-methylisoxazol-4-yl)carbonyl]amino}-5-phenyl-1-(4-pyridin-2-ylbenzyl)pentyl]amino}carbonyl)-2,2-dimethylpropylcarbamate;

methyl(1S)-1-({[(1S,3S,4S)-4-{[(3,5-dimethylisoxazol-4-yl)carbonyl]amino}-3-hydroxy-5-phenyl-1-(4-pyridin-2-ylbenzyl)pentyl]amino}carbonyl)-2,2-dimethylpropylcarbamate;

methyl(1S)-1-[({(1S,2S,4S)-1-benzyl-2-hydroxy-5-phenyl-4-[(thien-2-ylcarbonyl)amino]pentyl}amino)carbonyl]-2,2-dimethylpropylcarbamate;

methyl(1S)-1-[({(1S,2S,4S)-1-benzyl-2-hydroxy-5-phenyl-4-[(thien-3-ylcarbonyl)amino]pentyl}amino)carbonyl]-2,2-dimethylpropylcarbamate;

methyl(1S)-1-{[((1S,2S,4S)-1-benzyl-2-hydroxy-4-{[(3-methylthien-2-yl)carbonyl]amino}-5-phenylpentyl)amino]carbonyl}-2,2-dimethylpropylcarbamate;

methyl(1S)-1-{[((1S,2S,4S)-1-benzyl-2-hydroxy-4-{[(5-methylthien-2-yl)carbonyl]amino}-5-phenylpentyl)amino]carbonyl}-2,2-dimethylpropylcarbamate;

methyl(1S)-1-{[((1S,2S,4S)-1-benzyl-2-hydroxy-{[(1-methyl-1H-pyrrol-2-yl)carbonyl]amino}-5-phenylpentyl)amino]carbonyl}-2,2-dimethylpropylcarbamate; and methyl(1S)-1-{[((1S,2S,4S)-1-benzyl-4-{[(3,5-dimethylisoxazol-4-yl)carbonyl]amino}-2-hydroxy-5-phenylpentyl)amino]carbonyl}-2,2-dimethylpropylcarbamate;

or a pharmaceutically acceptable salt form, prodrug or stereoisomer, thereof.

In an eighth embodiment the present invention provides a compound of formula (VIII)

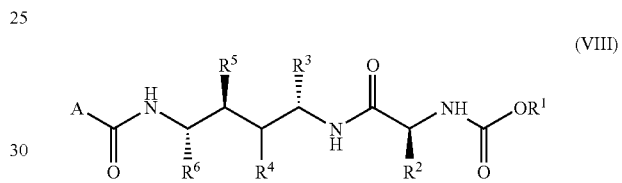

or a pharmaceutically acceptable salt form, prodrug or stereoisomer thereof, wherein:

A is

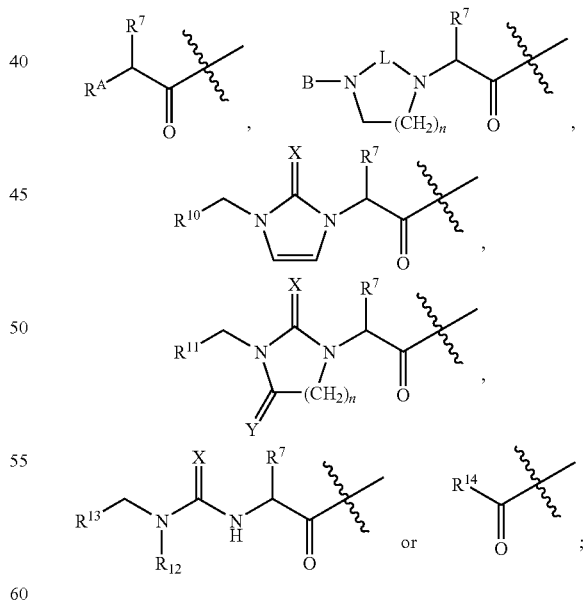

X is O, S or NH;
Y is O, S or NH;
B is H or —$CH_2R^9$;
L is —C(=O), —C(=S), —C(=NH) or —S(O)$_2$;
$R^4$ is —N(H)C(O)$R^8$, —O($R_a$), —OC(O)O$R_a$, —N$R_aR_b$, —N($R_b$)S(O)$_2R_a$, —N($R_b$)alkylN($R_b$)S(O)$_2R_a$, —N($R_b$)

alkylN($R_b$)C(O)O$R_a$, —N($R_b$)alkylN($R_b$)C(O)N$R_aR_b$, -alkylSR$_a$, -alkylS(O)R$_a$ or -alkylS(O)$_2$R$_a$;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —OR$_a$, —SR$_a$, —SOR$_a$, —SO$_2$R$_a$, —NR$_aR_b$, —NR$_b$C(O)R$_a$—N(R$_b$)C(O)OR$_a$, —N(R$_a$)C(=N)NR$_aR_b$, —N(R$_a$)C(O)NR$_aR_b$, —C(O)NR$_aR_b$, —C(O)OR$_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNR$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_aR_b$, -alkylN(R$_b$)C(O)R$_a$, -alkylN(R$_b$)C(O)OR$_a$, -alkylN(R$_a$)C(=N)NR$_aR_b$, -alkylN(R$_a$)C(O)NR$_aR_b$, -alkylC(O)NR$_aR_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$;

$R^4$ is H and $R^5$ is OR$^{16}$; or
$R^5$ is H and $R^4$ is OR$^6$; or
$R^4$ and $R^5$ are —OR$^{16}$;

$R^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_aR_b$, -alkylN(R$_b$)C(O)R$_a$, -alkylN(R$_b$)C(O)OR$_a$, -alkylN(R$_a$)C(=N)NR$_aR_b$, -alkylN(R$_a$)C(O)NR$_aR_b$, -alkylC(O)NR$_aR_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —NH$_2$, N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^7$ is —N($R_b$)C(O)O$R_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —O$R_a$, OC(O)$R_a$, —S$R_a$, —SO$R_a$, —SO$_2$$R_a$, —N$R_a$$R_b$, —N($R_b$)C(O)$R_a$, —N($R_b$)C(O)O$R_a$, —N($R_a$)C(=N)N$R_a$$R_b$, —N($R_a$)C(O)N$R_a$$R_b$, —C(O)N$R_a$$R_b$, —C(O)O$R_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^8$ is —O$R_a$, —N$R_a$$R_b$, —N($R_b$)C(O)O$R_a$, -alkylO$R_a$, -alkylOC(O)$R_a$, or —O-alkylC(O)$R_a$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —O$R_a$, —S$R_a$, —SO$R_a$, —SO$_2$$R_a$, —SO$_2$N$R_a$, —SO$_2$O$R_a$, —N$R_a$$R_b$, —N($R_b$)C(O)$R_a$, —N($R_b$)SO$_2$$R_a$, —N($R_b$)SO$_2$N$R_a$$R_b$, —N($R_b$)C(O)N$R_a$$R_b$, —N($R_b$)C(O)O$R_a$, —C(O)$R_a$, —C(O)N$R_a$$R_b$, —C(O)O$R_a$, haloalkyl, nitroalkyl, cynaoalkyl, formylalkyl, -alkylO$R_a$, -alkyl-O—P(O)(O$R_a$)(O$R_a$), -alkylN$R_a$$R_b$, -alkylN($R_b$)C(O)O$R_a$, -alkylN($R_b$)SO$_2$N$R_a$$R_b$, -alkylN($R_b$)C(O)$R_a$, -alkylN($R_b$)C(O)N$R_a$$R_b$, -alkylN($R_b$)SO$_2$$R_a$, -alkylC(O)O$R_a$, -alkylC(O)$R_a$, -alkylC(O)N$R_a$$R_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —O$R_a$, —S$R_a$, —SO$R_a$, SO$_2$$R_a$, —SO$_2$N$R_a$, —SO$_2$O$R_a$, —N$R_a$$R_b$, —N($R_b$)C(O)$R_a$, —N($R_b$)SO$_2$$R_a$, —N($R_b$)SO$_2$N$R_a$$R_b$, —N($R_b$)C(O)N$R_a$$R_b$, —N($R_b$)C(O)O$R_a$, —C(O)$R_a$, —C(O)N$R_a$$R_b$, —C(O)O$R_a$, haloalkyl, nitroalkyl, cynaoalkyl, formylalkyl, -alkylO$R_a$, -alkyl-O—P(O)(O$R_a$)(O$R_a$), -alkylN$R_a$$R_b$, -alkylN($R_b$)C(O)O$R_a$, -alkylN($R_b$)SO$_2$N$R_a$$R_b$, -alkylN($R_b$)C(O)$R_a$, -alkylN($R_b$)C(O)N$R_a$$R_b$, -alkylN($R_b$)SO$_2$$R_a$, -alkylC(O)O$R_a$, -alkylC(O)$R_a$, -alkylC(O)N$R_a$$R_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —O$R_a$, —S$R_a$, —SO$R_a$, —SO$_2$$R_a$, —SO$_2$N$R_a$, —SO$_2$O$R_a$, —N$R_a$$R_b$, —N($R_b$)C(O)$R_a$, —N($R_b$)SO$_2$$R_a$, —N($R_b$)SO$_2$N$R_a$$R_b$, —N($R_b$)C(O)N$R_a$$R_b$, —N($R_b$)C(O)O$R_a$, —C(O)$R_a$, —C(O)N$R_a$$R_b$, —C(O)O$R_a$, haloalkyl, nitroalkyl, cynaoalkyl, formylalkyl, -alkylO$R_a$, -alkyl-O—P(O)(O$R_a$)(O$R_a$), -alkylN$R_a$$R_b$, -alkylN($R_b$)C(O)O$R_a$, -alkylN($R_b$)SO$_2$N$R_a$$R_b$, -alkylN($R_b$)C(O)$R_a$, -alkylN($R_b$)C(O)N$R_a$$R_b$, -alkylN($R_b$)SO$_2$$R_a$, -alkylC(O)O$R_a$, -alkylC(O)$R_a$, -alkylC(O)N$R_a$$R_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —O$R_a$, —S$R_a$, —SO$R_a$, —SO$_2$$R_a$, —SO$_2$N$R_a$, SO$_2$O$R_a$, —N$R_a$$R_b$, —N($R_b$)C(O)$R_a$, —N($R_b$)C(O)O$R_a$, —C(O)N$R_a$$R_b$, —C(O)O$R_a$, haloalkyl, nitroalkyl, cynaoalkyl, -alkylO$R_a$, -alkyl-O—P(O)(O$R_a$)(O$R_a$), -alkylN$R_a$$R_b$, -alkylN($R_b$)C(O)$R_a$, -alkylN($R_b$)C(O)N$R_a$$R_b$, -alkylN($R_b$)SO$_2$$R_a$, -alkylC(O)O$R_a$, -alkyl-C(O)N$R_a$$R_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{14}$ is —OR$_a$, -alkylOR$_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —S(O)$_2$NR$_a$R$_b$, —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{16}$ is hydrogen or R$^{15}$;

R$^{15}$ is

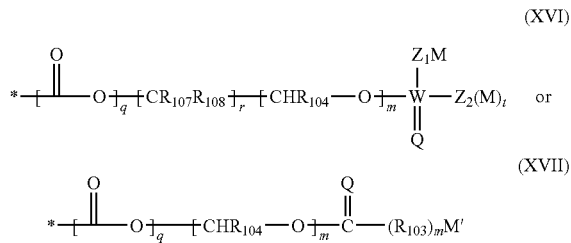

(XVI)

(XVII)

R$_{103}$ is C(R$_{105}$)$_2$, O or —N(R$_{105}$);

R$_{104}$ is hydrogen, alkyl, haloalkyl, alkoxycarbonyl, aminocarbonyl, alkylaminocarbonyl or dialkylaminocarbonyl, each M is independently selected from the group consisting of H, —N(R$_{105}$)$_2$, alkyl, alkenyl, and R$_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, Z$_1$ and Z$_2$ are —CH$_2$;

Z$_1$ is CH$_2$, O, S, —N(R$_{105}$), or, when M is absent, H;

Z$_2$ is CH$_2$, O, S or —N(R$_{105}$);

Q is O or S;

W is P or S; wherein when W is S, Z$_1$ and Z$_2$ are not S;

M' is H, alkyl, alkenyl or R$_{106}$; wherein 1 to 4 —CH$_2$ radicals of the alkyl or alkenyl is optionally replaced by a heteroatom group selected from O, S, S(O), SO$_2$, or N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{10}$, —SOR$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

each R$_{107}$ and R$_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

R$_a$ and R$_b$ at each occurrence are independently selected from the group consisting of hydrogen, alkyl, alkenyl, alkynyl, cycloalkyl, aryl, heteroaryl and heterocycle; wherein each R$_a$ and R$_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$; alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl), —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)

N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (VIII) wherein X is O; Y is O and L, B, $R^4$, $R^1$, $R^{1a}$, $R^2$, $R^{2a}$, $R^3$, $R^{3a}$, $R^4$, $R^5$, $R^6$, $R^{6a}$, $R^7$, $R^{7a}$, $R^8$, $R^9$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and n are defined in formula (VIII).

For example, the present invention provides a compound of formula (VIII) wherein X is O, Y is O, $R^4$ is H, $R^5$ is $OR^{16}$; $R^2$ is alkyl; and L, B, $R^4$, $R^1$, $R^{1a}$, $R^3$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, M', $R_{106}$, $R_{107}$, $R_{108}$, q, m, m', m", r, t, $R_a$, $R_b$, $R_c$, and n are defined in formula (VIII).

For example, the present invention provides a compound of formula (VIII) wherein X is O, Y is O, $R^4$ is H, $R^5$ is $OR^{16}$, $R^2$ is alkyl, $R^3$ is arylalkyl; and L, B, $R^4$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and n are defined in formula (VIII).

For example, the present invention provides a compound of formula (VIII) wherein X is O, Y is O, $R^4$ is H, $R^5$ is $OR^{16}$, $R^2$ is alkyl, $R^3$ is arylalkyl substituted with 0 or one $R^{3a}$; and L, B, $R^4$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a R_b$, $R_c$, and defined in formula (VIII).

For example, the present invention provides a compound of formula (VIII) wherein X is O, Y is O, $R^4$ is H, $R^5$ is $OR^{16}$, $R^2$ is alkyl, $R^1$ is arylalkyl substituted with 0 or one $R^{3a}$ is aryl or heteroaryl; and L, B, $R^4$, $R^1$, $R^{1a}$, $R^{3a}$, $R^6$, $R_{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, n and the substituents of $R^{3a}$ are defined in formula (VIII).

For example, the present invention provides a compound of formula (VIII) wherein X is O, Y is O, $R^4$ is H, $R^5$ is $OR^{16}$, $R^2$ is alkyl, $R^3$ is arylalkyl substituted with 0 or one $R^{3a}$, wherein, $R^{3a}$ is aryl or heteroaryl, $R^1$ is alkyl; and L, B, $R^4$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, n and the substituents of $R^{3a}$ are defined in formula (VIII).

For example, the present invention provides a compound of formula (VIII) wherein X is O, Y is O, $R^4$ is H, $R^5$ is $OR^{16}$, $R^2$ is alkyl, $R^3$ is arylalkyl substituted with 0 or one $R^{3a}$ wherein $R^{3a}$ is aryl or heteroaryl, $R^1$ is alkyl, and $R^6$ is arylalkyl substituted with 0 or one $R^{6a}$ wherein $R^{6a}$ is aryl or heteroaryl; and L, B, $R^4$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, n and the substituents of $R^{3a}$ and $R^{6a}$ are defined in formula (VIII).

For example, the present invention provides a compound of formula (VIII) wherein X is O, Y is O, $R^4$ is H, $R^5$ is $OR^{16}$, $R^2$ is alkyl, $R^1$ is alkyl, each $R_{104}$ is independently hydrogen or alkyl, each $R_{105}$ is independently hydrogen or alkyl, each M is independently hydrogen or alkyl, $Z_1$ and $Z_2$ are O, Q is O, W is P, $R^6$ is arylalkyl substituted with 0 or one $R^{6a}$ wherein $R^{6a}$ is aryl or heteroaryl, $R^3$ is arylalkyl substituted with $R^{3a}$ wherein $R^{3a}$ is aryl or heteroaryl; and L, B, $R^4$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, M', $R_{106}$, $R_{107}$, $R_{108}$, q, m, m', m", r, t, $R_a$, $R_b$, $R_c$, n and the substituents of $R^{3a}$ and $R^{6a}$ are defined in formula (VIII).

In a ninth embodiment the present invention provides a compound of formula (IX)

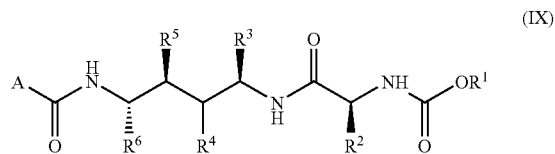

(IX)

or a pharmaceutically acceptable salt form, prodrug or stereoisomer thereof, wherein:

A is

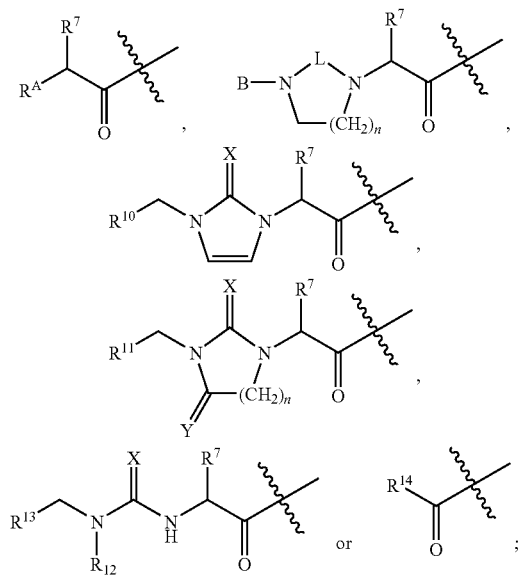

X is O, S or NH;
Y is O, S or NH;
B is H or —CH$_2$R$^9$;
L is —C(=O), —C(=S), —C(=NH) or —S(O)$_2$;
$R^A$ is —N(H)C(O)R$^8$, —O(R$_a$), —OC(O)OR$_a$, —NR$_a$R$_b$, —N(R$_b$)S(O)$_2$R$_a$, —N(R$_b$)alkylN(R$_b$)S(O)$_2$R$_a$, —N(R$_b$)alkylN(R$_b$)C(O)OR$_a$, —N(R$_b$)alkylN(R$_b$)C(O)NR$_a$R$_b$, -alkylSR$_a$, -alkylS(O)R$_a$ or —alkylS(O)$_2$R$_a$;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^4$ is H and $R^5$ is OR$^6$; or
$R^5$ is H and $R^4$ is OR$^{16}$; or
$R^4$ and $R^5$ are —OR$^{16}$;

$R^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N (alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^8$ is —OR$_a$, —NR$_a$R$_b$, —N(R$_b$)C(O)OR$_a$, -alkylOR$_a$, -alkylOC(O)R$_a$, or -alkylC(O)R$_a$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)C(O)OR$_a$, —C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkyl-C(O)NR$_a$R$_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{14}$ is —OR$_a$, -alkylOR$_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —S(O)$_2$NR$_a$R$_b$, —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)

N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{16}$ is hydrogen or $R^{15}$;

$R^{15}$ is

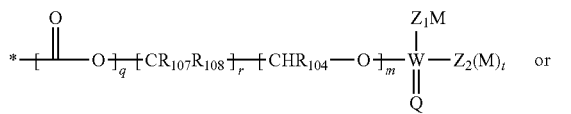 (XVI)

or

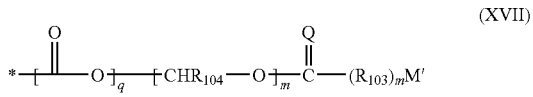 (XVII)

$R_{103}$ is C($R_{105}$)$_2$, O or —N($R_{105}$);

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —N($R_{105}$)$_2$, alkyl, alkenyl, and $R_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N($R_{105}$); and wherein any hydrogen in said alkyl, alkenyl or $R_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, Z$_1$ and Z$_2$ are —CH$_2$;

$Z_1$ is CH$_2$, O, S, N($R_{105}$), or, when M is absent, H;

$Z_2$ is CH$_2$, O, S or —N($R_{105}$);

Q is O or S;

W is P or S; wherein when W is S, $Z_1$ and $Z_2$ are not S;

M' is H, alkyl, alkenyl or $R_{106}$; wherein 1 to 4 —CH$_2$ radicals of the alkyl or alkenyl is optionally replaced by a heteroatom group selected from O, S, S(O), SO$_2$, or N($R_{105}$); and wherein any hydrogen in said alkyl, alkenyl or $R_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N($R_{105}$); and wherein any of said ring system is substituted with 0, 1, 2, 3, 4, 5 or 6 substituents selected from the group consisting of hydroxy, alkyl, alkoxy, and —OC(O)alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N($R_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (IX) wherein L is —C(=O) or —C(=S), X is O; Y is O; and L, B, $R^A$, $R^1$, $R^{1a}$, $R^2$, $R^{2a}$, $R^3$, $R^{3a}$, $R^4$, $R^5$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and n are defined in formula (IX).

For example, the present invention provides a compound of formula (IX) wherein X is O, Y is O, $R^4$ is H, $R^5$ is $OR^{16}$, $R^2$ is alkyl; and L, B, $R^A$, $R^1$, $R^{1a}$, $R^3$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (IX).

For example, the present invention provides a compound of formula (IX) wherein X is O, Y is O, $R^4$ is H, $R^5$ is $OR^{16}$, $R^2$ is alkyl, $R^3$ is arylalkyl; and L, B, $R^A$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of the aryl moiety of arylalkyl of $R^3$ are defined in formula (IX).

For example, the present invention provides a compound of formula (IX) wherein X is O, Y is O, $R^4$ is H, $R^5$ is $OR^{16}$, $R^2$ is alkyl and $R^3$ is arylalkyl wherein the aryl moiety of the arylalkyl is substituted with 0 or one $R^{3a}$; and L, B, $R^A$, $R^1$, $R^{1a}$, $R^3$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (IX).

For example, the present invention provides a compound of formula (IX) wherein X is O, Y is O, $R^4$ is H, $R^5$ is $OR^{16}$, $R^2$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (IX).

For example, the present invention provides a compound of formula (IX) wherein X is O, Y is O, $R^4$ is H, $R^5$ is $OR^{16}$, $R^2$ is alkyl, $R^1$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^A$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (IX).

For example, the present invention provides a compound of formula (IX) wherein X is O, Y is O, $R^4$ is H, $R^5$ is $OR^{16}$, $R^2$ is alkyl, $R^1$ is alkyl, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^A$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (IX).

For example, the present invention provides a compound of formula (IX) wherein X is O, Y is O, $R^4$ is H, $R^5$ is $OR^{16}$, $R^2$ is alkyl, $R^1$ is alkyl, each $R_{104}$ is independently hydrogen or alkyl, each $R_{105}$ is independently hydrogen or alkyl, each M is independently hydrogen or alkyl, $Z_1$ and $Z_2$ are O, Q is O, W is P, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^A$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (IX).

In a tenth embodiment, the present invention provides a compound of formula (X)

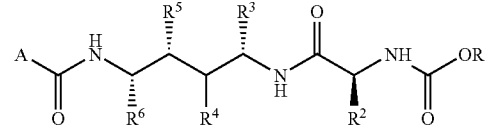

(X)

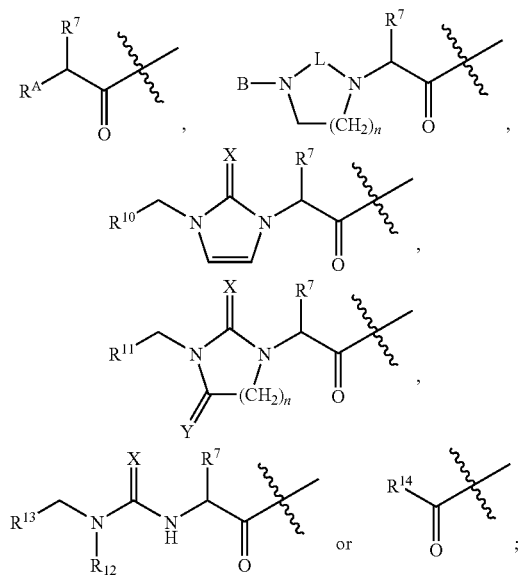

or a pharmaceutically acceptable salt form, prodrug or stereoisomer thereof, wherein:

A is

X is O, S or NH;

Y is O, S or NH;

B is H or $-CH_2R^9$;

L is $-C(=O)$, $-C(=S)$, $-C(=NH)$ or $-S(O)_2$;

$R^A$ is $-N(H)C(O)R^8$, $-O(R_a)$, $-OC(O)OR_a$, $-NR_aR_b$, $-N(R_b)S(O)_2R_a$, $-N(R_b)$alkylN$(R_b)S(O)_2R_a$, $-N(R_b)$alkylN$(R_b)C(O)OR_a$, $-N(R_b)$alkylN$(R_b)C(O)NR_aR_b$, -alkylSR$_a$, -alkylS(O)R$_a$ or -alkylS(O)$_2R_a$;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, $-NH_2$, $-N(H)$(alkyl), $-N(alkyl)_2$, $-SH$, $-S(alkyl)$, $-SO_2$(alkyl), $-N(H)C(O)$alkyl, $-N(alkyl)C(O)$alkyl, $-N(H)C(O)NH_2$, $-N(H)C(O)N(H)$(alkyl), $-N(H)C(O)N(alkyl)_2$, $-C(O)OH$, $-C(O)O$alkyl, $-C(O)NH_2$, $-C(O)N(H)$(alkyl), $-C(O)N(alkyl)_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, $-NH_2$, $-N(H)$(alkyl), $-N(alkyl)_2$, $-SH$, $-S(alkyl)$, $-SO_2$(alkyl), $-N(H)C(O)$alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$—N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^4$ is H and $R^5$ is OR$^{16}$; or
$R^5$ is H and $R^4$ is OR$^{16}$; or
$R^4$ and $R^5$ are —OR$^{16}$;

$R^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^8$ is —$OR_a$, —$NR_aR_b$, —$N(R_b)C(O)OR_a$, -alkyl$OR_a$, -alkylOC(O)$R_a$, or —O-alkylC(O)$R_a$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —$N(R_b)C(O)R_a$, —$N(R_b)SO_2R_a$, —$N(R_b)SO_2NR_aR_b$, —$N(R_b)C(O)NR_aR_b$, —$N(R_b)C(O)OR_a$, —$C(O)R_a$, —$C(O)NR_aR_b$, —$C(O)OR_a$, haloalkyl, nitroalkyl, cynaoalkyl, formylalkyl, -alkyl$OR_a$, -alkyl-O—P(O)($OR_a$)($OR_a$), -alkylN$R_aR_b$, -alkylN($R_b$)C(O)$OR_a$, -alkylN($R_b$)$SO_2NR_aR_b$, -alkylN($R_b$)C(O)$R_a$, -alkylN($R_b$)C(O)$NR_aR_b$, -alkylN($R_b$)$SO_2R_a$, -alkylC(O)$OR_a$, -alkylC(O)$R_a$, -alkylC(O)$NR_aR_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —$N(R_b)C(O)R_a$, —$N(R_b)SO_2R_a$, —$N(R_b)SO_2NR_aR_b$, —$N(R_b)C(O)NR_aR_b$, —$N(R_b)C(O)OR_a$, —$C(O)R_a$, —$C(O)NR_aR_b$, —$C(O)OR_a$, haloalkyl, nitroalkyl, cynaoalkyl, formylalkyl, -alkyl$OR_a$, -alkyl-O—P(O)($OR_a$)($OR_a$), -alkylN$R_aR_b$, alkylN($R_b$)C(O)$OR_a$, -alkylN($R_b$)$SO_2NR_aR_b$, -alkylN($R_b$)C(O)$R_a$, -alkylN($R_b$)C(O)$NR_aR_b$, -alkylN($R_b$)$SO_2R_a$, -alkylC(O)$OR_a$, -alkylC(O)$R_a$, -alkylC(O)$NR_aR_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, $R_a$, —$SR_a$, —$SOR_a$, —$SO_2R_a$, —$SO_2NR_a$, —$SO_2OR_a$, —$NR_aR_b$, —$N(R_b)C(O)R_a$, —$N(R_b)SO_2R_a$, —$N(R_b)SO_2NR_aR_b$, —$N(R_b)C(O)NR_aR_b$, —$N(R_b)C(O)OR_a$, —$C(O)R_a$, —$C(O)NR_aR_b$, —$C(O)OR_a$, haloalkyl, nitroalkyl, cynaoalkyl, formylalkyl, -alkyl$OR_a$, -alkyl-O—P(O)($OR_a$)($OR_a$), -alkylN$R_aR_b$, -alkylN($R_b$)C(O)$OR_a$, -alkylN($R_b$)$SO_2NR_aR_b$, -alkylN($R_b$)C(O)$R_a$, -alkylN($R_b$)C(O)$NR_aR_b$, -alkylN($R_b$)$SO_2R_a$, -alkylC(O)$OR_a$, -alkylC(O)$R_a$, -alkylC(O)$NR_aR_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —$OR_a$, —$SR_a$, —$SOR_a$, —$SO_2R_a$, —$SO_2NR_a$, $SO_2OR_a$, —$NR_aR_b$, —$N(R_b)C(O)R_a$, —$N(R_b)C(O)OR_a$, —$C(O)NR_aR_b$, —$C(O)OR_a$, haloalkyl, nitroalkyl, cynaoalkyl, -alkyl$OR_a$, -alkyl-O—P(O)($OR_a$)($OR_a$), -alkylN$R_aR_b$, -alkylN($R_b$)C(O)$R_a$, -alkylN($R_b$)C(O)$NR_aR_b$, -alkylN($R_b$)$SO_2R_a$, -alkylC(O)$OR_a$, -alkyl-C(O)$NR_aR_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{14}$ is —$OR_a$, -alkyl$OR_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —S(O)$_2NR_aR_b$, —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{16}$ is hydrogen or $R^{15}$;

$R^{15}$ is

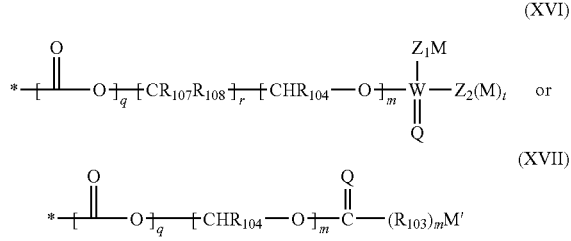

(XVI)

(XVII)

$R_{103}$ is $C(R_{105})_2$, O or $-N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, $-N(R_{105})_2$, alkyl, alkenyl, and $R_{106}$; wherein 1 to 4 $-CH_2$ radicals of the alkyl or alkenyl, other than the $-CH_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$, $NO_2$ and phenyl; provided that when M is $-N(R_{105})_2$, $Z_1$ and $Z_2$ are $-CH_2$;

$Z_1$ is $CH_2$, O, S, $-N(R_{105})$, or, when M is absent, H;

$Z_2$ is $CH_2$, O, S or $-N(R_{105})$;

Q is O or S;

W is P or S; wherein when W is S, $Z_1$ and $Z_2$ are not S;

M' is H, alkyl, alkenyl or $R_{106}$; wherein 1 to 4 $-CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $-OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $-OR_{105}$, $-R_{105}$, $-N(R_{105})_2$, $-N(R_{105})C(O)R_{105}$, $-CN$, $-C(O)OR_{105}$, $-C(O)N(R_{105})_2$, halo and $-CF_3$;

each $R_{107}$ and $R_{108}$ are independently selected from the group consisting of hydrogen and alkyl;

q is 0 or 1;

m is 0 or 1;

m' is 0 or 1;

m'' is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, alkyl, alkenyl, alkynyl, hydroxy, alkoxy, $-NH_2$, $-N(H)(alkyl)$, $-N(alkyl)$, $-SH$, $-S(alkyl)$, $-SO_2(alkyl)$, $-N(H)C(O)$alkyl, $-N(alkyl)C(O)$alkyl, $-N(H)C(O)NH_2$, $-N(H)C(O)N(H)(alkyl)$, $-N(H)C(O)N(alkyl)_2$, $-C(O)OH$, $-C(O)O$alkyl, $-C(O)NH_2$, $-C(O)N(H)(alkyl)$, $-C(O)N(alkyl)_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, $-NH_2$, $-N(H)(alkyl)$, $-N(alkyl)_2$, $-SH$, $-S(alkyl)$, $-SO_2(alkyl)$, $-N(H)C(O)$alkyl, $-N(alkyl)C(O)$alkyl, $-N(H)C(O)NH_2$, $-N(H)C(O)N(H)(alkyl)$, $-N(H)C(O)N(alkyl)_2$, $-C(O)OH$, $-C(O)O$alkyl, $-C(O)NH_2$, $-C(O)N(H)(alkyl)$, $-C(O)N(alkyl)_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, $-NH_2$, $-N(H)(alkyl)$, $-N(alkyl)_2$, $-SH$, $-S(alkyl)$, $-SO_2(alkyl)$, $-N(H)C(O)$alkyl, $-N(alkyl)C(O)$alkyl, $-N(H)C(O)NH_2$, $-N(H)C(O)N(H)(alkyl)$, $-N(H)C(O)N(alkyl)_2$, $-C(O)OH$, $-C(O)O$alkyl, $-C(O)NH_2$, $-C(O)N(H)(alkyl)$, $-C(O)N(alkyl)_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (X) wherein L is $-C(=O)$ or $-C(=S)$, X is O; Y is O; and L, B, $R^4$, $R^1$, $R^{1a}$, $R^2$, $R^{2a}$, $R^3$, $R^{3a}$, $R^4$, $R^5$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (X).

For example, the present invention provides a compound of formula (X) wherein X is O, Y is O, $R^4$ is H, $R^5$ is $OR^{16}$, $R^2$ is alkyl; and L, B, $R^A$, $R^1$, $R^{1a}$, $R^3$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (X).

For example, the present invention provides a compound of formula (X) wherein X is O, Y is O, R is H, $R^5$ is $OR^{16}$, $R^2$ is alkyl, $R^3$ is arylalkyl; and L, B, $R^4$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of the aryl moiety of arylalkyl of $R^3$ are defined in formula (X).

For example, the present invention provides a compound of formula (X) wherein X is O, Y is O, $R^4$ is H, $R^5$ is $OR^{16}$, $R^2$ is alkyl and $R^3$ is arylalkyl wherein the aryl moiety of the arylalkyl is substituted with 0 or one $R^{3a}$; and L, B, $R^4$, $R^1$, $R^{1a}$, $R_{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (X).

For example, the present invention provides a compound of formula (X) wherein X is O, Y is O, $R^4$ is H, $R^5$ is $OR^{16}$, $R^2$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^4$, $R^1$, $R^{1a}$, $R^6$, $R^{6a}$, $R^7$, $R^{7a}$, $R^8$, $R^9$, $R^{9a}$, $R^{10}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (X).

For example, the present invention provides a compound of formula (IX) wherein X is O, Y is O, $R^4$ is H, $R^5$ is $OR^{16}$, $R^2$ is alkyl, $R^1$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^4$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (X).

For example, the present invention provides a compound of formula (X) wherein X is O, Y is O, $R^4$ is H, $R^5$ is $OR^{16}$, $R^2$ is alkyl, $R^1$ is alkyl, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^4$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (X).

For example, the present invention provides a compound of formula (X) wherein X is O, Y is O, $R^4$ is H, $R^5$ is $OR^{16}$, $R^1$ is alkyl, $R^1$ is alkyl, each $R_{104}$ is independently hydrogen or alkyl, each $R_{105}$ is independently hydrogen or alkyl, each M is independently hydrogen or alkyl, $Z_1$ and $Z_2$ are O, Q is O, W is P, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^4$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (X).

In an eleventh embodiment, the present invention provides a compound of formula (XI)

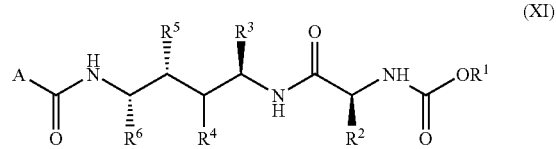

(XI)

or a pharmaceutically acceptable salt form, prodrug or stereoisomer thereof, wherein:

A is

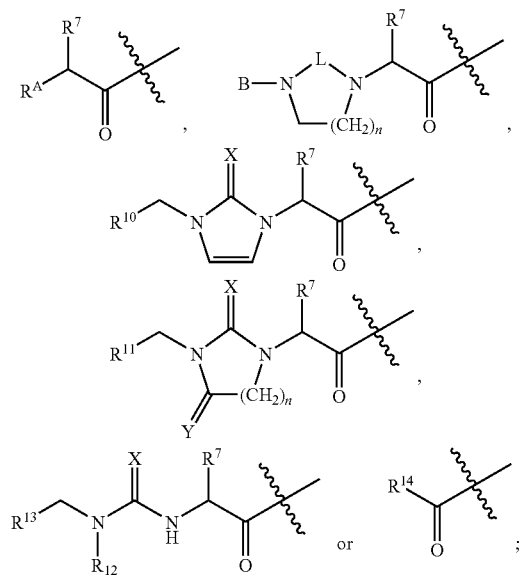

X is O, S or NH;

Y is O, S or NH;

B is H or $-CH_2R^9$;

L is $-C(=O)$, $-C(=S)$, $-C(=NH)$ or $-S(O)_2$;

$R^A$ is $-N(H)C(O)R^8$, $-O(R_a)$, $-OC(O)OR_a$, $-NR_aR_b$, $-N(R_b)S(O)_2R_a$, $-N(R_b)$alkylN$(R_b)S(O)_2R_a$, $-N(R_b)$alkylN$(R_b)C(O)OR_a$, $-N(R_b)$alkylN$(R_b)C(O)NR_aR_b$, -alkylSR$_a$, -alkylS(O)R$_a$ or -alkylS(O)$_2R_a$;

$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, $-NH_2$, $-N(H)($alkyl$)$, $-N($alkyl$)_2$, $-SH$, $-S($alkyl$)$, $-SO_2($alkyl$)$, $-N(H)C(O)$alkyl, $-N($alkyl$)C(O)$alkyl, $-N(H)C(O)NH_2$, $-N(H)C(O)N(H)($alkyl$)$, $-N(H)C(O)N($alkyl$)_2$, $-C(O)OH$, $-C(O)O$alkyl, $-C(O)NH_2$, $-C(O)N(H)($alkyl$)$, $-C(O)N($alkyl$)_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, $-NH_2$, $-N(H)($alkyl$)$, $-N($alkyl$)_2$, $-SH$, $-S($alkyl$)$, $-SO_2($alkyl$)$, $-N(H)C(O)$alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^2$ is alkyl, alkenyl, alkynyl, cycloalkyl, cycloalkenyl, heterocycle, aryl or heteroaryl; wherein each R$^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$—N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{2a}$;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^4$ is H and R$^5$ is OR$^{16}$; or
R$^5$ is H and R$^4$ is OR$^{16}$; or
R$^4$ and R$^5$ are —OR$^{16}$;

R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^8$ is —$OR_a$, —$NR_aR_b$, —$N(R_b)C(O)OR_a$, -alkyl$OR_a$, -alkylOC(O)$R_a$, or -alkylC(O)$R_a$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —$N(R_b)C(O)R_a$, —$N(R_b)SO_2R_a$, —$N(R_b)SO_2NR_aR_b$, —$N(R_b)C(O)NR_aR_b$, —$N(R_b)C(O)OR_a$, —C(O)$R_a$, —C(O)$NR_aR_b$, —C(O)$OR_a$, haloalkyl, nitroalkyl, cynaoalkyl, formylalkyl, -alkyl$OR_a$, -alkyl-O—P(O)(O$R_a$)(O$R_a$), -alkylN$R_aR_b$, -alkylN($R_b$)C(O)O$R_a$, -alkylN($R_b$)SO$_2$N$R_aR_b$, -alkylN($R_b$)C(O)$R_a$, -alkylN($R_b$)C(O)N$R_aR_b$, -alkylN($R_b$)SO$_2R_a$, -alkylC(O)O$R_a$, -alkylC(O)$R_a$, -alkylC(O)N$R_aR_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —$N(R_b)C(O)R_a$, —$N(R_b)SO_2R_a$, —$N(R_b)SO_2NR_aR_b$, —$N(R_b)C(O)NR_aR_b$, —$N(R_b)C(O)OR_a$, —C(O)$R_a$, —C(O)$NR_aR_b$, —C(O)$OR_a$, haloalkyl, nitroalkyl, cynaoalkyl, formylalkyl, -alkyl$OR_a$, -alkyl-O—P(O)(O$R_a$)(O$R_a$), -alkylN$R_aR_b$, -alkylN($R_b$)C(O)O$R_a$, -alkylN($R_b$)SO$_2$N$R_aR_b$, -alkylN($R_b$)C(O)$R_a$, -alkylN($R_b$)C(O)N$R_aR_b$, -alkylN($R_b$)SO$_2R_a$, -alkylC(O)O$R_a$, -alkylC(O)$R_a$, -alkylC(O)N$R_aR_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —$N(R_b)$C(O)$R_a$, —$N(R_b)SO_2R_a$, N($R_b$)SO$_2$N$R_aR_b$, —$N(R_b)$C(O)N$R_aR_b$, —$N(R_b)$C(O)O$R_a$, —C(O)$R_a$, —C(O)N$R_aR_b$, —C(O)O$R_a$, haloalkyl, nitroalkyl, cynaoalkyl, formylalkyl, -alkyl$OR_a$, -alkyl-O—P(O)(O$R_a$)(O$R_a$), -alkylN$R_aR_b$, -alkylN($R_b$)C(O)O$R_a$, -alkylN($R_b$)SO$_2$N$R_aR_b$, -alkylN($R_b$)C(O)$R_a$, -alkylN($R_b$)C(O)N$R_aR_b$, -alkylN($R_b$)SO$_2R_a$, -alkylC(O)O$R_a$, -alkylC(O)$R_a$, -alkylC(O)N$R_aR_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —$OR_a$, —$SR_a$, —$SOR_a$, —$SO_2R_a$, —$SO_2NR_a$, —$SO_2OR_a$, —$NR_aR_b$, —$N(R_b)C(O)R_a$, —$N(R_b)C(O)OR_a$, —C(O)N$R_aR_b$, —C(O)O$R_a$, haloalkyl, nitroalkyl, cynaoalkyl, -alkyl$OR_a$, -alkyl-O—P(O)(O$R_a$)(O$R_a$), -alkylN$R_aR_b$, -alkylN($R_b$)C(O)$R_a$, -alkylN($R_b$)C(O)N$R_b$, -alkylN($R_b$)SO$_2R_a$, -alkylC(O)O$R_a$, -alkyl-C(O)N$R_aR_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{14}$ is —$OR_a$, -alkyl$OR_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —SO$_2$(alkyl), —S(O)$_2$N$R_aR_b$, —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{16}$ is hydrogen or $R^{15}$;

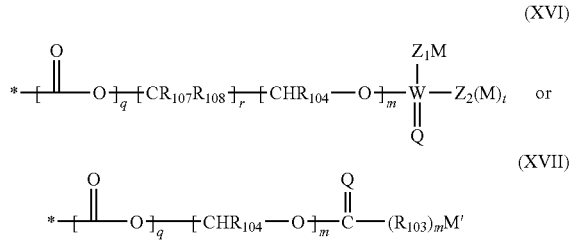

(XVI)

(XVII)

$R_{103}$ is $C(R_{105})_2$, O or $-N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, $-N(R_{105})_2$, alkyl, alkenyl, and $R_{106}$; wherein 1 to 4 $-CH_2$ radicals of the alkyl or alkenyl, other than the $-CH_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$, $NO_2$ and phenyl; provided that when M is $-N(R_{105})_2$, $Z_1$ and $Z_2$ are $-CH_2$;

$Z_1$ is $CH_2$, O, S, $-N(R_{105})$, or, when M is absent, H;

$Z_2$ is $CH_2$, O, S or $-N(R_{105})$;

Q is O or S;

W is P or S; wherein when W is S, $Z_1$ and $Z_2$ are not S;

M' is H, alkyl, alkenyl or $R_{106}$; wherein 1 to 4 $-CH_2$ radicals of the alkyl or alkenyl is optionally replaced by a heteroatom group selected from O, S, S(O), $SO_2$, or $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $-OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $-OR_{105}$, $-R_{105}$, $-N(R_{105})_2$, $-N(R_{105})C(O)R_{105}$, $-CN$, $-C(O)OR_{105}$, $-C(O)N(R_{105})_2$, halo and $-CF_3$; each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, alkyl, alkenyl, alkynyl, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, haloalkyl, hydroxyalkyl, alkoxyalkyl, -alkylNH_2, -alkylN(H)(alkyl), -alkylN(alkyl)_2, -alkylN(H)C(O)NH_2, -alkylN(H)C(O)N(H)(alkyl), -alkylN(H)C(O)N(alkyl)_2, -alkylC(O)OH, -alkylC(O)Oalkyl, -alkylC(O)NH_2, -alkylC(O)N(H)(alkyl), -alkylC(O)N(alkyl)_2 and $R_c$; alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, cyanoalkyl, formylalkyl, nitroalkyl, haloalkyl, hydroxyalkyl, alkoxyalkyl, -alkylNH_2, -alkylN(H)(alkyl), -alkylN(alkyl)_2, -alkylN(H)C(O)NH_2, -alkylN(H)C(O)N(H)(alkyl), -alkylN(H)C(O)N(alkyl)_2, -alkylC(O)OH, -alkylC(O)Oalkyl, -alkylC(O)NH_2, -alkylC(O)N(H)(alkyl), -alkylC(O)N(alkyl)_2 and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, $-NH_2$, $-N(H)(alkyl)$, $-N(alkyl)_2$, $-SH$, $-S(alkyl)$, $-SO_2(alkyl)$, $-N(H)C(O)alkyl$, $-N(alkyl)C(O)alkyl$, $-N(H)C(O)NH_2$, $-N(H)C(O)N(H)(alkyl)$, $-N(H)C(O)N(alkyl)_2$, $-C(O)OH$, $-C(O)Oalkyl$, $-C(O)NH_2$, $-C(O)N(H)(alkyl)$, $-C(O)N(alkyl)_2$, haloalkyl, hydroxyalkyl, alkoxyalkyl, -alkyl-NH_2, -alkyl-N(H)(alkyl), -alkyl-N(alkyl)_2, -alkyl-N(H)C(O)NH_2, -alkyl-N(H)C(O)N(H)(alkyl), -alkyl-N(H)C(O)N(alkyl)_2, -alkyl-C(O)OH, -alkyl-C(O)Oalkyl, -alkyl-C(O)NH_2, -alkyl-C(O)N(H)(alkyl) and -alkyl-C(O)N(alkyl)_2; and n is 1 or 2.

For example, the present invention provides a compound of formula (XI) wherein L is $-C(=O)$ or $-C(=S)$, X is O; Y is O; and L, B, $R^A$, $R^1$, $R^{1a}$, $R^2$, $R^{2a}$, $R^3$, $R^{3a}$, $R^4$, $R^5$, $R^6$, $R^{6a}$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{15a}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and n are defined in formula (XI).

For example, the present invention provides a compound of formula (XI) wherein X is O, Y is O, $R^4$ is H, $R^5$ is $OR^{16}$, $R^2$ is alkyl; and L, B, $R^A$, $R^1$, $R^{1a}$, $R^3$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R_{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_c$, and n are defined in formula (XI).

For example, the present invention provides a compound of formula (XI) wherein X is O, Y is O, R is H, R$^5$ is OR$^{16}$, R$^2$ is alkyl, R$^3$ is arylalkyl; and L, B, R$^A$, R$^1$, R$^{1a}$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{12a}$, R$^{13}$, R$^{13a}$, R$^{14}$, R$^{14a}$, R$^{15}$, R$^{15a}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_a$, R$_b$, R$_c$, n and the substituents of the aryl moiety of arylalkyl of R$^3$ are defined in formula (XI).

For example, the present invention provides a compound of formula (XI) wherein X is O, Y is O, R$^4$ is H, R$^5$ is OR$^{16}$, R$^2$ is alkyl and R$^3$ is arylalkyl wherein the aryl moiety of the arylalkyl is substituted with 0 or one R$^{3a}$; and L, B, R$^A$, R$^1$, R$^{1a}$, R$^{3a}$, R$^6$, R$^{6a}$, R$^7$, R$^{7a}$, R$^8$, R$^9$, R$^{9a}$, R$^{10}$ R$^{10a}$, R$^{11}$, R$^{11a}$, R$^{12}$, R$^{12a}$, R$^{13}$, R$^{13a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$, and n are defined in formula (XI).

For example, the present invention provides a compound of formula (XI) wherein X is O, Y is O, R$^4$ is H, R$^5$ is OR$^{16}$, R$^2$ is alkyl, R$^3$ is arylalkyl wherein the aryl moiety of the arylalkyl is substituted with 0 or one R$^{3a}$ wherein R$^{3a}$ is aryl or heteroaryl; and L, B, R$^A$, R$^1$, R$^{1a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{12a}$, R$^{13}$, R$^{13a}$, R$^{14}$, R$^{15}$, R$^{16}$, R$_{103}$, R$_{104}$, R$^{105}$, M, Z$_1$, Z$_2$, Q, W, M', R$_{106}$, R$_{107}$, R$_{108}$, q, m, m', m'', r, t, R$_a$, R$_b$, R$_c$, n and the substituents of R$^{3a}$ are defined in formula (XI).

For example, the present invention provides a compound of formula (XI) wherein X is O, Y is O, R$^4$ is H, R$^5$ is OR$^{16}$, R$^2$ is alkyl, R$^1$ is alkyl, R$^3$ is arylalkyl wherein the aryl moiety of the arylalkyl is substituted with 0 or one R$^{3a}$ wherein R$^{3a}$ is aryl or heteroaryl; and L, B, R$^A$, R$^6$, R$^{6a}$, R$^7$, R$^{7a}$, R$^8$, R$^{8a}$, R$^9$, R$^{9a}$, R$^{10}$, R$^{10a}$, R$^{11}$, R$^{11a}$, R$^{12}$, R$^{12a}$, R$^{13}$, R$^{13a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_a$, n and the substituents of R$^{3a}$ are defined in formula (XI).

For example, the present invention provides a compound of formula (XI) wherein X is O, Y is O, R$^4$ is H, R$^5$ is OR$^{16}$, R$^2$ is alkyl, R$^1$ is alkyl, R$^6$ is arylalkyl substituted with 0 or one R$^{6a}$ wherein R$^{6a}$ is aryl or heteroaryl, and R$^3$ is arylalkyl wherein the aryl moiety of the arylalkyl is substituted with 0 or one R$^{3a}$ wherein R$^{3a}$ is aryl or heteroaryl; and L, B, R$^A$, R$^7$, R$^{7a}$, R$^8$, R$^9$, R$^{9a}$, R$^{10}$, R$^{10a}$, R$^{11}$, R$^{11a}$, R$^{12}$, R$^{12a}$, R$^{13}$, R$^{13a}$, R$^{14}$, R$^{15}$, R$^{16}$, R$_{103}$, R$_{104}$, R$_{105}$, M, Z$_1$, Z$_2$, Q, W, M', R$_{106}$, R$_{107}$, R$_{108}$, q, m, m', m'', r, t, R$_a$, R$_b$, R$_c$, n and the substituents of R$^{3a}$ and R$^{6a}$ are defined in formula (XI).

For example, the present invention provides a compound of formula (XI) wherein X is O, Y is O, R$^4$ is H, R$^5$ is OR$^{16}$, R$^2$ is alkyl, R$^1$ is alkyl, each R$_{104}$ is independently hydrogen or alkyl each R$_{105}$ is independently hydrogen or alkyl, each M is independently hydrogen or alkyl, Z$_1$ and Z$_2$ are O, Q is O, W is P, R$^6$ is arylalkyl substituted with 0 or one R$^{6a}$ wherein R$^{6a}$ is aryl or heteroaryl, and R$^3$ is arylalkyl wherein the aryl moiety of the arylalkyl is substituted with 0 or one R$^{3a}$ wherein R$^{3a}$ is aryl or heteroaryl; and L, B, R$^A$, R$^7$, R$^{7a}$, R$^8$, R$^9$, R$^{9a}$, R$^{10}$, R$^{10a}$, R$^{11}$, R$^{11a}$, R$^{12}$, R$^{12a}$, R$^{13}$, R$^{13a}$, R$^{14}$, R$^{15}$, R$^{16}$, R$_{103}$, M', R$_{106}$, R$_{107}$, R$_{108}$, q, m, m', m'', r, t, R$_a$, R$_b$, R$_c$, n and the substituents of R$^{3a}$ and R$^{6a}$ are defined in formula (XI).

In a twelfth embodiment the present invention provides a compound of formula (XII)

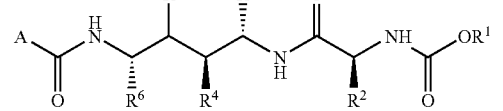

or a pharmaceutically acceptable salt form, prodrug or stereoisomer thereof, wherein:

A is

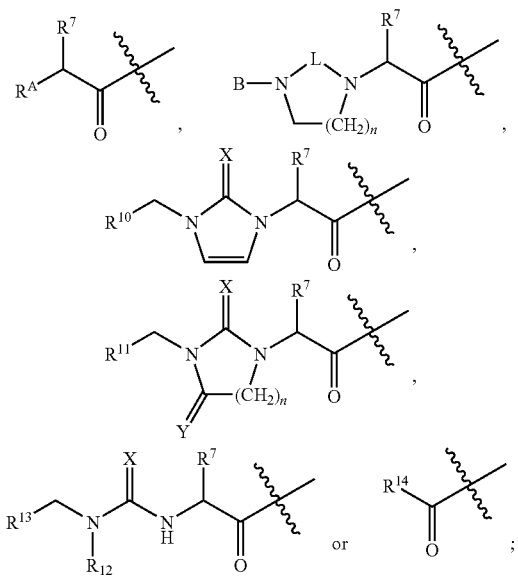

X is O, S or NH;
Y is O, S or NH;
B is H or —CH$_2$R$^9$;
L is —C(=O), —C(=S), —C(=NH) or —S(O)$_2$;
R$^A$ is —N(H)C(O)R$^8$, —O(R$_a$), —OC(O)OR$_a$, —NR$_a$R$_b$, —N(R$_b$)S(O)$_2$R$_a$, —N(R$_b$)alkylN(R$_b$)S(O)$_2$R$_a$, —N(R$_b$)alkylN(R$_b$)C(O)OR$_a$, —N(R$_b$)alkylN(R$_b$)C(O)NR$_a$R$_b$, -alkylSR$_a$, -alkylS(O)R$_a$ or -alkylS(O)$_2$R$_a$;
R$^1$ is alkyl, alkenyl, alkynyl, cycloalkyl, cycloalkenyl, heterocycle, aryl or heteroaryl; wherein each R$^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and R$^{1a}$;
R$^{1a}$ is cycloalkyl, cycloalkenyl, heterocycle, aryl or heteroaryl; wherein each R$^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_{a-N(Rb)}$C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^4$ is H and $R^5$ is OR$^{16}$; or
$R^5$ is H and $R^4$ is OR$^{16}$; or
$R^4$ and $R^5$ are —OR$^{16}$;

$R^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —NH$_2$, N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^8$ is —$OR_a$, —$NR_aR_b$, —$N(R_b)C(O)OR_a$, -alkyl$OR_a$, -alkylOC(O)$R_a$, or —O-alkylC(O)$R_a$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —N(R)C(O)$R_a$, —N($R_b$)$SO_2R_a$, —N($R_b$)$SO_2NR_aR_b$, —N($R_b$)C(O)N$R_aR_b$, —N($R_b$)C(O)O$R_a$, —C(O)$R_a$, —C(O)N$R_aR_b$, —C(O)O$R_a$, haloalkyl, nitroalkyl, cynaoalkyl, formylalkyl, -alkyl$OR_a$, -alkyl-O—P(O)(O$R_a$)(O$R_a$), -alkylN$R_aR_b$, -alkylN($R_b$)C(O)O$R_a$, -alkylN($R_b$)$SO_2NR_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkylC(O)$R_a$, -alkylC(O)N$R_aR_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, —$SO_2NR_a$, —$SO_2OR_a$, —$NR_aR_b$, —N($R_b$)C(O)$R_a$, —N($R_b$)$SO_2R_a$, —N($R_b$)$SO_2NR_aR_b$, —N($R_b$)C(O)N$R_aR_b$, —N($R_b$)C(O)O$R_a$, —C(O)$R_a$, —C(O)N$R_aR_b$, —C(O)O$R_a$, haloalkyl, nitroalkyl, cynaoalkyl, formylalkyl, -alkyl$OR_a$, -alkyl-O—P(O)(O$R_a$)(O$R_a$), -alkylN$R_aR_b$, -alkylN($R_b$)C(O)O$R_a$, -alkylN($R_b$)$SO_2NR_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkylC(O)$R_a$, -alkylC(O)N$R_aR_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, $SO_2R_a$, —$SO_2NR_a$, —$SO_2OR_a$, —$NR_aR_b$, —N($R_b$)C(O)$R_a$, —N($R_b$)$SO_2R_a$, —N($R_b$)$SO_2NR_aR_b$, —N($R_b$)C(O)N$R_aR_b$, —N($R_b$)C(O)O$R_a$, —C(O)$R_a$, —C(O)N$R_aR_b$, —C(O)O$R_a$, haloalkyl, nitroalkyl, cynaoalkyl, formylalkyl, -alkyl$OR_a$, -alkyl-O—P(O)(O$R_a$)(O$R_a$), -alkylN$R_aR_b$, -alkylN($R_b$)C(O)O$R_a$, -alkylN($R_b$)$SO_2NR_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkylC(O)$R_a$, -alkylC(O)N$R_aR_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —$OR_a$, —$SR_a$, —$SOR_a$, —$SO_2R_a$, —$SO_2NR_a$, —$SO_2OR_a$, —$NR_aR_b$, —N($R_b$)C(O)$R_a$, —N($R_b$)C(O)O$R_a$, —C(O)N$R_aR_b$, —C(O)O$R_a$, haloalkyl, nitroalkyl, cynaoalkyl, -alkyl$OR_a$, -alkyl-O—P(O)(O$R_a$)(O$R_a$), -alkylN$R_aR_b$, -alkylN($R_b$)C(O)$R_a$, -alkylN($R_b$)C(O)N$R_aR_b$, -alkylN($R_b$)$SO_2R_a$, -alkylC(O)O$R_a$, -alkyl-C(O)N$R_aR_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{14}$ is —$OR_a$, -alkyl$OR_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —S(O)$_2$N$R_aR^b$, —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkylC(O)N(alkyl)$_2$;

$R^{16}$ is hydrogen or $R^{15}$;

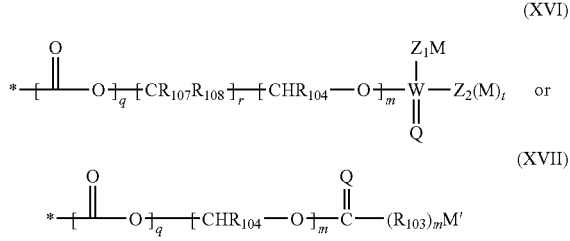

$R_{103}$ is $C(R_{105})_2$, O or —N($R_{105}$);

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —N($R_{105}$)$_2$, alkyl, alkenyl, and $R_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N($R_{105}$); and wherein any hydrogen in said alkyl, alkenyl or $R_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo —CF$_3$, NO$_2$ and phenyl; provided that when M is —N(R$_{105}$)$_2$, Z$_1$ and Z$_2$ are —CH$_2$;

Z$_1$ is CH$_2$, O, S, N(R$_{105}$), or, when M is absent, H;

Z$_2$ is CH$_2$, O, S or —N(R$_{105}$);

Q is O or S;

W is P or S; wherein when W is S, Z$_1$ and Z$_2$ are not S;

M' is H, alkyl, alkenyl or R$_{106}$; wherein 1 to 4 —CH$_2$ radicals of the alkyl or alkenyl is optionally replaced by a heteroatom group selected from O, S, S(O), SO, or N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)N(R$_{105}$)$_2$, halo and —CF$_3$;

each R$_{107}$ and R$_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

R$^a$ and R$^b$ at each occurrence are independently selected from the group consisting of hydrogen, alkyl, alkenyl, alkynyl, cycloalkyl, aryl, heteroaryl and heterocycle; wherein each R$_a$ and R$_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

R$_c$ is aryl, heteroaryl or heterocycle; wherein each R$_a$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (XII) wherein L is —C(=O) or —C(=S), X is O; Y is O; and L, B, R$^A$, R$^1$, R$^{1a}$, R$^2$, R$^{2a}$, R$^3$, R$^{3a}$, R$^4$, R$^5$, R$^6$, R$^{6a}$, R$^7$, R$^{7a}$, R$^8$, R$^9$, R$^{9a}$, R$^{10}$, R$_{10a}$, R$^{11}$, R$^{11a}$, R$^{12}$, R$^{12a}$, R$^{13}$, R$^{13a}$, R$^{14}$, R$^{15}$, R$^{16}$, R$_{103}$, R$_{104}$, R$_{105}$, M, Z$_a$, Z$_2$, Q, W, M', R$_{106}$, R$_{107}$, R$_{108}$, q, m, m', m", r, t, R$_a$, R$_b$, R$_a$, and n are defined in formula (XII).

For example, the present invention provides a compound of formula (XII) wherein X is O, Y is O, R$^4$ is H, R$^5$ is OR$^{16}$, R$^2$ is alkyl; and L, B, R$^A$, R$^1$, R$^{1a}$, R$^3$, R$^{3a}$, R$^6$, R$^{6a}$, R$^7$, R$^{7a}$, R$^8$, R$^9$, R$^{9a}$, R$^{10}$, R$^{10a}$, R$^{11}$, R$^{11a}$, R$^{12}$, R$^{12a}$, R$^{13}$, R$^{13a}$, R$^{14}$, R$^{15}$, R$^{16}$, R$_{103}$, R$_{104}$, R$_{105, M, Z1}$, Z$_2$, Q, W, M', R$_{106}$, R$_{107}$, R$_{108}$, q, m, m', m", r, t, R$_a$, R$_b$, R$_a$, and n are defined in formula (XII).

For example, the present invention provides a compound of formula (XII) wherein X is O, Y is O, $R^4$ is H, $R^5$ is $OR^{16}$, $R^2$ is alkyl, $R^3$ is arylalkyl; and L, B, $R^A$, $R^1$, $R^{1a}$, $R^{3a}$, $R^6$, $R^{6a}$, $R^7$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_a$, $Z_2$, Q, W, M', $R_{106}$, $R_{107}$, $R_{108}$, q, m, m', m'', r, t, $R_a$, $R_b$, $R_c$, n and the substituents of the aryl moiety of arylalkyl of $R^3$ are defined in formula (XII).

For example, the present invention provides a compound of formula (XII) wherein X is O, Y is O, $R^4$ is H, $R^5$ is $OR^{16}$, $R^2$ is alkyl and $R^3$ is arylalkyl wherein the aryl moiety of the arylalkyl is substituted with 0 or one $R^{3a}$; and L, B, $R^A$, $R^1$, $R^{1a}$, $R^3$, $R^{3a}$, $R^6$, $R^{6a}$, $R^7$, $R^{7a}$, $R^8$, $R^9$, $R_{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (XII).

For example, the present invention provides a compound of formula (XII) wherein X is O, Y is O, $R^4$ is H, $R^5$ is $OR^{16}$, $R^2$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_a$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (XII).

For example, the present invention provides a compound of formula (XII) wherein X is O, Y is O, $R^4$ is H, $R^5$ is $OR^{16}$, $R^2$ is alkyl, $R^1$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^A$, $R^6$, $R^{6a}$, $R^7$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R^{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (XII).

For example, the present invention provides a compound of formula (XII) wherein X is O, Y is O, $R^4$ is H, $R^5$ is $OR^{16}$, $R^2$ is alkyl, $R^1$ is alkyl, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^A$, $R^7$, $R^{7a}$, $R^8$, $R^9$, $R^{9a}$, $R^{10}$, $R^{10a}$, $R^{11}$, $R_{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (XII).

For example, the present invention provides a compound of formula (XII) wherein X is O, Y is O, $R^4$ is H, $R^5$ is $OR^{16}$, $R^2$ is alkyl, $R^1$ is alkyl, each $R_{104}$ is independently hydrogen or alkyl, each $R_{105}$ is independently hydrogen or alkyl, each M is independently hydrogen or alkyl, $Z_1$ and $Z_2$ are O, Q is O, W is P, It is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^A$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (XII).

In a thirteenth embodiment the present invention provides a compound of formula (XIII)

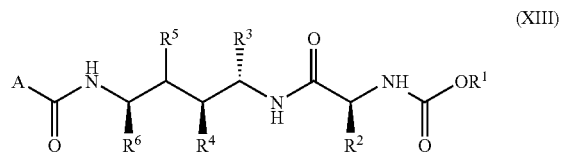

(XIII)

or a pharmaceutically acceptable salt form, prodrug or stereoisomer thereof, wherein:

A is

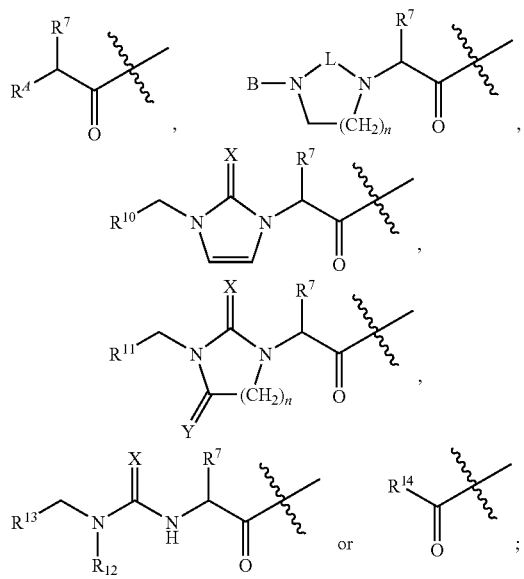

X is O, S or NH;
Y is O, S or NH;
B is H or $-CH_2R^9$;
L is $-C(=O)$, $-C(=S)$, $C(=NH)$ or $-S(O)_2$;
$R^A$ is $-N(H)C(O)R^8$, $-O(R_a)$, $-OC(O)OR_a$, $-NR_aR_b$, $-N(R_b)S(O)_2R_a$, $-N(R_b)$alkylN$(R_b)S(O)_2R_a$, $-N(R_b)$alkylN$(R_b)C(O)OR_a$, $-N(R_b)$alkylN$(R_b)C(O)NR_aR_b$, -alkylSR$_a$, -alkylS(O)R$_a$ or -alkylS(O)$_2R_a$;
$R^1$ is alkyl, alkenyl, alkynyl, cycloalkyl, cycloalkenyl, heterocycle, aryl or heteroaryl; wherein each $R^1$ is substituted with 0, 1 or 2 substituents independently selected from the group consisting of cyano, halo, nitro, oxo, alkyl, alkenyl, alkynyl, hydroxy, alkoxy, $-NH_2$, $-N(H)$(alkyl), $-N$(alkyl)$_2$, $-SH$, $-S$(alkyl), $-SO_2$(alkyl), $-N(H)C(O)$alkyl, $-N$(alkyl)C(O)alkyl, $-N(H)C(O)NH_2$, $-N(H)C(O)N(H)$(alkyl), $-N(H)C(O)N$(alkyl)$_2$, $-C(O)OH$, $-C(O)O$alkyl, $-C(O)NH_2$, $-C(O)N(H)$(alkyl), $-C(O)N$(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and $R^{1a}$;

$R^{1a}$ is cycloalkyl, cycloalkenyl, heterocycle, aryl or heteroaryl; wherein each $R^{1a}$ is substituted with 0, 1, 2, 3 or 4 substituents independently selected from the group consisting of cyano, halo, nitro, oxo, alkyl, alkenyl, alkynyl, hydroxy, alkoxy, $-NH_2$, $-N(H)$(alkyl), $-N$(alkyl)$_2$, $-SH$, $-S$(alkyl), $-SO_2$(alkyl), $-N(H)C(O)$alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^2$ is alkyl, alkenyl, alkynyl, cycloalkyl, cycloalkenyl, heterocycle, aryl or heteroaryl; wherein each $R^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{2a}$;

$R^{2a}$ is cycloalkyl, cycloalkenyl, heterocycle, aryl or heteroaryl; wherein each $R^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R^{3a}$;

$R^{3a}$ is cycloalkyl, cycloalkenyl, heterocycle, aryl or heteroaryl; wherein each $R^{3a}$ is substituted with 0, 1, 2, 3 or 4 substituents independently selected from the group consisting of cyano, halo, oxo, alkyl, alkenyl, hydroxy, alkoxy, —NH$_2$, N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^4$ is H and $R^5$ is OR$^{16}$; or
$R^5$ is H and $R^4$ is OR$^{16}$; or
$R^4$ and $R^5$ are —OR$^{16}$;

R is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$ and $R^{6a}$;

$R^{6a}$ is cycloalkyl, cycloalkenyl, heterocycle, aryl or heteroaryl; wherein each $R^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

$R^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^8$ is —OR$_a$, —NR$_a$R$_b$, —N(R$_b$)C(O)OR$_a$, -alkylOR$_a$, -alkylOC(O)R$_a$, or —O-alkylC(O)R$_a$;

R$^9$ is alkyl, alkenyl, alkynyl, cycloalkyl, cycloalkenyl, aryl, heteroaryl or heterocycle; wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$ and R$^{9a}$;

R$^{9a}$ is cycloalkyl, cycloalkenyl, heterocycle, aryl or heteroaryl; wherein each R$^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{10}$ is alkyl, alkenyl, alkynyl, cycloalkyl, cycloalkenyl, aryl, heteroaryl or heterocycle; wherein each R$^{10}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$R$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{10a}$;

R$^{10a}$ is cycloalkyl, cycloalkenyl, heterocycle, aryl or heteroaryl; wherein each R$^{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{11}$ is alkyl, alkenyl, alkynyl, cycloalkyl, cycloalkenyl, aryl, heteroaryl or heterocycle; wherein each R$^{11}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{11a}$;

R$^{11a}$ is cycloalkyl, cycloalkenyl, heterocycle, aryl or heteroaryl; wherein each R$^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{12}$ is alkyl, alkenyl, cycloalkyl, cycloalkenyl, cycloalkylalkyl or cycloalkenylalkyl; wherein each R$^{12}$ is substituted with 0, 1 or 2 substituents independently selected from the group consisting of hydroxy, alkoxy and halo;

R$^{13}$ is alkyl, alkenyl, alkynyl, cycloalkyl, cycloalkenyl, aryl, heteroaryl or heterocycle; wherein each R$^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)C(O)OR$_a$, —C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkyl-C(O)NR$_a$R$_b$ and R$^{13a}$;

R$^{13a}$ is cycloalkyl, cycloalkenyl, heterocycle, aryl or heteroaryl; wherein each R$^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{14}$ is —OR$_a$, -alkylOR$_a$, aryl, heteroaryl or heterocycle; wherein the aryl, heteroaryl and heterocycle are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —S(O)$_2$NR$_a$R$_b$, —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{16}$ is hydrogen or R$^{15}$;

R$^{15}$ is

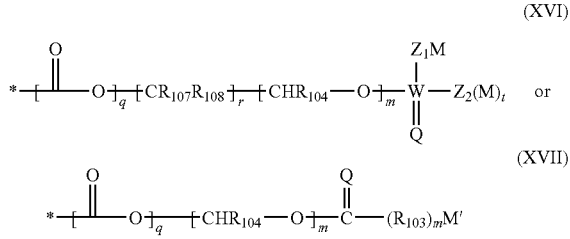

$R_{103}$ is $C(R_{105})_2$, O or —N($R_{105}$);

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —N($R_{105}$)$_2$, alkyl, alkenyl, and $R_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N($R_{105}$); and wherein any hydrogen in said alkyl, alkenyl or $R_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, $Z_a$ and $Z_2$ are —CH$_2$;

$Z_1$ is CH$_2$, O, S, —N($R_{105}$), or, when M is absent, H;

$Z_2$ is CH$_2$, O, S or —N($R_{105}$);

Q is O or S;

W is P or S; wherein when W is S, $Z_a$ and $Z_2$ are not S;

M' is H, alkyl, alkenyl or $R_{106}$; wherein 1 to 4 —CH$_2$ radicals of the alkyl or alkenyl is optionally replaced by a heteroatom group selected from O, S, S(O), SO$_2$, or N($R_{105}$); and wherein any hydrogen in said alkyl, alkenyl or $R_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N($R_{105}$); and wherein any of said ring system is substituted with 0, 1, 2, 3, 4, 5 or 6 substituents selected from the group consisting of hydroxy, alkyl, alkoxy, and —OC(O)alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N($R_{105}$); and wherein any one of said ring systems is substituted with 0, 1, 2 or 3 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound of formula (XIII) wherein L is —C(=O) or —C(=S), X is O; Y is O; and L, B, $R^4$, $R^1$, $R^{1a}$, $R^2$, $R^{2a}$, $R^3$, $R^{3a}$, $R^4$, $R^5$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m", r, t, $R_a$, $R_b$, $R_a$, and n are defined in formula (XIII).

For example, the present invention provides a compound of formula (XIII) wherein X is O, Y is O, $R^4$ is H, $R^5$ is OR$^{16}$, $R^2$ is alkyl; and L, B, $R^4$, $R^1$, $R^{1a}$, $R^3$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (XIII).

For example, the present invention provides a compound of formula (XIII) wherein X is O, Y is O, $R^4$ is H, $R^5$ is $OR^{16}$ $R^2$ is alkyl, $R^3$ is arylalkyl; and L, B, $R^A$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of the aryl moiety of arylalkyl of $R^3$ are defined in formula (XIII).

For example, the present invention provides a compound of formula (XIII) wherein X is O, Y is O, $R^4$ is H, $R^5$ is $OR^{16}$, $R^2$ is alkyl and $R^3$ is arylalkyl wherein the aryl moiety of the arylalkyl is substituted with 0 or one $R^{3a}$; and L, B, $R^A$, $R^1$, $R^{1a}$, $R^{3a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, and n are defined in formula (XIII).

For example, the present invention provides a compound of formula (XIII) wherein X is O, Y is O, $R^4$ is H, $R^5$ is $OR^{16}$, $R^2$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^A$, $R^1$, $R^{1a}$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ are defined in formula (XIII).

For example, the present invention provides a compound of formula (XIII) wherein X is O, Y is O, $R^4$ is H, $R^5$ is $OR^{16}$, $R^2$ is alkyl, $R^1$ is alkyl, $R^3$ is arylalkyl wherein the aryl moiety of the arylalkyl is substituted with 0 or one $R^{3a}$ wherein $R^{3a}$ is aryl or heteroaryl; and L, B, $R^A$, $R^6$, $R^{6a}$, $R^7$, $R^{7a}$, $R^8$, $R^9$, $R^{9a}$, $R^{10}$, $R^{10a}$, $R^{11}$, $R^{11a}$, $R^{12}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$ q, m, m', m'', r, t, $R_a$, $R_b$, $R_c$, n and the substituents of $R^{3a}$ are defined in formula (XIII).

For example, the present invention provides a compound of formula (XIII) wherein X is O, Y is O, $R^4$ is H, $R^5$ is $OR^{16}$, $R^2$ is alkyl, $R^1$ is alkyl, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^A$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, $R_{104}$, $R_{105}$, M, $Z_1$, $Z_2$, Q, W, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (XIII).

For example, the present invention provides a compound of formula (XIII) wherein X is O, Y is O, $R^4$ is H, $R^5$ is $OR^{16}$, $R^2$ is alkyl, $R^1$ is alkyl, each $R_{104}$ is independently hydrogen or alkyl, each $R_{105}$ is independently hydrogen or alkyl, each M is independently hydrogen or alkyl, $Z_1$ and $Z_2$ are O, Q is O, W is P, $R^6$ is arylalkyl substituted with 0 or one $R^{6a}$ wherein $R^{6a}$ is aryl or heteroaryl, and $R^3$ is arylalkyl wherein the aryl moiety of the arylalkyl is substituted with 0 or one $R^{3a}$ wherein $R^{3a}$ is aryl or heteroaryl; and L, B, $R^A$, $R^7$, $R^{7a}$, $R^8$, $R^9$, $R^{9a}$, $R^{10}$, $R^{10a}$, $R^{11}$, $R^{11a}$, $R^{12}$, $R^{12a}$, $R^{13}$, $R^{13a}$, $R^{14}$, $R^{15}$, $R^{16}$, $R_{103}$, M', $R_{106}$, $R_{107}$, $R_{108}$, q, m, m', m'', r, t, $R_a$, $R_b$, $R_c$, n and the substituents of $R^{3a}$ and $R^{6a}$ are defined in formula (XIII).

In a fourteenth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, and a pharmaceutically acceptable carrier.

For example, the present invention of the fourteenth embodiment provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt, prodrug or stereoisomer thereof, and a pharmaceutically acceptable carrier.

For example, the present invention of the fourteenth embodiment provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt, prodrug or stereoisomer thereof, and a pharmaceutically acceptable carrier.

For example, the present invention of the fourteenth embodiment provides a pharmaceutical composition comprising a therapeutically effective amount of Methyl(1S,4S,5S,7S,10S)-4-benzyl-1,10-ditert-butyl-5-hydroxy-2,9,12-trioxo-7-[2-pyridinyl)benzyl]-13-oxa-3,8,11-triazatetradec-1-ylcarbamate, or a pharmaceutically acceptable salt, prodrug or stereoisomer thereof, and a pharmaceutically acceptable carrier.

For example, the present invention of the fourteenth embodiment provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt, prodrug or stereoisomer thereof, and a pharmaceutically acceptable carrier.

For example, the present invention of the fourteenth embodiment provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt, prodrug or stereoisomer thereof, and a pharmaceutically acceptable carrier.

In a fifteenth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three, four, five or six second HIV protease inhibitors, and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-benzyl-2-oxo-1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt, prodrug or stereoisomer thereof, one, two, three, four, five or six second HIV protease inhibitors and a pharmaceutically acceptable carrier.

For example, the present invention provides a pharmaceutical composition comprising a therapeutically effective amount of methyl(1S)-1-[({(1S,3S,4S)-4-{[(2S)-2-(3-{[6-(1-imidazolidinyl)-3,3-dimethylbutanoyl]amino}-3-hydroxy-5-phenyl-1-[4-(2-pyridinyl)benzyl]pentyl}amino)

carbonyl]-2,2-dimethylpropylcarbamate, or a pharmaceutically acceptable salt, prodrug or stereoisomer thereof, one, two, three, four, five or six second HIV protease inhibitors and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,1-triazatetradec-1-ylcarbamate, a pharmaceutically acceptable salt, prodrug or stereoisomer thereof, one, two, three, four, five or six second HIV protease inhibitors and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt, prodrug or stereoisomer thereof, one, two, three, four, five or six second HIV protease inhibitors and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt, prodrug or stereoisomer thereof, one, two, three, four, five or six second HIV protease inhibitors and a pharmaceutically acceptable carrier.

For example, the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt, prodrug or stereoisomer thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

For example, the present invention provides a pharmaceutical composition comprising a therapeutically effective amount of methyl(1S,4S,5S,7S,10S)-4-benzyl-1,10bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two, three, four, five or six second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, and a pharmaceutically acceptable carrier.

In a sixteenth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, stereoisomer, ester, salt of an ester, prodrug, salt of a prodrug, or combination thereof, one, two, three, four, five or six HIV reverse transcriptase inhibitors, and a pharmaceutically acceptable carrier.

For example, the present invention provides a pharmaceutical composition comprising a therapeutically effective amount of methyl(15)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV reverse transcriptase inhibitors and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer, ester thereof, one, two, three, four, five or six HIV reverese transcriptase inhibitors and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer, ester thereof, one, two, three, four, five or six HIV reverese transcriptase inhibitors and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three, four, five or six HIV reverese transcriptase inhibitors and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two, three, four, five or six HIV reverese transcriptase inhibitors and a pharmaceutically acceptable carrier.

For example, the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceuticals acceptable salt form, prodrug or stereoisomer thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC083), DPC-961, MIV-150, TMC-120 and TMC-125, and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two, three, four, five or six HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutically acceptable carrier.

In a seventeenth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three, four, five or six HIV entry/fusion inhibitors and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV entry/fusion inhibitors and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV entry/fusion inhibitors and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two, three, four, five or six HIV entry/fusion inhibitors and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three, four, five or six HIV entry/fusion inhibitors and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form or stereoisomer thereof, one, two, three, four, five or six HIV entry/fusion inhibitors and a pharmaceutically acceptable carrier.

For example, the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

For example, the present invention provides a pharmaceutical composition comprising a therapeutically effective amount of methyl(1S)-1-[({(1S,3S,4S)-4-{[(2S)-2-(2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

For example, the present invention provides a pharmaceutical composition comprising a therapeutically effective amount of Methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three, four, five or six HIV entry/fusion inhibitors selected from the group consisting of enfuvirtide (T-20), T-1249, PRO 2000, PRO 542, PRO 140, AMD-3 100, BMS-806, FP21399, GW873140, Schering C (SCH-C), Schering D (SCH-D), TNX-355 and UK-427857, and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two, three, four, five or six HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutically acceptable carrier.

In an eighteenth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three, four, five or six HIV integrase inhibitors and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[(6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV integrase inhibitors and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV integrase inhibitors and a pharmaceutically acceptable carrier.

For example, the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three or four HIV integrase inhibitors selected from the group consisting of S-1360, zintevir (AR-177), L-870812 and L-870810, and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three or four HIV integrase inhibitors selected from the group consisting of S-1360, zintevir (AR-177), L-870812 and L-870810, and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three or four HIV integrase inhibitors selected from the group consisting of S-1360, zintevir (AR-177), L-870812 and L-870810, and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, a pharmaceutically acceptable salt form, prodrug or stereoisomer thereof, one, two, three or four HIV integrase inhibitors selected from the group consisting of S-1360, zintevir (AR-177), L-870812 and L-870810, and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three or four HIV integrase inhibitors selected from the group consisting of S-1360, zintevir (AR-177), L-870812 and L-870810, and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two, three or four HIV integrase inhibitors selected from the group consisting of S-1360, zintevir (AR-177), L-870812 and L-870810, and a pharmaceutically acceptable carrier.

In a nineteenth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two, three, four, five or six HIV budding/maturation inhibitors and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV budding/maturation inhibitors and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two, three, four, five or six HIV budding/maturation inhibitors and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two, three, four, five or six HIV budding/maturation inhibitors and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two, three, four, five or six HIV budding/maturation inhibitors and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two, three, four, five or six HIV budding/maturation inhibitors and a pharmaceutically acceptable carrier.

For example, the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, PA-457, and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, PA-457, and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl] pentyl}amino)carbonyl]-2,2-dimethylpropylcarbamate, or a pharmaceutically acceptable salt form, prodrug or stereoisomer thereof, PA-457, and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, PA-457, and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, PA-457, and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, PA-457, and a pharmaceutically acceptable carrier.

In a twentieth embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two or three second HIV protease inhibitor, one, two or three HIV reverese transcriptase inhibitor and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl ]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two or three second HIV protease inhibitor, one, two or three HIV reverse transcriptase inhibitor and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl] pentyl}amino)carbonyl]-2,2-dimethylpropylcarbamate, or a pharmaceutically acceptable salt form, prodrug or stereoisomer thereof, one, two or three second HIV protease inhibitor, one, two or three HIV reverse transcriptase inhibitor and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two or three second HIV protease inhibitor, one, two or three HIV reverse transcriptase inhibitor and a pharmaceutically acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two or three second HIV protease inhibitor, one, two or three HIV reverse transcriptase inhibitor and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two or three second HIV protease inhibitor, one, two or three HIV reverse transcriptase inhibitor and a pharmaceutically acceptable carrier.

For example, the present invention provides a pharmaceutical composition comprising a therapeutically effective amount of a compound, or combination of compounds of formulae (I), (II), (III), (IV), (V), (VI), (VII), (VIII), (IX), (X), (XI), (XII) or (XIII), or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutical acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl ]amino}-5-phenyl-1-[4-(2-pyridinyl)benzyl]pentyl}amino)carbonyl]-2, 2-dimethylpropylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutical acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl]pentyl}amino)carbonyl]-2,2-dimethylpropylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutical acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutical acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutical acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV reverse transcriptase inhibitors selected from the group consisting of lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120 and TMC-125, and a pharmaceutical acceptable carrier.

In a twenty-first embodiment the present invention provides a pharmaceutical composition comprising a therapeutically effective amount of a compound, or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof, one, two or three second HIV protease inhibitor, one, two or three HIV entry/fusion inhibitor and a pharmaceutically acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two or three second HIV protease inhibitor, one, two or three HIV entry/fusion inhibitor and a pharmaceutically acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl]pentyl}amino)carbonyl]-2,2-dimethylpropylcarbamate, or a pharmaceutically acceptable salt form, prodrug or stereoisomer thereof, one, two or three second HIV protease inhibitor, one, two or three HIV entry/fusion inhibitor and a pharmaceutically acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two or three second HIV protease inhibitor, one, two or three HIV entry/fusion inhibitor and a pharmaceutically acceptable carrier.

For example, the present invention provides a pharmaceutical composition comprising a therapeutically effective amount of methyl(1S,4S,5S,7S,10S)-4-benzyl-1,1-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two or three second HIV protease inhibitor, one, two or three HIV entry/fusion inhibitor and a pharmaceutically acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two or three second HIV protease inhibitor, one, two or three HIV entry/fusion inhibitor and a pharmaceutically acceptable carrier.

For example, the present invention provides a pharmaceutical composition comprising a therapeutically effective amount of a compound, or combination of compounds of formulae (I), (II), (III), (IV), (V), (VI), (VII), (VIII), (IX), (X), (XI), (XII) or (XIII), or a pharmaceutically acceptable salt form, prodrug or stereoisomer thereof, one, two or three, second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutical acceptable carrier.

For example, the present invention provides a pharmaceutical composition comprising a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutical acceptable carrier.

For example, the present invention provides a pharmaceutical composition comprising a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl] pentyl}amino)carbonyl]-2,2-dimethylpropylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutical acceptable carrier.

For example, the present invention provides a pharmaceutical composition comprising a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD3100, BMS-806, FP21399, GW873140, Schering C (SCH-C), Schering D (SCH-D), TNX-355 and UK-427857, and a pharmaceutical acceptable carrier.

For example, the present invention provides a pharmaceutical composition comprising a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD-3100, BMS-806, FP21399, GW873140, Schering C (SCH-C), Schering D (SCH-D), TNX-355 and UK-427857, and a pharmaceutical acceptable carrier.

For example, the present invention provides a pharmaceutical composition comprising a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof, one, two or three second HIV protease inhibitors selected from the group consisting of ritonavir, lopinavir, saquinavir, amprenavir, fosamprenavir, nelfinavir, tipranavir, indinavir, atazanavir, TMC-126, TMC-114, mozenavir (DMP-450), JE-2147 (AG1776), L-756423, RO0334649, KNI-272, DPC-681, DPC-684 and GW640385X, one, two or three HIV entry/fusion inhibitors selected from the group consisting of enfuvirtide (T-20), T-1249, PRO 2000, PRO 542, PRO 140, AMD3100, BMS-806, FP21399, GW873140, Schering C (SCH-C), Schering D (SCH-D), TNX-355 and UK-427857, and a pharmaceutical acceptable carrier.

In a twenty-second embodiment the present invention provides a method of inhibiting the replication of an HIV virus comprising contacting said virus with a therapeutically effective amount of a compound or combination of compounds of formula (I), (II), (III), (IV), (V), (VI), (VII), (VIII), (IX), (X), (XI), (XII) or (XIII), or a pharmaceutically acceptable salt form, prodrug or stereoisomer thereof.

For example, the present invention provides a method of inhibiting the replication of an HIV virus comprising contacting said virus with a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof.

For example, the present invention provides a method of inhibiting the replication of an HIV virus comprising contacting said virus with a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl]pentyl}amino)carbonyl]-2,2-dimethylpropylcarbamate, or a pharmaceutically acceptable salt form, prodrug or stereoisomer thereof.

For example, the present invention provides a method of inhibiting the replication of an HIV virus comprising contacting said virus with a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof.

For example, the present invention provides a method of inhibiting the replication of an HIV virus comprising contacting said virus with a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof.

For example, the present invention provides a method of inhibiting the replication of an HIV virus comprising contacting said virus with a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof.

In a twenty-third embodiment the present invention provides a method of inhibiting HIV protease comprising contacting said HIV protease with a therapeutically effective amount of a compound or combination of compounds of formula (I), (II), (III), (IV), (V), (VI), (VII), (VIII), (IX), (X), (XI), (XII) or (XIII), or a pharmaceutically acceptable salt form, prodrug or streoisomer thereof.

For example, the present invention provides a method of inhibiting HIV protease comprising contacting said HIV protease with a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl) benzyl]pentyl}amino)carbonyl]-2,2-dimethylpropylcarbamate, or a pharmaceutically acceptable salt form, prodrug or stereoisomer thereof.

For example, the present invention provides a method of inhibiting HIV protease comprising contacting said HIV protease with a therapeutically effective amount of methyl(1S)-1-[({(1S,3S,4S)-4-{[(2S)-2-(3-benzyl-2-oxo-1-imidazolidinyl)-3,3-dimethylbutanoyl ]amino}-3-hydroxy-5-phenyl-1-[4-(2-pyridinyl)benzyl]pentyl}amino)carbonyl ]-2,2-dimethylpropylcarbamate, or a pharmaceutically acceptable salt form, prodrug or stereoisomer thereof.

For example, the present invention provides a method of inhibiting HIV protease comprising contacting said HIV protease with a therapeutically effective amount of methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate, or a pharmaceutically acceptable salt form, prodrug or stereoisomer thereof.

For example, the present invention provides a method of inhibiting HIV protease comprising contacting said HIV protease with a therapeutically effective amount of methyl(1S,4S,5S,7S,10S)-4-benzyl-1,10-bis(tert-butyl)-2,9,12-trioxo-5-[(phosphonooxy)methoxy ]-7-(4-pyridin-2-ylbenzyl)-13-oxa-3,8,11-triazatetradec-1-ylcarbamate, or a pharmaceutically acceptable salt form, prodrug or stereoisomer thereof.

For example, the present invention provides a method of inhibiting HIV protease comprising contacting said HIV protease with a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof.

In a twenty-fourth embodiment the present invention provides a method of treating or preventing an HIV infection comprising administering to a patient in need of such treatment a therapeutically effective amount of a compound or combination of compounds of formula (I), (II), (III), (IV), (V), (VI), (VII), (VIII), (IX), (X), (XI), (XII) or (XIII), or a pharmaceutically acceptable salt form, prodrug or streoisomer thereof.

For example, the present invention provides a method of treating or preventing an HIV infection comprising administering to a patient in need of such treatment a therapeutically effective amount of methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino }-5-phenyl-1-[4-(2-pyridinyl)benzyl]pentyl}amino)carbonyl]-2,2-dimethylpropylcarbamate, or a pharmaceutically acceptable salt form, prodrug or stereoisomer thereof.

For example, the present invention provides a method of treating or preventing an HIV infection comprising administering to a patient in need of such treatment a therapeutically effective amount of methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl) benzyl]pentyl}amino)carbonyl]-2,2-dimethylpropylcarbamate, or a pharmaceutically acceptable salt form, prodrug or stereoisomer thereof.

For example, the present invention provides a method of treating or preventing an HIV infection comprising administering to a patient in need of such treatment a therapeutically effective amount of methyl(1S,4S,5S,7S,10S)-4-benzyl-1,10-ditert-butyl-5-hydroxy-2,9,12-trioxo-7-[4-(2-pyridinyl) benzyl]-13-oxa-3,8,11-triazatetradec-1-ylcarbamate, or a pharmaceutically acceptable salt form, prodrug or stereoisomer thereof.

For example, the present invention provides a method of treating or preventing an HIV infection comprising administering to a patient in need of such treatment a therapeutically effective amount of methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate, or a pharmaceutically acceptable salt form, prodrug or stereoisomer thereof.

For example, the present invention provides a method of treating or preventing an HIV infection comprising administering to a patient in need of such treatment a therapeutically effective amount of disodium(3S,5S,8S)-8-tert-butyl-3-((1S)-1-{[N-(methoxycarbonyl)-3-methyl-L-valyl]amino}-2-phenylethyl)-7,10-dioxo-5-(4-pyridin-2-ylbenzyl)-2,11-dioxa-6,9-diazadodec-1-ylphosphonate, or a pharmaceutically acceptable salt form, prodrug or stereoisomer thereof.

In a twenty-fifth embodiment the present invention provides a method of inhibiting the replication of an HIV virus comprising contacting said virus with any one of the pharmaceutical compositions disclosed hereinabove.

In a twenty-sixth embodiment the present invention provides a method of inhibiting HIV protease comprising contacting said HIV protease with any one of the pharmaceutical compositions disclosed hereinabove.

In a twenty-seventh embodiment the present invention provides a method of treating or preventing an HIV infection comprising administering to a patient in need of such treatment any one of the pharmaceutical compositions disclosed hereinabove.

In a twenty-eighth embodiment the present invention provides an HIV protease inhibiting compound comprising a substituent of the formula (XIV):

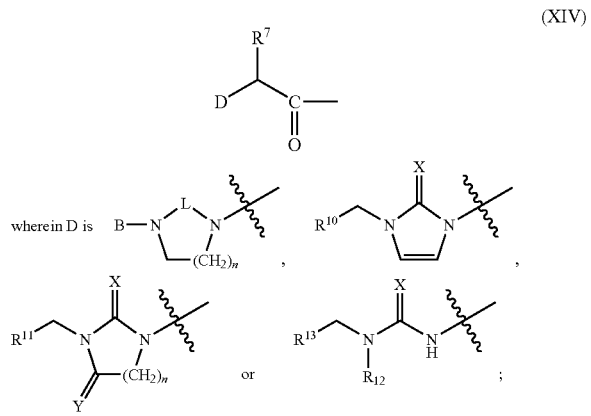

(XIV)

X is O, S or NH;
Y is O, S or NH;
B is H or —CH$_2$R$^9$;
L is —C(=O), —C(=S), —C(=NH) or —S(O)$_2$;
R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;
R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^9$ is alkyl, alkenyl, alkynyl, cycloalkyl, cycloalkenyl, aryl, heteroaryl or heterocycle; wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cyanoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$;

R$^{9a}$ is cycloalkyl, cycloalkenyl, heterocycle, aryl or heteroaryl; wherein each R$^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{10}$ is alkyl, alkenyl, alkynyl, cycloalkyl, cycloalkenyl, aryl, heteroaryl or heterocycle; wherein each R$^{10}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{10a}$;

R$^{10a}$ is cycloalkyl, cycloalkenyl, heterocycle, aryl or heteroaryl; wherein each R$^{10a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{11}$ is alkyl, alkenyl, alkynyl, cycloalkyl, cycloalkenyl, aryl, heteroaryl or heterocycle; wherein each R$^{11}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C (O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylN-R$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{11a}$;

R$^{11a}$ is cycloalkyl, cycloalkenyl, heterocycle, aryl or heteroaryl; wherein each R$^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^{12}$ is alkyl, alkenyl, cycloalkyl, cycloalkenyl, cycloalkylalkyl or cycloalkenylalkyl; wherein each R$^{12}$ is substituted with 0, 1 or 2 substituents independently selected from the group consisting of hydroxy, alkoxy and halo;

R$^{13}$ is alkyl, alkenyl, alkynyl, cycloalkyl, cycloalkenyl, aryl, heteroaryl or heterocycle; wherein each R$^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)C(O)OR$_a$, —C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkyl-C(O)NR$_a$R$_b$ and R$^{13a}$;

R$^{13a}$ is cycloalkyl, cycloalkenyl, heterocycle, aryl or heteroaryl; wherein each R$^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$_a$ and R$_b$ at each occurrence are independently selected from the group consisting of hydrogen, alkyl, alkenyl, alkynyl, cycloalkyl, aryl, heteroaryl and heterocycle; wherein each R$_a$ and R$_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, -S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

For example, the present invention provides a compound comprising a substituent of formula (XIV) wherein L is —C(═O) or —C(═S), X is O, Y is O; and B, R$^7$, R$^{7a}$, R$^9$, R$^9$, R$^{10}$, R$^{10a}$, R$^{11}$, R$^{11a}$, R$^{12}$, R$^{13}$, R$^{13a}$, R$_a$, R$_b$, R$_c$ and n are as defined in formula (XIV).

For example, the present invention provides a compound comprising a substituent of formula (XIV) wherein L is —C(═O) or —C(═S), X is O, Y is O, R$^7$ is alkyl; and B, R$^{7a}$, R$^9$, R$^{9a}$, R$^{10}$, R$^{10a}$, R$^{11}$, R$^{11a}$, R$^{12}$, R$^{13}$, R$^{13a}$, R$_a$, R$_b$, R$_c$, n and substituents of R$^7$ are as defined in formula (XIV).

For example, the present invention provides a compound comprising a substituent of formula (XIV) wherein L is —C(═O) or —C(═S), X is O, Y is O, R$^7$ is alkyl, R$^{12}$ is alkyl, and B, R$^{7a}$, R$^9$, R$^{9a}$, R$^{10}$, R$^{10a}$, R$^{11}$, R$^{11a}$, R$^{13}$, R$^{13a}$, R$_a$, R$_b$, R$_c$, n and substituents of R$^7$ are as defined in formula (XIV).

For example, the present invention provides a compound comprising a substituent of formula (XIV) wherein L is —C(═O) or —C(═S), X is O, Y is O, R$^7$ is alkyl, R$^{12}$ is alkyl, R$^9$, R$^{10}$, R$^{11}$ and R$^{13}$ are independently selected from the group consisting of aryl and heteroaryl; and B, R$^7$, R$^{7a}$, R$^{9a}$, R$^{10a}$, R$^{11a}$, R$^{13a}$, R$_a$, R$_b$, R$_c$ n and substituents of R$^7$, R$^9$, R$^{10}$, R$^{11}$ and R$^{13}$, are as defined in formula (XIV).

For example, the present invention provides a compound comprising a substituent of formula (XIV) wherein L is —C(═O) or —C(═S), X is O, Y is O, R$^7$ is alkyl, R$^{12}$ is alkyl and R$^9$, R$^{10}$, R$^{11}$ and R$^{13}$ are independently selected from the group consisting of thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl and indazolyl; and B, R$^7$, R$^{7a}$, R$^{9a}$, R$^{10a}$, R$^{11a}$, R$^{13a}$, R$_a$, R$_b$, R$_c$ n and substituents of R$^7$, R$^9$, R$^{10}$, R$^{11}$ and R$^{13}$, are as defined in formula (XIV).

For example, the present invention provides a compound comprising a substituent of formula (XIV) wherein L is —C(=O) or —C(=S), X is O, Y is O, $R^7$ is C1, C2, C3, C4 or C5 alkyl, $R^{12}$ is alkyl, and $R^9$, $R^{10}$, $R^{11}$ and $R^{13}$ are independently selected from the group consisting of thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl and indazolyl, and B, $R^7$, $R^{7a}$, $R^{9a}$, $R^{10a}$, $R^{11a}$, $R^{13a}$, $R_a$, $R_b$, $R_c$ n and substituents of $R^7$, $R^9$, $R^{10}$, $R^{11}$ and $R^{13}$, are as defined in formula (XIV).

For example, the present invention provides a compound comprising a substituent of formula (XIV) wherein L is —C(=O) or —C(=S), X is O, Y is O, $R^7$ is tert-butyl, 1-methylpropyl or isopropyl, $R^{12}$ is alkyl, $R^9$, $R^{10}$, $R^{11}$ and $R^{13}$ are independently selected from the group consisting of thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl and indazolyl; and B, $R^7$, $R^{7a}$, $R^{9a}$, $R^{10a}$, $R^{11a}$, $R^{13a}$, $R_a$, $R_b$, $R_c$ n and substituents of $R^7$, $R^9$, $R^{10}$, $R^{11}$ and $R^{13}$, are as defined in formula (XIV).

For example, the present invention provides a compound comprising a substituent of formula (XIV) wherein L is —C(=O) or —C(=S), X is O, Y is O, $R^7$ is tert-butyl, 1-methylpropyl or isopropyl, $R^{12}$ is methyl or ethyl, $R^9$, $R^{10}$, $R^{11}$ and $R^{13}$ are independently selected from the group consisting of thienyl, furanyl, pyrrolyl, thiazolyl, oxazolyl, imidazolyl, pyrazolyl, isothiazolyl, isoxazolyl, isoquinolinyl, quinolinyl, pyridyl, phenyl, pyridoimidazolyl, benzimiazolyl, benzothienyl, benzthiazolyl and indazolyl; and B, $R^7$, $R^{7a}$, $R^{9a}$, $R^{10a}$, $R^{11a}$, $R^{13a}$, $R_a$, $R_b$, $R_c$ n and substituents of $R^7$, $R^9$, $R^{10}$, $R^{11}$ and $R^{13}$, are as defined in formula (XIV).

HIV protease inhibiting compounds comprising a substituent of the formula (XIV) can be prepared by coupling a suitable intermediate or precursor molecule having an amino group (—$NH_2$ or —NHR* wherein R* is alkyl), a hydroxy group (—OH) or a thiol group (—SH) to the compound of formula (XV) or a salt or an activated ester derivative thereof:

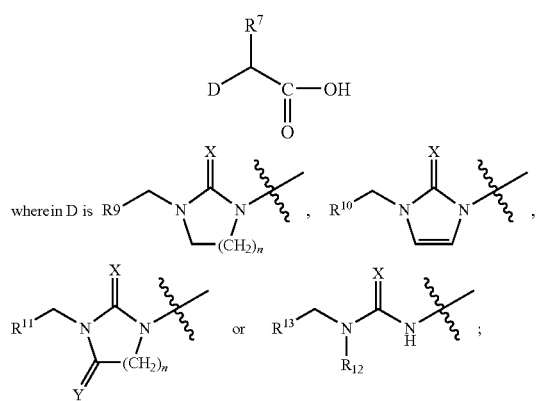

(XV)

X is O, S or NH;
Y is O, S or NH;
B is H or —$CH_2R^9$;
L is —C(=O), —C(=S), —C(=NH) or —S(O)$_2$;
$R^7$ is —$N(R_b)C(O)OR_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —$OR_a$, —$OC(O)R_a$, —$SR_a$, —$SOR_a$, —$SO_2R_a$, —$NR_aR_b$, —$N(R_b)C(O)R_a$, —$N(R_b)$ $C(O)OR_a$, —$N(R_a)C(=N)NR_aR_b$, —$N(R_a)C(O)NR_aR_b$, —$C(O)NR_aR_b$, —$C(O)OR_a$ and $R^{7a}$;

$R^{7a}$ is cycloalkyl, cycloalkenyl, heterocycle, aryl or heteroaryl; wherein each $R^{7a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N (H)(alkyl), —N(H)C(O)N(alkyl)$_2$, —C(O)OH, —C(O) Oalkyl, —C(O)$NH_2$, —C(O)N(H)(alkyl), —C(O)N (alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkyl-C(O)N(alkyl)$_2$;

$R^9$ is alkyl, alkenyl, alkynyl, cycloalkyl, cycloalkenyl, aryl, heteroaryl or heterocycle; wherein each $R^9$ is substituted with 0, 1, 2 or 3 substituents independently selected from the group consisting of alkyl, alkenyl, alkynyl, cyano, formyl, halo, nitro, oxo, —$OR_a$, —$SR_a$, —$SOR_a$, —$SO_2R_a$, $SO_2NR_a$, —$SO_2OR_a$, $NR_aR_b$, —$N(R_b)C(O)R_a$, —$N(R_b)SO_2R_a$, —$N(R_b)SO_2NR_aR_b$, —$N(R_b)C(O)$ $NR_aR_b$, —$N(R_b)C(O)OR_a$, —$C(O)R_a$, —$C(O)NR_aR_b$, —$C(O)OR_a$, haloalkyl, nitroalkyl, cynaoalkyl, formylalkyl, -alkyl$OR_a$, -alkyl-O—$P(O)(OR_a)(OR_a)$, -alkylN-$R_aR_b$, -alkylN($R_b$)C(O)$OR_a$, -alkylN($R_b$)$SO_2NR_aR_b$, -alkylN($R_b$)C(O)$R_a$, -alkylN($R_b$)C(O)$NR_aR_b$, -alkylN ($R_b$)$SO_2R_a$, -alkylC(O)$OR_a$, -alkylC(O)$R_a$, -alkylC(O) $NR_aR_b$ and $R^{9a}$;

$R^{9a}$ is cycloalkyl, cycloalkenyl, heterocycle, aryl or heteroaryl; wherein each $R^{9a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N (H)(alkyl), —N(H)C(O)N(alkyl)$_2$, —C(O)OH, —C(O) Oalkyl, —C(O)$NH_2$, —C(O)N(H)(alkyl), —C(O)N (alkyl)$_2$, cyanoalkyl, haloalkyl, hydroxyalkyl, alkoxyalkyl, -alkyl$NH_2$, -alkylN(H)(alkyl), -alkylN(alkyl)$_2$, -alkylN(H) C(O)$NH_2$, -alkylN(H)C(O)N(H)(alkyl), -alkylN(H)C(O) N(alkyl)$_2$, -alkylC(O)OH, -alkylC(O)Oalkyl, -alkylC(O) $NH_2$, -alkylC(O)N(H)(alkyl) and -alkylC(O)N(alkyl)$_2$;

$R^{10}$ is alkyl, alkenyl, alkynyl, cycloalkyl, cycloalkenyl, aryl, heteroaryl or heterocycle; wherein each $R^{10}$ is substituted with 0, 1, 2 or 3 substituents independently selected from the group consisting of alkyl, alkenyl, alkynyl, cyano, formyl, halo, nitro, oxo, —OR, —$SR_a$, —$SOR_a$, —$SO_2R_a$, —$SO_2NR_a$, —$SO_2OR_a$, —$NR_aR_b$, —$N(R_b)C(O)R_a$, —$N(R_b)SO_2R_a$, —$N(R_b)SO_2NR_aR_b$, —$N(R_b)C(O)$ $NR_aR_b$, —$N(R_b)C(O)OR_a$, —$C(O)R_a$, —$C(O)NR_aR_b$, —$C(O)OR_a$, haloalkyl, nitroalkyl, cynaoalkyl, formylalkyl, -alkyl$OR_a$, -alkyl-O—$P(O)(OR_a)(OR_a)$, -alkylN-$R_aR_b$, -alkylN($R_b$)C(O)$OR_a$, -alkylN($R_b$)$SO_2NR_aR_b$, -alkylN($R_b$)C(O)$R_a$, -alkylN($R_b$)C(O)$NR_aR_b$, -alkylN ($R_b$)$SO_2R_a$, -alkylC(O)$OR_a$, -alkylC(O)$R_a$, -alkylC(O) $NR_aR_b$ and $R^{10a}$;

$R^{10a}$ is cycloalkyl, cycloalkenyl, heterocycle, aryl or heteroaryl; wherein each $R^{10a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), —N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N (H)(alkyl), —N(H)C(O)N(alkyl)$_2$, —C(O)OH, —C(O) Oalkyl, —C(O)$NH_2$, —C(O)N(H)(alkyl), —C(O)N (alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{11}$ is alkyl, alkenyl, alkynyl, cycloalkyl, cycloalkenyl, aryl, heteroaryl or heterocycle; wherein each $R^{11}$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and $R^{11a}$;

$R^{11a}$ is cycloalkyl, cycloalkenyl, heterocycle, aryl or heteroaryl; wherein each $R^{11a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

$R^{12}$ is alkyl, alkenyl, cycloalkyl, cycloalkenyl, cycloalkylalkyl or cycloalkenylalkyl; wherein each $R^{12}$ is substituted with 0, 1 or 2 substituents independently selected from the group consisting of hydroxy, alkoxy and halo;

$R^{13}$ is alkyl, alkenyl, alkynyl, cycloalkyl, cycloalkenyl, aryl, heteroaryl or heterocycle; wherein each $R^{13}$ is substituted with 0, 1, 2 or 3 substituents independently selected from the group consisting of alkyl, alkenyl, alkynyl, cyano, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)C(O)OR$_a$, —C(O)NR$_a$R$_b$, —C(O)OR$_a$, haloalkyl, nitroalkyl, cynaoalkyl, -alkylOR$_a$, -alkyl-O—P(O)(OR$_a$)(OR$_a$), -alkylNR$_a$R$_b$, -alkylN(R$_b$)C(O)R$_a$, -alkylN(H)C(O)NR$_a$R$_b$, -alkylN(R$_b$)SO$_2$R$_a$, -alkylC(O)OR$_a$, -alkyl-C(O)NR$_a$R$_b$ and $R^{13a}$;

$R^{13a}$ is cycloalkyl, cycloalkenyl, heterocycle, aryl or heteroaryl; wherein each $R^{13a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$_a$ and R$_b$ at each occurrence are independently selected from the group consisting of hydrogen, alkyl, alkenyl, alkynyl, cycloalkyl, aryl, heteroaryl and heterocycle; wherein each R$_a$ and R$_b$, at each occurrence, is independently substituted with 0, 1, 2 or 3 substituents independently selected from the group consisting of cyano, nitro, halo, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

The present invention is also related to the process of preparing a compound of formula (XVIII)

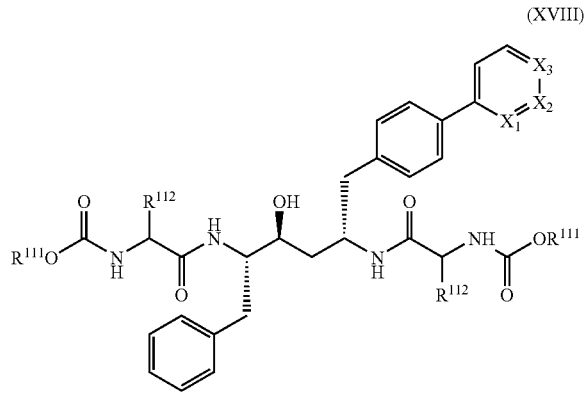

(XVIII)

wherein
X$_1$ is CH or N;
X$_2$ is CH or N;

$X_3$ is CH or N; provided only one of $X_1, X_2, X_3$ is N and the other two are CH;

$R^{112}$ is alkyl, alkenyl, alkynyl, cycloalkyl, cycloalkenyl heterocycle, aryl or heteroaryl; wherein each $R^{112}$ is substituted with 0, 1 or 2 substituents independently selected from the group consisting of halo, —$OR_{a'}$, —$SR_{a'}$, —$SO_{a'}$, —$SO_2R_{a'}$, —$NR_aR_{b'}$, —$N(R_{b'})C(O)R_{a'}$, —$N(R_{b'})C(O)OR_{a'}$, —$N(R_{b'})C(=N)NR_aR_{b'}$, —$N(R_{b'})C(O)NR_aR_{b'}$, —$C(O)NR_{a'}R_{b'}$, —$C(O)OR_{a'}$, and $R^{112a}$;

$R^{112a}$ is cycloalkyl, cycloalkenyl, heterocycle, aryl or heteroaryl; wherein each $R^{112a}$ is substituted with 0, 1, 2, 3 or 4 substituents independently selected from the group consisting of cyano, halo, nitro, oxo, alkyl, alkenyl, alkynyl, hydroxy, alkoxy, —$NH_2$, —N(H)(alkyl), -N(alkyl)$_2$, —SH, —S(alkyl), —$SO_2$(alkyl), —N(H)C(O)alkyl, —N(alkyl)C(O)alkyl, —N(H)C(O)$NH_2$, —N(H)C(O)N(H)(alkyl), —N(H)C(O)N(alkyl)$_2$, —C(O)OH, —C(O)Oalkyl, —C(O)$NH_2$, —C(O)N(H)(alkyl), —C(O)N(alkyl)$_2$, haloalkyl, hydroxyalkyl, alkoxyalkyl, -alkyl$NH_2$, -alkylN(H)(alkyl), -alkylN(alkyl)$_2$, -alkylN(H)C(O)$NH_2$, -alkylN(H)C(O)N(H)(alkyl), -alkylN(H)C(O)N(alkyl)$_2$, -alkylC(O)OH, -alkylC(O)Oalkyl, -alkylC(O)$NH_2$, -alkylC(O)N(H)(alkyl) and -alkyl-C(O)N(alkyl)$_2$;

$R^{111}$ is $C_1$-$C_6$ alkyl or phenylmethyl; and $R_{a'}$ and $R_{b'}$ are each independently selected from the group consisting of hydrogen and alkyl.

wherein the process comprises the steps of:
(a) contacting a compound of formula (i)

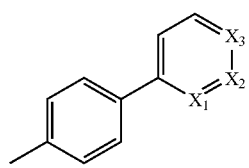
(i)

with potassium tert-butoxide and n-butyl lithium in a first solvent;

(b) contacting a first base with ketonitrile of formula (ii)

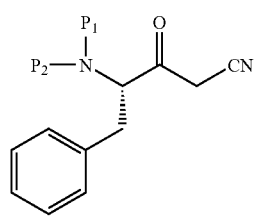
(ii)

wherein $P_1$ and $P_2$ are nitrogen protecting group and $P_1$ and $P_2$ can be the same or different, in the first solvent;

(c) contacting the product of step (b) with the product of step (a) to provide a compound of formula (iii)

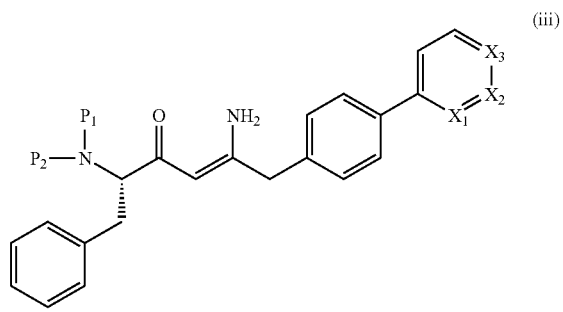
(iii)

(d) contacting the compound of formula (iii) with a first reducing agent and an acid in a second solvent;

(e) contacting the product of step (d) in the second solvent with a second reducing agent, to provide a compound of formula (iv);

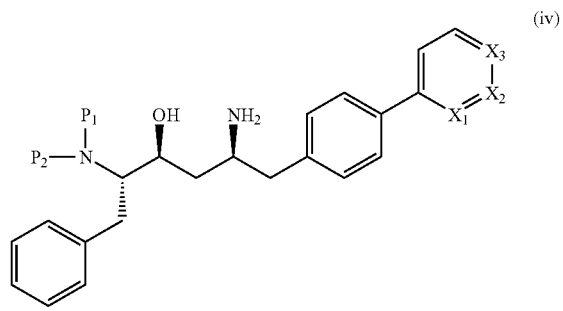
(iv)

(f) contacting the compound of formula (iv) with a hydrogen source and a catalyst in a third solvent to provide a compound of formula (v);

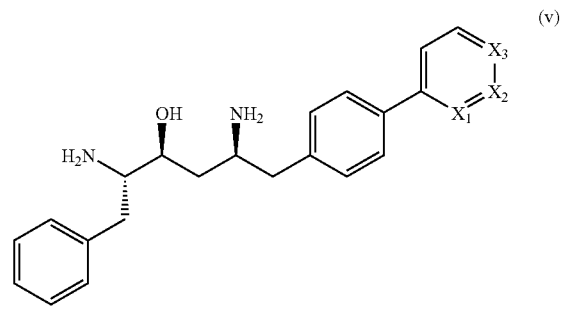
(v)

and
(g) contacting the compound of formula (v) with a compound of formula (vi),

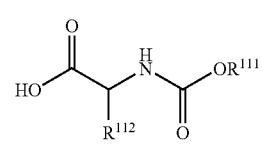
(vi)

a coupling reagent and a second base in a fourth solvent to provide the compound of formula (XVIII).

In step (a), about one to about 1.6 molar equivalent of potassium tert-butoxide is first 20 mixed with about one equivalent of the compound of formula (i) in a first solvent for a period of about 5 minutes to about 30 minutes, followed by the addition of about one to about 1.6 molar equivalents of n-butyl lithium. Alternatively potassium tert-butoxide and n-butyl lithium can be premixed in the first solvent, followed by the addition of the compound of formula (i). The temperature at which the mixings can be carried out is from about −78° C. to about 0° C., preferably at a temperature from about −25° C. to about 0° C. and most preferably at a temperature from about −20° C. to about −10° C. After complete mixing of all three reagents, the reaction mixture can be stirred at a temperature from about room temperature to about 35° C., preferably at about room temperature, for a period of about 30 minutes to about 3 hours, preferably for about 1 hour.

The first solvent used in step (a) refers to any organic solvent that will allow the reaction in step (a) to proceed to completion or substantially to completion. Examples of the first solvent include, but are not limited to, tetrahydrofuran, tert-butyl methyl ether and dimethyl ether preferably tetrahydrofuran.

About one equivalent of ketonitrile of formula (ii) in the first solvent is pre-cooled to a temperature of about −10° C. to about 10° C., preferably at about −5° C. to about 5° C., followed by addition of a first base at a temperature from about −10° C. to about 10° C., preferably at about −5° C. to about 5° C. The mixture is then stirred at a temperature from about −10° C. to about 10° C., preferably at about −5° C. to about 5° C., for a period from about 15 minutes to about 1 hour, preferably for about 30 minutes.

Examples of the first base in step (a) include, but are not limited to tert-butyl magnesium chloride and tert-butyl magnesium bromide, preferably tert-butyl magnesium chloride.

The product of step (b) is treated with the product of step (a) at a temperature from about −10° C. to about 10° C., preferably at about −5° C. to about 5° C. and the reaction mixture is stirred a temperature from about 10° C. to about 25° C., preferably at about 25° C., for about 1 hour to about 24 hours, preferably for about 20 hours. The product of step (c) is isolated by first quenching the reaction mixture with saturated ammonium chloride solution, diluting the solution with ethyl acetate, stirring the solution, separating the aqueous phase from the organic phase; wash the organic phase sequentially with ammonium chloride; drying the organic phase over sodium sulfate; and concentrating the organic phase to provide the compound of formula (iii).

The compound of formula (iii) in a second solvent is cooled to a temperature from about −20° C. to about 10° C., preferably at a temperature from about −15° C. to about 0° C., and most preferably at about −15° C., followed by addition of an acid. The mixture is cooled to a temperature from about −20° C. to about 10° C., preferably at a temperature from about −15° C. to about 0° C., and most preferably at about −15° C., followed by the addition of about 5 molar equivalents of a first reducing agent. The mixture is stirred for a period from about 1 hour to about 24 hours, preferably about 3 hours, at a temperature from about −20° C. to about 10° C., preferably at a temperature from about −15° C. to about 0° C., and most preferably at about −15° C.

The second solvent is a mixture of solvents selected from an alcohol (for example isopropyl alcohol, ethanol, methanol, and the like) and an amide (for example, N,N-dimethylformamide, dimethylacetamide, and the like). Preferred second solvent is a mixture of dimethylacetamide and isopropyl alcohol in a ratio of about 10:1 (volume:volume).

Examples of the acid used in step (d) include, but are not limited to, methane sulfonic acid, acetic acid, and sulfuric acid. Preferred acid for step (d) is methane sulfonic acid.

Examples of the first reducing agent include, but are not limited to, sodium triacetoxyborohydride, sodium borohydride. Preferred first reducing agent is sodium triacetoxyborohydride.

The reaction in step (d) is quenched with the addition of about 10 to about 15 molar equivalents of an organic amine. The reaction mixture is stirred at a temperature from about −20° C. to about 0° C., preferably at about −15° C., for a period of about 15 minutes to about 2 hours, preferably for about 1 hour. Examples of the organic amine include, but are not limited to, triethylamine, triethanolamine, and diisopropyl ethylamine. A preferred organic amine is triethanolamine.

The product of step (d) can be reacted with a second reducing agent, either in situ or after isolation. Preferred procedure is to mix the second reducing agent with the product of step (d) in the second solvent, after quenching with the organic amine, without isolation of the product of step (d).

Examples of the second reducing agent used in step (e) include, but are not limited to, sodium borohydride and lithium borohydride. Preferred second reducing agent is sodium borohydride.

The reduction reaction between the second reducing agent and the product of step (d) is conducted at a temperature from about −20° C. to about room temperature, preferably at a temperature from about −15° C. to about 0 C, most preferably at a temperature from about −15° C. to about −10° C., for a period from about 1 hour to about 30 hours, preferably for a period from about 10 to about 24 hours.

The product from step (e) is isolated by quenching the reaction mixture with water, extracting with isopropyl acetate, separating the organic phase from aqueous phase, extracting the isolated isopropyl acetate with dilute $H_3PO_4$ solution (preferably at a concentration of about 0.35 to about 1%, most preferably 0.3%), adjusting the pH of the isolated aqueous layer to about 6-7 with a base such as sodium carbonate, extracting with isopropyl acetate, washing the isolated organic phase with 5% aqueous $KH_2PO_4$, drying over a drying agent such as sodium sulfate or magnesium sulfate, filtering and concentrating to provide compounds of formula (iv).

$P_1$ and $P_2$ in compounds of formula (iv) are nitrogen protecting groups and can be the same or different. Examples of nitrogen protecting groups that can be employed in this process include, but are not limited to, 9-fluorenylmethyl oxycarbonyl, tert-butyloxycarbonyl, benzyl oxycarbonyl, p-methoxybenzyl oxycarbonyl, 3,5-dimethoxybenzyl oxycarbonyl and benzyl. Preferred nitrogen protecting group are tert-butyloxycarbonyl, benzyl oxycarbonyl and benzyl. Most preferred nitrogen protecting group is benzyl.

Compounds of formula (iv) can be converted to compounds of formula (v) by reacting with a deprotecting reagent. Examples of the deprotecting agent are well known in the art and are illustrated in Protective Groups in Organic Synthesis, $3^{rd}$ edition, T. W. Greene, P. G. M. Wuts, John Wiley & Sons, Inc., 1998. In the case wherein both $P_1$ and $P_2$ are benzyl, compounds of formula (iv) can be converted to compounds of formula (v) by reacting with a hydrogen source and a catalyst in a third solvent.

Examples of the third solvent include, but are not limited to, ethyl acetate, isopropyl alcohol, methanol, ethanol tetrahydrofuran, and dioxane. A preferred third solvent is methanol.

Examples of the hydrogen source include, but are not limited to, hydrogen gas, ammonium formate, and formic acid. Preferred hydrogen source is ammonium formate.

Examples of the catalyst include, but are not limited to, palladium on carbon, palladium hydroxide on carbon, and platinum oxide. Preferred catalyst is palladium on carbon.

The reaction is generally conducted at a temperature from about room temperature to about 80° C., preferably at a temperature from about 35° C. to about 70° C., most preferably at a temperature from about 50° C. to about 65° C., for a period from about 1 hour to about 20 hours, preferably for a period from about 8 to about 15 hours, under an inert atmosphere (e.g. nitrogen or argon gas).

The product of step (f) is isolated by filtering the reaction mixture, concentrating the filtrate, diluting the concentrate in dichloromethane, washing with aqueous sodium bicarbonate, separating the aqueous phase from the organic phase, drying the organic phase over sodium sulfate, filtering and concentrating the organic phase.

Compounds of formula (XVIII) can be obtained from compounds of formula (v) by reacting with compounds of formula (vi), a coupling reagent and a second base in a fourth solvent.

Examples of the coupling reagent include, but are not limited to, O-benzotriazol-1-yl-N,N,N',N'-tetramethyluronium hexafluorophosphate (HBTU), O-benzotriazol-1-yl-N,N,N',N'-tetramethyluronium tetrafluoroborate (TBTU), bis(2-oxo-3-oxazolidinyl)phosphinic chloride (BOPCl), benzotriazol-1-yloxytris(dimethylamino)phosphonium hexafluorophosphate (BOP), 1-hydroxybenzotriazole hydrate (HOBT), 3-hydroxy-1,2,3-benzotriazin-4(3H)-one (HOOBT) and 1,3-di-tert-butylcarbodiimide. Preferred coupling reagent for step (g) is O-benzotriazol-1-yl-N,N,N',N'-tetramethyluronium hexafluorophosphate (HBTU).

Examples of the second base include, but are not limited to, triethylamine, diisopropylethylamine, sodium carbonate, potassium carbonate. Preferred second base for the reaction is diisopropylethylamine.

Examples of the fourth solvent include acetonitrile, ethyl acetate, dichloromethane, tetrahydrofuran, dioxane, and mixtures thereof. Preferred fourth solvent is a mixture of ethyl acetate and acetonitrile in a ratio of about 10:1 (volume:volume).

A mixture of compound of formula (vi), coupling reagent, and the second base in a molar ratio of about 2:2:6 in the fourth solvent is stirred at about room temperature for a period of about 30 minutes to about 3 hours, followed by addition of about 1 equivalent of the compound of formula (v) in ethyl acetate. The reaction mixture is stirred for a period from about 8 hours to about 24 hours, preferably 24 hours, at a temperature from about room temperature to about 50° C., preferably at about room temperature. The product is isolated by filtering, dissolving the isolated solid in acetonitrile at a temperature from about 70° C. to about 80° C., cooling the solution to about room temperature, stirring the cooled solution for a period of about 30 minutes to about 2 hours, filtering, washing the isolated solid with acetonitrile and drying the solid.

The term "nitrogen protecting group", "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 2nd edition, John Wiley & Sons, New York (1991). N protecting groups comprise acyl groups such as formyl, acetyl, propionyl, pivaloyl, t-butylacetyl, 2-chlorcacetyl, 2-bromoacetyl, trifluoroacetyl, trichloroacetyl, phthalyl, o-nitrophenoxyacetyl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu-S(O)—) and the like; carbamate forming groups such as benzyloxycarbonyl, p-chlorobezzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

As used herein, the terms "S" and "R" configuration are as defined by the IUPAC 1974 Recommendations for Section E, Fundamental Stereochemistry, Pure Appl. Chem. (1976) 45, 13-30.

The compounds of the invention can comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, esters, amides, solvates and hydrates of the compounds of formula (I), (II), (III), (IV), (V), (VI), (VII), (VIII), (IX), (X), (XI), (XII) or (XIII) are meant to be included in this invention.

When any variable (for example X, $R_{103}$, $R_{104}$, $R_{105}$, $R_{106}$, $R_{107}$, $R_{108}$, $R_a$, $R_b$, $R_c$, M, Q, etc.) occurs more than one time in any substituent or in the compound of formula (I), (II), (III), (IV), (V), (VI), (VII), (VIII), (IX), (X), (XI), (XII), (XIII), (XIV), (XV), (XVI), (XVII) or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

The compounds of the present invention can be used in the form of salts derived from inorganic or organic acids. These salts include but are not limited to the following: 4-acetamidobenzoate, acetate, adipate, alginate, carbonate, 4-chlorobenzenesulfonate, citrate, aspartate, benzoate, benzenesulfonate, bisulfate, butyrate, camphorate, camphorsulfonate, cholate, digluconate, cyclopentanepropionate, dichloroacetate, dodecylsulfate, ethanedisulfonate, ethanesulfonate, ethylsuccinate, formate, fumarate, galactarate, D-gluconate, D-glucuronate, glucoheptanoate, glutarate, lycerophosphate, glycolate, hemisulfate, heptanoate, hexanoate, hydrochloride, hydrobromide, hydroiodide, 2-hydroxyethanesulfonate (isethionate), 3-hydroxy-2-naphthoate, 1-hydroxy-2-naphthoate, lactate, lactobionate, laurate, maleate, malonate, mandelate, methanesulfonate, nicotinate, 1,5-naphthalene-disulfonate, 2-naphthalene-sulfonate, oleate, oxalate, pamoate, palmitate, pectinate, persulfate, 3-phenylpropionate, picrate, pivalate, propionate, L-pyroglutamate, sebacate, stearate, succinate, tartrate, terephthalate, thiocyanate, p-toluenesulfonate, undecanoate, undecylenoate and valerate. Also, the basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Other salts include salts with alkali metals or alkaline earth metals, such as aluminum, sodium, lithium, potassium, calcium, magnesium or zinc or with organic bases such as diethylethanolamine, diethanolamine, ethylenediamine, guanidine, meglumine, olamine (ethnolamine), piperazine, piperidine, triethylamine, tromethamine, benzathine, benzene-ethanamine, adenine, cytosine, diethylamine, glucosamine, guanine, nicotinamide, hydrabamine, tributylamine, deanol, epolamine or triethanolamine.

Representative salts of the compounds of the present invention include, but not limited to, hydrochloride, bis hydrochloride, mosodium, disodium, methanesulfonate, sulfonate, phosphonate, isethionate and trifluoroacetate.

The compounds of the present invention can also be used in the form of prodrugs. Examples of such prodrugs include compounds wherein one, two or three hydroxy groups in the compound of this invention are functionalized with $R^{15}$ wherein $R^{15}$ is

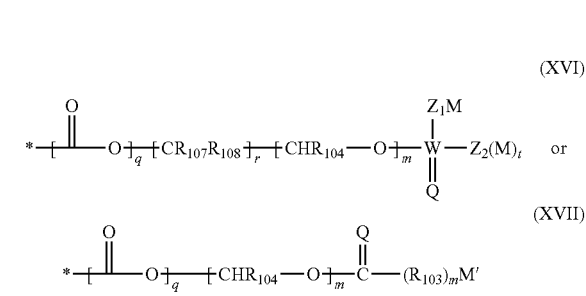

$R_{103}$ is $C(R_{105})_2$, O or —$N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —$N(R_{105})_2$, alkyl, alkenyl, and $R_{106}$; wherein 1 to 4 —$CH_2$ radicals of the alkyl or alkenyl, other than the —$CH_2$ radical that is bound to Z, is optionally replaced by a heteroatom group selected from the group consisting of O, S, S(O), $SO_2$ and $N(R_{105})$; and wherein any hydrogen in said alkyl, alkenyl or $R_{106}$ is optionally replaced with a substituent selected from the group consisting of oxo, —$OR_{105}$, —$R_{105}$, —$N(R_{105})_2$, —CN, —C(O)$OR_{105}$, —C(O)$N(R_{105})_2$, —$SO_2N(R_{105})$, —$N(R_{105})C(O)R_{105}$, —C(O)$R_{105}$, —$SR_{105}$, —S(O)$R_{105}$, —$SO_2R_{105}$, —$OCF_3$, —$SR_{106}$, —$SOR_{106}$, —$SO_2R_{106}$, —$N(R_{105})SO_2R_{105}$, halo, —$CF_3$, $NO_2$ and phenyl; provided that when M is —$N(R_{105})_2$, $Z_1$ and $Z_2$ are —$CH_2$;

$Z_1$ is $CH_2$, O, S, —$N(R_{105})$, or, when M is absent H;

$Z_2$ is $CH_2$, O, S or —$N(R_{105})$;

Q is O or S;

W is P or S; wherein when W is S, $Z_1$ and $Z_2$ are not S;

M' is H, alkyl, alkenyl or $R_{106}$; wherein 1 to 4 $H_2$ radicals of the alkyl or alkenyl is optionally replaced by a heteroatom group selected from O, S, S(O), SO, or $N(R_{105})$; and wherein any hydrogen in said alkyl, alkenyl or $R_{106}$ is optionally replaced with a substituent selected from the group consisting of oxo, $-OR_{105}$, $-R_{105}$, $-N(R_{105})_2$, $-CN$, $-C(O)OR_{105}$, $-C(O)N(R_{105})_2$, $-SO_2N(R_{105})$, $-N(R_{105})C(O)R_{105}$, $-C(O)R_{105}$, $-SR_{105}$, $-S(O)R_{105}$, $-SO_2R_{105}$, $-OCF_3$, $-SR_{106}$, $-SOR_{106}$, $-SO_2R_{106}$, $-N(R_{105})SO_2R_{105}$, halo, $-CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, $SO_2$ and $N(R_{105})$; and wherein any of said ring system is substituted with 0, 1, 2, 3, 4, 5 or 6 substituents selected from the group consisting of hydroxy, alkyl, alkoxy, and $-OC(O)$alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, $SO_2$, and $N(R_{105})$; and wherein any one of said ring systems is substituted with 0, 1, 2, 3 or 4 substituents selected from the group consisting of oxo, $-OR_{105}$, $-R_{105}$, $-N(R_{105})_2$, $-N(R_{105})C(O)R_{105}$, $-CN$, $-C(O)OR_{105}$, $-C(O)N(R_{105})_2$, halo and $-CF_3$;

each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4; and t is 0 or 1.

It will be understood by those of skill in the art that component M or M' in the formulae (XVI) and (XVII) set forth herein will have either a covalent, a covalent/zwitterionic, or an ionic association with either $Z_1$, $Z_2$ or $R_{103}$ depending upon the actual choice for M or M'. When M or M' is hydrogen, alkyl, alkenyl or $R_{106}$, then M or M', is covalently bound to $-R_{103}$ $Z_1$, or $Z_2$. If M is a mono or bivalent metal or other charged species (i.e. $NH_4^+$), there is an ionic interaction between M and $Z_1$ or $Z_2$ and the resulting compound is a salt.

These prodrugs of the compound of the present invention serve to increase the solubility of these compounds in the gastrointestinal tract. These prodrugs also serve to increase solubility for intravenous administration of the compound. These prodrugs may be prepared by using conventional synthetic techniques. One of skill in the art would be well aware of conventional synthetic reagents to convert one or more of the hydroxy groups of the compounds of the present invention to a desired prodrug, functionalized by the substituents of formula (XVI) or (XVII) as defined above.

The prodrugs of this invention are metabolized in vivo to provide the compound of this invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention are useful for inhibiting retroviral protease, in particular HIV protease, in vitro or in vivo (especially in mammals and in particular in humans). The compounds of the present invention are also useful for the inhibition of retroviruses in vivo, especially human immunodeficiency virus (HIV). The compounds of the present invention are also useful for the treatment or prophylaxis of diseases caused by retroviruses, especially acquired immune deficiency syndrome or an HIV infection in a human or other mammal.

Total daily dose administered to a human or other mammal host in single or divided doses may be in amounts, for example, from 0.001 to 300 mg/kg body weight daily and more usually 0.1 to 20 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, sublingually, by inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coating.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono-or multi-lamellar hydrated liquid crystals that are dispersed in an aqueous medium. Any nontoxic, physiologically acceptable and metabolizable lipid capable of forming liposomes can be used. The present compositions in liposome form can contain, in addition to the compound of the present invention, stabilizers, preservatives, excipients, and the like. The preferred lipids are the phospholipids and phosphatidyl cholines (lecithins), both natureal and synthetic.

Methods to form liposomes are known in the art. See, for example, Prescott, Ed., Methods in Cell Biology, Volume XIV, Academic Press, New York, N.Y. (1976), p. 33.

While the compound of the invention can be administered as the sole active pharmaceutical agent, it can also be used in combination with one or more immunomodulators, antiviral agents, other antiinfective agents or vaccines. Other antiviral agents to be administered in combination with a compound of the present invention include AL-721, beta interferon, polymannoacetate, reverse transcriptase inhibitors (for example, BCH-189, AzdU, carbovir, ddA, d4C, d4T (stavudine), 3TC (lamivudine) DP-AZT, FLT (fluorothymidine), BCH1189, 5-halo-3'-thia-dideoxycytidine, PMEA, bis-POMPMEA, zidovudine (AZT), MSA-300, trovirdine, R82193, L-697, 661, BI-RG-587 (nevirapine), abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150, TMC-120, and TMC-125 and the like), retroviral protease inhibitors (for example, HIV protease inhibitors such as ritonavir, lopinavir, saquinavir, amprenavir (VX-478), fosamprenavir, nelfmavir (AG1343), tipranavir, indinavir, atazanovir, TMC-126, TMC-114, mozenavir (DMP-450), JE-2147 (AG1776), L-756423, R00334649, KNI-272, DPC-681, DPC-684, GW640385X, SC-52151, BMS 186,318, SC-55389a, BELA 1096 BS, DMP-323, KNI-227, and the like), HEPT compounds, L,697, 639, R82150, U87201E and the like), HIV integrase inhibitors (S-1360, zintevir (AR-177), L-870812 L-870810 and the like), TAT inhibitors (for example, RO-247429 and the like), trisodium phosphonoformate, HPA-23, eflonithine, Peptide T, Reticulose (nucleophosphoprotein), ansamycin LM 427, trimetrexate, UA001, ribavirin, alpha interferon, oxetanocin, oxetanocin-G, cylobut-G, cyclobut-A, ara-M, BW882C87, foscarnet, BW256U87, BW348U87, L-693,989, BV ara-U, CMV triclonal antibodies, FIAC, HOE-602, HPMPC, MSL-109, TI-23, trifluridine, vidarabine, famciclovir, penciclovir, acyclovir, ganciclor, castanosperminem rCD4/CD4-IgG, CD4-PE40, butyl-DNJ, hypericin, oxamyristic acid, dextran sulfate and pentosan polysulfate. Other agents that can be administered in combination with the compound of the present invention include HIV entry/fusion inhibitor (for example, enfuivirtide (T-20), T-1249, PRO 2000, PRO 542, PRO 140, AMD-3100, BMS-806, FP21399, GW873140, Schering C (SCH-C), Schering D (SCH-D), TNX-355, UK-427857, and the like) and HIV budding/maturation inhibitor such as PA-457. Immunomodulators that can be administered in combination with the compound of the present invention include bropiriiine, Ampligen, anti-human alpha interferon antibody, colony stimulting factor, CL246, 738, Imreg-1, Imreg-2, diethydithiocarbamate, interleukin-2, alpha-interferon, inosine pranobex, methionine enkephalin, muramyl-tripeptide, TP-5, erythropoietin, naltrexone, tumor necrosis factor, beta interferon, gamma interferon, interleukin-3, interleukin-4, autologous CD8+ infusion, alpha interferon immunoglobulin, IGF-1, anti-Leu3A, autovaccination, biostimulation, extracorporeal photophoresis, cyclosporin, rapamycin, FK-565, FK-506, GCSF, GM-CSF, hyperthermia, isopinosine, IVIG, HIVIG, passive immunotherapy and polio vaccine hyperimmunization. Other antiinfective agents that can be administered in combination with the compound of the present invention include pentamidine isethionate. Any of a variety of HIV or AIDS vaccines (for example, gp120 (recombinant), Env 2-3 (gp120), HIVAC-1e (gp120), gp160 (recombinant), VaxSyn HIV-1 (gp160), Immuno-Ag (gp160), HGP-30, HIV-Immunogen, p24 (recombinant), VaxSyn HIV-1 (p24)) can be used in combination with the compound of the present invention.

Other agents that can be used in combination with the compound of this invention are ansamycin LM 427, apurinic acid, ABPP, Al-721, carrisyn, AS-101, avarol, azimexon, colchicine, compound Q, CS-85, N-acetyl cysteine, (2-oxothiazolidine-4-carboxylate), D-penicillamine, diphenylhydantoin, EL-10, erythropoieten, fusidic acid, glucan, HPA-23, human growth hormone, hydroxchloroquine, iscador, L-ofloxacin or other quinolone antibiotics, lentinan, lithium carbonate, MM-1, monolaurin, MTP-PE, naltrexone, neurotropin, ozone, PAI, panax ginseng, pentofylline, pentoxifylline, Peptide T, pine cone extract, polymannoacetate, reticulose, retrogen, ribavirin, ribozymes, RS-47, Sdc-28, silicotungstate, THA, thymic humoral factor, thymopentin, thymosin fraction 5, thymosin alpha one, thymostimulin, UA001, uridine, vitamin B12 and wobemugos.

Other agents that can be used in combination with the compound of this invention are antifungals such as amphotericin B, clotrimazole, flucytosine, fluconazole, itraconazole, ketoconazole and nystatin and the like.

Other agents that can be used in combination with the compound of this invention are antibacterials such as amikacin sulfate, azithromycin, ciprofloxacin, tosufloxacin, clarithromycin, clofazirnine, ethambutol, isoniazid, pyrazinamide, rifabutin, rifampin, streptomycin and TLC G-65 and the like.

Other agents that can be used in combination with the compound of this invention are anti-neoplastics such as alpha interferon, COMP (cyclophosphamide, vincristine, methotrexate and prednisone), etoposide, mBACOD (methotrexate, bleomycin, doxorubicin, cyclophosphamide, vincristine and dexamethasone), PRO-MACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, pentosan polysulfate, platelet factor 4 and SP-PG and the like.

Other agents that can be used in combination with the compound of this invention are drugs for treating neurological disease such as peptide T, ritalin, lithium, elavil, phenytoin, carbamazipine, mexitetine, heparin and cytosine arabinoside and the like.

Other agents that can be used in combination with the compound of this invention are anti-protozoals such as albendazole, azithromycin, clarithromycin, clindamycin, corticosteroids, dapsone, DIMP, eflornithine, 566C80, fansidar, furazolidone, L,671,329, letrazuril, metronidazole, paromycin, pefloxacin, pentamidine, piritrexim, primaquine, pyrimethamine, somatostatin, spiramycin, sulfadiazine, trimethoprim, TMP/SMX, trimetrexate and WR 6026 and the like.

For example, a compound or combination of compounds of this invention, or a pharmaceutically acceptable salt form, prodrug or stereoisomer thereof can be administered in combination with ritonavir or its pharmaceutically acceptable salt form or prodrug thereof. Such a combination is especially useful for inhibiting HIV protease in a human. Such a combination is also especially useful for inhibiting or treating an HIV infection in a human. When used in such a combination the compound of this invention (or a pharmaceutically acceptable salt form or prodrug thereof) and ritonavir (or a pharmaceutically acceptable salt form or prodrug thereof) can be administered as separate agents at the same or different times or they can be formulated as a single pharmaceutical composition comprising both active ingredients, or as separate pharmaceutical compositions each comprising an active ingredient and the pharmaceutical compositions can be administered at the same or different time.

When administered in combination with a compound, or combination of compounds of this invention (or a pharmaceutically acceptable salt form or prodrug thereof), ritonavir (or a pharmaceutically acceptable salt form or prodrug thereof) causes an improvement in the pharmacokinetics (i.e., increases half-life, increases the time to peak plasma concentration, increases blood levels) of the compound of this invention.

Another combination can comprise of a compound, or combination of compounds of the present invention with ritonavir and one or more reverse transcriptase inhibitors (for example, lamivudine, stavudine, zidovudine, abacavir, zalcitabine, didanosine, tenofovir, emtricitabine, amdoxovir, elvucitabine, alovudine, MIV-210, Racivir (±-FTC), D-D4FC (Reverset, DPC-817), SPD754, nevirapine, delavirdine, efavirenz, capravirine, emivirine, calanolide A, GW5634, BMS-56190 (DPC-083), DPC-961, MIV-150 TMC-120, TMC-125 and the like). Yet another combination can comprise of a compound, or combination of compounds of the present invention with ritonavir and one or more HIV entry/fusion inhibitors. Such combinations are useful for inhibiting or treating an HIV infection in a human. When used in such a combination the compound or combination of compounds of the present invention and ritonavir and one or more reverse transcriptase inhibitors or HIV entry/fusion inhibitors can be administered as separate agents at the same or different times or they can be formulated as a single pharmaceutical composition comprising two or more of the compounds, or formulated as separate pharmaceutical compositions each comprising one or more of the active ingredients and that the pharmaceutical compositions can be administered at the same or different time.

It will be understood that agents which can be combined with the compound of the present invention for the inhibition, treatment or prophylaxis of AIDS or an HIV infection are not limited to those listed above, but include in principle any agents useful for the treatment or prophylaxis of AIDS or an HIV infection.

When administered as a combination, the therapeutic agents can be formulated as separate compositions which are given at the same time or different times, or the therapeutic agents can be given as a single composition.

Antiviral Activity

Determination of Activity Against Wild-type HIV or the Passaged Variants

MT4 cells were infected with 0.003 multiplicity of infection (MOI) of wild-type HIV-1 or the passaged mutant variants at $1\times10^6$ cells/mL for 1 h, washed twice to remove unabsorbed virus and resuspended to $1\times10^5$ cells/mL of medium, seeded in a 96-well plate at 100 μL/well, and treated with an equal volume of solution of inhibitor in a series of half log dilutions in RPMI 1640 (Rosewell Park Memorial Institute) media (Gibco) containing 10% fetal bovine serum (FBS), in triplicate. The final concentration of DMSO in all wells was 0.5%. The virus control culture was treated in an identical manner except no inhibitor was added to the medium. The cell control was incubated in the absence of inhibitor or virus. Plates were incubated for 5 days in a $CO_2$ incubator at 37° C. On day 5, stock solution of 3-[4,5-dimethylthiazol-2-yl]-2,5-diphenyltetrazolium bromide (MTT) (4 mg/mL in PBS, Sigma cat. #M 5655) was added to each well at 25 μL per well. Plates were further incubated for 4 hrs, then treated with 20% sodium dodecyl sulfate (SDS) plus 0.02 N HCl at 50 μL per well to lyse the cells. After an overnight incubation, optical density (O.D.) was measured by reading the plates at 570/650 nm wavelengths on a Bio-Tek microtitre plate reader. Percent cytopathic effect (CPE) reduction was calculated from the formula below:

((O.D. test well–O.D. infected control well)/(O.D. uninfected control well–O.D. infected control well))×100

$EC_{50}$ values were determined from the plot of log (Fa/Fu) vs. log (compound concentration) using the median-effect equation (Chou, 1975, Proc. Int. Cong. Pharmacol. $6^{th}$ p. 619) wherein Fa is the fraction inhibited by the compound, and Fu is the fraction uninhibited (1−Fa).

When tested by the above method, the compounds of the present invention exhibit $EC_{50}$ in the range of 0.7 nM to >3.2 μM.

Determination of Anti-HIV Activity in the Presence of Human Serum

The above antiviral assay was performed in 96-well tissue culture plates containing 50% human serum (HS) (Sigma) plus 10% FBS (Gibco/BRL, Grand Island, N.Y.). Compounds were dissolved in DMSO, diluted at half log concentrations in DMSO, then transferred to media without serum at four times the final concentration. These solutions were added to 96-well plates at 50 μL per well, in triplicate. Cells were separately infected with 0.003 MOI of HIV-1 at $1\times10^6$ cells/mL for 1 hour, washed twice to remove unadsorbed virus and resuspended to $2\times10^5$ cells/mL of media without serum. The cell suspension (50 μL) was seeded at $1\times10^4$ cells per well. Uninfected cells were included as control. Final DMSO concentration in all wells was 0.5% including uninfected and infected control wells. Cultures were incubated for 5 days in a $CO_2$ incubator at 37° C. $EC_{50}$ values were measured using MTT uptake as described above.

When tested by the above method, compounds of the present invention exhibit $EC_{50}$ in the range of 5 nM to >3.2 μM.

Generation of HIV-1 Resistant to ABT-378/r (A17) by in vitro Passage

MT4 cells ($2\times10^6$) were infected with pNL4-3 at an MOI of 0.03 for 2 h, washed, then cultured in the presence of ABT- 378 and ritonavir at concentration ratio of 5:1. The concentration of ABT-378 and ritonavir used in the initial passage was 1 nM and 0.2 nM respectively. Viral replication was monitored by determination of p24 antigen levels in the culture supernatant (Abbott Laboratories), as well as by observation for any cytopathic effect (CPE) present in the cultures. When p24 antigen levels were positive, the viral supernatant was harvested for the proceeding passage. Following each passage, the drug concentrations in the subsequent passage were gradually increased. After 5 months of selection, 1.5 µM of ABT-378 can be used in the final passage. The A17 virus was generated after 17 passages of pNL43 in the presence of ABT-378 and ritonavir at concentration ratio of 5:1.

When tested by the above method, compounds of the present invention inhibit the A17 virus with $EC_{50}$ in the range of 0.3 nM to >3.2 µM.

Synthetic Methods

Abbreviations which have been used in the descriptions of the schemes and the examples that follow are: DMF is N,N-dimethylformamide, DMSO is dimethylsulfoxide, THF is tetrahydrofuran, NMMO is 4-methylmorpholine N-oxide, HOBT is 1-hydroxybenzotriazole hydrate, DCC is 1,3-dicyclohexylcarbodiimide, EDAC is 1-(3-dimethylaminopropyl)-3-ethylcarbodiimide hydrochloride, DMAP is 4-(dimethylamino)pyridine, TFA is trifluoroacetic acid, DEPBT is 3-(diethoxyphosphoryloxy)-1,2,3-benzotriazin-4(3H)-one, DPPA is diphenylphosphoryl azide, NMM is N-methylmorpholine, DIBAL is diisobutyl aluminum hydride, EtOAc is ethyl acetate and TBAF is tetrabutyl ammonium fluoride.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art. The groups A, X, Y, L, B, $R^A$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R_{104}$, $R_{105}$, $R_{106}$, $R_{107}$, $R_{108}$, $R_a$, $R_b$, $R_c$, $Z_1$, $Z_2$, M, M', m, m', m'', t, r and n are as defined above unless otherwise noted below.

This invention is intended to encompass compounds having formula (I), (II), (III), (IV), (V), (VI), (VII), (VIII), (IX), (X), (XI), (XII) or (XIII), when prepared by synthetic processes or by metabolic processes. Preparation of the compounds of the invention by metabolic processes includes those occurring in the human or animal body (in vivo) or processes occurring in vitro.

Compounds of the invention can be prepared according to the methods described in Schemes 1-8 as shown below.

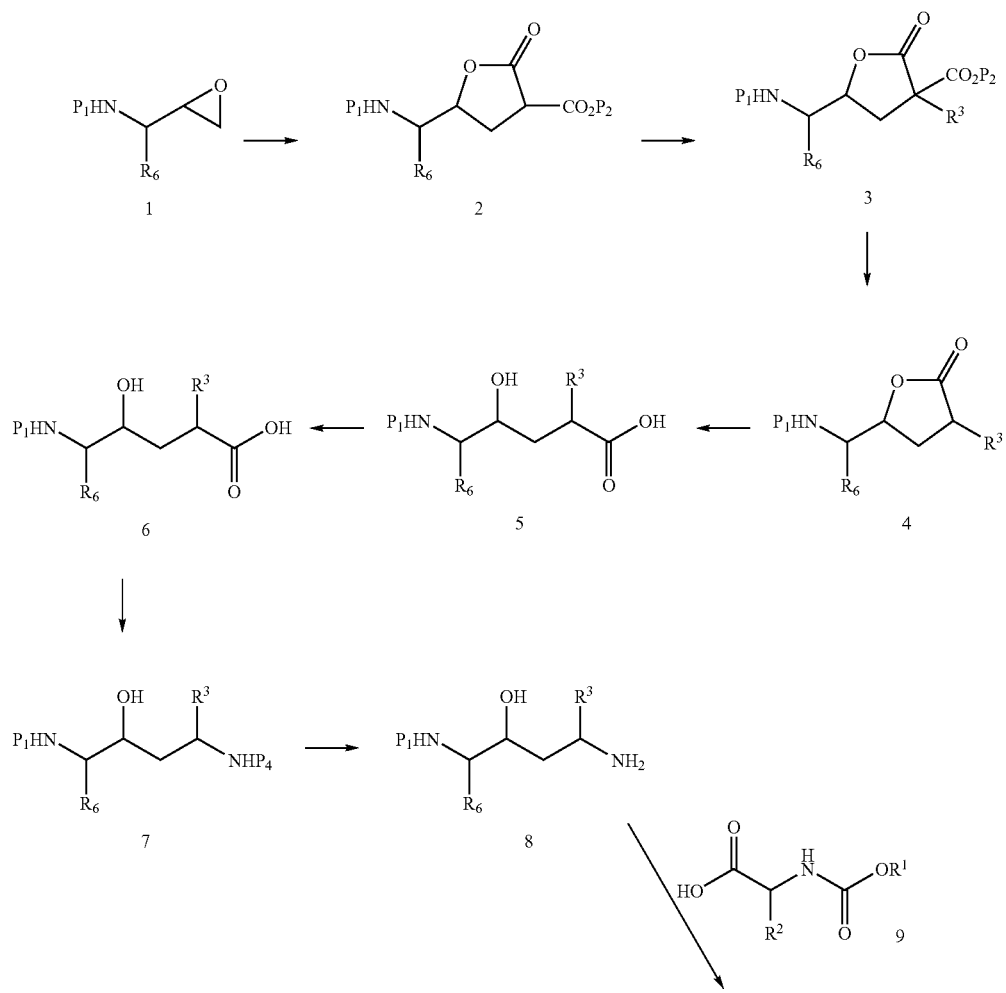

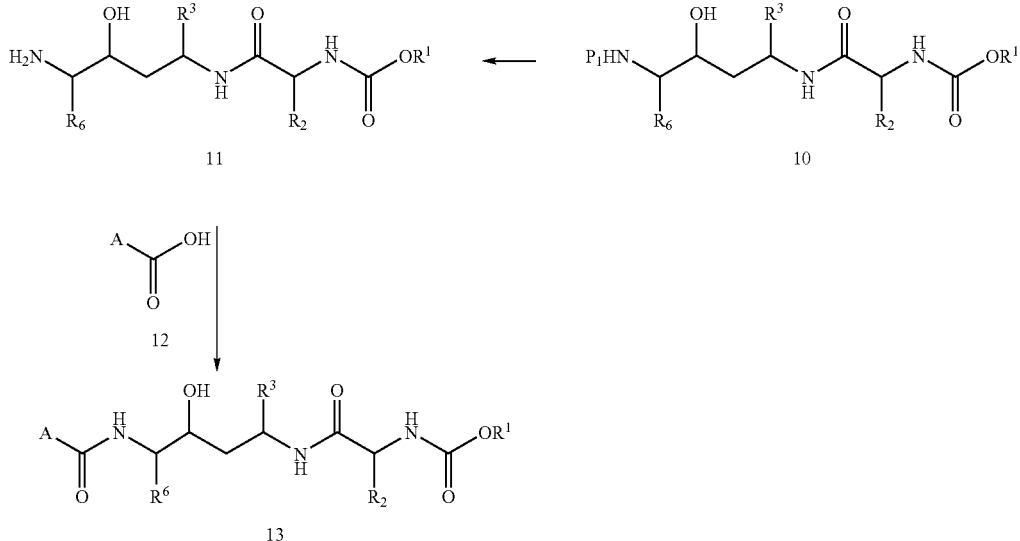

Compounds of formula (1) wherein $P_1$ is an N-protecting group, for example 1-tert-butyloxycarbonyl or benzyloxycarbonyl, can be treated with a dialkyl malonate and a base in an alcoholic solvent such as, but not limited to, methanol or ethanol, at a temperature of about −15° C. to about 30° C. to give compounds of formula (2), wherein $P_2$ is a carboxyl protecting group, for example ethyl, methyl, benzyl, tert-butyl, and the like. Examples of the dialkyl malonate are, but are not limited to, diethyl malonate, dimethyl malonate or dibenzyl malonate. Examples of the base include, but are not limited to, sodium methoxide, sodium ethoxide and sodium tert-butoxide.

Compounds of formula (2) can be isolated or reacted in-situ with an alkylating agent of formula $R^3X$, wherein X is F, Br, Cl or I, and the like, in the presence of a base, in a solvent such as ethanol, methanol, THF, dioxane, DMF, or mixtures thereof, at a temperature from about 25° C. to about 80° C., to give compounds of formula (3). Examples of the base include, but are not limited to, sodium methoxide, sodium ethoxide and sodium tert-butoxide, $NaNH_2$, lithium bis(trimethylsilyl)amide and lithium diisopropylamide.

Compounds of formula (3) can be converted to compounds of formula (4) by (a) reacting compounds of formula (3) with a base, in a solvent such as, but not limited to, THF, DMF, methanol, ethanol or water, and mixtures thereof, at a temperature from about 25° C. to about 100° C., and (b) heating the product of step (a) at reflux in a high boiling solvent such as, but not limited to, benzene, toluene, xylene, DMF or acetic acid. Examples of the base include, but are not limited to, lithium hydroxide, sodium hydroxide, potassium hydroxide and potassium carbonate.

Transformation of compounds of formula (4) to compounds of formula (6), wherein $P_3$ is a hydroxyl protecting group (for example, tert-butyldimethyl silyl) can be achieved in a one-step or stepwise manner by (a) contacting compounds of formula (4) with a first base in a solvent such as, but not limited to, N-methylpyrrolidinone, DMF, THF, dioxane at a temperature from about 0° C. to about 50° C., and (b) contacting the product of step (b) with a silylating agent and a second base in an inert solvent such as, but not limited to, ethyl acetate, THF, dichloromethane, DMF, NMP, acetonitrile, isopropyl acetate or toluene, and the like, at a temperature from about −10° C. to about 60° C. Examples of the first base include, but are not limited to, inorganic bases such as sodium hydroxide, lithium hydroxide, potassium hydroxide, and the like, optionally in the presence of 4-N,N-(dimethylamino)pyridine (DMAP). Examples of the second base include, but are not limited to, organic amine bases such as imidazole, 1-methylimidazole, 2-methylimidazole, 2-isopropylimidazole, 4-methylimidazole, 4-nitroimidazole, pyridine, N,N-dimethylaminopyridine, 2,6-lutidine, 1,2,4-triazole, pyrrole, 3-methylpyrrole, triethylamine or N-methylmorpholine and the like. Examples of the silylating agent include, but are not limited to, trimethylsilyl chloride, trimethylsilyl triflate, tert-butyldimethylsilyl chloride, and tert-butyldimethylsilyl triflate.

Compounds of formula (6) can be converted to compounds of formula (7), wherein $P_4$ is an N-protecting group (for example benzyloxy carbonyl), in a one-step or stepwise manner, by (a) treating compounds of formula (6) with diphenylphosphoryl azide and a base such as, but not limited to, triethylamine, diisoproylethylamine, N-methylmorpholine, and the like in a solvent, or mixture of solvents, such as xylene, toluene, benzene or DMF, and the like, at a temperature from about 80° C. to about 150° C., (b) treating the product of step (b) with an alcohol at a temperature from about 80° C. to about 150° C., in a solvent, in a solvent, or mixture of solvents, such as xylene, toluene, benzene or DMF, and the like, and (c) treating the product of step(b) with a desilylating agent in a solvent, or mixture of solvents, such as THF, DMF, ethyl acetate, dichloromethane, acetone, acetonitrile, methanol or diethyl ether, and the like, at a temperature from about 0° C. to about 50° C. Examples of the alcohol include, but are not limited to, tertbutyl alcohol and benzyl alcohol. Examples of the desilylating agent include, but are not limited to, tetrabutyl ammonium fluoride, acetic acid, formic acid, HCl, HF and citric acid.

Removal of the $P_4$ benzyloxy carbonyl group of (7) (for example, using hydrogen and a hydrogenation catalyst or Pd/C and a formic acid salt (for example, ammonium formate and the like) or Pd/C and formic acid and the like) provides (8). Examples of the hydrogenation catalyst include, but are not limited to, Pd/C, Raney nickel, platinum metal and its oxides.

Compounds of formula (8) are reacted with carboxylic acids of formula (9) and an activating agent, optionally in the presence of 1-Hydroxy-7-azabenzotriazole (HOAT), 1-hydroxybenzotriazole hydrate (HOBT) or 3-hydroxy-1,2,3-benzotriazin-4(3H)-one (HOOBT), and optionally in the presence of an inorganic base (for example, sodium bicarbonate, sodium carbonate, potassium bicarbonate, potassium carbonate, sodium hydroxide, potassium hydroxide, and the like) in an inert solvent (for example, 1:1 ethyl acetate/water or sopropyl acetate/water or toluene/water or THF/water and the like) at about room temperature, or an organic amine base (for example, imidazole, 1-methylimidazole, 2-methylimidazole, 2-isopropylimidazole, 4-methylimidazole, 4-nitroimidazole, pyridine, 4-(dimethylamino)pyridine, 1,2,4-triazole, pyrrole, 3-methylpyrrole, triethylamine or N-methylmorpholine and the like) in an inert solvent (for example, ethyl acetate, isopropyl acetate, THF, toluene, acetonitrile, DMF, dichloromethane and the like) at a temperature from about 0° C. to about 50° C. to provide compound (10). Examples of the activating agent include, but are not limited to, 1,1'-carbonyldiimidazole (CDI), 1,3-dicyclohexylcarbodiimide (DCC), 1,3-diisopropylcarbodiimide, 1-(3-dimethylaminopropyl)-3-ethylcarbodiimide hydrochloride (EDAC), DEPBT (3-(diethoxyphosphoryloxy)-1,2,3-benzotriazin-4(3H)-one), benzotriazol-1-yl-oxy-tris-pyrrolidino-phosphoniumhexafluorophosphate (PyBOP), and 1,3-di-tert-butylcarbodiimide. Alternatively, a salt or an activated ester derivative of acid (9) (for example, the acid chloride, prepared by reaction of the carboxylic acid with thionyl chloride in ethyl acetate or THF or oxalyl chloride in toluene/DMF) can be reacted with (8).

Removal of tert-butoxycabonyl group can be accomplished by treating compounds of formula (10) with an acid (for example, trifluoroacetic acid, hydrochloric acid, methanesulfonic acid, toluenesulfonic acid, sulfuric acid, aluminum chloride and the like) in an inert solvent (for example, dioxane, dichloromethane, chloroform, methanol, THF, acetonitrile and the like) at a temperature from about 0° C. to about room temperature, to provide (11).

Compounds of formula (11) can be reacted with acids of formula (12), or its salts, using the conditions for the transformation of (8) to (10), to provide compounds of formula (13).

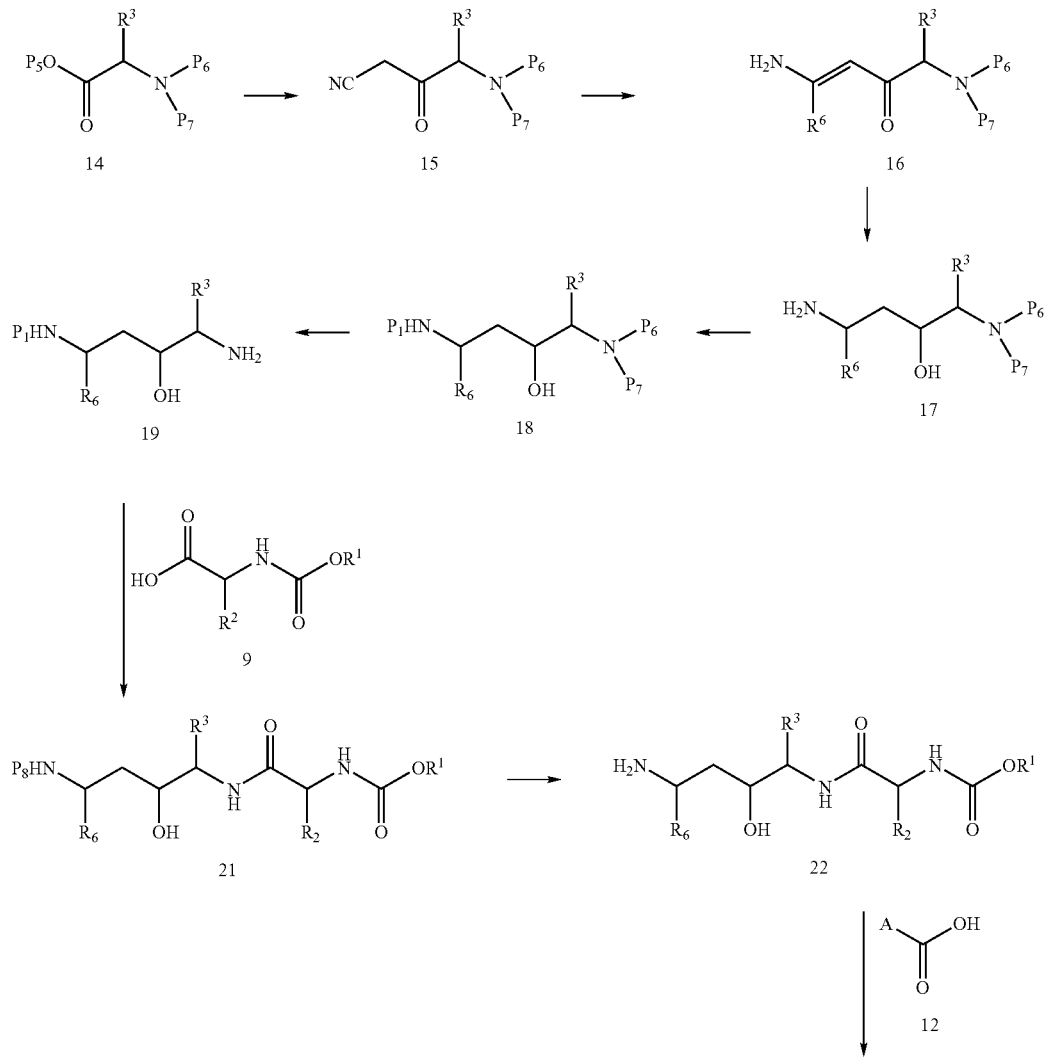

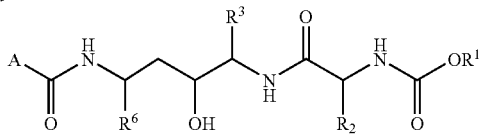

Protected amino acids of formula (14), wherein $P_5$ is lower alkyls, $P_6$ and $P_7$ are N-protecting groups (preferably, $P_6$ and $P_7$ are benzyl) is reacted with sodioacetonitrile (formed in-situ from acetonitrile and a base such as $NaNH_2$) or lithioacetonitrile (formed in-situ from acetonitrile and a base such as lithium bis(trimethylsilyl)amide, or lithium diisopropylamide, and the like) in a solvent, or mixtures of solvents, such as acetonitrile or THF, and the like, at a temperature of about −40° C. to provide ketonitrile (15). Addition of an organometallic reagent of formula $R^6MX$, wherein M is a metal such as magnesium, and X is Cl, Br or I, in an inert solvent such as, but not limited to, dichloromethane, THF, diethyl ether, methyl tert-butyl ether, at a temperature from about 0° C. to about room temperature. Examples of the organometallic reagent include, but are not limited to, benzyl magnesium chloride and methylmagnesium bromide. Reduction of (16) to compounds of formula (17) can be accomplished by reaction with a reducing agent in an inert solvent, or mixtures of solvents, such as ethyl acetate, THF, dichloromethane, ethyl acetate, diethyl ether and the like, at a temperature from about −10° C. to about room temperature. Examples of reducing agents include, but are not limited to, hydrogen in the presence of a catalyst (for example, Pd/C, Raney nickel, platinum metal or its oxides and the like), metallic hydrides such as lithium aluminum hydride and sodium borohydride. The amino group can subsequently be protected to provide compound (18), wherein $P_8$ is tert-butoxycarbonyl, by conditions that are well known in the art.

N-Debenzylation of compounds of formula (18) wherein $P_6$ and $P_7$ are benzyl to provide compounds of formula (19) can be achieved using the conditions for the transformation of compounds of formula (7) to compounds of formula (8).

Conversion of compounds of formula (19) to compounds of formula (23) can be achieved using the conditions for the transformation of compounds of formula (8) to compounds of formula (13)

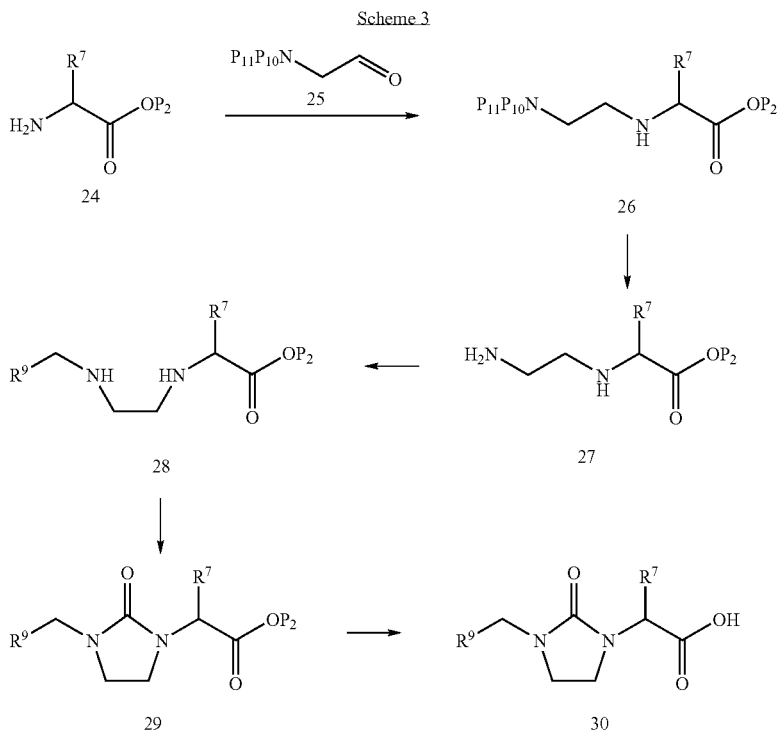

Scheme 3

Amino acid esters of formula (24), wherein $P_2$ is lower alkyls (for example methyl, ethyl, tert-butyl and the like), can be treated with a suitably protected aldehyde of formula (25) (for example, $P_{10}$ and $P_{11}$ together with the nitrogen atom they are attached, form a phthalimido group) in the presence of a reducing agent, optionally under acidic conditions (for example, in the presence of acetic acid or hydrochloric acid), in an inert solvent, or mixture of solvents, such as methyl sulfoxide, methanol, dichloromethane, and the like, at a temperature from about room temperature to about 50° C., to provide compounds of formula (26). Examples of the reducing agent include, but are not limited to, sodium triacetoxyborohydride, sodium borohydride, sodium cyanoborohydride, and $BH_3$-pyridine.

Removal of the phthalimido group can be achieved by treatment with hydrazine in a suitable solvent such as ethanol and the like, at a temperature of about room temperature to about 100° C., to provide compounds of formula (27).

Compounds of formula (27) can be converted to compounds of formula (28) by (a) treating compounds of formula (27) with an aldehyde having formula $R^9CHO$, optionally in the presence of a drying agent (for example, magnesium sulfate, silica gel and the like) in an inert solvent, or mixture of solvents, such as dichloromethane, benzene, toluene, methanol, ethanol, methyl sulfoxide, and the like, at a temperature from about room temperature to about 100° C., and (b) reacting the product of step (a) with a reducing agent at about room temperature. Examples of the reducing agent include, but are not limited to, sodium triacetoxyborohydride, sodium borohydride, sodium cyanoborohydride, and $BH_3$-pyridine.

The diamine of formula (28) can be treated with a carbonylating agent in an inert solvent, or mixture of solvents, such as dichloromethane, 1,2 dichloroethane, toluene, acetonitrile, and the like, at a temperature from about room temperature to about 100° C., to provide compounds of formula (29). Examples of the carbonylating agent include, but not are limited to, 4-nitrophenyl carbonate, phosphene, diphosgene, triphosgene, carbonyl diimidazole and disuccinimidyl carbonate.

Conversion of compounds of formula (29) to the corresponding acids having formula (30) can be achieved by acid hydrolysis (for example acetic acid, trifluoroacetic acid, toluenesulfonic acid, formic acid, hydrochloric acid and the like) or base hydrolysis (for example sodium hydroxide, potassium hydroxide, lithium hydroxide, cesium carbonate, and the like) in a solvent, or mixture of solvents such as DMF, toluene, benzene, dichloromethane, ethyl acetate, water, methanol and the like, at a temperature from about 0° C. to about 100° C.

Scheme 4

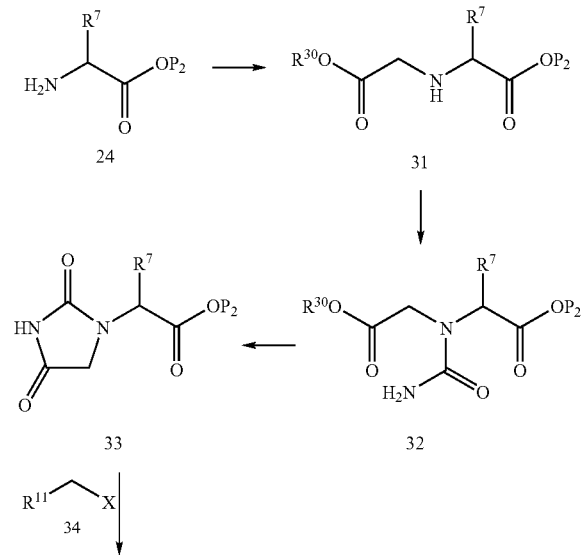

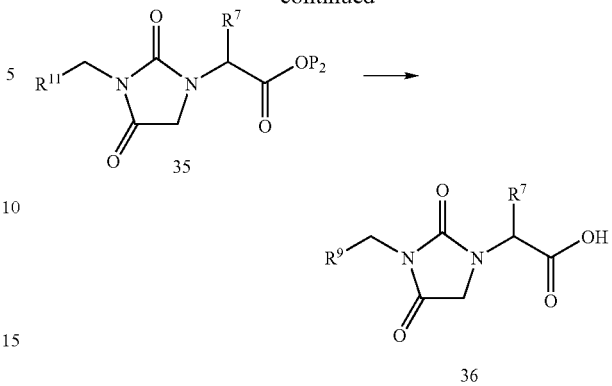

Amino acid esters having formula (24), wherein $P_2$ is lower alkyls (for example, methyl, ethyl, tert-butyl and the like) can be treated with compounds of formula $R^{30}C(O)CH_2X$, wherein $R^{30}$ is lower alkyls and X is Br, Cl, or I, in an inert solvent, or mixture of solvents, such as DMF, dichloromethane, 1,2-dichloroethane, acetonitrile, toluene, benzene, diethyl ether and the like, at a temperature of about room temperature to about 50° C., to provide (31).

Compounds of formula (31) can be converted to compounds of formula (32) by (a) treating with compounds of formula $XSO_2NCO$ (for example chlorosulfonyl isocyanate), wherein X is Br, Cl, or I, in an inert solvent, or mixture of solvents, such as dichloromethane, 1,2-dichloroethane, dioxane, toluene, DMF, THF diethyl ether and the like, at a temperature from about –10° C. to about room temperature, and (b) treating the product of step (a) with water at about room temperature. Alternatively, (31) can be reacted with a carbonylating agent such as, but not limited to, 4-nitrophenyl carbonate, phosphene, diphosgene, triphosgene, carbonyl diimidazole, disuccinimidyl carbonate, followed by reaction with ammonia.

Cyclization of the compounds of formula (32) to provide compounds of formula (33) can be achieved be treating with an organic amine base such as triethylamine, diisopropylethylamine, imidazole, pyridine, N-methylmorpholine and the like, or an inorganic base such as sodium bicarbonate, sodium carbonate, cesium carbonate and the like, in an inert solvent, or mixture of solvents, such as methanol, ethanol, DMF, dioxane, xylene, THF and the like, at a temperature from about room temperature to about 100° C.

Imides of formula (33) can be converted to compounds of formula (35) by (a) deprotonation with a base in an inert solvent, or mixture of solvents, such as DMF, THF, diethyl ether, tert-butyl methyl ether, and the like, at a temperature from about –78° C. to about 0° C., and (b) treating product of step (a) with an alkyl halide of formula (34), wherein X is Cl, Br or I, at a temperature from about room temperature to about 100° C. Examples of the base include, but are not limited to, sodium hydride, potassium hydride, lithium diisopropyl amide, lithium bis(trimethylsilyl)amide.

Alternatively, compounds of formula (33) can be converted to compounds of formula (35) by treating with an alcohol having formula $R^{11}CH_2OH$, in the presence of triphenylphosphine and diethyl azodicarboxylate, in an inert solvent such as dichloromethane, THF, dioxane or DMF, at a temperature of about 0° C. to about 25° C.

Conversion of compounds of formula (35) to compounds of formula (36) can be achieved by using the conditions for the transformation of compounds of formula (29) to compounds of formula (30).

can be accomplished with vanadium(III) chloride-THF complex and zinc at about room temperature in an inert solvent, such as dichloromethane, THF, diethyl ether, 1,2-dichloroethane, and the like.

Scheme 5

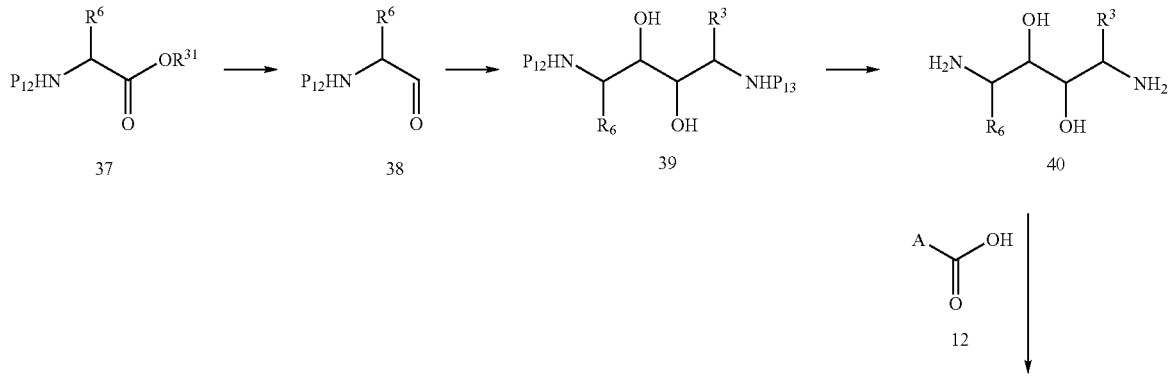

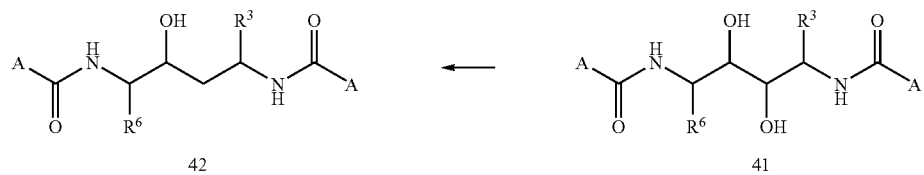

Protected amino acids of formula (37), wherein $P_{12}$ is an N-protecting group (for example benzyloxycarbonyl, benzyl, tert-butyloxycarbonyl, and the like) and $R^{31}$ is hydrogen or lower alkyls (for example, methyl, ethyl and the like), can be converted to compounds of formula (38) by (a) treating with a reducing agent in an inert solvent such as dichloromethane, diethyl ether, THF, tert-butyl methyl ether, and the like, at a temperature from about −78° C. to about room temperature, and (b) treating the product of step (a) with an oxidizing agent in an inert solvent, such as dichloromethane, diethyl ether, THF, tertbutyl methyl ether, and the like, at a temperature from about 0° C. to about room temperature. Examples of the reducing agent include, but are not limited to, lithium aluminum hydride, lithium borohydride, sodium borohydride and diisobutylaluminum hydride. Examples of the oxidizing agent include, but are not limited to, oxalyl chloride/methyl sulfoxide/triethylamine, Jones reagent, Cr(VI) reagents such as pyridinium chlorochromate, $SO_3$/pyridine, $MnO_2$ and $KMnO_4$.

Compounds of formula (38) can condense with itself, or an aldehyde of formula $P_{13}N(H)CH(R^3)CHO$ (prepared from the corresponding carboxylic acids or esters using the conditions for the transformation of (37) to (38)), wherein $P_{13}$ is a N-protecting group, and may be the same as or different from $P_{12}$, to give a diols having formula (39). The transformation N-Deprotection of compounds of formula (39) can be performed in a stepwise manner (if $P_{12}$ is different from $P_{13}$) or in one step (if $P_{12}$ is the same as $P_{13}$) using the conditions for the transformation of (7) to (8), if the N-protecting groups are benzyl or tert-benzyloxycarbonyl, or using the conditions for the transformation of (10) to (11), if the N protecting groups are tert-butyloxycarbonyl.

The compounds of formula (41) can be prepared from (40) and carboxylic acids of formula (12), or its salt, using standard peptide coupling conditions (see the conditions for the transformation of (8) to (10)). The compounds of formula (41) can be converted to compounds of formula (42) by (a) treating with a thiocarbonylating agent in an inert solvent such as THF, dichloromethane, 1,2-dichloroethane, diethyl ether, toluene, xylene, and the like, at a temperature from about room temperature to about 100° C., and (b) treating products of step (b) with tributyltin hydride and 2,2' azobisisobutyronitrile in an inert solvent, such as THF, dichloromethane, 1,2-dichloroethane, diethyl ether, toluene, xylene, and the like, at a temperature from about room temperature to about 150° C. Examples of the thiocarbonylating agent include, but are not limited to, thiocarbonyldiimidazole, and thiophosgene/4-(dimethylamino)pyridine.

Scheme 6

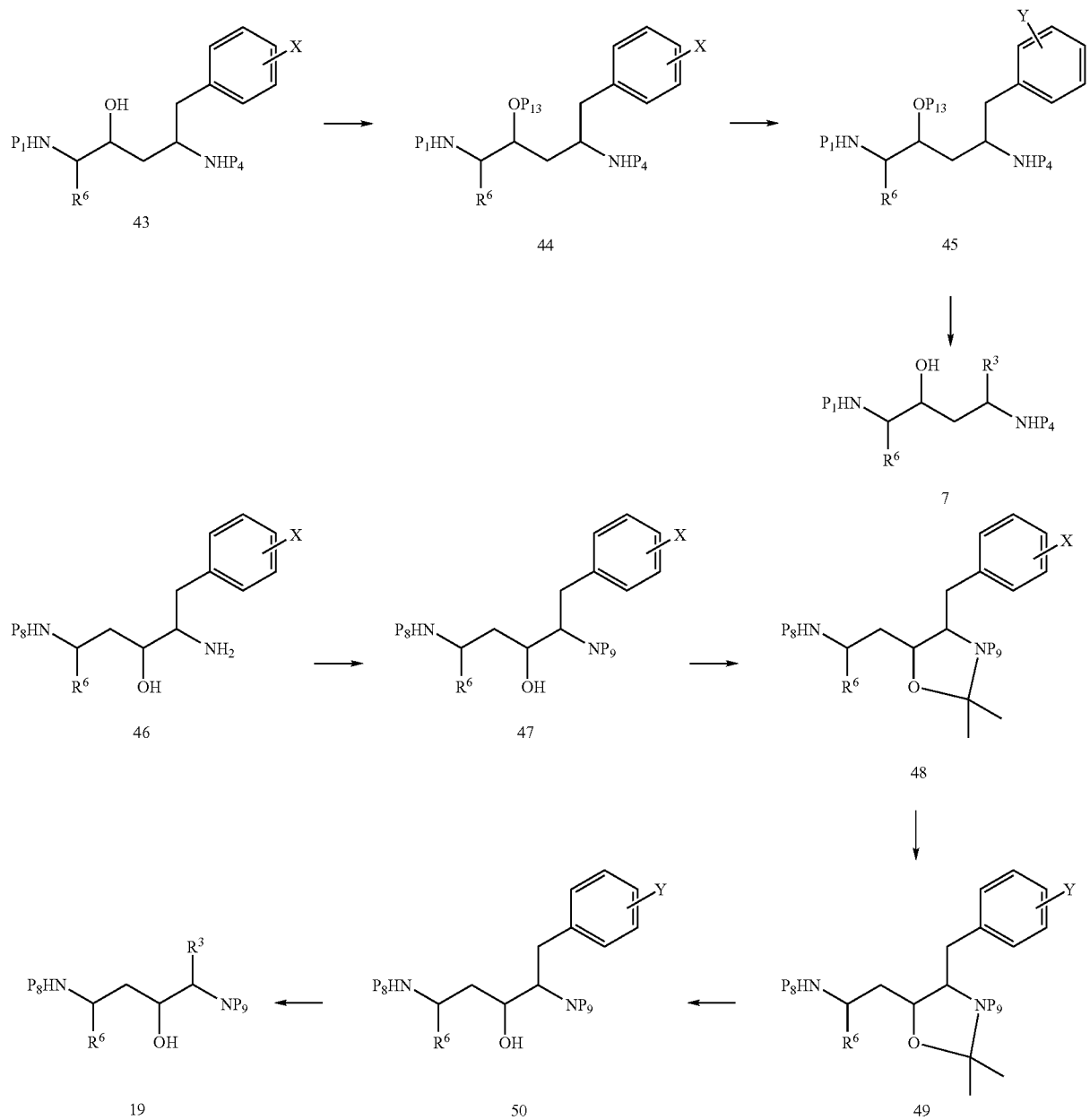

Compounds of formula (43) wherein X is Br, I, Cl or triflate can be converted to compounds of formula (44), wherein $P_{13}$ is a hydroxyl protecting group (for example, trialkyl silyl, methoxymethyl, and the like) by using the conditions for the transformation of (5) to (6). Treatment of compounds of formula (44) with compounds of formula Y—$X^1$, wherein Y is aryl or heteroaryl, and $X^1$ is Br, I, Cl, B(OH)$_2$, or Sn(lower alkyl)$_3$, and a palladium catalyst, optionally in the presence of a base (for example cesium carbonate, triethylamine, and the like), and optionally in the presence of CuI, provide compounds of formula (45). Examples of the palladium catalyst include, but are not limited to, tetrakis(triphenylphosphine) Pd(0), dichlorobis(triphenylphosphine)Pd(II), Pd on carbon, Pd(OAc), tris(dibenzylideneacetone)dipalladium(0), or any of the above with additional phosphine ligands such as, 2-(dicyclohexylphosphino)biphenyl or 2-(di-tert-butylphosphino) biphenyl. Compounds of formula (45) can be converted to compounds of formula (7), wherein $R^3$ is arylalkyl and wherein the aryl moiety of the arylalkyl is substituted by aryl or heteroaryl, by treatment with a desilylating agent such as, but not limited to, tetrabutyl ammonium fluoride, acetic acid, formic acid, HCl, HF and citric acid in a solvent, or mixture of solvents, such as THF, DMF, ethyl acetate, dichloromethane, acetone, acetonitrile, methanol or diethyl ether, and the like, at a temperature from about 25° C. to about 50° C.

Compounds of formula (47) wherein $P_9$ is tert-benzyloxycarbonyl, can be obtained from compounds of formula (46) using conditions well known in the art. The compounds of formula (47) can be converted to compounds of formula (48) by treatment with excess 2,2-dimethoxypropane in the presence of an acid (for example, toluenesulfonic acid, acetic acid, sulfuric acid, and the like) at a temperature from about 0° C. to about room temperature, optionally in the presence of an inert solvent such as dichloromethane, toluene, benzene, acetone, and the like. Transformation of (48) to compounds of formula (49), wherein Y is aryl or heteroaryl, can be accomplished by the conditions for the conversion of (44) to (45). Compounds of formula (49) can be converted to compounds of formula (50) by acid hydrolysis (for example acetic acid, trifluoroacetic acid, toluenesulfonic acid, formic acid, hydrochloric acid and the like) in solvent, or mixture of solvents, such as water, methanol, isopropyl alcohol, ethanol, dichloromethane, THF, acetonitrle, toluene, benzene, 1,2-dichloroethane, ethyl acetate, and the like, at a temperature from about room temperature to about 100° C. Compounds of formula (50) can be de-protected by employing the conditions for the conversion of (7) to (8) as illustrated in scheme 1, to provide compounds of formula (19) wherein $R^3$ is arylalkyl and wherein the aryl moiety of the arylalkyl is substituted with aryl or heteroaryl.

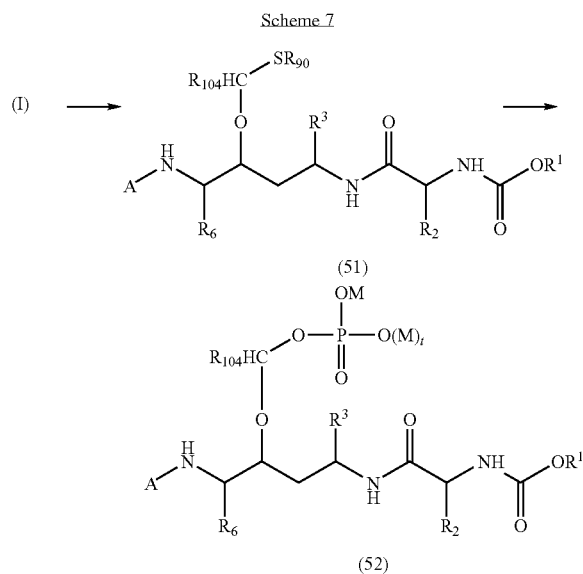

Compounds of formula (I) wherein $R^4$ is H and $R^5$ is $OR^{16}$ wherein $R^{16}$ is H can be converted to compounds of formula (52) wherein t is 1, and each M is independently hydrogen, alkyl or benzyl, and wherein both M can be the same or different via the following two step reaction: (a) reacting the starting material with an alkyl sulfide having formula H—$CHR_{104}$—$SR_{90}$, wherein $R_{90}$ is alkyl, an oxidizing agent, and with or without a base in a solvent to provide compounds of formula (51), and (b) reaction compounds of formula (51) with phosphoric acid to provide compounds of formula (Ia) wherein both M are hydrogen, or with the corresponding monoester or diester of the phosphoric acid to provide compounds of formula (52) wherein one or both M are alkyl or benzyl and the other is hydrogen and wherein both M can be the same or different.

Step (a) can be can be performed in a solvent such as, but is not limited to, acetonitrile or tetrahydrofuran, at a temperature from about −10° C. to about 50° C. Examples of alkyl sulfides include, but are not limited to, methyl sulfide, ethyl sulfide, butylsulfide and t-butyl methyl sulfide. Examples of suitable oxidizing agents include, but are not limited to, benzoyl peroxide, N-chlorosuccinimide and N-chloro-N-methylacetamide. Examples of bases include, but are not limited to, triethylamine, diisopropylethylamine, tributylamine, morpholine and 1-methylimidazole. Alternatively, the thioethers of formula (51) can be prepared from an alkyl sulfoxide, such as dimethyl sulfoxide, and an acid anhydride such as acetic anhydride in a solvent such as acetonitrile, acetic acid or dimethyl sulfoxide at a temperature from about 20° C. to about 50° C. Compounds of formula (51) can also be prepared by treatment of compounds of formula (I) wherein $R^4$ is H and $R^5$ is OH, with a haloalkyl alkyl sulfide having formula X—$CHR_{104}$—$SR_{90}$, wherein X is Cl, Br, F or I, in the presence of a base in a solvent and optionally in the presence of a silver salt such as $AgNO_3$. An example of a suitable haloalkyl alkyl sulfide includes, but is not limited to, chloromethyl methyl sulfide. Examples of suitable bases include, but are not limited to metal hydrides (for example sodium hydride and the like), lithium bis(trimethylsilyl)amide, sodium bis(trimethylsilyl)amide, and potassium bis(trimethylsilyl)amide. The reaction can be performed in a solvent such as, but not limited to, tetrahydrofuran, N,N-dimethylformamide or diethyl ether at a temperature from about −78° C. to about the reflux temperature of the solvent employed.

Step (b) is generally performed by contacting compounds of formula (51) with reagent 1, and with or without a dehydrating reagent, in a solvent. Examples of reagents 1 include, but are not limited to, N-iodosuccinimide, N-chlorosuccinimide, N-bromosuccinimide, iodonium dicollidine triflate, methyl iodide, $AgNO_3$ and trimethylsilyl chloride. Examples of dehydrating agents include, but are not limited to, molecular sieves, magnesium sulfate, $Na_2SO_4$, and $K_2CO_3$. The reaction can be performed in a solvent such as, but not limited to, ethyl acetate, tetrahydrofuran, N,N-dimethylformamide or acetonitrile at a temperature from about −40° C. to about room temperature.

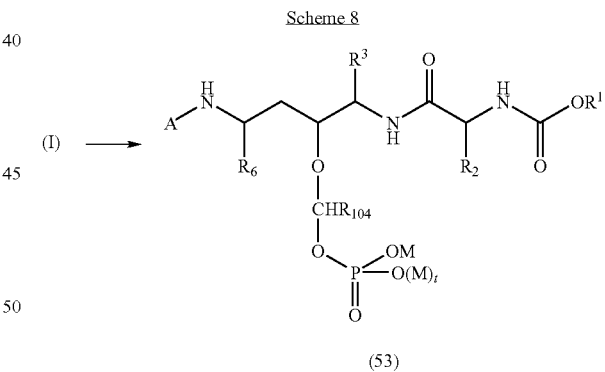

Using similar methodology, compounds of formula (I) wherein $R^4$ is OH and $R^5$ is H can be transformed to compounds of formula (53) wherein t is 1, and each M is independently hydrogen, alkyl or benzyl and wherein both M can be the same or different.

Compounds of formula (I) wherein $R^{15}$ is formula (XVI), $Z_1$ is O, $Z_2$ is O, W is P, Q is O, t is 1, and at least one M is hydrogen and the other is hydrogen, alkyl or benzyl, can be converted to the corresponding mono or dibasic salts wherein (a) t is 1, one of M's is a movalentcation (for example, sodium, potassium, ammonium, triethylammonium and the like), and the other is hydrogen, alkyl or benzyl, or both M are movalent cation (for example, sodium, potassium, ammonium, triethylammonium and the like) and that both M can be the same or different, or (b) t is 0, M is a monovalent or divalent cation, (for example calcium, barium, magnesium and the like) by reacting with about half, one or two equivalents of a variety of inorganic and organic bases, either in situ or after isolation of the compound of formula (I) wherein $R^{15}$ is formula (XVI), $Z_1$ is O, $Z_2$ is O, W is P, Q is O, t is 1, and at least one M is hydrogen and the other is hydrogen, alkyl or benzyl, from the reaction mixtures, it is understood that when t is 0, the oxygen that is adjacent to $(M)_t$ is a charged specie, and that the counter ion may be located elsewhere in the same molecule or the net negative charge is balanced by another molecule of compound of formula (I) that is bearing a net charge of −1. The salts can be obtained via a one step reaction or stepwise from compounds of formula (I) wherein $R^{15}$ is formula (XVI), $Z_1$ is O, $Z_2$ is O, W is P, Q is O, t is 1, and at least one M is hydrogen and the other is hydrogen, alkyl or benzyl. The reaction can be performed in aqueous solvent medium or in a suitable organic solvent such as methanol or ethanol. Typically the reaction is carried out at a temperature from about −10° C. to about 70° C. for about 5 minutes to about 48 hours. Upon evaporation of the solvent, the desired solid salt is obtained with or without further purification such as chromatography.

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purpose of illustration of certain preferred embodiments and are presented to provide what is believed to be the most useful and readily understood description of its procedures and conceptual aspects.

Compounds of the invention were named by ACD/ChemSketch version 4.01 (developed by Advanced Chemistry Development, Inc., Toronto, ON, Canada) or were given names consistent with ACD nomenclature.

EXAMPLE 1 methyl(1S,4R,6S,7S,10S)-7-benzyl-1,10-ditert-butyl-6-hydroxy-2,9,12-trioxo-4-[4-(2-pyridinyl)benzyl]-13-oxa-3,8,11-triazatetradec-1-ylcarbamate

EXAMPLE 1A tert-butyl(1S)-1-{(2S)-5-oxo-4-[4-(2-pyridinyl)benzyl]tetrahydro-2-furanyl}-2-phenylethylcarbamate A solution of tert-Butyl (1S)-1-[(2R)-oxiran-2-yl]-2-phenylethylcarbamate (10.0 g, 38.0 mmol) and diethyl malonate (5.8 ml, 38.2 mmol) in ethanol (30 mL) at 0° C. was treated with sodium ethoxide (17 mL, 21% in ethanol) over 10 minutes. The reaction was warmed to 25° C. and stirred for 2 hours, treated with additional diethyl malonate (0.58 mL, 3.4 mmol) and stirred for 1 hour. The reaction was cooled to 0° C., and solid 2-[4-(bromomethyl)phenyl]pyridine (9.43 g, 38.0 mmol) was added in four increments over 10 minutes. To this suspension was added ethanol (20 mL) and the mixture was stirred at 25° C. for 16 hours. The reaction mixture was treated with LiOH monohydrate (4.6 g, 109.6 mmol) solution in water (30 mL), stirred at 25° C. for 16 hours, cooled to 0° C., adjusted to pH 5 by addition of 4N HCl and partitioned between dichloromethane and water. The organic phase was washed with brine and dried over $MgSO_4$, filtered and concentrated. A solution of the concentrate in toluene (100 mL) was heated at reflux for 16 hours, cooled to 25° C. and concentrated to afford the title compound (21.4 g).

EXAMPLE 1B (4S,5S)-5-[(tert-butoxycarbonyl)amino]-4-{[tert-butyl(dimethyl)silyl]oxy}-6-phenyl-2-[4-(2-pyridinyl)benzyl]hexanoic acid A solution of the product from Example 1A (21.4 g) in dioxane (100 mL) was treated with sodium hydroxide solution (57 mL, 1N), stirred at 25° C. for 30 minutes and concentrated. The concentrate was cooled to 0° C., and acidified to pH 5 with 4N HCl. The mixture was partitioned between dichloromethane and water, and the organic phase layer was washed with brine, dried over $MgSO_4$, filtered and concentrated. A solution of the residue in N,N-dimethylformamide (100 mL) was treated with imidazole (21 g, 308.5 mmol) and t-butyldimethylsilyl chloride (23 g, 152.6 mmol), stirred at 25° C. for 16 hours and concentrated. The residue was combined with ice and acidified with 4N HCl to pH 3. Ethyl acetate (50 mL) was added to permit stirring during the acidification. The mixture was extracted with ethyl acetate, washed with brine, dried over $MgSO_4$, filtered, and concentrated. The residue was chromatographed on silica gel eluting with a gradient of 200%-100% ethyl acetate in chloroform, followed by elution with 5% methanol in ethyl acetate to give the title product (11.3 g, 49% yield).

EXAMPLE 1C

Benzyl (1S,3S,4S)-4-[(tert-butoxycarbonyl)amino]-3-hydroxy-5-phenyl-1-[4-(2-pyridinyl)benzyl]pentylcarbamate A solution of the product from Example 1B (11.3 g, 18.7 mmol) in toluene (190 mL) was treated with DPPA (8.1 mL, 37.6 mmol) and triethylamine (5.2 mL, 37.3 mmol), heated at reflux for 2 hours, treated with benzyl alcohol (5.8 mL, 56.0 mmol), heated at reflux for an additional 16 hours, cooled to 25° C. and concentrated. The residue was treated with a solution of TBAF in THF (94 mL, 1N), stirred at 25° C. for 40 hours and concentrated. The mixture was partitioned between ethyl acetate and water. The organic phase was washed with brine, dried over $MgSO_4$, filtered and concentrated. The residue was chromatographed on silica gel eluting with 50% ethyl acetate in chloroform to give 4.2 g (38% yield) of the lower Rf product by TLC (35% ethyl acetate in dichloromethane).

EXAMPLE 1D

Benzyl (1R,3S,4S)-4-[(tert-butoxycarbonyl)amino]-3-hydroxy-5-phenyl-1-[4-(2-pyridinyl)benzyl]pentylcarbamate A solution of the product from Example 1B (11.3 g, 18.7 mmol) in toluene (190 mL) was treated with DPPA (8.1 mL, 37.6 mmol) and triethylamine (5.2 mL, 37.3 mmol), heated at reflux for 2 hours, treated with benzyl alcohol (5.8 mL, 56.0 mmol), heated at reflux for an additional 16 hours, cooled to 25° C. and concentrated. The residue was treated with a solution of tetrabutylammonium fluoride in THF (94 mL, 1N), stirred at 25° C. for 40 hours and concentrated. The mixture was partitioned between ethyl acetate and water. The organic phase was washed with brine, dried over MgSO₄, filtered and concentrated. The residue was chromatographed on silica gel eluting with 50% ethyl acetate in chloroform to give 2.6 g (23% yield) of the higher Rf product by TLC (35% ethyl acetate in dichloromethane).

EXAMPLE 1E tert-butyl(1S,2S,4R)-4-amino-1-benzyl-2-hydroxy-5-[4-(2-pyridinyl)phenyl]pentylcarbamate A solution of the product from Example 1D (2.6 g, 4.4 mmol) in a mixture of methanol (22 mL) and ethyl acetate (22 mL) was treated with Pd(OH)₂ on carbon (0.8 g, 20% Pd by wt.) and HCl solution (1.0 mL, 4N in dioxane), stirred under a hydrogen atmosphere (balloon pressure) at 25° C. for 16 hours, filtered through celite®, rinsed with methanol and concentrated to give the title product (1.7 g) as the hydrochloride salt.

EXAMPLE 1F (2S)-2-[(methoxycarbonyl)amino]-3,3-dimethylbutanoic acid

A solution of L-tert-Leucine (25 g, 190.58 mmol) in a mixture of dioxane (100 mL) and aqueous NaOH solution (315 mL, 2N) was treated dropwise with methyl chloroformate (29.3 mL, 379.19 mmol), keeping the internal temperature below 50° C. The mixture was warmed to 60° C. and stirred for 18 hours, cooled to 25° C. and extracted with dichloromethane. The aqueous phase was cooled to 0° C. and the pH was adjusted to about 1-2 with concentrated HCl. The mixture was partitioned between ethyl acetate and water. The combined organic extracts were washed with brine, dried over MgSO₄, filtered and concentrated. A solution of the concentrate in ether was treated with hexanes to afford the crystalline product (33.22 g, 92% yield), which was collected by filtration.

EXAMPLE 1G tert-butyl(1S,2S,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A solution of the product of Example 1E (1.7 g) in THF (33 mL) was treated with the product of Example 1F (0.81 g, 4.3 mmol), DEPBT (1.5 g, 5.0 mmol), and N,N-diisopropylethylamine (2.9 mL, 16.6 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane to give the title compound (1.55 g, 74% yield).

EXAMPLE 1H methyl(1S)-1-[({(1R,3S,4S)-4-amino-3-hydroxy-5-phenyl-1-[4-(2-pyridinyl)benzyl]pentyl}amino)carbonyl]-2,2-dimethylpropylcarbamate A solution of the product of Example 1G (1.55 g, 2.45 mmol) in dichloromethane (12.5 mL) was treated with trifluoroacetic acid (12.5 mL), stirred at 25° C. for 1 hour and concentrated. The concentrate was partitioned between ethyl acetate and saturated NaHCO₃ solution. The organic phase extract was washed with brine, dried over MgSO₄, filtered and concentrated to give the title compound (1.4 g) which was used without further purification.

EXAMPLE 1I methyl(1S,4R,6S,7S,10S)-7-benzyl-1,10-ditert-butyl-6-hydroxy-2,9,12-trioxo-4-[4-(2-pyridinyl)benzyl]-13-oxa-3,8,11-triazatetradec-1-ylcarbamate A solution of the product of Example 1H (0.18 g, 0.33 mmol) in THF (3.3 mL) was treated with the product of Example 1F (0.11 g, 0.60 mmol), DEPBT (0.15 g, 0.50 mmol), and N,N-diisopropylethylamine (0.29 mL, 1.66 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0%-75% ethyl acetate in chloroform to give the title product (0.19 g, 81% yield). ¹H NMR (300 MHz, DMSO-d₆), δ ppm 0.75 (s, 9 H), 0.78 (s, 9 H), 1.28 (m, 2 H), 1.55 (m, 1 H), 2.70 (m, 4 H), 3.55 (d, J=11.77 Hz, 6 H), 3.85 (m, 3 H), 4.15 (m, 1 H), 4.80 (d, J=5.15 Hz, 1 H), 6.75 (d, J=9.19 Hz, 1 H), 6.86 (d, J=9.56 Hz, 1 H), 7.13 (m, 5 H), 7.22 (d, J=8.46 Hz, 2 H), 7.32 (m, 1 H), 7.52 (d, *8.82 Hz, 1 H), 7.88 (m, 5 H), 8.64 (d, j=4.41 Hz, 1 H).

EXAMPLE 2 methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate Method A

EXAMPLE 2A tert-butyl(1S,2S,4S)-4-amino-1-benzyl-2-hydroxy-5-[4-(2-pyridinyl)phenyl]pentylcarbamate A solution of the product of Example 1C (4.2 g, 7.0 mmol) in a mixture of methanol (35 mL) and ethyl acetate (35 mL) was treated with Pd(OH)₂ on carbon (1.4 g, 20% Pd by wt.) and HCl solution (1.8 mL, 4N in dioxane), and the reaction was stirred under a hydrogen atmosphere (balloon pressure) for 16 hours at 25° C. The reaction mixture was filtered through a bed of celite®, rinsed with methanol and concentrated to give the title compound as the hydrochloride salt (3.7 g).

EXAMPLE 2B tert-butyl(1S,2S,4S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A solution of the product of Example 2A (3.7 g, 7.4) in THF (75 mL) was treated with the product from Example 1F (1.39 g, 7.4 mmol), DEPBT (3.3 g, 11.0 mmol), and N,N-diisopropylethylamine (6.4 mL, 36.7 mmol), stirred at 25° C. for 16 hours, and partitioned between ethyl acetate and 10% Na₂CO₃ solution. The organic phase was washed with additional 10% Na$_2$CO$_3$ solution and brine, dried over MgSO$_4$, filtered and concentrated. The residue was chromatographed on silica gel eluting with 33%-100% ethyl acetate in chloroform to give the title compound (3.5 g, 75% yield).

EXAMPLE 2C methyl(1S)-1-[({(1S,3S,4S)-4-amino-3-hydroxy-5-phenyl-1-[4-(2-pyridinyl)benzyl]pentyl}amino)carbonyl]-2,2-dimethylpropylcarbamate A solution of the product of Example 2B (3.5 g, 5.5 mmol) in dichloromethane (40 mL) was treated with trifluoroacetic acid (20 mL), stirred at 25° C. for 1 hour, and concentrated. The concentrate was partitioned between ethyl acetate and saturated NaHCO$_3$ solution. The organic phase was washed with brine, dried over MgSO$_4$, filtered and concentrated to afford the crude product (3.19 g).

EXAMPLE 2D methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate A solution of the product of Example 2C (1.6 g, 3.0 mmol) in THF (30 mL) was treated with the product of Example 1F (0.57 g, 3.0 mmol), DEPBT (1.35 g, 4.5 mmol), and N,N-diisopropylethylamine (2.6 mL, 14.9 mmol), stirred at 25° C. for 3 hours and partitioned between ethyl acetate and 10% Na$_2$CO$_3$ solution. The organic phase was washed with additional 10% Na$_2$CO$_3$ solution and brine, dried over MgSO$_4$ filtered and concentrated. The residue was chromatographed on silica gel eluting with 50% ethyl acetate in chloroform, followed by. 5% methanol in chloroform to give the title compound (1.59 g, 75% yield). $^1$H NMR (300 MHz, DMSO-d$_6$), δ ppm 0.79 (s, 9 H), 0.82 (s, 9 H), 1.51 (m, 2 H), 2.51 (m, 1 H),2.72 (m, 3 H), 3.49 (s, 3 H), 3.55 (s, 3 H), 3.63 (m, 1 H), 3.82 (d, J=9.93 Hz, 1 H), 3.90 (d, J=9.56 Hz, 1 H), 4.04 (m, 2 H), 4.86 (d, J=5.88 Hz, 1 H), 6.60 (d, J=9.93 Hz, 1 H), 6.78 (d, J=9.19 Hz, 1 H), 7.16 (m, 7 H), 7.31 (m, 1 H), 7.54 (d, J=8.46 Hz, 1 H), 7.83 (m, 5 H), 8.63 (d, J=4.78 Hz, 1 H).

Method B

A mixture of (2S)-2-[(methoxycarbonyl)amino]-3,3-dimethyl-butanoic acid (4.5 g, 23.7 mmol), HBTU (9.0 g, 23.7 mmol) and diisopropylethylamine (11.8 mL, 67.5 mmol) in ethyl acetate (120 mL) and acetonitrile (24 mL) was stirred at 25° C. for 1 hr, treated with the product of Example 111-14 (12.1 g, 22.5 mmol) and stirred at room temperature overnight. The reaction mixture was filtered and the solid was washed with ethyl acetate (90 mL). The isolated white solid was dissolved in acetonitrile (150 mL) at 70° C. After mixing at 70° C. for 1 hr, the solution was cooled down to room temperature and stirred for 2 hrs and filtered. The isolated solid was washed with acetonitrile (80 mL) and dried to afford the title compound as a white solid. Yield: 91%. $^1$H NMR (DMSO-d$_6$) δ ppm 0.79 (s, 9H), 0.81(s, 9H), 1.52(m, 2H), 2.51 (m, 1H), 2.72 (m, 3H), 3.48 (s, 3H), 3.54 (s, 3H), 3.63 (m, 1H), 3.81 (d, J=8 Hz, 1H), 3.89 (d, J=8 Hz, 1H), 4.00-4.20 (m, 2H), 4.85 (d, J=8 Hz, 1H), 6.58 (d, J=8 Hz, 1H), 6.76 (d, J=8 Hz, 1H), 7.107.18 (m, 7H), 7.30 (m, 1H), 7.53 (m, 1H), 7.81-7.87 (m, 5H), 8.60-8.62 (d, J=8Hz, 1H).

Method C

EXAMPLE 2-1

(2S)-5-amino-2-(dibenzylamino)-1-phenyl-6-(4-pyridin-2-ylphenyl)hex-4-en-3-one

Part I Potassium tert-butoxide (26.5 g, 1.6 equivalents) in tetrahydrofuran (250 mL) under N$_2$ at about −17° C. was treated with 2-(p-tolyl)pyridine (25 g, 1 equivalent), stirred at −17° C. for about 10 minutes, and treated dropwise with of n-butyl lithium (2.5 M in hexane, 94.5 mL 1.6 equivalent), maintaining the internal temperature at about <−13° C. After the addition was completed, the reaction mixture was warmed up to room temperature and stirred for 1 hr.

Part II A solution of commercially available 4S-4-dibenzylamino-3-oxo-5-phenyl-pentanenitrile (50 g, 0.92 equivalent) in tetrahydrofuran (250 mL) was cooled to about 2° C., treated with tert-butyl magnesium chloride (143 mL), stirred at about 2° C. for 30 min, treated with the solution from Part I at about 2° C. and stirred at about 25° C. overnight. The reaction mixture was quenched with saturated NH$_4$Cl solution at 5° C. and diluted with 250 mL of ethyl acetate. The isolated organic layer was washed with aqueous NH$_4$Cl and brine. Assay yield: 57.4 g. Yield: 78.7%. The isolated organic layer was concentrated to yield the crude title compound.

EXAMPLE 2-2

(2S,3S,5S)-5-amino-2-(dibenzylamino)-1-phenyl-6-(4-pyridin-2-ylphenyl)hexan-3-ol To a jacketed round bottom 1L flask was added 27.5 g (1 eq) of the product of Example 2-1, 300 mL of dimethylacetamide and 30 mL of isopropyl alcohol. The reaction solution was cooled to about −16° C. and treated with 33 mL (10 eq) of methanesulfonic acid slowly (The reaction was exothermal, temperature raised to 9° C.). The mixture was cooled to about −16° C., treated with 54.1 g (5 equivalents) of sodium triacetoxylborohydride. Mixed at −16° C. for about 2 hrs and 30 min, HPLC showed the first reduction was completed. 67.9 mL (10 equivalents) of triethanolamine was then added slowly (exothermal). The mixture was stirred at about −16° C. for 1 hr. 7.7 g of sodium borohydride was added in 7 portions. The reaction mixture was stirred at −16° C. until the reduction was completed as indicated by HPLC (Column: YMC QDS-AQ 15 cm, flow 1 ml/1 min, Gradient system: 0-15 min, 80% 0.03M HK$_2$PO$_4$/20% CH$_3$CN/to 20% 0.03M HK$_2$PO$_4$/80% CH$_3$CN, 15-20 hold at 20% 0.03M HK$_2$PO$_4$/80% CH$_3$CN, 20-21 min, 20% 0.03M HK$_2$PO$_4$/80% CH$_3$CN to 80% 0.03M HK$_2$PO$_4$/20% CH$_3$CN, 21-23 min, hold at 80% 0.03M HK$_2$PO$_4$/20% CH$_3$CN), treated with 100 mL of water, stirred at room temperature overnight and diluted with 300 mL of dichloromethane to the reaction mixture. The isolated dichloromethane layer (Assay: 23 g, yield: 83.5%. ds: 95% as measured by HPLC (Column: YMC QDS-AQ 15 cm, flow 1 ml/1 min, Gradient system: 0-15 min, 80% 0.03M HK$_2$PO$_4$/20% CH$_3$CN/ to 20% 0.03M HK$_2$PO$_4$/80% CH$_3$CN, 15-20 hold at 20% 0.03M HK$_2$PO$_4$/80% CH$_3$CN, 20-21 min, 20% 0.03M HK$_2$PO$_4$/80% CH$_3$CN to 80% 0.03M HK$_2$PO$_4$/20% CH$_3$CN, 21-23 min, hold at 80% 0.03M HK$_2$PO$_4$/20% CH$_3$CN) was extracted with 0.3% H$_3$PO$_4$ solution (3×200 mL). The pH of the isolated aqueous layer was adjusted to 6-7 with sodium carbonate. The resulting solution was extracted with dichloromethane (2×300 ml). The combined isolated dichloromethane layers were washed with 200 mL of 5% aqueous KH$_2$PO$_4$, dried (Na$_2$SO$_4$) and concentrated. The resulting residue was dissolved in 100 mL of isopropyl acetate and washed sequentially with 100 mL of 5% KH$_2$PO$_4$ and brine. The isopropyl acetate solution was concentrated and 21.2 g of the title compound was obtained as a yellow foam.

EXAMPLE 2-3

(2S,3S,5S)-2,5-diamino-1-phenyl-6-(4-pyridin-2-ylphenyl)hexan-3-ol

A solution of the product of Example 2-2 (3.8 g) in methanol (65 mL) in a three-necked round bottom flask equipped with a condenser was flushed with nitrogen, treated with water (5 mL), ammonium formate (2.5 g) and Pd/C (1.0 g), and stirred under nitrogen at 60° C. for 12 hours. The reaction mixture was cooled, filtered, and concentrated. A solution of the residue in dichloromethane (100 mL) was washed with saturated aqueous NaHCO$_3$ (3×50 mL). The isolated dichloromethane layer was concentrated to afford 3.3 g of the crude product.

EXAMPLE 2-4 methyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate A mixture of (2S)-2-[(methoxycarbonyl)amino]-3,3-dimethyl-butanoic acid (2.6 g, 2.05 equivalents), O-benzotriazol-1-yl-N,N,N',N'-tetramethyluronium hexafluorophosphate (5.1 g, 2.05 eq), diisopropylethylamine (6.9 mL, 6 equivalents) in ethyl acetate (30 mL) and acetonitrile (3 mL) was stirred at room temperature for 2 hrs until the suspension turned to a clear solution, treated with a solution of the product of Example 2-3 (3.3 g) in ethyl acetate (10 mL), stirred at room temperature overnight, and filtered. The isolated white solid was dissolved in acetonitrile (45 mL) at 75° C. After mixing at 75° C. for 1 hr, the solution was cooled down to room temperature and stirred for 2 hrs and filtered. The isolated solid was washed with acetonitrile (30 mL) and dried to afford the title compound as a white solid. Potency: 96%. Yield over two steps: 70%. $^1$H NMR (DMSO-d$_6$) δ ppm 0.79 (s, 9H), 0.81(s, 9H),1.52(m, 2H), 2.51 (m, 1H), 2.72 (m, 3H), 3.48 (s, 3H), 3.54 (s, 3H), 3.63 (m, 1H), 3.81 (d, J=8 Hz, 1H), 3.89 (d, J=8 Hz, 1H), 4.00-4.20 (m, 2H), 4.85 (d, J=8 Hz, 1H), 6.58 (d, J=8 Hz, 1H), 6.76 (d, J=8 Hz, 1H), 7.107.18 (m, 7H), 7.30 (m, 1H), 7.53 (m, 1H), 7.81-7.87 (m, 5H), 8.608.62 (d, J=8Hz, 1H).

EXAMPLE 3 methyl(1S)-1-{[((1S,3S,4S)-1-benzyl-3-hydroxy-4-{[(2S)-3-methyl-2-(2-oxo-3-{[2-(2-pyridinyl)-1,3-thiazol-4-yl]methyl}-1-imidazolidinyl)pentanoyl]amino}-5-phenylpentyl)amino]carbonyl}-2,2-dimethylpropylcarbamate

EXAMPLE 3A 9H-fluoren-9-ylmethyl(1S,2S,4S)-1-benzyl-2-hydroxy-4-[(tert-butoxycarbonyl)amino]-5-phenylpentylcarbamate A solution of the product of Example 126 (1.0 g, 2.0 mmol) in a mixture of dioxane (15 mL) and water (5 mL) was treated with sodium bicarbonate (0.37 g, 4.4 mmol) and N-(9-fluorenylmethyloxycarbonyloxy)-succinimide (0.74 g, 2.2 mmol), stirred at 25° C. for 16 hours and partitioned between ethyl acetate and diluted sodium bicarbonate solution. The organic phase was washed with brine and dried over MgSO$_4$, filtered and concentrated to give the title compound (1.37 g), which was used without further purification.

EXAMPLE 3B 9H-fluoren-9-ylmethyl(1S,2S,4S)-4-amino-1-benzyl-2-hydroxy-5-phenylpentylcarbamate A solution containing the product of Example 3A (0.92 g, 1.5 mmol) in dioxane (5 mL) was treated with HCl solution (15 mL, 4 N in dioxane) at 0° C., stirred at 25° C. for 1 hour and concentrated. The residue was triturated with hexanes to give the title compound as the hydrochloride salt (0.82 g).

EXAMPLE 3C methyl(1S)-1-{[((1S,3S,4S)-1-benzyl-4-{[(9H-fluoren-9-ylmethoxy)carbonyl]amino}-3-hydroxy-5-phenylpentyl)amino]carbonyl}-2,2-dimethylpropyl-carbamate A solution of the product of Example 3B (0.150 g, 0.276 mmol) in DMF (3 mL) was treated with the product of Example 1F (0.052 g, 0.275 mmol), EDAC (0.080 g, 0.417 mmol), HOBT (0.055, 0.407 mmol), and NMM (0.090 mL, 0.819 mmol) at 0° C., stirred at 25° C. for 2 hours, and partitioned between ethyl acetate and water. The organic phase was washed with 10% citric acid, diluted sodium bicarbonate, and brine, dried over MgSO$_4$, filtered and concentrated. The concentrate was purified by reversed phase chromatography on a C18 column, eluting with a gradient starting with 5%-100% acetonitrile in water (0.1% TFA) to give the title compound (0.130 g, 70% yield).

EXAMPLE 3D methyl(1S)-1-({[(1S,3S,4S)-4-amino-1-benzyl-3-hydroxy-5-phenylpentyl]amino}carbonyl)-2,2-dimethylpropylcarbamate A solution of the product of Example 3C (0.130 g, 0.192 mmol) in DMF (6 mL) was treated with diethylamine (1.5 mL), stirred at 25° C. for 1 hour, and partitioned between ethyl acetate and water. The organic phase was washed with brine, dried over MgSO$_4$, filtered and concentrated. The residue was chromatographed on silica gel eluting with a gradient starting with ethyl acetate and ending with methanol to give the title compound (0.52 g, 60% yield).

EXAMPLE 3E (1,3-dioxo-1,3-dihydro-2H-isoindol-2-yl)acetaldehyde

A solution of phthalimidoacetaldehyde diethyl acetal (39.6 g, 150.4 mmol) in a mixture of THF (80 mL) and aqueous HCl (50 mL, 10%) was heated at 75° C. for 5 hours, cooled to 25° C. and partitioned between ethyl acetate and half-saturated NaHCO$_3$. The organic phase was washed with brine, dried over MgSO₄, filtered and concentrated to give the title compound (36.81 g), which was used without further purification.

EXAMPLE 3F tert-butyl(2S,3S)-2-{[2-(1,3-dioxo-1,3-dihydro-2H-isoindol-2-yl)ethyl]amino}-3-methylpentanoate A solution of the product of Example 3E (36.81 g) in methanol (50 mL) was treated with L-iso-leucine tert-butyl ester hydrochloride (30 g, 134 mmol), sodium cyanoborohydride (16.9 g, 268 mmol), and acetic acid (4.6 ml, 80.4 mmol), stirred at 25° C. for 3 hours and concentrated. The concentrate was partitioned between dichloromethane and saturated NaHCO₃. The organic phase was washed with brine and dried over MgSO₄, filtered and concentrated. The residue was chromatographed on silica gel, eluting with a gradient starting with 10%-66% ethyl acetate in hexanes to give the title compound (28.44 g, 59% yield).

EXAMPLE 3G tert-butyl(2S,3S)-2-[(2-aminoethyl)amino]-3-methylpentanoate

A solution of the product of Example 3F (28.44 g, 78.9 mmol) in ethanol (400 mL) was treated with hydrazine hydrate (25 mL, 789 mmol), stirred at 70° C. for 2 hours, cooled to 25° C. The solid precipitate was dissolved by addition of aqueous NaOH solution (200 mL, 1 N). The reaction was partitioned between dichloromethane and water. The aqueous was extracted three times with dichloromethane. The combined organic extracts were dried over MgSO₄, filtered and concentrated to give the title compound (15.4 g, 85% yield), which was used without further purification.

EXAMPLE 3H 2-pyridinecarbothioamide

A solution of pyridine-2-carboxamide (3.1 g, 25.4 mmol) in toluene (25 mL) was treated with Laweson's reagent (5.1 g, 12.6 mmol), heated at 85° C. for 64 hours, cooled to 25° C., and partitioned between ethyl acetate and water. The organic phase was washed with brine, dried over MgSO₄, filtered and concentrated to give the title compound, which was used without further purification.

EXAMPLE 3I ethyl 2-(2-pyridinyl)-1,3-thiazole-4-carboxylate

A solution of the product of Example 3H (25.4 mmol) in ethanol (50 mL) was treated with ethyl bromopyruvate (3 mL, 23.9 mmol) and molecular sieves (10 g, 3 Å), heated at reflux for 16 hours, cooled to 25° C., filtered and concentrated. The concentrate was partitioned between ethyl acetate and saturated NaHCO₃, and the organic phase was washed with brine, dried over MgSO₄, filtered and concentrated. The residue was chromatographed on silica gel eluting with 0-25% ethyl acetate in dichloromethane to give the title compound (1.98 g, 33% yield).

EXAMPLE 3J 2-(2-pyridinyl)-1,3-thiazole-4-carbaldehyde

A solution containing the product of Example 3I (0.91 g, 3.9 mmol) in dichloromethane (13 mL) was treated dropwise with DIBAL (7.4 mL, 1 M in dichloromethane) at −78° C., stirred at −78° C. for 1 hour, treated with acetic acid (0.8 mL) and warmed to 25° C. A 10% solution of aqueous sodium potassium tartrate was added and the mixture was stirred vigorously for 1 hour. The reaction mixture was partitioned between chloroform and water, and the organic phase was washed with brine, dried over MgSO₄, filtered and concentrated. The residue was chromatographed on silica gel eluting with 0-10% ethyl acetate in dichloromethane to give the title compound (0.39 g, 53% yield).

EXAMPLE 3K tert-butyl(2S,3S)-3-methyl-2-(2-oxo-3-{[2-(2-pyridinyl)-1,3-thiazol-4-yl]methyl}-1-imidazolidinyl)pentanoate A solution containing the product of Example 3G (0.30 g, 1.30 mmol) in a mixture of benzene (3 mL) and ethanol (3 mL) was treated with the product of Example 3J (0.25 g, 1.31 mmol), heated at 70° C. for 16 hours, cooled to 25° C., treated with sodium borohydride (0.15 g, 3.97 mmol), stirred at 25° C. for 3 hours, quenched with sodium bicarbonate solution and partitioned between ethyl acetate and water. The organic phase was washed with brine, dried over MgSO₄, filtered and concentrated. A solution of the residue (1.3 mmol) in 1,2-dichloroethane (50 mL) was treated with bis(4-nitrophenyl) carbonate (0.425 g, 1.40 mmol) and triethylamine (0.225 ml, 1.83 mmol), heated at 70° C. for 16 hours, and partitioned between ethyl acetate and saturated NaHCO₃. The organic phase was washed with brine, dried over MgSO₄, filtered and concentrated. The residue was chromatographed on silica gel eluting with 0-35% ethyl acetate in dichloromethane to give the title compound (0.214 g, 38% yield).

EXAMPLE 3L (2S,3S)-3-methyl-2-(2-oxo-3-{[2-(2-pyridinyl)-1,3-thiazol-4-yl]methyl}-1-imidazolidinyl)pentanoic acid trifluoroacetate A solution containing the product of Example 3K (0.214 g, 0.50 mmol) in dichloromethane (2 mL) was treated with trifluoracetic acid (2 mL), stirred at 25° C. for 1 hour and concentrated. The residue was chromatographed on silica gel eluting with 0-15% methanol in dichloromethane to give the title compound (0.24 g) as the trifluoroacetic acid salt.

EXAMPLE 3M methyl(1S)-1-{[((1S,3S,4S)-1-benzyl-3-hydroxy4-{[(2S)-3-methyl-2-(2-oxo-3-{[2-(2-pyridinyl)-1,3-thiazol-4-yl]methyl}-1-imidazolidinyl)pentanoyl]amino}-5-phenylpentyl)amino]carbonyl}-2,2-dimethylpropylcarbamate A solution containing the product from Example 3D (0.025 g, 0.055 mmol) in DMF (0.5 mL) was treated with the product from Example 3L (0.021 g, 0.056 mmol), EDAC (0.020 g, 0.104 mmol), HOBT (0.015 g, 0.111 mmol), and NMM (0.020 mL, 0.182 mmol) at 0° C., stirred at 25° C. for 16 hours, and partitioned between ethyl acetate and water. The organic phase was washed with 10% citric acid, diluted sodium bicarbonate, and brine, dried over MgSO₄, filtered and concentrated. The residue was purified by reversed phase chromatography on a C18 column, eluting with 5-100% acetonitrile in water (0.1% TFA) to give the title compound (0.028 g, 63% yield). $^1$H NMR (300 MHz, DMSO-d$_6$), δ ppm 0.79 (m, 15 H), 0.95 (m, 1 H), 1.29 (m, 1 H), 1.49 (m, 2 H), 1.80 (m, 1 H), 2.68 (m, 4 H), 3.03 (m, 1 H), 3.17(m, 2 H), 3.55 (s, 3 H), 3.63 (m, 3 H), 3.94 (d, J=11.03 Hz, 2 H), 4.12 (m, 2 H), 4.47 (m, 2 H), 6.62 (d, J=9.93 Hz, 1 H), 7.07 (m, 10 H), 7.25 (d, J=9.56 Hz, 1 H), 7.48 (m, 1 H), 7.57 (s, 1 H), 7.75 (d, J=8.46 Hz, 1 H), 7.93 (m, 1 H), 8.10 (d, J=8.09 Hz, 1 H), 8.62 (d, J=4.04 Hz, 1 H).

EXAMPLE 4 methyl(1S)-1-({[(1S,3S,4S)-1-benzyl-3-hydroxy-4-({(2S)-3-methyl-2-[2-[oxo-3-(4-quinolinylmethyl)-1-imidazolidinyl]pentanoyl}amino)-5-phenylpentyl]amino}carbonyl)-2,2-dimethylpropylcarbamate

EXAMPLE 4A (2S,3S)-3-methyl-2-[2-oxo-3-(4-quinolinylmethyl)-1-imidazolidinyl]pentanoic acid trifluoroacetate A solution containing the product from Example 3G (2.0 g, 8.69 mmol) in a mixture of benzene (40 mL) and ethanol (40 mL) was treated with 4-quinolinecarboxaldehyde (1.4 g, 8.91 mmol), heated at 70° C. for 2 hours, cooled to 25° C., treated with sodium borohydride (1.0 g, 26.75 mmol), stirred at 25° C. for 16 hours, quenched with sodium bicarbonate solution and partitioned between ethyl acetate and water. The organic phase was washed with brine, dried over MgSO$_4$, filtered and concentrated. A solution of the residue (8.69 mmol) in 1,2-dichloroethane (300 mL) was treated with bis(4-nitrophenyl) carbonate (3.0 g, 9.86 mmol), heated at 70° C. for 16 hours, and partitioned between ethyl acetate and saturated NaHCO$_3$. The organic phase was washed with brine, dried over MgSO$_4$, filtered and concentrated. A solution of the residue (8.69 mmol) in dichloromethane (40 mL) was treated with trifluoroacetic acid (40 mL), stirred at 25° C. for 1 hour and concentrated. The residue was chromatographed on silica gel eluting with 0-5% methanol in dichloromethane. A second purification using reversed phase chromatography on a C18 column, eluting with 5-100% acetonitrile in water (0.1% TFA) afforded the title compound (1.91 g, 48% yield).

EXAMPLE 4B methyl(1S)-1-({[(1S,3S,4S)-1-benzyl-3-hydroxy-4-({(2S)-3-methyl-2-[2-oxo-3-(4-quinolinylmethyl)-1-imidazolidinyl]pentanoyl}amino)-5-phenylpentyl]amino}carbonyl)-2,2-dimethylpropylcarbamate A solution containing the product from Example 3D (0.078 g, 0.171 mmol) in DMF (0.5 mL) was treated with the product from Example 4A (0.070 g, 0.205 mmol), EDAC (0.050 g, 0.261 mmol), HOBT (0.035 g, 0.259 mmol), and NMM (0.060 mL, 0.546 mmol) at 0° C., stirred at 25° C. for 16 hours and partitioned between ethyl acetate and water. The organic phase was washed with 10% citric acid, diluted sodium bicarbonate, and brine, dried over MgSO$_4$, filtered and concentrated. The residue was purified by reversed phase chromatography on a C18 column, eluting with 5-100% acetonitrile in water (0.1% TFA) to give the title compound (0.030 g, 23% yield). $^1$H NMR (300 MHz, DMSO-d$_6$), δ ppm 0.79 (m, 15 H), 1.00 (m, 1 H), 1.25 (m, 1 H), 1.51 (m, 2 H), 1.82 (m, 1 H), 2.64 (m, 5 H), 3.02 (m, 1 H), 3.55 (s, 3 H), 3.63 (m, 1 H), 3.82 (d, J=9.93 Hz, 1 H), 3.99 (d, J=11.03 Hz, 1 H), 4.13 (m, 2 H), 4.64 (d, J=7.72 Hz, 1 H), 4.80 (m, 2 H), 6.62 (d, J=9.93 Hz, 1 H), 6.98 (m, 5 H), 7.14 (m, 5 H), 7.32 (d, J=9.56 Hz, 1 H), 7.41 (d, J=4.41 Hz, 1 H), 7.62 (t, J=7.54 Hz, 1 H), 7.76 (m, 2 H), 8.06 (d, J=7.72 Hz, 1 H), 8.30 (d, J=8.46 Hz, 1 H), 8.88 (d, J=4.41 Hz, 1 H).

EXAMPLE 5 methyl(1S)-1-({[(1S,3S,4S)-1-benzyl-3-hydroxy-4-({(2S)-3-methyl-2-[2-oxo-3-(4-quinolinylmethyl)-1-imidazolidinyl]pentanoyl}amino)-5-phenylpentyl]amino}carbonyl)-2-methylbutylcarbamate

EXAMPLE 5A (2S,3S)-2-[(methoxycarbonyl)amino]-3-methylpentanoic acid

A solution of L-iso-Leucine (7.43 g, 56.6 mmol) in a mixture of dioxane (28 mL) and aqueous NaOH solution (93.5 mL, 2N) was treated with methyl chloroformate (8.75 mL, 113.3 mmol) dropwise, not allowing the internal temperature to rise above 50° C. The mixture was warmed to 60° C. and stirred for 18 hours, cooled to 25° C., and extracted with dichloromethane. The aqueous phase was cooled to 0° C., and its pH was adjusted to 1-2 with HCl (4 N). The mixture was partitioned between ethyl acetate and water, and the organic phase was washed with brine, dried over Na$_2$SO$_4$, filtered and concentrated to give the crude product (10 g).

EXAMPLE 5B methyl(1S,2S)-1-{[((1S,3S,4S)-1-benzyl-4-{[(9H-fluoren-9-ylmethoxy)carbonyl]amino}-3-hydroxy-5-phenylpentyl)amino]carbonyl}-2-methylbutylcarbamate A solution containing the product from Example 3B (0.150 g, 0.276 mmol) in DMF (3 mL) was treated with the product from Example 5A (0.063 g, 0.333 mmol), EDAC (0.080 g, 0.417 mmol), HOBT (0.055, 0.407 mmol), and NMM (0.090 mL, 0.819 mmol) at 0° C., stirred at 25° C. for 16 hours, and partitioned between ethyl acetate and water. The organic phase was washed with 10% citric acid, dilute sodium bicarbonate solution, and brine, dried over MgSO$_4$, filtered and concentrated. The concentrate was purified by reversed phase chromatography on a C18 column, eluting with 5%-100% acetonitrile in water (0.1% TFA) to give the title compound (0.107 g, 57% yield).

EXAMPLE 5C methyl(1S,2S)-1-({[(1S,3S,4S)-4-amino-1-benzyl-3-hydroxy-5-phenylpentyl]amino}carbonyl)-2-methylbutylcarbamate A solution containing the product from Example 5B (0.107 g, 0.158 mmol) in DMF (6 mL) was treated with diethylamine (1.5 mL), stirred at 25° C. for 1 hour, and partitioned between ethyl acetate and water. The organic phase was washed with brine, dried over MgSO$_4$, filtered and concentrated to give the title compound, which was used without further purification.

EXAMPLE 5D methyl(1S)-1-({[(1S,3S,4S)-1-benzyl-3-hydroxy-4-({(2S)-3-methyl-2-[2-oxo-3-(4-quinolinylmethyl)-1-imidazolidinyl]pentanoyl}amino)-5-phenylpentyl]amino}carbonyl)-2-methylbutylcarbamate A solution containing the product from Example 5C (0.078 g, 0.171 mmol) in DMF (0.5 mL) was treated with the product from Example 4A (0.070 g, 0.205 mmol), EDAC (0.050 g, 0.261 mmol), HOBT (0.035 g, 0.259 mmol), and NMM (0.060 mL, 0.546 mmol) at 0° C., stirred at 25° C. for 16 hours, and partitioned between ethyl acetate and water. The organic phase was washed with 10% citric acid, diluted sodium bicarbonate, and brine, dried over MgSO$_4$, filtered and concentrated. The residue was purified by reversed phase chromatography on a C18 column eluting with 5-100% acetonitrile in water (0.1% TFA) to give the title compound (0.030 g, 23% yield). $^1$H NMR (300 MHz, DMSO-d$_6$), δ ppm 0.76 (m, 12 H), 1.00 (m, 2 H), 1.29 (m, 2 H), 1.49 (m, 3 H), 1.81 (m, 1 H), 2.65 (m, 5 H), 3.01 (m, 3 H), 3.54 (s, 3 H), 3.61 (m, 1 H), 3.75 (t, J=8.82 Hz, 1 H), 3.99 (d, J=11.03 Hz, 1 H), 4.13 (m, 2 H), 4.62 (d, J=7.35 Hz, 1 H), 4.80 (m, 2 H), 6.89 (d, J=9.56 Hz, 1 H), 6.98 (m, 5 H), 7.15 (m, 5 H), 7.32 (d, J=9.93 Hz, 1 H), 7.41 (d, J=4.41 Hz, 1 H), 7.66 (m, 2 H), 7.77 (t, J=6.99 Hz, 1 H), 8.06 (d, J=7.72 Hz, 1 H), 8.30 (d, J=8.09 Hz, 1 H), 8.88 (d, J=4.41 Hz, 1 H).

EXAMPLE 6 methyl(1S)-1-{[((1S,3S,4S)-1-benzyl-3-hydroxy-4-{[(2S)-2-(3-{[2-(methoxymethyl)-1,3-thiazol-4-yl]methyl}-2-oxo-1-imidazolidinyl)-3,3-dimethylbutanoyl]amino}-5-phenylpentyl)amino]carbonyl}-2,2-dimethylpropylcarbamate

EXAMPLE 6A tert-butyl(1S,3S,4S)-4-amino-1-benzyl-3-hydroxy-5-phenylpentylcarbamate The product from Example 126 (20 g, 39.8 mmol) was partitioned between ethyl acetate and saturated NaHCO$_3$ solution with stirring for 30 minutes. The solid white amine was collected by filtration and the aqueous was extracted twice with portions of ethyl acetate. The solid material collected was dissolved in warm ethyl acetate and this solution was combined with the organic phase extracts, dried over sodium sulfate, filtered and concentrated to give the free amine (14.15 g).

EXAMPLE 6B 2-methoxyethanethioamide

A solution containing methoxyacetyl chloride (10 g, 92.15 mmol) and ammonium acetate (7.1 g, 92.11 mmol) in acetone (250 mL) was stirred at 25° C. for 16 hours, treated with phosphorous pentasulfide (4.1 g, 9.22 mmol), stirred at 25° C. for 64 hours, concentrated and partitioned between ethyl acetate and water. The organic phase was washed with brine, dried over MgSO$_4$, filtered and concentrated to give the title compound (7.0 g, 72% yield), which was used without further purification.

EXAMPLE 6C ethyl 2-(methoxymethyl)-1,3-thiazole-4-carboxylate

A solution containing the product from Example 6B (7 g, 66.6 mmol) in acetone (270 mL) was treated with ethyl bromopyruvate (8.4 mL, 66.6 mmol) and magnesium sulfate (7.9 g, 66.6 mmol), heated at reflux for 16 hours, cooled to 25° C., filtered and concentrated. The residue was chromatographed on silica gel eluting with chloroform to give the title compound (7.6 g, 57% yield).

EXAMPLE 6D 2-(methoxymethyl)-1,3-thiazole-4-carbaldehyde

A solution containing the product from Example 6C (7.4 g, 36.8 mmol) in dichloromethane (40 mL) was treated with DIBAL (73.6 mL, 1 M in dichloromethane) dropwise at −78° C. over 2 hours, stirred at −78° C. for 2 hours, treated with acetic acid (10 mL) at −78° C. and warmed to 25° C. A 10% solution of aqueous sodium potassium tartrate was added and the mixture was stirred vigorously for 1 hour. The reaction mixture was partitioned between chloroform and water. The organic phase was washed with brine, dried over MgSO$_4$, filtered and concentrated. The residue was chromatographed on silica gel eluting with 0-100% ethyl acetate/dichloromethane to give the title compound (5.78 g, 71% yield).

EXAMPLE 6E tert-butyl (2S)-2-{[2-(1,3-dioxo-1,3-dihydro-2H-isoindol-2-yl)ethyl]amino}-3,3-dimethylbutanoate A solution of the product of Example 3E (9.34 g, 49.4 mmol) in methanol (33 mL) was treated with L-tert-leucine tert-butyl ester hydrochloride (10 g, 44.9 mmol), sodium cyanoborohydride (5.6 g, 89.8 mmol), and acetic acid (1.5 ml, 26.2 mmol), stirred at 25° C. for 4 hours, and partitioned between chloroform and saturated NaHCO$_3$. The organic phase was washed with brine, dried over MgSO$_4$, filtered and concentrated. The residue was chromatographed on silica gel, eluting with first with 66% chloroform in hexanes and then with 33% ethyl acetate in chloroform to give the title compound (10.5 g, 59% yield).

EXAMPLE 6F tert-butyl (2S)-2-[(2-aminoethyl)amino]-3,3-dimethylbutanoate

A solution of the product from Example 6E (10.5 g, 29.1 mmol) in ethanol (290 mL) was treated with hydrazine hydrate (9 mL, 290 mmol), heated at 70° C. for 2 hours and cooled to 25° C. The solid precipitate was dissolved by addition of aqueous NaOH solution (150 mL, 1 N). The reaction mixture was partitioned between chloroform and water, and the aqueous was extracted three times with chloroform. The combined organic extracts were dried over MgSO$_4$, filtered and concentrated to give the diamine (7.0 g, quantitative), which was used without further purification.

EXAMPLE 6G tert-butyl(2S)-2-(3-{[2-(methoxymethyl)-1,3-thiazol-4-yl]methyl}-2-oxo-1-imidazolidinyl)-3,3-dimethylbutanoate A solution containing the product from Example 6F (1.0 g, 4.34 mmol) in a mixture of benzene (12 mL) and ethanol (12 mL) was treated with the product from Example 6D (0.682 g, 4.34 mmol), heated at 50° C. for 1.5 hours, cooled to 25° C., treated with sodium borohydride (0.329 g, 8.68 mmol), stirred at 25° C. for 1.5 hours, quenched with sodium bicarbonate solution, and partitioned between ethyl acetate and water. The organic phase was washed with brine, dried over $MgSO_4$, filtered and concentrated. A solution of the residue (4.34 mmol) in toluene (25 mL) was treated with bis(4-nitrophenyl) carbonate (1.58 g, 5.21 mmol), heated at 60° C. for 16 hours, and partitioned between ethyl acetate and saturated $NaHCO_3$. The organic phase was washed with brine, dried over $MgSO_4$, filtered and concentrated to give the title compound (1.28 g, 74% yield), which was used without further purification.

EXAMPLE 6H (2S)-2-(3-{[2-(methoxymethyl)-1,3-thiazol-4-yl]methyl}-2-oxo-1-imidazolidinyl)-3,3-dimethylbutanoic acid trifluoroacetate A solution containing the product from Example 6G (1.28 g, 3.2 mmol) in dichloromethane (10 mL) was treated with trifluoracetic acid (5 mL), stirred at 25° C. for 4 hours and concentrated. The residue was chromatographed on silica gel eluting with 0-5% methanol in dichloromethane to give the title compound (1.2 g) as the trifluoroacetic acid salt.

EXAMPLE 6I tert-butyl(1S,3S,4S)-1-benzyl-3-hydroxy-4-{[(2S)-2-(3-{[2-(methoxymethyl)-1,3-thiazol-4-yl]methyl}-2-oxo-1-imidazolidinyl)-3,3-dimethylbutanoyl]amino}-5-phenylpentylcarbamate A solution of the product from Example 6A (0.034 g, 0.089 mmol) in THF (0.9 mL) was treated with the product from Example 6H (0.035 g, 0.103 mmol), DEPBT (0.040 g, 0.134 mmol), and N,N-diisopropylethylamine (0.075 mL, 0.431 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography using C18 column, eluting with 5-100% acetonitrile in water (0.1% TFA) to give the title compound (0.047 g, 75% yield).

EXAMPLE 6J methyl(1S)-1-{[((1S,3S,4S)-1-benzyl-3-hydroxy-4-{[(2S)-2-(3-{[2-(methoxymethyl)-1,3-thiazol-4-yl]methyl}-2-oxo-1-imidazolidinyl)-3,3-dimethylbutanoyl]amino}-5-phenylpentyl)amino]carbonyl}-2,2-dimethylpropylcarbamate A solution containing the product from Example 6I (0.047 g, 0.066 mmol) in dichloromethane (1 mL) was treated with trifluoracetic acid (1 mL), stirred at 25° C. for 1 hour, concentrated, and partitioned between ethyl acetate and saturated $NaHCO_3$. The organic phase was washed with brine and dried over $MgSO_4$, filtered and concentrated. A solution of the residue (0.030 g, 0.049 mmol) in DMF (0.5 mL) was treated with the product from Example 1F (0.010 g, 0.053 mmol), EDAC (0.020 g, 0.104 mmol), HOBT (0.015 g, 0.111 mmol), and NMM (0.016 mL, 0.146 mmol) at 0° C., stirred at 25° C. for 16 hours, and partitioned between ethyl acetate and water. The organic phase was washed with 10% citric acid, diluted sodium bicarbonate, and brine, and dried over $MgSO_4$, filtered and concentrated. The residue was purified by reversed phase chromatography on a C18 column, eluting with 5-100% acetonitrile in water (0.1% TFA) to give the title compound (0.031 g, 79% yield). $^1$H NMR (300 MHz, DMSO-$d_6$), δ ppm 0.82 (s, 9 H), 0.89 (s, 9 H), 1.25 (m, 1 H), 1.50 (m, 2 H), 2.37 (m, 1H), 2.65 (d, J=7.35 Hz, 2 H), 2.73 (d, J=9.56 Hz, 1 H), 3.02 (m, 2 H), 3.19 (m, 1 H), 3.38 (s, 3 H), 3.55 (s, 3 H), 3.85 (m, 3 H), 4.08 (m, 3 H), 4.38 (m, 2 H), 4.68 (s, 2 H), 6.61 (d, J=9.93 Hz, 1 H), 7.08 (m, 10 H), 7.43 (m, 2 H), 7.74 (d, J=8.46 Hz, 1 H).

EXAMPLE 7 methyl(1S)-1-[({(1S,3S,4S)-1-benzyl-3-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate

EXAMPLE 7A tert-butyl(2S,3S)-3-methyl-2-{3-[(6-methyl-2-pyridinyl)methyl]-2-oxo-1-imidazolidinyl}pentanoate A solution containing the product from Example 3G (6.18 g, 26.9 mmol) in dichloromethane (160 mL) was treated with 6-methyl-2-pyridinecarboxaldehyde (3.25 g, 26.8 mmol) and magnesium sulfate (16.3 g, 135.4 mmol) g), stirred at 25° C. for 18 hours, filtered and concentrated. A solution of the residue in methanol (160 mL) was treated with sodium borohydride (1.2 g, 31.7 mmol), stirred at 25° C. for 1 hour, quenched with water, stirred for 15 minutes, and followed by evaporation of the solvent. The concentrate was partitioned between ethyl acetate and saturated $NaHCO_3$, and the organic phase was washed with brine and dried over $MgSO_4$, filtered and concentrated. A solution of the residue (9.1 g, 26.8 mmol) in 1,2-dichloroethane (550 mL) was treated with N,N-disuccinimidyl carbonate (8.24 g, 32.2 mmol) and triethylamine (3.7 mL, 26.5 mmol), stirred at 25° C. for 68 hours, partitioned with 10% $Na_2CO_3$, and the organic phase was washed with additional 10% $Na_2CO_3$ solution and brine, dried over $MgSO_4$, filtered and concentrated. The residue was chromatographed on silica gel eluting with 0-100% ethyl acetate/dichloroform to give the title compound (6.15 g, 63% yield).

EXAMPLE 7B (2S,3S)-3-methyl-2-{3-[(6-methyl-2-pyridinyl)methyl]-2-oxo-1-imidazolidinyl}pentanoic acid A solution containing the product from Example 7A (6.15 g, 17.0 mmol) in dichloromethane (150 mL) was treated with trifluoracetic acid (50 mL), stirred at 25° C. for 2 hours and concentrated. The residue was purified by reversed phase chromatography on a C18 column, eluting with 5-100% acetonitrile in water (0.1% TFA) to give the title compound (6.0 g, 84% yield) as the trifluoroacetic acid salt.

EXAMPLE 7C tert-butyl(1S,3S,4S)-1-benzyl-3-hydroxy-4-[((2S,3S)-3-methyl-2-{3-[(6-methyl-2-pyridinyl)methyl]-2-oxo-1-imidazolidinyl}pentanoyl)amino]-5-phenylpentylcarbamate

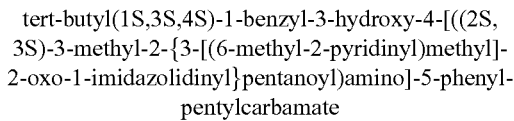

A solution of the product from Example 6A (0.046 g, 0.119 mmol) in THF (0.9 mL) was treated with the product from Example 7B (0.050 g, 0.119 mmol), EDAC (0.035 g, 0.183 mmol), HOBT (0.025 g, 0.185 mmol), and NMM (0.040 mL, 0.364 mmol) at 0° C., stirred at 25° C. for 16 hours, and partitioned between ethyl acetate and water. The organic phase was washed with 10% citric acid, dilute sodium bicarbonate solution, and brine, dried over MgSO₄, filtered and concentrated. The residue was purified by reversed phase chromatography on a C18 column, eluting with 5-100% acetonitrile in water (0.1% TFA) to give the title compound (0.080 g, 100% yield).

EXAMPLE 7D methyl(1S)-1-[({(1S,3S,4S)-1-benzyl-3-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate

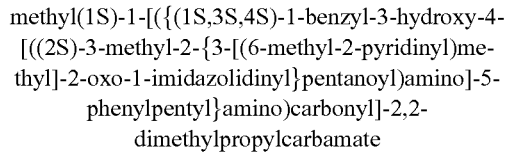

A solution containing the product from Example 7C (0.080 g, 0.119 mmol) in dichloromethane (1 mL) was treated with trifluoroacetic acid (1 mL), stirred at 25° C. for 1 hour and concentrated. The concentrate was partitioned between ethyl acetate and saturated NaHCO₃. The organic phase was washed with brine, dried over MgSO₄, filtered and concentrated. A solution of the residue (0.056 g, 0.098 mmol) in DMF (1 mL) was treated with the product from Example 1F (0.020 g, 0.106 mmol), EDAC (0.030 g, 0.156 mmol), HOBT (0.020 g, 0.148 mmol), and NMM (0.030 mL, 0.273 mmol) at 0° C., stirred at 25° C. for 16 hours, and partitioned between ethyl acetate and water. The organic phase was washed with 10% citric acid, dilute sodium bicarbonate, and brine, and dried over MgSO₄, filtered and concentrated. The residue was purified by reversed phase chromatography on a C18 column, eluting with 5-100% acetonitrile in water (0.1% TFA) to give the title compound (0.049 g, 67% yield). ¹H NMR (300 MHz, DMSO-d₆), δ ppm 0.79 (m, 15 H), 0.93 (m, 2 H), 1.31 (m, 1 H), 1.50 (m, 2 H), 1.82 (m, 1 H), 2.45 (s, 3 H), 2.67 (m, 4 H), 3.06 (m, 3 H), 3.55 (s, 3 H), 3.64 (m, 1 H), 3.82 (d, J=9.93 Hz, 1 H), 3.93 (d, J=11.03 Hz, 1 H), 4.13 (m, 2 H), 4.35 (s, 2 H), 4.64 (d, J=7.35 Hz, 1 H), 6.62 (d, J=9.93 Hz, 1 H), 7.02 (d, J=7.72 Hz, 1 H), 7.13 (m, 11 H), 7.26 (d, J=9.93 Hz, 1 H), 7.66 (t, J=7.72 Hz, 1 H), 7.75 (d, J=8.46 Hz, 1 H).

EXAMPLE 8 methyl(1S)-1-[({(1S,2S,4S)-1-benzyl-2-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate

EXAMPLE 8A methyl(1S)-1-[({(1S,2S,4S)-1-benzyl-4-[(tert-butoxycarbonyl)amino]-2-hydroxy-5-phenylpentyl}amino)carbonyl]-2,2-dimethylpropylcarbamate

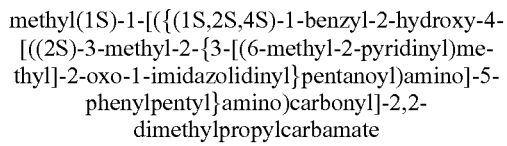

A solution of the product from Example 1F (7.0 g, 37.0 mmol), EDAC (8.5 g, 44.3 mmol), HOBT (6.0 g, 44.4 mmol), and NMM (8.0 mL, 72.8 mmol) in DMF (30 mL) was stirred at 25° C. for 1 hour, treated with a solution of the product from Example 6A (14.15 g, 36.8 mmol) in DMF (30 mL), stirred at 25° C. for 16 hours, concentrated, and partitioned between ethyl acetate and saturated NaHCO₃. The organic phase was washed with saturated NaHCO₃ and brine, and concentrated. The solution of the residue in hot methanol (20 mL) and water (10 mL) was allowed to cool and stand for 16 hours. The solids were collected by filtration and rinsed several times with hexanes, followed by drying under vacuum to give the title compound (16.97 g, 77% yield).

EXAMPLE 8B methyl(1S)-1-({[(1S,2S,4S)-4-amino-1-benzyl-2-hydroxy-5-phenylpentyl]amino}carbonyl)-2,2-dimethylpropylcarbamate

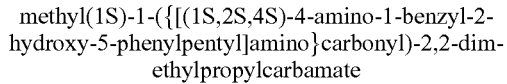

A solution containing the product from Example 8A (16.97 g, 30.6 mmol) in THF (150 mL) was treated with HCl solution (50 mL, 4 N in dioxane), stirred at 60° C. for 2 hours, cooled and adjusted to pH 8 with 10% NaOH solution. The reaction mixture was partitioned between ethyl acetate and water, and the organic phase was washed with brine and concentrated to give the title compound (13.74 g).

EXAMPLE 8C methyl(1S)-1-[({(1S,2S,4S)-1-benzyl-2-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2,2-dimethylpropylcarbamate

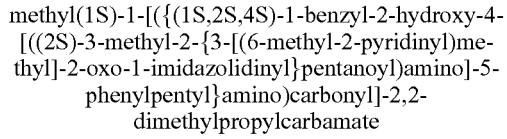

A solution containing the product from Example 8B (5.67 g, 12.5 mmol) in THF (124 mL) was treated with the product from Example 7B (3.8 g, 12.5 mmol), DEPBT (5.59 g, 18.7 mmol), and N,N-diisopropylethylamine (10.8 mL, 62.0 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with a gradient starting with dichloromethane and ending with acetone to give the title compound (4.42 g, 48% yield). ¹H NMR (300 MHz, DMSO-d₆), δ ppm 0.68 (d, J=6.25 Hz, 3 H), 0.82 (m, 14 H), 0.92 (m, 1 H), 1.30 (m, 1 H), 1.50 (m, 2 H), 1.79 (m, 1 H), 2.43 (m, 3 H), 2.68 (m, 3 H), 2.89 (m, 1 H), 3.10 (m, 3 H), 3.57 (m, 3 H), 3.89 (m, 2 H), 4.13 (m, 2 H), 4.34 (s, 2 H), 4.79 (d, J=5.52 Hz, 1 H), 6.80 (d, J=9.56 Hz, 1 H), 7.11 (m, 12 H), 7.50 (d, J=8.82 Hz, 1 H), 7.66 (t, J=7.54 Hz, 1 H), 7.83 (d, J=9.19 Hz, 1 H).

EXAMPLE 9 methyl(1S)-1-[({(1S,2S,4S)-1-benzyl-2-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2-methylbutylcarbamate

EXAMPLE 9A methyl(1S,2S)-1-[({(1S,2S,4S)-1-benzyl-4-[(tert-butoxycarbonyl)amino]-2-hydroxy-5-phenylpentyl}amino)carbonyl]-2-methylbutylcarbamate A solution of the product from Example 6A (0.50 g, 1.30 mmol) in THF (13 mL) was treated with the product from Example 5A (0.30 g, 1.59 mmol), DEPBT (0.45 g, 1.50 mmol), and N,N-diisopropylethylamine (1.1 mL, 6.31 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated to give the title compound, used without further purification.

EXAMPLE 9B methyl(1S,2S)-1-({[(1S,2S,4S)-4-amino-1-benzyl-2-hydroxy-5-phenylpentyl]amino}carbonyl)-2-methylbutylcarbamate A solution containing the crude product from Example 9A in THF (150 mL) was treated with an HCl solution (5 mL, 4 N in dioxane), and the mixture was heated at 60° C. for 2 hours, cooled to 25° C. and concentrated. The concentrate was partitioned between ethyl acetate and saturated NaHCO$_3$. The organic phase was washed with brine, dried over MgSO$_4$, filtered and concentrated to give the title compound (0.36 g, 61% yield).

EXAMPLE 9C methyl(1S)-1-[({(1S,2S,4S)-1-benzyl-2-hydroxy-4-[((2S)-3-methyl-2-{3-[(6-methyl-2-pyridinyl)methyl]-2-oxo-1-imidazolidinyl}pentanoyl)amino]-5-phenylpentyl}amino)carbonyl]-2-methylbutylcarbamate A solution containing the product from Example 9B (0.36 g, 0.79 mmol) in THF (8 mL) was treated with the product from Example 7B (0.33 g, 0.79 mmol), DEPBT (0.355 g, 1.19 mmol), and N,N-diisopropylethylamine (0.70 mL, 4.02 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-50% acetone/dichloromethane to give the title compound (0.264 g, 45% yield). $^1$H NMR (300 MHz, DMSO-d$_6$), δ ppm 0.75 (m, 12 H), 0.94 (m, 2 H), 1.29 (m, 2 H), 1.46 (m, 2 H), 1.62 (m, 1 H), 1.80 (m, 1 H), 2.43 (m, 4 H), 2.68 (m, 3 H), 2.88 (m, 1 H), 3.08 (m, 3 H), 3.56 (m, 4 H), 3.84 (m, 2 H), 4.15 (m, 2 H), 4.34 (s, 2 H), 4.84 (d, J=5.88 Hz, 1 H), 7.03 (m, 7 H), 7.15 (m, 6 H), 7.39 (d, J=9.19 Hz, 1 H), 7.66 (t, J=7.72 Hz, 1 H), 7.83 (d, J=8.82 Hz, 1 H).

EXAMPLE 10 methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-phenylpentyl}amino)carbonyl]-2,2-dimethylpropylcarbamate

EXAMPLE 10A tert-butyl(2S)-3,3-dimethyl-2-[(2-{[(6-methyl-2-pyridinyl)methyl]amino}ethyl)amino]butanoate A solution containing the product from Example 6F (2.0 g, 8.68 mmol) in dichloromethane (40 mL) was treated with 6-methyl-2-pyridinecarboxaldehyde (1.04 g, 8.59 mmol) and magnesium sulfate (6.0 g, 49.85 mmol), stirred at 25° C. for 4 hours, filtered and concentrated. A solution of the residue in methanol (40 mL) at 0° C. was treated with sodium borohydride (0.5 g, 13.22 mmol), stirred at 25° C. for 1.5 hours, and concentrated. The concentrate was partitioned between dichloromethane and water, and the aqueous was extracted three times with dichloromethane. The combined organic phase was dried over NaSO$_4$, filtered and concentrated. The residue was chromatographed on silica gel, eluting with 10% methanol in chloroform, to give the title compound (2.48 g, 85% yield).

EXAMPLE 10B tert-butyl(2S)-3,3-dimethyl-2-{3-[(6-methyl-2-pyridinyl)methyl]-2-oxo-1-imidazolidinyl}butanoate A solution containing the product from Example 10A (1.76 g, 5.25 mmol) in 1,2-dichloroethane (210 mL) was treated with N,N-disuccinimidyl carbonate (1.61 g, 6.28 mmol) and triethylamine (0.75 mL, 5.38 mmol), stirred at 25° C. for 16 hours, and partitioned with 10% Na$_2$CO$_3$. The aqueous phase was extracted with additional dichloromethane. The combined organic phase was dried over MgSO$_4$, filtered and concentrated. The residue was chromatographed on silica gel eluting with 0-25% methyl tert-butyl ether/dichloromethane to give the title compound (1.33 g, 70% yield).

EXAMPLE 10C (2S)-3,3-dimethyl-2-{3-[(6-methyl-2-pyridinyl)methyl]-2-oxo-1-imidazolidinyl}butanoic acid A solution containing the product from Example 10B (1.33 g, 3.68 mmol) in dichloromethane (20 mL) was treated with trifluoracetic acid (20 mL), stirred at 25° C. for 2 hours and concentrated. The residue was purified by reversed phase chromatography on a C18 column, eluting with 0-100% acetonitrile/water (0.1% TFA) to give the title compound (1.44 g, 94% yield) as the trifluoroacetic acid salt.

EXAMPLE 10D (2S)-3,3-dimethyl-2-{3-[(6-methyl-2-pyridinyl)methyl]-2-oxo-1-imidazolidinyl}butanoic acid A solution containing the product from Example 10B (10 g, 27.7 mmol) in dichloromethane (100 ml) at −5° C. was slowly treated with an HCl solution in dioxane (200 mL, 4 N), stirred at 40° C. for 6 hrs, stirred at 25° C. for 16 hours concentrated to give the title compound as a hydrochloride salt (10 g, quantitative).

EXAMPLE 10E methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-phenylpentyl}amino)carbonyl]-2,2-dimethylpropylcarbamate A solution containing the product from Example 8B (1.36 g, 2.99 mmol) in THF (30 mL) was treated with the product from Example 10D (1.25 g, 2.98 mmol), DEPBT (1.34 g, 4.48 mmol), and N,N-diisopropylethylamine (2.6 mL, 14.9 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by elution with 5% methanol in ethyl acetate. The material obtained after concentration of all the desired fractions was re-chromatographed on silica gel eluting with 0-50% acetone/dichloromethane to give the title compound (1.57 g, 71% yield). $^1$H NMR (300 MHz, DMSO-$d_6$), δ ppm 0.84 (s, 9 H), 0.87 (s, 9 H), 1.51 (m, 2 H), 2.41 (m, 5 H), 2.65 (dd, J=13.05, 2.76 Hz, 1 H), 2.72 (d, J=7.35 Hz, 2 H), 2.97 (m, 1 H), 3.08 (q, J=8.58 Hz, 1 H), 3.24 (m, 1 H), 3.58 (m, 3 H), 3.91 (d, J=9.19 Hz, 1 H), 3.97 (s, 1 H), 4.16 (m, 2 H), 4.34 (d, J=2.94 Hz, 2 H), 4.80 (d, J=5.52 Hz, 1 H), 6.81 (d, J=9.56 Hz, 1 H), 7.07 (m, 6 H), 7.16 (m, 7 H), 7.50 (d, J=9.19 Hz, 1 H), 7.68 (t, J=7.72 Hz, 1 H), 7.89 (d, J=9.19 Hz, 1 H).

EXAMPLE 11 methyl(1S)-1-[({(1S,2S,4S)-1-benzyl-2-hydroxy-4-[((2S)-3-methyl-2-{3-[(2-methyl-1,3-thiazol-5-yl)methyl]-2-oxo-1-imidazolidinyl}pentanoyl)amino]-5-phenylpentyl}amino)carbonyl]-2,2-dimethylpropylcarbamate

EXAMPLE 11A tert-butyl(1S,2S,4S)-4-amino-1-benzyl-2-hydroxy-5-phenylpentylcarbamate A solution of the product from Example 127 (5 g, 17.6 mmol) in toluene (70 mL) was treated with phenyl boronic acid (2.14 g, 17.6 mmol), stirred at reflux until the theoretical amount of water (0.317 mL) was collected in a Dean-Stark trap. The reaction mixture was cooled to 25° C. and concentrated to dryness, treated with dichloromethane (70 mL) and di-tert-butyl-dicarbonate (4.0 mL, 17.6 mmol), stirred at 25° C. for 18 hours, treated with sodium hydroxide solution (35 mL, 1 N), and stirred for 10 minutes. The organic phase was washed with water, dried over $Na_2SO_4$, filtered and concentrated. The residue was chromatographed on silica gel, eluting with isopropyl amine in dichloromethane to give the title compound (2.23 g, 33% yield).

EXAMPLE 11B 2-methyl-1,3-thiazole-4-carbaldehyde

A solution of ethyl 2-methylthiazole-4-carboxylate (1.00 g, 5.8 mmol) in toluene (18 mL) at −78° C. was treated dropwise with a diisobutyl aluminum hydride solution in dichloromethane (11.1 mL, 1 M) over 30 minutes, stirred at −78° C. for 4 hours, quenched with acetic acid (0.46 mL), warmed to 25° C. and concentrated. The concentrate was treated with dichloromethane and Rochelle's salt, stirred vigorously until a clear, two-phase solution formed (approximately 10 minutes). The layers were separated and organic layer was washed with 10% $NaHCO_3$, brine, dried over $Na_2SO_4$, filtered and concentrated. The residue was chromatographed on silica gel, eluting with 14% ethyl acetate in hexanes to give the title compound (0.28 g, 38% yield).

EXAMPLE 11C tert-butyl(2S,3S)-3-methyl-2-{3-[(2-methyl-1,3-thiazol-4-yl)methyl]-2-oxo-1-imidazolidinyl}pentanoate A solution containing the product from Example 3G (1.81 g, 7.9 mmol) in a mixture of benzene (8 mL) and methanol (8 mL) was treated with the product from Example 11B (1.0 g, 7.9 mmol), stirred at 50° C. for 1 hour, cooled to 25° C. and treated with sodium borohydride (0.60 g, 15.7 mmol), stirred at 25° C. for 1 hour, quenched with sodium bicarbonate solution and partitioned between ethyl acetate and water. The organic phase was washed with brine, dried over $Na_2SO_4$, filtered and concentrated. A solution of the residue (7.9 mmol) in toluene (16 mL) was treated with bis(4-nitrophenyl) carbonate (2.87 g, 9.4 mmol), stirred at reflux for 16 hours, cooled to 25° C. and partitioned between ethyl acetate and 10% $K_2CO_3$. The organic phase was washed with brine, dried over $Na_2SO_4$, filtered and concentrated. The residue was chromatographed on silica gel eluting with 1% methanol in chloroform to give the title compound (2.0 g, 69% yield).

EXAMPLE 11D (2S,3S)-3-methyl-2-{3-[(2-methyl-1,3-thiazol-4-yl)methyl]-2-oxo-1-imidazolidinyl}pentanoic acid A solution containing the product from Example 11C (2.0 g, 5.4 mmol) in dichloromethane (14 mL) was treated with trifluoracetic acid (7 mL), stirred at 25° C. for 3 hours and concentrated to give the title compound as a trifluoroacetic acid salt.

EXAMPLE 11E tert-butyl(1S,2S,4S)-1-benzyl-2-hydroxy-4-[((2S, 3S)-3-methyl-2-{3-[(2-methyl-1,3-thiazol-4-yl)methyl]-2-oxo-1-imidazolidinyl}pentanoyl)amino]-5-phenylpentylcarbamate A solution containing the product from Example 11A (0.42 g, 1.09 mmol) in THF (5 mL) was treated with the product from Example 11D (0.34 g, 1.09 mmol), DEPBT (0.65 g, 2.2 mmol), and N,N-diisopropylethylamine (0.57 mL, 3.3 mmol), stirred at 25° C. for 4 hours and partitioned between dichloromethane and 10% $Na_2CO_3$ solution. The organic phase was washed with additional 10% Na₂CO₃ solution and brine, dried over Na₂SO₄, filtered and concentrated. The residue was chromatographed on silica gel, eluting with 2% methanol in chloroform to give the title compound (0.27 g, 36% yield).

EXAMPLE 11F (2S,3S)-N-[(1S,3S,4S)-4-amino-1-benzyl-3-hydroxy-5-phenylpentyl]-3-methyl-2-{3-[(2-methyl-1,3-thiazol-4-yl)methyl]-2-oxo-1-imidazolidinyl}pentanamide A solution containing the product from Example 11E (0.27 g, 0.4 mmol) in THF (4 mL) was treated with an HCl solution (0.70 mL, 4 N in dioxane), heated at 60° C. for 3 hours, cooled to 25° C., and concentrated to give the title compound as the hydrochloride salt.

EXAMPLE 11G methyl(1S)-1-[({(1S,2S,4S)-1-benzyl-2-hydroxy-4-[((2S)-3-methyl-2-{3-[(2-methyl-1,3-thiazol-5-yl)methyl]-2-oxo-1-imidazolidinyl}pentanoyl)amino]-5-phenylpentyl}amino)carbonyl]-2,2-dimethylpropylcarbamate A solution containing the product from Example 11F (0.23 g, 0.4 mmol) in THF (5 mL) was treated with the product from Example 1F (0.08 g, 0.4 mmol), DEPBT (0.24 g, 0.8 mmol), and N,N-diisopropylethylamine (0.21 mL, 1.2 mmol), stirred at 25° C. for 64 hours, and partitioned between chloroform and 10% Na₂CO₃ solution. The organic phase was washed with additional 10% Na₂CO₃ solution and brine, dried over Na₂SO₄, filtered and concentrated. The residue was chromatographed on silica gel, eluting with 2% methanol in chloroform to give the title compound (0.13 g, 44% yield). ¹H NMR (300 MHz, CDCl₃), δ ppm 0.77 (d, J=6.25 Hz, 3 H), 0.85 (t, J=7.35 Hz, 4 H), 0.92 (s, 10 H), 1.00 (m, 1 H), 1.41 (m, 1 H), 2.01 (m, 1 H), 2.68 (s, 3 H), 2.71 (d, J=7.35 Hz, 2 H), 2.82 (dd, J=7.35, 1.84 Hz, 2 H), 3.00 (m, 1 H), 3.17 (m, 3 H), 3.66 (m, 6 H), 3.77 (d, J=8.82 Hz, 1 H), 3.94 (s, 1 H), 4.07 (m, 2 H), 4.40 (s, 2 H), 5.23 (s, 1 H), 6.05 (d, J=9.19 Hz, 1 H), 6.48 (d, J=8.46 Hz, 1 H), 6.91 (s, 1 H), 7.15 (m, 11 H).

EXAMPLE 12 methyl(1S)-1-{[((1S,2S,4S)-1-benzyl-2-hydroxy-4-{[(2S)-3-methyl-2-(2-oxo-3-{[2-(3-pyridinyl)-1,3-thiazol-4-yl]methyl}-1-imidazolidinyl)pentanoyl]amino}-5-phenylpentyl)amino]carbonyl}-2,2-dimethylpropylcarbamate A solution containing the product from Example 8B (0.275 g, 0.56 mmol) in THF (6 mL) was treated with the product from Example 3L (0.227 g, 0.61 mmol), DEPBT (0.275 g, 0.92 mmol), and N,N-diisopropylethylamine (0.55 mL, 3.16 mmol), stirred at 25° C. for 64 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane, followed by elution with 5% methanol in ethyl acetate to give the title compound (0.378 g, 77% yield). ¹H NMR (300 MHz, DMSO-d₆), δ ppm 0.67 (d, J=6.62 Hz, 3 H), 0.80 (m, 14 H), 0.94 (m, 1 H), 1.29 (m, 1 H), 1.49 (m, 2 H), 1.78 (m, 1 H), 2.42 (m, 1 H), 2.68 (m, 3 H), 2.86 (m, 1 H), 3.13 (m, 4 H), 3.58 (m, 4 H), 3.89 (m, 2 H), 4.12 (m, 2 H), 4.47 (s, 2 H), 4.79 (d, J=5.52 Hz, 1 H), 6.80 (d, J=9.19 Hz, 1 H), 7.07 (m, 7 H), 7.52 (m, 2 H), 7.57 (s, 1 H), 7.82 (d, J=8.82 Hz, 1 H), 8.29 (m, 1 H), 8.66 (dd, J=4.78, 1.84 Hz, 1 H), 9.13 (d, J=1.47 Hz, 1 H).

EXAMPLE 13 methyl(1S)-1-[({(1S,2S,4S)-1-benzyl-2-hydroxy-4-[((2S)-3-methyl-2-{3-[(6-methyl-3-pyridinyl)methyl]-2-oxo-1-imidazolidinyl}pentanoyl)amino]-5-phenylpentyl}amino)carbonyl]-2,2-dimethylpropylcarbamate

EXAMPLE 13A 6-methylnicotinaldehyde

A solution of methyl 6-methylnicotinate (0.5 g, 3.3 mmol) in THF (16 mL) at 0° C. was treated dropwise with lithium aluminum hydride in THF (6.6 mL, 1 M), stirred at 0° C. for 1.5 hours, treated with ethyl acetate (3 mL), and stirred at 25° C. The reaction was partitioned between ethyl acetate and saturated NaHCO₃, and the organic phase was washed with brine and dried over MgSO₄, filtered and concentrated. A solution of the residue (0.395 g) in dichloromethane (16 mL) was treated with MnO₂ (2 g), stirred at 25° C. for 68 hours, and filtered through celite® to give the title compound (0.326 g, 80% yield), which was used without further purification.

EXAMPLE 13B tert-butyl(2S,3S)-3-methyl-2-{3-[(6-methyl-3-pyridinyl)methyl]-2-oxo-1-imidazolidinyl}pentanoate A solution containing the product from Example 3G (0.55 g, 2.39 mmol) in a mixture of benzene (6 mL) and ethanol (6 mL) was treated with the product from Example 13A (0.265 g, 2.19 mmol), stirred at 70° C. for 2 hours, cooled to 25° C., treated with sodium borohydride (0.25 g, 6.61 mmol), stirred at 25° C. for 3 hours, and partitioned between ethyl acetate and saturated NaHCO₃. The organic phase was washed with brine, dried over MgSO₄, filtered and concentrated. A solution of the residue (2.19 mmol) in 1,2-dichloroethane (90 mL) was treated with N,N-disuccinimidyl carbonate (0.675 g, 2.63 mmol) and triethylamine (0.30 mL, 2.15 mmol), stirred at 25° C. for 16 hours, and partitioned with 10% NaCO₃. The aqueous phase was extracted with additional dichloromethane. The combined organic phase was dried over MgSO₄, filtered and concentrated. The residue was chromatographed on silica gel eluting with 0-100% ethyl acetate/dichloromethane to give the title compound (0.392 g, 49% yield).

EXAMPLE 13C (2S,3S)-3-methyl-2-{3-[(6-methyl-3-pyridinyl)methyl]-2-oxo-1-imidazolidinyl}pentanoate A solution containing the product from Example 13B (0.39 g, 1.08 mmol) in dichloromethane (5 mL) was treated with trifluoracetic acid (5 mL), stirred at 25° C. for 2 hours and concentrated. The concentrate was purified by reversed phase chromatography on a C18 column, eluting with 0-100% acetonitrile/water (0.1% TFA) give the title compound (0.536 g, quantitative) as the trifluoroacetic acid salt.

EXAMPLE 13D methyl(1S)-1-[({(1S,2S,4S)-1-benzyl-2-hydroxy-4-[((2S)-3-methyl-2-{3-[(6-methyl-3-pyridinyl)methyl]-2-oxo-1-imidazolidinyl}pentanoyl)amino]-5-phenylpentyl}amino)carbonyl]-2,2-dimethylpropylcarbamate A solution containing the product from Example 8B (0.29 g, 0.64 mmol) in THF (6 mL) was treated with the product from Example 13C (0.27 g, 0.64 mmol), DEPBT (0.300 g, 1.00 mmol), and N,N-diisopropylethylamine (0.60 mL, 3.44 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by elution with 5% methanol in ethyl acetate to give the title compound (0.345 g, 73% yield). $^1$H NMR(300 MHz, DMSO-$d_6$), δ ppm 0.67 (d, J=6.25 Hz, 3 H), 0.85 (m, 13 H), 1.21 (m, 1 H), 1.49 (m, 2 H), 1.77 (m, 1 H), 2.41 (m, 4 H), 2.68 (m, 3 H), 2.84 (m, 1 H), 2.93 (m, 1 H), 3.01 (m, 2 H), 3.57 (m, 3 H), 3.89 (m, 3 H), 4.11 (m, 2 H), 4.28 (s, 2 H), 4.79 (d, J=5.52 Hz, 1 H), 6.80 (d, J=9.93 Hz, 1 H), 7.03 (s, 5 H), 7.17 (m, 6 H), 7.52 (m, 2 H), 7.83 (d, J=8.82 Hz, 1 H), 8.35 (d, J=2.21 Hz, 1 H).

EXAMPLE 14 methyl(1S)-1-[({(1S,2S,4S)-1-benzyl-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenylpentyl}amino)carbonyl]-2,2-dimethylpropylcarbamate

EXAMPLE 14A tert-butyl(2S)-3,3-dimethyl-2-{3-[(2-methyl-1,3-thiazol-4-yl)methyl]-2-oxo-1-imidazolidinyl}butanoate A solution containing the product from Example 6F (0.82 g, 3.5 mmol) in a mixture of benzene (12 mL) and methanol (12 mL) was treated with the product from Example 11B (0.45 g, 3.5 mmol), heated at 50° C. for 1 hour, cooled to 25° C., treated with sodium borohydride (0.27 g, 7.1 mmol), stirred at 25° C. for 1 hour, quenched with sodium bicarbonate solution and partitioned between ethyl acetate and water. The organic phase was washed with brine and dried over $Na_2SO_4$, filtered and concentrated. A solution containing the residue (3.5 mmol) in toluene (20 mL) was treated with bis(4-nitrophenyl) carbonate (1.29 g, 4.2 mmol), heated at reflux for 16 hours, cooled to 25° C., and partitioned between ethyl acetate and 10% $K_2CO_3$. The organic phase was washed with brine and dried over $Na_2SO_4$, filtered and concentrated to give the title compound, which was used without further purification.

EXAMPLE 14B (2S)-3,3-dimethyl-2-{3-[(2-methyl-1,3-thiazol-4-yl)methyl]-2-oxo-1-imidazolidinyl}butanoic acid A solution containing the product from Example 14A (3.5 mmol) in dichloromethane (4 mL) was treated with trifluoracetic acid (3 mL), stirred at 25° C. for 3 hours and concentrated. The residue was chromatographed on silica gel eluting with 2% methanol in chloroform to give the title compound as the trifluoroacetic acid salt (0.88 g, 80% yield).

EXAMPLE 14C tert-butyl(1S,2S,4S)-1-benzyl-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenylpentylcarbamate A solution containing the product from Example 11A (0.37 g, 1.0 mmol) in THF (5 mL) was treated with the product of Example 14B (0.30 g, 1.0 mmol), DEPBT (0.58 g, 1.9 mmol), and N,N-diisopropylethylamine (0.57 mL, 3.3 mmol), stirred at 25° C. for 4 hours, and partitioned between dichloromethane and 10% $Na_2CO_3$ solution. The organic phase was washed with additional 10% $Na_2CO_3$ solution and brine, dried over $Na_2SO_4$, filtered and concentrated. The residue was chromatographed on silica gel, eluting with 2% methanol in chloroform to give the title compound (0.63 g, 97% yield).

EXAMPLE 14D (2S)-N-[(1S,3S,4S)-4-amino-1-benzyl-3-hydroxy-5-phenylpentyl]-3,3-dimethyl-2-{3-[(2-methyl-1,3-thiazol-4-yl)methyl]-2-oxo-1-imidazolidinyl}butamide A solution containing the product from Example 14C (0.63 g, 0.9 mmol) in THF (5 mL) was treated with an HCl solution (0.1.6 mL, 4 N in dioxane), heated at 60° C. for 3 hours, cooled to 25° C. and concentrated. The residue was treated with ethanol (10 mL) and concentrated. This process was repeated an additional time to give the title compound as the hydrochloride salt.

EXAMPLE 14E methyl(1S)-1-[({(1S,2S,4S)-1-benzyl-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenylpentyl}amino)carbonyl]-2,2-dimethylpropylcarbamate A solution containing the product from Example 14D (0.9 mmol) in THF (5 mL) was treated with the product from Example 1F (0.176 g, 0.9 mmol), DEPBT (0.556 g, 1.86 mmol), and N,N-diisopropylethylamine (0.486 mL, 2.79 mmol), stirred at 25° C. for 48 hours, and partitioned between dichloromethane and 10% $Na_2CO_3$ solution. The organic phase was washed with additional 10% $Na_2CO_3$ solution and brine, dried over $Na_2SO_4$, filtered and concentrated. The residue was chromatographed on silica gel, eluting with 2% methanol in chloroform to give the title compound (0.31 g, 44% yield). $^1$H NMR (300 MHz, CDCl$_3$), δ ppm 0.94 (s, 9 H), 1.00 (s, 9 H), 2.74 (m, 9 H), 3.13 (m, 2 H), 3.40 (m, 1 H), 3.63 (m, 1 H), 3.68 (s, 3 H), 3.78 (d, J=9.19 Hz, 1 H), 3.83 (d, J=4.04 Hz, 1 H), 3.96 (s, 1 H), 4.10 (m, 2 H), 4.44 (d, J=2.21 Hz, 2 ), 5.27 (d, J=8.46 Hz, 1 H), 6.05 (d, J=9.19 Hz, 1 H), 6.14 (d, J=9.19 Hz, 1 H), 6.93 (s, 1 H), 7.16 (m, 11 H).

EXAMPLE 15 methyl(1S)-1-[({(1S,2S,4S)-1-benzyl-2-hydroxy-4-[((2s)-3-methyl-2-{3-[(2-methyl-3-pyridinyl)methyl]-2-oxo-1-imidazolidinyl}pentanoyl)amino]-5-phenylpentyl}amino)carbonyl]-2,2-dimethylpropylcarbamate

EXAMPLE 15A 2-methylnicotinaldehyde

A solution of methyl 2-methylnicotinate (0.5 g, 3.3 mmol) in THF (16 mL) at 0° C. was treated dropwise with lithium aluminum hydride in THF (6.6 mL, 1 M), stirred at 0° C. for 1.5 hours, treated with ethyl acetate (3 mL), warmed to 25° C., and partitioned between ethyl acetate and saturated NaHCO$_3$. The organic phase was washed with brine, dried over MgSO$_4$, filtered and concentrated. A solution of the residue (0.391 g) in dichloromethane (16 mL) was treated with MnO$_2$ (2 g), stirred at 25° C. for 68 hours, filtered through celite®, and the solvent was evaporated to give the title compound (0.303 g, 75% yield), which was used without further purification.

EXAMPLE 15B tert-butyl(2S,3S)-3-methyl-2-{3-[(2-methyl-3-pyridinyl)methyl]-2-oxo-1-imidazolidinyl}pentanoate A solution containing the product from Example 3G (2.4 g, 10.43 mmol) in dichloromethane (24 mL) was treated with the product from Example 15A (1.3 g, 10.74 mmol) and MgSO$_4$ (4.6 g, 38.21 mmol), stirred at 25° C. for 2.5 hours, filtered and concentrated. A solution of the residue in methanol (24 mL) at 0° C. was treated with sodium borohydride (0.5 g, 13.2 mmol), and stirred at 25° C. for 3 hours. The solvent was concentrated and the reaction was partitioned between ethyl acetate and saturated NaHCO$_3$, and the organic phase was washed with brine and dried over MgSO$_4$, filtered and concentrated. A solution of the residue (3.4 g) in 1,2 dichloroethane (30 mL was treated with bis(4-nitrophenyl) carbonate (3.8 g, 12.5 mmol), heated at 60° C. for 16 hours, and partitioned between ethyl acetate and saturated NaHCO$_3$. The organic phase was washed with brine, dried over MgSO$_4$, filtered and concentrated. The residue was chromatographed on silica gel eluting with ethyl acetate to give the title compound (2.31 g, 60% yield).

EXAMPLE 15C (2S,3S)-3-methyl-2-{3-[(2-methyl-3-pyridinyl)methyl]-2-oxo-1-imidazolidinyl}pentanoic acid A solution containing the product from Example 15B (2.3 g, 6.37 mmol) in dichloromethane (15 mL) was treated with trifluoracetic acid (15 mL), stirred at 25° C. for 5.5 hours and concentrated to give the title compound (3.42 g) as the trifluoroacetic acid salt, which was used without further purification.

EXAMPLE 15D methyl(1S)-1-[({(1S,2S,4S)-1-benzyl-2-hydroxy-4-[((2S)-3-methyl-2-{3-[(2-methyl-3-pyridinyl)methyl]-2-oxo-1-imidazolidinyl}pentanoyl)amino]-5-phenylpentyl}amino)carbonyl]-2,2-dimethylpropylcarbamate A solution containing the product from Example 8B (2.0 g, 4.40 mmol) in DMF (10 mL) was treated with the product from Example 15C (1.34 g, 4.39 mmol), EDAC (1.01 g, 5.27 mmol), HOBT (0.7 g, 5.19 mmol), and NMM (0.96 mL, 8.72 mmol), stirred at 25° C. for 16 hours, treated with Example 15C (0.13 g), EDAC (0.5 g), HOBT (0.35 g), NMM (1 mL), and DMF (5 mL), stirred for 64 hours at 25° C. and concentrated. The concentrate was partitioned between ethyl acetate and saturated NaHCO$_3$. The organic phase was washed with brine, dried over Na$_2$SO$_4$, filtered and concentrated. The residue was chromatographed on silica gel eluting with 0-4% methanol/dichloromethane to give the title compound (1.76 g, 54% yield). $^1$H NMR (300 MHz, DMSO-d$_6$), δ ppm 0.68 (d, J=6.62 Hz, 3 H), 0.81 (m, 15 H), 1.26 (m, 1 H), 1.49 (m, 2 H), 1.78 (m, 1 H), 2.45 (m, 5 H), 2.70 (m, 3 H), 2.90 (m, 2 H), 3.04 (m, 2 H), 3.59 (m, 4 H), 3.87 (m, 2 H), 4.13 (m, 2 H), 4.31 (s, 2 H), 4.79 (d, J=5.52 Hz, 1 H), 6.80 (d, J=9.19 Hz, 1 H), 7.05 (s, 3 H), 7.19 (m, 5 H), 7.51 (m, 2 H), 7.86 (d, J=8.82 Hz, 1 H), 8.36 (d, J=3.68 Hz, 1 H).

EXAMPLE 16 methyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 2C (1.0 g, 1.88 mmol) in THF (19 mL) was treated with the product from Example 10B (0.83 g, 1.98 mmol), DEPBT (0.84 g, 2.8 mmol), and N,N-diisopropylethylamine (1.6 mL, 9.2 mmol), stirred at 25° C. for 16 hours, and partitioned between a mixture of dichloromethane and ethyl acetate (2:1, respectively) and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by elution with 0-5% methanol in ethyl acetate to give the title compound (1.15 g, 75% yield). $^1$H NMR (300 MHz, DMSO-d$_6$), δ ppm 0.83 (s, 9 H), 0.90 (s, 9 H), 1.55 (m, 2 H), 2.38 (q, J=9.44 Hz, 1 H), 2.46 (s, 3 H), 2.57 (m, 1 H), 2.67 (d, J=7.35 Hz, 2 H), 2.79 (m, 1 H), 2.97 (m, 1 H), 3.09 (q, J=8.95 Hz, 1 H), 3.21 (m, 1 H), 3.50 (s, 3 H), 3.67 (m, 1 H), 3.85 (d, J=9.93 Hz, 1 H), 4.12 (m, 3 H), 4.35 (m, 2 H), 4.54 (d, J=7.72 Hz, 1 H), 6.63 (d, J=9.56 Hz, 1 H), 7.09 (m, 7 H), 7.22 (d, J=8.09 Hz, 2 H), 7.31 (m, 1 H), 7.49 (d, J=9.56 Hz, 1 H), 7.69 (t, J=7.54 Hz, 1 H), 7.86 (m, 5 H), 8.63 (d, J=4.78 Hz, 1 H).

EXAMPLE 17 methyl(1S)-1-{[((1S,2S,4S)-1-benzyl-2-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenylpentyl)amino]carbonyl}-2,2-dimethylpropylcarbamate

EXAMPLE 17A methyl 6-(hydroxymethyl)-2-pyridinecarboxylate

A suspension of dimethyl 2,6-pyridine-dicarboxylate (50 g, 0.25 mol) in methanol (400 mL) and tetrahydrofuran (150 mL) was heated to dissolve and while the solution was still hot, it was treated in portions with sodium borohydride (9.1 g, 0.24 mol). The mixture was stirred for 1 hour after the addition, cooled to 25° C., quenched with 10% citric acid (80 mL), stirred for 15 minutes, filtered, and concentrated. A solution of the concentrate in dichloromethane was dried over sodium sulfate, filtered, and concentrated. A solution of the residue in hot ethyl acetate was allowed to stand for 16 hours at 25° C. The resulting precipitate (23 g) was collected by filtration. The mother liquor was concentrated and the resulting solid was purified by flash chromatography on silica gel eluting with 10% methanol in dichloromethane to give the crude white solid (24 g). The solid was crystallized in ethyl acetate to give a total yield of the title compound (36 g, 84% yield).

EXAMPLE 17B methyl 6-formyl-2-pyridinecarboxylate

A solution of the product from Example 17A (8 g, 48 mmol) in dichloromethane (200 mL) was treated with electrolytic manganese dioxide (41.67 g, 0.48 mol). The mixture was stirred for 4 days at 25° C. and filtered through celite. The filtrate was concentrated under reduced pressure and the residue was purified by chromatography on silica gel eluting with 5% methanol in dichloromethane to give the title compound as a white solid (6.9 g, 87% yield).

EXAMPLE 17C methyl 6-{[(2-{[(1S)-1-(tert-butoxycarbonyl)-2,2-dimethylpropyl]amino}ethyl)amino]methyl}-2-pyridinecarboxylate A suspension containing the product from Example 17B (6 g, 36.4 mmol), the product from Example 6F (8.37 g, 36.4 mmol), and magnesium sulfate (21.9 g, 0.18 mol) in dichloromethane (80 mL) was stirred at 25° C. for 4 hours, filtered, and concentrated. A solution of the residue in methanol (80 mL) was treated with sodium borohydride (1.58 g, 41.9 mmol) at 0° C., stirred 0.5 hour at 0° C., quenched with acetone (2 mL), concentrated, treated with 1M sodium bicarbonate and extracted with ethyl acetate. The organic phase was concentrated and the residue was chromatographed on silica gel eluting with 8% methanol in dichloromethane to give the title compound (10.27 g).

EXAMPLE 17D methyl 6-({3-[(1S)-1-(tert-butoxycarbonyl)-2,2-dimethylpropyl]-2-oxo-1-imidazolidinyl}methyl)-2-pyridinecarboxylate A solution of the product from Example 17C (10.27 g, 27.1 mmol), bis (4-nitrophenyl) carbonate (8.24 g, 27.1 mmol), in toluene (100 mL) was heated at 110° C. for 16 hours, cooled to 25° C., treated with 1M sodium bicarbonate, and extracted with ethyl acetate. The organic phase layer was concentrated and the residue was purified by flash chromatography on silica gel eluting with 60% ethyl acetate in hexane to give the title compound as a white solid (9.44 g, 64% yield).

EXAMPLE 17E tert-butyl(2S)-2-(3-{[6-(1-hydroxy-1-methylethyl)-2-pyridinyl]methyl}-2-oxo-1-imidazolidinyl)-3,3-dimethylbutanoate A solution of the product from Example 17D (9 g, 22.2 mmol) in tetrahydrofuran (200 mL) at 0° C. was treated with a solution of methylmagnesium bromide in diethyl ether (3M, 37 mL, 111 mmol), stirred for 1.5 hours at 0° C., quenched with 10% citric acid (20 mL), and extracted with ethyl acetate. The organic phase was concentrated, and the residue was purified by flash chromatography on silica gel eluting with 20-70% ethyl acetate in hexane to give the title compound (7.2 g, 80% yield).

EXAMPLE 17F (2S)-2-(3-{[6-(1-hydroxy-1-methylethyl)-2-pyridinyl]methyl}-2-oxo-1-imidazolidinyl)-3,3-dimethylbutanoic acid The product from Example 17E (7.2 g, 17.8 mmol) at 25° C. was treated with 90% trifluoroacetic acid in water (30 mL). The reaction mixture was stirred at 25° C. for 3 hours and concentrated. A solution of the residue in water (2 mL) was chromatographed on silica gel eluting with 5% methanol/dichloromethane to give the title compound as the trifluoroacetic acid salt (7.4 g, 89.9% yield).

EXAMPLE 17G methyl(1S)-1-{[(((1S,2S,4S)-1-benzyl-2-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenylpentyl)amino]carbonyl}-2,2-dimethylpropylcarbamate A solution containing the product from Example 8B (1.7 g, 3.73 mmol) in THF (25 mL) was treated with the product from Example 17F (1.8 g, 3.88 mmol), DEPBT (2.32 g, 7.46 mmol), and triethylamine (1.35 mL, 9.32 mmol), stirred at 25° C. for 16 hours, quenched with sodium bicarbonate solution (1M), and extracted with ethyl acetate. The organic phase layer was decanted and concentrated. The residue was chromatographed on a silica gel column eluting with 2% methanol/ethyl acetate to give the title compound (1.73 g, 57% yield). $^1$H NMR (300 MHz, CD$_3$OD) δ ppm 0.91 (s, 9 H), 0.95 (s, 9 H), 1.24 (m, 1 H), 1.35 (m, 2 H), 1.53 (s, 6 H), 1.66 (m, 1 H), 2.01 (s, 1 H,) 2.42 (m, 1 H), 2.87 (m, 2 H), 3.08 (m, 1 H), 3.24 (m, 1 H), 3.66 (s, 2 H), 3.76 (m, 1 H), 3.92 (s, 1 H), 3.98 (s, 1 H), 4.09 (m, 1 H), 4.25 (dd, J=8.64, 7.17 Hz, 1 H), 4.36 (m, J=8.82 Hz, 1 H), 4.43 (s, 1 H), 4.58 (s, 1 H), 4.63 (s, 1 H), 7.14 (m, 11 H), 7.53 (d, J=6.99 Hz, 1 H), 7.77 (t, J=7.91 Hz, 1 H).

EXAMPLE 18 methyl(1S)-1-[({(1S,3S,4S)-3-hydroxy-4-[((2S)-3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 2C (0.01 g, 0.019 mmol) in THF (0.2 mL) was treated with the product from Example 7B (0.009 g, 0.021 mmol), DEPBT (0.009 g, 0.030 mmol), and N,N-diisopropylethylamine (0.016 mL, 0.092 mmol), stirred at 25° C. for 16 hours and partitioned between a mixture of dichloromethane, ethyl acetate (2:1, respectively) and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with a gradient starting with 5-100% acetonitrile in water (0.1% TFA). The product was partitioned between a mixture of dichloromethane and ethyl acetate (2:1, respectively) and saturated NaHCO$_3$ solution. The organic phase was washed with brine, dried over MgSO$_4$, filtered and concentrated to give the title compound (0.0076 g, 51% yield). $^1$H NMR (300 MHz, DMSO-d$_6$), δ ppm 0.82 (m, 18 H), 1.31 (m, 3 H), 1.52 (m, 2 H), 1.80 (m, 1 H), 2.45 (s, 3 H), 2.67 (m, 4 H), 3.09 (m, 4 H), 3.50 (s, 1 H), 3.66 (m, 1 H), 3.84 (d, J=9.93 Hz, 1 H), 3.93 (d, J=11.03 Hz, 1 H), 4.14 (m, 1 H), 4.35 (s, 1 H), 4.67 (d, J=7.35 Hz, 1 H), 6.64 (d, J=9.93 Hz, 1 H), 7.21 (m, 12 H), 7.66 (t, J=7.72 Hz, 1 H), 7.86 (m, 4 H), 8.63 (d, J=4.78 Hz, 1 H).

EXAMPLE 19 methyl(1S)-1-{[(((1S,2S,4S)-1-benzyl-4-{[(2S)-3,3-dimethyl-2-(2-oxo-3-{[2-(3-pyridinyl)-1,3-thiazol-4-yl]methyl})-1-imidazolidinyl)butanoyl]amino}-2-hydroxy-5-phenylpentyl)amino]carbonyl}-2,2-dimethylpropylcarbamate

EXAMPLE 19A ethyl 2-(3-pyridinyl)-1,3-thiazole-4-carboxylate

A solution containing thionicotinamide (30 g, 217.1 mmol) in ethanol (540 mL) was treated with ethyl bromopyruvate (30.3 mL, 241.4 mmol), heated at 70° C. for 3 hours, cooled to 25° C., concentrated and partitioned between chloroform and saturated NaHCO$_3$. The organic phase was washed with brine, dried over MgSO$_4$, filtered and concentrated. The residue was chromatographed on silica gel eluting with chloroform and then with 15% methanol in chloroform containing 1% ammonium hydroxide to give the product (36.3 g, 71% yield).

EXAMPLE 19B 2-(3-pyridinyl)-1,3-thiazole-4-carbaldehyde

A solution containing the product from Example 19A (20 g, 85.5 mmol) in dichloromethane (340 mL) was treated dropwise with DIBAL (86 mL, 1 M in dichloromethane) at −78° C., stirred at −78° C. for 2 hours, treated with DIBAL (43 mL, 1 M in dichloromethane), stirred at −78° C. for 1 hour, treated with methanol (20 mL) at −78° C., warmed to 25° C., treated with dichloromethane (250 mL), saturated aqueous sodium potassium tartrate (350 mL), and pH 7 buffer (300 mL), stirred vigorously with a mechanical stirrer for 16 hours, and filtered through celite®. The aqueous phase was washed with chloroform, and the combined organic phase was washed with brine and dried over MgSO$_4$, filtered and concentrated. The residue was chromatographed on silica gel eluting 0-4% methanol/chloroform to give the title compound (11.61 g, 71% yield).

EXAMPLE 19C tert-butyl(2S)-3,3-dimethyl-2-(2-oxo-3-{[2-(3-pyridinyl)-1,3-thiazol-4-yl]methyl}-1-imidazolidinyl)butanoate A solution containing the product from Example 6F (0.855 g, 3.72 mmol) in a mixture of benzene (10 mL) and ethanol (10 mL) was treated with the product from Example 19B (0.70 g, 3.72 mmol), heated at 70° C. for 1 hour, cooled to 25° C. and treated with sodium borohydride (0.422 g, 11.16 mmol), stirred at 25° C. for 2 hours, quenched with sodium bicarbonate solution and partitioned between ethyl acetate and water. The organic phase was washed with brine, dried over MgSO$_4$, filtered and concentrated. A solution of the residue (3.72 mmol) in toluene (85 mL) was treated with bis(4-nitrophenyl) carbonate (1.36 g, 4.47 mmol), heated at 100° C. for 24 hours, cooled to 25° C., and partitioned between ethyl acetate and 10% K$_2$CO$_3$. The organic phase was washed several times with 10% K$_2$CO$_3$, and with brine, dried over MgSO$_4$, filtered and concentrated. The residue was chromatographed on silica gel eluting with 40% chloroform in hexanes to give the title compound (0.61 g, 39% yield).

EXAMPLE 19D (2S)-3,3-dimethyl-2-(2-oxo-3-{[2-(3-pyridinyl)-1,3-thiazol-4-yl]methyl}-1-imidazolidinyl)butanoic acid A solution containing the product from Example 19C (0.61 g, 1.42 mmol) in dichloromethane (7 mL) was treated with trifluoracetic acid (4 mL), stirred at 25° C. for 1 hour, concentrated, and azeotroped several times with toluene to give the title compound as the trifluoroacetic acid salt, which was used without further purification.

EXAMPLE 19E methyl(1S)-1-{[(((1S,2S,4S)-1-benzyl-4-{[(2S)-3,3-dimethyl-2-(2-oxo-3-{[2-(3-pyridinyl)-1,3-thiazol-4-yl]methyl}-1-imidazolidinyl)butanoyl]amino}-2-hydroxy-5-phenylpentyl)amino]carbonyl}-2,2-dimethylpropylcarbamate A solution containing the product from Example 8B (1.4 g, 3.08 mmol) in THF (30 mL) was treated with the product from Example 19D (1.5 g, 3.07 mmol), DEPBT (1.4 g, 4.68 mmol), and N,N-diisopropylethylamine (2.75 mL, 15.78 mmol), stirred at 25° C. for 16 hours, and partitioned between dichloromethane and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate. The product was then purified by reversed phase chromatography on a C18 column eluting with a gradient starting with 5-100% acetonitrile in water (0.1% TFA). The product was partitioned between dichloromethane and saturated NaHCO$_3$ solution. The organic phase was washed brine, dried over MgSO$_4$, filtered and concentrated to give the title compound (1.49 g, 60% yield). $^1$H NMR (300 MHz, DMSO-d$_6$), δ ppm 0.84 (s, 9 H), 0.86 (s, 9 H), 1.49 (m, 2 H), 2.39 (m, 2 H), 2.62 (m, 1 H), 2.72 (d, J=6.99 Hz, 2 H), 3.16 (m, 3 H), 3.57 (m, 4 H), 3.91 (d, J=9.56 Hz, 1 H), 3.98 (s, 1 H), 4.17 (m, 2 H), 4.48 (m, 2 H), 4.80 (d, J=5.52 Hz, 1 H), 6.81 (d, J=9.19 Hz, 1 H), 6.94 (m, 1 H), 7.04 (m, 4 H), 7.15 (m, 5 H), 7.52 (m, 2 H), 7.59 (s, 1 H), 7.88 (d, J=9.56 Hz, 1 H), 8.30 (m, 1 H), 8.66 (dd, J=4.78, 1.47 Hz, 1 H), 9.14 (d, J=1.47 Hz, 1 H).

EXAMPLE 20 methyl(1S)-1-({[(1S,2S,4S)-1-benzyl-4-({(2S)-3,3-dimethyl-2-[2-oxo-3-(3-pyridinylmethyl)-1-imidazolidinyl]butanoyl}amino)-2-hydroxy-5-phenylpentyl]amino}carbonyl)-2,2-dimethylpropylcarbamate

EXAMPLE 20A (2S)-3,3-dimethyl-2-[2-oxo-3-(3-pyridinylmethyl)-1-imidazolidinyl]butanoic acid A solution containing the product from Example 6F (0.10 g, 0.43 mmol) in a mixture of benzene (1.6 mL) and methanol (1.66 mL) was treated with pyridine-3-carboxaldehyde (0.041 mL, 0.43 mmol), stirred at 50° C. for 18 hours, cooled to 25° C., treated with sodium borohydride (0.033 g, 0.87 mmol), stirred at 25° C. for 1 hour, quenched with saturated NaHCO$_3$, stirred for 1 hour, and partitioned between ethyl acetate and saturated NaHCO$_3$. The organic phase was washed with brine, dried over MgSO$_4$, filtered and concentrated. A solution of the residue (0.127 g, 0.40 mmol) in 1,2-dichloroethane (7 mL) was treated with N,N-disuccinimidyl carbonate (0.134 g, 0.52 mmol) and triethylamine (0.07 mL, 0.50 mmol), stirred at 25° C. for 16 hours, diluted with chloroform and partitioned with 10% Na$_2$CO$_3$. The organic phase was washed with brine, dried over MgSO$_4$, filtered and concentrated. A solution of the residue (0.146 g) in dichloromethane (2 mL) was treated with trifluoroacetic acid (2 mL), stirred at 25° C. for 2 hours, concentrated, and azeotroped with toluene several times to give the title compound (0.252 g), as the trifluoroacetic acid salt.

EXAMPLE 20B methyl(1S)-1-({[(1S,2S,4S)-1-benzyl-4-({(2S)-3,3-dimethyl-2-[2-oxo-3-(3-pyridinylmethyl)-1-imidazolidinyl]butanoyl}amino)-2-hydroxy-5-phenylpentyl]amino}carbonyl)-2,2-dimethylpropylcarbamate A solution containing the product from Example 8B (2.0 g, 4.40 mmol) in DMF (10 mL) was treated with the product from Example 20A (1.78 g, 4.39 mmol), EDAC (1.01 g, 5.27 mmol), HOBT (0.7 g, 5.19 mmol), and NMM (0.96 mL, 8.72 mmol), stirred at 25° C. for 16 hours, additional acid (0.17 g), EDAC (0.42 g), HOBT (0.3 g), NMM (0.5 mL), and DMF (5 mL) was added, stirred for 16 hours at 25° C., and concentrated. The reaction was partitioned between ethyl acetate and water. The organic phase was washed with brine and dried over Na$_2$SO$_4$, filtered and concentrated. The residue was chromatographed on silica gel eluting with 3% methanol in dichloromethane to give the title compound (2.0 g, 62% yield). $^1$H NMR (300 MHz, DMSO-d$_6$), δ ppm 0.85 (d, J=1.47 Hz, 18 H), 1.01 (m, 1 H), 1.51 (m, 2 H), 2.39 (m, 2 H), 2.66 (m, 1 H), 2.72 (d, >6.99 Hz, 2 H), 2.90 (m, 2 H), 3.21 (m, 1 H), 3.58 (m, 3 H), 3.91 (d, J=9.93 Hz, 1 H), 3.96 (s, 1 H), 4.19 (m, 2 H), 4.34 (d, J=2.94 Hz, 2 H), 4.80 (d, J=5.52 Hz, 1 H), 6.81 (d, J=9.93 Hz, 1 H), 7.02 (m, 5 H), 7.14 (m, 5 H), 7.40 (dd, J=8.09, 4.78 Hz, 1 H), 7.50 (d, J=9.19 Hz, 1 H), 7.67 (m, 1 H), 7.89 (d, J=9.19 Hz, 1 H), 8.51 (d, J=2.94 Hz, 2 H).

EXAMPLE 21 methyl(1S)-1-[({(1S,3S,4S)-3-hydroxy-4-[((2S)-3-methyl-2-{3-[(2-methyl-3-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 2C (1.1 g, 2.07 mmol) in THF (20 mL) was treated with the product from Example 15C (0.87 g, 2.07 mmol), DEPBT (0.93 g, 3.11 mmol), and N,N-diisopropylethylamine (1.8 mL, 10.33 mmol), stirred at 25° C. for 3 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with a gradient starting with 0-100% ethyl acetate/dichloromethane, followed by 0-10% methanol in ethyl acetate to give the title compound (1.17 g, 69% yield). $^1$H NMR (300 MHz, DMSO-d$_6$), δ ppm 0.83 (m, 18 H), 1.29 (m, 1 H), 1.53 (m, 2 H), 1.80 (m, 1 H), 2.48 (s, 3 H), 2.72 (m, 3 H), 2.96 (m, 3 H), 3.50 (s, 3 H), 3.65 (m, 1 H), 3.84 (d, J=9.93 Hz, 1 H), 3.94 (d, J=11.03 Hz, 1 H), 4.15 (m, 2 H), 4.32 (s, 2 H), 4.67 (d, J=7.35 Hz, 1 H), 6.64 (d, J=9.93 Hz, 1 H), 7.09 (m, 5 H), 7.22 (m, 3 H), 7.31 (m, 2 H), 7.52 (dd, J=7.72, 1.47 Hz, 1 H), 7.86 (m, 5 H), 8.36 (dd, J=4.78, 1.47 Hz, 1 H), 8.63 (d, J=4.41 Hz, 1 H).

EXAMPLE 22 methyl(1S)-1-[({(1S,3S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-phenylpentyl}amino)carbonyl]-2,2-dimethylpropylcarbamate

EXAMPLE 22A tert-butyl(1S,3S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-phenylpentylcarbamate A solution of the product from Example 6A (3.0 g, 7.81 mmol) in THF (80 mL) was treated with the product from Example 10D (2.93 g, 8.57 mmol), DEPBT (3.5 g, 11.71 mmol), and N,N-diisopropylethylamine (7 mL, 40.19 mmol) and the mixture was stirred at 25° C. for 3 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The product was used without further purification.

EXAMPLE 22B methyl(1S)-1-[({(1S,3S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-phenylpentyl}amino)carbonyl]-2,2-dimethylpropylcarbamate A solution of the product from Example 22A (7.81 mmol) in dichloromethane (20 mL) was treated with trifluoroacetic acid (20 mL), and the mixture was stirred at 25° C. for 1 hour. The solvent was concentrated and the reaction was partitioned between ethyl acetate and 10% Na$_2$CO$_3$, and the organic phase was washed with brine and dried over MgSO$_4$, filtered and concentrated. A solution of the residue (7.81 mmol) in THF (80 mL) was treated with the product from Example 1F (1.6 g, 8.47 mmol), DEPBT (3.5 g, 11.71 mmol), and N,N-diisopropylethylamine (6.8 mL, 39.04 mmol) and the mixture was stirred at 25° C. for 5 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The product was purified by chromatography on silica gel eluting with a gradient starting with 0-100% ethyl acetate/dichloromethane, followed by 0-10% methanol in ethyl acetate. The product was then purified by reversed phase chromatography on a C18 column eluting with a gradient starting with 5-100% acetonitrile in water (0.1% TFA). The product was, partitioned between ethyl acetate and 10% Na$_2$CO$_3$ solution. The organic phase was washed brine, dried over MgSO$_4$, filtered and concentrated to give the title compound (1.32 g, 23% yield). $^1$H NMR (300 MHz, DMSO-d$_6$), δ ppm 0.82 (s, 9 H), 0.91 (s, 9 H), 1.25 (m, 1 H), 1.51 (m, 2 H), 2.36 (m, 1 H), 2.46 (s, 3 H), 2.70 (m, 3 H), 2.96 (m, 1 H), 3.09 (m, 1 H), 3.23 (m, 1 H), 3.55 (s, 3 H), 3.65 (m, 1 H), 3.83 (d, J=9.93 Hz, 1 H), 4.14 (m, 3 H), 4.35 (m, 2 H), 4.50 (d, J=7.72 Hz, 1 H), 6.64 (d, J=9.93 Hz, 1 H), 7.09 (m, 12 H), 7.47 (d, J=9.19 Hz, 1 H), 7.71 (m, 2 H).

EXAMPLE 23 methyl(1S)-1-[({(1S,2S,4S)-4-[((2S)-3,3-dimethyl-2-{3-[(6-methyl-2-pyridinyl(methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate

EXAMPLE 23A benzyl(2S)-3-[4-(benzyloxy)phenyl]-2-(dibenzylamino)propanoate

A suspension of L-Tyrosine (20 g, 110.4 mmol) in a mixture of water and ethanol (2:1, respectively, 120 mL) was treated with potassium carbonate (76.3 g, 552.1 mmol) and benzyl chloride (63.5 mL, 551.8 mmol), and the mixture was heated at reflux for 68 hours. The reaction was cooled to 25° C., treated with a mixture of hexanes and THF (1:1, 500 mL), followed by water. The mixture was partitioned and the organic phase was washed two times with a mixture of water and methanol (2:1, respectively) and then with brine, dried over MgSO$_4$, filtered and concentrated. The crude product (53.5 g) was used without further purification.

EXAMPLE 23B (4S)-5-[4-(benzyloxy)phenyl]-4-(dibenzylamino)-3-oxopentanenitrile A solution of sodium bis(trimethylsilyl) amide (1 M in THF, 330 mL) at −45° C., was treated dropwise with acetonitrile (18.8 mL, 360 mmol) and the mixture was stirred for 15 minutes at −45° C. and then cooled to −78 ° C., treated dropwise with a solution of the product from Example 23A (53.5 g, 110 mmol) in THF (150 mL), warmed to −45° C., stirred for 1 hour, treated with solid NH$_4$Cl (40 g), warmed to 5° C., treated with water, warmed to 25° C. and partitioned between ethyl acetate and water. The organic phase was washed with brine and dried over MgSO$_4$, filtered and concentrated. Precipitation from ethanol gave the product (19.0 g, 36% yield).

EXAMPLE 23C (2S)-5-amino-1-[4-(benzyloxy)phenyl]-2-(dibenzylamino)-6-phenyl-4-hexen-3-one A solution containing the product from Example 23B (19.0 g, 40.1 mmol) in THF (48 mL) was treated dropwise with a solution of benzyl magnesium bromide (120 mL, 1 M in ether) at 0° C. The mixture was allowed to warm to 25° C. and was stirred for 16 hours. The reaction was cooled to 0° C. and quenched with 10% citric acid, followed by partitioning between ethyl acetate and water. The organic phase was washed with brine and dried over MgSO$_4$, filtered and concentrated to give the crude product (23.2 g), which was used without further purification.

EXAMPLE 23D (2S,3S,5S)-5-amino-1-[4-(benzyloxy)phenyl]-2-(dibenzylamino)-6-phenyl-3-hexanol (i) A suspension of NaBH$_4$ (6.07 g, 160.4 mmol) in THF (170 mL) at −10° C. was treated with methanesulfonic acid (26.0 mL, 401.0 mmol) dropwise. After complete addition, a solution containing the product from Example 23C (23.2 g, 40.1 mmol) in a mixture of THF (60 mL) and water (6 mL) was added and the mixture was stirred at −10° C. for 18 hours.

(ii) A suspension of NaBH$_4$ (6.07 g, 160.4 mmol) in THF (170 mL) at 0° C. was treated dropwise with trifluoroacetic acid (15.4 mL, 200.5 mmol), stirred at 0° C. for 30 minutes, treated with the solution from step (i), warmed to 25° C., stirred for 3 hours, treated with a mixture of NaBH$_4$ (6.07 g, 160.4 mmol) and trifluoroacetic acid (15.4 mL, 200.5 mmol) prepared as described above, warmed to 25° C. and stirred for 2 hours. The reaction was cooled to 0° C. and quenched cautiously by slow addition of NaOH solution (300 mL, 3 N), followed by partitioning between tert-butyl methyl ether and water. The organic phase was washed with NaOH solution (0.5 N), NH$_4$Cl solution, and brine, dried over MgSO$_4$, filtered and concentrated to give the crude product (22.9 g), which was used without further purification.

EXAMPLE 23E tert-butyl(1S,3S,4S)-1-benzyl-5-[4-(benzyloxy)phenyl]-4-(dibenzylamino)-3-hydroxypentylcarbamate A solution containing the product from Example 23D (22.9 g, 40.1 mmol) intert-butyl methyl ether (200 mL) was treated with 10% K$_2$CO$_3$ (95 mL) and di-tert-butyl dicarbonate (14.0 g, 64.2 mmol), and stirred at 25° C. for 2 hours. The organic phase layer was washed with water and brine, dried over MgSO$_4$, filtered and concentrated. The residue was chromatographed on silica gel eluting with 20% hexanes in chloroform and then with 10% ethyl acetate in chloroform to give the title compound (12.3 g, 46% yield).

EXAMPLE 23F tert-butyl (1S,3S,4S)-4-amino-1-benzyl-3-hydroxy-5-(4-hydroxyphenyl)pentylcarbamate A solution containing the product from Example 23E (12.3 g, 18.4 mmol) in THF (169 mL) was treated with 10% Pd on carbon (2.5 g) and ammonium formate (6.9 g, 109.4 mmol) and the mixture was heated at reflux for 1.5 hours. Additional 10% Pd on carbon (1.25 g) and NH$_4$CO$_2$H (3.45 g) were added and the mixture was heated at reflux for 2.5 hours. The reaction was concentrated and partitioned between chloroform and water and the solution was adjusted to pH 10 with NaHCO$_3$ solution. The organic phase was washed with brine and dried over MgSO$_4$, filtered and concentrated to give the title compound (6.1 g, 82% yield), which was used without further purification.

EXAMPLE 23G benzyl(1S,2S,4S)-4-[(tert-butoxycarbonyl)amino]-2-hydroxy-1-(4-hydroxybenzyl)-5-phenylpentylcarbamate A solution containing the product from Example 23F (6.1 g, 15.2 mmol) in THF (150 mL) was treated with N-(benzyloxycarbonyloxy)succinimide (3.4 g, 13.6 mmol) and N,N-diisopropylethylamine (3.3 mL, 19.0 mmol), stirred at 25° C. for 68 hours and concentrated. The residue was chromatographed on silica gel eluting with 33% ethyl acetate in chloroform and then with 10% methanol in chloroform to give the title compound (5.1 g, 63% yield).

EXAMPLE 23H

4-{(2S,3S,5S)-2-{[(benzyloxy)carbonyl]amino}-5-[(tert-butoxycarbonyl)amino]-3-hydroxy-6-phenylhexyl}phenyl trifluoromethanesulfonate A solution containing the product from Example 23G (5.1 g, 9.6 mmol) in dichloromethane (50 mL) was treated with N-Phenyltrifluoromethanesulfonimide (4.1 g, 11.5 mmol) and DMAP (1.4 g, 11.5 mmol), heated at reflux for 1 hour, cooled to 25° C. and chromatographed on silica gel eluting with 0-50% ethyl acetate/chloroform to give the title compound (4.7 g, 74% yield).

EXAMPLE 23I benzyl(4S,5S)-5-{(2S)-2-[(tert-butoxycarbonyl)amino]-3-phenylpropyl}-2,2-dimethyl-4-{4-[(trifluoroacetyl)oxy]benzyl}-1,3-oxazolidine-3-carboxylate A solution containing the product from Example 23H (4.7 g, 7.1 mmol) in 2,2-dimethoxypropane (70 mL) was treated with p-toluenesulfonic acid monohydrate (0.067 g, 0.35 mmol), and the mixture was stirred at 25° C. for 1 hour. Triethylamine (0.3 mL, 2.15 mmol) was added, and the reaction was partitioned between ethyl acetate and water. The organic phase was washed with brine and dried over MgSO$_4$, filtered and concentrated to give the title compound (4.83 g, 97% yield), which was used without further purification.

EXAMPLE 23J benzyl(1S,2S,4S)-4-[(tert-butoxycarbonyl)amino]-2-hydroxy-5-phenyl-1-[4-(2-pyridinyl)benzyl]pentylcarbamate A solution containing the product from Example 23I (2.65 g, 3.75 mmol) in DMF (20 mL) was treated with LiCl (1.6 g, 37.74 mmol), dichlorobis(triphenylphosphine)palladium(II) (0.5 g, 0.71 mmol), and 2-tri-n-butylstannylpyridine (2.6 mL, 11.30 mmol), heated at 100° C. for 16 hours, cooled and partitioned between ethyl acetate and water. The organic phase was washed with brine and dried over MgSO$_4$, filtered and concentrated. A solution of the residue in THF (30 mL) and aqueous HCl (30 mL, 1 N) was stirred at 50° C. for 48 hours, cooled to 0° C. and adjusted to pH 8 with 3 N NaOH solution. The reaction mixture was partitioned between ethyl acetate and water, and the organic phase was washed with brine and dried over MgSO$_4$, filtered and concentrated. A solution of the residue in THF (30 mL) was treated with triethylamine (1 mL, 13.6 mmol) and di-tert-butyl dicarbonate (0.82 g, 3.75 mmol), stirred at 25° C. for 16 hours, and partitioned between ethyl acetate and saturated NaHCO$_3$. The organic phase was washed with brine and dried over MgSO$_4$, filtered and concentrated. The residue was chromatographed on silica gel eluting with 0-100% ethyl acetate/dichloromethane to give the title compound (0.568 g, 25% yield).

EXAMPLE 23K benzyl(2S)-3-(4-bromophenyl)-2-(dibenzylamino)propanoate

A suspension of L-p-bromophenylalanine (5 g, 20.5 mmol) in a mixture of water and ethanol (2:1, respectively, 20 mL) was treated with potassium carbonate (9.3 g, 67.3 mmol) and benzyl chloride (7.77 mL, 67.5 mmol), heated at reflux for 16 hours, cooled to 25° C. and treated with a mixture of hexanes and THF (1:1, 100 mL), followed by addition of water. The mixture was partitioned and the organic phase was washed two times with a mixture of water and methanol (2:1, respectively) and then with brine, dried over MgSO$_4$, filtered and concentrated. The crude product (11.23 g) was used without further purification.

EXAMPLE 23L benzyl(2S)-2-(dibenzylamino)-3-[4-(2-pyridinyl)phenyl]propanoate A solution containing the product from Example 23K (11.0 g, 20.5 mmol) in DMF (90 mL) was treated with LiCl (8 g, 188.7 mmol), tetrakis(triphenylphosphine)palladium(0) (5 g, 4.3 mmol), and 2-tri-n-butylstannylpyridine (22 g, 59.8 mmol), heated at 80° C. for 16 hours, cooled, filtered and concentrated. The residue was partitioned between ethyl acetate and water, and the organic phase was washed with brine and dried over MgSO$_4$, filtered and concentrated. The residue was purified by chromatography on silica gel eluting with a gradient 0-25% ethyl acetate/hexanes to give the title compound (7.6 g, 72% yield).

EXAMPLE 23M (4S)-4-(dibenzylamino)-3-oxo-5-[4-(2-pyridinyl)phenyl]pentanenitrile A solution of sodium bis(trimethylsilyl) amide (1 M in THF, 50 mL) at −45° C., was treated with a solution of acetonitrile (2.81 mL, 53.4 mmol) in THF (10 mL) dropwise and the mixture was stirred for 15 minutes at −45° C. and then cooled to −78° C., treated dropwise with a solution of the product from Example 23L (7.6 g, 14.8 mmol) in THF (20 mL), stirred at −45° C. for 1 hour, treated with solid NH$_4$Cl (10 g), warmed to 5° C., followed by the addition of water. The mixture was allowed to warm to 25° C. and was partitioned between ethyl acetate and water. The organic phase was washed with brine and dried over MgSO$_4$, filtered and concentrated. The residue was titurated with ethanol and the resulting solid was filtered and dried to give the title compound (4.3 g, 62% yield).

EXAMPLE 23N (2S,4E)-5-amino-2-(dibenzylamino)-6-phenyl-1-[4-(2-pyridinyl)phenyl]-4-hexen-3-one A solution containing the product from Example 23M (4.3 g, 9.65 mmol) in THF (15 mL) was treated dropwise with a solution of benzyl magnesium bromide (30 mL, 1 M in ether) at 0° C., warmed to 25° C., stirred for 16 hours, cooled to 0° C., quenched with 10% citric acid, and partitioned between ethyl acetate and water. The organic phase was washed with brine and dried over MgSO$_4$, filtered and concentrated to give the crude product (6.18 g), which was used without further purification.

EXAMPLE 23O (2S,3S,5S)-5-amino-2-(dibenzylamino)-6-phenyl-1-[4-(2-pyridinyl)phenyl]-3-hexanol (i) A suspension of NaBH$_4$ (1.75 g, 46.3 mmol) in THF (45 mL) at −10° C. was treated with methanesulfonic acid (7.46 mL, 114.9 mmol) dropwise. After complete addition, a solution containing the product from Example 23N (6.18 g, 9.65 mmol) in a mixture of THF (16 mL) and water (1.6 mL) was added and the mixture was stirred at −10° C. for 16 hours.

(ii) A suspension of NaBH$_4$ (1.75 g, 46.3 mmol) in THF (45 mL) at 0° C. was treated with trifluoroacetic acid (4.4 mL, 57.1 mmol) dropwise, stirred at 0° C. for 30 minutes, treated with a solution of step (i), warmed to 25° C., stirred for 16 hours, treated with a suspension of NaBH$_4$ (1.75 g, 46.3 mmol) and trifluoroacetic acid (4.4 mL, 57.1 mmol) prepared as described above at 0° C., warmed to 25° C. and stirred for 16 hours. The reaction mixture was cooled to 0° C. and quenched cautiously by slow addition of NaOH solution (65 mL, 3 N), followed by partitioning between tert-butyl methyl ether and water. The organic phase was washed with NaOH solution (0.5 N), NH$_4$Cl solution, and brine, dried over MgSO$_4$, filtered and concentrated to give the crude product, which was used without further purification.

EXAMPLE 23P tert-butyl(1S,3S,4S)-1-benzyl-4-(dibenzylamino)-3-hydroxy-5-[4-(2-pyridinyl)phenyl]pentylcarbamate A solution containing the product from Example 23O (9.65 mmol) in tert-butyl methyl ether (50 mL) was treated with 10% K$_2$CO$_3$ (23 mL) and ditert-butyl dicarbonate (3.5 g, 16.0 mmol) and the mixture was stirred at 25° C. for 1 hour. The reaction mixture was diluted with tert-butyl methyl ether and the organic phase layer was washed with water and brine, dried over MgSO$_4$, filtered and concentrated. The residue was chromatographed on silica gel eluting with 0-50% ethyl acetate/hexanes to give the title compound (2.7 g, 43% yield).

EXAMPLE 23Q tert-butyl(1S,3S,4S)-4-amino-1-benzyl-3-hydroxy-5-[4-(2-pyridinyl)phenyl]pentylcarbamate Method 1 A solution containing the product from Example 23J (0.568 g, 0.95 mmol) in a mixture of ethyl acetate (5 mL) and methanol (5 mL) was treated with Pd(OH)$_2$ on carbon (0.2 g, 20% Pd by wt.) and HCl solution (0.25 mL, 4N in dioxane), stirred under a hydrogen atmosphere (balloon pressure) for 16 hours at 25° C., filtered through a bed of celite®, rinsed with a mixture of 50% ethyl acetate in methanol, and concentrated. The residue was partitioned between ethyl acetate and saturated NaHCO$_3$. The organic phase was washed with brine and dried over MgSO$_4$, filtered and concentrated to give the title compound (0.442 g), which was used without further purification.

Method 2 A solution containing the product from Example 23P (2.7 g, 4.21 mmol) in a mixture of methanol (20 mL) and ethyl acetate (20 mL) was treated with 20% Pd(OH)$_2$ on carbon (1 g) and an HCl solution in dioxane (2 mL, 4 N), stirred under an atmosphere of hydrogen (balloon pressure) for 16 hours at 25° C., heated to 60° C. for 6 hours. The reaction cooled and filtered through celite®, and concentrated. The residue was partitioned between dichloromethane and half-saturated NaHCO$_3$. The organic phase was dried over MgSO$_4$, filtered and concentrated to give the title compound, which was used without further purification.

EXAMPLE 23R tert-butyl(1S,3S,4S)-1-benzyl-3-hydroxy-4-({(2S)-2-[(methoxycarbonyl)amino]-3,3-dimethylbutanoyl}amino)-5-[4-(2-pyridinyl)phenyl]pentylcarbamate A solution containing the product from Example 23Q (0.442 g, 0.95 mmol) in THF (10 mL) was treated with the product from Example 1F (0.20 g, 1.06 mmol), DEPBT (0.45 g, 1.50 mmol), and N,N-diisopropylethylamine (0.85 mL, 4.88 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-75% ethyl acetate/dichloromethane to give the title compound (0.34 g, 56% yield).

EXAMPLE 23S methyl(1S)-1-[({(1S,2S,4S)-4-amino-2-hydroxy-5-phenyl-1-[4-(2-pyridinyl)benzyl]pentyl}amino)carbonyl]-2,2-dimethylpropylcarbamate A solution containing the product from Example 23R (0.34 g, 0.54 mmol) in dichloromethane (5 mL) was treated with trifluoroacetic acid (5 mL), stirred at 25° C. for 1 hour, and concentrated. The residue was partitioned between dichloromethane and saturated NaHCO$_3$ solution. The organic phase was washed with brine, dried over MgSO$_4$, filtered and concentrated. The crude product (0.251 g) was used without further purification.

EXAMPLE 23T methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate A solution containing the product from Example 23S (0.075 g, 0.14 mmol) in THF (1.5 mL) was treated with the product from Example 10D (0.073 g, 0.21 mmol), DEPBT (0.09 g, 0.30 mmol), and N,N-diisopropylethylamine (0.125 mL, 0.72 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The concentrate was purified by reversed phase chromatography on a C18 column eluting with a gradient starting with 5-100% acetonitrile in water (0.1% TFA). The product was partitioned between dichloromethane and saturated NaHCO$_3$ solution. The organic phase was washed with brine, dried over MgSO$_4$, filtered and concentrated. The residue was then chromatographed on silica gel eluting with 0-100% ethyl acetate/dichloromethane, followed by 0-10% methanol in ethyl acetate, to give the title compound (0.063 g, 54% yield). $^1$H NMR (300 MHz, DMSO-d$_6$), δ ppm 0.83 (s, 9 H), 0.86 (s, 9 H), 1.53 (m, 2 H), 2.39 (m, 1 H), 2.45 (m, 3 H), 2.48 (m, 1 H), 2.66 (d, J=10.66 Hz, 1 H), 2.78 (d, J=6.99 Hz, 2 H), 2.96 (m, 1 H), 3.07 (q, J=8.70 Hz, 1 H), 3.23 (m, 1 H), 3.50 (s, 3 H), 3.62 (m, 1 H), 3.95 (d, J=8.1 Hz, 1H), 3.96 (s, 1 H), 4.19 (m, 2 H), 4.34 (m, 2 H), 4.83 (d, J=5.52 Hz, 1 H), 6.79 (d, J=9.56 Hz, 1 H), 7.05 (m, 6 H), 7.15 (d, J=7.35 Hz, 1 H), 7.30 (m, 3 H), 7.58 (d, J=9.19 Hz, 1 H), 7.68 (t, J=7.72 Hz, 1 H), 7.86 (m, 5 H), 8.63 (d, J=4.78 Hz, 1 H).

EXAMPLE 24 methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate

EXAMPLE 24A tert-butyl(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentylcarbamate A solution containing the product from Example 2A (0.185 g, 0.37 mmol) in THF (3.5 mL) was treated with the product from Example 10D (0.127 g, 0.37 mmol), DEPBT (0.167 g, 0.56 mmol), and N,N-diisopropylethylamine (0.32 mL, 1.84 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The product was purified by reversed phase chromatography on a C18 column eluting with 5-100% acetonitrile in water (0.1% TFA). The product was partitioned between dichloromethane and saturated NaHCO$_3$ solution. The organic phase was washed brine, dried over MgSO$_4$, filtered and concentrated. The residue was then chromatographed on silica gel eluting with 0-10% methanol/chloroform to give the title compound (0.129 g, 46% yield).

EXAMPLE 24B methyl(1S)-1-[({(1S,2S,4S)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate A solution containing the product from Example 24A (0.129 g, 0.17 mmol) in dichloromethane (0.8 mL) was treated with trifluoroacetic acid (0.8 mL), stirred at 25° C. for 1 hour and concentrated. A solution of the residue (0.17 mmol) in THF (1.8 mL) was treated with the product from Example 1F (0.033g, 0.17 mmol), DEPBT (0.077 g, 0.26 mmol), and N,N-diisopropylethylamine (0.30 mL, 1.72 mmol), stirred at 25° C. for 18 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-5% methanol/ethyl acetate to give the title compound (0.057 g, 40% yield). $^1$H NMR (300 MHz, DMSO-d$_6$), δ ppm 0.85 (d, J=1.10 Hz, 18 H), 1.55 (m, 2 H), 2.43 (m, 5 H), 2.72 (m, 4 H), 2.95 (m, 1 H), 3.19 (m, 1 H), 3.58 (m, 4 H), 3.93 (d, J=9.56 Hz, 1 H), 3.99 (s, 1 H), 4.28 (m, 4 H), 4.84 (d, J=5.52 Hz, 1 H), 6.82 (d, J=9.93 Hz, 1 H), 6.97 (d, J=7.72 Hz, 1 H), 7.16 (m, 8 H), 7.29 (m, 1 H), 7.52 (d, J=8.82 Hz, 1 H), 7.61 (t, J=7.72 Hz, 1 H), 7.79 (m, 4 H), 7.95 (d, J=8.82 Hz, 1 H), 8.61 (d, J=4.78 Hz, 1 H).

EXAMPLE 25 methyl(1S,4S,5S,7S,10S)-7-benzyl-1,10-ditert-butyl-5-hydroxy-2,9,12-trioxo-4-[4-(2-pyridinyl)benzyl]-13-oxa-3,8,11-triazatetradec-1-ylcarbamate A solution of the product from Example 23S (0.025 g, 0.047 mmol) in THF (0.5 mL) was treated with the product from Example 1F (0.010g, 0.053 mmol), DEPBT (0.020 g, 0.067 mmol), and N,N-diisopropylethylamine (0.040 mL, 0.229 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give the title compound (0.015 g, 45% yield). $^1$H NMR (300 MHz, DMSO-d$_6$), δ ppm 0.77 (s, 9 H), 0.83 (s, 9 H), 1.48 (m, 2 H), 2.74 (m, 3 H), 3.50 (s, 3 H), 3.54 (s, 3 H), 3.64 (m, 1 H), 3.79 (d, J=9.19 Hz, 1 H), 3.93 (d, J=956 Hz, 1 H), 4.09 (m, 2 H), 4.85 (d, J=5.88 Hz, 1 H), 6.60 (d, J=9.93 Hz, 1 H), 6.75 (d, J=9.93 Hz, 1 H), 7.11 (m, 5 H), 7.31 (m, 3 H), 7.59 (d, J=9.19 Hz, 1 H), 7.74 (d, J=8.82 Hz, 1 H), 7.86 (m, 4 H), 8.63 (d, J=4.41 Hz, 1 H).

EXAMPLE 26

1:1 mixture of (3R,3aS,6aR) and (3S,3aR,6aS)-hexahydrofuro[2,3-b]furan-3-yl(1S,3S,4S)-1-benzyl-3-hydroxy-4-({(2S)-2-[(methoxycarbonyl)amino]-3,3-dimethylbutanoyl}amino)-5-[4-(2-pyridinyl)phenyl]pentylcarbamate

EXAMPLE 26A

1:1 mixture of (3R,3aS,6aR)-hexahydrofuro[2,3-b]furan-3-yl 4-nitrophenyl carbonate and (3S,3aR,6aS)-hexahydrofuro[2,3-b]furan-3-yl 4-nitrophenyl carbonate A solution of (3S,3aR,6aS)- and (3R,3aS,6aR)-3-hydroxy-4H-hexahydrofuro[2,3-b]furan (prepared as described in: Gosh, A. K.; Kincaid, J. F.; Walters, D. E.; Chen, Y.; Chaudhuri, N. C.; Thompson, W. J.; Culberson, C.; Fitzgerald, P. M. D.; Lee. H. Y.; McKee, S. P.; Munson, P. M.; Duong, T. T.; Darke, P. L.; Zugay, J. A.; Schleif, W. A.; Axel, M. G.; Lin, J.; Huff, J. R. *Journal of Medicinal Chemistry* 1996, 39, 3278-3290.) (1.5 g, 11.5 mmol) in dichloromethane (40 mL) at 0° C. was treated with NMM (1.9 mL, 17.3 mmol) and 4-nitrophenyl chloroformate (2.9 g, 14.4 mmol), stirred for 16 hours at 0° C. and concentrated. The residue was chromatographed on silica gel, eluting with 25% ethyl acetate in hexanes to give the title compound (2.91 g, 86% yield).

EXAMPLE 26B (3R)-hexahydrofuro[2,3-b]furan-3-yl (1S,3S,4S)-1-benzyl-3-hydroxy-4-({(2S)-2-[(methoxycarbonyl)amino]-3,3-dimethylbutanoyl}amino)-5-[4-(2-pyridinyl)phenyl]pentylcarbamate and (3R,3aR,6aS)-hexahydrofuro[2,3-b]furan-3-yl (1S,3S,4S)-1-benzyl-3-hydroxy-4-({(2S)-2-[(methoxycarbonyl)amino]-3,3-dimethylbutanoyl}amino)-5-[4-(2-pyridinyl)phenyl]pentylcarbamate A solution of the product from Example 23S (0.05 g, 0.094 mmol) in THF (0.5 mL) was treated with triethylamine (0.025 mL, 0.179 mmol) and the product from Example 26A (0.040 g, 0.135 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane to give the title compound (0.050 g, 77% yield). $^1$H NMR (300 MHz, DMSO-$d_6$), δ ppm 0.86 (d, J=4.78 Hz, 9 H), 1.28 (m, 2 H), 1.56 (m, 3 H), 2.62 (m, 2 H), 2.79 (m, 3 H), 3.41 (m, 1 H), 3.51 (s, 3 H), 3.58 (m, 1 H), 3.72 (m, 3 H), 3.93 (m, 1 H), 4.18 (m, 1 H), 4.80 (m, 2 H), 5.47 (d, J=4.78 Hz, 1 H), 6.84 (t, J=9.93 Hz, 1 H), 7.16 (m, 6 H), 7.31 (d, J=8.46 Hz, 3 H), 7.59 (d, J=9.19 Hz, 1 H), 7.89 (m, 4 H), 8.63 (d, J=4.78 Hz, 1 H).

EXAMPLE 27

1:1 mixture of (3R,3aS,6aR)-hexahydrofuro[2,3-b]furan-3-yl (1S,2S,4S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate and (3R,3aR,6aS)-hexahydrofuro[2,3-b]furan-3-yl (1S,2S,4S)-1-benzyl-2-hydroxy-4-({(2S)-2-[(methoxycarbonyl)amino]-3,3-dimethylbutanoyl}amino)-5-(2-pyridinyl)phenyl]pentylcarbamate A solution of the product from Example 2C (0.025 g, 0.047 mmol) in THF (0.25 mL) was treated with triethylamine (0.013 mL, 0.093 mmol) and the product from Example 26A (0.020 g, 0.067 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane to give the title compound (0.024 g, 74% yield). $^1$H NMR (300 MHz, DMSO-$d_6$), δ ppm 0.84 (d, J=9.19 Hz, 9 H), 1.44 (m, 5 H), 2.73 (m, 5 H), 3.49 (m, 3 H), 3.73 (m, 6 H), 4.19 (m, 1 H), 4.68 (dd, J=17.65, 6.25 Hz, 1 H), 4.82 (m, 1 H), 5.49 (m, 1 H), 6.70 (t, J=9.74 Hz, 1 H), 6.86 (t, J=8.82 Hz, 1 H), 7.19 (m, 7 H), 7.31 (m, 1 H), 7.88 (m, 5 H), 8.63 (d, J=4.78 Hz, 1 H).

EXAMPLE 28 methyl(1S)-1-[({(1S,2S,4S)-2-hydroxy-4-[((2S)-3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 23S (0.025 g, 0.047 mmol) in THF (0.5 mL) was treated with the product from Example 7B (0.025 g, 0.060 mmol), DEPBT (0.025 g, 0.084 mmol), and N,N-diisopropylethylamine (0.040 mL, 0.230 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by eluting with 0-10% methanol in ethyl acetate to give the title compound (0.021 g, 54% yield). $^1$H NMR (300 MHz, DMSO-$d_6$), δ ppm 0.60 (d, J=6.62 Hz, 3 H), 0.73 (t, J=7.17 Hz, 3 H), 0.87 (m, 10 H), 1.27 (m, 1 H), 1.54 (m, 2 H), 1.75 (m, 1 H), 2.43 (m, 4 H), 2.66 (m, 1 H), 2.77 (d, J=6.99 Hz, 2 H), 2.91 (m, 1 H), 3.12 (m, 3 H), 3.51 (s, 3 H), 3.59 (m, 1 H), 3.85 (d, J=11.03 Hz, 1 H), 3.94 (d, J=9.56 Hz, 1 H), 4.14 (m, 2 H), 4.33 (s, 2 H), 4.81 (d, J=5.15 Hz, 1 H), 6.80 (d, J=9.56 Hz, 1 H), 7.07 (m, 7 H), 7.30 (d, J=7.72 Hz, 3 H), 7.58 (d, J=8.82 Hz, 1 H), 7.65 (t, J=7.54 Hz, 1 H), 7.87 (m, 5 H), 8.63 (d, J=4.04 Hz, 1 H).

EXAMPLE 29 methyl(1S)-1-[({(1R,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 1H (0.176 g, 0.33 mmol) in THF (3.3 mL) was treated with the product from Example 10D (0.113 g, 0.33 mmol), DEPBT (0.148 g, 0.49 mmol), and N,N-diisopropylethylamine (0.29 mL, 1.66 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with a gradient starting with 5-100% acetonitrile in water (0.1% TFA). The product was partitioned between ethyl acetate and saturated $NaHCO_3$, and the organic phase was washed with brine and dried over $MgSO_4$, filtered and concentrated to give the title compound (0.176 g, 65% Meld). $^1$H NMR (300 MHz, DMSO-$d_6$), δ ppm 0.80 (s, 9 H), 0.88 (s, 9 H), 1.29 (m, 2 H), 1.53 (m, 1 H), 2.45 (s, 3 H), 2.66 (m, 3 H), 2.83 (dd, J=13.79, 6.07 Hz, 1 H), 3.03 (m, 2 H), 3.23 (m, 1 H), 3.53 (m, 4 H), 3.84 (d, J=9.56 Hz, 1 H), 4.01 (m, 2 H), 4.16 (m, 1 H), 4.34 (m, 2 H), 4.44 (d, J=6.99 Hz, 1 H), 6.88 (d, J=9.56 Hz, 1 H), 7.09 (m, 7 H), 7.24 (d, J=8.09 Hz, 2 H), 7.32 (m, 1 H), 7.54 (d, J=9.56 Hz, 1 H), 7.67 (t, J=7.72 Hz, 1 H), 7.89 (m, 5 H), 8.64 (d, J=4.04 Hz, 1 H).

EXAMPLE 30 methyl(1R,4S,5S,7S,10S)-4-benzyl-10-tert-butyl-5-hydroxy-1-[1-methyl-1-(methylsulfanyl)ethyl]-2,9,12-trioxo-7-[4-(2-pyridinyl)benzyl]-13-oxa-3,8,11-triazatetradec-1-ylcarbamate

EXAMPLE 30A (2R)-2-[(methoxycarbonyl)amino]-3-methyl-3-(methylsulfanyl)butanoic acid A solution of L-penicillamine (0.5 g, 3.35 mmol) in methanol (3.3 mL) at 0° C. was treated with aqueous NaOH solution (3.7 mL, 1 N) and methyl iodide (0.23 mL, 3.69 mmol), stirred at 0° C. for 16 hours, treated with additional aqueous NaOH solution (3.5 mL, 3 N) at 0° C., followed by methyl chloroformate (0.5 mL, 6.47 mmol), warmed to 25° C. and stirred for 3 hours, and partitioned between ethyl acetate and water. The organic phase was washed with brine and dried over MgSO$_4$, filtered and concentrated to give the title compound (0.428 g, 58% yield), which was used without further purification.

EXAMPLE 30B methyl(1R,4S,5S,7S,10S)-4-benzyl-10-tert-butyl-5-hydroxy-1-[1-methyl-1-(methylsulfanyl)ethyl]-2,9,12-trioxo-7-[4-(2-pyridinyl)benzyl]-13-oxa-3,8,11-triazatetradec-1-ylcarbamate A solution containing the product from Example 2C (0.10 g, 0.18 mmol) in THF (2 mL) was treated with the product from Example 30A (0.05 g, 0.226 mmol), DEPBT (0.085 g, 0.28 mmol), and N,N-diisopropylethylamine (0.165 mL, 0.947 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give the title compound (0.052 g, 38% yield). $^1$H NMR (300 MHz, DMSO-d$_6$), δ ppm 0.80 (s, 9 H), 1.10 (s, 3 H), 1.21 (s, 3 H), 1.54 (m, 2 H), 1.98 (s, 3 H), 2.57 (m, 1 H), 2.75 (m, 3 H), 3.49 (s, 3 H), 3.56 (s, 3 H), 3.64 (m, 1 H), 3.82 (d, J=9.56 Hz, 1 H), 4.17 (m, 3 H), 4.83 (d, J=5.88 Hz, 1 H), 6.61 (d, J=9.56 Hz, 1 H), 6.90 (d, J=9.56 Hz, 1 H), 7.15 (m, 7 H), 7.31 (m, 1 H), 7.84 (m, 6 H), 8.63 (d, J=4.78 Hz, 1 H).

EXAMPLE 31 methyl(1R,4S,5S,7S,10S)-4-benzyl-10-tert-butyl-5-hydroxy-1-[1-methyl-1-(methylsulfonyl)ethyl]-2,9,12-trioxo-7-[4-(2-pyridinyl)benzyl]-13-oxa-3,8,11-triazatetradec-1-ylcarbamate A solution of the product from Example 30B (0.015 g, 0.020 mmol) in a mixture of acetone and water (3:1, respectively, 0.20 mL) and THF (0.10 mL) was treated with 4-methylmorpholine N-oxide (0.014 g, 0.120 mmol) and aqueous OSO$_4$ solution (0.033 mL, 4%), stirred at 25° C. for 16 hours, and partitioned between ethyl acetate and water. The organic phase was washed with brine and dried over MgSO$_4$, filtered and concentrated. The residue was chromatographed on silica gel eluting with 0-100% ethyl acetate/dichloromethane to give the title compound (0.013 g, 83% yield). H NMR (300 MHz, DMSO-d$_6$), δ ppm 0.82 (s, 9 H), 1.14 (s, 3 H), 1.26 (s, 3 H), 1.50 (m, 2 H), 2.57 (m, 1 H), 2.75 (m, 3 H), 2.88 (s, 3 H), 3.50 (s, 3 H), 3.57 (s, 3 H), 3.69 (m, 1 H), 3.83 (d, J=10.30 Hz, 1 H), 4.03 (m, 1 H), 4.16 (m, 1 H), 4.69 (d, J=10.30 Hz, 1 H), 4.89 (d, J=5.52 Hz, 1 H), 6.64 (d, J=9.56 Hz, 1 H), 7.16 (m, 8 H), 7.31 (m, 1 H), 7.85 (m, 5 H), 8.01 (d, J=9.19 Hz, 1 H), 8.63 (d, J=4.41 Hz, 1 H).

EXAMPLE 32 methyl(1R,4S,6S,7S,10S)-4-benzyl-10-tert-butyl-6-hydroxy-1-[1-methyl-1-(methylsulfanyl)ethyl]-2,9,12-trioxo-7-[4-(2-pyridinyl)benzyl]-13-oxa-3,8,11-triazatetradec-1-ylcarbamate A solution containing the product from Example 23S (0.025 g, 0.047 mmol) in THF (0.5 mL) was treated with the product from Example 30A (0.0125 g, 0.056 mmol), DEPBT (0.021 g, 0.070 mmol), and N,N-diisopropylethylamine (0.040 mL, 0.230 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give the title compound (0.024 g, 69% yield). $^1$H NMR (300 MHz, DMSO-d$_6$), δ ppm 0.84 (s, 9 H), 1.08 (s, 3 H), 1.11 (s, 3 H), 1.50 (m, 2 H), 1.93 (s, 3 H), 2.45 (m, 1 H), 2.75 (m, 3 H), 3.51 (s, 3 H), 3.56 (s, 3 H), 3.67 (m, 1 H), 394 (d, J=9.5 Hz, 1 H), 4.10 (d, J=10.30 Hz, 3 H), 4.84 (d, J=5.88 Hz, 1 H), 6.79 (dd, J=15.81, 9.93 Hz, 2 H), 7.09 (m, 5 H), 7.30 (d, J=7.35 Hz, 3 H), 7.57 (s, 1 H), 7.87 (m, 5 H), 8.63 (d, J=4.41 Hz, 1 H).

EXAMPLE 33 methyl(1R,4S,6S,7S,10S)-4-benzyl-10-tert-butyl-6-hydroxy-1-[1-methyl-1-(methylsulfonyl)ethyl]-2,9,12-trioxo-7-[4-(2-pyridinyl)benzyl]-13-oxa-3,8,11-triazatetradec-1-ylcarbamate A solution of the product from Example 32 (0.015 g, 0.020 mmol) in a mixture of acetone and water (3:1, respectively, 0.20 mL) and THF (0.15 mL) was treated with 4-methylmorpholine N-oxide (0.014 g, 0.120 mmol) and aqueous OSO$_4$ solution (0.030 mL, 4%), stirred at 25° C. for 16 hours, and partitioned between ethyl acetate and water. The organic phase was washed with brine and dried over MgSO$_4$, filtered and concentrated. The residue was chromatographed on silica gel eluting with 0-100% ethyl acetate/dichloromethane, followed by 0-5% methanol in ethyl acetate, to give the title compound (0.012 g, 77% yield). $^1$H NMR (300 MHz, DMSO-d$_6$), δ ppm 0.85 (s, 9 H), 1.05 (s, 3 H), 1.25 (s, 3 H), 1.50 (m, 2 H), 2.79 (m, 8 H), 3.51 (s, 3 H), 3.56 (s, 3 H), 3.95 (d, J=9.19 Hz, 1 H), 4.08 (m, 2 H), 4.53 (d, J=10.30 Hz, 1 H), 4.88 (d, J=5.88 Hz, 1 H), 6.79 (d, J=9.93 Hz, 1 H), 7.11 (m, 6 H), 7.31 (m, 3 H), 7.62 (d, J=9.56 Hz, 1 H), 7.86 (m, 4 H), 8.17 (d, J=8.82 Hz, 1 H), 8.63 (d, J=4.41 Hz, 1 H).

EXAMPLE 34 methyl(1S)-1-[({(1S,3S,4S)-4-{[(2S)-3,3-dimethyl-2-(2-oxo-3-{[2-(3-pyridinyl)-1,3-thiazol-4-yl]methyl}-1-imidazolidinyl)butanoyl]amino}-3-hydroxy-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 19D (0.030 g, 0.061 mmol), DEPBT (0.020 g, 0.067 mmol), and N,N-diisopropylethylamine (0.040 mL, 0.230 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.029 g, 70% yield). $^1$H NMR (300 MHz, DMSO-d$_6$), δ ppm 0.83 (s, 9 H), 0.89 (s, 9 H), 1.54 (m, 2 H), 2.34 (m, 1 H), 2.63 (m, 2 H), 2.79 (m, 1 H), 3.16 (m, 4 H), 3.50 (s, 3 H), 3.65 (m, 1 H), 3.85 (d, J=9.93 Hz, 1 H), 4.14 (m, 3 H), 4.50 (m, 3 H), 6.63 (d, J=9.56 Hz, 1 H), 6.98 (m, 1 H), 7.06 (m, 4 H), 7.22 (d, J=8.09 Hz, 2

H), 7.31 (m, 1 H), 7.52 (m, 2 H), 7.61 (s, 1 H), 7.87 (m, 5 H), 8.31 (m, 1 H), 8.65 (m, 2 H), 9.14 (d, J=1.84 Hz, 1 H).

EXAMPLE 35 methyl(1S)-1-[({(1S,2S,4S)-4-{[(2S)-3,3-dimethyl-2-(2-oxo-3-{[2-(3-pyridinyl)-1,3-thiazol-4-yl]methyl}-1-imidazolidinyl)butanoyl]amino}-2-hydroxy-5-phenyl-1-[4-(2-pyridinyl)benzyl]pentyl}amino)carbonyl]-2,2-dimethylpropylcarbamate A solution containing the product from Example 23S (0.025 g, 0.047 mmol) in THF (0.5 mL) was treated with the product from Example 19D (0.030 g, 0.061 mmol), DEPBT (0.020 g, 0.067 mmol), and N,N-diisopropylethylamine (0.040 mL, 0.230 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 0-5% methanol in ethyl acetate, to give the title compound (0.021 g, 50% yield). $^1H$ NMR (300 MHz, DMSO-$d_6$), δ ppm 0.82 (s, 9 H), 0.86 (s, 9 H), 1.53 (m, 2 H), 2.40 (m, 1 H), 2.64 (d, J=13.97 Hz, 1 H), 2.77 (d, J=6.62 Hz, 2 H), 3.15 (m, 4 H), 3.51 (s, 3 H), 3.62 (m, 1 H), 3.96 (m, 2 H), 4.18 (m, 2 H), 4.47 (m, 2 H), 4.82 (d, J=5.52 Hz, 1 H), 6.79 (d, J=9.56 Hz, 1 H), 6.95 (m, 1 H), 7.03 (m, 4 H), 7.30 (m, 3 H), 7.54 (m, 3 H), 7.87 (m, 5 H), 8.30 (m, 1 H), 8.65 (m, 2 H), 9.14 (d, J=1.47 Hz, 1 H).

EXAMPLE 36 methyl(1S)-1-[({(1S,3S,4S)-3-hydroxy-4-[((2S)-3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate

EXAMPLE 36A tert-butyl(2S,3S)-2-[(2-ethoxy-2-oxoethyl)amino]-3-methylpentanoate A solution of L-iso-leucine tert-butyl ester hydrochloride (5 g, 22.34 mmol) in DMF (30 mL) was treated with triethylamine (3.1 mL, 22.34 mmol), stirred for 1 hour at 25° C., filtered to remove solid salts, and the filtrate was treated with triethylamine (9.3 mL, 67.0 mmol) and ethyl bromoacetate (9.9 mL, 67.0 mmol), and the reaction was stirred for 3 hours at 25° C. The reaction mixture was partitioned between ethyl acetate and water, and the organic phase was washed with brine and dried over $MgSO_4$, filtered and concentrated to give the title compound (5.7 g, 93% yield), which was used without further purification.

EXAMPLE 36B tert-butyl(2S,3S)-2-[(aminocarbonyl)(2-ethoxy-2-oxoethyl)amino]-3-methylpentanoate A solution containing the product from Example 36A (5.7 g, 20.9 mmol) in dichloromethane (60 mL) at 0° C. was treated with chlorosulfonyl isocyanate (2.7 mL, 31.0 mmol) and the mixture was stirred at 0° C. for 16 hours. Water (60 mL) was added to the cold reaction and the mixture was warmed to 25° C. and stirred for 4 hours. The reaction was partitioned between dichloromethane and water, and the organic phase was washed with brine and dried over $MgSO_4$, filtered and concentrated to give the title compound (6.83 g), which was used without further purification.

EXAMPLE 36C tert-butyl(2S,3S)-2-(2,4dioxo-1-imidazolidinyl)-3-methylpentanoate A solution containing the product from Example 36B (6.8 g, 20.9 mmol) in methanol (30 mL) was treated with triethylamine (5.6 mL, 40.2 mmol), stirred at 50° C. for 2 hours, and concentrated. The residue was chromatographed on silica gel eluting with 0-30% ethyl acetate/dichloromethane to give the title compound (2.53 g, 47% yield).

EXAMPLE 36D tert-butyl(2S,3S)-3-methyl-2-{3-[(6-methyl-2-pyridinyl)methyl]-2,4dioxo-1-imidazolidinyl}pentanoate A solution containing the product from Example 36C (0.107 g, 0.396 mmol) in dichloromethane (2 mL) at 0° C. was treated with 6-methyl-2-pyridinemethanol (0.053 g, 0.435 mmol), triphenylphosphine (0.135 g, 0.515 mmol), followed by diethyl azodicarboxylate (0.080 mL, 0.515 mmol), stirred at 25° C. for 16 hours. Water (2 mL) was added and the reaction was stirred for 2 hours at 25° C. The reaction mixture was partitioned between dichloromethane and water, and the organic phase was washed with brine and dried over $MgSO_4$, filtered and concentrated. The residue was chromatographed on silica gel eluting with 0-30% ethyl acetate/dichloromethane to give the title compound (0.154 g, 94% yield).

EXAMPLE 36E (2S,3S)-3-methyl-2-{3-[(6-methyl-2-pyridinyl)methyl]-2,4-dioxo-1-imidazolidinyl}pentanoic acid A solution containing the product from Example 36D (0.154 g, 0.410 mmol) in dichloromethane (3 mL) was treated with trifluoracetic acid (3 mL), stirred at 25° C. for 16 hours and concentrated. The residue was purified by reversed phase chromatography on a C18 column eluting with a gradient starting with 5-100% acetonitrile in water (0.1% TFA) to give the title compound (0.153 g) as the trifluoroacetic acid salt.

EXAMPLE 36F methyl(1S)-1-[({(1S,3S,4S)-3-hydroxy-4-[((2S)-3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 36E (0.020 g, 0.061 mmol), DEPBT (0.021 g, 0.071 mmol), and N,N-diisopropylethylamine (0.041 mL, 0.235 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 0-10% methanol in ethyl acetate, to give the title compound (0.026 g, 68% yield). $^1$H NMR (300 MHz, DMSO-d$_6$), δ ppm 0.76 (m, 18 H), 1.16 (m, 1 H), 1.29 (m, 1 H), 1.52 (m, 1 H), 1.76 (s, 1 H), 2.39 (s, 3 H), 2.68 (m, 4 H), 3.20 (m, 2 H), 3.50 (s, 3 H), 3.83 (m, 2 H), 4.13 (m, 2 H), 4.67 (m, 2 H), 6.66 (d, J=9.56 Hz, 1 H), 7.07 (m, 7 H), 7.22 (d, J=8.09 Hz, 2 H), 7.31 (m, 1 H), 7.66 (t, J=7.72 Hz, 1 H), 7.86 (m, 6 H), 8.63 (d, J=4.04 Hz, 1 H).

EXAMPLE 37 methyl(1S)-1-[({(1S,2S,4S)-2-hydroxy-4-[((2S)-3-methyl-2-{3-[(6-methyl-2-pyridinyl)methyl]-2,4-dioxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 23S (0.025 g, 0.047 mmol) in THF (0.5 mL) was treated with the product from Example 36E (0.020 g, 0.061 mmol), DEPBT (0.021 g, 0.071 mmol), and N,N-diisopropylethylamine (0.041 mL, 0.235 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-10% methanol in ethyl acetate, to give the title compound (0.025 g, 64% yield). $^1$H NMR (300 MHz, DMSO-d$_6$), δ ppm 0.57 (d, J=6.62 Hz, 3 H), 0.71 (t, J=7.17 Hz, 3 H), 0.82 (m, 12 H), 1.26 (m, 1 H), 1.54 (m, 2 H), 1.73 (m, 1 H), 2.33 (m, 4 H), 2.76 (m, 3 H), 3.51 (s, 3 H), 3.59 (m, 1 H), 3.82 (d, J=18.38 Hz, 1 H), 4.01 (m, 2 H), 4.18 (s, 1 H), 4.67 (m, 2 H), 4.87 (d, J=5.15 Hz, 1 H), 6.82 (d, J=9.56 Hz, 1 H), 7.02 (m, 6 H), 7.12 (d, J=7.72 Hz, 1 H), 7.30 (d, J=8.46 Hz, 3 H), 7.64 (m, 2 H), 7.87 (m, 4 H), 8.09 (d, J=9.19 Hz, 1 H), 8.63 (d, J=4.04 Hz, 1 H).

EXAMPLE 38 methyl(1S)-1-[({(1S,3S,4S)-4-{[(2,6-dimethylphenoxy)acetyl]amino}-3-hydroxy-5-phenyl-1-[4-(2-pyridinyl)benzyl]pentyl}amino)carbonyl]-2,2-dimethylpropylcarbamate A solution containing the product from Example 2C (0.020 g, 0.038 mmol) in THF (0.4 mL) was treated with 2,6-dimethylphenoxy acetic acid (U.S. Pat. No. 5,914,332, see Example 1H) (0.008 g, 0.044 mmol), DEPBT (0.017 g, 0.057 mmol), and N,N-diisopropylethylamine (0.030 mL, 0.172 mmol), stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-80% ethyl acetate/chloroform to give the title compound (0.021 g, 77% yield). $^1$H NMR (300 MHz, DMSO-d$_6$), δ ppm 0.83 (s, 9 H), 1.52 (m, 2 H), 2.08 (s, 6 H), 2.72 (m, 2 H), 2.80 (m, 2 H), 3.51 (s, 3 H), 3.72 (m, 1 H), 3.85 (d, J=9.19 Hz, 1 H), 4.01 (s, 2 H), 4.22 (m, 2 H), 5.05 (d, J=5.88 Hz, 1 H), 6.71 (d, J=9.93 Hz, 1 H), 6.92 (m, 3 H), 7.26 (m, 8 H), 7.45 (d, J=9.56 Hz, 1 H), 7.85 (m, 5 H), 8.62 (d, J=4.78 Hz, 1 H).

EXAMPLE 39 methyl(1S)-1-[({(1S,2S,4S)-4-{[(2,6-dimethylphenoxy)acetyl]amino}-2-hydroxy-5-phenyl-1-[4-(2-pyridinyl)benzyl]pentyl}amino)carbonyl]-2,2-dimethylpropylcarbamate A solution containing the product from Example 23S (0.020 g, 0.038 mmol) in THF (0.4 mL) was treated with 2,6-dimethylphenoxy acetic acid (U.S. Pat. No. 5,914,332, see Example 1H) (0.008 g, 0.044 mmol), DEPBT (0.017 g, 0.057 mmol), and N,N-diisopropylethylamine (0.030 mL, 0.172 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-80% ethyl acetate/chloroform to give the title compound (0.016 g, 61% yield). $^1$H NMR (300 MHz, DMSO-d$_6$), δ ppm 0.86 (s, 9 H), 1.63 (m, 2 H), 2.07 (s, 6 H), 2.78 (m, 4 H), 3.51 (s, 3 H), 3.62 (m, 1 H), 3.94 (m, 3 H), 4.25 (m, 2 H), 4.87 (d, J=5.15 Hz, 1 H), 6.89 (m, 4 H), 7.19 (m, 5 H), 7.31 (m, 3 H), 7.61 (d, *8.46 Hz, 1 H), 7.84 (m, 5 H), 8.62 (d, J=4.41 Hz, 1 H).

EXAMPLE 40 methyl(1S)-1-[({(1S,3S,4S)-3-hydroxy-4-({(2S)-2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate

EXAMPLE 40A imidazo[1,5-a]pyridine-3-carbaldehyde

To imidazo[1,5-a]pyridine (2.337 g, 19.78 mmol) in tetrahydrofuran (40 mL) was added n-butyl lithium (2.5 M in hexane, 15.76 mL, 39.4 mmol) at −40° C. The mixture was stirred at −40° C. for 3.5 hours, followed by the addition of dimethylformamide (3.1 mL, 40 mmol). The reaction mixture was stirred at 25° C. overnight and quenched with water. The mixture was then partitioned between dichloromethane (80 mL) and water (15 mL). The organic phase layer was dried with anhydrous sodium sulfate, filtered and concentrated in vacuo. The crude material was purified by chromatography eluting with 0-50% ethyl acetate/dichloromethane to give the title compound (1.78 g, 62% yield).

EXAMPLE 40B tert-butyl (2S)-2-[3-(imidazo[1,5-a]pyridin-3-ylmethyl)-2-oxo-1-imidazolidinyl]-3,3-dimethylbutanoate A solution of the product from Example 40A (1.809 g, 12.38 mmol) and the product from Example 6F (2.85 g, 12.38 mmol) in ethanol (35 mL) and benzene (35 mL) was treated with molecular sieves (3 Å, 1.5 g). The mixture was stirred at 60° C. overnight and cooled to 25° C. To the reaction mixture was added sodium borohydride (1.407 g, 37.19 mmol) and then stirred for 3 hours at 25° C. The reaction mixture was quenched with an aqueous solution of saturated ammonium chloride at 0° C. The mixture was partitioned between water (50 mL) and ethyl acetate (100 mL). The organic phase layer was separated and washed with water and brine, dried with anhydrous sodium sulfate, filtered and concentrated. The residue was treated with 1,2-dichloroethane (247 mL), N,N-diisopropylethylamine (2.2 mL, 12.63 mmol) and N,N'-disuccinimidyl carbonate (3.823 g, 14.92 mmol). The solution was stirred at 25° C. overnight and then washed with a solution of 10% sodium carbonate (3×50 mL) and water (50 mL). The organic phase layer was dried with anhydrous sodium sulfate, filtered and concentrated in vacuo The crude material was purified by chromatography eluting with 0-100% ethyl acetate/dichloromethane to give the title compound (3 g, 63% yield).

EXAMPLE 40C (2S)-2-[3-(imidazo[1,5-a]pyridin-3-ylmethyl)-2-oxo-1-imidazolidinyl]-3,3-dimethylbutanoic acid A solution containing the product from Example 40B (0.039 g, 0.096 mmol) in dichloromethane (0.5 mL) was treated with trifluoracetic acid (0.5 mL), and the mixture was stirred at 25° C. for 2 hours. The solvent was concentrated and azeotroped with toluene to give the title compound as the trifluoroacetic acid salt, which was used without further purification.

EXAMPLE 40D methyl(1S)-1-[({(1S,3S,4S)-3-hydroxy-4-({(2S)-2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate A solution containing the product from Example 2C (0.021 g, 0.048 mmol) in THF (0.5 mL) was treated with the product from Example 40C (0.020 g; 0.061 mmol), DEPBT (0.021 g, 0.071 mmol), and N,N-diisopropylethylamine (0.042 mL, 0.235 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The reaction was partitioned between ethyl acetate and saturated NaHCO$_3$, and the organic phase was washed with brine and dried over MgSO$_4$, filtered and concentrated to give the title compound (0.018 g, 42% yield). $^1$H NMR (300 MHz, DMSO-d$_6$), δ ppm 0.83 (s, 9 H), 0.86 (s, 9 H), 1.26 (m, 1 H), 1.53 (m, 2 H), 2.58 (m, 3 H), 2.77 (m, 2 H), 3.03 (m, 2 H), 3.50 (s, 3 H), 3.65 (m, 1 H), 3.84 (d, J=9.93 Hz, 1 H), 4.13 (m, 3 H), 4.52 (m, 2 H), 4.92 (d, 15.44 Hz, 1 H), 6.64 (t, J=7.54 Hz, 3 H), 6.71 (m, 1 H), 6.83 (m, 4 H), 7.22 (d, J=8.09 Hz, 2 H), 7.31 (m, 1 H), 7.41 (m, 2 H), 7.59 (d, J=9.19 Hz, 1 H), 7.86 (m, 5 H), 8.35 (d, J=7.35 Hz, 1 H), 8.63 (d, J=4.78 Hz, 1 H).

EXAMPLE 41 methyl(1S)-1-[({(1S,2S,4S)-2-hydroxy-4-({(2S)-2-[3-(imidazo[1,5-a]pyridin-3-ylmethyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate A solution containing the product from Example 23S (0.021 g, 0.048 mmol) in THF (0.5 mL) was treated with the product from Example 40C (0.020 g, 0.061 mmol), DEPBT (0.021 g, 0.071 mmol), and N,N-diisopropylethylamine (0.042 mL, 0.235 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The reaction was partitioned between ethyl acetate and saturated NaHCO$_3$, and the organic phase was washed with brine and dried over MgSO$_4$, filtered and concentrated to give the title compound (0.019 g, 47% yield). $^1$H NMR (300 MHz, DMSO-d$_6$), δ ppm 0.79 (s, 9 H), 0.86 (s, 9 H), 1.28 (m, 1 H), 1.51 (m, 2 H), 2.09 (m, 1 H), 2.26 (m, 1 H), 2.80 (m, 3 H), 2.97 (m, 1 H), 3.09 (m, 1 H), 3.50 (s, 3 H), 3.61 (m, 1 H), 3.95 (m, 2 H), 4.16 (m, 2 H), 4.52 (d, J=15.44 Hz, 1 H), 4.85 (m, 2 H), 6.65 (m, 3 H), 6.78 (m, 3 H), 6.87 (d, J=6.99 Hz, 2 H), 7.30 (m, 3 H), 7.38 (s, 1 H), 7.58 (d, J=9.19 Hz, 2 H), 7.85 (m, 5 H), 8.33 (d, J=6.99 Hz, 1 H), 8.63 (d, J=4.41 Hz, 1 H).

EXAMPLE 42 methyl(1S)-1-[({(1S,3S,4S)-4-({(2S)-3,3-dimethyl-2-[2-oxo-3-(4-quinolinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate

EXAMPLE 42A tert-butyl(2S)-3,3-dimethyl-2-[2-oxo-3-(4-quinolinylmethyl)-1-imidazolidinyl]butanoate A solution containing the product from Example 6F (0.367 g, 1.59 mmol) in a mixture of benzene (5 mL) and methanol (5 mL) was treated with 4-quinolinecarboxaldehyde (0.25 g, 1.59 mmol), heated at 50° C. for 3 hours, cooled to 25° C. and treated with sodium borohydride (0.12 g, 3.18 mmol), stirred at 25° C. for 2 hours, quenched with sodium bicarbonate solution and partitioned between ethyl acetate and water. The organic phase was washed with brine and dried over MgSO$_4$, filtered and concentrated. A solution of the concentrate (1.59 mmol) in toluene (10 mL) was treated with bis(4-nitrophenyl) carbonate (0.58 g, 1.9 mmol), heated at 100° C. for 16 hours, cooled and partitioned between ethyl acetate and saturated Na$_2$CO$_3$. The organic phase was washed with brine and dried over MgSO$_4$, filtered and concentrated. The residue was chromatographed on silica gel eluting with 0-20% acetone/dichloromethane to give the title compound (0.355 g, 57% yield).

EXAMPLE 42B (2S)-3,3-dimethyl-2-[2-oxo-3-(4-quinolinylmethyl)-1-imidazolidinyl]butanoic acid A solution containing the product from Example 42A (0.355 g, 0.89 mmol) in dichloromethane (4 mL) was treated with trifluoracetic acid (4 mL), and the mixture was stirred at 25° C. for 2 hours. The solvent was concentrated and azeotroped with toluene several times to give the crude product as the trifluoroacetic acid salt, which was used without further purification.

EXAMPLE 42C methyl(1S)-1-[({(1S,3S,4S)-4-({(2S)-3,3-dimethyl-2-[2-oxo-3-(quinolinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 42B (0.024 g, 0.070 mmol), DEPBT (0.021 g, 0.070 mmol), and N,N-diisopropylethylamine (0.041 mL, 0.235 mmol) and the mixture was stirred at 25° C. for 2 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.027 g, 67% yield). $^1$H NMR (500 MHz, DMSO-d$_6$), δppm 0.82(s, 9H), 0.89(s, 9H), 1.55 (m, 2H), 2.27(m, 1H), 2.65-2.60(m, 3H), 2.77(m, 1H), 2.85(m, 1H), 3.03(m, 1 H), 3.17(m, 1H), 3.49(s, 3H), 3.65(m, 1H), 3.84(d, J=8.79 Hz, 1H), 4.08(d, J=33.69 Hz, 3H), 4.52(d, J=7.81 Hz, 1H), 4.79(dd, J=152.34, 15.63 Hz, 2H), 6.57(d, J=8.79 Hz, 1H), 6.81(t, J=7.32 Hz, 2H), 6.90(t, J=7.08 Hz, 1H), 6.96(d, J=6.84 Hz, 2H), 7.22(d, J=7.81 Hz, 2H), 7.29(m, 1H), 7.46-7.42(m, 2H), 7.63(t, J=7.57 Hz, 1H), 7.90-7.76(m, 5H), 8.06(d, J=7.81 Hz, 1H), 8.31(d, J=8.30 Hz, 1H), 8.62(d, J=3.91 Hz, 1H), 8.90(d, J=4.39 Hz, 1H).

EXAMPLE 43 methyl(1S)-1-[({(1S,2S,4S)-4-({(2S)-3,3-dimethyl-2-[2-oxo-3-(4-quinolinylmethyl)-1-imidazolidinyl]butanoyl}amino)-2-hydroxy-5-phenyl-1-[4-(2-pyridinyl)benzyl]pentyl}amino)carbonyl]-2,2-dimethylpropylcarbamate A solution containing the product from Example 23S (0.025 g, 0.047 mmol) in THF (0.5 mL) was treated with the product from Example 42B (0.024 g, 0.070 mmol), DEPBT (0.021 g, 0.070 mmol), and N,N-diisopropylethylamine (0.041 mL, 0.235 mmol) and the mixture was stirred at 25° C. for 2 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.015 g, 37% yield). $^1$H NMR (500 MHz, DMSO-d$_6$), δ ppm 0.83(s, 9H), 0.85(s, 9H), 1.61-1.50(m, 2H), 2.41-2.31(m, 2H), 2.69-2.59(m, 1H), 2.78(bs, 2H), 2.88(m, 1H), 3.03-2.95(m, 1H), 3.23-3.14(m, 1H), 3.50(s, 3H), 3.61(m, 1H), 3.94(m, 1H), 4.00(s, 1H), 4.18(m, 2H), 4.81(bs, 1H), 4.92-4.64(dd, J=15.63, 126.95 Hz, 2H), 6.87-6.73(m, 4H), 6.96(m, 2H), 7.29(m, 3 H), 7.41 (bs, 1H), 7.61-7.54(m, 2H), 7.89-7.77(m, 5H), 8.05(d, J=7.81 Hz, 1H), 8.29(d, J=7.32 Hz, 1H), 8.62(bs, 1H), 8.89(bs, 1H).

EXAMPLE 44 methyl(1S)-1-[({(1S,2S,4S)-2-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate A solution containing the product from Example 23S (0.025 g, 0.047 mmol) in THF (0.5 mL) was treated with the product from Example 17F (0.030 g, 0.066 mmol), DEPBT (0.021 g, 0.070 mmol), and N,N-diisopropylethylamine (0.041 mL, 0.235 mmol) and the mixture was stirred at 25° C. for 2 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.026 g, 64% yield). $^1$H NMR (300 MHz, DMSO-d$_6$), δ ppm 0.82 (s, 9 H), 0.86 (s, 9 H), 1.42 (d, J=4.78 Hz, 6 H), 1.55 (m, 2 H), 2.39 (m, 2 H), 2.65 (d, J=13.24 Hz, 1 H), 2.78 (d, J=6.25 Hz, 2 H), 2.98 (m, 1 H), 3.20 (m, 3 H), 3.51 (s, 3 H), 3.61 (m, 1 H), 3.98 (m, 2 H), 4.19 (m, 2 H), 4.39 (m, 2 H), 4.82 (d, J=5.52 Hz, 1 H), 6.78 (d, J=9.19 Hz, 1 H), 7.06 (m, 6 H), 7.31 (m, 3 H), 7.55 (m, 2 H), 7.76 (t, J=7.72 Hz, 1 H), 7.86 (m, 5 H), 8.63 (d, J=4.04 Hz, 1 H).

EXAMPLE 45 methyl(1S)-1-[({(1S,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 17F (0.030 g, 0.066 mmol), DEPBT (0.021 g, 0.070 mmol), and N,N-diisopropylethylamine (0.041 mL, 0.235 mmol) and the mixture was stirred at 25° C. for 2 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.035 g, 86% yield). $^1$H NMR (300 MHz, DMSO-d$_6$), δ ppm 0.83 (s, 9 H), 0.90 (s, 9 H), 1.43 (d, J=5.15 Hz, 6 H), 1.53 (m, 2 H), 2.36 (m, 1 H), 2.65 (m, 3 H), 2.79 (m, 1 H), 2.99 (m, 1 H), 3.20 (m, 3 H), 3.50 (s, 3 H), 3.65 (m, 1 H), 3.85 (d, J=9.93 Hz, 1 H), 4.05 (m, 3 H), 4.45 (m, 3 H), 6.63 (d, J=9.93 Hz, 1 H), 7.08 (m, 6 H), 7.22 (d, J=8.09 Hz, 2 H), 7.31 (m, 1 H), 7.46 (d, J=9.56 Hz, 1 H), 7.54 (d, J=7.72 Hz, 1 H), 7.83 (m, 6 H), 8.64 (d, J=4.78 Hz, 1 H).

EXAMPLE 46 methyl(1S)-1-[({(1R,3S,4S)-4-[((2S)-3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate

EXAMPLE 46A tert-butyl(2S)-2-[(2-ethoxy-2-oxoethyl)amino]-3,3-dimethylbutanoate

A solution of L-tert-leucine tert-butyl ester hydrochloride (5 g, 22.34 mmol) in DMF (25 mL) was treated with triethylamine (3.1 mL, 22.34 mmol) and the mixture was stirred for 1 hour. The reaction was filtered to remove solid salts, and the filtrate was treated with triethylamine (9.3 mL, 67.0 mmol) and ethyl bromoacetate (9.9 mL, 67.0 mmol), and the reaction was stirred for 3 hours at 25° C. The solvent was concentrated and the reaction was partitioned between dichloromethane and water. The organic phase was washed with brine and dried over MgSO$_4$, filtered and concentrated. The residue was chromatographed on silica gel eluting with 0-20% ethyl acetate/hexane to give the title compound (5.47 g, 90% yield).

EXAMPLE 46B tert-butyl(2S)-2-[(aminocarbonyl)(2-ethoxy-2-oxoethyl)amino]-3,3-dimethylbutanoate A solution containing the product from Example 46A (5.74 g, 20.0 mmol) in dichloromethane (40 mL) at 0° C. was treated with chlorosulfonyl isocyanate (2.26 mL, 26.0 mmol) and the mixture was stirred at 0° C. for 2 hours. Water (40 mL) was added to the cold reaction and the mixture was warmed to 25° C. and stirred for 2 hours. The reaction mixture was partitioned between dichloromethane and water, and the organic phase was washed with brine and dried over MgSO$_4$, filtered and concentrated to give the title compound, which was used without further purification.

EXAMPLE 46C tert-butyl(2S)-2-(2,4-dioxo-1-imidazolidinyl)-3,3-dimethylbutanoate A solution containing the product from Example 46B (20.0 mmol) in methanol (30 mL) was treated with triethylamine (5.6 mL, 40.2 mmol), stirred at 50° C. for 2 hours, and concentrated. The residue was chromatographed on silica gel eluting with 0-30% ethyl acetate/dichloromethane to give the title compound (4.57 g, 85% yield).

EXAMPLE 46D tert-butyl(2S)-3,3-dimethyl-2-{3-[(6-methyl-2-pyridinyl)methyl]-2,4-dioxo-1-imidazolidinyl}butanoate A solution containing the product from Example 46C (0.112 g, 0.413 mmol) in dichloromethane (3 mL) at 0° C. was treated with 6-methyl-2-pyridinemethanol (0.056 g, 0.454 mmol), triphenylphosphine (0.141 g, 0.537 mmol), followed by diethyl azodicarboxylate (0.084 mL, 0.537 mmol), stirred at 25° C. for 16 hours, treated with water (3 mL), stirred for 2 hours at 25° C., and partitioned between dichloromethane and water. The organic phase was washed with brine and dried over MgSO$_4$, filtered and concentrated. The residue was chromatographed on silica gel eluting with 0-30% ethyl acetate/dichloromethane to give the title compound (0.151 g, 97% yield).

EXAMPLE 46E (2S)-3,3-dimethyl-2-{3-[(6-methyl-2-pyridinyl)methyl]-2,4-dioxo-1-imidazolidinyl}butanoic acid A solution containing the product from Example 46D (0.151 g, 0.403 mmol) in dichloromethane (3 mL) was treated with trifluoroacetic acid (3 mL), and the mixture was stirred at 25° C. for 16 hours. The solvent was concentrated and the product was purified by reversed phase chromatography on a C18 column eluting with a gradient starting with 5-100% acetonitrile in water (0.1% TFA) to give the title compound (0.141 g, 81% yield) as the trifluoroacetic acid salt.

EXAMPLE 46F methyl(1S)-1-[({(1R,3S,4S)-4-[((2S)-3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 46E (0.020 g, 0.046 mmol), DEPBT (0.017 g, 0.057 mmol), and N,N-diisopropylethylamine (0.030 mL, 0.172 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give the title compound (0.023 g, 73% yield). $^1$H NMR (300 MHz, DMSO-d$_6$), δ ppm 0.82 (s, 9 H), 0.87 (s, 9 H), 1.32 (m, 1 H), 1.53 (t, J=11.40 Hz, 1 H), 2.41 (s, 3 H), 2.63 (m, 3 H), 2.85 (m, 1 H), 3.16 (d, J=18.02 Hz, 1 H), 3.60 (m, 5 H), 3.90 (m, 3 H), 4.19 (m, 1 H), 4.35 (s, 1 H), 4.68 (m, 2 H), 6.90 (d, J=9.93 Hz, 1 H), 7.03 (m, 6 H), 7.16 (d, J=7.72 Hz, 1 H), 7.25 (d, J=8.09 Hz, 2 H), 7.34 (m, 1 H), 7.69 (t, J=7.72 Hz, 1 H), 7.93 (m, 6 H), 8.65 (d, J=4.78 Hz, 1 H).

EXAMPLE 47

1:1 mixture of (3R,3aS,6aR)-hexahydrofuro[2,3-b]furan-3-yl(1S,2S,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate and (3R,3aR,6aS)-hexahydrofuro[2,3-b]furan-3-yl(1S,2S,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A solution of the product from Example 1H (0.020 g, 0.038 mmol) in THF (0.25 mL) was treated with N,N-diisopropylethylamine (0.015 mL, 0.086 mmol) and the product from Example 26A (0.017 g, 0.058 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give the title compound (0.018 g, 70% yield). $^1$H NMR(300 MHz, DMSO-d$_6$), δ ppm 0.76 (d, J=3.31 Hz, 9 H), 1.43 (m, 3 H), 2.68 (m, 5 H), 3.71 (m, 12 H), 4.18 (m, 1 H), 4.85 (m, 1 H), 5.52 (m, 1 H), 6.89 (m, 1 H), 6.99 (m, 1 H), 7.23 (m, 8 H), 7.94 (m, 5 H), 8.65 (d, J=4.78 Hz, 1 H).

EXAMPLE 48 methyl(1S)-1-[({(1R,3S,4S)-4-{[(2S)-3,3-dimethyl-2-(2-oxo-3-{[2-(3-pyridinyl)-1,3-thiazol-4-yl]methyl}-1-imidazolidinyl)butanoyl]amino}-3-hydroxy-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 19D (0. 022 g, 0.045 mmol), DEPBT (0.017 g, 0.057 mmol), and N,N-diisopropylethylamine (0.030 mL, 172 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-7.5% methanol in ethyl acetate to give the title compound (0.026 g, 78% yield). $^1$H NMR (300 MHz, DMSO-d$_6$), δ ppm 0.80 (s, 9 H), 0.88 (s, 9 H), 1.46 (m, 2 H), 2.44 (d, J=8.82 Hz, 1 H), 263 (m, 3 H), 2.83 (m, 1 H), 3.15 (m, 3 H), 3.54 (m, 4 H), 3.84 (d, J=9.56 Hz, 1 H), 3.93 (m, 1 H), 4.04 (s, 1 H), 4.18 (m, 1 H), 4.46 (m, 3 H), 6.88 (d, J=9.56 Hz, 1 H), 6.96 (m, 1 H), 7.06 (m, 4 H), 7.24 (d, J=8.46 Hz, 2 H), 7.32 (m, 1 H), 7.53 (m, 2 H), 7.60 (s, 1 H), 7.89 (m, 5 H), 8.29 (m, 1 H), 8.65 (m, 2 H), 9.13 (d, J=1.47 Hz, 1 H).

EXAMPLE 49 methyl(1S)-1-[({(1R,3S,4S)-4-{[(2,6-dimethylphenoxy)acetyl]amino}-3-hydroxy-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with 2,6-dimethylphenoxy acetic acid (U.S. Pat. No. 5,914,332, see Example 1H) (0.008 g, 0.044 mmol), DEPBT (0.017 g, 0.057 mmol), and N,N-diisopropylethylamine (0.030 mL, 0.172 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give the title compound (0.019 g, 73% yield). $^1$H NMR (300 MHz, DMSO-d$_6$), δ ppm 0.76 (s, 9 H), 1.41 (t, J=11.77 Hz, 1 H), 1.58 (m, 1 H), 2.10 (s, 6 H), 2.77 (m, 4 H), 3.57 (s, 3 H), 3.65 (m, 1 H), 3.81 (d, J=9.56 Hz, 1 H), 4.07 (m, 4 H), 5.02 (d, J=5.52 Hz, 1 H), 6.92 (m, 4 H), 7.25 (m, 8 H), 7.56 (d, J=9.56 Hz, 1 H), 7.85 (m, 3 H), 7.96 (d, J=8.46 Hz, 2 H), 8.64 (d, J=4.41 Hz, 1 H).

EXAMPLE 50 methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl}amino)carbonyl]-2,2-dimethylpropylcarbamate Method A A solution containing the product of Example 1H (0.72 g, 1.35 mmol) in THF (12 mL) was treated with the product from Example 17F (0.54 g, 1.16 mmol), DEPBT (0.52 g, 1.74 mmol), and N,N-diisopropylethylamine (1.0 mL, 5.74 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 50-100% ethyl acetate in chloroform to give the title compound (0.84 g, 84% yield). $^1$H NMR (300 MHz, DMSO-d$_6$), δ ppm 0.79 (s, 9 H), 0.87 (s, 9 H), 1.37 (m, 1 H), 1.41 (s, 3 H), 1.43 (s, 3 H), 1.52 (m, 1 H), 2.48 (m, 1H), 2.64 (m, 3 H), 2.83 (dd, J=14.0, 6.6 Hz, 1 H), 3.01 (m, 1 H), 3.15 (m, 1 H), 3.23 (m, 1 H), 3.53 (m, 1 H), 3.56 (s, 3H), 3.83 (d, J=9.56 Hz, 1 H), 3.93 (m, 1 H), 4.02 (s, 1 H), 4.17 (m, 1 H), 4.39 (m, 3 H), 5.15 (s, 1 H), 6.87 (d, J=10.30 Hz, 1 H), 7.08 (m, 6 H), 7.24 (d, J=8.46 Hz, 2 H), 7.32 (m, 1 H), 7.52 (m, 2 H), 7.75 (t, J=7.72 Hz, 1 H), 7.89 (m, 3 H), 7.95 (d, J=8.46 Hz, 2 H), 8.64 (d, J=4.78 Hz, 1 H).

Method B

EXAMPLE 50-1 methyl 6-(hydroxymethyl)pyridine-2-carboxylate

A suspension of dimethyl 2,6-pyridine-dicarboxylate (100 g, 513 mmol) in methanol (800 mL) and tetrahydrofuran (300 mL) was heated to dissolve and while the solution was still hot, it was treated in portions with sodium borohydride (18.2 g, 479 mmol) over 1 hour. The mixture was stirred for 1 hour at room temperature, cooled to 0-5° C., and quenched with 10% citric acid (160 mL), stirred for another 15 minutes, and filtered. The filtrate was concentrated, dissolved in dichloromethane, dried (sodium sulfate), filtered, and concentrated to a white solid. The solid was heated to dissolve in ethyl acetate (100 mL), stirred for 16 hours at room temperature, filtered and concentrated to give the title compound (44.5 g, 56% yield). $^1$H NMR (CDCl$_3$) δ ppm 3.50(s, 1H), 4.00 (s, 3 H), 4.86 (s, 2 H), 7.52 (d, 1 H), 7.85 (t, 1 H), 8.04 (d, 1 H).

EXAMPLE 50-2 methyl 6-formylpyridine-2-carboxylate

To a solution of 2M oxalyl chloride/dichloromethane (236 mL, 462 mmol) in dichloromethane (800 mL) at −45° C. was slowly added dimethylsulfoxide (48.4 mL, 682 mmol) keeping temperature below −45° C. The mixture was stirred for 30 minutes at −45° C. after the addition, and a solution of the product of Example 50-1 (46 g, 276 mmol) in dichloromethane (160 mL) was added dropwise, stirred for 30 minutes at −45° C., treated with triethylamine (175 mL, 1256 mmol), stirred for 15 minutes at −45° C., removed dry ice bath, stirred at −40 to −50 C for 30 minutes, and quenched with pH 7 phosphate buffer solution (250 mL). The organic layer was separated and concentrated. This residue was heated to dissolve in ethyl acetate (100 mL), cooled to room temperature, stirred at room temperature for 1-2 hours and 1 hour at 0° C. The resulting precipitate was filtered and washed with cold ethyl acetate (100 mL) to give the title compound (30 g, 69%). $^1$H NMR (CDCl$_3$) δ ppm 4.07 (s, 3 H), 8.05 (m, 1 H), 8.16 (m, 1 H), 8.36 (m, 1 H), 10.18 (d, 1 H).

EXAMPLE 50-3 methyl 6-{[(2-{[(1R)-1-(tert-butoxycarbonyl)-2,2-dimethylpropyl]amino}ethyl)amino]methyl}pyridine-2-carboxylate A suspension of the product of Example 50-2 (40 g, 242 mmol), the product of Example 111-3 (64 g, 278 mmol), and magnesium sulfate (144 g, 1.2 mol) in dichloromethane (600 mL) was stirred at room temperature overnight, filtered and the filtrate was concentrated. The resulting residue was dissolved in methanol (600 mL) and treated with sodium borohydride (10.56 g, 277 mmol) at 0° C. The mixture was stirred for 0.5 hour at 0° C., quenched with acetone (10 mL), concentrated, treated with ethyl acetate (1 L), and washed with NaHCO$_3$ (2×200 mL). The organic layer was dried over MgSO$_4$, filtered and concentrated to give the crude product (113 g). The residue was chromatographed on silica gel (750 g), eluted with 4 L of 30% ethyl acetate in hexane, 4 L of 50% ethyl acetate in hexane, then 8 L of 10% methanol in dichloromethane to afford the title compound (85 gm, 92.5% yield). $^1$H NMR (CDCl$_3$): δ ppm 0.96 (s, 9 H), 1.47 (s, 9 H), 2.54 (m, 1 H), 2.76 (m, 4 H), 3.99 (s, 3 H), 4.02 (d, 2 H), 7.62 (d, 1 H), 7.80 (t, 1 H), 7.99 (d, 1 H).

EXAMPLE 50-4 methyl 6-({3-[(1S)-1-(tert-butoxycarbonyl)-2,2-dimethylpropyl]-2-oxoimidazolidin-1-yl}methyl)pyridine-2-carboxylate A solution of the product of Example 50-3 (92 g, 243 mmol), disuccinimidyl carbonate (78 g, 304 mmol), and triethylamine (41 mL, 294 mmol) in 1,2-dichloroethane (1.8 L) was stirred at room temperature for 16 hours. The mixture was diluted with dichloroethane (200 mL), washed with saturated NaHCO$_3$ (2×500 mL), and brine (200 mL), dried over MgSO$_4$, filtered and concentrated. The residue was triturated with hexane (550 mL) and ethyl acetate (50 mL) at room temperature for two hours to give the title compound as a white solid (85 gm, 98% yield). $^1$H NMR (CDCl$_3$): δ ppm 1.10 (s, 9 H), 1.48 (s, 9 H), 3.34 (m, 2 H), 3.62 (m, 1 H), 3.88 (m, 1 H), 4.00 (s, 3 H), 4.42 (s, 1 H), 4.64 (s, 2 H), 7.52 (d, 1 H), 7.81 (t, 1 H), 8.03 (d, 1 H).

EXAMPLE 50-5 tert-butyl(2S)-2-(3-{[6-(1-hydroxy-1-methylethyl)pyridin-2-yl]methyl}-2-oxoimidazolidin-1-yl)-3,3-dimethylbutanoate A solution of the product of Example 50-4 (46 g, 114 mmol) in tetrahydrofuran(1 L) at 0° C. was treated with methylmagnesium bromide in diethyl ether (3M, 190 mL, 570 mmol), stirred for 1 hour at 0° C., quenched with 10% citric acid (160 mL), and extracted with ethyl acetate (200 mL). The aqueous layer was washed with ethyl acetate (200 mL). The combined organic layer was washed with brine (200 mL), dried over MgSO$_4$, filtered and concentrated to 54.7 g of crude material. The crude material was filtered through silica pad, washed with ethyl acetate (1.2 L), and concentrated. The residue was crystallized from hexane (400 mL) to give the title compound as solid (30 gm, 69%). $^1$H NMR (CDCl$_3$): δ ppm 1.09 (s, 9 H), 1.47 (s, 9 H), 1.47 (s, 9 H), 1.52 (s, 6 H), 3.34 (m, 2 H), 3.62 (m, 1 H), 3.89 (m, 1 H), 4.41 (s, 1 H), 4.53 (m, 2 H), 5.20 (s, 1 H), 7.21 (m, 2 H), 7.67 (t, 1 H).

EXAMPLE 50-6

(2S)-2-(3-{[6-(1-hydroxy-1-methylethyl)pyridin-2-yl]methyl}-2-oxoimidazolidin-1-yl)-3,3-dimethylbutanoic acid The product of Example 50-5 (61 g, 150.6 mmol) at 25° C. was treated with 90% trifluoroacetic acid in water (300 mL). The reaction was stirred at 25° C. for 5 hours and concentrated to give 118 g of residue. The residue was loaded on 600 g of silica gel, eluted with 4 L of 5% methanol in dichloromethane, then with 4 L of 10% methanol in dichloromethane. The desired fractions were combined and concentrated to give 100 g of crude material. The crude material was crystallized from diethyl ether (350 mL) to afford 54 g of the trifluoroacetic acid salt of the title compound, 77% yield. $^1$H NMR (CDCl$_3$): δ ppm 1.10 (s, 9 H,) 1.63 (s, 6 H), 3.48 (m, 2 H), 3.65 (m, 1 H), 3.87 (m, 1H), 4.33 (s, 1 H), 4.78 (q, 2 H), 7.54 (d, 1 H), 7.61 (d, 1 H), 8.12 (t, 1 H), 9.2(w, 3H).

EXAMPLE 50-7

N$^1$-[(1R,3S,4S)-4-amino-3-hydroxy-5-phenyl-1-(4-pyridin-2-ylbenzyl)pentyl]-N$^2$-(methoxymethyl)-3-methyl-L-valinamide The product of Example 111-13A (21.746 g; 27:1 diastereomeric ratio) in isopropyl acetate (217 mL) was treated with concentrated hydrochloric acid (43.5 of mL), stirred at room temperature for 5 minutes, and diluted with water (168 mL). The aqueous layer was diluted with chloroform (440 mL) and the pH was adjusted to about 10 with K$_2$CO$_3$ (52.5 g). The chloroform layer was concentrated to oil, chased with ethanol (220 mL) to a solid. The solid was crystallized from 105 mL of ethanol/105 mL of water to give 16.57 g of the title compound. $^1$H NMR (CDCl$_3$) δ ppm 0.89 (s, 9 H,) 1.55 (m, 1H), 1.75 (m, 1 H), 2.36 (m, 1 H), 2.78 (m, 2 H), 2.88 (m, 1H), 3.02 (m, 1H), 3.50 (m, 1H), 3.65 (s, 3H), 3.85 (d, 1H), 4.54 (m, 1 H), 5.45 (d, 1 H), 6.63, (d, 1H), 7.18 (m, 4H), 7.28 (m, 4 H), 7.70 (m, 2 H), 7.90(d, 2H), 8.66 (d, 1H).

EXAMPLE 50-8 methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1-[4-(2-pyridinyl)benzyl]pentyl]amino)carbonyl]-2,2-dimethylpropylcarbamate A mixture of the product of Example 50-6 ( 16.27 g, 35 mmol, 1.1 equivalents), DEPBT (13.37 g, 45 mmol, 1.4 equivalents), tetrahydrofuran (170 mL), and K$_2$CO$_3$(8.82 g, 64 mmol, 2 equivalents) was stirred for 2.5 hours at 20° C., treated with a solution of the product of Example 50-7 (17 g, 32 mmol, 1 equivalent) in tetrahydrofuran (170 mL), stirred at 20° C. for 15 hours, treated with 10% Na$_2$CO$_3$ (340 mL), stirred at 20° C. for 6 hours, and extracted with ethyl acetate (340 mL). The organic phase was washed with 10% brine (340 mL) and 20% brine (340 mL), and concentrated. The residue was chromatographed on silica gel (260 gm silica gel, eluted with dichloromethane, 2.5% of methanol in dichloromethane, 5% methanol in dichloromethane, 7.5% methanol in dichloromethane, and 10% methanol in dichloromethane). The desired fractions were pooled, concentrated to foam, chased with ethyl acetate (250 mL) to oil, then twice with dichloromethane. 28.4 gm of solid was removed from the flask. The remaining solid was dissolved in heptanes (100 mL) at 100° C., cooled to 75° C., after 30 minutes added 100 mL of ethyl acetate and 100 mL of heptanes, held at 80° C. for 15 minutes, cooled to room temperature, filtered to give crystalline seeds. 28.4 gm of amorphous solid was slurried in 150 mL of heptanes and 25 mL of ethyl acetate at 100° C., cooled to 75° C., added seeds from the small lot, added 50 mL of ethyl acetate, heated to 85° C., cooled to room temperature, filtered and washed with 2×50 mL of heptanes, dried to give 26.6 gm of the title compound. $^1$H NMR(DMSO-d$_6$) δ ppm 0.79 (s, 9 H,) 0.88 (s, 9H), 1.37 (m, 1H), 1.40 (s, 3H), 1.42 (s, 3H), 1.53 (m, 1H), 2.45 (m, 1H), 2.63 (m, 3H), 2.82 (m, 1H), 2.99 (m, 1H), 3.17 (m, 2H), 3.53 (m, 3H), 3.57 (s, 3H), 3.82 (d, 1 H), 3.93 (m, 1 H), 4.01 (s, 1 H), 4.17 (m, 1H), 4.38 (m, 3H), 5.17 (s, 1 H), 6.85 (d, 1H), 7.05 (m, 6H), 7.22 (d, 2 H), 7.30 (t, 1 H), 7.51 (m, 2H), 7.73 (t, 1H), 7.85 (m, 3H), 7.94 (d, 2H), 8.62(d, 1H).

EXAMPLE 51 methyl(1S)-1-[({(1S,3S,4S)-4-[((2S)-3,3-dimethyl-2-{3-[(6-methyl-2-pyridinyl)methyl]-2,4-dioxo-1-imidazolidinyl}butanoyl)amino]-3-hydroxy-5-phenyl-1-[4-(2-pyridinyl)benzyl]pentyl}amino) carbonyl]-2,2-dimethylpropylcarbamate A solution containing the product from Example 2C (0.020 g, 0.038 mmol) in THF (0.4 mL) was treated with the product from Example 46E (0.020 g, 0.046 mmol), DEPBT (0.017 g, 0.057 mmol), and N,N-diisopropylethylamine (0.035 mL, 0.201 mmol), stirred at 25° C. for 1 hour, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane to give the title compound (0.020 g, 64% yield). $^1$H NMR (300 MHz, DMSO-$d_6$), δ ppm 0.85 (s, 9 H), 0.88 (s, 9 H), 1.54 (m, 2 H), 2.41 (s, 3 H), 2.65 (m, 4 H), 3.08 (d, J=18.02 Hz, 1 H), 3.51 (s, 3 H), 3.72 (m, 1 H), 3.89 (m, 2 H), 4.17 (m, 2 H), 4.39 (s, 1 H), 4.67 (m, 3 H), 6.66 (d, J=9.93 Hz, 1 H), 7.06 (m, 7 H), 7.23 (d, J=8.46 Hz, 2 H), 7.31 (m, 1 H), 7.66 (t, J=7.54 Hz, 1 H), 7.87 (m, 6 H), 8.64 (d, J=4.41 Hz, 1 H).

EXAMPLE 52 methyl(1S)-1-[({(1S,2S,4S)-4-[((2S)-3,3-dimethyl-2-{3-[(6-methyl-2-pyridinyl)methyl]-2,4-dioxo-1-imidazolidinyl}butanoyl)amino]-2-hydroxy-5-phenyl-1-[4-(2-pyridinyl)benzyl]pentyl}amino) carbonyl]-2,2-dimethylpropylcarbamate A solution containing the product from Example 23S (0.020 g, 0.038 mmol) in THF (0.4 mL) was treated with the product from Example 46E (0.020 g, 0.046 mmol), DEPBT (0.017 g, 0.057 mmol), and N,N-diisopropylethylamine (0.035 mL, 0.201 mmol), stirred at 25° C. for 1 hour, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane to give the title compound (0.021 g, 67% yield). $^1$H NMR (300 MHz, DMSO-$d_6$), δ ppm 0.80 (s, 9 H), 0.88 (s, 9 H), 1.55 (m, 2 H), 2.29 (m, 1 H), 2.39 (s, 3H), 2.75 (m, 3 H), 3.15 (d, J=18.38 Hz, 1 H), 3.52 (s, 3 H), 3.61 (m, 1 H), 3.94 (m, 2 H), 4.19 (m, 3 H), 4.68 (d, J=10.30 Hz, 2 H), 4.89 (d, J=5.52 Hz, 1 H), 6.83 (d, J=9.93 Hz, 1 H), 7.00 (m, 6 H), 7.13 (d, J=7.72 Hz, 1 H), 7.31 (m, 3 H), 7.64 (m, 2 H), 7.88 (m, 4 H), 8.09 (d, J=9.19 Hz, 1 H), 8.63 (d, J=4.78 Hz, 1 H).

EXAMPLE 53 methyl(1S)-1-[({(1R,3S,4)-4-({(2S)-3,3-dimethyl-2-[2-oxo-3-(4-quinolinylmethyl)-1-imidazolidinyl] butanoyl}amino)-3-hydroxy-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 42B (0.020 g, 0.045 mmol), DEPBT (0.017 g, 0.057 mmol), and N,N-diisopropylethylamine (0.035 mL, 0.201 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 0-0.5% methanol in ethyl acetate, to give the title compound (0.021 g, 65% yield). $^1$H NMR (300 MHz, DMSO-$d_6$), δ ppm 0.81 (s, 9 H), 0.89 (s, 9 H), 1.26 (m, 1 H), 1.37 (m, 1 H), 1.53 (m, 1 H), 2.30 (m, 1 H), 2.65 (m, 2 H), 2.85 (m, 2 H), 3.00 (m, 1 H), 3.18 (m, 1 H), 3.53 (m, 4 H), 3.84 (d, J=9.56 Hz, 1 H), 3.94 (m, 1 H), 4.05 (m, 1 H), 4.19 (m, 1 H), 4.44 (d, J=7.35 Hz, 1 H), 4.63 (d, J=15.44 Hz, 1 H), 4.95 (d, J=15.44 Hz, 1 H), 6.87 (m, 6 H), 7.25 (d, J=8.46 Hz, 2 H), 7.32 (m, 1 H), 7.43 (d, J=4.41 Hz, 1 H), 7.60 (m, 2 H), 7.86 (m, 6 H), 8.06 (d, J=7.72 Hz, 1 H), 8.30 (d, J=8.09 Hz, 1 H), 8.65 (m, 1 H), 8.90 (d, J=4.04 Hz, 1 H).

EXAMPLE 54 methyl(1S)-1-[({(1S,3S,4S)-4-({(2S)-3,3-dimethyl-2-[(phenoxyacetyl)amino]butanoyl}amino)-3-hydroxy-5-phenyl-1-[4-(2-pyridinyl)benzyl] pentyl}amino)carbonyl]-2,2-dimethylpropylcarbamate

EXAMPLE 54A tert-butyl(2S)-3,3-dimethyl-2-[(phenoxyacetyl) amino]butanoate

A solution of L-tert-Leucine tert-butyl ester hydrochloride (0.20 g, 0.90 mmol) in THF (9 mL) at 0° C. was treated with triethylamine (0.38 mL, 2.73 mmol) and phenoxyacetyl chloride (0.14 mL, 1.01 mmol), stirred at 0° C. for 15 minutes and then at 25° C. for 2 hours. The reaction mixture was partitioned between ethyl acetate and water. The organic phase was washed with brine and dried over $MgSO_4$, filtered and concentrated. The residue was chromatographed on silica gel eluting with 0-10% ethyl acetate/chloroform to give the title compound (0.23 g, 80% yield).

EXAMPLE 54B (2S)-3,3-dimethyl-2-[(phenoxyacetyl)amino]butanoic acid

A solution of the product from Example 54A (0.012 g, 0.038 mmol) in dichloromethane (0.2 mL) was treated with trifluoroacetic acid (0.2 mL) and the reaction was stirred at 25° C. for 1 hour and concentrated. The concentrate was azeotroped with toluene to give the title compound, which was used without further purification.

EXAMPLE 54C methyl(1S)-1-[({(1S,3S,4S)-4-({(2S)-3,3-dimethyl-2-[(phenoxyacetyl)amino]butanoyl}amino)-3-hydroxy-5-phenyl-1-[4-(2-pyridinyl)benzyl] pentyl}amino)carbonyl]-2,2-dimethylpropylcarbamate A solution containing the product from Example 2C (0.020 g, 0.038 mmol) in THF (0.4 mL) was treated with the product from Example 54B (0.038 mmol), DEPBT (0.016 g, 0.054 mmol), and N,N-diisopropylethylamine (0.032 mL, 0.184 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA) to give the title compound (0.011 g, 38% yield). $^1$H NMR (300 MHz, DMSO-d$_6$), δ ppm 0.80 (d, J=2.94 Hz, 18 H), 1.53 (m, 2 H), 2.55 (m, 1 H), 2.73 (m, 3 H), 3.49 (s, 3 H), 3.65 (m, 1 H), 3.82 (d, J=9.93 Hz, 1 H), 4.05 (m, 1 H), 4.15 (m, 1 H), 4.33 (d, J=9.56 Hz, 1 H), 4.53 (m, 2 H), 4.81 (d, J=5.88 Hz, 1 H), 6.61 (d, J=9.56 Hz, 1 H), 6.95 (m, 3 H), 7.11 (m, 1 H), 7.18 (m, 6 H), 7.31 (m, 3 H), 7.48 (d, 9.56 Hz, 1 H), 7.84 (m, 6 H), 8.64 (d, J=4.41 Hz, 1 H).

EXAMPLE 55 methyl(1S,4S,6S,7S,10S)-7-benzyl-1,10-ditert-butyl-6-hydroxy-2,9,12-trioxo-4-[4-(2-pyridinyl)benzyl]-14-oxa-3,8,11-triazapentadec-1-ylcarbamate

EXAMPLE 55A tert-butyl(2S)-2-[(methoxyacetyl)amino]-3,3-dimethylbutanoate

A solution of L-tert-Leucine tert-butyl ester hydrochloride (0.20 g, 0.90 mmol) in THF (9 mL) at 0° C. was treated with triethylamine (0.38 mL, 2.73 mmol) and methoxyacetyl chloride (0.09 mL, 0.98 mmol), stirred at 0° C. for 15 minutes and then at 25° C. for 2 hours. The reaction was partitioned between ethyl acetate and water. The organic phase was washed with brine and dried over MgSO$_4$, filtered and concentrated. The residue was chromatographed on silica gel eluting with 0-33% ethyl acetate/chloroform to give the title compound (0.266 g).

EXAMPLE 55B (2S)-2-[(methoxyacetyl)amino]-3,3-dimethylbutanoic acid

A solution of the product from Example 55A (0.012 g, 0.038 mmol) in dichloromethane (0.2 mL) was treated with trifluoroacetic acid (0.2 mL), stirred at 25° C. for 1 hour and concentrated. The residue was azeotroped with toluene to give the title compound, which was used without further purification.

EXAMPLE 55C methyl(1S,4S,6S,7S,10S)-7-benzyl-1,10-ditert-butyl-6-hydroxy-2,9,12-trioxo-4-[4-(2-pyridinyl)benzyl]-14-oxa-3,8,11-triazapentadec-1-ylcarbamate A solution containing the product from Example 2C (0.020 g, 0.038 mmol) in THF (0.4 mL) was treated with the product from Example 55B (0.038 mmol), DEPBT (0.016 g, 0.054 mmol), and N,N-diisopropylethylamine (0.032 mL, 0.184 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA) to give the title compound (0.011 g, 38% yield). $^1$H NMR (300 MHz, DMSO-d$_6$), δ ppm 0.81 (s, 9 H), 0.84 (s, 9 H), 1.52 (m, 2 H), 2.56 (m, 1 H), 2.74 (m, 3 H), 3.26 (s, 3 H), 3.49 (s, 3 H), 3.66 (m, 1 H), 3.82 (m, 3 H), 4.03 (m, 1 H), 4.16 (m, 1 H), 4.31 (d, J=9.56 Hz, 1 H), 4.83 (d, J=5.88 Hz, 1 H), 6.62 (d, J=9.56 Hz, 1 H), 7.14 (m, 8 H), 7.31 (m, 1 H), 7.85 (m, 6 H), 8.63 (d, J=4.41 Hz, 1 H).

EXAMPLE 56 methyl(1S)-1-[({(1S,3S,4S)-3-hydroxy-4-[((2S)-2-{3-[(2-isopropyl-1,3-thiazol-4-yl)methyl]-2,4-dioxo-1-imidazolidinyl}-3-methylpentanoyl)amino]-5-phenyl-1-[4-(2-pyridinyl)benzyl]pentyl}amino)carbonyl]-2,2-dimethylpropylcarbamate

EXAMPLE 56A 2-methylpropanethioamide

A solution containing isobutyramide (10 g, 115 mmol) in THF (250 mL) was treated with phosphorous pentasulfide (4.1 g, 9.22 mmol), stirred at 25° C. for 64 hours, concentrated and partitioned between ethyl acetate and water. The organic phase was washed with brine and dried over MgSO$_4$, filtered and concentrated to give the title compound (8.6 g, 73% yield), which was used without further purification.

EXAMPLE 56B ethyl 2-isopropyl-1,3-thiazole-4-carboxylate

A solution containing the product from Example 56A (8.6 g, 83.5 mmol) in ethanol (250 mL) was treated with ethyl bromopyruvate (12.6 mL, 100 mmol), and the mixture was heated at 70° C. for 3 hours, cooled to 25° C., concentrated, and partitioned between dichloromethane and saturated NaHCO$_3$. The organic phase was washed with brine and dried over MgSO$_4$, filtered and concentrated to give the title compound (18 g, 57% yield), which was used without further purification.

EXAMPLE 56C (2-isopropyl-1,3-thiazol-4-yl)methanol

A solution containing the product from Example 56B (18 g, 90.5mmol) in dichloromethane (100 mL) was treated with diisobutyl aluminum hydride (150 mL, 1 M in dichloromethane) dropwise at −78° C. over 2 hours and the mixture was stirred at −78° C. for 2 hours. Acetic acid (10 mL) was added at −78° C. and the mixture was warmed to 25° C. A 10% solution of aqueous sodium potassium tartrate was added and the mixture was stirred vigorously for 1 hour. The reaction was partitioned between dichloromethane and water, and the organic phase was washed with brine and dried over MgSO$_4$, filtered and concentrated. The residue was chromatographed on silica gel eluting with 0-5% ethyl acetate/dichloromethane to give the title compound (3.84 g, 27% yield).

EXAMPLE 56D tert-butyl(2S,3S)-2-{3-[(2-isopropyl-1,3-thiazol-4-yl)methyl]-2,4-dioxo-1-imidazolinyl}-3-methylpentanoate A solution containing the product from Example 36C (0.076 g, 0.281 mmol) in dichloromethane (2 mL) at 0° C.

was treated with the product from Example 56C (0.049 g, 0.309 mmol), triphenylphosphine (0.096 g, 0.365 mmol), followed by diethyl azodicarboxylate (0.057 mL, 0.365 mmol), stirred at 25° C. for 16 hours. Water (3 mL) was added and the reaction was stirred for 2 hours at 25° C. The reaction mixture was partitioned between dichloromethane and water, and the organic phase was washed with brine and dried over MgSO$_4$, filtered and concentrated. The residue was purified by reversed phase chromatography on a C18 column eluting with 5-100% acetonitrile in water (0.1% TFA) to give the title compound (0.090 g, 78% yield).

EXAMPLE 56E (2S,3S)-2-{3-[(2-isopropyl-1,3-thiazol-4-yl)methyl]-2,4-dioxo-1-imidazolidinyl}-3-methylpentanoic acid A solution containing the product from Example 56D (0.090 g, 0.220 mmol) in dichloromethane (2 mL) was treated with trifluoracetic acid (2 mL), stirred at 25° C. for 16 hours, and concentrated. The residue was purified by reversed phase chromatography on a C18 column eluting with 5-100% acetonitrile in water (0.1% TFA) to give the title compound (0.1 g) as the trifluoroacetic acid salt.

EXAMPLE 56F methyl(1S)-1-[({(1S,3S,4S)-3-hydroxy-4-[((2S)-2-{3-[(2-isopropyl-1,3-thiazol-4-yl)methyl]-2,4-dioxo-1-imidazolidinyl}-3-methylpentanoyl)amino]-5-phenyl-1-[4-(2-pyridinyl)benzyl]pentyl}amino)carbonyl]-2,2-dimethylpropylcarbamate A solution containing the product from Example 2C (0.030 g, 0.056 mmol) in THF (0.5 mL) was treated with the product from Example 56E (0.026 g, 0.073 mmol), DEPBT (0.025 g, 0.085 mmol), and N,N-diisopropylethylamine (0.049 mL, 0.282 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by elution with 0-5% methanol in ethyl acetate to give the title compound (0.033 g, 67% yield). $^1$H NMR (300 MHz, DMSO-d$_6$), δ ppm 0.66 (d, J=6.62 Hz, 3 H), 0.73 (t, J=7.35 Hz, 3 H), 0.88 (m, 12 H), 1.26 (s, 3 H), 1.29 (s, 3 H), 1.50 (m, 2 H), 1.73 (m, 1 H), 2.69 (m, 4 H), 3.10 (d, J=18.38 Hz, 1 H), 3.50 (s, 3 H), 3.78 (m, 3 H) 4.17 (m, 3 H), 4.66 (m, 3 H), 6.67 (d, J=9.93 Hz, 1 H), 6.99 (m, 3 H), 7.07 (m, 2 H), 7.23 (m, 3 H), 7.31 (m, 1 H), 7.85 (m, 6 H), 8.63 (d, J=4.41 Hz, 1 H).

EXAMPLE 57 methyl(1S)-1-[({(1S,3S,4S)-4-{[(2S)-2-(2,4-dioxo-3-{[2-(3-pyridinyl)-1,3-thiazol-4-yl]methyl}-1-imidazolidinyl)-3-methylpentanoyl]amino}-3-hydroxy-5-phenyl-1-[4-(2-pyridinyl)benzyl]pentyl}amino)carbonyl]-2,2-dimethylpropylcarbamate

EXAMPLE 57A

[2-(3-pyridinyl)-1,3-thiazol-4-yl]methanol

A solution containing the product from Example 19 B (0.20 g, 1.05 mmol) in a mixture of THF (1.5 mL) and methanol (1.5 mL) was treated with NaBH$_4$ (0.052 g, 1.37 mmol), stirred at 25° C. for 2 hours, quenched with saturated ammonium chloride solution and concentrated. The concentrate was partitioned between ethyl acetate and saturated NaHCO$_3$. The organic phase was washed with brine and dried over MgSO$_4$, filtered and concentrated to give the title compound (0.063 g, 31% yield).

EXAMPLE 57B tert-butyl(2S,3S)-2-(2,4-dioxo-3-{[2-(3-pyridinyl)-1,3-thiazol-4-yl]methyl}-1-imidazolidinyl)-3-methylpentanoate A solution containing the product from Example 36C (0.081 g, 0.30 mmol) in dichloromethane (2 mL) at 0° C. was treated with the product from Example 57A (0.063 g, 0.33 mmol), triphenylphosphine (0.103 g, 0.39 mmol), followed by diethyl azodicarboxylate (0.061 mL, 0.39 mmol), stirred at 25° C. for 16 hours. Water (3 mL) was added and the reaction was stirred for 2 hours at 25° C. The reaction mixture was partitioned between dichloromethane and water, and the organic phase was washed with brine and dried over MgSO$_4$, filtered and concentrated, to give the crude product, which was used without further purification.

EXAMPLE 57C (2S,3S)-2-(2,4dioxo-3-{[2-(3-pyridinyl)-1,3-thiazol-4-yl]methyl}-1-imidazolidinyl)-3-methylpentanoic acid A solution containing the product from Example 57B (0.090 g, 0.220 mmol) in dichloromethane (2 mL) was treated with trifluoracetic acid (2 mL), stirred at 25° C. for 16 hours, and concentrated. The residue was purified by reversed phase chromatography on a C18 column eluting with 5-100% acetonitrile in water (0.1% TFA) to give the title compound (0.131 g, 90% yield) as the trifluoroacetic acid salt.

EXAMPLE 57D methyl(1S)-1-[({(1S,3S,4S)-4-{[(2S)-2-(2,4-dioxo-3-{[2-(3-pyridinyl)-1,3-thiazol-4-yl]methyl}-1-imidazolidinyl)-3-methylpentanoyl]amino}-3-hydroxy-5-phenyl-1-[4-(2-pyridinyl)benzyl]pentyl}amino)carbonyl]-2,2-dimethylpropylcarbamate A solution containing the product from Example 2C (0.030 g, 0.056 mmol) in THF (0.5 mL) was treated with the product from Example 57C (0.036 g, 0.073 mmol), DEPBT (0.025 g, 0.085 mmol), and N,N-diisopropylethylamine (0.049 mL, 0.282 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by elution with 0-5% methanol in ethyl acetate to give the title compound (0.044g, 86% yield). $^1$H NMR (300 MHz, DMSO-d$_6$), δ ppm 0.67 (d, J=6.62 Hz, 3 H), 0.73 (t, J=7.35 Hz, 3 H), 0.90 (m, 12 H), 1.25 (m, 1 H), 1.52 (m, 2 H), 1.75 (m, 1 H), 2.69 (m, 3 H), 3.15 (m, 1 H), 3.50 (s, 3 H), 3.78 (m, 2 H), 4.16 (m, 3 H), 4.67 (d, J=6.62 Hz, 1 H), 4.78 (m, 2 H), 6.67 (d, J=9.93 Hz, 1 H), 6.96 (m, 3 H), 7.07 (m, 2 H), 7.22 (d, J=8.09 Hz, 2 H), 7.31 (m, 1 H), 7.51 (dd, J=7.91, 4.96 Hz, 1 H), 7.64 (s, 1 H), 7.86 (m, 6 H), 8.24 (m, 1 H), 8.64 (m, 2 H), 9.08 (d, J=1.84 Hz, 1 H).

EXAMPLE 58 methyl(1S)-1-[({(1S,3S,4S)-4-{[(2S)-3,3-dimethyl-2-({[(6-methyl-3-pyridinyl)oxy]acetyl}amino)butanoyl]amino}-3-hydroxy-5-phenyl-1-[4-(2-pyridinyl)benzyl]pentyl}amino)carbonyl]-2,2-dimethylpropylcarbamate

EXAMPLE 58A

[(6-methyl-3-pyridinyl)oxy]acetic acid

A solution containing ethyl 6-methyl-3-pyridyloxyacetate (0.026 g, 0.13 mmol) in a mixture of THF (0.5 mL) and water (0.5 mL) was treated with lithium hydroxide monohydrate (0.008 g, 0.19 mmol), stirred at 25° C. for 18 hours, aid concentrated to give the crude product, which was used without purification.

EXAMPLE 58B methyl(1S,4S,6S,7S,10S)-7-benzyl-1,10-ditert-butyl-6-hydroxy-14,14-dimethyl-2,9,12-trioxo-4-[4-(2-pyridinyl)benzyl]-13-oxa-3,8,11-triazapentadec-1-ylcarbamate A solution containing the product from Example 2C (0.050 g, 0.094 mmol) in THF (0.5 mL) was treated with Boc-L-tert-leucine (0.022 g, 0.096 mmol), DEPBT (0.042 g, 0.140 mmol), and N,N-diisopropylethylamine (0.08 mL, 0.459 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with a gradient starting with 50-100% ethyl acetate/chloroform to give the title compound (0.058 g, 83% yield).

EXAMPLE 58C methyl(1S)-1-[({(1S,3S,4S)-4-{[(2S)-2-amino-3,3-dimethylbutanoyl]amino}-3-hydroxy-5-phenyl-1-[4-(2-pyridinyl)benzyl]pentyl}amino)carbonyl]-2,2-dimethylpropylcarbamate A solution containing the product from Example 58B (0.058 g, 0.078 mmol) in dichloromethane (0.5 mL) was treated with trifluoroacetic acid (0.5 mL), stirred at 25° C. for 1 hour, and concentrated. The residue was azeotroped with toluene to give the title compound as the trifluoroacetic acid salt, which was used without further purification.

EXAMPLE 58D methyl(1S)-1-[({(1S,3S,4S)-4-{[(2S)-3,3-dimethyl-2-({[(6-methyl-3-pyridinyl)oxy]acetyl}amino)butanoyl]amino}-3-hydroxy-5-phenyl-1-[4-(2-pyridinyl)benzyl]pentyl}amino)carbonyl]-2,2-dimethylpropylcarbamate A solution containing the product from Example 58C (0.03 g, 0.04 mmol) in THF (0.5 mL) was treated with the product from Example 58A (0.13 mmol), DEPBT (0.017 g, 0.12 mmol), and N,N-diisopropylethylamine (0.033 mL, 0.39 mmol), stirred at 25° C. for 18 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA) to give the title compound (0.016 g, 52% yield). $^1H$ NMR (300 MHz, DMSO-$d_6$), δ ppm 0.80 (s, 9 H), 0.83 (s, 9 H), 1.25 (m, 1 H), 1.52 (m, 2 H), 2.38 (s, 3 H), 2.71 (m, 3 H), 3.49 (s, 3 H), 3.65 (m, 1 H), 3.82 (d, J=9.93 Hz, 1 H), 4.10 (m, 2 H), 4.32 (d, J=9.56 Hz, 1 H), 4.58 (m, 2 H), 4.81 (d, J=5.88 Hz, 1 H), 6.61 (d, J=9.56 Hz, 1 H), 7.17 (m, 9 H), 7.31 (m, 1 H), 7.61 (d, J=9.56 Hz, 1 H), 7.83 (m, 6 H), 8.14 (d, J=2.94 Hz, 1 H), 8.63 (d, J=4.41 Hz, 1 H).

EXAMPLE 59 methyl(1S)-1-[({(1R,3S,4S)-4-[((2S)-3,3-dimethyl-2-{3-[(1-methyl-1H-benzimidazol-2-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate

EXAMPLE 59A 2,2-dimethoxy-N-[(1-methyl-1H-benzimidazol-2-yl)methyl]ethanamine A solution of 1-methyl-2-formylbenzimidazole (1 g) in methanol (27 mL) and acetic acid (0.54 mL) was treated with aminoacetaldehyde diethylacetal (0.9 g, 1 eq.) and NaCNBH$_3$ (0.85 g, 2 eq.) at 25° C., stirred for 1 hour. The mixture was partitioned between water and ethyl acetate. The organic phase layer was separated, washed sequentially with saturated NaHCO$_3$ and brine, and concentrated. The residue was chromatographed on silica gel, eluting with 8% methanol/dichloromethane to give the title compound (1.2 g 64% yield).

EXAMPLE 59B 9H-fluoren-9-ylmethyl 2,2-dimethoxyethyl[(1-methyl-1H-benzimidazol-2-yl)methyl]carbamate A solution of the product of Example 59A (1.2 g) in dichloromethane (30 mL) was treated with 9-fluorenylmethyl succinimide (1.6 g, 1.05 eq.) at 0° C. for 16 hours. The mixture was partitioned between water and ethyl acetate. The organic phase layer was separated, washed sequentially with 10% NaHCO$_3$ and brine, dried over Na$_2$SO$_4$, filtered and concentrated. The residue was chromatographed on silica gel, eluting with ethyl acetate: dichloromethane (1:1) to give 1.83 g (84% yield) of the title compound.

EXAMPLE 59C 9H-fluoren-9-ylmethyl(1-methyl-1H-benzimidazol-2-yl)methyl(2-oxoethyl)carbamate A solution of the product of Example 59B (0.2 g) in tetrahydrofuran (0.2 mL) was treated with 30% HCl (0.2 mL), stirred at 75° C. for 6 hours, cooled to 25° C. and concentrated. The residue was partitioned between 10% NaHCO$_3$ and ethyl acetate, the organic phase layer was separated and washed with brine, dried over Na$_2$SO$_4$, filtered and concentrated to give the title compound (175 mg).

EXAMPLE 59D tert-butyl(2S)-2-[(2-{[(9H-fluoren-9-ylmethoxy)carbonyl][(1-methyl-1H-benzimidazol-2-yl)methyl]amino}ethyl)amino]-3,3-dimethylbutanoate A solution of the product of Example 59C (0.178 g) and (1)-methyl t-leucinate hydrochloride (76.1 mg, 1 eq.) in methanol (1.7 mL) and acetic acid (17 µL) was treated with NaCNBH$_3$ (54 mg, 2 eq.) at 25° C. for 3.5 hours. The mixture was partitioned between water and ethyl acetate. The organic phase layer was separated and washed with IN NaHCO$_3$ and brine, and concentrated. The residue was chromatographed on silica gel, eluting with ethyl acetate:dichloromethane (3:1) to give 0.19 g (83% yield) of the title compound.

EXAMPLE 59E tert-butyl(2S)-3,3-dimethyl-2-{3-[(1-methyl-1H-benzimidazol-2-yl)methyl]-2-oxo-1-imidazolidinyl}butanoate A solution of the product of Example 59D (0.19 g) in N,N-dimethylformamide (3.5 mL) was treated with diethylamine (0.35 mL), stirred at 25° C. for 1.5 hours and concentrated. A solution of the residue in 1,2-dichloroethane (7 mL) was treated with bis-(p-nitrophenyl) carbonate (0.128 g, 1.2 eq.), stirred at 60° C. for 16 hours and concentrated. The residue was chromatographed on silica gel, eluting with ethyl acetate:dichloromethane (3:2) to give 80 mg (64% yield) of the title compound.

EXAMPLE 59F (2S)-3,3-dimethyl-2-{3-[(1-methyl-1H-benzimidazol-2-yl)methyl]-2-oxo-1-imidazolidinyl}butanoic acid A solution containing the product from Example 59E (0.025 g, 0.070 mmol) in a mixture of THF (0.3 mL) and water (0.3 mL) was treated with lithium hydroxide monohydrate (0.004 g, 0.094 mmol), and the mixture was stirred at 25° C. for 18 hours. The solvent was concentrated to give the crude product, which was used without purification.

EXAMPLE 59G methyl(1S)-1-[({(1R,3S,4S)-4-[((2S)-3,3-dimethyl-2-{3-[(1-methyl-1H-benzimidazol-2-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 1H (0.025 g, 0.047 mmol) in THF (0.5 mL) was treated with the product from Example 59F(0.070 mmol), DEPBT (0.021 g, 0.070 mmol), and N,N-diisopropylethylamine (0.041 mL, 0.240 mmol) and the mixture was stirred at 25° C. for 2 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The product was purified by reversed phase chromatography on a C18 column eluting with 5-100% acetonitrile in water (0.1% TFA). The reaction was partitioned between ethyl acetate and saturated NaHCO$_3$, and the organic phase was washed with brine and dried over MgSO$_4$, filtered and concentrated, to give the title compound (0.021 g, 50% yield). $^1$H NMR (300 MHz, DMSO-d$_6$), δ ppm 0.81 (s, 9 H), 0.88 (s, 9 H), 1.38 (m, 1 H), 1.53 (m, 1 H), 2.40 (m, 1 H), 2.64 (m, 3 H), 2.83 (m, 1 H), 3.12 (m, 4 H), 3.54 (m, 4 H), 3.82 (m, 3 H), 3.95 (m, 1 H), 4.03 (s, 1 H), 4.18 (m, 1 H), 4.43 (d, J=6.99 Hz, 1 H), 4.60 (m, 2 H), 6.92 (m, 4 H), 7.04 (m, 2 H), 7.21 (m, 4 H), 7.32 (m, 1 H), 7.58 (m, 3 H), 7.89 (m, 5 H), 8.65 (d, J=4.41 Hz, 1 H).

EXAMPLE 60 methyl(1S)-1-[({(1R,3S,4S)-4-[((2S)-3,3-dimethyl-2-{3-[(2-methyl-1,3-thiazol-4-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 1H (0.030 g, 0.056 mmol) in THF (0.5 mL) was treated with the product from Example 14B (0.023 g, 0.073 mmol), DEPBT (0.025 g, 0.085 mmol), and N,N-diisopropylethylamine (0.049 mL, 0.282 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by elution with 0-5% methanol in ethyl acetate to give the title compound (0.044 g, 94% yield). $^1$H NMR (300 MHz, DMSO-d$_6$), δ ppm 0.80 (s, 9 H), 0.89 (m, 9 H), 1.38 (m, 1 H), 1.53 (m, 1 H), 2.43 (m, 1 H), 2.63 (m, 6 H), 2.83 (m, 1 H), 3.03 (m, 2 H), 3.20 (m, 1 H), 3.53 (m, 4 H), 3.94 (m, 3 H), 4.36 (m, 4 H), 6.88 (d, J=9.56 Hz, 1 H), 7.05 (m, 5 H), 7.24 (m, 3 H), 7.32 (m, 1 H), 7.51 (d, J=9.56 Hz, 1 H), 7.89 (m, 5 H), 8.65 (d, J=4.78 Hz, 1 H).

EXAMPLE 61

3-pyridinylmethyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate

EXAMPLE 61A tert-butyl(2S)-3,3-dimethyl-2-{[(3-pyridinylmethoxy)carbonyl]amino}butanoate A solution containing L-tert-leucine tert-butyl ester hydrochloride (0.20 g, 0.90 mmol) in THF (9 mL) was treated with [(3-pyridinyl)methyl](4-nitrophenyl)carbonate (0.27 g, 0.99 mmol) and triethylamine (0.38 mL, 2.73 mmol), and the mixture was stirred at 25° C. for 16 hours. The reaction mixture was partitioned between ethyl acetate and saturated NaHCO$_3$, and the organic phase was washed with brine and dried over MgSO$_4$, filtered and concentrated. The residue was chromatographed on silica gel eluting 0-66% ethyl acetate in chloroform to give the title compound (0.080 g, 28% yield).

EXAMPLE 61B (2S)-3,3-dimethyl-2-{[(3-pyridinylmethoxy)carbonyl]amino}butanoic acid A solution containing the product from Example 61A (0.017 g, 0.052 mmol) in dichloromethane (0.2 mL) was treated with trifluoroacetic acid (0.2 mL), and the mixture was stirred at 25° C. for 2 hours. The solvent was concentrated and the residue was dissolved in toluene and concentrated several times to give the title compound as the trifluoroacetic acid salt, which was used without further purification.

EXAMPLE 61C 3-pyridinylmethyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate A solution containing the product from Example 2C (0.025 g, 0.047 mmol) in THF (0.5 mL) was treated with the product from Example 61B (0.052 mmol), DEPBT (0.021 g, 0.071 mmol), and N,N-diisopropylethylamine (0.041 mL, 0.235 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-5% methanol in chloroform to give the title compound (0.024 g, 65% yield). $^1$H NMR (300 MHz, DMSO-d$_6$) δ ppm 0.79(m, 9H), 0.83(m, 9H), 1.59-1.46 (m, 2H), 2.80-2.70(m, 3H), 3.49(s, 3H), 3.69-3.60(m, 1H), 3.84-3.80(d, J=9.56 Hz, 1H), 3.96-3.93(d, J=9.93Hz, 1H), 4.22-4.00(m, 2H), 4.88-4.86(d, J=5.52 Hz, 1H), 5.14-5.04(m, 2H), 6.62-6.59(d, J=9.56 Hz, 1H), 7.03-7.00(d, J=9.93 Hz, 1H), 7.20-7.06(m, 7H), 7.33-7.28(m, 1H), 7.43-7.39(m, 1H), 7.59-7.56(d, J=9.19 Hz, 1H), 7.82-7.77(m, 2H), 7.89-7.84(m, 4H), 8.54-8.53(m, 1H), 8.64-8.60(m, 2H).

EXAMPLE 62 benzyl(1S,4S,5S,7S,10S)-4-benzyl-1,10-ditert-butyl-5-hydroxy-2,9,12-trioxo-7-[4-(2-pyridinyl)benzyl]-13-oxa-3,8,11-triazatetradec-1-ylcarbamate A solution containing the product from Example 58C (0.011 g, 0.014 mmol) in THF (0.2 mL) was treated with N-(benzyloxycarbonyloxy)succinimide (0.005 g, 0.020 mmol) and triethylamine (0.006 mL, 0.043 mmol) and the mixture was stirred at 25° C. for 3 hours. The reaction was partitioned between ethyl acetate and saturated NaHCO$_3$, and the organic phase was washed with brine and dried over MgSO$_4$, filtered and concentrated. The residue was chromatographed on silica gel eluting with 0-10% methanol in chloroform to give the title compound (0.006 g, 55% yield). $^1$H NMR (300 MHz, DMSO-d$_6$) δ ppm 0.80(m, 9H), 0.83(m, 9H), 1.59-1.46(m, 2H), 2.80-2.70(m, 3H), 3.49(s, 3H), 3.69-3.60(m, 1H), 3.84-3.80(d, J=9.56 Hz, 1H), 3.96-3.93(d, J=9.93 Hz, 1H), 4.22-4.00(m, 2H), 4.88-4.86(d, J=5.52 Hz, 1H), 5.05(s, 2H), 6.62-6.58(d, J=9.56 Hz, 1H), 6.96-6.93(d, J=9.93 Hz, 1H), 7.20-7.17(m, 8H), 7.38-7.29(m, 5H), 7.59-7.58(d, J=8.82 Hz, 1H), 7.82-7.78(m, 1H), 7.89-7.84(m, 4H), 8.64-8.63(m, 1H).

EXAMPLE 63 methyl(1S,4S,6S,7S,10S)-7-benzyl-1,10-ditert-butyl-6-hydroxy-13-methyl-2,9,12-trioxo-14-phenyl-4-[4-(2-pyridinyl)benzyl]-3,8,11,13-tetraazatetradec-1-ylcarbamate

EXAMPLE 63A methyl(2S)-3,3-dimethyl-2-{[(4-nitrophenoxy)carbonyl]amino}butanoate A solution of L-tert-leucine methyl ester hydrochloride (0.300 g, 1.65 mmol) in dichloromethane (4 mL) at 0° C. was treated with 4-nitrophenyl chloroformate (0.366, 1.82 mmol) and N-methyl morpholine (0.380 mL, 3.46 mmol), and the mixture was stirred at 25° C. for 64 hours. The reaction was partitioned between dichloromethane and saturated NaHCO$_3$, and the organic phase was washed with brine and dried over MgSO$_4$, filtered and concentrated to give the title compound (0.562 g, quantitative), which was used without further purification.

EXAMPLE 63B methyl(2S)-2-({[benzyl(methyl)amino]carbonyl}amino)-3,3-dimethylbutanoate A solution containing the product from Example 63A (0.075 g, 0.242 mmol) in toluene (0.5 mL) was treated with N-benzylmethylamine (0.035 mL, 2.71 mmol), and the mixture was stirred at 80° C. for 1 hour. The reaction was partitioned between ethyl acetate and 10% Na$_2$CO$_3$, and the organic phase was washed with brine and dried over MgSO$_4$, filtered and concentrated. The residue was chromatographed on silica gel eluting with 0-20% ethyl acetate in dichloromethane to give the title compound (0.046 g, 65% yield).

EXAMPLE 63C (2S)-2-({[benzyl(methyl)amino]carbonyl}amino)-3,3-dimethylbutanoic acid A solution containing the product from Example 63B (0.046 g, 0.057 mmol) in dioxane (1.6 mL) was treated with an aqueous solution of lithium hydroxide (0.63 mL, 0.5 N), and the mixture was stirred at 25° C. for 16 hours. An aqueous HCl solution (0.60 mL, 1N) was added, the reaction mixture was partitioned between ethyl acetate and water, and the organic phase was washed with brine and dried over MgSO$_4$, filtered and concentrated to give the crude product, which was used without further purification.

EXAMPLE 63D methyl(1S,4S,6S,7S,10S)-7-benzyl-1,10-ditert-butyl-6-hydroxy-13-methyl-2,9,12-trioxo-14-phenyl-4-[4-(2-pyridinyl)benzyl]-3,8,11,13-tetraazatetradec-1-ylcarbamate A solution containing the product from Example 2C (0.020 g, 0.038 mmol) in THF (0.4 mL) was treated with the product from Example 63C (0.013 g, 0.047 mmol), DEPBT (0.017 g, 0.057 mmol), and N,N-diisopropylethylamine (0.035 mL, 0.201 mmol) and the mixture was stirred at 25° C. for 45 minutes. The mixture was partitioned between ethyl acetate and 10% Na$_2$CO$_3$ solution. The organic phase was washed with additional 10% Na₂CO₃ solution and brine, dried over MgSO₄, filtered and concentrated. The residue was chromatographed on silica gel eluting with 0-100% ethyl acetate/dichloromethane to give the title compound (0.017 g, 57% yield). ¹H NMR (300 MHz, DMSO-d) δ ppm 0.80(s, 9H), 0.81(s, 9H), 1.58-1.49(m, 2H), 2.74-2.72(m, 3H), 2.79(s, 3H), 3.49(s, 3H), 3.67-3.61(m, 1H), 3.84-3.81(d, J=9.93 Hz, 1H), 4.12-3.99(m, 1H), 4.16-4.13(d, J=8.82 Hz, 2H), 4.44(s, 2H), 4.82-4.80(d, J=5.88 Hz, 1H), 5.40-5.37(d, J=9.19 Hz, 1H), 6.62-6.59(d, J=9.93 Hz, 1H), 7.35-7.10(m, 13H), 7.67-7.64(d, J=8.82 Hz, 1H), 7.82-7.77(m, 1H), 7.88-7.84(m, 4H), 8.63 (d, J=4.41 Hz, 1 H).

EXAMPLE 64 methyl(1S,4R,6S,7S,10S)-7-benzyl-1,10-ditert-butyl-6-hydroxy-13-methyl-2,9,12-trioxo-14-phenyl-4-[4-(2-pyridinyl)benzyl]-3,8,11,13-tetraazatetradec-1-ylcarbamate A solution containing the product from Example 1H (0.020 g, 0.038 mmol) in THF (0.4 mL) was treated with the product from Example 63C (0.013 g, 0.047 mmol), DEPBT (0.017 g, 0.057 mmol), and N,N-diisopropylethylamine (0.035 mL, 0.201 mmol) and the mixture was stirred at 25° C. for 16 hours. The mixture was partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane to give the title compound (0.022 g, 74% yield). ¹H NMR (300 MHz, DMSO-d₆) δ ppm 0.75(m, 9H), 0.78(m, 9H), 1.35-1.22(m, 1H), 1.65-1.54(m, 1H), 2.77-2.60 (m, 4H), 2.79(s, 3H), 3.57(s, 3H), 3.83-3.77(m, 1H), 3.94-3.83(m, 1H), 4.09-4.06(d, J=8.82 Hz, 1H), 4.21-4.10(m, 1H), 4.51-4.38(m, 2H), 4.77-4.75(d, J=5.52 Hz, 1H), 5.43-5.40(d, J=8.82 Hz, 1H), 6.85-6.82(d, J=9.52 Hz, 1H), 7.26-7.10(m, 10H), 7.35-7.30(m, 1H). 3H), 7.60-7.57(d, J=9.19, 1H), 7.79-7.77(d, J=7.72 Hz, 1H), 7.93-7.82(m, 4H), 8.65-8.62(m, 1H).

EXAMPLE 65 methyl(1S)-1-[({(1S,3S,4S)-4-({(2S)-3,3-dimethyl-2-[3-(2-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate

EXAMPLE 65A (2S)-3,3-dimethyl-2-[3-(2-methylbenzyl)-2-oxo-1-imidazolidinyl]butanoic acid A solution containing the product from Example 6F (0.150 g, 0.65 mmol) in a mixture of toluene (2.5 mL) and methanol (2.5 mL) was treated with o-tolualdehyde (0.081 mL, 0.687 mmol), and the mixture was stirred at 50° C. for 18 hours. The reaction was cooled to 25° C. and sodium borohydride (0.049 g, 1.29 mmol) was added and the reaction was stirred at 25° C. for 1 hour. The reaction mixture was quenched with 1N NaHCO₃, stirred for 1 hour, and partitioned between ethyl acetate and water. The organic phase was washed with brine and dried over MgSO₄, filtered and concentrated. A solution containing the residue (0.220 g) in 1,2-dichloroethane (10 mL) was treated with N,N-disuccinimidyl carbonate (0.20 g, 0.781 mmol) and triethylamine (0.11 mL, 0.789 mmol), stirred at 25° C. for 68 hours, and partitioned with 10% Na₂CO₃, and the aqueous was extracted with additional dichloromethane. The organic phase was dried over MgSO₄, filtered and concentrated. A solution containing the concentrate (0.245 g) in dichloromethane (2.5 mL) was treated with trifluoracetic acid (2.5 mL), stirred at 25° C. for 2 hours and concentrated to give the title compound, which was used without further purification.

EXAMPLE 65B methyl(1S)-1-[({(1S,3S,4S)-4-({(2S)-3,3-dimethyl-2-[3-(2-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.025 g, 0.047 mmol)in THF (0.5 mL) was treated with the product from Example 65A (0.014 g, 0.046 mmol), DEPBT (0.021 g, 0.071 mmol), and N,N-diisopropylethylamine (0.041 mL, 0.235 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was purified by reversed phase chromatography on a C18 column eluting with 5-100% acetonitrile in water (0.1% TFA). The product was partitioned between ethyl acetate and saturated NaHCO₃ solution. The organic phase was washed brine, dried over MgSO₄, filtered and concentrated to give the title compound (0.020 g, 49% yield). ¹H NMR (300 MHz, DMSO-d₆) δ ppm 0.83(m, 9H), 0.89(m, 9H), 1.62-1.48(m, 2H), 2.31(s, 3H), 2.34-2.24(m, 1H), 2.62-2.53(m, 1H), 2.68-2.65(m, 2H), 2.84-2.73(m, 2H), 2.97-2.88(m, 1H), 3.22-3.12 (m, 1H), 3.50(s, 3H), 3.70-3.62(m, 1H), 3.87-3.83(d, J=9.93 Hz, 1H), 4.08(s, 1H), 4.43-4.12(m, 4H), 4.55-4.52(d, J=7.72 Hz, 1H), 6.65-6.62(d, J=9.56 Hz, 1H), 7.01-6.99(m, 3H), 7.09-7.08(m, 2H), 7.24-7.20(m, 5H), 7.32-7.29(m, 1H), 7.49-7.46(d, J=9.56 Hz, 1H), 7.91-7.82(m, 5H), 8.64-8.63(d, J=4.41 Hz, 1H).

EXAMPLE 66 methyl(1S)-1-[({(1S,3S,4S)-4-({(2S)-3,3-dimethyl-2-[3-(3-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate

EXAMPLE 66A (2S)-3,3-dimethyl-2-[3-(3-methylbenzyl)-2-oxo-1-imidazolidinyl]butanoic acid A solution containing the product from Example 6F (0.150 g, 0.65 mmol) in a mixture of toluene (2.5 mL) and methanol (2.5 mL) was treated with m-tolualdehyde (0.080 mL, 0.692 mmol), stirred at 50° C. for 18 hours, cooled to 25° C., treated with sodium borohydride (0.049 g, 1.29 mmol), stirred at 25° C. for 1 hour, quenched with 1N NaHCO₃, stirred for 1 hour, and partitioned between ethyl acetate and water. The organic phase was washed with brine and dried over MgSO₄, filtered and concentrated. A solution of the concentrate (0.211 g) in 1,2-dichloroethane (10 mL) was treated with N,N-disuccinimidyl carbonate (0.20 g, 0.781 mmol) and triethylamine (0.11 mL, 0.789 mmol), stirred at 25° C. for 68 hours, and partitioned with 10% Na₂CO₃. The aqueous was extracted with additional chloroform. The combined organic phase was dried over MgSO$_4$, filtered and concentrated. A solution of the concentrate (0.254 g) in dichloromethane (2.5 mL) was treated with trifluoracetic acid (2.5 mL), and the mixture was stirred at 25° C. for 2 hours. The solvent was concentrated to give the title compound, which was used without further purification.

EXAMPLE 66B methyl(1S)-1-[({(1S,3S,4S)-4-({(2S)-3,3-dimethyl-2-[3-(3-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 66A (0.014 g, 0.046 mmol), DEPBT (0.021 g, 0.071 mmol), and N,N-diisopropylethylamine (0.041 mL, 0.235 mmol) and the mixture was stirred at 25° C. for 16 hours. The mixture was partitioned between ethyl acetate aid 10% Na$_2$CO$_3$ solution. The organic phase was washed with additional 10% Na$_2$CO$_3$ solution and brine, dried over MgSO$_4$, filtered and concentrated. The product was purified by reversed phase chromatography on a C18 column eluting with 5-100% acetonitrile in water (0.1% TFA). The product was partitioned between ethyl acetate and saturated NaHCO$_3$ solution. The organic phase was washed brine, dried over MgSO$_4$, filtered and concentrated to give the title compound (0.018 g, 44% yield). $^1$H NMR (300 MHz, DMSO-d$_6$) δ ppm 0.83(m, 9H), 0.89(m, 9H), 1.62-1.48(m, 2H), 2.31(s, 3H), 2.34-2.24(m, 1H), 2.62-2.53(m, 1H), 2.68-2.65(m, 2H), 2.97-2.73(m, 3H), 3.22-3.12(m, 1H), 3.50(s, 3H), 3.70-3.62(m, 1H), 3.87-3.83(d, J=9.93 Hz, 1H), 4.08(s, 1H), 4.33-4.11(m, 4H), 4.56-4.53(d, J=7.72 Hz, 1H), 6.65-6.62(d, J=9.56 Hz, 1H), 7.04-7.02(m, 3H), 7.11-7.07(m, 4H), 7.25-7.21(m, 4H), 7.33-7.28(m, 1H), 7.49-7.46(d, J=9.56 Hz, 1H), 7.91-7.82(m, 4H), 8.64-8.63(d, J=4.04 Hz, 1H).

EXAMPLE 67 methyl(1S)-1-[({(1S,2S,4S)-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate

EXAMPLE 67A benzyl(4S,5S)-5-{(2S)-2-[(tert-butoxycarbonyl)amino]-3-phenylpropyl}-2,2-dimethyl-4-[4-(3-pyridinyl)benzyl]-1,3-oxazolidine-3-carboxylate A solution containing the product from Example 23I(0.200 g, 0.283 mmol) in DMF (3 mL) was treated with LiCl (0.120 g, 2.83 mmol), dichlorobis(triphenylphosphine)palladium (II) (0.060 g, 0.085 mmol), and 3-tri-n-butylstannylpyridine (0.200 mL, 0.870 mmol), heated at 100° C. for 16 hours, cooled and partitioned between ethyl acetate and water. The organic phase was washed with brine and dried over MgSO$_4$, filtered and concentrated. The residue was chromatographed on silica gel eluting with 0-25% ethyl acetate in dichloromethane to give the title compound (0.130 g, 72% yield).

EXAMPLE 67B tert-butyl(1S,3S,4S)-4-amino-1-benzyl-3-hydroxy-5-[4-(3-pyridinyl)phenyl]pentylcarbamate A solution containing the product from Example 67A (0.130 g, 0.205 mmol) in methanol (3 mL) was treated with Pd(OH)$_2$ on carbon (0.040 g, 20% Pd by wt.) and HCl solution (0.150 mL, 4N in dioxane), stirred under a hydrogen atmosphere (balloon pressure) for 2.5 hours at 25° C., filtered through a bed of celite® and rinsed with methanol. The filtrate was concentrated to give the title compound as the hydrochloride salt.

EXAMPLE 67C tert-butyl(1S,3S,4S)-1-benzyl-3-hydroxy-4-({(2S)-2-[(methoxycarbonyl)amino]-3,3-dimethylbutanoyl}amino)-5-[4-(3-pyridinyl)phenyl]pentylcarbamate A solution containing the product from Example 67B (0.205 mmol) in THF (2 mL) was treated with the product from Example 1F (0.046 g, 0.243 mmol), DEPBT (0.10 g, 0.334 mmol), and N,N-diisopropylethylamine (0.350 mL, 2.01 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated to give the title compound (0.073 g), which was used without further purification.

EXAMPLE 67D methyl(1S)-1-[({(1S,2S,4S)-4-amino-2-hydroxy-5-phenyl-1-[4-(3-pyridinyl)benzyl]pentyl}amino)carbonyl]-2,2-dimethylpropylcarbamate A solution containing the product from Example 67C (0.073 g) in dichloromethane (5 mL) was treated with trifluoroacetic acid (5 mL) and the mixture was stirred at 25° C. for 1 hour. The solvent was concentrated and the residue was purified by reversed phase chromatography on a C18 column eluting with 5-100% acetonitrile in water (0.1% TFA) to give the title compound as the trifluoroacetic acid salt (0.073 g, 47% yield).

EXAMPLE 67E methyl(1S)-1-[({(1S,2S,4S)-4-[((2S)-3,3-dimethyl-2-{3-[(2-methyl-1,3-thiazol-4-yl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate A solution containing the product from Example 67D (0.025 g, 0.033 mmol) in THF (0.4 mL) was treated with the product from Example 14B (0.017 g, 0.039 mmol), DEPBT (0.017 g, 0.057 mmol), and N,N-diisopropylethylamine (0.060 mL, 0.344 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate to give the title compound (0.01 g). $^1$H NMR (300 MHz, DMSO-d$_6$), δ ppm 0.81 (s, 9 H), 0.86 (s, 9 H), 1.53 (m, 2 H), 2.39 (m, 2 H), 2.66 (m, 4 H), 2.77 (d, J=6.99 Hz, 2 H), 3.00 (m, 2 H), 3.19 (m, 1 H), 3.49 (s, 3 H), 3.61 (m, 1 H), 3.93 (m, 2 H), 4.32 (m, 4 H), 4.83 (d, J=5.15 Hz, 1 H), 6.81 (d, J=9.19 Hz, 1 H), 7.03 (m, 5 H), 7.21 (s, 1 H), 7.32 (d, J=8.09 Hz, 2 H), 7.46 (dd, J=7.72, 4.78 Hz, 1 H), 7.55 (m, 3 H), 7.87 (d, J=8.82 Hz, 1 H), 8.01 (d, J=8.09 Hz, 1 H), 8.53 (d, J=4.41 Hz, 1 H), 8.83 (d, J=1.84 Hz, 1 H).

EXAMPLE 68 methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-2-pyridinyl)benzyl]-5-phenylpentyl}amino)carbonyl]-2,2-dimethylpropylcarbamate

EXAMPLE 68A 2-methyl-6-(tributylstannyl)pyridine

A solution containing 2-bromo-6-methylpyridine (1.48 g, 8.63 mmol) in ether (15 mL) at −78° C. was treated with n-butyllithium (5.39 mL, 1.6 M in hexanes) dropwise, stirred at −78° C. for 1 hour, treated with tributyltin chloride (4.21 mL, 12.94 mmol), stirred at −78° C. for 4 hours, quenched with saturated ammonium chloride solution, and partitioned between ether and water. The organic phase was washed with brine and dried over MgSO$_4$, filtered and concentrated. The residue was purified by chromatography on neutral alumina eluting with 10% ethyl acetate in dichloromethane to give the title compound.

EXAMPLE 68B benzyl(4S,5S)-5-{(2S)-2-[(tert-butoxycarbonyl)amino]-3-phenylpropyl}-2,2-dimethyl-4-[4-(6-methyl-2-pyridinyl)benzyl]-1,3-oxazolidine-3-carboxylate A solution containing the product from Example 23I (0.113 g, 0.160 mmol) in DMF (1.5 mL) was treated with LiCl (0.068 g, 1.60 mmol), dichlorobis(triphenylphosphine)palladium(II) (0.034 g, 0.048 mmol), and the product from Example 68A (0.367 g, 0.961 mmol), heated at 110° C. for 16 hours, cooled and partitioned between ethyl acetate and water. The organic phase was washed with brine and dried over MgSO$_4$, filtered and concentrated. The residue was chromatographed on silica gel eluting with 0-50% ethyl acetate in dichloromethane to give the title compound (0.102 g, 98% yield).

EXAMPLE 68C benzyl(1S,2S,4S)-4-amino-2-hydroxy-1-[4-(6-methyl-2-pyridinyl)benzyl]-5-phenylpentylcarbamate A solution containing the product from Example 68B (0.07 g, 0.108 mmol) in a mixture of THF (0.5 mL), methanol (0.3 mL), and aqueous HCl (0.5 mL, 1 N) was stirred at 50° C. for 16 hours. The solvent was removed under reduced pressure to give the title compound as the hydrochloride salt, which was used without further purification.

EXAMPLE 68D benzyl(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-2-pyridinyl)benzyl]-5-phenylpentylcarbamate A solution containing the product from Example 68C (0.108 mmol) in THF (0.5 mL) was treated with the product from Example 10D (0.048 g, 0.14 mmol), DEPBT (0.048 g, 0.162 mmol), and N,N-diisopropylethylamine (0.281 mL, 1.62 mmol), stirred at 25° C. for 3 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate to give the title compound (0.048 g, 56% yield).

EXAMPLE 68E (2S)-N-{(1S,3S,4S)-4-amino-1-benzyl-3-hydroxy-5-[4-(6-methyl-2-pyridinyl)phenyl]pentyl}-3,3-dimethyl-2-{3-[(6-methyl-2-pyridinyl)methyl]-2-oxo-1-imidazolidinyl}butanamide A solution containing the product from Example 68D (0.046 g, 0.058 mmol) in a mixture of ethyl acetate (0.25 mL) and methanol (0.25 mL) was treated with Pd(OH)$_2$ on carbon (0.012 g, 20% Pd by wt.) and HCl solution (0.058 mL, 4N in dioxane), stirred under a hydrogen atmosphere (balloon pressure) at 25° C. for 16 hours, filtered through a bed of celite® and rinsed with methanol. The solvent was concentrated to give the crude product as the hydrochloride salt, which was used without further purification.

EXAMPLE 68F methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-2-pyridinyl)benzyl]-5-phenylpentyl}amino)carbonyl]-2,2-dimethylpropylcarbamate A solution containing the product from Example 68E (0.058 mmol) in THF (0.5 mL) was treated with the product from Example 1F (0.013 g, 0.069 mmol), DEPBT (0.026 g, 0.087 mmol), and N,N-diisopropylethylamine (0.100 mL, 0.577 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate, to give the title compound (0.033 g, 69% yield). $^1$H NMR (300 MHz, DMSO-d$_6$), δ ppm 0.84 (s, 9 H), 0.87 (s, 9 H), 1.53 (m, 3 H), 2.42 (m, 5 H), 2.74 (m, 4 H), 3.05 (m, 2 H), 3.24 (m, 2 H), 3.60 (m, 4 H), 3.97 (m, 2 H), 4.19 (m, 2 H), 4.34 (m, 2 H), 4.81 (d, J=5.15 Hz, 1 H), 6.78 (d, J=9.19 Hz, 1 H), 7.02 (m, 6 H), 7.16 (m, 2 H), 7.29 (d, J=8.09 Hz, 2 H), 7.69 (m, 4 H), 7.89 (d, J=8.09 Hz, 3 H).

EXAMPLE 69 methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(3-pyridinyl)benzyl]pentyl}amino)carbonyl]-2,2-dimethylpropylcarbamate A solution containing the product from Example 67D (0.025 g, 0.033 mmol) in THF (0.4 mL) was treated with the product from Example 10D (0.016 g, 0.047 mmol), DEPBT (0.017 g, 0.057 mmol), and N,N-diisopropylethylamine (0.060 mL, 0.344 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by elution with 0.5% methanol in ethyl acetate to give the title compound (0.015 g, 56% yield). $^1$H NMR (300 MHz, DMSO-$d_6$) δ ppm 0.84(s, 9H), 0.86(s, 9H), 1.59-1.50(m, 2H), 2.48-2.35(m, 2H), 2.46(s, 3H), 2.70-2.62(m, 1H), 2.79-2.77 (m, 2H), 3.00-2.92(m, 1H), 3.13-3.02(m, 1H), 3.28-3.18(m, 1H), 3.49(s, 3H), 3.67-3.58(m, 1H), 3.95-3.93(m, 1H), 3.97 (s, 1H), 4.27-4.12(m, 2H), 4.40-4.26(m, 2H), 4.84-4.82(d, J=5.52 Hz, 1H), 6.83-6.80 (d, J=9.56 Hz, 1H), 7.05-7.02 (m, 5H), 7.16-7.14(d, J=7.72 Hz, 1H), 7.34-7.33(d, J=8.09 Hz, 2H), 7.49-7.44(dd, J=8.27, 4.96 Hz, 1H), 7.59-7.53(m, 3H), 7.70-7.65(t, J=7.54 Hz, 1H), 7.91-7.88(d, J=9.19 Hz, 1H), 8.03-7.99(m, J=6.07, 2.39 Hz, 1H), 8.55-8.53(dd, J=4.78, 1.47 Hz, 1H), 8.84-8.83(d, J=1.84 Hz, 1H).

EXAMPLE 70 methyl(1S)-1-[({(1S,2S,4S)-4-{[(2S)-2-(3-benzyl-2-oxo-1-imidazolidinyl)-3,3-dimethylbutanoyl]amino}-2-hydroxy-5-phenyl-1-[4-(3-pyridinyl)benzyl]pentyl}amino)carbonyl]-2,2-dimethylpropylcarbamate

EXAMPLE 70A (2S)-2-(3-benzyl-2-oxo-1-imidazolidinyl)-3,3-dimethylbutanoic acid A solution containing the product from Example 6F (1.0 g, 4.35 mmol) in a mixture of benzene (10 mL) and ethanol (10 mL) was treated with benzaldehyde (0.46 mL, 4.55 mmol), stirred at 70° C. for 16 hours, cooled to 25° C., treated with sodium borohydride (0.50 g, 13.22 mmol), stirred at 25° C. for 3 hours, quenched with 1N $NaHCO_3$ and stirred for 1 hour, and partitioned between ethyl acetate and saturated $NaHCO_3$. The organic phase was washed with brine and dried over $MgSO_4$, filtered and concentrated. A solution of the concentrate (4.35 mmol) in 1,2-dichloroethane (175 mL) was treated with N,N-disuccinimidyl carbonate (1.34 g, 5.23 mmol) and triethylamine (0.60 mL, 4.30 mmol), stirred at 25° C. for 16 hours, and partitioned with 10% $Na_2CO_3$. The aqueous was extracted with additional dichloromethane. The combined organic phase was dried over $MgSO_4$, filtered and concentrated. A solution of the concentrate (4.35 mmol) in dichloromethane (25 mL) was treated with trifluoracetic acid (25 mL), and the mixture was stirred at 25° C. for 2 hours. The solvent was concentrated, and the residue was purified by reversed phase chromatography on a C18 column eluting with a gradient starting with 0-100% acetonitrile/water (0.1% TFA) to give the title compound (0.76 g, 60% yield).

EXAMPLE 70B methyl(1S)-1-[({(1S,2S,4S)-4-{[(2S)-2-(3-benzyl-2-oxo-1-imidazolidinyl)-3,3-dimethylbutanoyl]amino}-2-hydroxy-5-phenyl-1-[4-(3-pyridinyl)benzyl]pentyl}amino)carbonyl]-2,2-dimethylpropylcarbamate A solution containing the product from Example 67D (0.025 g, 0.033 mmol) in THF (0.4 mL) was treated with the product from Example 70A (0.014 g, 0.048 mmol), DEPBT (0.017 g, 0.057 mmol), and N,N-diisopropylethylamine (0.060 mL, 0.344 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by elution with 0.5% methanol in ethyl acetate to give the title compound (0.013 g, 49% yield). $^1$H NMR (300 MHz, DMSO-$d_6$) δ ppm 0.83(s, 9H), 0.86(s, 9H), 1.58-1.49(m, 2H), 2.45-2.35(m, 2H), 2.70-2.60(m, 1H), 2.99-2.74(m, 4H), 3.24-3.15(m, 1H), 3.49(s, 3H), 3.67-3.58(m, 1H), 3.96-3.93(d, J=9.93 Hz, 1H), 3.97(s, 1H), 4.27-4.11(m, 2H), 4.30(s, 2H), 4.84-4.82(d, J=5.88 Hz, 1H), 6.83-6.80(d, J=9.19 Hz, 1H), 7.06-7.03(m, 5H), 7.40-7.25(m, 6H), 7.49-7.44(dd, J=8.27, 4.96 Hz, 1H), 7.58-7.52(m, 3H), 7.91-7.88(d, J=8.82 Hz, 1H), 8.03-7.99(m, 1H), 8.55-8.52(dd, J=4.78, 1.47 Hz, 1H), 8.84-8.83(d, J=2.21 Hz, 1H).

EXAMPLE 71 methyl(1S)-1-[({(1S,3S,4S)-3-hydroxy-4-({(2S)-2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate

EXAMPLE 71A (2S)-2-[3-(3-methoxybenzyl)-2-oxo-1-imidazolidinyl]-3,3-dimethylbutanoic acid A solution containing the product from Example 6F (0.150 g, 0.65 mmol) in a mixture of toluene (2.5 mL) and methanol (2.5 mL) was treated with m-anisaldehyde (0.083 mL, 0.68 mmol), stirred at 50° C. for 18 hours, cooled to 25° C., treated with sodium borohydride (0.049 g, 1.29 mmol), stirred at 25° C. for 1 hour, quenched with 1N $NaHCO_3$ and stirred for 1 hour, and partitioned between ethyl acetate and water. The organic phase was washed with brine and dried over $MgSO_4$, filtered and concentrated. A solution of the concentrate (0.242 g) in 1,2-dichloroethane (10 mL) was treated with N,N-disuccinimidyl carbonate (0.20 g, 0.781 mmol) and triethylamine (0.11 mL, 0.789 mmol), stirred at 25° C. for 68 hours, and partitioned with 10% $Na_2CO_3$. The aqueous was extracted with additional chloroform. The combined organic phase was dried over $MgSO_4$, filtered and concentrated. A solution of the concentrate (0.265 g) in dichloromethane (2.5 mL) was treated with trifluoracetic acid (2.5 mL), stirred at 25° C. for 2 hours, and concentrated to give the title compound, which was used without further purification.

EXAMPLE 71B methyl(1S)-1-[({(1S,3S,4S)-3-hydroxy-4-({(2S)-2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 71A (0.020 g, 0.062 mmol), DEPBT (0.021 g, 0.071 mmol), and N,N-diisopropylethylamine (0.041 mL, 0.235 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with a gradient starting with 5-100% acetonitrile in water (0.1% TFA). The product was partitioned between ethyl acetate and saturated NaHCO$_3$ solution. The organic phase was washed brine, dried over MgSO$_4$, filtered and concentrated to give the title compound (0.024 g, 59% yield). $^1$H NMR (300 MHz, DMSO-d$_6$), δ ppm 0.83 (s, 9 H), 0.89 (s, 9 H), 1.55 (m, 2 H), 2.32 (m, 1 H), 2.80 (m, 6 H), 3.18 (m, 1 H), 3.50 (s, 3 H), 3.65 (m, 1 H), 3.74 (s, 3 H), 3.85 (d, J=9.93 Hz, 1 H), 4.20 (m, 5 H), 4.54 (d, J=7.72 Hz, 1 H), 6.63 (d, J=9.93 Hz, 1 H), 6.85 (m, 3 H), 7.08 (m, 5 H), 7.28 (m, 4 H), 7.48 (d, J=9.56 Hz, 1 H), 7.86 (m, 5 H), 8.63 (d, J=4.78 Hz, 1 H).

EXAMPLE 72 methyl(1S)-1-[({(1R,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate A solution containing the product from Example 1H (0.040 g, 0.075 mmol) in THF (0.6 mL) was treated with the product from Example 70A (0.027 g, 0.092 mmol), DEPBT (0.034 g, 0.114 mmol), and N,N-diisopropylethylamine (0.066 mL, 0.379 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by elution with 0-5% methanol in ethyl acetate to give the title compound (0.045 g, 73% yield). $^1$H NMR (300 MHz, DMSO-d$_6$), δ ppm 0.80 (s, 9 H), 0.87 (s, 9 H), 1.38 (t, J=11.58 Hz, 1 H), 1.54 (m, 1 H), 2.41 (m, 1 H), 2.64 (m, 3 H), 2.87 (m, 3 H), 3.19 (m, 1 H), 3.53 (m, 4 H), 3.84 (d, J=9.56 Hz, 1 H), 3.95 (m, 1 H), 4.04 (s, 1 H), 4.18 (m, 1 H), 4.29 (m, 2 H), 4.45 (d, J=7.35 Hz, 1 H), 6.88 (d, J=9.56 Hz, 1 H), 7.05 (m, 5 H), 7.30 (m, 8 H), 7.53 (d, J=9.56 Hz, 1 H), 7.90 (m, 5 H), 8.65 (d, J=4.41 Hz, 1 H).

EXAMPLE 73 methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(4-pyridinyl)benzyl]pentyl}amino)carbonyl]-2,2-dimethylpropylcarbamate

EXAMPLE 73A benzyl(4S,5S)-5-{(2S)-2-[(tert-butoxycarbonyl)amino]-3-phenylpropyl}-2,2-dimethyl-4-[4-(4-pyridinyl)benzyl]-1,3-oxazolidine-3-carboxylate A solution containing the product from Example 23I (0.64 g, 0.906 mmol) in DMF (10 mL) was treated with LiCl (0.384 g, 9.06 mmol), dichlorobis(triphenylphosphine)palladium (II) (0.19 g, 0.271 mmol), and 4-(tri-n-butylstannyl)pyridine (1.0 g, 2.72 mmol), heated at 100° C. for 16 hours, cooled and partitioned between ethyl acetate and water. The organic phase was washed with brine and dried over MgSO$_4$, filtered and concentrated. The residue was chromatographed on silica gel eluting with 0-25% ethyl acetate in dichloromethane to give the title compound (0.28 g, 49% yield).

EXAMPLE 73B benzyl(1S,2S,4S)-4-amino-2-hydroxy-5-phenyl-1-[4-(4-pyridinyl)benzyl]pentylcarbamate A solution containing the product from Example 73A (0.28 g, 0.441 mmol) in a mixture of THF (5 mL), methanol (5 mL), and aqueous HCl (5 mL, 1 N) was stirred at 60° C. for 16 hours, and concentrated to give the title compound as the hydrochloride salt, which was used without further purification.

EXAMPLE 73C benzyl(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-5-phenyl-1-[4-(4-pyridinyl)benzyl]pentylcarbamate A solution containing the product from Example 73B (0.441 mmol) in THF (4.5 mL) was treated with the product from Example 10D (0.18 g, 0.526 mmol), DEPBT (0.20 g, 0.669 mmol), and N,N-diisopropylethylamine (0.75 mL, 4.31 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 7.5% methanol in ethyl acetate to give the title compound (0.095 g, 28% yield).

EXAMPLE 73D (2S)-N-{(1S,3S,4S)-4-amino-1-benzyl-3-hydroxy-5-[4-(4-pyridinyl)phenyl]pentyl}-3,3-dimethyl-2-{3-[(6-methyl-2-pyridinyl)methyl]-2-oxo-1-imidazolidinyl}butanamide A solution containing the product from Example 73C (0.095 g, 0.121 mmol) in methanol (1.5 mL) was treated with Pd(OH)$_2$ on carbon (0.075 g, 20% Pd by wt.) and HCl solution (0.090 mL, 4N in dioxane), stirred under a hydrogen atmosphere (balloon pressure) at 25° C. for 16 hours, filtered through a bed of celite® and rinsed with methanol. The solvent was concentrated to give the title compound as the hydrochloride salt, which was used without further purification.

EXAMPLE 73E methyl(1S)-1-[({(1S,2S,4S)-4-[((2S)-3,3-dimethyl-2-{3-[(6-methyl-]-2-oxo-1-imidazolidinyl}butanoyl)amino]-2-hydroxy-5-phenyl-1-[4-(4-pyridinyl)benzyl]pentyl}amino)carbonyl]-2,2-dimethylpropylcarbamate A solution containing the product from Example 73D (0.121 mmol) in THF (1.2 mL) was treated with the product from Example 1F (0.030 g, 0.159 mmol), DEPBT (0.055 g, 0.184 mmol), and N,N-diisopropylethylamine (0.225 mL, 2.35 mmol), stirred at 25° C. for 4 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-10% methanol in ethyl acetate, to give the title compound (0.048 g, 48% yield). $^1$H NMR (300 MHz, DMSO-d$_6$) δ ppm 0.83(s, 9H), 0.86(s, 9H), 1.59-1.50(m, 2H), 2.48-2.35(m, 2H), 2.46 (s, 3H), 2.70-2.62(m, 1H), 2.79-2.77(m, 2H), 3.00-2.92(m, 1H), 3.13-3.02(m, 1H), 3.28-3.18(m, 1H), 3.49(s, 3H), 3.67-3.58(m, 1H), 3.95-3.93(m, 1H), 3.97(s, 1H), 4.27-4.12(m, 2H), 4.40-4.26(m, 2H), 4.84-4.82(m, 1H), 6.83-6.80(d, J=9.93 Hz, 1H), 7.09-7.00(m, 5H), 7.16-7.14(d, J=7.35 Hz, 1H), 7.36-7.33(d, J=8.09 Hz, 2H), 7.74-7.53(m, 6H), 7.92-7.89(d, J=9.19 Hz, 1H), 8.62-8.60(d, J=5.88 Hz, 2H).

EXAMPLE 74 methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate

EXAMPLE 74A 5-methyl-2-(tributylstannyl)pyridine

A solution containing 2-bromo-5-methylpyridine (1.42 g, 8.23 mmol) in ether (15 mL) at −78° C. was treated with n-butyllithium (5.14 mL, 1.6 M in hexanes) dropwise, stirred at −78° C. for 1 hour, treated with tributyltin chloride (3.35 mL, 12.35 mmol), stirred at 0° C. for 4 hours, quenched with saturated ammonium chloride solution and partitioned between ether and water. The organic phase was washed with brine and dried over MgSO$_4$, filtered and concentrated. The residue was purified by chromatography on neutral alumina eluting with 10% ethyl acetate in dichloromethane to give the title compound.

EXAMPLE 74B benzyl(4S,5S)-5-{(2S)-2-[(tert-butoxycarbonyl)amino]-3-phenylpropyl}-2,2-dimethyl-4-[4-(5-methyl-2-pyridinyl)benzyl]-1,3-oxazolidine-3-carboxylate A solution containing the product from Example 23I (0.114 g, 0.162 mmol) in DMF (1.6 mL) was treated with LiCl (0.068 g, 1.60 mmol), dichlorobis(triphenylphosphine)palladium(II) (0.034 g, 0.048 mmol), and the product from Example 74A (0.367 g, 0.961 mmol), heated at 100° C. for 16 hours, cooled and partitioned between ethyl acetate and water. The organic phase was washed with brine and dried over MgSO$_4$, filtered and concentrated. The residue was chromatographed on silica gel eluting with 0-15% ethyl acetate in dichloromethane. The product was purified by reversed phase chromatography on a C18 column eluting with 5-100% acetonitrile in water (0.1% TFA) to give the title compound (0.044 g, 42% yield).

EXAMPLE 74C benzyl(1S,2S,4S)-4-amino-2-hydroxy-1-[4-(5-methyl-2-pyridinyl)benzyl]-5-phenylpentylcarbamate A solution containing the product from Example 74B (0.044 g, 0.068 mmol) in a mixture of THF (0.3 mL), methanol (0.2 mL), and aqueous HCl (0.4 mL, 1 N) was stirred at 50° C. for 16 hours. The solvent was removed under reduced pressure to give the title compound as the hydrochloride salt, which was used without further purification.

EXAMPLE 74D benzyl(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(5-methyl-2-pyridinyl)benzyl]-5-phenylpentylcarbamate A solution containing the product from Example 74C (0.068 mmol) in THF (0.5 mL) was treated with the product from Example 10D (0.030 g, 0.088 mmol), DEPBT (0.030 g, 0.102 mmol), and N,N-diisopropylethylamine (0.177 mL, 1.02 mmol), stirred at 25° C. for 3 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate to give the title compound (0.033 g, 61% yield).

EXAMPLE 74E (2S)-N-{(1S,3S,4S)-4-amino-1-benzyl-3-hydroxy-5-[4-(5-methyl-2-pyridinyl)phenyl]pentyl}-3,3-dimethyl-2-{3-[(6-methyl-2-pyridinyl)methyl]-2-oxo-1-imidazolidinyl}butanamide A solution containing the product from Example 74D (0.033 g, 0.041 mmol) in a mixture of ethyl acetate (0.25 mL) and methanol (0.25 mL) was treated with Pd(OH)$_2$ on carbon (0.009 g, 20% Pd by wt.) and HCl solution (0.041 mL, 4N in dioxane), stirred under a hydrogen atmosphere (balloon pressure) at 25° C. for 16 hours, filtered through a bed of celite® and rinsed with methanol. The solvent was concentrated to give the title compound as the hydrochloride salt, which was used without further purification.

EXAMPLE 74F methyl(1S)-1-[({(1S,2S,4S)-4-[((2S)-3,3-dimethyl-2-{3-[(6-methyl-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate A solution containing the product from Example 74E (0.041 mmol) in THF (0.5 mL) was treated with the product from Example 1F (0.010 g, 0.053 mmol), DEPBT (0.018 g, 0.061 mmol), and N,N-diisopropylethylamine (0.071 mL, 0.408 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 0-100% ethyl acetate/dichloromethane, followed by 0-5% methanol in ethyl acetate, to give the title compound (0.024 g, 70% yield). $^1$H NMR (300 MHz, DMSO-$d_6$) δ ppm 0.83(m, 9H), 0.86(m, 9H), 1.60-1.47(m, 2H), 2.32(s, 3H), 2.46-2.39 (m, 2H), 2.46(s, 3H), 2.682.64(m, 1H), 2.78-2.76(d, J=6.62 Hz, 2H), 2.99-2.91(m, 1H), 3.12-3.03(m, 1H), 3.27-3.18(m, 1H), 3.52(s, 3H), 3.65-3.57(m, 1H), 3.96-3.94(m, 2H), 4.26-4.11(m, 2H), 4.40-4.28(m, 2H), 4.84-4.82(d, J=5.52 Hz, 1H), 6.81-6.78(d, J=9.93 Hz, 1H), 7.05-7.0(m, 5H), 7.16-7.14(d, J=7.72 Hz, 1H), 7.30-7.27(d, J=8.09 Hz, 2H), 7.59-7.56(m, 1 H), 7.70-7.65 (m, 2H), 7.79-7.77(d, J=8.46 Hz, 1H), 7.91-7.86(m, 3H) 8.46(bs, 1H).

EXAMPLE 75 methyl(1S)-1-[({(1S,3S,4S)-3-hydroxy-4-({(2S)-2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate

EXAMPLE 75A (2S)-2-[3-(2-methoxybenzyl)-2-oxo-1-imidazolidinyl]-3,3-dimethylbutanoic acid A solution containing the product from Example 6F (0.150 g, 0.65 mmol) in a mixture of toluene (2.5 mL) and methanol (2.5 mL) was treated with o-anisaldehyde (0.079 mL, 0.68 mmol), and the mixture was stirred at 50° C. for 18 hours. The reaction was cooled to 25° C. and sodium borohydride (0.049 g, 1.29 mmol) was added and the reaction was stirred at 25° C. for 1 hour. The reaction was quenched with 1N $NaHCO_3$ and stirred for 1 hour. The reaction was partitioned between ethyl acetate and water, and the organic phase was washed with brine and dried over $MgSO_4$, filtered and concentrated. A solution of the concentrate (0.261 g) in 1,2-dichloroethane (10 mL) was treated with N,N-disuccinimidyl carbonate (0.20 g, 0.781 mmol) and triethylamine (0.11 mL, 0.789 mmol), and the mixture was stirred at 25° C. for 18 hours. The reaction was partitioned with 10% $Na_2CO_3$, and the aqueous was extracted with additional chloroform. The organic phase was dried over $MgSO_4$, filtered and concentrated. A solution of the concentrate (0.319 g) in dichloromethane (2.5 mL) was treated with trifluoracetic acid (2.5 mL), and the mixture was stirred at 25° C. for 1 hour. The solvent was concentrated to give the title compound (0.371 g), which was used without further purification.

EXAMPLE 75B methyl(1S)-1-[({(1S,3S,4S)-3-hydroxy-4-({(2S)-2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 75A (0.020 g, 0.062 mmol), DEPBT (0.021 g, 0.071 mmol), and N,N-diisopropylethylamine (0.041 mL, 0.235 mmol) and the mixture was stirred at 25° C. for 2 hours. The mixture was partitioned between ethyl acetate and 10% $Na_2CO_3$ solution. The organic phase was washed with additional 10% $Na_2CO_3$ solution and brine, dried over $MgSO_4$, filtered and concentrated. The product was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.024 g, 59% yield). $^1$H NMR (300 MHz, DMSO-$d_6$), δ ppm 0.83 (s, 9 H), 0.89 (s, 9 H), 1.26 (m, 1 H), 1.38 (m, 1 H), 1.54 (m, 2 H), 2.33 (m, 1 H), 2.83 (m, 5 H), 3.18 (m, 1 H), 3.50 (s, 3 H), 3.66 (m, 1 H), 3.83 (m, 4 H), 4.25 (m, 4 H), 4.53 (d, J=7.72 Hz, 1 H), 6.63 (d, J=9.93 Hz, 1 H), 6.95 (t, J=6.99 Hz, 1 H), 7.18 (m, 11 H), 7.45 (d, J=9.19 Hz, 1 H), 7.86 (m, 5 H), 8.63 (d, J=4.41 Hz, 1 H).

EXAMPLE 76 methyl(1S)-1-[({(1R,3S,4S)-4-({(2S)-3,3-dimethyl-2-[3-(2-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 65A (0.023 g, 0.076 mmol), DEPBT (0.017 g, 0.057 mmol), and N,N-diisopropylethylamine (0.033 mL, 0.189 mmol) and the mixture was stirred at 25° C. for 2 hours. The mixture was partitioned between ethyl acetate and 10% $Na_2CO_3$ solution. The organic phase was washed with additional 10% $Na_2CO_3$ solution and brine, dried over $MgSO_4$, filtered and concentrated. The product was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.013 g, 42% yield). $^1$H NMR (300 MHz, DMSO-$d_6$), δ ppm 0.80 (s, 9 H), 0.89 (m, 9 H), 1.46 (m, 2 H), 2.29 (s, 3 H), 2.38 (m, 1 H), 2.76 (m, 5 H), 3.22 (m, 2 H), 3.53 (m, 4 H), 3.84 (d, J=9.93 Hz, 1 H), 3.95 (m, 1 H), 4.02 (s, 1 H), 4.18 (m, 2 H), 4.41 (m, 2 H), 6.88 (d, J=9.56 Hz, 1 H), 7.04 (m, 5 H), 7.21 (m, 6 H), 7.32 (m, 1 H), 7.53 (d, J=9.56 Hz, 1 H), 7.89 (m, 5 H), 8.65 (d, J=4.04 Hz, 1 H).

EXAMPLE 77 methyl(1S)-1-[({(1R,3S,4S)-4-({(2S)-3,3-dimethyl-2-[3-(3-methylbenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 66A (0.023 g, 0.076 mmol), DEPBT (0.017 g, 0.057 mmol), and N,N-diisopropylethylamine (0.033 mL, 0.189 mmol) and the mixture was stirred at 25° C. for 2 hours. The mixture was partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.013 g, 42% yield). $^1$H NMR (300 MHz, DMSO-$d_6$), δ ppm 0.80 (s, 9 H), 0.89 (m, 9 H), 1.47 (m, 2 H), 2.28 (s, 3 H), 2.39 (m, 1 H), 2.78 (m, 6 H), 3.22 (m, 1 H), 3.54 (m, 4 H), 3.84 (d, J=9.93 Hz, 1 H), 3.93 (m, 1 H), 4.04 (s, 1 H), 4.25 (m, 3 H), 4.45 (d, J=6.99 Hz, 1 H), 6.88 (d, J=9.93 Hz, 1 H), 7.05 (m, 7 H), 7.24 (m, 4 H), 7.32 (m, 1 H), 7.54 (d, J=9.56 Hz, 1 H), 7.89 (m, 5 H), 8.65 (d, J=4.41 Hz, 1 H).

EXAMPLE 78 methyl(1S)-1-[({(1R,3S,4S)-3-hydroxy-4-({(2S)-2-[3-(2-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 75A (0.018 g, 0.056 mmol), DEPBT (0.017 g, 0.057 mmol), and N,N-diisopropylethylamine (0.033 mL, 0.189 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.016 g, 47% yield). $^1$H NMR (300 MHz, DMSO-$d_6$), δ ppm 0.80 (s, 9 H), 0.89 (m, 9 H), 1.26 (m, 1 H), 1.39 (m, 1 H), 1.54 (m, 1 H), 2.41 (m, 1 H), 2.65 (m, 2 H), 2.89 (m, 3 H), 3.20 (m, 1 H), 3.54 (m, 4 H), 3.81 (m, 4 H), 3.93 (m, 1 H), 4.02 (m, 1 H), 4.28 (m, 3 H), 4.44 (d, J=7.35 Hz, 1 H), 6.91 (m, 2 H), 7.04 (m, 6 H), 7.14 (d, J=7.35 Hz, 1 H), 7.28 (m, 4 H), 7.51 (d, J=9.93 Hz, 1 H), 7.90 (m, 5 H), 8.65 (d, J=4.04 Hz, 1 H).

EXAMPLE 79 methyl(1S)-1-[({(1R,3S,4S)-3-hydroxy-4-({(2S)-2-[3-(3-methoxybenzyl)-2-oxo-1-imidazolidinyl]-3,3-dimethylbutanoyl}amino)-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 71A (0.018 g, 0.056 mmol), DEPBT (0.017 g, 0.057 mmol), and N,N-diisopropylethylamine (0.033 mL, 0.189 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.018 g, 54% yield). $^1$H NMR (300 MHz, DMSO-$d_6$), δ ppm 0.80 (s, 9 H), 0.87 (s, 9 H), 1.25 (m, 1 H), 1.39 (m, 1 H), 1.54 (m, 1 H), 2.42 (m, 1 H), 2.64 (m, 3 H), 2.89 (m, 2 H), 3.21 (m, 1 H), 3.54 (m, 4 H), 3.72 (s, 3 H), 3.84 (d, J=9.56 Hz, 1 H), 3.96 (m, 1 H), 4.04 (s, 1 H), 4.18 (m, 1 H), 4.27 (s, 2 H), 4.44 (d, J=6.99 Hz, 1 H), 6.85 (m, 4 H), 7.06 (m, 5 H), 7.29 (m, 4 H), 7.54 (d, J=9.56 Hz, 1 H), 7.89 (m, 5 H), 8.65 (d, J=4.41 Hz, 1 H).

EXAMPLE 80 methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(4-methyl-2-pyridinyl)benzyl]-5-phenylpentyl}amino)carbonyl]-2,2-dimethylpropylcarbamate

EXAMPLE 80A 4-methyl-2-(tributylstannyl)pyridine

A solution containing 2-bromo-4-methylpyridine (1.46 g, 8.49 mmol) in ether (15 mL) at −78° C. was treated with n-butyllithium (5.57 mL, 1.6 M in hexanes) dropwise, stirred at −78° C. for 1 hour, treated with tributyltin chloride (3.45 mL, 12.74 mmol), stirred at 0° C. for 4 hours, quenched with saturated ammonium chloride solution and partitioned between ether and water. The organic phase was washed with brine and dried over $MgSO_4$, filtered and concentrated. The residue was purified by chromatography on neutral alumina eluting with 10% ethyl acetate in dichloromethane to give the title compound.

EXAMPLE 80B benzyl(4S,5S)-5-{(2S)-2-[(tert-butoxycarbonyl)amino]-3-phenylpropyl}-2,2-dimethyl-4-[4-(4-methyl-2-pyridinyl)benzyl]-1,3-oxazolidine-3-carboxylate A solution containing the product from Example 23I (0.183 g, 0.259 mmol) in DMF (2.6 mL) was treated with LiCl (0.110 g, 2.59 mmol), dichlorobis(triphenylphosphine)palladium(II) (0.055 g, 0.078 mmol), and the product from Example 80A (0.495 g, 1.29 mmol), heated at 100° C. for 16 hours, cooled and partitioned between ethyl acetate and water. The organic phase was washed with brine and dried over $MgSO_4$, filtered and concentrated. The residue was chromatographed on silica gel eluting with 0-10% ethyl acetate in dichloromethane, to give the title compound (0.065 g, 39% yield).

EXAMPLE 80C benzyl(1S,2S,4S)-4-amino-2-hydroxy-1-[4-(4-methyl-2-pyridinyl)benzyl]-5-phenylpentylcarbamate A solution containing the product from Example 80B (0.065 g, 0.100 mmol) in a mixture of THF (0.3 mL), methanol (0.3 mL), and aqueous HCl (0.5 mL, 1 N) was stirred at 50° C. for 16 hours. The solvent was removed under reduced pressure to give the title compound as the hydrochloride salt, which was used without further purification.

EXAMPLE 80D benzyl(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(4-methyl-2-pyridinyl)benzyl]-5-phenylpentylcarbamate A solution of the product from Example 80C (0.100 mmol) in THF (1 mL) was treated with the product from Example 10D (0.044 g, 0.13 mmol), DEPBT (0.044 g, 0.15 mmol), and N,N-diisopropylethylamine (0.261 mL, 1.5 mmol), stirred at 25° C. for 1.5 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-3% methanol in ethyl acetate to give the title compound (0.054 g, 68% yield).

EXAMPLE 80E (2S)-N-{(1S,3S,4S)-4-amino-1-benzyl-3-hydroxy-5-[4-(4-methyl-2-pyridinyl)phenyl]pentyl}-3,3-dimethyl-2-{3-[(6-methyl-2-pyridinyl)methyl]-2-oxo-1-imidazolidinyl}butanamide A solution containing the product from Example 80D (0.054 g, 0.068 mmol) in a mixture of ethyl acetate (0.3 mL) and methanol (0.3 mL) was treated with Pd(OH)$_2$ on carbon (0.014 g, 20% Pd by wt.) and HCl solution (0.068 mL, 4N in dioxane), stirred under a hydrogen atmosphere (balloon pressure) at 25° C. for 16 hours, filtered through a bed of celite® and rinsed with methanol. The solvent was concentrated to give the title compound as the hydrochloride salt, which was used without further purification.

EXAMPLE 80F methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(4-methyl-2-pyridinyl)benzyl]-5-phenylpentyl}amino)carbonyl]-2,2-dimethylpropylcarbamate A solution containing the product from Example 80E (0.068 mmol) in THF (0.65 mL) was treated with the product from Example 1F (0.017 g, 0.088 mmol), DEPBT (0.030 g, 0.102 mmol), and N,N-diisopropylethylamine (0.118 mL, 0.678 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate, to give the title compound (0.036 g, 64% yield). $^1$H NMR (300 MHz, DMSO-d$_6$), δ ppm 0.83 (s, 9 H), 0.86 (s, 9 H), 1.53 (m, 2 H), 2.42 (m, 8 H), 2.73 (m, 3 H), 3.03 (m, 2 H), 3.23 (m, 1 H), 3.52 (s, 3 H), 3.62 (m, 1 H), 3.94 (m, 2 H), 4.18 (m, 2 H), 4.34 (m, 2 H), 4.83 (d, J=5.88 Hz, 1 H), 6.79 (d, J=9.56 Hz, 1 H), 7.05 (m, 6 H), 7.16 (m, 2 H), 7.29 (d, J=8.09 Hz, 2 H), 7.58 (d, J=8.46 Hz, 1 H), 7.69 (m, 2 H), 7.90 (d, J=8.46 Hz, 3 H), 8.48 (d, J=4.78 Hz, 1 H).

EXAMPLE 81 methyl(1S)-1-[({(1S,2S,4S)-4-{[(2S)-2-(3-benzyl-2-oxo-1-imidazolidinyl)-3,3-dimethylbutanoyl]amino}-2-hydroxy-5-phenyl-1-[4-(2-pyridinyl)benzyl]pentyl}amino)carbonyl]-2,2-dimethylpropylcarbamate A solution containing the product from Example 23S (0.020 g, 0.038 mmol) in THF (0.4 mL) was treated with the product from Example 70A (0.013 g, 0.045 mmol), DEPBT (0.017 g, 0.057 mmol), and N,N-diisopropylethylamine (0.039 mL, 0.224 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by elution with 5% methanol in ethyl acetate to give the title compound (0.009 g, 30% yield). $^1$H NMR (300 MHz, CDCl$_3$), δ ppm 0.96 (s, 9 H), 1.00 (s, 9 H), 1.27 (m, 1 H), 2.62 (dd, J=13.79, 8.64 Hz, 1 H), 2.85 (m, 5 H), 3.03 (q, J=8.58 Hz, 1 H), 3.39 (m, 1 H), 3.64 (m, 4 H), 3.82 (d, J=9.19 Hz, 1 H), 3.94 (m, 1 H), 4.00 (s, 1 H), 4.11 (m, 2 H), 4.35 (m, 2 H), 5.31 (m, 1 H), 6.13 (m, 2 H), 7.10 (m, 5 H), 7.21 (m, 2 H), 7.33 (m, 7 H), 7.74 (m, 2 H), 7.89 (d, J=8.46 Hz, 2 H), 8.68 (d, J=4.78 Hz, 1 H).

EXAMPLE 82 methyl(1S)-1-[({(1S,3S,4S)-4-[((2S)-3,3-dimethyl-2-{3-[(2-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate

EXAMPLE 82A (2S)-3,3-dimethyl-2-{3-[(2-methyl-3-pyridinyl)methyl]-2-oxo-1-imidazolidinyl}butanoic acid A solution containing the product from Example 6F (0.150 g, 0.65 mmol) in a mixture of toluene (2.5 mL) and methanol (2.5 mL) was treated with the product from Example 15A (0.079 mL, 0.65 mmol), stirred at 50° C. for 18 hours, cooled to 25° C., treated with sodium borohydride (0.049 g, 1.29 mmol), stirred at 25° C. for 1 hour, quenched with 1N NaHCO$_3$, stirred for 1 hour, and partitioned between ethyl acetate and water. The organic phase was washed with brine and dried over MgSO$_4$, filtered and concentrated. A solution of the concentrate (0.214 g) in 1,2-dichloroethane (10 mL) was treated with N,N-disuccinimidyl carbonate (0.20 g, 0.781 mmol) and triethylamine (0.11 mL, 0.789 mmol), stirred at 25° C. for 16 hours, and partitioned with 10% Na$_2$CO$_3$. The aqueous was extracted with additional chloroform. The combined organic phase was dried over MgSO$_4$, filtered and concentrated. A solution of the concentrate (0.268 g) in dichloromethane (2.5 mL) was treated with trifluoroacetic acid (2.5 mL), and the mixture was stirred at 25° C. for 2 hours. The solvent was concentrated to give the title compound (0.430 g) as the trifluoroacetic acid salt, which was used without further purification.

EXAMPLE 82B methyl(1S)-1-[({(1S,3S,4S)-4-[((2S)-3,3-dimethyl-2-{3-[(2-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 2C (0.020 g, 0.038 mmol) in THF (0.4 mL) was treated with the product from Example 82A (0.025 g, 0.082 mmol), DEPBT (0.017 g, 0.057 mmol), and N,N-diisopropylethylamine (0.033 mL, 0.189 mmol) and the mixture was stirred at 25° C. for 16 hours. The mixture was partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.016 g, 52% yield). $^1$H NMR (300 MHz, DMSO-$d_6$), δ ppm 0.83 (s, 9 H), 0.89 (s, 9 H), 1.26 (m, 2 H), 1.54 (m, 2 H), 2.32 (m, 1 H), 2.61 (m, 4 H), 2.81 (m, 2 H), 2.96 (q, J=8.95 Hz, 1 H), 3.21 (m, 1 H), 3.50 (s, 3 H), 3.66 (m, 1 H), 3.85 (d, J=9.93 Hz, 1 H), 4.08 (s, 1 H), 4.21 (m, 3 H), 4.42 (m, 1 H), 4.55 (d, J=7.72 Hz, 1 H), 6.65 (d, J=9.93 Hz, 1 H), 7.00 (m, 3 H), 7.10 (m, 2 H), 7.24 (m, 3 H), 7.31 (m, 1 H), 7.54 (m, 2 H), 7.87 (m, 5 H), 8.38 (dd, J=4.78, 1.47 Hz, 1 H), 8.64 (d, J=4.41 Hz, 1 H).

EXAMPLE 83 methyl(1S)-1-[({(1S,3S,4S)-4-[((2S)-3,3-dimethyl-2-{3-[(6-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate

EXAMPLE 83A (2S)-3,3-dimethyl-2-{3-[(6-methyl-3-pyridinyl)methyl]-2-oxo-1-imidazolidinyl}butanoic acid A solution containing the product from Example 6F (0.150 g, 0.65 mmol) in a mixture of toluene (2.5 mL) and methanol (2.5 mL) was treated with the product from Example 13A (0.079 mL, 0.65 mmol), stirred at 50° C. for 16 hours, cooled to 25° C., treated with sodium borohydride (0.049 g, 1.29 mmol), stirred at 25° C. for 1 hour, quenched with 1N $NaHCO_3$ and stirred for 1 hour, and partitioned between ethyl acetate and water. The organic phase was washed with brine and dried over $MgSO_4$, filtered and concentrated. A solution of the concentrate (0.194 g) in 1,2-dichloroethane (10 mL) was treated with N,N-disuccinimidyl carbonate (0.20 g, 0.781 mmol) and triethylamine (0.11 mL, 0.789 mmol), stirred at 25° C. for 16 hours, and partitioned with 10% $Na_2CO_3$. The aqueous was extracted with additional chloroform. The combined organic phase was dried over $MgSO_4$, filtered and concentrated. A solution of the concentrate (0.223 g) in dichloromethane (2.5 mL) was treated with trifluoroacetic acid (2.5 mL), and the mixture was stirred at 25° C. for 2 hours. The solvent was concentrated to give the title compound (0.379 g) as the trifluoroacetic acid salt, which was used without further purification.

EXAMPLE 83B methyl(1S)-1-[({(1S,3S,4S)-4-[((2S)-3,3-dimethyl-2-{3-[(6-methyl-3-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 2C (0.020 g, 0.038 mmol) in THF (0.4 mL) was treated with the product from Example 83A (0.025 g, 0.082 mmol), DEPBT (0.017 g, 0.057 mmol), and N,N-diisopropylethylamine (0.033 mL, 0.189 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.014 g, 45% yield). $^1$H NMR (300 MHz, DMSO-$d_6$), δ ppm 0.83 (s, 9 H), 0.88 (s, 9 H), 1.25 (m, 1 H), 1.54 (m, 2 H), 2.32 (m, 1 H), 2.45 (s, 3 H), 2.63 (m, 2 H), 2.89 (m, 3 H), 3.18 (m, 1 H), 3.50 (s, 3 H), 3.66 (m, 1 H), 3.85 (d, J=9.93 Hz, 1 H), 4.13 (m, 3 H), 4.30 (s, 2 H), 4.55 (d, J=7.35 Hz 1 H), 6.65 (d, J=9.56 Hz, 1 H), 7.07 (m, 5 H), 7.28 (m, 4 H), 7.54 (m, 2 H), 7.86 (m, 5 H), 8.37 (d, J=1.84 Hz, 1 H), 8.63 (d, J=4.41 Hz, 1 H).

EXAMPLE 84 methyl(1S)-1-[({(1S,3S,4S)-4-({(2S)-3,3-dimethyl-2-[2-oxo-3-(3-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.015 g, 0.028 mmol) in THF (0.3 mL) was treated with the product from Example 20A (0.019 g, 0.047 mmol), DEPBT (0.013 g, 0.043 mmol), and N,N-diisopropylethylamine (0.025 mL, 0.144 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by reversed phase chromatography on a C18 column eluting with 5-100% acetonitrile in water (0.1% TFA). The product was partitioned between ethyl acetate and saturated $NaHCO_3$ solution. The organic phase was washed brine, dried over $MgSO_4$, filtered and concentrated to give the title compound (0.013 g, 55% yield). $^1$H NMR (300 MHz, DMSO-$d_6$), δ ppm 0.83 (s, 9 H), 0.88 (s, 9 H), 126 (m, 1 H), 1.54 (m, 2 H), 2.32 (m, 1 H), 2.77 (m, 5 H), 3.18 (m, 1 H), 3.50 (s, 3 H), 3.66 (m, 1 H), 3.85 (d, J=9.93 Hz, 1 H), 4.28 (m, 5 H), 4.55 (d, J=7.72 Hz, 1 H), 6.65 (d, J=9.93 Hz, 1 H), 7.03 (m, 2 H), 7.10 (m, 2 H), 7.22 (d, J=8.46 Hz, 2 H), 7.31 (m, 1 H), 7.41 (dd, J=7.72, 5.15 Hz, 1 H), 7.51 (d, J=9.56 Hz, 1 H), 7.68 (m, 1 H), 7.86 (m, 6 H), 8.52 (m, 2 H), 8.63 (d, J=4.41 Hz, 1 H).

EXAMPLE 85 methyl(1S)-1-[({(1S,3S,4S)-4-({(2S)-3,3-dimethyl-2-[2-oxo-3-(4-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate

EXAMPLE 85A (2S)-3,3-dimethyl-2-[2-oxo-3-(4-pyridinylmethyl)-1-imidazolidinyl]butanoic acid A solution containing the product from Example 6F (0.10 g, 0.43 mmol) in a mixture of benzene (1.6 mL) and methanol (1.66 mL) was treated with pyridine-4-carboxaldehyde (0.041 mL, 0.43 mmol), stirred at 50° C. for 18 hours, cooled to 25° C., treated with sodium borohydride (0.033 g, 0.87 mmol), stirred at 25° C. for 1 hour, quenched with saturated NaHCO$_3$, stirred for 1 hour, and partitioned between ethyl acetate and saturated NaHCO$_3$. The organic phase was washed with brine and dried over MgSO$_4$, filtered and concentrated. A solution of the concentrate (0.43 mmol) in 1,2-dichloroethane (7 mL) was treated with N,N-disuccinimidyl carbonate (0.134 g, 0.52 mmol) and triethylamine (0.07 mL, 0.50 mmol), and the mixture was stirred at 25° C. for 16 hours. The reaction was diluted with chloroform and partitioned with 10% Na$_2$CO$_3$. The organic phase was washed with brine, dried over MgSO$_4$, filtered and concentrated. A solution containing the resulting residue (0.43 mmol) in dichloromethane (2 mL) was treated with trifluoroacetic acid (2 mL), and the mixture was stirred at 25° C. for 2 hours. The solvent was concentrated, and the product was dissolved in toluene and concentrated several times to give the title compound (0.259 g), as the trifluoroacetic acid salt.

EXAMPLE 85B methyl(1S)-1-[({(1S,3S,4S)-4-({(2S)-3,3-dimethyl-2-[2-oxo-3-(4-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.015 g, 0.028 mmol) in THF (0.3 mL) was treated with the product from Example 85A (0.019 g, 0.047 mmol), DEPBT (0.013 g, 0.043 mmol), and N,N-diisopropylethylamine (0.07 mL, 0.402 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The product was partitioned between ethyl acetate and saturated NaHCO$_3$ solution. The organic phase was washed brine, dried over MgSO$_4$, filtered and concentrated to give the title compound (0.010 g, 44% yield). $^1$H NMR (300 MHz, DMSO-d$_6$), δ ppm 0.83 (s, 9 H), 0.90 (s, 9 H), 1.27 (m, 1 H), 1.55 (m, 2 H), 2.41 (m, 1 H), 2.83 (m, 5 H), 3.24 (m, 1 H), 3.50 (s, 3 H), 3.67 (m, 1 H), 3.85 (d, J=9.93 Hz, 1 H), 4.18 (m, 5 H), 4.56 (d, J=7.35 Hz, 1 H), 6.65 (d, J=9.93 Hz, 1 H), 7.11 (m, 5 H), 7.28 (m, 5 H), 7.54 (d, J=9.19 Hz, 1 H), 7.87 (m, 5 H), 8.56 (d, J=5.88 Hz, 2 H), 8.64 (d, J=4.41 Hz, 1 H).

EXAMPLE 86 methyl(1S)-1-[({(1S,3S,4S)-4-({(2S)-3,3-dimethyl-2-[2-oxo-3-(2-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate

EXAMPLE 86A (2S)-3,3-dimethyl-2-[2-oxo-3-(2-pyridinylmethyl)-1-imidazolidinyl]butanoic acid A solution containing the product from Example 6F (0.10 g, 0.43 mmol) in a mixture of benzene (1.6 mL) and methanol (1.66 mL) was treated with pyridine-2-carboxaldehyde (0.041 mL, 0.43 mmol), stirred at 50° C. for 18 hours, cooled to 25° C., treated with sodium borohydride (0.033 g, 0.87 mmol), stirred at 25° C. for 1 hour, quenched with saturated NaHCO$_3$, stirred for 1 hour, and partitioned between ethyl acetate and saturated NaHCO$_3$. The organic phase was washed with brine and dried over MgSO$_4$, filtered and concentrated. A solution of the concentrate (0.43 mmol) in 1,2-dichloroethane (7 mL) was treated with N,N-disuccinimidyl carbonate (0.134 g, 0.52 mmol) and triethylamine (0.07 mL, 0.50 mmol), stirred at 25° C. for 16 hours, diluted with chloroform and partitioned with 10% Na$_2$CO$_3$. The organic phase was washed with brine, dried over MgSO$_4$, filtered and concentrated. A solution of the concentrate (0.43 mmol) in dichloromethane (2 mL) was treated with trifluoroacetic acid (2 mL), stirred at 25° C. for 2 hours, concentrated, and azeotroped several times with toluene to give the title compound (0.201 g), as the trifluoroacetic acid salt.

EXAMPLE 86B methyl(1S)-1-[({(1S,3S,4S)-4-({(2S)-3,3-dimethyl-2-[2-oxo-3-(2-pyridinylmethyl)-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.015 g, 0.028 mmol) in THF (0.3 mL) was treated with the product from Example 85A (0.019 g, 0.047 mmol), DEPBT (0.013 g, 0.043 mmol), and N,N-diisopropylethylamine (0.025 mL, 0.144 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The product was partitioned between ethyl acetate and saturated NaHCO$_3$ solution. The organic phase was washed brine, dried over MgSO$_4$, filtered and concentrated to give the title compound (0.011 g, 48% yield). $^1$H NMR (300 MHz, DMSO-d$_6$) δ ppm 0.83(s, 9H), 0.90(s, 9H), 1.60-1.51(m, 2H), 2.44-2.35(q, J=9.07 Hz, 1H), 2.61-2.54(m, 1H), 2.69-2.66(d, J=6.99 Hz, 2H), 2.81-2.76(m, 1H), 3.01-2.94(m, 1H), 3.14-3.05(m, 1H), 3.26-3.19(m, 1H), 3.50(s, 3H), 3.70-3.62(m, 1H), 3.86-3.83 (d, J=9.56 Hz, 1H), 4.08(s, 1H), 4.25-4.11(m, 2H), 4.47-4.34 (m, 2H), 4.57-4.54(d, J=7.72 Hz, 1H), 6.65-6.63(d, J=9.17 Hz, 1H), 7.10-7.06(m, 5H), 7.26-7.21(m, 3H), 7.32-7.28(m, 2H), 7.51-7.48(d, J=9.56 Hz, 1H), 7.91-7.79(m, 6H), 8.55-8.54(d, J=3.68 Hz, 1H), 8.64-8.63(d, J=4.41 Hz, 1H).

EXAMPLE 87 methyl(1S,4S,5S,7S,10S)-7-benzyl-1,10-ditert-butyl-5-hydroxy-4-[4-(6-methyl-3-pyridinyl)benzyl]-2,9,12-trioxo-13-oxa-3,8,11-triazatetradec-1-ylcarbamate

EXAMPLE 87A 2-methyl-5-(tributylstannyl)pyridine

A solution containing 5-bromo-2-methylpyridine (1.2 g, 6.98 mmol) in ether (14 mL) at −78° C. was treated with n-butyllithium (5.2 mL, 1.6 M in hexanes) dropwise, stirred at −78° C. for 1 hour, treated with tributyltin chloride (2.25 mL, 8.30 mmol), stirred at −78° C. for 0.5 hours, and then at 0° C. for 0.5 hours. The reaction was quenched with saturated ammonium chloride solution and the reaction was partitioned between ether and water, and the organic phase was washed with brine and dried over $MgSO_4$, filtered and concentrated to give the title compound (2.97 g), which was used without further purification.

EXAMPLE 87B benzyl(4S,5S)-5-{(2S)-2-[(tert-butoxycarbonyl)amino]-3-phenylpropyl}-2,2-dimethyl-4-[4-(6-methyl-3-pyridinyl)benzyl]-1,3-oxazolidine-3-carboxylate A solution containing the product from Example 23I (0.25 g, 0.354 mmol) in DMF (3.5 mL) was treated with LiCl (0.15 g, 3.54 mmol), dichlorobis(triphenylphosphine)palladium (II) (0.075 g, 0.107 mmol), and the product from Example 87A (0.40 mL, 1.67 mmol), heated at 100° C. for 16 hours, cooled and partitioned between ethyl acetate and water. The organic phase was washed with brine and dried over $MgSO_4$, filtered and concentrated. The residue was chromatographed on silica gel eluting with 0-25% ethyl acetate in dichloromethane to give the title compound (0.193 g, 84% yield).

EXAMPLE 87C benzyl(1S,2S,4S)-4-amino-2-hydroxy-1-[4-(6-methyl-3-pyridinyl)benzyl]-5-phenylpentylcarbamate A solution containing the product from Example 87B (0.193 g, 0.297 mmol) in a mixture of THF (2 mL), methanol (2 mL), and aqueous HCl (2 mL, 1 N) was stirred at 60° C. for 16 hours. The solvent was removed under reduced pressure to give the title compound as the hydrochloride salt, which was used without further purification.

EXAMPLE 87D (2S,3S,5S)-2,5-diamino-1-[4-(6-methyl-3-pyridinyl)phenyl]-6-phenyl-3-hexanol A solution containing the product from Example 87C (0.086 g, 0.148 mmol) in methanol (1.5 mL) was treated with $Pd(OH)_2$ on carbon (0.020 g, 20% Pd by wt.) and HCl solution (0.11 mL, 4N in dioxane), stirred under a hydrogen atmosphere (balloon pressure) at 25° C. for 16 hours, filtered through a bed of celite® and rinsed with methanol. The solvent was concentrated to give the title compound as the hydrochloride salt, which was used without further purification.

EXAMPLE 87E methyl(1S,4S,5S,7S,10S)-7-benzyl-1,10-ditert-butyl-5-hydroxy-4-[4-(6-methyl-3-pyridinyl)benzyl]-2,9,12-trioxo-13-oxa-3,8,11-triazatetradec-1-ylcarbamate A solution containing the product from Example 87D (0.148 mmol) in THF (1.5 mL) was treated with the product from Example 1F (0.070 g, 0.370 mmol), DEPBT (0.14 g, 0.468 mmol), and N,N-diisopropylethylamine (0.26 mL, 1.49 mmol) and the mixture was stirred at 25° C. for 16 hours. The mixture was partitioned between ethyl acetate and 10% $Na_2CO_3$ solution. The organic phase was washed with additional 10% $Na_2CO_3$ solution and brine, dried over $MgSO_4$, filtered and concentrated. The product was purified by chromatography on silica gel eluting with 0-100% ethyl acetate/dichloromethane, followed by 0-5% methanol in ethyl acetate, to give the title compound (0.060 g, 56% yield). $^1$H NMR (300 MHz, DMSO-$d_6$) δ ppm 0.77(s, 9H), 0.83(s, 9H), 1.56-1.54(m, 2H), 2.77-2.69(m, 3H), 3.49(s, 3H), 3.54(s, 3H), 3.67-3.60(m, 1H), 3.81-3.78(d, J=9.93 Hz, 1H), 3.95-3.92(d, J=9.56 Hz, 1H), 4.16-4.02(m, 2H), 4.86-4.84(d, J=5.88 Hz, 1H), 6.64-6.61(d, J=9.93 Hz, 1H), 6.81-6.78(d, J=9.93 Hz, 1H), 7.15-7.07(m, 5H), 7.33-7.28(m, 3H), 7.52-7.49(d, J=8.09 Hz, 2H), 7.60-7.58(d, J=8.82 Hz, 1H), 7.76-7.73(d, J=8.09 Hz, 1H), 7.91-7.88(dd, J=8.09, 2.57 Hz, 1H), 8.70-8.69 (d, J=2.21 Hz, 1H).

EXAMPLE 88 methyl(1S)-1-[({(1S,2S,4S)-4-[((2S)-3,3-dimethyl-2-{3-[(6-methyl]-2-oxo-1-imidazolidinyl}butanoyl)amino]-2-hydroxy-1-[4-(6-methyl-3-pyridinyl)benzyl]-5-phenylpentyl}amino)carbonyl]-2,2-dimethylpropylcarbamate

EXAMPLE 88A benzyl(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-3-pyridinyl)benzyl]-5-phenylpentylcarbamate A solution containing the product from Example 87C (0.086 g, 0.148 mmol) in THF (1.5 mL) was treated with the product from Example 10D (0.060 g, 0.176 mmol), DEPBT (0.067 g, 0.224 mmol), and N,N-diisopropylethylamine (0.26 mL, 1.49 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 0-100% ethyl acetate/dichloromethane, followed by 0-5% methanol in ethyl acetate, to give the title compound (0.079 g, 67% yield).

EXAMPLE 88B (2S)-N-{(1S,3S,4S)-4-amino-1-benzyl-3-hydroxy-5-[4-(6-methyl-3-pyridinyl)phenyl]pentyl}-3,3-dimethyl-2-{3-[(6-methyl-2-pyridinyl)methyl]-2-oxo-1-imidazolidinyl}butanamide A solution containing the product from Example 88A (0.079 g, 0.099 mmol) in methanol (1.5 mL) was treated with Pd(OH)$_2$ on carbon (0.040 g, 20% Pd by wt.) and HCl solution (0.075 mL, 4N in dioxane), stirred under a hydrogen atmosphere (balloon pressure) at 25° C. for 16 hours, filtered through a bed of celite® and rinsed with methanol. The solvent was concentrated to give the title compound as the hydrochloride salt, which was used without further purification.

EXAMPLE 88C methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methyl-3-pyridinyl)benzyl]-5-phenylpentyl}amino)carbonyl]-2,2-dimethylpropylcarbamate A solution containing the product from Example 88B (0.099 mmol) in THF (1 mL) was treated with the product from Example 1F (0.022 g, 0.116 mmol), DEPBT (0.045 g, 0.151 mmol), and N,N-diisopropylethylamine (0.175 mL, 1.00 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate, to give the title compound (0.064 g, 77% yield). $^1$H NMR (300 MHz, DMSO-d$_6$) δ ppm 0.83(s, 9H), 0.86(s, 9H), 1.59-1.49(m, 2H), 2.46-2.34(m, 2H), 2.46 (s, 3H), 2.49(s, 3H), 2.67-2.64(m, 1H), 2.77-2.75(d, J=6.99 Hz, 2H), 2.99-2.91(m, 1H), 3.12-3.03(m, 1H), 3.26-3.17(m, 1H), 3.50(s, 3H), 3.66-3.58(m, 1H), 3.96-3.93(m, 2H), 4.25-4.13(m, 2H), 4.40-4.28(m, 2H), 4.84-4.82(d, J=5.52 Hz, 1H), 6.84-6.81(d, J=9.56 Hz, 1H), 705-7.01(m, 6H), 7.16-7.14(d, J=7.72 Hz, 1H), 7.33-7.29(dd, J=8.09, 4.04 Hz, 3H), 7.51-7.49(d, J=8.09 Hz, 2H), 7.59-7.56(d, J=8.45 Hz, 1H), 7.71-7.65(t, J=7.72 Hz, 1H), 7.91-7.88(m, 2H), 8.69(d, J=2.21 Hz, 1H).

EXAMPLE 89 methyl(1S)-1-[({(1S,2S,4S)-4-[((2S)-3,3-dimethyl-2-{3-[(2-methyl-1,3-thiazol-4-yl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate

EXAMPLE 89A tert-butyl(1S,3S,4S)-4-amino-1-benzyl-3-hydroxy-5-[4-(5-methyl-2-pyridinyl)phenyl]pentylcarbamate A solution containing the product from Example 74B (0.312 g, 0.48 mmol) in methanol (5 mL) was treated with Pd(OH)$_2$ on carbon (0.10 g, 20% Pd by wt.) and HCl solution (0.240 mL, 4N in dioxane), stirred under a hydrogen atmosphere (balloon pressure) at 25° C. for 16 hours, filtered through a bed of celite®, rinsed with methanol and concentrated. The residue was purified by reversed phase chromatography on a C18 column eluting with 5-100% acetonitrile in water (0.1% TFA) to give the title compound as the hydrochloride salt (0.178 g, 53% yield).

EXAMPLE 89B tert-butyl(1S,3S,4S)-1-benzyl-3-hydroxy-4-({(2S)-2-[(methoxycarbonyl)amino]-3,3-dimethylbutanoyl}amino)-5-[4-(5-methyl-2-pyridinyl)phenyl]pentylcarbamate A solution containing the product from Example 89A (0.178 g, 0.302 mmol) in THF (4 mL) was treated with the product from Example 1F (0.074 g, 0.393 mmol), DEPBT (0.136 g, 0.454 mmol), and N,N-diisopropylethylamine (0.527 mL, 3.02 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated to give the title compound, which was used without further purification.

EXAMPLE 89C methyl(1S)-1-[({(1S,2S,4S)-4-amino-2-hydroxy-1-[4-(5-methyl-2-pyridinyl)benzyl]-5-phenylpentyl}amino)carbonyl]-2,2-dimethylpropylcarbamate A solution containing the product from Example 89B (0.302 mmol) in dichloromethane (2.5 mL) was treated with trifluoroacetic acid (2.5 mL), stirred at 25° C. for 16 hours and concentrated. The residue was purified by reversed phase chromatography on a C18 column eluting with 5-100% acetonitrile in water (0.1% TFA). The product was partitioned between ether and dilute ammonium hydroxide, and the organic phase was dried over MgSO$_4$ filtered and concentrated to give the title compound (0.068 g, 42% yield).

EXAMPLE 89D methyl(1S)-1-[({(1S,2S,4S)-4-[((2S)-3,3-dimethyl-2-{3-[(2-methyl-1,3-thiazol-4-yl)methyl]-2-oxo-1-imidazolidinyl}butanoyl)amino]-2-hydroxy-1-[4-(5-methyl-2-pyridinyl)benzyl]-5-phenylpentyl}amino)carbonyl]-2,2-dimethylpropylcarbamate A solution containing the product from Example 89C (0.040 g, 0.073 mmol) in THF (0.7 mL) was treated with the product from Example 14B (0.030 g, 0.095 mmol), DEPBT (0.033 g, 0.110 mmol), and N,N-diisopropylethylamine (0.064 mL, 0.365 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate, to give the title compound (0.037 g, 60% yield). $^1$H NMR (300 MHz, DMSO-d$_6$) δ ppm 0.81(s, 9H), 0.86(s, 9H), 1.57-1.45(m, 2H), 2.32(s, 3H), 2.45-2.37(m, 2H), 2.64(s, 3H), 2.69-2.58(m, 1H), 2.77-2.75(m, 2H), 3.09-2.92(m, 2H), 3.26-3.17(m, 1H), 3.52(s, 3H), 3.66-3.54(m, 1H), 3.97-3.94(m, 2H), 4.23-4.07(m, 2H), 4.42-4.23(m, 2H), 4.82(bs, 1H), 6.58-6.54(J=8.09 Hz, 1H), 6.82-6.79(d, J=9.56 Hz, 1H), 7.08-6.95(m, 5H), 7.21(s, 1H), 7.29-7.27(d, J=8.09

Hz, 2H), 7.60-7.57(d, J=8.82 Hz, 1H), 7.68-7.64(dd, J=8.09, 2.21 Hz, 1H), 7.79-7.77(d, J=8.09 Hz, 1H), 7.89-7.86(d, J=8.46 Hz, 2H), 8.47-8.46(d, J=2.21 Hz, 1H),

EXAMPLE 90 methyl(1S,4S,5S,7S,10S)-7-benzyl-1,10-ditert-butyl-5-hydroxy-4-[4-(5-methyl-2-pyridinyl)benzyl]-2,9,12-trioxo-13-oxa-3,8,11-triazatetradec-1-ylcarbamate A solution containing the product from Example 89C (0.032 g, 0.059 mmol) in THF (0.5 mL) was treated with the product from Example 1F (0.014 g, 0.076 mmol), DEPBT (0.034 g, 0.114 mmol), and N,N-diisopropylethylamine (0.066 mL, 0.38 mmol) and the mixture was stirred at 25° C. for 16 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate, to give the title compound (0.028 g, 61% yield). $^1$H NMR (300 MHz, DMSO-d$_6$) δ ppm 0.77 (s, 9H), 0.83(s, 9H), 1.58-1.39(m, 2H), 2.32(s, 3H), 2.77-2.69(m, 3H), 3.51(s, 3H), 3.54(s, 3H), 3.67-3.60(m, 1H), 3.81-3.78(d, J=9.93 Hz, 1H), 3.95-3.92(d, J=9.93 Hz, 1H), 4.17-4.01(m, 2H), 4.86-4.84(d, J=5.52 Hz, 1H), 6.63-6.60(d, J=9.56 Hz, 1H), 6.78-6.75(d, J=9.93 Hz, 1H), 7.14-7.06(m, 5H), 7.29-7.26(d, J=8.46 Hz, 2H), 7.61-7.58(d, J=9.19 Hz, 1H), 7.68-7.65(m, 1H), 7.80-7.73(m, 2H), 7.90-7.87(d, J=8.09 Hz, 2H), 8.47(s, 1H).

EXAMPLE 91 methyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2-methylbutylcarbamate

EXAMPLE 91A tert-butyl(1S,2S,4S)-1-benzyl-2-hydroxy-4-({(2S,3S)-2-[(methoxycarbonyl)amino]-3-methylpentanoyl}amino)-5-[4-(2-pyridinyl)phenyl]pentylcarbamate A solution containing the product from Example 2A (0.030 g, 0.060 mmol) in THF (0.6 mL) was treated with the product from Example 5A (0.014 g, 0.074 mmol), DEPBT (0.030 g, 0.100 mmol), and N,N-diisopropylethylamine (0.050 mL, 0.287 mmol) and the mixture was stirred at 25° C. for 4 hours. The mixture was partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 33-100% ethyl acetate in chloroform to give the title compound (0.025 g, 66% yield).

EXAMPLE 91B methyl(1S,2S)-1-[({(1S,3S,4S)-4-amino-3-hydroxy-5-phenyl-1-[4-(2-pyridinyl)benzyl]pentyl}amino)carbonyl]-2-methylbutylcarbamate A solution containing the product from Example 2B (0.025 g, 0.040 mmol) in dichloromethane (1 mL) was treated with trifluoroacetic acid (1 mL) and the mixture was stirred at 25° C. for 1 hour. The solvent was concentrated and the mixture was partitioned between ethyl acetate and saturated NaHCO$_3$ solution. The organic phase was washed with brine, dried over MgSO$_4$, filtered and concentrated.

EXAMPLE 91C methyl(1S)-1-[({(1S,3S,4S)-4-[((2S)-3,3-dimethyl-2-{3-[(6-methyl-]-2-oxo-1-imidazolidinyl}butanoyl)amino]-3-hydroxy-5-phenyl-1-[4-(2-pyridinyl)benzyl]pentyl}amino)carbonyl]-2-methylbutylcarbamate A solution containing the product from Example 91B (0.040 mmol) in THF (0.4 mL) was treated with the product from Example 10D (0.016 g, 0.047 mmol), DEPBT (0.018 g, 0.060 mmol), and N,N-diisopropylethylamine (0.035 mL, 0.201 mmol) and the mixture was stirred at 25° C. for 16 hours. The mixture was partitioned between ethyl acetate and 10% NaCO$_3$ solution. The organic phase was washed with additional 10% Na$_2$CO$_3$ solution and brine, dried over MgSO$_4$, filtered and concentrated. The residue was chromatographed on silica gel eluting with 50% ethyl acetate in chloroform, followed by 5% methanol in chloroform to give the title compound (0.007 g, 22% yield). $^1$H NMR (300 MHz, DMSO-d$_6$) δ ppm 0.77-0.69(m, 6H), 0.90(s, 9H), 1.06-0.80 (m, 2H), 1.40-1.22(m, 1H), 1.67-1.48(m, 2H), 2.40-2.33(m, 1H), 2.46(s, 3H), 2.68-2.57(m, 3H), 2.82-2.70(m, 1H), 3.01-2.92(m, 1H), 3.13-3.04(m, 1H), 3.27-3.17(m, 1H), 3.52(s, 3H), 3.68-3.74(m, 1H), 3.80-3.74(m, 1H), 4.08(s, 1H), 4.25-4.11(m, 2H), 4.41-4.29(m, 2H), 4.53-4.51(d, J=7.72 Hz, 1H), 6.94-6.91(d, J=9.19 Hz, 1H), 7.17-7.03(m, 6H), 7.25-7.23(d, J=8.09 Hz, 2H), 7.33-7.29(m, 1H), 7.51-7.48(d, J=9.56 Hz, 1H), 7.71-7.66(t, J=7.72 Hz, 1H), 7.79-7.75(d, J=9.19 Hz, 1H), 7.947.85(m, 4H), 8.64-8.63(m, 1H).

EXAMPLE 92 methyl(1S,4S,5S,7S,10S)-4-benzyl-1,10-ditert-butyl-5-hydroxy-7-[4-(5-pyridinyl)benzyl]-2,9,12-trioxo-13-oxa-3,8,11-triazatetradec-1-ylcarbamate

EXAMPLE 92A ethyl(5S)-3-(4-bromobenzyl)-5-{(1S)-1-[(tert-butoxycarbonyl)amino]-2-phenylethyl}-2-oxotetrahydro-3-furancarboxylate A solution of tert-Butyl(1S)-1-[(2R)-oxiran-2-yl]-2-phenylethylcarbamate (10.0 g, 38.0 mmol) and diethyl malonate (5.8 ml, 38.2 mmol) in ethanol (30 mL) at 0° C. was treated with a solution of NaOEt (13.5 mL, 21% in ethanol) over 10 minutes. The reaction was warmed to 25° C. and stirred for 18 hours. The reaction was re-cooled to 0° C. and treated with a solution of 4-bromobenzyl bromide (9.5 g, 38.0 mmol) in ethanol (40 mL), stirred at 50° C. for 3 hours, cooled to 0° C. and adjusted to neutral pH by addition of 4N HCl. The ethanol was removed under reduced pressure and the residue was partitioned between chloroform and water. The organic phase was washed with brine and dried over MgSO$_4$, filtered and concentrated to give the title compound (22.4 g), which was used without further purification.

EXAMPLE 92B tert-butyl(1S)-1-[(2S)-4-(4-bromobenzyl)-5-oxotetrahydro-2-furanyl]-2-phenylethylcarbamate A solution of the product from Example 92A (22.4 g) in ethanol (120 mL) was treated with LiOH monohydrate (8.0 g, 190.7 mmol) solution in water (30 mL) and the mixture was stirred at 25° C. for 16 hours. The mixture was cooled to 0° C., adjusted to pH 5 by addition of 4N HCl and partitioned between dichloromethane and water. The organic phase was washed with brine and dried over $MgSO_4$, filtered and concentrated. A solution of the concentrate in toluene (400 mL) was then heated at reflux for 18 hours, cooled and concentrated to give the title compound (18.4 g), which was used without further purification.

EXAMPLE 92C (4S,5s)-2-(4-bromobenzyl)-5-[(tert-butoxycarbonyl)amino]-4-{[tert-butyl(dimethyl)silyl]oxy}-6-phenylhexanoic acid A solution containing the product from Example 92B (18.4 g) in dioxane (190 mL) was treated with sodium hydroxide solution (45 mL, 1N) for 1 hour at 25° C. The mixture was cooled to 0° C., and acidified to pH 5 using 4N HCl, and concentrated under reduced pressure. The concentrate was partitioned between chloroform and water. The organic phase layer was washed with brine, dried over $MgSO_4$, and concentrated. A solution of the residue (22 g) in dioxane (115 mL) was treated with imidazole (19 g, 279 mmol) and t-butyldimethylsilyl chloride (35 g, 232 mmol), stirred at 25° C. for 18 hours and concentrated. The residue was combined with ice, acidified with 4N HCl to pH 3, and extracted with ethyl acetate. The organic phase was washed with brine, dried over $MgSO_4$, filtered, and concentrated. A solution of the residue in a mixture of THF (180 mL), acetic acid (180 mL), and water (60 mL) was stirred for 1 hour at 25° C. and concentrated. The residue was chromatographed on silica gel eluting with 0-50% ethyl acetate in chloroform to give the title compound (14.18 g, 60% yield).

EXAMPLE 92D tert-butyl(1S,2S,4S)-1-benzyl-4-{[benzyloxycarbonyl]amino}-5-(4-bromophenyl)-2-{[tert-butyl(dimethyl)silyl]oxy}pentylcarbamate A solution of the product from Example 92C (14.1 g, 23.3 mmol) in toluene (230 mL) was treated with DPPA (10.0 mL, 46.4 mmol) and triethylamine (6.5 mL, 46.6 mmol), heated at reflux for 2 hours, treated with benzyl alcohol (7.2 mL, 69.9 mmol), heated at reflux for an additional 16 hours, cooled and concentrated. The residue was purified by chromatography on silica gel, eluting with 20% ethyl acetate in hexanes to give the higher Rf product (2.94 g, 18% yield).

EXAMPLE 92E tert-butyl(1S,2S,4R)-1-benzyl-4-{[(benzyloxy)carbonyl]amino}-5-(4-bromophenyl)-2-{[tert-butyl(dimethyl)silyl]oxy}pentylcarbamate A solution of the product from Example 92C (14.1 g, 23.3 mmol) in toluene (230 mL) was treated with diphenylphosphoryl azide (10.0 mL, 46.4 mmol) and triethylamine (6.5 mL, 46.6 mmol), heated at reflux for 2 hours, treated with benzyl alcohol (7.2 mL, 69.9 mmol), heated at reflux for an additional 16 hours, cooled and concentrated. The residue was purified by chromatography on silica gel, eluting with 20% ethyl acetate in hexanes to give the lower Rf product (3.21 g, 19% yield).

EXAMPLE 92F tert-butyl(1S,2S,4S)-1-benzyl-4-{[(benzyloxy)carbonyl]amino}-2-{[tert-butyl(dimethyl)silyl]oxy}-5-[4-(5-methyl-2-pyridinyl)phenyl]pentylcarbamate A solution containing the product from Example 92D (0.50 g, 0.703 mmol) in DMF (7 mL) was treated with LiCl (0.30 g, 7.08 mmol), dichlorobis(triphenylphosphine)palladium(II) (0.15 g, 0.213 mmol), and the product from Example 74A (0.805 g, 2.11 mmol), heated at 100° C. for 16 hours, cooled, filtered through celite®, and partitioned between ethyl acetate and water. The organic phase was washed with brine and dried over $MgSO_4$, filtered and concentrated. The residue was chromatographed on silica gel eluting with 0-20% ethyl acetate in chloroform to give the title compound (0.374 g, 74% yield).

EXAMPLE 92G tert-butyl(1S,2S,4S)-1-benzyl-4-{[(benzyloxy)carbonyl]amino}-2-hydroxy-5-[4-(5-methyl-2-pyridinyl)phenyl]pentylcarbamate The product from Example 92F (0.374 g, 0.517 mmol) was treated with TBAF solution in THF (2 mL, 1N), stirred at 25° C. for 16 hours, concentrated and partitioned between ethyl acetate and water. The organic phase was washed with brined, dried over $MgSO_4$, filtered and concentrated. The residue was chromatographed on silica gel eluting with 0-20% ethyl acetate in chloroform, to give the title compound (0.198 g, 63% yield).

EXAMPLE 92H tert-butyl(1S,2S,4S)-4-amino-1-benzyl-2-hydroxy-5-[4-(5-methyl-2-pyridinyl)phenyl]pentylcarbamate A solution containing the product from Example 92G (0.198 g, 0.325 mmol) in a mixture of methanol (1.6 mL) and ethyl acetate (1.6 mL) was treated with $Pd(OH)_2$ on carbon (0.060 g, 20% Pd by wt.) and HCl solution (0.080 mL, 4N in dioxane), stirred under a hydrogen atmosphere (balloon pressure) at 25° C. for 18 hours, filtered through a bed of celite® and rinsed with methanol. The solvent was concentrated to give the title compound as the hydrochloride salt, which was used without further purification.

EXAMPLE 92I tert-butyl(1S,2S,4S)-1-benzyl-2-hydroxy-4-({(2S)-2-[(methoxycarbonyl)amino]-3,3-dimethylbutanoyl}amino)-5-[4-(5-methyl-2-pyridinyl)phenyl]pentylcarbamate A solution containing the product from Example 92H (0.325 mmol) in THF (3.3 mL) was treated with the product from Example 1F (0.068 g, 0.360 mmol), DEPBT (0.146 g, 0.488 mmol), and N,N-diisopropylethylamine (0.28 mL, 1.61 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-80% ethyl acetate in chloroform to give the title compound (0.120 g, 56% yield).

EXAMPLE 92J methyl(1S)-1-[({(1S,3S,4S)-4-amino-3-hydroxy-1-[4-(5-methyl-2-pyridinyl)benzyl]-5-phenylpentyl}amino)carbonyl]-2,2-dimethylpropylcarbamate A solution containing the product from Example 92I (0.120 g, 0.183 mmol) in dichloromethane (1 mL) was treated with trifluoroacetic acid (1 mL), stirred at 25° C. for 1 hour. The solvent was concentrated and the mixture was partitioned between chloroform and saturated NaHCO$_3$ solution. The organic phase was washed with brine, dried over MgSO$_4$, filtered and concentrated, and the crude product (0.098 g) was used without further purification.

EXAMPLE 92K methyl(1S,4S,5S,7S,10S)-4-benzyl-1,10-ditert-butyl-5-hydroxy-7-[4-(5-methyl-2-pyridinyl)benzyl]-2,9,12-trioxo-13-oxa-3,8,11-triazatetradec-1-ylcarbamate A solution containing the product from Example 92J (0.049 g, 0.090 mmol) in THF (1 mL) was treated with the product from Example 1F (0.018 g, 0.095 mmol), DEPBT (0.040 g, 0.133 mmol), and N,N-diisopropylethylamine (0.080 mL, 0.459 mmol), stirred at 25° C. for 3 days, and partitioned between ethyl acetate and 10% Na$_2$CO$_3$ solution. The organic phase was washed with additional 10% Na$_2$CO$_3$ solution and brine, dried over MgSO$_4$, filtered and concentrated. The reaction was purified by reversed phase chromatography on a C18 column eluting with 5-100% acetonitrile in water (0.1% TFA). The product was partitioned between ethyl acetate and 10% Na$_2$CO$_3$, and the organic phase was washed with brine and dried over MgSO$_4$, filtered and concentrated to give the title compound (0.047 g, 73% yield). $^1$H NMR (300 MHz, DMSO-d$_6$) δ ppm 0.79(s, 9H), 0.82(s, 9H), 1.58-1.43(m, 2H), 2.32(s, 3H), 2.79-2.68(m, 3H), 3.49(s, 3H), 3.55(s, 3H), 3.67-3.59(m, 1H), 3.843.80(d, J=9.93 Hz, 1H), 3.92-3.89(d, J=9.93 Hz, 1H), 4.19-4.01(m, 2H), 4.87-4.85(d, J=5.88 Hz, 1H), 6.63-6.60(d, J=9.19 Hz, 1H), 6.81-6.77(d, J=9.56 Hz, 1H), 7.19-7.12(m, 5H), 7.56-7.53(d, J=8.82 Hz, 1H), 7.68-7.64(m, 1H), 7.81-7.76(m, 3H), 7.86-7.83(d, J=8.09 Hz, 2H), 8.47(bs, 1H).

EXAMPLE 93 methyl(1S)-1-[({(1S,3S,4S)-4-{[(2S)-2-(3-benzyl-2-oxo-1-imidazolidinyl)-3,3-dimethylbutanoyl]amino}-3-hydroxy-1-[4-(5-methyl-2-pyridinyl)benzyl]-5-phenylpentyl}amino)carbonyl]-2,2-dimethylpropylcarbamate A solution containing the product from Example 92J (0.050 g, 0.092 mmol) in THF (1 mL) was treated with the product from Example 70A (0.028 g, 0.097 mmol), DEPBT (0.041 g, 0.137 mmol), and N,N-diisopropylethylamine (0.080 mL, 0.459 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The product was partitioned between ethyl acetate and saturated NaHCO$_3$, and the organic phase was washed with brine and dried over MgSO$_4$, filtered and concentrated to give the title compound (0.036 g, 48% yield). $^1$H NMR (300 MHz, DMSO-d$_6$) δ ppm 0.83(s, 9H), 0.89(s, 9H), 1.60-1.49(m, 2H), 2.32(s, 3H), 2.60-2.53(m, 1H), 2.68-2.65(d, J=6.99 Hz, 2H), 2.88-2.75(m, 2H), 2.96-2.90(q, J=8.70 Hz, 1H), 3.24-3.15(m, 1H), 3.51(s, 3H), 3.71-3.61(m, 1H), 3.87-3.83(d, J=9.56 Hz, 1H), 4.09(s, 1H), 4.22-4.11 (m, 2H), 4.31(s, 2H), 4.56-4.53(d, J=7.72 Hz, 1H), 6.67-6.63(d, J=9.56 Hz, 1H), 7.08-7.02(m, 5H), 7.21-7.19(d, J=8.46 Hz, 2H), 7.31-7.26(m, 3H), 7.40-7.35(m, 2H), 7.50-7.46 (d, J=9.56 Hz, 1H), 7.68-7.64(dd, J=8.27, 2.02 Hz, 1H), 7.82-7.77(m, 2H), 7.88-7.85(d, J=8.09 Hz, 2H), 8.47-8.46(d, J=2.21 Hz, 1H).

EXAMPLE 94 methyl(1S)-1-[({(1S,2S,4R)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate

EXAMPLE 94A tert-butyl(1S,2S,4R)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentylcarbamate A solution containing the product from Example 1E (0.050 g, 0.101 mmol) in THF (1 mL) was treated with the product from Example 10D (0.034 g, 0.100 mmol), DEPBT (0.045 g, 0.151 mmol), and N,N-diisopropylethylamine (0.090 mL, 0.517 mmol), stirred at 25° C. for 4 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The product was partitioned between dichloromethane and saturated NaHCO$_3$ solution. The organic phase was washed brine, dried over MgSO$_4$, filtered and concentrated. The residue was then chromatographed on silica gel eluting with 0-10% methanol in chloroform, to give the title compound (0.042 g, 56% yield).

EXAMPLE 94B methyl(1S)-1-[({(1S,2S,4R)-1-benzyl-4-[((2S)-3,3-dimethyl-2-{3-[(6-methyl-2-pyridinyl)methyl]-2-oxo-1-imidazolidinyl}butanoyl)amino]-2-hydroxy-5-[4-(2-pyridinyl)phenyl]pentyl}amino)carbonyl]-2,2-dimethylpropylcarbamate A solution containing the product from Example 94A (0.042 g, 0.056 mmol) in dichloromethane (0.3 mL) was treated with trifluoroacetic acid (0.3 mL) and the mixture was stirred at 25° C. for 1 hour. The solvent was concentrated and the residue was dissolved in toluene and concentrated several times. A solution of the residue (0.056 mmol) in THF (0.6 mL) was treated with the product from Example 1F (0.011 g, 0.058 mmol), DEPBT (0.025 g, 0.083 mmol), and N,N-diisopropylethylamine (0.049 mL, 0.281 mmol), stirred at 25° C. for 2 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The product was partitioned between ethyl acetate and saturated NaHCO$_3$, and the organic phase was washed with brine and dried over MgSO$_4$, filtered and concentrated to give the title compound (0.023 g, 48% yield). $^1$H NMR (300 MHz, DMSO-d$_6$) δ ppm 0.77(s, 9H), 0.81(s, 9H), 1.41-1.31(m, 1H), 1.59-1.49(m, 1H), 2.43(s, 3H), 2.70-2.59(m, 3H), 2.88-2.77(m, 1H), 3.25-3.12(m, 2H), 3.53(s, 3H), 3.64-3.44(m, 2H), 3.94-3.84(m, 2H), 4.08(s, 1H), 4.19-4.10(m, 2H), 4.43-4.26(m, 2H), 6.77-6.73(d, J=9.56 Hz, 1H), 7.03-7.01(d, J=7.72 Hz, 1H), 7.18-7.09(m, 5H), 7.28-7.25(d, J=8.46 Hz, 2H), 7.34-7.30(m, 2H), 7.53-7.50(d, J=9.93 Hz, 1H), 7.65-7.60(t, J=7.72 Hz, 1H), 7.92-7.83(m, 2H), 7.97-7.95(d, J=8.09 Hz, 2H), 8.17-8.15(d, J=8.46 Hz, 1H), 8.65-8.64(d, J=4.78 Hz, 1H).

EXAMPLE 95

1:1 mixture of methyl(1R,4S,5S,7S,10S)-4-benzyl-10-tert-butyl-5-hydroxy-1-[1-methyl-1-(R)-methylsulfinyl)ethyl]-2,9,12-trioxo-7-[4-(2-pyridinyl)benzyl]-13-oxa-3,8,11-triazatetradec-1-ylcarbamate and methyl(1R,4S,5S,7S,10S)-4-benzyl-10-tert-butyl-5-hydroxy-1-[1-methyl-1-((S)-methylsulfinyl)ethyl]-2,9,12-trioxo-7-[4-(2-pyridinyl)benzyl]-13-oxa-3,8,11-triazatetradec-1-ylcarbamate A solution containing the product from Example 30B (0.015 g, 0.020 mmol)in a mixture of THF (0.15 mL), acetone (0.15 mL), and water (0.05 mL) was treated with NMO (0.003 g, 0.026 mmol) and aqueous osmium tetroxide solution (0.030 mL, 4%), was stirred for 16 hours at 25° C., and partitioned between ethyl acetate and water. The organic phase was washed with brine and dried over MgSO$_4$, filtered and concentrated. The residue was chromatographed on silica gel eluting with 0-100% ethyl acetate/dichloromethane, followed by 0-10% methanol in dichloromethane to give the title compound (0.006 g, 39% yield). $^1$H NMR (300 MHz, DMSO-d$_6$), δ ppm 0.81 (s, 9 H), 1.02 (m, 7 H), 1.50 (m, 2 H), 2.29 (s, 1 H), 2.38 (s, 2 H), 2.76 (m, 3 H), 3.50 (s, 3 H), 3.55 (s, 3 H), 3.68 (m, 1 H), 3.83 (d, J=9.93 Hz, 1 H), 4.08 (m, 2 H), 4.33 (m, 1 H), 5.01 (d, J=5.15 Hz, 1 H), 6.63 (d, J=9.56 Hz, 1 H), 7.22 (m, 9 H), 7.86 (m, 6 H), 8.63 (d, J=4.41 Hz, 1 H).

EXAMPLE 96 methyl(1S)-1-[({(1S,2S,4S)-2-hydroxy-4-[((2S)-3-methyl-2-{3-[(1-methyl-1H-benzimidazol-2-yl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate

EXAMPLE 96A tert-butyl(2S,3S)-2-[(2-{[(9H-fluoren-9-ylmethoxy)carbonyl][(1-methyl-1H-benzimidazol-2-yl)methyl]amino}ethyl)amino]-3-methylpentanoate A solution of the product of Example 59C (0.81 mmol ) and (L)-methyl iso-leucinate hydrochloride (0.182 g, 0.813 mmol) in methanol (3.2 mL) and acetic acid (0.032 mL) was treated with NaCNBH$_3$ (0.104 g, 1.65 mmol), stirred at 25° C. for 1 hour, and partitioned between water and dichloromethane. The organic phase layer was separated and washed with 1N NaHCO$_3$ and brine, dried over Na$_2$SO$_4$, filtered and concentrated. The crude product was used without further purification.

EXAMPLE 96B tert-butyl(2S,3S)-3-methyl-2-{3-[(1-methyl-1H-benzimidazol-2-yl)methyl]-2-oxo-1-imidazolidinyl}pentanoate A solution of the product of Example 96A (0.81 mmol) in N,N-dimethylformamide (5 mL) was treated with diethylamine (0.8 mL), stirred at 25° C. for 2 hours and concentrated. A solution of the residue in 1,2-dichloroethane (16 mL) was treated with bis-(p-nitrophenyl)carbonate (0.296 g, 0.973 mmol), stirred at 60° C. for 16 hours and concentrated. The residue was chromatographed on silica gel, eluting with 0-100% ethyl acetate/dichloromethane to give the title compound (0.192 g, 59% yield).

EXAMPLE 96C (2S,3S)-3-methyl-2-{3-[(1-methyl-1H-benzimidazol-2-yl)methyl]-2-oxo-1-imidazolidinyl}pentanoic acid A solution containing the product from Example 96B (0.037 g, 0.093 mmol) in dichloromethane (0.45 mL) was treated with trifluoroacetic acid (0.45 mL), stirred for 2 hours at 25° C. The solvent was concentrated and the residue was dissolve in ethyl acetate and concentrated to give the title compound as the trifluoroacetic acid salt, which was used without purification.

EXAMPLE 96D methyl(1S)-1-[({(1S,2S,4S)-2-hydroxy-4-[((2S)-3-methyl-2-{3-[(1-methyl-1H-benzimidazol-2-yl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 23S (0.020 g, 0.038 mmol) in THF (0.5 mL) was treated with the product from Example 96C (0.021 g, 0.046 mmol), DEPBT (0.017 g, 0.057 mmol), and N,N-diisopropylethylamine (0.035 mL, 0.201 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.022 g, 68% yield). $^1$H NMR (300 MHz, DMSO-d$_6$), δ ppm 0.60 (d, J=6.25 Hz, 3 H), 0.72 (t, J=7.35 Hz, 3 H), 0.85 (m, 12 H), 1.24 (m, 1 H), 1.51 (m, 2 H), 1.73 (m, 1 H), 2.67 (m, 1 H), 2.77 (d, J=6.62 Hz, 2 H), 2.89 (m, 1 H), 3.08 (m, 2 H), 3.51 (s, 3 H), 3.59 (m, 1 H), 3.77 (s, 3 H), 3.85 (d, J=11.03 Hz, 1 H), 3.94 (d, J=9.93 Hz, 1 H), 4.15 (m, 2 H), 4.59 (s, 2 H), 4.82 (d, J=5.52 Hz, 1 H), 6.80 (d, J=10.30 Hz, 1 H), 6.99 (m, 5 H), 7.24 (m, 5 H), 7.56 (m, 3 H), 7.88 (m, 5 H), 8.63 (d, J=4.41 Hz, 1 H).

EXAMPLE 97 methyl(1S)-1-[({(1S,2S,4S)-2-hydroxy-4-[((2S)-2-{3-[(2-isopropyl-1,3-thiazol-4-yl)methyl]-2-oxo-1-imidazolidinyl}-3-methylpentanoyl)amino]-5-phenyl-1-[4-(2-pyridinyl)benzyl]pentyl}amino)carbonyl]-2,2-dimethylpropylcarbamate

EXAMPLE 97A 2-isopropyl-1,3-thiazole-4-carbaldehyde

A solution containing the product from Example 56B (18 g, 90.5 mmol) in dichloromethane (100 mL) was treated with DIBAL (150 mL, 1 M in dichloromethane) dropwise at −78° C. over 2 hours, stirred at −78° C. for 2 hours, treated with acetic acid (10 mL), warmed to 25° C., treated with 10% solution of aqueous sodium potassium tartrate, stirred vigorously for 1 hour, and partitioned between dichloromethane and water. The organic phase was washed with brine and dried over $MgSO_4$, filtered and concentrated. The residue was chromatographed on silica gel eluting 0-5% ethyl acetate in dichloromethane to give the title compound (5.24 g, 40% yield).

EXAMPLE 97B tert-butyl(2S,3S)-2-{3-[(2-isopropyl-1,3-thiazol-4-yl)methyl]-2-oxo-1-imidazolidinyl}-3-methylpentanoate A solution containing the product from Example 3G (1.304 g, 5.66 mmol) in a mixture of benzene (15 mL) and methanol (15 mL) was treated with the product from Example 97A (1.05 g, 6.79 mmol), was heated at 50° C. for 3 hours, cooled to 0° C., treated with sodium borohydride (0.428 g, 11.32 mmol), stirred at 25° C. for 16 hours, quenched with sodium bicarbonate solution, and partitioned between ethyl acetate and water. The organic phase was washed with brine and dried over $MgSO_4$, filtered and concentrated. A solution of the concentrate (5.66 mmol) in toluene (30 mL) was treated with bis(4-nitrophenyl)carbonate (2.066 g, 6.79 mmol), heated at 100° C. for 16 hours, cooled and partitioned between ethyl acetate and saturated $NaHCO_3$. The organic phase was washed with brine and dried over $MgSO_4$, filtered and concentrated. The residue was chromatographed on silica gel eluting with 0-25% ethyl acetate in dichloromethane to give the title compound (1.68 g, 75% yield).

EXAMPLE 97C (2S,3S)-2-{3-[(2-isopropyl-1,3-thiazol-4-yl)methyl]-2-oxo-1-imidazolidinyl}-3-methylpentanoic acid A solution containing the product from Example 97B (1.68 g, 4.25 mmol) in dichloromethane (14 mL) was treated with trifluoroacetic acid (7 mL), was stirred at 25° C. for 2 hours, and concentrated to give the title compound as the trifluoroacetic acid salt, which was used without further purification.

EXAMPLE 97D methyl(1S)-1-[({(1S,2S,4S)-2-hydroxy-4-[((2S)-2-{3-[(2-isopropyl-1,3-thiazol-4-yl)methyl]-2-oxo-1-imidazolidinyl}-3-methylpentanoyl)amino]-5-phenyl-1-[4-(2-pyridinyl)benzyl]pentyl}amino)carbonyl]-2,2-dimethylpropylcarbamate A solution containing the product from Example 23S (0.020 g, 0.038 mmol) in THF (0.5 mL) was treated with the product from Example 97C (0.020 g, 0.044 mmol), DEPBT (0.017 g, 0.057 mmol), and N,N-diisopropylethylamine (0.035 mL, 0.201 mmol), stirred at 25° C. for 1 hour, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 0-5% methanol in ethyl acetate, to give the title compound (0.024 g, 75% yield). $^1$H NMR (300 MHz, DMSO-$d_6$), δ ppm 0.59 (d, J=6.25 Hz, 3 H), 0.72 (t, J=7.17 Hz, 3 H), 0.86 (s, 10 H), 1.28 (m, 7 H), 1.52 (m, 2 H), 1.72 (m, 1 H), 2.41 (m, 1 H), 6.25 (m, 1 H), 2.80 (m, 3 H), 3.07 (m, 4 H), 3.51 (s, 3 H), 3.59 (m, 1 H), 3.83 (d, J=11.03 Hz, 1 H), 3.94 (d, J=9.56 Hz, 1 H), 4.14 (m, 2 H), 4.33 (m, 2 H), 4.80 (d, J=5.52 Hz, 1 H), 6.79 (d, J=9.19 Hz, 1 H), 7.04 (s, 5 H), 7.22 (s, 1 H), 7.31 (m, 3 H), 7.58 (d, J=8.46 Hz, 1 H), 7.86 (m, 5 H), 8.63 (d, J=4.04 Hz, 1 H).

EXAMPLE 98 methyl(1S)-1-[({(1R,3S,4S)-3-hydroxy-4-[((2S)-3-methyl-2-{3-[(6-methyl-2-pyridinyl)methyl]-2-oxo-1-imidazolidinyl}pentanoyl)amino]-5-phenyl-1-[4-(2-pyridinyl)benzyl]pentyl}amino)carbonyl]-2,2-dimethylpropylcarbamate A solution containing the product from Example 1H (0.020 g, 0.038 mmol) in THF (0.4 mL) was treated with the product from Example 7B (0.020 g, 0.048 mmol), DEPBT (0.017 g, 0.057 mmol), and N,N-diisopropylethylamine (0.035 mL, 0.201 mmol), stirred at 25° C. for 1 hour, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 0-5% methanol in ethyl acetate, to give the title compound (0.025 g, 81% yield). $^1$H NMR (300 MHz, DMSO-$d_6$), δ ppm 0.83 (m, 16 H), 1.29 (m, 2 H), 1.55 (m, 1 H), 1.80 (m, 1 H), 2.44 (s, 3 H), 2.71 (m, 5 H), 3.09 (m, 3 H), 3.54 (m, 4 H), 3.85 (m, 3 H), 4.18 (m, 1 H), 4.33 (s, 2 H), 4.56 (d, J=6.99 Hz, 1 H), 6.88 (d, J=9.56 Hz, 1 H), 7.01 (d, J=7.35 Hz, 1 H), 7.12 (m, 6 H), 7.23 (d, J=8.09 Hz, 2 H), 7.32 (m, 2 H), 7.64 (t, J=7.72 Hz, 1 H), 7.88 (m, 5 H), 8.64 (d, J=4.78 Hz, 1 H).

EXAMPLE 99 methyl(1S)-1-[({(1S,3S,4S)-4-[((2S)-3,3-dimethyl-2-{3-[(1-methyl-1H-benzimidazol-2-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 2C (0.025 g, 0.047 mmol) in THF (0.5 mL) was treated with the product from Example 59F (0.020 g, 0.061 mmol), DEPBT (0.021 g, 0.071 mmol), and N,N-diisopropylethylamine (0.041 mL, 0.235 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The reaction was purified by reversed phase chromatography on a C18 column eluting with 5-100% acetonitrile in water (0.1% TFA). The residue was partitioned between ethyl acetate and saturated NaHCO₃, and the organic phase was washed with brine and dried over MgSO₄, filtered and concentrated to give the title compound (0.006 g, 14% yield). ¹H NMR (300 MHz, DMSO-d₆), δ ppm 0.83 (s, 9 H), 0.89 (s, 9 H), 1.26 (m, 1 H), 1.52 (m, 2 H), 2.32 (m, 1 H), 2.70 (m, 4 H), 2.98 (m, 1 H), 3.09 (m, 2 H), 3.46 (s, 1 H), 3.50 (s, 3 H), 3.81 (s, 3 H), 4.15 (m, 3 H), 4.53 (dd, J=11.40, 3.68 Hz, 2 H), 4.70 (d, J=15.44 Hz, 1 H), 6.63 (d, J=9.56 Hz, 1 H), 6.93 (m, 3 H), 7.07 (d, J=6.62 Hz, 2 H), 7.24 (m, 6 H), 7.59 (m, 3 H), 7.88 (m, 4 H), 8.63 (d, J=3.31 Hz, 1 H).

EXAMPLE 100 methyl(1S)-1-[({(1S,2S,4S)-4-[((2S)-3,3-dimethyl-2-{3-[(1-methyl-1H-benzimidazol-2-yl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate A solution containing the product from Example 23S (0.011 g, 0.021 mmol) in THF (0.3 mL) was treated with the product from Example 59F (0.007 g, 0.020 mmol), DEPBT (0.009 g, 0.030 mmol), and N,N-diisopropylethylamine (0.018 mL, 0.103 mmol), stirred at 25° C. for 3 hours, and partitioned between ethyl acetate and 10% Na₂CO₃ solution. The organic phase was washed with additional 10% Na₂CO₃ solution and brine, dried over MgSO₄, filtered and concentrated. The residue was purified by reversed phase chromatography on a C18 column eluting with 5-100% acetonitrile in water (0.1% TFA). The product was partitioned between ethyl acetate and saturated NaHCO₃, and the organic phase was washed with brine and dried over MgSO₄, filtered and concentrated to give the title compound (0.009 g, 51% yield). ¹H NMR (300 MHz, DMSO-d₆), δ ppm 0.82 (s, 9 H), 0.86 (s, 9 H), 1.27 (m, 1 H), 1.53 (m, 2 H), 2.36 (m, 2 H), 2.72 (m, 3 H), 2.98 (m, 1 H), 3.10 (m, 1 H), 3.48 (d, J=13.97 Hz, 3 H), 3.61 (m, 1 H), 3.80 (s, 3 H), 3.93 (m, 2 H), 4.16 (m, 2 H), 4.60 (m, 2 H), 4.83 (d, J=5.52 Hz, 1 H), 6.91 (m, 4 H), 7.02 (m, 2 H), 7.20 (m, 2 H), 7.29 (m, 3 H), 7.58 (m, 3 H), 7.87 (m, 5 H), 8.63 (d, J=4.78 Hz, 1 H).

EXAMPLE 101 methyl(1S)-1-[({(1S,3S,4S)-3-hydroxy-4-[((2S)-2-{3-[(2-isopropyl-1,3-thiazol-4-yl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate

EXAMPLE 101A tert-butyl(2S)-2-{3-[(2-isopropyl-1,3-thiazol-4-yl)methyl]-2-oxo-1-imidazolidinyl}-3,3-dimethylbutanoate A solution containing the product from Example 6F (0.060 g, 0.253 mmol) in a mixture of benzene (0.7 mL) and methanol (0.7 mL) was treated with the product from Example 97A (0.043 g, 0.278 mmol), heated at 50° C. for 3 hours, cooled to 0° C., treated with sodium borohydride (0.019 g, 0.506 mmol), stirred at 25° C. for 16 hours, quenched with sodium bicarbonate solution and partitioned between ethyl acetate and water. The organic phase was washed with brine and dried over MgSO₄, filtered and concentrated. A solution of the concentrate (0.253 mmol) in toluene (1.5 mL) was treated with bis(4-nitrophenyl)carbonate (0.092 g, 0.304 mmol), heated at 100° C. for 16 hours, cooled and partitioned between ethyl acetate and saturated NaHCO₃. The organic phase was washed with brine and dried over MgSO₄, filtered and concentrated. The residue was chromatographed on silica gel eluting with 0-25% ethyl acetate in dichloromethane to give the title compound (0.075 g, 75% yield).

EXAMPLE 101B (2S)-2-{3-[(2-isopropyl-1,3-thiazol-4-yl)methyl]-2-oxo-1-imidazolidinyl}-3,3-dimethylbutanoic acid A solution containing the product from Example 97B (0.075 g, 0.190 mmol) in dichloromethane (0.5 mL) was treated with trifluoracetic acid (0.5 mL), was stirred at 25° C. for 2 hours, and concentrated to give the title compound as the trifluoroacetic acid salt, which was used without further purification.

EXAMPLE 101C methyl(1S)-1-[({(1S,3S,4S)-3-hydroxy-4-[((2S)-2-{3-[(2-isopropyl-1,3-thiazol-4-yl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate A solution containing the product from Example 2C (0.020 g, 0.038 mmol) in THF (0.5 mL) was treated with the product from Example 101B (0.015 g, 0.045 mmol), DEPBT (0.017 g, 0.057 mmol), and N,N-diisopropylethylamine (0.033 mL, 0.189 mmol), stirred at 25° C. for 2 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane, followed by 0-5% methanol in ethyl acetate, to give the title compound (0.019 g, 59% yield). ¹H NMR (300 MHz, DMSO-d₆), δ ppm 0.83 (s, 9 H), 0.88 (s, 9 H), 1.31 (m, 6 H), 1.53 (m, 2 H), 2.30 (m, 1 H), 2.62 (m, 3 H), 2.79 (m, 1 H), 3.02 (m, 2 H), 3.22 (m, 2 H), 3.50 (s, 3 H), 3.66 (m, 1 H), 3.85 (d, J=9.56 Hz, 1 H), 4.20 (m, 4 H), 4.45 (m, 1 H), 4.53 (d, J=7.35 Hz, 1 H), 6.63 (d, J=9.93 Hz, 1 H), 7.03 (m, 5 H), 7.28 (m, 4 H), 7.45 (d, J=9.56 Hz, 1 H), 7.86 (m, 5 H), 8.64 (d, J=4.41 Hz, 1 H)

EXAMPLE 102 methyl(1S)-1-[({(1S,2S,4S)-2-hydroxy-4-[((2S)-2-{3-[(2-isopropyl-1,3-thiazol-4-yl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate A solution containing the product from Example 23S (0.018 g, 0.033 mmol) in THF (0.5 mL) was treated with the product from Example 101B (0.014 g, 0.041 mmol), DEPBT (0.015 g, 0.051 mmol), and N,N-diisopropylethylamine (0.030 mL, 0.171 mmol), stirred at 25° C. for 2 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane, followed by 0-5% methanol in ethyl acetate, to give the title compound (0.018 g, 62% yield). ¹H NMR (300 MHz, DMSO-d₆), δ ppm 0.81 (s, 9 H), 0.86 (s, 9 H), 1.32 (d, J=6.99 Hz, 6 H), 1.52 (m, 2 H), 2.38 (m, 2 H), 2.64 (d, J=9.93 Hz, 1 H), 2.77 (d, J=6.99

Hz, 2 H), 3.01 (m, 2 H), 3.23 (m, 2 H), 3.51 (s, 3 H), 3.61 (m, 1 H), 3.95 (m, 2 H), 4.30 (m, 4 H), 4.82 (d, J=5.52 Hz, 1 H), 6.79 (d, J=9.19 Hz, 1 H), 7.00 (m, 5 H), 7.24 (s, 1 H), 7.30 (m, 3 H), 7.58 (d, J=9.56 Hz, 1 H), 7.87 (m, 5 H), 8.63 (d, J=4.41 Hz, 1 H).

EXAMPLE 103 methyl(1S,4S,5S,7S,10S)-7-benzyl-1,10-ditert-butyl-5-hydroxy-2,9,12-trioxo-4-[4-(3-pyridinyl)benzyl]-13-oxa-3,8,11-triazatetradec-1-ylcarbamate

EXAMPLE 103A benzyl(1S,2S,4S)-4-amino-2-hydroxy-5-phenyl-1-[4-(3-pyridinyl)benzyl]pentylcarbamate A solution containing the product from Example 67A (0.059 g, 0.093 mmol) in a mixture of methanol (3 mL) and aqueous HCl (1 mL, 1 N) was stirred at 50° C. for 2 hours, and concentrated to give the title compound as the hydrochloride salt, which was used without further purification.

EXAMPLE 103B (2S,3S,5S)-2,5-diamino-6-phenyl-1-[4-(3-pyridinyl)phenyl]-3-hexanol A solution containing the product from Example 103A (0.093 mmol) in methanol (2 mL) was treated with Pd(OH)$_2$ on carbon (0.050 g, 20% Pd by wt.) and HCl solution (0.040 mL, 4N in dioxane), stirred under a hydrogen atmosphere (balloon pressure) at 25° C. for 2 hours, filtered through a bed of celite®, rinsed with methanol, and concentrated to give the title compound as the hydrochloride salt, which was used without further purification.

EXAMPLE 103C methyl(1S,4S,5S,7S,10S)-7-benzyl-1,10-ditert-butyl-5-hydroxy-2,9,12-trioxo-4-[4-(3-pyridinyl)benzyl]-13-oxa-3,8,11-triazatetradec-1-ylcarbamate A solution containing the product from Example 103B (0.093 mmol) in THF (1 mL) was treated with the product from Example 1F (0.040 g, 0.211 mmol), DEPBT (0.085 g, 0.284 mmol), and N,N-diisopropylethylamine (0.175 mL, 1.00 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate, to give the title compound (0.035 g, 55% yield). $^1$H NMR (300 MHz, DMSO-d$_6$), δ ppm 0.77 (s, 9 H), 0.83 (s, 9 H), 1.50 (m, 2 H), 2.73 (m, 4 H), 3.48 (s, 3 H), 3.54 (s, 3 H), 3.64 (m, 1 H), 3.80 (d, J=10.30 Hz, 1 H), 3.93 (d, J=9.19 Hz, 1 H), 4.12 (m, 2 H), 4.84 (d, J=5.52 Hz, 1 H), 6.61 (d, J=9.56 Hz, 1 H), 6.78 (d, J=8.82 Hz, 1 H), 7.11 (m, 5 H), 7.32 (d, J=8.09 Hz, 2 H), 7.47 (dd, J=7.72, 5.15 Hz, 1 H), 7.56 (m, 3 H), 7.73 (d, J=8.46 Hz, 1 H), 8.01 (m, 1 H), 8.54 (dd, J=4.60, 1.65 Hz, 1 H), 8.84 (d, J=1.84 Hz, 1 H).

EXAMPLE 104 methyl(1S,4S,5S,7S,10S)-7-benzyl-1,10-ditert-butyl-5-hydroxy-2,9,12-trioxo-4-[4-(4-pyridinyl)benzyl]-13-oxa-3,8,11-triazatetradec-1-ylcarbamate

EXAMPLE 104A benzyl(1S,2S,4S)-2-hydroxy-4-({(2S)-2-[(methoxycarbonyl)amino]-3,3-dimethylbutanoyl}amino)-5-phenyl-1-[4-(4-pyridinyl)benzyl]pentylcarbamate A solution containing the product from Example 73B (0.045 mmol) in THF (0.45 mL) was treated with the product from Example 1F (0.010 g, 0.053 mmol), DEPBT (0.020 g, 0.067 mmol), and N,N-diisopropylethylamine (0.080 mL, 0.459 mmol), stirred at 25° C. for 0.5 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated to give the title compound, which was used without further purification.

EXAMPLE 104B methyl(1S)-1-[({(1S,3S,4S)-4-amino-1-benzyl-3-hydroxy-5-[4-(4-pyridinyl)phenyl]pentyl}amino)carbonyl]-2,2-dimethylpropylcarbamate A solution containing the product from Example 104A (0.045 mmol) in methanol (0.5 mL) was treated with Pd(OH)$_2$ on carbon (0.010 g, 20% Pd by wt.) and HCl solution (0.035 mL, 4N in dioxane), stirred under a hydrogen atmosphere (balloon pressure) for 4 hours at 25° C., filtered through a bed of celite®, rinsed with methanol, and concentrated to give the title compound as the hydrochloride salt, which was used without further purification.

EXAMPLE 104C methyl(1S,4S,5S,7S,10S)-7-benzyl-1,10-ditert-butyl-5-hydroxy-2,9,12-trioxo-4-[4-(4-pyridinyl)benzyl]-13-oxa-3,8,11-triazatetradec-1-ylcarbamate A solution containing the product from Example 104B (0.045 mmol) in THF (0.45 mL) was treated with the product from Example 1F (0.010 g, 0.053 mmol), DEPBT (0.020 g 0.067 mmol), and N,N-diisopropylethylamine (0.080 mL, 0.459 mmol), stirred at 25° C. for 1 hour, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was purified by reversed phase chromatography on a C18 column eluting with 5-100% acetonitrile in water (0.1% TFA). The product was partitioned between ethyl acetate and saturated NaHCO$_3$, and the organic phase was washed with brine and dried over MgSO$_4$, filtered and concentrated to give the title compound (0.008 g, 25% yield). $^1$H NMR (300 MHz, DMSO-d$_6$), δ ppm 0.77 (s, 9 H), 0.82 (s, 9 H), 1.48 (m, 2 H), 2.75 (m, 4 H), 3.49 (s, 3 H), 3.54 (s, 3 H), 3.63 (m, 1 H), 3.80(d, J=9.93 Hz, 1 H), 3.93 (d, J=9.56 Hz, 1 H), 4.10 (m, 2 H), 4.85 (d, J=5.52 Hz, 1 H), 6.60 (d, J=9.19 Hz, 1 H), 6.76 (d, J=10.30 Hz, 1 H), 7.10 (m, 5 H), 7.33 (d, J=8.09 Hz, 2 H), 7.64 (m, 6 H), 8.61 (m, 2 H).

EXAMPLE 105 methyl(1S)-1-[({(1S,3S,4S)-4-[((2S)-3,3-dimethyl-2-{3-[(2-methyl-1,3-thiazol-4-yl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 2C (0.044 g, 0.082 mmol) in THF (0.7 mL) was treated with the product from Example 14B (0.033 g, 0.107 mmol), DEPBT (0.037 g, 0.124 mmol), and N,N-diisopropylethylamine (0.072 mL, 0.412 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 0-100% ethyl acetate dichloromethane, followed by 0-5% methanol in ethyl acetate, to give the title compound (0.056 g, 83% yield). $^1$H NMR (300 MHz, DMSO-$d_6$), δ ppm 0.83 (s, 9 H), 0.88 (s, 9 H), 1.54 (m, 2 H), 2.36 (q, J=9.31 Hz, 1 H), 2.61 (m, 5 H), 2.78 (m, 1 H), 3.01 (m, 2 H), 3.22 (m, 2 H), 3.50 (s, 3 H), 3.66 (m, 1 H), 3.85 (d, J=9.56 Hz, 1 H), 4.17 (m, 4 H), 4.41 (m, 1 H), 4.54 (d, J=7.35 Hz, 1 H), 6.63 (d, J=9.56 Hz, 1 H), 7.06 (m, 5 H), 7.21 (s, 1 H), 7.24 (s, 2 H), 7.31 (m, 1 H), 7.45 (d, J=9.56 Hz, 1 H), 7.87 (m, 5 H), 8.63 (d, J=4.41 Hz, 1 H).

EXAMPLE 106 methyl(1S)-1-[({(1S,2S,4S)-4-[((2S)-3,3-dimethyl-2-{3-[(2-methyl-1,3thiazol-4-yl)methyl]-2-oxo-1-imidazolidinyl}butanoyl)amino]-2-hydroxy-5-phenyl-1-[4-(2-pyridinyl)benzyl]pentyl}amino)carbonyl]-2,2-dimethylpropylcarbamate A solution containing the product from Example 23S (0.038 g, 0.071 mmol) in THF (0.7 mL) was treated with the product from Example 14B (0.029 g, 0.092 mmol), DEPBT (0.032 g, 0.107 mmol), and N,N-diisopropylethylamine (0.062 mL, 0.355 mmol) stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 0-100% ethyl acetate/dichloromethane, followed by 0-5% methanol in ethyl acetate, to give the title compound (0.041 g, 70% yield). $^1$H NMR (300 MHz, DMSO-$d_6$), δ ppm 0.81 (s, 9 H), 0.86 (s, 9 H), 1.53 (m, 2 H), 2.39 (m, 2 H), 2.64 (m, 4 H), 2.77 (d, J=6.62 Hz, 2 H), 3.00 (m, 2 H), 3.19 (m, 1 H), 3.51 (s, 3 H), 3.61 (m, 1 H), 3.96 (m, 2 H), 4.32 (m, 4 H), 4.82 (d, J=5.52 Hz, 1 H), 6.79 (d, J=9.56 Hz, 1 H), 7.04 (m, 5 H), 7.21 (s, 1 H), 7.30 (m, 3 H), 7.58 (d, J=8.82 Hz, 1 H), 7.87 (m, 5 H), 8.63 (d, J=4.78 Hz, 1 H).

EXAMPLE 107 methyl(1S)-1-[({(1S,3R,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate

EXAMPLE 107A ethyl(5R)-5-{(1S)-1-[(tert-butoxycarbonyl)amino]-2-phenylethyl}-2-oxotetrahydro-3-furancarboxylate A solution of tert-Butyl(1S)-1-[(2S)-oxiran-2-yl]-2-phenylethylcarbamate (10.0 g, 38.0 mmol) and diethyl malonate (9.0 ml, 59.3 mmol) in ethanol (27 mL) at 0° C. was treated with a solution of NaOEt (16 mL, 21% in ethanol) over 10 minutes, stirred at 70° C. for 2 hours, cooled to 0° C. and quenched with 10% citric acid solution, and partitioned between ethyl acetate and water. The organic phase was washed with saturated $NaHCO_3$ and brine, dried over $MgSO_4$, filtered and concentrated. The residue was chromatographed on silica gel eluting with 0-35% ethyl acetate in hexanes to give the title compound (13.3 g, 93% yield).

EXAMPLE 107B tert-butyl(1S)-1-{(2R)-5-oxo-4-[4-(2-pyridinyl)benzyl]tetrahydro-2-furanyl}-2-phenylethylcarbamate A solution of the product from Example 107A (13.3 g, 35.27 mmol) in ethanol (140 mL) at 0° C. was treated with a solution of NaOEt (14.9 mL, 21% in ethanol) and solid 2-[4-(bromomethyl)phenyl]pyridine (12.05 g, 48.59 mmol), stirred at 25° C. for 16 hours, treated with a solution of LiOH monohydrate (8.9 g, 212.11 mmol) in water (35 mL), stirred at 25° C. for 5 hours, cooled to 0° C., adjusted to pH 5 by addition of 10% citric acid and then partitioned between dichloromethane and water. The organic phase was washed with brine and dried over $MgSO_4$, filtered and concentrated. A solution of the concentrate in toluene (1 L) was heated at reflux for 16 hours, cooled and concentrated to give the title compound (10.55 g, 63% yield), which was used without further purification.

EXAMPLE 107C (4R,5S)-5-[(tert-butoxycarbonyl)amino]-4-{[tert-butyl(dimethyl)silyl]oxy}-6-phenyl-2-[4-(2-pyridinyl)benzyl]hexanoic acid A solution containing the product from Example 107B (10.55 g, 22.35 mmol) in a mixture of dioxane (130 mL) and water (65 mL) was treated with sodium hydroxide solution (33.5 mL, 1N), stirred for 30 minutes at 25° C., concentrated, cooled to 0° C., acidified to pH 5 using 10% citric acid, and partitioned between dichloromethane and water. The organic phase layer was washed with brine, dried over $Na_2SO_4$, filtered and concentrated. A solution of the concentrate in dimethylformamide (130 mL) was treated with imidazole (18.3 g, 268.80 mmol) and t-butyldimethylsilyl chloride (20.2 g, 134.01 mmol), stirred at 25° C. for 16 hours, and concentrated. The concentrate was combined with ice and extracted with ethyl acetate. The organic phase was washed with 10% citric acid and brine, dried over $MgSO_4$, filtered, and concentrated. A solution of the residue in a mixture of THF (100 mL), acetic acid (100 mL) and water (33 mL) was stirred at 25° C. for 2 hours, and concentrated under reduced pressure. The residue was dissolved in toluene and concentrated several times, followed by drying under high vacuum to give the title compound, which was used without further purification.

EXAMPLE 107D benzyl(3R,4S)-4-[(tert-butoxycarbonyl)amino]-3-hydroxy-5-phenyl-1-[4-(2-pyridinyl)benzyl]pentylcarbamate A solution of the product from Example 107C (22.35 mmol) in toluene (500 mL) was treated with DPPA (5.3 mL, 24.59 mmol) and triethylamine (3.75 mL, 26.90 mmol) was heated at reflux for 2 hours, cooled to 25° C., treated with benzyl alcohol (6.9 mL, 66.68 mmol), heated at reflux for an additional 16 hours, cooled and concentrated. A solution of the concentrate in THF (100 mL) was treated with TBAF solution in THF (67 mL, 1N), stirred at 25° C. for 40 hours, concentrated, and partitioned between ethyl acetate and water. The organic phase was washed with brined, dried over MgSO$_4$, filtered and concentrated, to give the title compound (4.98 g, 37% yield), which was used without further purification.

EXAMPLE 107E tert-butyl(1S,2R)-4-amino-1-benzyl-2-hydroxy-5-[4-(2-pyridinyl)phenyl]pentylcarbamate A solution containing the product from Example 107D (0.5 g, 0.840 mmol) in a mixture of methanol (4 mL) and ethyl acetate (4 mL) was treated with Pd(OH)$_2$ on carbon (0.175 g, 20% Pd by wt.) and HCl solution (0.40 mL, 4N in dioxane), stirred under a hydrogen atmosphere (balloon pressure) at 25° C. for 2 hours, filtered through a bed of celite®, rinsed with methanol, and concentrated to give the title compound as the hydrochloride salt.

EXAMPLE 107F tert-butyl(1S,2R,4S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A solution containing the product from Example 107E (0.840 mmol) in THF (8 mL) was treated with the product from Example 1F (0.175 g, 0.926 mmol), DEPBT (0.375 g, 1.194 mmol), and N,N-diisopropylethylamine (0.75 mL, 4.31 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give a mixture of products (0.254 g, 48% yield). A portion of the mixture (0.112 g) was chromatographed on silica gel eluting with 0-100% tert-butyl methyl ether/dichloromethane, to give the lower Rf compound (0.033 g).

EXAMPLE 107G tert-butyl(1S,2R,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A solution containing the product from Example 107E (0.840 mmol) in THF (8 mL) was treated with the product from Example 1F (0.175 g, 0.926 mmol), DEPBT (0.375 g, 1.194 mmol), and N,N-diisopropylethylamine (0.75 mL, 4.31 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane to give a mixture of products (0.254 g, 48% yield). A portion of the mixture (0.112 g) was chromatographed on silica gel eluting with 0-100% tert-butyl methyl ether/dichloromethane, to give the higher Rf compound (0.042 g).

EXAMPLE 107H methyl(1S)-1-[({(1S,3R,4S)-4-amino-3-hydroxy-5-phenyl-1-[4-(2-pyridinyl)benzyl]pentyl}amino)carbonyl]-2,2-dimethylpropylcarbamate A solution containing the product from Example 107F (0.033 g, 0.052 mmol) in dichloromethane (1 mL) was treated with trifluoroacetic acid (1 mL), stirred at 25° C. for 1 hour, concentrated, and partitioned between ethyl acetate and saturated NaHCO$_3$ solution. The organic phase was washed with brine, dried over MgSO$_4$, filtered and concentrated.

EXAMPLE 107I methyl(1S)-1-[({(1S,3R,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 107H (0.052 mmol) in THF (0.6 mL) was treated with the product from Example 10D (0.021 g, 0.063 mmol), DEPBT (0.024 g, 0.078 mmol), and N,N-diisopropylethylamine (0.045 mL, 0.261 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate, to give the title compound (0.024 g, 56% yield). $^1$H NMR (300 MHz, DMSO-d$_6$), δ ppm 0.71 (s, 6 H); 0.89 (m, 12 H), 1.25 (s, 1 H), 1.48 (m, 1 H), 1.71 (m, 1 H), 2.46 (m, 3 H), 2.63 (m, 1 H), 2.74 (m, 1 H), 2.98 (m, 3 H), 3.22 (m, 1 H), 3.50 (m, 5 H), 3.82 (m, 2 H), 4.02 (s, 1 H), 4.20 (m, 1 H), 4.38 (m, 2 H), 4.91 (d, J=6.62 Hz, 1 H), 6.77 (d, J=9.93 Hz, 1 H), 7.06 (m, 5 H), 7.16 (d, J=7.72 Hz, 1 H), 7.26 (d, J=8.46 Hz, 1 H), 7.32 (m, 3 H), 7.69 (m, 1 H), 7.87 (m, 6 H), 8.64 (d, J=4.78 Hz, 1 H).

EXAMPLE 108 methyl(1S)-1-[({(1R,3R,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate

EXAMPLE 108A methyl(1S)-1-[({(1R,3R,4S)-4-amino-3-hydroxy-5-phenyl-1-[4-(2-pyridinyl)benzyl]pentyl}amino)carbonyl]-2,2-dimethylpropylcarbamate A solution containing the product from Example 107G (0.042 g, 0.066 mmol) in dichloromethane (1 mL) was treated with trifluoroacetic acid (1 mL), stirred at 25° C. for 1 hour, concentrated, and partitioned between ethyl acetate and saturated NaHCO₃ solution. The organic phase was washed with brine, dried over MgSO₄, filtered and concentrated.

EXAMPLE 108B methyl(1S)-1-[({(1R,3R,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 108A (0.066 mmol) in THF (0.7 mL) was treated with the product from Example 10D (0.027 g, 0.080 mmol), DEPBT (0.030 g, 0.100 mmol), and N,N-diisopropylethylamine (0.057 mL, 0.332 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane, followed by 0-5% methanol in ethyl acetate, to give the title compound (0.027 g, 49% yield). ¹H NMR (300 MHz, DMSO-d₆), δ ppm 0.88 (d, J=1.10 Hz, 18 H), 1.25 (s, 1 H), 1.51 (m, 2 H), 2.46 (s, 3 H), 2.75 (d, J=6.25 Hz, 2 H), 2.87 (m, 1 H), 3.05 (m, 2 H), 3.23 (m, 1 H), 3.48 (m, 5 H), 3.84 (m, 2 H), 3.99 (s, 1 H), 4.14 (m, 1 H), 4.36 (m, 2 H), 4.67 (d, J=5.52 Hz, 1 H), 6.81 (d, J=9.56 Hz, 1 H), 7.02 (m, 5 H), 7.15 (d, J=7.72 Hz, 1 H), 7.30 (m, 4 H), 7.67 (m, 2 H), 7.87 (m, 5 H), 8.64 (d, J=4.78 Hz, 1 H).

EXAMPLE 109 methyl(1S,4S,6S,7S,10S)-7-benzyl-10-sec-butyl-1-tert-butyl-6-hydroxy-13-methyl-14-(2-methyl-1,3-thiazol-4-yl)-2,9,12-trioxo-4-[4-(2-pyridinyl)benzyl]-3,8,11,13-tetraazatetradec-1-ylcarbamate

EXAMPLE 109A 4-(chloromethyl)-2-methyl-1,3-thiazole

A solution of thioacetamide (2.45 g, 32.6 mmol) in 2-propanol (130 mL) was treated with dichloroacetone (4.14 g, 32.6 mmol) and heated at 60° C. for 2 hours, cooled and concentrated under reduced pressure. The solid product was added cautiously to a saturated NaHCO₃ solution (gas evolution) and the mixture was partitioned between chloroform and saturated NaHCO₃. The organic phase was washed with water, dried over Na₂SO₄, filtered and concentrated. The residue was purified by chromatography on silica gel eluting with chloroform to give the title compound.

EXAMPLE 109B

N-methyl(2-methyl-1,3-thiazol-4-yl)methanamine

An aqueous solution of methylamine (18 mL, 40%) was treated with the product from Example 109A (2.0 g, 13.5 mmol) in portions over 0.5 hours, stirred at 25° C. for 16 hours, and concentrated. The residue was chromatographed on silica gel eluting with 5% methanol in chloroform to give the title compound (1.23 g, 64% yield).

EXAMPLE 109C methyl(2S,3S)-3-methyl-2-{[(4-nitrophenoxy)carbonyl]amino}pentanoate A solution of L-iso-leucine methyl ester hydrochloride (2.5 g, 13.75 mmol) in dichloromethane (35 mL) at 0° C. was treated with 4-nitrophenyl chloroformate (3.05, 15.13 mmol) and 4-methylmorpholine (3.2 mL, 29.11 mmol), stirred at 25° C. for 64 hours, and partitioned between dichloromethane and saturated NaHCO₃. The organic phase was washed with brine and dried over MgSO₄, filtered and concentrated to give the title compound (4.19 g, 98% yield).

EXAMPLE 109D methyl(2S,3S)-3-methyl-2-[({methyl[(2-methyl-1,3-thiazol-4-yl)methyl]amino}carbonyl)amino]pentanoate A solution containing the product from Example 109B (0.200 g, 1.4 mmol) in THF (6 mL) was treated with the product from Example 109C (0.415 g, 1.4 mmol), triethylamine (0.196 mL, 1.4 mmol), and DMAP (0.020 g, 0.16 mmol) at 25° C., stirred at reflux for 1 hour, cooled and concentrated. The residue was partitioned between ethyl acetate and 5% K₂CO₃. The organic phase was washed with brine and dried over Na₂SO₄, filtered and concentrated to give the title compound (0.38 mg, 86% yield).

EXAMPLE 109E (2S,3S)-3-methyl-2-[({methyl[(2-methyl-1,3-thiazol-4-yl)methyl]amino}carbonyl)amino]pentanoic acid A solution of the product from Example 109D (0.38 g, 1.2 mmol) in dioxane (5 mL) was treated with an aqueous solution of lithium hydroxide (5.0 mL, 0.5 M), stirred for 0.5 hours at 25° C., treated with aqueous HCl (2.5 mL, 1 N), and partitioned between ethyl acetate and water. The organic phase was washed with brine and dried over Na₂SO₄, filtered and concentrated to give the title compound.

EXAMPLE 109F methyl(1S,4S,6S,7S,10S)-7-benzyl-10-sec-butyl-1-tert-butyl-6-hydroxy-13-methyl-14-(2-methyl-1,3-thiazol-4-yl)-2,9,12-trioxo-4-[4-(2-pyridinyl)benzyl]-3,8,11,13-tetraazatetradec-ylcarbamate A solution containing the product from Example 2C (0.025 g, 0.047 mmol) in THF (0.5 mL) was treated with the product from Example 109E (0.018 g, 0.061 mmol), DEPBT (0.021 g, 0.071 mmol), and N,N-diisopropylethylamine (0.041 mL, 0.235 mmol), stirred at 25° C. for 2 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane, followed by 0-10% methanol in ethyl acetate, to give the title compound (0.030 g, 78% yield). ¹H NMR (300 MHz, DMSO-d₆), δ ppm 0.78 (m, 16 H), 1.01 (m, 1 H), 1.36 (m, 1 H), 1.50 (m, 2 H), 1.70 (m, 1 H), 2.61 (s, 3 H), 2.73 (m, 3 H), 2.86 (s, 3 H), 3.49 (s, 3 H), 3.62 (m, 1 H), 3.83 (d, J=9.93 Hz, 1 H), 3.98 (t, J=7.91 Hz, 1 H), 4.11 (m, 2 H), 4.43 (m, 2 H), 4.86 (d, J=5.88 Hz, 1 H), 6.19 (d, J=8.09 Hz, 1 H), 6.62 (d, J=9.56 Hz, 1 H), 7.16 (m, 8 H), 7.31 (m, 1 H), 7.42 (d, J=9.19 Hz, 1 H), 7.77 (d, J=8.09 Hz, 1 H), 7.85 (m, 4 H), 8.63 (d, J=4.78 Hz, 1 H).

EXAMPLE 110 methyl(1S,4S,5S,7S,10S)-7-benzyl-10-sec-butyl-1-tert-butyl-5-hydroxy-13-methyl-14-(2-methyl-1,3-thiazol-4-yl)-2,9,12-trioxo-4-[4-(2-pyridinyl)benzyl]-3,8,11,13-tetraazatetradec-1-ylcarbamate A solution containing the product from Example 23S (0.025 g, 0.047 mmol) in THF (0.5 mL) was treated with the product from Example 109E (0.018 g, 0.061 mmol), DEPBT (0.021 g, 0.071 mmol), and N,N-diisopropylethylamine (0.041 mL, 0.235 mmol), stirred at 25° C. for 2 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 0-10% methanol in ethyl acetate. The product was then purified by reversed phase chromatography on a C18 column eluting with 5-100% acetonitrile in water (0.1% TFA). The product was partitioned between ethyl acetate and saturated $NaHCO_3$, and the organic phase was washed with brine and dried over $MgSO_4$, filtered and concentrated to give the title compound (0.011 g, 29% yield). $^1$H NMR (300 MHz, DMSO-$d_6$), δ ppm 0.64 (d, J=6.62 Hz, 3 H), 0.72 (t, J=7.35 Hz, 3 H), 0.83 (s, 9 H), 0.93 (m, 1 H), 1.28 (m, 2 H), 1.49 (m, 2 H), 1.60 (m, 1 H), 2.61 (s, 3 H), 2.73 (m, 3 H), 2.84 (s, 3 H), 3.50 (s, 3 H), 3.62 (m, 1 H), 3.91 (m, 2 H), 4.10 (m, 2 H), 4.41 (m, 2 H), 4.80 (d, J=5.52 Hz, 1 H), 6.01 (d, J=8.46 Hz, 1 H), 6.76 (d, J=9.93 Hz, 1 H), 7.12 (m, 6 H), 7.31 (m, 3 H), 7.60 (m, 2 H), 7.86 (m, 4 H), 8.63 (d, J=4.41 Hz, 1 H).

EXAMPLE 111 methyl(1S)-1-[({(1S,3S,4S)-4-{[(2S)-2-(3-benzyl-2-oxo-1-imidazolidinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate Method A A solution containing the product from Example 2C (1.09 g, 2.05 mmol) in THF (20 mL) was treated with the product from Example 70A (0.71 g, 2.45 mmol), DEPBT (1.0 g, 3.34 mmol), and N,N-diisopropylethylamine (2.0 mL, 11.5 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The residue was chromatographed on silica gel eluting with 0-100% ethyl acetate/dichloromethane, followed by 1% methanol in ethyl acetate to give the title compound (1.197g, 73% yield). $^1$H NMR (300 MHz, DMSO-$d_6$), δ ppm 0.83 (s, 9 H), 0.89 (s, 9 H), 1.56 (m, 2 H), 2.33 (q, J=9.2 Hz, 1 H), 2.58 (dd, J=13.6, 8.8 Hz, 1H), 2.67 (m, 2H), 2.78 (dd, J=13.6, 3.3 Hz, 1H), 2.84 (m, 1 H), 2.94 (q, J=9.2 Hz, 1 H), 3.19 (m, 1 H), 3.50 (s, 3 H), 3.67 (m, 1 H), 3.85 (d, J=9.93 Hz, 1 H), 4.09 (s, 1 H), 4.19 (m, 2 H), 4.31 (s, 2 H), 4.55 (d, J=7.72 Hz, 1 H), 6.63 (d, J=9.56 Hz, 1 H), 7.07 (m, 5 H), 7.22 (d, J=8.5 Hz, 2 H), 7.29 (m, 4 H), 7.36 (m, 2 H), 7.47 (d, J=9.56 Hz, 1 H), 7.85 (m, 3H), 7.89 (d, J=8.5 Hz, 2 H ), 8.63 (d, J=4.78 Hz, 1 H).

Method B

EXAMPLE 111-1

(1,3-dioxo-1,3-dihydro-2H-isoindol-2-yl)acetaldehyde

Phthalimidoacetaldehyde diethyl acetal (75 g, 284.8 mmol) was added in one portion to 450 mL of 2N HCl in a 1 L 3-necked round bottom flask equipped with mechanical stirring. The suspension was heated to 70° C. By the time the internal temperature reached 70° C., the reaction mixture was clear and starting material was consumed as determined by HPLC. The reaction mixture was stirred at 70° C. for 30 minutes. The reaction mixture was allowed to cool to ambient temperature with stirring overnight, at which time the solid product had precipitated. The reaction was diluted with 400 mL of water and mixed for 3 hours. The solid was filtered and washed with 1 L of water, air dried, and dried in a vacuum oven at ambient temperature with a nitrogen bleed to afford the title compound (46.5 g, 86.4% yield). $^1$H NMR (CDCl$_3$): δ 9.65 (s, 1 H), 7.94 (m, 2 H), 7.75 (m, 2 H), 4.58 (s, 2 H).

EXAMPLE 111-2 tert-butyl N-[2-(1,3-dioxo-1,3-dihydro-2H-isoindol-2-yl)ethyl]-3-methyl-L-valinate A solution of the product of Example 111-1 (46.5 g, 246.0 mmol) in tetrahydrofuran (900 mL) was treated with L-tert-leucine-t-butyl ester hydrochloride salt (66.1 g, 295.2 mmol, 1.2 equivalents) stirred at 20° C. for 2 hours, treated with sodium triacetoxyborohydrodride (78.2 g, 369.0 mmol, 1.5 equivalents) portionwise over 5 minutes (slightly exothermic), stirred at 20° C. for 2 hours, diluted with ethyl acetate (1 L) and washed with water (1 L). The organic layer was washed with water (1 L), 10% NaHCO$_3$ (2×1 L) and brine (1 L). The organic layer was dried over MgSO$_4$, filtered, and concentrated to afford the title compound (87 g, 98.2% yield). $^1$H NMR (CDCl$_3$): δ 7.82 (m, 2 H), 7.70 (m, 2 H), 3.77 (t, 2 H), 2.92 (m, 1 H), 2.73(s, 1H), 2.68(m, 1H), 1.44(s, 9H), 0.86(s, 9H).

EXAMPLE 111-3 tert-butyl N-(2-aminoethyl)-3-methyl-L-valinate

The product of Example 111-2 (87 g, 241.6 mmol) was taken up in ethanol (2 L) in a 3-necked, 3L round bottom flask equipped with mechanical stirring under N$_2$. Hydrazine (anhydrous, 68.3 mL, 2.17 mol, 9 equivalents) was added. The reaction mixture was heated to 75° C., which resulted in the formation of a very thick suspension. The addition of more ethanol was necessary in order to continue effective stirring. The reaction was stirred for 1 hour at 75° C. until consumption of starting material was complete as determined by HPLC. The thick suspension was cooled to ambient temperature and quenched with 1 L of 0.5N NaOH solution. The mixture was diluted with 0.5N NaOH (2 L) and extracted with dichloromethane (2×2 L). The combined organic layer was washed with brine (1 L), dried over MgSO$_4$, filtered and concentrated to oil. The oil was chased with heptanes to remove ethanol and pump dried to afford light yellow oil (50.2 g, 93.2% yield). $^1$H NMR (CDCl$_3$): δ 2.73(m, 4H), 2.45(m, 1H), 1.64(s, 9H), 0.96(s, 9H).

EXAMPLE 111-4 tert-butyl
N-[2-(benzylamino)ethyl]-3-methyl-L-valinate

A solution of benzaldehyde (23 g, 217 mmol) and the product of Example 111-3 (50 g, 217 mmol, 1 equivalent) in 50:50 mixture of toluene and methanol (total volume=1400 mL), stirred at 50° C. overnight, cooled to –3° C., treated with NaBH$_4$ (16.6 g, 434 mmol, 2equivalents) slowly over 5 hours, and stirred at room temperature for 16 hours. The reaction mixture was quenched with a saturated NaHCO$_3$ solution (1400 mL) and extracted with ethyl acetate (1.3 L). The layers were separated and the aqueous layer was extracted with ethyl acetate (850 mL). The organic layers were combined, washed with brine (900 mL), and concentrated. The residue was dissolved in heptanes (700 mL), decanted inorganic salt, distilled to oil and chased to yield 69.4 g of crude material. $^1$H NMR (CDCl$_3$): δ 7.05-7.3(m, 7H), 3.75(d, 2H), 2.4-2.8(m, 5H), 1.4(s, 9H), 0.87(s, 9H).

EXAMPLE 111-5 tert-butyl(2S)-2-(3-benzyl-2-oxoimidazolidin-1-yl)-
3,3-dimethylbutanoate

A solution of the product of Example 111-4 in 1,2-dichloroethane (1325 mL) was treated with triethylamine (37.5 mL, 269 mmol, 1.25 equivalents) and N,N-disuccinimidyl carbonate (68.9 g, 269 mmol, 1.25 eq). The reaction mixture was stirred at 20° C. overnight, washed with 10% Na$_2$CO$_3$ (2×1.5 L). The aqueous was back-extracted with dichloromethane (600 mL). The organics were combined and washed with 1.5 L of brine. The organic layer was concentrated to yield 76.8 gm of crude material. $^1$H NMR (CDCl$_3$): δ 7.15-7.3(m, 5H), 4.25-4.4(m, 3H), 3.75(m, 1H), 3.67(residual dichloroethane), 3.48(m, 1H), 3.1(m, 2H), 1.4(s, 9H), 1.0(s, 9H).

EXAMPLE 111-6

(2S)-2-(3-benzyl-2-oxoimidazolidin-1-yl)-3,3-dim-
ethylbutanoic acid

To a solution of the product of Example 111-5 in dichloromethane (1.5 L) was added triflouroacetic acid (810 mL). The mixture was stirred at room temperature for 3 hours and concentrated. The residue was chased with heptanes (4×500 mL). The product was partitioned between dichloromethane (1.5 L) and 5% KH$_2$PO$_4$ (1.1 L). The organic layer was washed with 5% KH$_2$PO$_4$ (900 mL) and brine (900 mL), and concentrated. A solution of the residue in dichloromethane (500 mL) was dried over MgSO$_4$, filtered and concentrated. The residue was recrystallized twice from isopropyl alcohol/water to afford the title compound. $^1$H NMR (DMSO-d$_6$): δ 7.2-7.4(m, 5H), 4.28(d, 2H), 4.21(s, 1H), 3.47-3.64(m, 2H), 3.08-3.2(m, 2H), 1.0(s, 9H).

EXAMPLE 111-7

2-[4-(bromomethyl)phenyl]pyridine

A mixture of 2-(p-tolyl) pyridine (118.88 g, 702.5 mmol), N-bromosuccinimide (131.29 g, 737.6 mmol, 1.05 equivalents) and CCl$_4$ (1190 mL) was treated with benzoyl peroxide (1.70 g, 7.03 mmol, 0.01 equivalents) under nitrogen, stirred at 70° C. for 1.5 hours, and then allowed to cool to ambient temperature with stirring overnight. The reaction mixture was filtered, washed with CCl$_4$ (2×250 mL), concentrated to oil, treated with isopropyl alcohol (420 mL) and cooled to –5° C. The resulting solid was filtered, washed with isopropyl alcohol (140 mL), and dried in a vacuum oven with a N$_2$ bleed to afford the title compound (111.91 g, 64.2% yield). $^1$H NMR (CDCl$_3$): δ 8.70(m, 1H), 7.99(m, 2H), 7.75(m, 2H), 7.52(m, 2H), 7.25(m, 1H), 4.58 (s, 2H).

EXAMPLE 111-8 tert-butyl(1S)-1-[(2S)-5-oxo-4-(4-pyridin-2-ylben-
zyl)tetrahydrofuran-2-yl]-2-phenylethylcarbamate 450 g of tert-Butyl (1S)-1-[(2R)-oxiran-2-yl]-2-phenylethylcarbamate was treated with 1.1 equivalents of diethyl malonate and 1.05 equivalents of sodium ethoxide in 1200 mL of ethanol at 5° C. for 0.5 hr, then at 25° C. for 5 hrs. The reaction mixture was quenched with acetic acid till the pH of the mixture was about 6. The reaction mixture was extracted with ethyl acetate (4 L) and the isolated organic phase was washed sequentially with 25% brine (4 L), 5% NaHCO$_3$ (5L), and 25% brine (4 L), dried over NaSO$_4$, filtered, concentrated and chased with 2 L of methyl tert-butyl ether to dryness. The oil was dissolved in 950 mL of methyl tert-butyl ether and warmed to 45° C., added heptane (4L) and cooled to –5° C. The solid was isolated by filtration to provide tert-butyl(1S)-1-[(2S)-5-oxotetrahydrofuran-2-yl]-2-phenylethylcarbamate. A mixture of the tert-butyl (1S)-1-[(2S)-5-oxotetrahydrofuran-2-yl]-2-phenylethylcarbamate (400 g, 1.028 mol), the product of Example 111-7 (321 g, 1.08 mol, 1.05 equivalents) in absolute ethanol (3.35 L) was cooled to 5° C. was treated with a solution of sodium ethoxide (77.5 g sodium ethoxide in 0.65 L of absolute ethanol, 1.05 equivalents) over 1 hour. The reaction mixture was stirred at 3° C. for 3 hours. Lithium hydroxide monohydrate (215.6 g, 5.138 mol, 5 equivalents) was added all at once and the temperature rose to 10° C. The mixture was stirred at 10° C. for 2 hours, treated with acetic acid (308.6 gm, 5.138 mol, 5 eq) and stirred at 60° C. for 17 hours. The reaction mixture was treated with distilled water (4 L) over 20 minutes while maintaining the internal temperature >55° C. The slurry was cooled slowly to 14° C. over 2.5 hours, filtered, washed with 1:1 ethanol:water (total volume=2 L), heptanes (2 L) and dried at 55° C. vacuum oven under N$_2$ for 40 hours to give the title compound (451.9 g, 91% yield). $^1$H NMR (CDCl$_3$): δ 8.65(m, 1H), 7.90(m, 2H), 7.65-7.75 (m, 2H), 7.17-7.30(m, 8H), 4.63(m, 1H), 4.32(m, 1H), 3.95(m, 1H), 3.32(m, 1H), 2.7-3.0(m, 4H), 2.10 (m, 1H), 1.74(m, 1H), 1.36 (s, 9H).

EXAMPLE 111-9

(4S,5S)-5-[(tert-butoxycarbonyl)amino]-4-{[tert-
butyl(dimethyl)silyl]oxy}-6-phenyl-2-(4-pyridin-2-
ylbenzyl)hexanoic acid A solution of the product of Example 111-8 (250 g, 529 mmol) in N-methylpyrrolidinone (2L) under N$_2$ was treated with milled lithium hydroxide monohydrate (33.3 g, 793.5 mmol, 1.5equivalents) and N,N-(dimethylamino)pyridine (6.5 g, 53 mmol, 0.1 equivalent) and stirred at 40° C. for 10 hrs. The reaction mixture was cooled to about 22° C., treated with imidazole (827.5 g, 12.2 mol, 23 equivalents) over 15 minutes, stirred at 22° C. for 30minutes, cooled to 6° C., and treated with t-butyldimethylsilyl chloride (876.94 g, 5.819 mol, 11 equivalents) over 45 minutes. This mixture was warmed to 22° C., stirred at 20° C. for 1.5 hours, and stirred at 40° C. overnight. The reaction mixture was cooled to 22° C., charged with 1.25 L of distilled water over 10 minutes and mixed for 2 hrs. The reaction mixture was charged with 1.25 L of brine, 1.25 L of ethyl acetate and 1.25 L of heptanes. The aqueous layer was extracted with 1.25 L of ethyl acetate and 1.25 L of heptanes. The combined organic layer was washed with brine (2×1.2 L), concentrated and chased with heptanes (1.4 L). The resulting oil was dissolved in N,N-dimethylformamide (812 mL), partitioned between heptanes (5.25 L) and 10% aqueous $K_2CO_3$ (1.25 L). The heptane layer was extracted with 10% $K_2CO_3$ (2×400 mL) and N,N-dimethylformamide (260 mL). The combined aqueous layer (DMF/$K_2CO_3$) was washed with 4×5L heptanes. The aqueous layer was cooled to 5° C., charged with 2.5L of toluene, adjusted to pH 5 with 5% HCl, and extracted with 1.6 L of toluene. The combined toluene layer was washed with brine (2×1.75 L), and water (2×1.75 L), concentrated to oil and chased with toluene (2×800 mL) to give the title compound. $^1$H NMR (CDCl$_3$): δ 8.50(m, 1H), 7.5-7.8(m, 4H), 7.0-7.2 (m, 8H), 4.6 (m, 1H), 3.6-4.0(m, 2H), 2.5-2.9(m, 4H), 2.25(s, residual toluene), 1.5-2.0(m, 2H), 1.0-1.3 (s+d, boc), 0.85(s, t-butyl), 0 (m, 6H).

EXAMPLE 111-10

Benzyl(3S,4S)-4-[(tert-butoxycarbonyl)amino]-3-hydroxy-5-phenyl-1-[4-(2-pyridinyl)benzyl]pentyl-carbamate To the product of Example 111-9 (274 g, 453 mmol) in toluene (2.65 L) were added triethylamine (126.5 mL, 906 mmol, 2 equivalents) and DPPA (128.5 g, 453 mmol, 1 equivalent). The mixture was stirred at 40° C. for 1 hour. Additional DPPA (6.3 mL, 17 mmol, 0.04 equivalent) was charged to the reaction mixture and mixed at 40° C. for 3 hours. Benzyl alcohol (147 g, 1.359 mol, 3 equivalents) was added and the mixture was heated at 105° C. for 10 hours then 22° C. for 7 hours. The reaction mixture was washed with 10% $Na_2CO_3$ (1.1 L), saturated NaHCO$_3$ (1.1 L), and water (4×3 L). The organic layer was concentrated. The residue was dissolved in tetrahydrofuran (500 mL), cooled to 5° C. and treated with 1M TBAF in tetrahydrofuran (2.5 L, 5.5 equivalents.) and the mixture was stirred at 5° C. for 2 hrs. The reaction mixture was quenched with 5% $KH_2PO_4$ (2.6 L) and water (1.1 L), extracted with ethyl acetate (5 L). The aqueous layer was extracted with ethyl acetate (3.2 L). The combined organic layers were washed with water (3×2.7 L) and concentrated. The resulting solid was chased with heptanes and methanol. The solid was dissolved in methanol (1.6 L) at 63° C., cooled to 22° C. and stirred at 22° C. until solids precipitated. The slurry was treated with 800 mL of distilled water, mixed at 22° C. for 3 hours, filtered, washed with 2:1 methanol:water (total volume=600 mL), and heptanes (700 mL). The wet cake was dried in 50° C. vacuum oven under $N_2$ to give the title compound (diastereomeric ratio=1.3:1 as determined by HPLC (Column: Zorbax C-8 25 cm, flow, Gradient system: 0-5 min, 0.1% $H_3PO_4$/10% $CH_3CN$/90% water to 0.1% $H_3PO_4$/90% $CH_3CN$/10% water, 5-12 hold at 0.1% $H_3PO_4$/90% $CH_3CN$/10% water, 12-13 min, 0.1% $H_3PO_4$/90% $CH_3CN$/10% water to 0.1% $H_3PO_4$/10% $CH_3CN$/90% water, 13-15 min, hold at 0.1% $H_3PO_4$/10% $CH_3CN$/90% water). $^1$H NMR (DMSO-d$_6$): δ 8.64(m, 1H), 7.81-7.97(m, 4H), 7.10-7.33(m, 14H), 6.27(m, 1H), 4.83-4.95(m, 2H), 4.60(d, 1H), 3.95(m, 1H), 3.80(m, 1H), 3.55(m, 1H), 2.57-2.77(m, 4H), 1.55(m, 2H), 1.27(s, 9H).

EXAMPLE 111-11

Benzyl(3S,4S)-4-[(tert-butoxycarbonyl)amino]-3-hydroxy-5-phenyl-1-[4-(2-pyridinyl)benzyl]pentyl-carbamate A mixture of the product of Example 111-10 (12 g, 20 mmol), ammonium formate (5.1 g, 81 mmol, 4 equivalents) and methanol (360 mL) was treated with Pd/C (4.8 gm, 40% loading) and stirred at ambient temperature under $N_2$ for 1.5 hr, filtered and concentrated. A solution of the residue in dichloromethane (150 mL) was washed with saturated NaHCO$_3$ (2×80 mL), and brine (2×50 ml). The dichloromethane layer was dried over Na$_2$SO$_4$ filtered and concentrated to give the title compound (8.75 g, 93% yield). $^1$H NMR (DMSO-d$_6$): δ 8.61(m, 1H), 7.96(d, 2H), 7.89(d, 1H), 7.82(m, 1H), 7.10-7.32(m, 8H), 6.25(d, 1H), 3.65(m, 1H), 3.55(m, 1H), 2.98(m, 1H), 2.51-2.81(m, 4H), 1.44(m, 1H), 1.15-1.35(s+s, 10H).

EXAMPLE 111-12 tert-butyl(1S,2S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A mixture of (2S)-2-[(methoxycarbonyl)amino]-3,3-dimethylbutanoic acid (Degussa, 8.74 g, 46.18 mmol, 1.1 equivalents), $K_2CO_3$ (11.60 g, 83.96 mmol, 2equivalents), DEPBT (15.08 g, 50.38 mmol, 1.2 equivalents) in ethyl acetate (400 mL) was stirred at room temperature under $N_2$ for 1 hour, treated with the product of Example 111-11 (20 g, 41.98 mmol) and stirred at room temperature under $N_2$ for 24 hrs. The reaction mixture was washed with $H_2O$ (200 mL), 10% NaHCO$_3$ (200 mL), and $H_2O$ (2×200 mL). The organic layer was concentrated, and the residue charged with ethyl acetate (30 mL), heated to 70° C. for 1 hr, added heptanes (120 mL) dropwise, stirred at 70° C. for 30 minutes, cooled to room temperature overnight. The slurry was filtered and washed with 100 mL of 1:1 heptane/ethyl acetate, and dried in 50° C. vacuum oven overnight to give the title compound.

EXAMPLE 111-13A tert-butyl(1S,2S,4R)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate A 12 L 3-necked round bottom flask was charged with 169.74 gm of the product of Example 111-12 and 3.5 L of methanol, warmed to 45° C., water (1.75 L) was slowly added, stirred at 45-48° C. for about 1 hour, and cooled to ambient temperature overnight. The slurry was filtered and washed with 2:1 methanol:water, suction dried for 1 hour and dried at 50° C. vacuum oven overnight to give 60.4 gm of the title compound (28:1 diastereomeric ratio as determined by HPLC (Column: XDB C8 15 cm, Eluent: $CH_3CN$/10 mM Na$_2$HPO$_4$ with $H_3PO_4$ adjusted to pH 7, Gradient: 10% $CH_3CN$ to 90% $CH_3CN$ in 15 min, then hold for 10 min, column oven temperature: 35° C.).

EXAMPLE 111-13B tert-butyl(1S,2S,4S)-1-benzyl-2-hydroxy-4-({(2S)-2-[(methoxycarbonyl)amino]-3,3-dimethylbutanoyl}amino)-5-[4-(2-pyridinyl)phenyl]pentylcarbamate The 7.6 L mother liquor from Example 111-13A was heated to 45° C. in a 12 L 3-necked flask, water (2.37 L) was added dropwise to make a 1:1 methanol:water solution, stirred at 45° C. for 2 hours, and cooled to ambient temperature overnight. The slurry was filtered, dried in 50° C. vacuum oven overnight to give 99.52 gm of the title compound (27:1 diastereomeric ratio as determined by HPLC (Column: XDB C8 15 cm, Eluent: $CH_3CN$/10 mM $Na_2HPO_4$ with $H_3PO_4$ adjusted to pH 7, Gradient: 10% $CH_3CN$ to 90% $CH_3CN$ in 15 min, then hold for 10 min, column oven temperature: 35° C.). $^1H$ NMR (CDCl3): δ 8.66(m, 1H), 7.90(d, 2H), 7.65-7.76 (m, 2H), 7.11-7.24(m, 8H), 5.74(d, 1H), 5.22 (d, 1H), 4.95(d, 1H), 4.27-4.45(m, 2H), 3.60-3.73(m, 5H), 3.47(m, 1H), 2.70-2.98(m, 4H), 1.82-1.93(m, 1H), 1.25-1.45(m, 10H), 0.75(s, 9H).

EXAMPLE 111-14 methyl(1S)-1-[({(1S,3S,4S)-4-amino-3-hydroxy-5-phenyl-1-[4-(2-pyridinyl)benzyl]pentyl}amino)carbonyl]-2,2-dimethylpropylcarbamate A suspension of the product of Example 111-13B (113.8 mmol) in isopropyl acetate 1050 mL was treated with concentrated HCl (72 mL, 869 mmol, 8 equivalents) and stirred at ambient temperature for 1 hour. The reaction mixture was charged with water (360 mL) and heptanes (900 mL) and the layers separated. The organic layer was extracted with water (360 mL). The combined aqueous layers was washed with 1:1 isopropyl acetate:heptanes (2×500 mL). The aqueous layer was charged with ethyl acetate (360 mL), cooled to <10° C., and adjusted the pH to 9 with 77 g of $Na_2CO_3$ while keeping the temperature at <10° C. and the layers separated. The aqueous layer was extracted with ethyl acetate (720 mL). The combined ethyl acetate layers was washed with saturated $NaHCO_3$ (350 mL), and brine (2×350 mL), dried over $Na_2SO_4$ filtered and concentrated to give the title compound. $^1H$ NMR (DMSO-$d_6$): δ 8.62(m, 1H), 7.81-7.97(m, 5H), 7.12-7.33(m, 9H), 6.87(d, 1H), 4.51(d, 1H), 4.15 (m, 1H), 3.80(d, 1H), 3.55(s, 3H), 2.60-2.84(m, 4H), 2.40(m, 1H), 1.65 (m, 1H), 1.50(m, 1H), 0.73(s, 9H).

EXAMPLE 111-15 methyl(1S)-1-[({(1S,3S,4S)-4-{[(2S)-2-(3-benzyl-2-oxo-1-imidazolinyl)-3,3-dimethylbutanoyl]amino}-3-hydroxy-5-phenyl-1-[4-(2-pyridinyl)benzyl]pentyl}amino)carbonyl]-2,2-dimethylpropylcarbamate A mixture of the product of Example 111-6 (30.7 g, 105.8 mmol, 1 equivalent), $K_2CO_3$ (29.2 g, 211.6 mmol, 2 equivalents), ethyl acetate (270 mL) and DEPBT (33.2 g, 299.23 mmol, 1.05 equivalent) was stirred at 20° C. for 30 minutes, treated with the product of Example 111-14 (56.4 g, 105.8 mmol) and stirred at 20° C. for 5 hours. Additional Example 1116 (4 g, 0.13 equivalent), DEPBT (6.4 g, 0.2 equivalent), $K_2CO_3$ (2.7 g, 0.18 equivalent) were added and the mixture was stirred at 20° C. overnight. The reaction mixture was quenched with water (300 mL), washed with 10% $Na_2CO_3$ (3×480 mL), 5% $KH_2PO_4$ (2×480 mL), and brine (480 mL), dried over $Na_2SO_4$, filtered and concentrated. The residue was crystallized from ethyl acetate (420 mL)/heptanes (840 mL) to provide 84 gm of the ethyl acetate solvate of the title compound. $^1H$ NMR (DMSO-$d_6$): δ 8.60(m, 1H), 7.85(m, 5H), 7.45 (m, 1H), 7.2-7.4 (m, 8H), 7.1 (m, 2H), 7.0(m, 3H), 6.6(d, 1H), 4.5(d, 1H), 4.3(d, 2H), 4.15(m, 2H), 4.07(s, 1H), 3.85(d, 1H), 3.65(m, 1H), 3.49(s, 3H), 3.17(m, 1H), 2.93(q, 1H), 2.8(m, 2H), 2.66(d, 2H), 2.57(m, 1H), 2.33(q, 1H), 1.55(m, 2H), 0.88 (s, 9H)), 0.82(s, 9H).

The ethyl acetate solvate of the title compound (90 g, 89.5 g by assay) was dissolved in 450 mL isopropyl alcohol, then charged with 1350 mL water to crystallize the desired compound. After filtration and drying, 85.3 g of the hydrate of the title compound was obtained.

EXAMPLE 112

1,2,5,6-tetradeoxy-2,5-bis({(2S)-2-[(methoxycarbonyl)amino]-3,3-dimethylbutanoyl}amino)-1,6-bis[4-(2-pyridinyl)phenyl]-L-iditol

EXAMPLE 112A methyl(2S)-3-(4-bromophenyl)-2-[(tert-butoxycarbonyl)amino]propanoate A mixture of (L)-4-bromophenylalanine (1.0 g, 4.1 mmol), $NaHCO_3$ (0.9 g, 10.7 mmol), and di-tert-butyldicarbonate (1.34 g, 6.1 mmol) in 4:1 1,4-dioxane:water (25 mL) was stirred at 25° C. for 18 hours, diluted with water (20 mL) and extracted with dichloromethane (50 mL). The aqueous phase was adjusted to pH 2 using 1N HCl, and extracted with ethyl acetate (2×50 mL). The combined organic phase was dried over $Na_2SO_4$, filtered and concentrated. A solution of the concentrate in methanol (20 mL) was cooled to 0° C., treated with a solution of trimethylsilyl diazomethane (2.0 M in $Et_2O$), stirred at 25° C. for 18 hours, then concentrated. The residue was chromatographed on silica gel, eluting with dichloromethane to afford the title compounds (1.15 g, 78%).

EXAMPLE 112B tert-butyl(1S)-2-hydroxy-1-[4-(2-pyridinyl)benzyl]ethylcarbamate (i) A solution containing the product from Example 112A (1.15 g, 3.2 mmol) in anhydrous THF (20 mL) at 0° C. was treated dropwise with a solution of lithium aluminumhydride (3.2 mL, 1N in THF), stirred at 0° C. for 1 h, treated with ethyl acetate (2 mL), washed with water (10 mL), 15% aq. NaOH, and water (10 mL), dried over $Na_2SO_4$, filtered and concentrated. The residue was purified by column chromatography on silica gel, eluting with 30-50% ethyl acetate in hexanes.

(ii) A solution of the product from step (i) (0.20 g, 0.61 mmol), 3-tri-n-butylstannyl)pyridine (0.9 g, 2.44 mmol), and dichlorobis(triphenylphosphine)palladium (0.13 g, 0.19 mmol) in dry acetonitrile (4 mL) was stirred at 80° C. for 18 hours, filtered and concentrated. The concentrate was chromatographed on silica gel, eluting with 30-60% ethyl acetate in hexanes to give the title compound (0.18 g, 90%).

EXAMPLE 112C 2,5-bis[(tert-butoxycarbonyl)amino]-1,2,5,6-tetradeoxy-1,6-bis[4-(2-pyridinyl)phenyl]-L-iditol (i) A solution of oxalyl chloride (0.42 mL, 2.0 M in $CH_2Cl_2$, 0.84 mmol) in anhydrous dichloromethane (2 mL) at −63° C. ($CHCl_3$-dry ice bath) was treated dropwise with a solution of DMSO (80 µL, 88 mg, 1.13 mmol) in dichloromethane (2 mL). To this solution was added dropwise a solution of the product from Example 112B (0.18 g, 0.55 mmol) in anhydrous dichloromethane (1 mL). The resulting mixture was stirred for 20 min at 63° C., treated with triethylamine (0.31 mL, 0.23 g, 2.22 mmol), stirred for 30 min at −63° C., warmed to 25° C., treated with 10% citric acid (5 mL) and hexanes (5 mL), and the layers were separated. The aqueous layer was washed with diethyl ether (2×5 mL). The combined organic layers were dried over $Na_2SO_4$, filtered and concentrated. The crude product was purified by column chromatography on silica gel, eluting with 1:1 ethyl acetate: hexanes to give the aldehyde (0.12 g, 67%).

(ii) A solution of vanadium (III) chloride-THF complex (1:3) in anhydrous $CH_2Cl_2$ (0.5 M, 0.4 mL, 0.2 mmol) under $N_2$ was treated with Zn (7 mg, 0.11 mmol), stirred at 25° C. for 30 min. To this mixture was added a solution of the aldehyde from step (i) (60 mg, 0.20 mmol) in anhydrous dichloromethane (0.5 mL), and the resulting mixture was stirred at 25° C. for 18 hours. The mixture was treated with 0.2 M HCl (2 mL), stirred at 25° C. for 1 h, extracted with dichloromethane (3×2 mL), dried over $Na_2SO_4$, filtered and concentrated. The crude product was chromatographed on silica gel, eluting 60-100% ethyl acetate in hexanes to give the title compound (11 mg, 9%).

EXAMPLE 112D 1,2,5,6-tetradeoxy-2,5-bis({(2S)-2-[(methoxycarbonyl)amino]-3,3-dimethylbutanoyl}amino)-1,6-bis[4-(2-pyridinyl)phenyl]-L-iditol A solution of the product from Example 112C (9 mg, 14 µmol) in a 1:1 mixture of methanol and 4N HCl (0.2 mL) was stirred at 25° C. for 4 hours, and concentrated in vacuo. A solution of the residue in dimethylformamide (0.2 mL) was treated with the product from Example 1F (7 mg, 40 µmol), DEPBT (18 mg, 60 µmol), and triethylamine (12 µL, 9 mg, 86 µmol), stirred at 25° C. for 18 hours, and partitioned between saturated $NaHCO_3$ (0.5 mL) and ethyl acetate (3×1 mL). The organic phase was dried over $Na_2SO_4$ filtered and concentrated. The residue was chromatographed on silica gel, eluting with 50-100% ethyl acetate in hexanes to afford the title compound (6 mg, 55%).

1H NMR (300 MHz, $CDCl_3$) δ ppm 0.81(s, 18H), 3.02(m, 4H), 3.49 (m, 2H), 3.59(s, 6H), 3.74(m, 2H), 4.14(m, 4H), 5.19(m, 2H), 6.33(m, 2H), 7.34 (d, J=8.09 Hz, 4H), 7.74(m, 6H), 7.88(d, J=8.46 Hz, 4H), 8.67(m, 2H).

EXAMPLE 113 methyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-1-[4-(6-methoxy-2-pyridinyl)benzyl]-5-phenylpentyl}amino)carbonyl]-2,2-dimethylpropylcarbamate

EXAMPLE 113A methyl 6-(tributylstannyl)-2-pyridinyl ether

A solution containing 2-bromo-6-methoxypyridine (0.65 mL, 5.3 mmol) in ether (11 mL) at −78° C. was treated with n-butyllithium (4.0 mL, 1.6 M in hexanes) dropwise, warmed to 0° C. for 10 minutes, cooled to −78° C., treated with tributyltin chloride (2.25 mL, 8.30 mmol), stirred at −78° C. for 0.5 hours, and then at 0° C. for 0.5 hours. The reaction was quenched with saturated ammonium chloride solution and partitioned between ether and water. The organic phase was washed with brine and dried over $MgSO_4$, filtered and concentrated to give the title compound.

EXAMPLE 113B benzyl(1S,3S,4S)-4-[(tert-butoxycarbonyl)amino]-3-{[tert-butyl(dimethyl)silyl]oxy}-1-[4-(6-methoxy-2-pyridinyl)benzyl]-5-phenylpentylcarbamate A solution containing the product from Example 92D (0.20 g, 0.28 mmol) in DMF (3 mL) was treated with LiCl (0.119 g, 2.8 mmol), dichlorobis(triphenylphosphine)palladium(II) (0.060 g, 0.085 mmol), and the product from Example 113A (0.336 g, 0.84 mmol), heated at 100° C. for 16 hours, cooled, filtered through celite®, and partitioned between ethyl acetate and water. The organic phase was washed with brine and dried over $MgSO_4$, filtered and concentrated to give the title compound.

EXAMPLE 113C benzyl(1S,3S,4S)-4-[(tert-butoxymethyl)amino]-3-hydroxy-1-[4-(6-methoxy-2-pyridinyl)benzyl]-5-phenylpentylcarbamate The product from Example 113B (0.28 mmol) was treated with TBAF solution in THF (1.4 mL, 1N), stirred at 25° C. for 16 hours, concentrated and partitioned between ethyl acetate and water. The organic phase was washed with brined, dried over $MgSO_4$, filtered and concentrated. The residue was chromatographed on silica gel eluting with 20% ethyl acetate in dichloromethane, to give the title compound (0.055 g, 31% yield).

EXAMPLE 113D benzyl(1S,3S,4S)-4-amino-3-hydroxy-1-[4-(6-methoxy-2-pyridinyl)benzyl]-5-phenylpentylcarbamate A solution of the product from Example 113C (0.093 g, 0.15 mmol) in THF (1 mL) was treated with an HCl solution (0.26 mL, 4 N in dioxane), stirred at 25° C. for 64 hours, and concentrated. The concentrate was treated with ethanol and concentrated several times to give the title compound as the hydrochloride salt.

EXAMPLE 113E benzyl(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-1-[4-(6-methoxy-2-pyridinyl)benzyl]-5-phenylpentylcarbamate A solution containing the product from Example 113D (0.049 mmol) in THF (0.5 mL) was treated with the product from Example 10D (0.017 g, 0.049 mmol), DEPBT (0.030 g, 0.099 mmol), and N,N-diisopropylethylamine (0.043 mL, 0.246 mmol), stirred at 25° C. for 5 hours, and partitioned between chloroform and 10% Na$_2$CO$_3$ solution. The organic phase was washed with additional 10% Na$_2$CO$_3$ solution and brine, dried over MgSO$_4$, filtered and concentrated.

EXAMPLE 113F (2S)-N-{(1S,2S,4S)-4-amino-1-benzyl-2-hydroxy-5-[4-(6-methoxy-2-pyridinyl)phenyl]pentyl}-3,3-dimethyl-2-{3-[(6-methyl-2-pyridinyl)methyl]-2-oxo-1-imidazolidinyl}butanamide A solution containing the product from Example 113E (0.049 mmol) in methanol (1 mL) was treated with Pd on carbon (0.005 g, 10% Pd by wt.) and HCl solution (0.050 ML, 4N in dioxane), stirred under a hydrogen atmosphere (balloon pressure) at 25° C. for 16 hours, filtered through a bed of celite®, rinsed with methanol, and concentrated to give the title compound as the hydrochloride salt.

EXAMPLE 113G methyl(1S)-1-[({(1S,3S,4S)-4-[((2S)-3,3-dimethyl-2-{3-[(6-methyl-2pyridinyl)methyl]-2-oxo-1-imidazolidinyl}butanoyl)amino]-3-hydroxy-1-[4-(6-methoxy-2-pyridinyl)benzyl]-5-phenylpentyl}amino)carbonyl]-2,2-dimethylpropylcarbamate A solution containing the product from Example 113F (0.049 mmol) in THF (0.5 mL) was treated with the product from Example 1F (0.010 g, 0.054 mmol), DEPBT (0.029 g, 0.098 mmol), and N,N-diisopropylethylamine (0.043 mL, 0.245 mmol), stirred at 25° C. for 16 hours, and partitioned between chloroform and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 2% methanol in chloroform. The product was purified by reversed phase chromatography on a C18 column eluting with 20-100% acetonitrile in water (0.1% TFA). The product was partitioned between ethyl acetate and saturated NaHCO$_3$, and the organic phase was washed with brine and dried over MgSO$_4$, filtered and concentrated to give the title compound (0.0065 g, 16% yield). $^1$NMR (300 MHz, CDCl$_3$) δ ppm 0.94(s, 9H), 0.98(s, 9H), 1.77-1.63(m, 2H), 2.69-2.59(m, 1H), 2.59(bs, 3H), 2.86-2.80(m, 4H), 3.21-3.04(m, 2H), 3.41-3.34(m, 1H), 3.62(s, 3H), 3.77-3.72(m, 2H), 4.02(s, 1H), 4.03(s, 3H), 4.34-4.16(m, 2H), 4.64-4.46(m, 2H), 5.36-5.34 (d, J-7.72 Hz, 1H), 6.04-6.01(d, J=7.35 Hz, 1H), 6.43-6.40(d, J=8.82 Hz, 1H), 6.68-6.66(d, J=7.72 Hz, 1H), 7.33-7.09(m, 10H), 7.64-7.59(m, 2H), 7.95-7.92(d, J=8.09 Hz, 2H).

EXAMPLE 114 methyl(1S)-1-[({(1S,3S,4S)-4-{[(2S)-2-(3-benzyl-2-oxo-1-imidazolidinyl)-3,3-dimethylbutanoyl]amino}-3-hydroxy-1-[4-(6-methoxy-2-pyridinyl)benzyl]-5-phenylpentyl}amino)carbonyl]-2,2-dimethylpropylcarbamate

EXAMPLE 114A benzyl(1S,3S,4S)-4-{[(2S)-2-(3-benzyl-2-oxo-1-imidazolidinyl)-3,3-dimethylbutanoyl]amino}-3-hydroxy-1-[4-(6-methoxy-2-pyridinyl)benzyl]-5-phenylpentylcarbamate A solution containing the product from Example 113D (0.049 mmol) in THF (0.5 mL) was treated with the product from Example 70A (0.016 g, 0.055 mmol), DEPBT (0.030 g, 0.099 mmol), and N,N-diisopropylethylamine (0.043 mL, 0.246 mmol), stirred at 25° C. for 5 hours, and partitioned between chloroform and 10% Na$_2$CO$_3$ solution. The organic phase was washed with additional 10% Na$_2$CO$_3$ solution and brine, dried over MgSO$_4$, filtered and concentrated.

EXAMPLE 114B (2S)-N-{(1S,2S,4S)-4-amino-1-benzyl-2-hydroxy-5-[4-(6-methoxy-2-pyridinyl)phenyl]pentyl}-2-(3-benzyl-2-oxo-1-imidazolidinyl)-3,3-dimethylbutanamide A solution containing the product from Example 114A (0.049 mmol) in methanol (1 mL) was treated with Pd on carbon (0.005 g, 10% Pd by wt.) and HCl solution (0.050 mL, 4N in dioxane), stirred under a hydrogen atmosphere (balloon pressure) at 25° C. for 3 hours, filtered through a bed of celite®, rinsed with methanol, and concentrated to give the title compound as the hydrochloride salt.

EXAMPLE 114C methyl(1S)-1-[({(1S,3S,4S)-4-{[(2S)-2-(3-benzyl-2-oxo-1-imidazolidinyl)-3,3-dimethylbutanoyl]amino}-3-hydroxy-1-[4-(6-methoxy-2-pyridinyl)benzyl]-5-phenylpentyl}amino)carbonyl]-2,2-dimethylpropylcarbamate A solution containing the product from Example 114B (0.049 mmol) in THF (0.5 mL) was treated with the product from Example 1F (0.010 g, 0.054 mmol), DEPBT (0.029 g, 0.098 mmol), and N,N-diisopropylethylamine (0.043 mL, 0.245 mmol), stirred at 25° C. for 16 hours, and partitioned between chloroform and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 2% methanol in chloroform. The product was purified by reversed phase chromatography on a C18 column eluting with 40-100% acetonitrile in water (0.1% TFA). The product was partitioned between ethyl acetate and saturated NaHCO$_3$, and the organic phase was washed with brine and dried over MgSO$_4$, filtered and concentrated to give the title compound (0.0065 g, 16% yield). $^1$H NMR (300 MHz, CDCl$_3$) δ ppm 0.94(s, 9H), 0.98(s, 9H), 1.77-1.63(m, 2H), 2.64-2.55(q, J=9.19 Hz, 1H), 2.95-2.81(m, 5H), 3.06-2.97(m, 1H), 3.37-3.30(m, 1H), 3.62(s, 3H), 3.78-3.71(m, 2H), 4.03(s, 4H), 4.31-4.16(m, 2H), 4.43-4.32(m, 2H), 5.38-5.35(d, J=7.35 Hz, 1H), 6.07-6.04(d, J=7.72 Hz, 1H), 6.43-6.40(d, J=9.19 Hz, 1H), 6.69-6.66(d, J=8.46 Hz, 1H), 7.18-7.06(m, 5H), 7.23-7.20(d, J=8.46 Hz, 2H), 7.37-7.26(m, 6H), 7.65-7.60(m, 1H), 7.95-7.92(d, J=8.46 Hz, 2H).

EXAMPLE 115 methyl(1S)-1-[({(1S,3S,4S)-4-[((2S)-2-{3-[(6-tert-butyl-2-pyridinyl)methyl]-2-oxo-1-imidazolidinyl}-3,3-dimethylbutanoyl)amino]-3-hydroxy-5-phenyl-1-[4-(2-pyridinyl)benzyl]pentyl}amino)carbonyl]-2,2-dimethylpropylcarbamate

EXAMPLE 115A 2,2-dimethyl-5-hexen-3-ol

A solution of trimethylacetaldehyde (10.2 mL, 90.9 mmol) in diethyl ether (200 mL) at 0° C. was treated with allylmagnesium bromide (100 mL, 1 M in ether), stirred at 0° C. for 1 hour, quenched with saturated ammonium chloride and extracted with diethyl ether. The organic phase was washed with brine and dried over $Na_2SO_4$, filtered and concentrated to give the title compound (11.6 g).

EXAMPLE 115B ethyl 5-(2-hydroxy-3,3-dimethylbutyl)-4,5-dihydro-3-isoxazolecarboxylate A solution containing the product from Example 115A (7.83 g, 61.1 mmol) and ethyl chloroimidoacetate (20.4 g, 134.4 mmol) at 0° C. in diethyl ether (180 mL) was treated with a solution of triethylamine (24.7 mL, 177.1 mmol) in diethyl ether (200 mL) over 2 hours, stirred at 0° C. for 1 hour, filtered and concentrated. The concentrate was purified by chromatography on silica gel eluting with 10% ethyl acetate in dichloromethane to give the title compound (6.76 g).

EXAMPLE 115C ethyl 5-(3,3-dimethyl-2-oxobutyl)-4,5-dihydro-3-isoxazolecarboxylate A solution of DMSO (3.94 mL, 55.6 mmol) in dichloromethane (90 mL) at –78° C. was treated dropwise with oxalyl chloride (20.8 mL, 2 M in dichloromethane), stirred at –78° C. for 15 minutes, treated with a solution of the product from Example 115B (6.76 g, 27.8 mmol) in dichloromethane (230 mL) over 10 minutes, stirred at –78° C. for 20 minutes, treated dropwise with triethylamine (16.7 mL, 119.5 mmol) at –78° C., and after 10 minutes the reaction was warmed to 0° C., and stirred for an additional 10 minutes. The reaction mixture was quenched with water and partitioned between dichloromethane and water. The organic phase was washed with brine and dried over $Na_2SO_4$, filtered and concentrated. The residue was chromatographed on silica gel eluting with 5% ethyl acetate in chloroform to give the title compound (4.9 g, 73% yield).

EXAMPLE 115D ethyl 6-tert-butyl-2-pyridinecarboxylate

A solution of the product from Example 115C (4.95 g, 20.5 mmol) in ethanol (400 mL) was treated with Raney nickel (20.10 g) and 48% $HBF_4$ solution (4.13 mL), and the reaction was shaken under a hydrogen atmosphere (50 psi) at 25° C. for 1 hour. The reaction mixture was filtered, diluted with water, basified with dilute NaOH solution, and partitioned between dichloromethane and water. The organic phase was washed with brine and dried over $MgSO_4$, filtered and concentrated. The residue was chromatographed on silica gel eluting with 10% ethyl acetate in hexane to give the title compound (1.1 g, 26% yield).

EXAMPLE 115E (6-tert-butyl-2-pyridinyl)methanol

A solution containing the product from Example 115D (1.1 g, 5.3 mmol) in THF (20 mL) at –30° C. was treated with a solution of lithium aluminum hydride (5.3 mL, 1 M in THF), stirred at –30° C. for 5 minutes, treated with water (0.20 mL), 15% NaOH (0.20 mL), and water (0.40 mL) sequentially, stirred for 15 minutes at 25° C., filtered, rinsed with ethyl acetate, and concentrated to give the title compound (0.88 g, quantitative).

EXAMPLE 115F 6-tert-butyl-2-pyridinecarbaldehyde

A solution of DMSO (0.90 mL, 12.7 mmol) in dichloromethane (10 mL) at –78° C. was treated with oxalyl chloride (3.1 mL, 2 M in dichloromethane) dropwise, stirred for an additional 15 minutes at –78° C., treated with a solution of the product from Example 115E (0.88 g, 5.3 mmol) in dichloromethane (14 mL) over 10 minutes, stirred for 20 minutes, treated dropwise with triethylamine (3.6 mL, 26.1 mmol) at –78° C., stirred for 10 minutes, warmed to 0° C., stirred for an additional 10 minutes, quenched with water and partitioned between dichloromethane and water. The organic phase was washed with brine and dried over $Na_2SO_4$, filtered and concentrated. The residue was chromatographed on silica gel eluting with 5% ethyl acetate in chloroform to give the title compound (0.77 g, 88% yield).

EXAMPLE 115G tert-butyl(2S)-2-{3-[(6-tert-butyl-2-pyridinyl)methyl]-2-oxo-1-imidazolidinyl}-3,3-dimethylbutanoate A solution containing the product from Example 6F (1.14 g, 5.0 mmol) in dichloromethane (12 mL) was treated with the product from Example 115F (0.77 mL, 4.7 mmol) and $MgSO_4$ (2.27 g, 18.9 mmol), stirred at 25° C. for 16 hours, filtered and concentrated. A solution of the residue in methanol (18 mL) was treated with sodium borohydride (0.27 g, 7.1 mmol), stirred at 25° C. for 1 hour, quenched with acetone (6 mL) and concentrated. The concentrate was partitioned between ethyl acetate and saturated $NaHCO_3$, and the organic phase was washed with brine and dried over $Na_2SO_4$, filtered and concentrated. A solution of the residue (4.7 mmol) in 1,2-dichloroethane (18 mL) was treated with N,N-disuccinimidyl carbonate (1.45 g, 5.70 mmol) and triethylamine (0.66 mL, 4.70 mmol), stirred at 25° C. for 16 hours, and partitioned with 10% $NaHCO_3$. The aqueous phase was extracted with additional dichloromethane. The combined organic phase was washed with brine, dried over $Na_2SO_4$, filtered and concentrated. The residue was chromatographed on silica gel eluting with 2% methanol in chloroform to give the title compound (1.42 g, 75% yield).

EXAMPLE 115H (2S)-2-{3-[(6-tert-butyl-2-pyridinyl)methyl]-2-oxo-1-imidazolidinyl}-3,3-dimethylbutanoic acid A solution containing the product from Example 115G (1.27 g, 3.15 mmol) in dichloromethane (6 mL) was treated with trifluoracetic acid (3 mL), stirred at 25° C. for 3 hours, and concentrated. The residue was dissolved in ethyl acetate and concentrated several times to give the crude product as the trifluoroacetic acid salt.

EXAMPLE 115I methyl(1S)-1-[({(1S,3S,4S)-4-[((2S)-2-{3-[(6-tert-butyl-2-pyridinyl)methyl]-2-oxo-1-imidazolidinyl}-3,3-dimethylbutanoyl)amino]-3-hydroxy-5-phenyl-1-[4-(2-pyridinyl)benzyl]pentyl}amino)carbonyl]-2,2-dimethylpropylcarbamate A solution containing the product from Example 2C (0.035 g, 0.066 mmol) in THF (0.66 mL) was treated with the product from Example 115H (0.035 g, 0.079 mmol), DEPBT (0.029 g, 0.098 mmol), and N,N-diisopropylethylamine (0.012 mL, 0.069 mmol), stirred at 25° C. for 16 hours, and partitioned between chloroform and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 0-100% ethyl acetate/dichloromethane, followed by 0-5% methanol in ethyl acetate to give the title compound (0.023 g, 40% yield). $^1$H NMR (300 MHz, DMSO-$d_6$) δ ppm 0.83(s, 9H), 0.90(s, 9H), 1.31(s, 9H), 1.60-1.47(m, 2H), 2.37-2.34(m, J=8.82 Hz, 1H), 2.61-2.53(m, 1H), 2.68-2.65(d, J=7.35 Hz, 2H), 2.80-2.76(m, 1H), 3.03-2.98(m, 1H), 3.24-3.16(m, 1H), 3.50(s, 3H), 3.70-3.60(m, 1H), 3.86-3.83(d, J=9.56 Hz, 1H), 4.08(s, 1H), 4.26-4.10(m, 2H), 4.47-4.33(m, 2H), 4.55-4.52(d, J=7.72 Hz, 1H), 6.67-6.63(d, J=9.93 Hz, 1H), 7.11-7.03(m, 6H), 7.23-7.21(d, J=8.09 Hz, 2H), 7.33-7.30(m, 2H), 7.49-7.45(d, J=9.56 Hz, 1H), 7.75-7.69(t, J=7.72 Hz, 1H), 7.91-7.82(m, 5H), 8.64-8.63(d, J=4.78 Hz, 1H).

EXAMPLE 116 methyl(1S,4S,5S,7S,10S)-1,10-ditert-butyl-5-hydroxy-2,9,12-trioxo-4,7-bis[4-(2-pyridinyl)benzyl]-13-oxa-3,8,11-triazatetradec-1-ylcarbamate (i) A solution of the product from Example 112D (14 mg, 18 μmol) and thiocarbonyldiimidazole (10 mg, 56 μmol) in anhydrous THF (0.3 mL) was stirred at 60° C. 3 days. The solvent was concentrated, and the crude product was purified on by column chromatography on silica gel, eluting with 50-80% ethyl acetate in hexanes (7.7 mg, 52%).

(ii) A solution of the product from step (i) in anhydrous toluene (0.2 mL) was treated with tributyltin hydride (5 μL, 17 μmol) and 2,2'-azobisisobutyronitrile (2 mg, 12 μmol). The resulting mixture was heated at reflux for 90 min, cooled to 25° C., and the crude product was purified by column chromatography on silica gel, eluting with 50-100% ethyl acetate in hexanes (2.6 mg, 36%). $^1$H NMR (300 MHz, CDCl$_3$) δ ppm 0.89(m, 18H), 2.34(m, 2H), 2.88 (m, 4H), 3.62(s, 6H), 3.80(m, 2H), 4.00(m, 1H), 4.18(m, 1H), 5.33(m, 2H), 6.08(m, 1H), 6.21(m, 1H), 7.31(m, 2H), 7.72(m, 6H), 7.89(m, 4H), 8.67(m, 2H).

EXAMPLE 117 methyl(1S)-1-[({(1R,3S,4S)-3-hydroxy-4-[((2S)-2-{3-[(6-isopropyl-2-pyridinyl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate

EXAMPLE 117A tert-butyl (2S)-2-{3-[(6-acetyl-2-pyridinyl)methyl]-2-oxo-1-imidazolidinyl}-3,3-dimethylbutanoate A solution of the product from Example 17D (1.95 g, 4.815 mmol) in tetrahydrofuran (50 mL) at −78° C. was treated methylmagnesium bromide in butyl ether (5.7 mL, 1 M). The mixture was stirred 0.5 hours at −78° C., quenched with acetone (3 mL) and 10% citric acid. The reaction mixture was partitioned between ethyl acetate and 1 N $NaHCO_3$, and the organic phase layer was decanted and concentrated. The residue was purified by flash chromatography on silica gel eluting with 25%-50% ethyl acetate in hexane give the title compound (1.6 g, 85% yield).

EXAMPLE 117B tert-butyl (2S)-2-{3-[(6-isopropenyl-2-pyridinyl)methyl]-2-oxo-1-imidazolidinyl}-3,3-dimethylbutanoate A solution of methyltriphenylphosphonium bromide (0.33 g, 0.923 mmol) in THF (2.5 mL) was treated with a solution of potassium tert-butoxide in THF (0.89 mL, 1 M) dropwise, stirred for 1 hour at 25° C., treated with a solution of the product from Example 117A (0.116 g, 0.298 mmol) in THF (2 mL), stirred at 25° C. for 16 hours, quenched with saturated ammonium chloride solution and partitioned between ethyl acetate and water. The organic phase was washed with brine and dried over $MgSO_4$, filtered and concentrated. The residue was chromatographed on silica gel eluting with 15%-25% ethyl acetate in hexane to give the title compound (0.040 g, 35% yield).

EXAMPLE 117C tert-butyl (2S)-2-{3-[(6-isopropyl-2-pyridinyl)methyl]-2-oxo-1-imidazolidinyl}-3,3-dimethylbutanoate A solution containing the product from Example 117B (0.038 g, 0.098 mmol) in methanol (1 mL) was treated with 10% Pd on carbon (0.005 g) and the reaction was stirred under an atmosphere of hydrogen (balloon pressure) for 2 hours. The reaction was filtered and the solvent was concentrated to give the title compound, which was used without further purification.

EXAMPLE 117D (2S)-2-{3-[(6-isopropyl-2-pyridinyl)methyl]-2-oxo-1-imidazolidinyl}-3,3-dimethylbutanoic acid A solution of the product from Example 117C (0.098 mmol) in dichloromethane (0.5 mL) was treated with trifluoroacetic acid (0.5 mL) and the mixture was stirred for 1 hour at 25° C. The solvent was removed under reduced pressure and the residue was purified by reversed phase chromatography on a C18 column eluting with 5-100% acetonitrile in water (0.1% TFA) to give the title compound as the trifluroacetic acid salt (0.022 g, 52% yield).

EXAMPLE 117E methyl(1S)-1-[({(1R,3S,4S)-3-hydroxy-4-[((2S)-2-{3-[(6-isopropyl-2-pyridinyl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate A solution containing the product from Example 1H (0.025 g, 0.046 mmol) in THF (0.5 mL) was treated with the product from Example 117D (0.022 g, 0.051 mmol), DEPBT (0.021 g, 0.070 mmol), and N,N-diisopropylethylamine (0.057 mL, 0.325 mmol), stirred at 25° C. for 16 hours, and partitioned between chloroform and 10% Na$_2$CO$_3$ solution. The organic phase was washed with additional 10% Na$_2$CO$_3$ solution and brine, dried over MgSO$_4$, filtered and concentrated. The product was purified by chromatography on silica gel eluting with 0-100% ethyl acetate/dichloromethane, followed by 0-5% methanol in ethyl acetate to give the title compound (0.024 g, 62% yield). $^1$H NMR (300 MHz, DMSO-d$_6$) δ ppm 0.80(s, 9H), 0.88(s, 9H), 1.27-1.25(d, J=6.99 Hz, 6H), 1.42-1.23(m, 1H), 1.58-1.47(m, 1H), 2.70-2.53(m, 3H), 2.87-2.78(m, 1H), 3.31-2.98(m, 4H), 3.57-3.50(m, 1H), 3.57(s, 3H), 3.85-3.82 (d, J=9.56 Hz, 1H), 3.99-3.87(m, 1H), 4.03(s, 1H), 4.20-4.10, 4.23-4.13(m, 2H), 4.45(s, 2H), 6.91-6.87(d, J=9.93 Hz, 1H), 7.10-7.06(m, 5H), 7.28-7.21(m, 4H), 7.44-7.37(m, 2H), 7.58-7.55(d, J=9.19 Hz, 1H), 7.97-7.86(m, 5H), 8.69-8.67(m, 1H).

EXAMPLE 118 methyl(1S)-1-[({(1R,3S,4S)-4-[((2S)-2-{3-[(6-tert-butyl-2-pyridinyl)methyl]-2-oxo-1-imidazolidinyl}-3,3-dimethylbutanoyl)amino]-3-hydroxy-5-phenyl-1-[4-(2-pyridinyl)benzyl]pentyl}amino)carbonyl]-2,2-dimethylpropylcarbamate A solution containing the product from Example 1H (0.019 g, 0.036 mmol) in THF (0.43 mL) was treated with the product from Example 115H (0.019 g, 0.043 mmol), DEPBT (0.016 g, 0.054 mmol), and N,N-diisopropylethylamine (0.063 mL, 0.360 mmol), stirred at 25° C. for 16 hours, and partitioned between chloroform and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate to give the title compound (0.012 g, 39% yield). $^1$H NMR (300 MHz, DMSO-d6) δ ppm 0.80(s, 9H), 0.88(s, 9H), 1.30(s, 9H), 1.42-1.23(m, 1H), 1.58-1.47(m, 1H), 2.47-2.42(m, 1H), 2.73-2.55(m, 2H), 2.87-2.78(m, 1H), 3.05-2.99(m, 1H), 3.31-3.18 (m, 1H), 3.57-3.50(m, 1H), 3.57(s, 3H), 3.85-3.82(d, J=9.56 Hz, 1H), 3.99-3.87(m, 1H), 4.02(s, 1H), 4.23-4.13(m, 1H), 4.44-4.32(m, 2H), 4.44-4.42(d, J=7.35 Hz, 1H), 6.90-6.87(d, J=9.19 Hz, 1H), 7.09-7.04(m, 6H), 7.25-7.22(d, J=8.46 Hz, 2H), 7.34-7.29(m, 2H), 7.54-7.51(d, J=9.91 Hz, 1H), 7.73-7.68(t, J=7.72 Hz, 1H), 7.90-7.83(m, 3H), 7.97-7.94(d, J=8.09 Hz, 2H), 8.65-8.64(m, 1H).

EXAMPLE 119 methyl(1S)-1-[({(1S,2S,4S)-4-{[(2S)-2-(3-benzyl-2-oxo-1-imidazolidinyl)-3,3-dimethylbutanoyl]amino}-2-hydroxy-1-[4-(6-methoxy-2-pyridinyl)benzyl]-5-phenylpentyl}amino)carbonyl]-2,2-dimethylpropylcarbamate

EXAMPLE 119A benzyl (4S,5S)-5-{(2S)-2-[(tert-butoxycarbonyl)amino]-3-phenylpropyl}-4-[4-(6-methoxy-2-pyridinyl)benzyl]-2,2-dimethyl-1,3-oxazolidine-3-carboxylate A solution containing the product from Example 23I (0.20 g, 0.28 mmol) in DMF (3 mL) was treated with LiCl (0.119 g, 2.8 mmol), dichlorobis(triphenylphosphine)palladium(II) (0.060 g, 0.085 mmol), and the product from Example 113A (0.338 g, 0.85 mmol), heated at 85° C. for 64 hours, cooled and partitioned between ethyl acetate and water. The organic phase was washed with brine and dried over MgSO$_4$, filtered and concentrated. The residue was chromatographed on silica gel eluting with 20% ethyl acetate in hexanes to give the title compound (0.097 g, 51% yield).

EXAMPLE 119B benzyl (1S,2S,4S)-4-amino-2-hydroxy-1-[4-(6-methoxy-2-pyridinyl)benzyl]-5-phenylpentylcarbamate A solution containing the product from Example 119A (0.095 g, 0.14 mmol) in THF (1 mL) was treated with a solution of HCl in dioxane (0.25 mL, 4 N), stirred at 50° C. for 16 hours, cooled and concentrated under reduced pressure. The residue was dissolved in ethanol and concentrated several times to give the title compound as hydrochloride salt, which was used without further purification.

EXAMPLE 119C benzyl (1S,2S,4S)-4-{[(2S)-2-(3-benzyl-2-oxo-1-imidazolidinyl)-3,3-dimethylbutanoyl]amino}-2-hydroxy-1-[4-(6-methoxy-2-pyridinyl)benzyl]-5-phenylpentylcarbamate A solution containing the product from Example 119B (0.048 mmol) in THF (2 mL) was treated with the product from Example 70A (0.014 g, 0.048 mmol), DEPBT (0.029 g, 0.095 mmol), and N,N-diisopropylethylamine (0.042 mL, 0.235 mmol), stirred at 25° C. for 5 hours. The mixture was partitioned between chloroform and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 2% methanol in chloroform to give the title compound (0.024 g, 62% yield).

EXAMPLE 119D (2S)—N-{(1S,3S,4S)-4-amino-1-benzyl-3-hydroxy-5-[4-(6-methoxy-2-pyridinyl)phenyl]pentyl}-2-(3-benzyl-2-oxo-1-imidazolidinyl)-3,3-dimethylbutanamide A solution containing the product from Example 119C (0.024 g, 0.030 mmol) in methanol (1 mL) was treated with 10% Pd on carbon (0.003 g) and HCl solution (0.030 mL, 4 N in dioxane), stirred under a hydrogen atmosphere (balloon pressure) at 25° C. for 16 hours, filtered through a bed of celite and rinsed with methanol. The solvent was concentrated to give the crude product as a hydrochloride salt, which was used without further purification.

EXAMPLE 119E methyl(1S)-1-[({(1S,2S,4S)-4-{[(2S)-2-(3-benzyl-2-oxo-1-imidazolidinyl)-3,3-dimethylbutanoyl]amino}-2-hydroxy-1-[4-(6-methoxy-2-pyridinyl)benzyl]-5-phenylpentyl}amino)carbonyl]-2,2-dimethylpropylcarbamate A solution containing the product from Example 119D (0.030 mmol) in THF (1 mL) was treated with the product from Example 1F (0.006 g, 0.033 mmol), DEPBT (0.018 g, 0.059 mmol), and N,N-diisopropylethylamine (0.026 mL, 0.148 mmol), stirred at 25° C. for 16 hours, and partitioned between chloroform and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 2% methanol in chloroform, to give the title compound. $^1H$ NMR (300 MHz, $CDCl_3$) δ ppm 0.96(s, 9H), 1.00(s, 9H), 1.67-1.55(m, 2H), 2.67-2.60(m, 1H), 2.96-2.73m, 5H), 3.08-2.99q, J=8.46 Hz, 1H), 3.43-3.36(m, 1H), 3.62(bs, 4H), 3.82-3.79(d, J=8.82 Hz, 1H), 4.00(s, 1H), 4.04(s, 3H), 4.16-4.09(m, 2H), 4.45-4.25(m, 2H), 5.34-5.27(m, 1H), 6.12-6.09(m, 2H), 6.69-6.66(d, J=8.09 Hz, 1H), 7.15-7.06(m, 6H), 7.36-7.23(m, 7H), 7.65-7.59(m, 1H), 7.95-7.92(d, J=8.09 Hz, 2H).

EXAMPLE 120 methyl(1S,4S,5S,7S,10S)-7-benzyl-1,10-ditert-butyl-5-hydroxy-4-[4-(6-methoxy-2-pyridinyl)benzyl]-2,9,12-trioxo-13-oxa-3,8,11-triazatetradec-1-ylcarbamate

EXAMPLE 120A benzyl(1S,2S,4S)-2-hydroxy-4-({(2S)-2-[(methoxycarbonyl)amino]-3,3-dimethylbutanoyl}amino)-1-[4-(6-methoxy-2-pyridinyl)benzyl]-5-phenylpentylcarbamate A solution containing the product from Example 119B (0.048 mmol) in THF (2 mL) was treated with the product from Example 1F (0.009 g, 0.048 mmol), DEPBT (0.029 g, 0.095 mmol), and N,N-diisopropylethylamine (0.042 mL, 0.235 mmol), stirred at 25° C. for 5 hours, and partitioned between chloroform and 10% $Na_2CO_3$ solution. The organic phase was washed with additional 10% $Na_2CO_3$ solution and brine, dried over $MgSO_4$, filtered and concentrated. The residue was chromatographed on silica gel eluting with 2% methanol in chloroform to give the title compound (0.028 g, 85% yield).

EXAMPLE 120B methyl(1S)-1-[({(1S,3S,4S)-4-amino-1-benzyl-3-hydroxy-5-[4-(6-methoxy-2-pyridinyl)phenyl]pentyl}amino)carbonyl]-2,2-dimethylpropylcarbamate A solution containing the product from Example 120A (0.028 g, 0.041 mmol) in methanol (1 mL) was treated with 10% Pd on carbon (0.003 g) and HCl solution (0.030 mL, 4 N in dioxane), and the reaction was stirred under a hydrogen atmosphere (balloon pressure) at 25° C. for 16 hours. The reaction was filtered through a bed of celite and rinsed with methanol. The solvent was concentrated to give the title compound as the hydrochloride salt, which was used without further purification.

EXAMPLE 120C methyl(1S,4S,5S,7S,10S)-7-benzyl-1,10-ditert-butyl-5-hydroxy-4-[4-(6-methoxy-2-pyridinyl)benzyl]-2,9,12-trioxo-13-oxa-3,8,11-triazatetradec-1-ylcarbamate A solution containing the product from Example 120B (0.041 mmol) in THF (1 mL) was treated with the product from Example 1F (0.009 g, 0.045 mmol), DEPBT (0.024 g, 0.082 mmol), and N,N-diisopropylethylamine (0.036 mL, 0.204 mmol) and the mixture was stirred at 25° C. for 16 hours. The mixture was partitioned between chloroform and 10% $Na_2CO_3$ solution. The organic phase was washed with additional 10% $Na_2CO_3$ solution and brine, dried over $MgSO_4$, filtered and concentrated. The residue was purified by chromatography on silica gel eluting with 2% methanol in chloroform, to give the title compound. $^1H$ NMR (300 MHz, $CDCl_3$) δ ppm 0.91(s, 9H), 0.94(s, 9H), 1.67-1.54(m, 2H), 2.80-2.74(m, 2H), 2.89-2.87(d, J=7.35 Hz, 2H), 3.62(s, 3H), 3.67(s, 3H), 3.74-3.61(m, 2H), 3.82-3.79(d, J=9.19 Hz, 1H), 4.00-3.93(m, 1H), 4.04(s, 3H), 4.13-4.04(m, 1H), 5.32-5.28(m, 2H), 5.96-5.94(d, J=6.99 Hz, 1H), 6.14-6.11(d, J=8.82 Hz, 1H), 6.69-6.67(d, J=7.72 Hz, 1H), 7.08-7.06(d, J=6.62 Hz, 2H), 7.33-7.15(m, 6H), 7.66-7.60(m, 1H), 7.95-7.92(d, J=8.09 Hz, 2H).

EXAMPLE 121 methyl(1S,4S,5S,7S,10S)-4-benzyl-1,10-ditert-butyl-5-hydroxy-7-[4-(6-methoxy-2-pyridinyl)benzyl]-2,9,12-trioxo-13-oxa-3,8,11-triazatetradec-1-ylcarbamate A solution of the product from Example 113C (0.074 g, 0.12 mmol) in THF (2 mL) was treated with an HCl solution (0.21 mL, 4 N in dioxane), and the reaction was stirred at 50° C. for 16 hours. The solvent was removed under reduced pressure and ethanol added and concentrated several times. A solution of the concentrate (0.12 mmol) in methanol (2 mL) was treated with Pd on carbon (0.007 g, 10% Pd by wt.), and the reaction was stirred under a hydrogen atmosphere (balloon pressure) at 25° C. for 16 hours. The reaction mixture was filtered through a bed of celite®, rinsed with methanol, and concentrated. A solution of the concentrate (0.12 mmol) in THF (0.5 mL) was treated with the product from Example 1F (0.047 g, 0.25 mmol), DEPBT (0.142 g, 0.47 mmol), and N,N-diisopropylethylamine (0.207 mL, 1.19 mmol), stirred at 25° C. for 16 hours, and partitioned between chloroform and 10% $Na_2CO_3$ solution. The organic phase was washed with additional 10% Na₂CO₃ solution and brine, dried over MgSO₄, filtered and concentrated. The residue was chromatographed on silica gel eluting with 1.5% methanol in chloroform, to give the title compound. ¹H NMR (300 MHz, CDCl₃) δ ppm 0.93(s, 18H), 1.65-1.58(m, 2H), 2.90-2.74(m, 4H), 3.63(s, 3H), 3.68(s, 3H), 3.80-3.63(m, 3H), 3.98-3.92 (m, 1H), 4.04(s, 3H), 4.20-4.11(m, 1H), 5.32-5.35(m, 2H), 6.02-6.00(d, J=8.09 Hz, 1H), 6.11-6.08(d, J=8.82 Hz, 1H), 6.69-6.67(d, J=7.72 Hz, 1H), 7.33-7.14(m, 8H), 7.65-7.60(m, 1H), 7.94-7.91(d, J=8.09 Hz, 2H).

EXAMPLE 122 methyl(1S)-1-[({(1S,2S,4S)-4-[((2S)-3,3-dimethyl-2-{3-[(6-methyl]-2-oxo-1-imidazolidinyl}butanoyl)amino]-2-hydroxy-1-[4-(6-methoxy-2-pyridinyl)benzyl]-5-phenylpentyl}amino)carbonyl]-2,2-dimethylpropylcarbamate

EXAMPLE 122A benzyl(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methoxy-2-pyridinyl)benzyl]-5-phenylpentylcarbamate A solution containing the product from Example 119B (0.048 mmol) in THF (2 mL) was treated with the product from Example 10D (0.016 g, 0.048 mmol), DEPBT (0.029 g, 0.095 mmol), and N,N-diisopropylethylamine (0.042 mL, 0.235 mmol), stirred at 25° C. for 5 hours, and partitioned between chloroform and 10% Na₂CO₃ solution. The organic phase was washed with additional 10% Na₂CO₃ solution and brine, dried over MgSO₄, filtered and concentrated. The residue was chromatographed on silica gel eluting with 2% methanol in chloroform to give the title compound (0.018 g, 47% yield).

EXAMPLE 122B (2S)-N-{(1S,3S,4S)-4-amino-1-benzyl-3-hydroxy-5-[4-(6-methoxy-2-pyridinyl)phenyl]pentyl}-3,3-dimethyl-2-{3-[(6-methyl-2-pyridinyl)methyl]-2-oxo-1-imidazolidinyl}butanamide A solution containing the product from Example 122A (0.018 g, 0.022 mmol) in methanol (1 mL) was treated with 10% Pd on carbon (0.002 g) and HCl solution (0.030 mL, 4 N in dioxane), stirred under a hydrogen atmosphere (balloon pressure) at 25° C. for 16 hours, filtered through a bed of celite and rinsed with methanol. The solvent was concentrated to give the crude product as the hydrochloride salt, which was used without further purification.

EXAMPLE 122C methyl(1S)-1-[({(1S,2S,4S)-4-[((2S)-3,3-dimethyl-2-{3-[(6-methyl-2-pyridinyl)methyl]-2-oxo-1-imidazolidinyl}butanoyl)amino]-2-hydroxy-1-[4-(6-methoxy-2-pyridinyl)benzyl]-5-phenylpentyl}amino)carbonyl]-2,2-dimethylpropylcarbamate A solution containing the product from Example 122B (0.022 mmol) in THF (1 mL) was treated with the product from Example 1F (0.005 g, 0.024 mmol), DEPBT (0.013 g, 0.044 mmol), and N,N-diisopropylethylamine (0.020 mL, 0.111 mmol), stirred at 25° C. for 16 hours, and partitioned between chloroform and 10% Na₂CO₃ solution. The organic phase was washed with additional 10% Na₂CO₃ solution and brine, dried over MgSO₄, filtered and concentrated. The residue was purified by chromatography on silica gel eluting with 2% methanol in chloroform, to give the title compound. ¹H NMR (300 MHz, CDCl₃) δ ppm 0.96(s, 9H), 1.01(s, 9H), 1.67-1.59(m, 2H), 2.55(s, 3H), 2.67-2.59(m, 1H), 2.84-2.73 (m, 2H), 2.91-2.89(d, J=7.72 Hz, 2H), 3.10-3.02(m, 1H), 3.23-3.14(q, J=8.95 Hz, 1H), 3.46-3.39(m, 1H), 3.68-3.62(m, 1H), 3.62(s, 3H), 3.82-3.79(d, J=9.19 Hz, 1H), 3.99(s, 1H), 4.04(s, 3H), 4.17-4.07(m, 2H), 4.59-4.34(m, 2H), 5.32-5.29 (d, J=8.46 Hz, 1H), 6.12-6.09(d, J=9.19 Hz, 1H), 6.21-6.11 (m, 1H), 6.68-6.66(d, J=7.72 Hz, 1H), 7.14-7.01(m, 7H), 7.33-7.27(m, 3H), 7.58-7.53(t, J=7.72 Hz, 1H), 7.64-7.61(m, 1H), 7.95-7.93(d, J=8.46 Hz, 2H).

EXAMPLE 123 methyl(1S)-1-[({(1S,3S,4S)-4-({(2S)-2-[3-(2-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate

EXAMPLE 123A (2S)-3,3-dimethyl-2-[3-(2-nitrobenzyl)-2-oxo-1-imidazolidinyl]butanoic acid A solution containing the product from Example 6F (0.162 g, 0.702 mmol) in a mixture of benzene (3.5 mL) and methanol (3.5 mL) was treated with 2-nitrobenzaldehyde (0.112 mL, 0.737 mmol), stirred at 50° C. for 16 hours, cooled to 25° C., treated with sodium borohydride (0.053 g, 1.4 mmol), stirred at 25° C. for 2 hours, quenched with saturated NaHCO₃, and partitioned between ethyl acetate and saturated NaHCO₃. The organic phase was washed with brine and dried over MgSO₄, filtered and concentrated. A solution of the concentrate (0.702 mmol) in 1,2-dichloroethane (7 mL) was treated with N,N-disuccinimidyl carbonate (0.216 g, 0.842 mmol) and triethylamine (0.117 mL, 0.842 mmol), stirred at 25° C. for 16 hours, diluted with dichloromethane and partitioned with 10% Na₂CO₃. The organic phase was washed with brine, dried over MgSO₄, filtered and concentrated. A solution of the concentrate (0.702 mmol) in dichloromethane (3.5 mL) was treated with trifluoracetic acid (3.5 mL), stirred at 25° C. for 2 hours and concentrated. The residue was purified by reversed phase chromatography on a C18 column eluting with a gradient starting with 5-100% acetonitrile in water (0.1% TFA), to give the title compound (0.12 g, 50% yield).

EXAMPLE 123B methyl(1S)-1-[({(1S,3S,4S)-4-({(2S)-3,3-dimethyl-2-[3-(2-nitrobenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.082 g, 0.154 mmol) in THF (1.5 mL) was treated with the product from Example 123A (0.057 g, 0.17 mmol), DEPBT (0.069 g, 0.231 mmol), and N,N-diisopropylethylamine (0.135 mL, 0.77 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% acetate/dichloromethane, followed by 0-5% methanol in ethyl acetate to give the title compound (0.080 g, 61% yield).

EXAMPLE 123C methyl(1S)-1-[({(1S,3S,4S)-4-({(2S)-2-[3-(2-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate A solution containing the product from Example 123B (0.027 g, 0.031 mmol) in ethanol (1 mL) was treated with 10% Pd on carbon (0.010 g), stirred under an atmosphere of hydrogen (balloon pressure) at 25° C. for 2.5 hours, filtered and concentrated under reduced pressure. The residue was purified by reversed phase chromatography on a C18 column eluting with 5-100% acetonitrile in water (0.1% TFA). The product was partitioned between ethyl acetate and saturated NaHCO₃, and the organic phase was washed with brine and dried over MgSO₄, filtered and concentrated to give the title compound (0.014 g, 55% yield). ¹H NMR (300 MHz, DMSO-d₆) δ ppm 0.84(s, 9H), 0.86(s, 9H), 1.63-1.46(m, 2H), 2.16-2.07(m, 1H), 2.65-2.54(m, 3H), 3.00-2.74(m, 3H), 3.18-3.08(m, 1H), 3.50(s, 3H), 3.71-3.62(m, 1H), 3.87-3.83(d, J=9.56 Hz, 1H), 4.05(s, 1H), 4.28-4.10(m, 4H), 4.53-4.51(d, J=7.72 Hz, 1H), 5.20(s, 2H), 6.56-6.51(t, J=7.35 Hz, 1H), 6.68-6.64(m, 2H), 7.08-6.92(m, 7H), 7.24-7.21(d, J=8.09 Hz, 2H), 7.33-7.29(m, 1H), 7.43-7.40(d, J=9.93 Hz, 1H), 7.91-7.82(m, 5H), 8.64-8.63(d, J=4.41 Hz, 1H).

EXAMPLE 124 methyl(1S)-1-[({(1S,3S,4S)-4-({(2S)-2-[3-(4-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate

EXAMPLE 124A (2S)-3,3-dimethyl-2-[3-(4-nitrobenzyl)-2-oxo-1-imidazolidinyl]butanoic acid A solution containing the product from Example 6F (0.161 g, 0.700 mmol) in a mixture of benzene (3.5 mL) and methanol (3.5 mL) was treated with 4-nitrobenzaldehyde (0.111 mL, 0.735 mmol), stirred at 50° C. for 16 hours, cooled to 25° C., treated with sodium borohydride (0.053 g, 1.4 mmol), stirred at 25° C. for 2 hours, quenched with saturated NaHCO₃, and partitioned between ethyl acetate and saturated NaHCO₃. The organic phase was washed with brine and dried over MgSO₄, filtered and concentrated. A solution of the concentrate (0.700 mmol) in 1,2-dichloroethane (7 mL) was treated with N,N-disuccinimidyl carbonate (0.215 g, 0.839 mmol) and triethylamine (0.117 mL, 0.842 mmol), stirred at 25° C. for 16 hours, diluted with dichloromethane and partitioned with 10% Na₂CO₃. The organic phase was washed with brine, dried over MgSO₄, filtered and concentrated. A solution containing of the concentrate (0.700 mmol) in dichloromethane (3 mL) was treated with trifluoracetic acid (3 mL), and the mixture was stirred at 25° C. for 2 hours. The solvent was concentrated, and the residue was purified by reversed phase chromatography on a C18 column eluting with a gradient starting with 5-100% acetonitrile in water (0.1 % TFA), to give the title compound (0.17 g, 62% yield).

EXAMPLE 124B methyl(1S)-1-[({(1S,3S,4S)-4-({(2S)-3,3-dimethyl-2-[3-(4-nitrobenzyl)-2-oxo-1-imidazolidinyl]butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.074 g, 0.138 mmol) in THF (1.5 mL) was treated with the product from Example 124A (0.051 g, 0.152 mmol), DEPBT (0.062 g, 0.207 mmol), and N,N-diisopropylethylamine (0.120 mL, 0.691 mmol), stirred at 25° C. for 16 hours, and partitioned between ethyl acetate and 10% Na₂CO₃ solution. The organic phase was washed with additional 10% Na₂CO₃ solution and brine, dried over MgSO₄, filtered and concentrated. The residue was chromatographed on silica gel eluting with 0-100% ethyl acetate/dichloromethane, followed by 0-5% methanol in ethyl acetate to give the title compound (0.066 g, 56% yield).

EXAMPLE 124C methyl(1S)-1-[({(1S,3S,4S)-4-({(2S)-2-[3-(4-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate A solution containing the product from Example 124B (0.065 g, 0.076 mmol) in ethanol (1.5 mL) was treated with 10% Pd on carbon (0.024 g), stirred under an atmosphere of hydrogen (balloon pressure) at 25° C. for 2.5 hours, filtered concentrated under reduced pressure. The residue was purified by reversed phase chromatography on a C18 column eluting with a gradient starting with 5-100% acetonitrile in water (0.1% TFA). The product was partitioned between ethyl acetate and saturated NaHCO₃, and the organic phase was washed with brine and dried over MgSO₄, filtered and concentrated to give the title compound (0.024 g, 39% yield). ¹H NMR (300 MHz, DMSO-d₆) δ ppm 0.83(s, 9H), 0.87(s, 9H), 1.60-1.48(m, 2H), 2.29-2.20(m, 1H), 2.67-2.53(m, 3H), 2.92-2.75(m, 3H), 3.16-3.08(m, 1H), 3.50(s, 3H), 3.71-3.61(m, 1H), 3.86-3.83(d, J=9.93 Hz, 1H), 4.07(s, 1H), 4.11(s, 2H), 4.23-4.09(m, 2H), 4.56-4.53(d, J=7.72 Hz, 1H), 5.00(s, 2H), 6.55-6.52(d, J=8.46 Hz, 2H), 6.67-6.64(d, J=9.93 Hz, 1H), 6.94-6.91(d, J=8.46 Hz, 2H), 7.10-7.02(m, 5H), 7.23-7.21(d, J=8.46 Hz, 2H), 7.33-7.29(m, 1H), 7.45-7.42(d, J=9.56 Hz, 1H), 7.91-7.82(m, 5H), 8.64-8.62(m, 1H).

EXAMPLE 125 methyl(1S)-1-[({(1S,3S,4S)-4-({(2S)-2-[3-(3-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate

EXAMPLE 125A tert-butyl(2S)-3,3-dimethyl-2-[3-(3-nitrobenzyl)-2-oxo-1-imidazolidinyl]butanoate A solution containing the product from Example 6F (0.215 g, 0.933 mmol) in a mixture of benzene (3 mL) and methanol (3 mL) was treated with 3-nitrobenzaldehyde (0.148 mL, 0.98 mmol), and the mixture was stirred at 50° C. for 16 hours, cooled to 25° C., treated with sodium borohydride (0.071 g, 1.88 mmol), stirred at 25° C. for 2 hours, quenched with saturated NaHCO$_3$, and partitioned between ethyl acetate and saturated NaHCO$_3$. The organic phase was washed with brine and dried over MgSO$_4$, filtered and concentrated. A solution of the concentrate (0.933 mmol) in 1,2-dichloroethane (9 mL) was treated with N,N-disuccinimidyl carbonate (0.287 g, 1.12 mmol) and triethylamine (0.156 mL, 1.12 mmol), stirred at 25° C. for 16 hours, diluted with dichloromethane and partitioned with 10% Na$_2$CO$_3$. The organic phase was washed with brine, dried over MgSO$_4$, filtered and concentrated. The residue was chromatographed on silica gel eluting with 0-25% ethyl acetate in hexane to give the title compound (0.209 g, 56% yield).

EXAMPLE 125B (2S)-3,3-dimethyl-2-[3-(3-nitrobenzyl)-2-oxo-1-imidazolidinyl]butanoic acid A solution containing the product from Example 125B (0.209 g, 0.53 mmol) in dichloromethane (2.5 mL) was treated with trifluoracetic acid (2.5 mL), and the mixture was stirred at 25° C. for 1 hour. The solvent was concentrated and the residue was dissolved in ethyl acetate and concentrated several times to give the crude product, which was used without further purification.

EXAMPLE 125C methyl(1S)-1-[({(1S,3S,4S)-4-({(2S)-3,3-dimethyl-2-[3-(3-nitrobenzyl)-2-oxo-1-imidazolidinyl] butanoyl}amino)-3-hydroxy-5-phenyl-1-[4-(2-pyridinyl)benzyl]pentyl}amino)carbonyl]-2,2-dimethylpropylcarbamate A solution containing the product from Example 2C (0.065 g, 0.123 mmol) in THF (1 mL) was treated with the product from Example 125B (0.049 g, 0.147 mmol), DEPBT (0.055 g, 0.185 mmol), and N,N-diisopropylethylamine (0.102 mL, 0.615 mmol), stirred at 25° C. for 16 hours, and partitioned between ethyl acetate and 10% Na$_2$CO$_3$ solution. The organic phase was washed with additional 10% Na$_2$CO$_3$ solution and brine, dried over MgSO$_4$, filtered and concentrated. The residue was chromatographed on silica gel eluting with 0-100% ethyl acetate/dichloromethane, followed by 0-5% methanol in ethyl acetate to give the title compound (0.077 g, 74% yield).

EXAMPLE 125D methyl(1S)-1-[({(1S,3S,4S)-4-({(2S)-2-[3-(3-aminobenzyl)-2-oxo-1-imidazolidinyl]-3,3-dimethylbutanoyl}amino)-3-hydroxy-5-phenyl-1-[4-(2-pyridinyl)benzyl]pentyl}amino)carbonyl]-2,2-dimethylpropylcarbamate A solution containing the product from Example 125C (0.077 g, 0.091 mmol) in ethanol (2 mL) was treated with 10% Pd on carbon (0.029 g), stirred under an atmosphere of hydrogen (balloon pressure) at 25° C. for 3 hours, filtered and concentrated under reduced pressure. The residue was purified by reversed phase chromatography on a C18 column eluting with 5-100% acetonitrile in water (0.1% TFA. The product was partitioned between ethyl acetate and saturated NaHCO$_3$, and the organic phase was washed with brine and dried over MgSO$_4$, filtered and concentrated to give the title compound (0.035 g, 47% yield). $^1$H NMR (300 MHz, DMSO-d$_6$) δ ppm 0.83(s, 9H), 0.89(s, 9H), 1.60-1.49(m, 2H), 2.38-2.28(m, 1H), 2.62-2.53(m, 1H), 2.68-2.66(m, 2H), 2.86-2.76(m, 2H), 2.98-2.89(q, J=9.19 Hz, 1H), 3.20-3.14(m, 1H), 3.50(s, 3H), 3.70-3.62(m, 1H), 3.86-3.83(d, J=9.93 Hz, 1H), 4.07(s, 1H), 4.14(s, 2H), 4.25-4.10(m, 2H), 4.55-4.53(d, J=7.35 Hz, 1H), 5.03(s, 2H), 6.42-6.39(d, J=7.35 Hz, 1H), 6.48-6.66(m, 2H), 6.62-6.59(d, J=9.93 Hz, 1H), 7.01-6.96(t, J=7.91 Hz, 1H), 7.11-7.04(m, 5H), 7.24-7.21(d, J=8.09 Hz, 2H), 7.33-7.28(m, 1H), 7.40-7.37(d, J=9.19 Hz, 1H), 7.91-7.80(m, 5H), 8.64-8.63(d, J=4.41 Hz, 1H).

EXAMPLE 126 tert-butyl(1S,3S,4S)-4-amino-1-benzyl-3-hydroxy-5-phenylpentylcarbamate, Succinate Salt The title compound was prepared from L-phenylalanine using the procedures as described in U.S. Pat. No. 5,914,332, Examples 1A to 1F-2.

EXAMPLE 127

(2S,3S,5S)-2,5-diamino-1,6-diphenyl-3-hexanol

The title compound was prepared from Cbz-L-phenylalaninol using the procedures as described in Kempf, D. J.; Marsh K. C.; Codacovi Fino, L.; Bryant, P.; Craig-Kennard, A.; Sham, H. L.; Zhao, C.; Vasavanonda, S.; Kohlbrenner, W. E.; Wideburg, N. E.; Saldivar, A.; Green, B. E.; Herrin, T.; Norbeck, D. W. *Bioorganic and Medicinal Chemistry* 1994, 2, 847-858, and in Kempf, D. J.; Sowin, T. J.; Doherty, E. M.; Hannick, S. M.; Codavoci, L.; Henry, R. F.; Green, B. E.; Spanton, S. G.; Norbeck, D. W. *Journal of Organic Chemistry* 1992, 57, 5692-5700.

EXAMPLE 128 methyl(1S)-1-[({(1S,3S,4S)-4-[((2S)-3,3-dimethyl-2-{3-[(6-methyl-]-2-oxo-1-imidazolidinyl}butanoyl) amino]-3-hydroxy-1-[4-(5-methyl-2-pyridinyl)benzyl]-5-phenylpentyl}amino)carbonyl]-2,2-dimethylpropylcarbamate

EXAMPLE 128A benzyl(3S,4S)-1-(4-bromobenzyl)-4-[(tert-butoxycarbonyl)amino]-3-hydroxy-5-phenylpentylcarbamate A solution of a mixture of the products from Examples 92D and Example 92E (prior to separation by chromatography) (2.4 g, 3.37 mmol) was treated with TBAF solution in THF (19 mL, 1N), stirred at 25° C. for 16 hours, concentrated, and partitioned between ethyl acetate and water. The organic was washed with brine, dried over MgSO$_4$, filtered and concentrated to give the product, which was used without further purification.

EXAMPLE 128B tert-butyl (4S,5S)-4-benzyl-5-[2-{[(benzyloxy)carbonyl]amino}-3-(4-bromophenyl)propyl]-2,2-dimethyl-1,3-oxazolidine-3-carboxylate A solution containing the product from Example 128A (3.37 mmol) in 2,2-dimethoxypropane (35 mL) was treated with p-toluenesulfonic acid monohydrate (0.032 g, 0.17 mmol), stirred at 25° C. for 1 hour, treated with triethylamine (0.14 mL, 1.0 mmol), and the reaction was partitioned between ethyl acetate and water. The organic phase was washed with brine, dried over $MgSO_4$, filtered and concentrated to give the product (1.16 g, 54% yield), which was used without further purification.

EXAMPLE 128C tert-butyl(4S,5S)-4-benzyl-5-{2-{[(benzyloxy)carbonyl]amino}-3-[4-(5-methyl-2-pyridinyl)phenyl]propyl}-2,2-dimethyl-1,3-oxazolidine-3-carboxylate A solution containing the product from Example 128B (0.50 g, 0.78 mmol) in DMF (8 mL) was treated with dichlorobis(triphenylphosphine)palladium(II) (0.165 g, 0.235 mmol), and the product from Example 74A (0.60 g, 1.63 mmol), stirred at 100° C. for 6 hours, cooled to 25° C., filtered through celite®, and partitioned between ethyl acetate and water. The organic was washed with brine, dried over $MgSO_4$, filtered and concentrated. The residue was chromatographed on silica gel eluting with 0-15% ethyl acetate in chloroform to give the product (0.322 g, 63% yield).

EXAMPLE 128D benzyl(3S,4S)-4-amino-3-hydroxy-1-[4-(5-methyl-2-pyridinyl)benzyl]-5-phenylpentylcarbamate A solution containing the product from Example 128C (0.322 g, 0.496 mmol) in a mixture of THF (5 mL), methanol (5 mL), and aqueous HCl (5 mL, 1 N) was stirred at 60° C. for 16 hours. The solvent was removed under reduced pressure to give the title compound as the hydrochloride salt.

EXAMPLE 128E benzyl(3S,4S)-4-[((2S)-3,3-dimethyl-2-{3-[(6-methyl-2-pyridinyl)methyl]-2-oxo-1imidazolidinyl}butanoyl)amino]-3-hydroxy-1-[4-(5-methyl-2-pyridinyl)benzyl]-5-phenylpentylcarbamate A solution containing the product from Example 128D (0.496 mmol) in THF (5 mL) was treated with the product from Example 10D (0.205 g, 0.600 mmol), DEPBT (0.225 g, 0.753 mmol), and N,N-diisopropylethylamine (0.875 mL, 5.02 mmol), stirred at 25° C. for 3 hours, and partitioned between ethyl acetate and 10% $Na_2CO_3$ solution. The organic phase was washed with additional 10% $Na_2CO_3$ solution and then brine, dried over $MgSO_4$, filtered and concentrated. The residue was chromatographed on silica gel eluting with 0-100% ethyl acetate/dichloromethane, followed by 50% methanol in ethyl acetate to give the product (0.127 g, 32% yield).

EXAMPLE 128F (2S)-N-{(1S,2S)-4-amino-1-benzyl-2-hydroxy-5-[4-(5-methyl-2-pyridinyl)phenyl]pentyl}-3,3-dimethyl-2-{3-[(6-methyl-2-pyridinyl)methyl]-2-oxo-1-imidazolidinyl}butanamide A solution containing the product from Example 128E (0.127 g, 0.159 mmol) in methanol (2 mL) was treated with $Pd(OH)_2$ on carbon (0.035 g, 20% Pd by wt.) and HCl solution (0.12 mL, 4N in dioxane), stirred under a hydrogen atmosphere (balloon pressure) at 25° C. for 16 hours, filtered through a bed of celite® and rinsed with methanol. The solvent was concentrated to give the title compound as the hydrochloride salt, which was used without further purification.

EXAMPLE 128G methyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-1-[4-(5-methyl-2-pyridinyl)benzyl]-5-phenylpentyl}amino)carbonyl]-2,2-dimethylpropylcarbamate A solution containing the product from Example 128F (0.159 mmol) in THF (1.6 mL) was treated with the product from Example 1F (0.036 g, 0.190 mmol), DEPBT (0.075 g, 0.251 mmol), and N,N-diisopropylethylamine (0.30 mL, 1.72 mmol), stirred at 25° C. for 16 hours, and partitioned between ethyl acetate and 10% $Na_2CO_3$ solution. The organic phase was washed with additional 10% $Na_2CO_3$ solution and brine, dried over $MgSO_4$, filtered and concentrated. The product was purified by chromatography on silica gel eluting with 0-50% acetone in dichloromethane, to give the lower Rf (50% acetone in dichloromethane) product of the mixture (0.01 g). $^1$H NMR (300 MHz, DMSO-$d_6$), δ ppm 0.83 (s, 9 H), 0.90 (s, 9 H), 1.55 (m, 2 H), 2.32 (s, 3H), 2.38 (q, J=9.2 Hz, 1 H), 2.46 (s, 3 H), 2.57 (m, 1 H), 2.67 (d, J=7.0 Hz, 2 H), 2.79 (m, 1 H), 2.97 (m, 1 H), 3.09 (q, J=8.95 Hz, 1 H), 3.21 (m, 1 H), 3.51 (s, 3 H), 3.67 (m, 1 H), 3.85 (d, J=9.6 Hz, 1 H), 4.08 (s, 1H), 4.12 (m, 3 H), 4.35 (m, 2 H), 4.54 (d, J=7.35 Hz, 1 H), 6.63 (d, J=9.56 Hz, 1 H), 7.09 (m, 5 H), 7.14 (d, J=7.7 Hz, 1 H), 7.18 (d, J=8.6 Hz, 2 H), 7.48 (d, J=9.56 Hz, 1 H), 7.66 (m, 1H), 7.68 (t, J=7.7 Hz, 1 H), 7.86 (m, 4 H), 8.46 (br s, 1 H).

EXAMPLE 129 methyl(1S)-1-[({(1R,3S,4S)-4-[((2S)-3,3-dimethyl-2-{3-[(6-methyl-2-pyridinyl)methyl]-2-oxo-1-imidazolidinyl}butanoyl)amino]-3-hydroxy-1-[4-(5-methyl-2-pyridinyl)benzyl]-5-phenylpentyl}amino)carbonyl]-2,2-dimethylpropylcarbamate A solution containing the product from Example 128F (0.159 mmol) in THF (1.6 mL) was treated with the product from Example 1F (0.036 g, 0.190 mmol), DEPBT (0.075 g, 0.251 mmol), and N,N-diisopropylethylamine (0.30 mL, 1.72 mmol), stirred at 25° C. for 16 hours, and partitioned between ethyl acetate and 10% $Na_2CO_3$ solution. The organic was washed with additional 10% $Na_2CO_3$ solution and then brine, dried over $MgSO_4$, filtered and concentrated. The residue was purified by chromatography on silica gel eluting with 0-50% acetone in dichloromethane, to give the higher Rf (50% acetone in dichloromethane) product of the mixture (0.01 g). $^1$H NMR (300 MHz, DMSO-$d_6$), δ ppm 0.80 (s, 9 H), 0.88 (s, 9 H), 1.37 (m, 1 H), 1.52 (m, 1 H), 2.32 (s, 3H), 2.45 (s, 3 H), 2.66 (m, 3 H), 2.83 (dd, J=13.79, 6.07 Hz, 1 H), 3.03 (m, 2 H), 3.23 (m, 1 H), 3.53 (m, 4 H), 3.83 (d, J=9.56 Hz, 1 H), 4.01 (m, 2 H), 4.03 (s, 1H), 4.16 (m, 1 H), 4.33 (m, 2 H), 4.43 (d, J=6.99 Hz, 1 H), 6.88 (d, J=9.56 Hz, 1 H), 7.09 (m, 5 H), 7.14 (d, J=7.35 Hz, 1 H), 7.21 (d, J=8.09 Hz, 2 H), 7.54 (d, J=9.56 Hz, 1 H), 7.67 (m, 2 H), 7.81 (m, 2 H), 7.93 (d, J=8.45 Hz, 2H), 8.48 (br s, 1 H).

EXAMPLE 130 tert-butyl 2-({(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropyl}amino)-2-oxoethylcarbamate

EXAMPLE 130A benzyl(1S,3S,4S)-4-amino-3-hydroxy-5-phenyl-1-[4-(2-pyridinyl)benzyl]pentylcarbamate A solution containing the product from Example 1C (0.088 g, 0.15 mmol) in a mixture of THF (2 mL) and aqueous HCl (0.26 mL, 4 N) was stirred at 25° C. for 16 hours, then heated at 60° C. for 2 hours, cooled and concentrated. The residue was treated with ethanol and concentrated several times to give the title compound as the hydrochloride salt, which was used without further purification.

EXAMPLE 130B benzyl(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentylcarbamate A solution containing the product from Example 130A (0.15 mmol) in DMF (1 mL) was treated with the product from Example 10D (0.045 g, 0.15 mmol), EDAC (0.072 g, 0.375 mmol), HOBT (0.051 g, 0.375 mmol), and NMM (0.222 mL, 2.02 mmol), stirred at 25° C. for 40 hours, and partitioned between ethyl acetate and water. The organic was washed with brine, dried over Na$_2$SO$_4$, filtered and concentrated. The residue was purified by chromatography on silica gel eluting with 1-5% methanol in chloroform, to give the product (0.067 g, 58% yield).

EXAMPLE 130C (2S)—N-{(1S,2S,4S)-4-amino-1-benzyl-2-hydroxy-5-[4-(2-pyridinyl)phenyl]pentyl}-3,3-dimethyl-2-{3-[(6-methyl-2-pyridinyl)methyl]-2-oxo-1-imidazolidinyl}butanamide A solution containing the product from Example 130B (0.067 g, 0.086 mmol) in methanol (3 mL) was treated with a solution of HCl in dioxane (0.025 mL, 4 M) and Pd on carbon (0.007 g, 10% Pd by wt.), stirred under a hydrogen atmosphere (balloon pressure) at 25° C. for 16 hours, filtered through a bed of celite® and rinsed with methanol. The solvent was concentrated to give the title compound as the hydrochloride salt (0.053 g), which was used without further purification.

EXAMPLE 130D tert-butyl(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropylcarbamate A solution containing the product from Example 130C (0.053 g, 0.081 mmol) in DMF (1 mL) was treated with Boc-L-tert-leucine (0.019 g, 0.081 mmol), EDAC (0.023 g, 0.122 mmol), HOBT (0.016 g, 0.122 mmol), and NMM (0.018 mL, 0.162 mmol), stirred at 25° C. for 40 hours, and partitioned between ethyl acetate and water. The organic phase was washed with brine, and then dried over MgSO$_4$, filtered and concentrated. The residue was purified by chromatography on silica gel eluting with 20% ethyl acetate in chloroform, to give the product (0.024 g, 34% yield).

EXAMPLE 130E (2S)-2-amino-N-{(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}-3,3-dimethylbutanamide A solution containing the product from Example 130D (0.024 g, 0.028 mmol) in a mixture of THF (1 mL) and aqueous HCl (0.050 mL, 4 N) was stirred at 25° C. for 16 hours, and concentrated under reduced pressure. The residue was treated with ethanol and concentrated several times to give the title compound as the hydrochloride salt, which was used without further purification.

EXAMPLE 130F tert-butyl 2-({(1S)-1-[({(1S,3S,4S)-4-[((2S)-3,3-dimethyl-2-{3-[(6-methyl-2-pyridinyl)methyl]-2-oxo-1-imidazolidinyl}butanoyl)amino]-3-hydroxy-5-phenyl-1-[4-(2-pyridinyl)benzyl]pentyl}amino)carbonyl]-2,2-dimethylpropyl}amino)-2-oxoethylcarbamate A solution containing the product from Example 130E (0.028 mmol) in DMF (1 mL) were added Boc-glycine (0.005 g, 0.028 mmol), EDAC (0.008 g, 0.042 mmol), HOBT (0.0056 g, 0.042 mmol), and NMM (0.018 mL, 0.162 mmol), stirred at 25° C. for 40 hours, and partitioned between ethyl acetate and water. The organic phase was washed with brine, dried over MgSO$_4$, filtered and concentrated. The residue was purified by chromatography on silica gel eluting with 2% methanol in chloroform, to give the product. ES-MS: m/z 920 [M+H]$^+$.

EXAMPLE 131 methyl(1S)-1-[({(1S,3S,4S)-3-hydroxy-4-[((2S)-2-{3-[(6-isopropyl-2-pyridinyl)methyl]-2-oxo-1-imidazolidinyl}-3,3-dimethylbutanoyl)amino]-5-phenyl-1-[4-(2-pyridinyl)benzyl]pentyl}amino)carbonyl]-2,2-dimethylpropylcarbamate A solution containing the product from Example 2C (0.025 g, 0.066 mmol) in THF (0.66 mL) was treated with the product from Example 117D (0.034 g, 0.079 mmol), DEPBT (0.030 g, 0.099 mmol), and N,N-diisopropylethylamine (0.115 mL, 0.658 mmol), stirred at 25° C. for 16 hours, and partitioned between chloroform and 10% Na$_2$CO$_3$ solution. The organic phase was washed with additional 10% Na$_2$CO$_3$ solution and brine, dried over MgSO$_4$, filtered and concentrated. The residue was purified by chromatography on silica gel eluting with 0-100% ethyl acetate/dichloromethane, followed by 0-5% methanol in ethyl acetate to give the product (0.030 g, 54% yield). $^1$H NMR (300 MHz, DMSO-d$_6$), δ ppm 0.82 (s, 9 H), 0.89 (s, 9 H), 1.21 (d, J=2.2 Hz, 3 H), 1.23 (d, J=2.2 Hz, 3 H), 1.41-1.57 (m, 2 H), 2.33 (q, J=8.5 Hz, 1 H), 2.57 (m, 1 H), 2.66 (d, J=7.0 Hz, 2 H), 2.79 (m, 1 H), 2.98 (m, 2 H), 3.19(m, 1 H), 3.50(s, 3 H), 3.66 (m, 1 H), 3.85 (d, J=9.56 Hz, 1 H), 4.08 (s, 1H), 4.13-4.25 (m, 2 H), 4.38 (m, 2 H), 4.53 (d, J=7.7 Hz, 1 H), 6.65 (d, J=9.55 Hz, 1 H), 7.03-7.13 (m, 7 H), 7.15-7.22 (m, 3H), 7.31 (m, 1 H), 7.47 (d, J=9.56 Hz, 1 H), 7.71 (t, J=7.7 Hz, 1 H), 7.81-7.90 (m, 3 H), 8.62 (m, 1 H).

EXAMPLE 132 methyl(1S)-1-[({(1S,3S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-[4-(2-pyridinyl)phenyl]pentyl}amino)carbonyl]-2,2-dimethylpropylcarbamate

EXAMPLE 132A tert-butyl(1S,3S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-[4-(2-pyridinyl)phenyl]pentylcarbamate A solution containing the product from Example 23Q (0.074 mmol) in THF (0.8 mL) was treated with the product from Example 10D (0.032 g, 0.094 mmol, DEPBT (0.035 g, 0.117 mmol), and N,N-diisopropylethylamine (0.10 mL, 0.574 mmol), stirred at 25° C. for 1 hour, and partitioned between chloroform and 10% Na$_2$CO$_3$ solution. The organic phase was washed with additional 10% Na$_2$CO$_3$ solution and then brine, dried over MgSO$_4$, filtered and concentrated. The product was purified by chromatography on silica gel eluting with 0-100% ethyl acetate/dichloromethane, followed by 0-0.5% methanol in ethyl acetate to give the product (0.017 g, 31% yield).

EXAMPLE 132B (2S)—N-{(1S,2S,4S)-4-amino-2-hydroxy-5-phenyl-1-[4-(2-pyridinyl)benzyl]pentyl}-3,3-dimethyl-2-{3-[(6-methyl-2-pyridinyl)methyl]-2-oxo-1-imidazolidinyl}butanamide A solution containing the product from Example 132A (0.017 g, 0.023 mmol) in dichloromethane (1 mL) was added trifluoroacetic acid (1 mL), and the mixture was stirred at 25° C. for 1 hour, and concentrated. The residue was partitioned between ethyl acetate and saturated NaHCO$_3$, and the organic phase was washed with brine and dried over MgSO$_4$, filtered and concentrated to give the product, which was used without further purification.

EXAMPLE 132C methyl(1S)-1-[({(1S,3S,4S)-1-benzyl-4-[((2S)-3,3-dimethyl-2-{3-[(6-methyl-2-pyridinyl)methyl]-2-oxo-1-imidazolidinyl}butanoyl)amino]-3-hydroxy-5-[4-(2-pyridinyl)phenyl]pentyl}amino)carbonyl]-2,2-dimethylpropylcarbamate A solution containing the product from Example 132B (0.023 mmol) in THF (0.25 mL) were added the product from Example 1F (0.005 g, 0.026 mmol), DEPBT (0.010 g, 0.033 mmol), and N,N-diisopropylethylamine (0.020 mL, 0.115 mmol), stirred at 25° C. for 16 hours, and partitioned between chloroform and 10% Na$_2$CO$_3$ solution. The organic phase was washed with additional 10% Na$_2$CO$_3$ solution and then brine, dried over MgSO$_4$, filtered and concentrated. The product was purified by chromatography on silica gel eluting with 0-100% ethyl acetate/dichloromethane, followed by 0-5% methanol in ethyl acetate to give the product. The product was re-purified by preparative TLC eluting with 5% methanol in ethyl acetate to give the title compound (0.002 g, 11% yield). $^1$H NMR (300 MHz, DMSO-d$_6$), δ ppm 0.82 (s, 9 H), 0.91 (s, 9 H), 1.25 (m, 1 H), 1.52 (m, 2 H), 2.41 (m, 1 H), 2.43 (s, 3 H), 2.74 (m, 3H), 2.97 (q, J=9.2 Hz, 1 H), 3.24 (m, 1 H), 3.54 (s, 3 H), 3.66 (m, 1 H), 3.82 (d, J=9.9 Hz, 2 H), 4.09 (s, 1 H), 4.17 (m, 1 H), 4.25 (d, J=16 Hz, 1 H), 4.35 (d, J=16 Hz, 1 H), 4.53 (d, J=7.4 Hz, 1 H), 6.63 (d, J=9.9 Hz, 1 H), 7.11 (m, 8 H), 7.21 (d, J=8.09 Hz, 2 H), 7.51 (d, J=8.56 Hz, 1 H), 7.62 (t, J=7.7 Hz, 1 H), 7.75 (m, 2H), 7.83 (d, J=8.09 Hz, 1 H), 8.60 (d, J=4.1 Hz, 1 H).

EXAMPLE 133 methyl(1S,4S,5S,7S,10S)-4-benzyl-1,10-disec-butyl-5-hydroxy-2,9,12-trioxo-7-[4-(2-pyridinyl)benzyl]-13-oxa-3,8,11-triazatetradec-1-ylcarbamate

EXAMPLE 133A tert-butyl(1S,2S,4S)-1-benzyl-4-[(tert-butoxycarbonyl)amino]-2-hydroxy-5-[4-(2-pyridinyl)phenyl]pentylcarbamate To a solution of the product from Example 1B (7.32 g, 12.1 mmol) in toluene (400 mL) were treated with DPPA (5.2 mL, 24.2 mmol) and triethylamine (3.4 mL, 24.4 mmol), heated at reflux for 2 hours, cooled, treated with tert-Butyl alcohol (41.6 mL), triethylamine (4 mL), and DMAP (0.30 g), heated at reflux for an additional 64 hours, cooled and concentrated. A solution of the residue in THF (60 mL) was treated with TBAF solution in THF (36 mL, 1N), stirred at 25° C. for 40 hours, concentrated and partitioned between ethyl acetate and water. The organic phase was washed with brined, dried over MgSO$_4$, filtered and concentrated. The residue was chromatographed on silica gel eluting with 0-50% ethyl acetate in dichloromethane to give 0.614 g (9% yield) of the lower Rf product by TLC (25% ethyl acetate in dichloromethane).

EXAMPLE 133B (2S,3S,5S)-2,5-diamino-1-phenyl-6-[4-(2-pyridinyl)phenyl]-3-hexanol A solution containing the product from Example 133A (0.60 g, 1.07 mmol) in dichloromethane (10 mL) was treated with trifluoroacetic acid (10 mL), stirred at 25° C. for 1 hour, concentrated and partitioned between chloroform and satu-

EXAMPLE 133C methyl(1S,4S,5S,7S,10S)-4-benzyl-1,10-disec-butyl-5-hydroxy-2,9,12-trioxo-7-[4-(2-pyridinyl)benzyl]-13-oxa-3,8,11-triazatetradec-1-ylcarbamate A solution containing the product from Example 133B (0.045 g, 0.125 mmol) in DMF (1.2 mL) was treated with the product from Example 5A (0.060 g, 0.317 mmol), EDAC (0.075 g, 0.391 mmol), HOBT (0.050 g, 0.370 mmol), and NMM (0.030 mL, 0.272 mmol), stirred at 25° C. for 16 hours, and partitioned between ethyl acetate and water. The organic phase was washed with brine, dried over MgSO$_4$, filtered and concentrated. The residue was purified by reversed phase chromatography on a C18 column, eluting with 5-100% acetonitrile in water (0.1% TFA). The product was partitioned between ethyl acetate and saturated NaHCO$_3$, and the organic phase was washed with brine and dried over MgSO$_4$, filtered and concentrated to give the product (0.0072 g, 8% yield). $^1$H NMR (300 MHz, DMSO-d$_6$), δ ppm 0.56 (d, J=7.0 Hz, 3H), 0.64 (t, J=7.0 Hz, 3H), 0.72 (t, J=8.5 Hz, 3H), 0.90-1.07 (m, 2H), 1.20-1.34 (m, 3H), 1.43-1.67 (m, 4H), 2.57 (m, 1H), 2.69-2.77 (m, 3H), 3.50 (s, 3H), 3.53 (s, 3H), 3.60 (m, 1H), 3.71-3.83 (m, 2H), 4.03-4.21 (m, 2H), 6.87 (d, J=9.2 Hz, 1H), 6.70 (d, J=8.5 Hz, 1H), 7.10-7.21 (m, 7H), 7.30 (m, 1H), 7.70 (d, J=8.8 Hz, 1H), 7.81-7.96 (m, 5H), 8.63 (m, 1H).

EXAMPLE 134 methyl(1S)-1-({[(1S,2S,4S)-1-benzyl-2-hydroxy-4-({(2S)-3-methyl-2-[2-oxo-3-(4-quinolinylmethyl)-1-imidazolidinyl]pentanoyl}amino)-5-phenylpentyl]amino}carbonyl)-2,2-dimethylpropylcarbamate

EXAMPLE 134A 9H-fluoren-9-ylmethyl(1S,2S,4S)-1-benzyl-2-hydroxy-4-({(2S,3S)-3-methyl-2-[2-oxo-3-(4-quinolinylmethyl)-1-imidazolidinyl]pentanoyl}amino)-5-phenylpentylcarbamate A solution containing the product from Example 3B (0.150 g, 0.276 mmol) in DMF (3 mL) was treated with the product from Example 4A (0.110 g, 0.332 mmol), EDAC (0.080 g, 0.417 mmol), HOBT (0.055, 0.407 mmol), and NMM (0.090 mL, 0.819 mmol) at 0° C., stirred at 25° C. for 16 hours, and partitioned between ethyl acetate and water. The organic phase was washed with 10% citric acid, dilute sodium bicarbonate, and brine, dried over MgSO$_4$ filtered and concentrated. The residue was purified by reversed phase chromatography on a C18 column, eluting with 5-100% acetonitrile in water (0.1% TFA) to give the product (0.122 g, 53% yield).

EXAMPLE 134B (2S,3S)-N-[(1S,3S,4S)-4-amino-1-benzyl-3-hydroxy-5-phenylpentyl]-3-methyl-2-[2-oxo-3-(4-quinolinylmethyl)-1-imidazolidinyl]pentanamide A solution containing the product from Example 134A (0.122 g, 0.147 mmol) in DMF (6 mL) was treated with diethylamine (1.5 mL), stirred at 25° C. for 1 hour, and partitioned between ethyl acetate and water. The organic phase was washed with brine and dried over MgSO$_4$, filtered and concentrated to give the title compounds.

EXAMPLE 134C methyl(1S)-1-({[(1S,2S,4S)-1-benzyl-2-hydroxy-4-({(2S)-3-methyl-2-[2-oxo-3-(4-quinolinylmethyl)-1-imidazolidinyl]pentanoyl}amino)-5-phenylpentyl]amino}carbonyl)-2,2-dimethylpropylcarbamate A solution containing the product from Example 134B (0.147 mmol) in DMF (2 mL) was treated with the product from Example 1F (0.035 g, 0.185 mmol), EDAC (0.045 g, 0.235 mmol), HOBT (0.030g, 0.222 mmol), and NMM (0.050 mL, 0.455 mmol) at 0° C., stirred at 25° C. for 16 hours, and partitioned between ethyl acetate and water. The organic phase was washed with 10% citric acid, dilute sodium bicarbonate, and brine, dried over MgSO$_4$, filtered and concentrated. The residue was purified by reversed phase chromatography on a C18 column, eluting with 5-100% acetonitrile in water (0.1% TFA) to give the title compound (0.019 g, 17% yield). $^1$H NMR (300 MHz, DMSO-d$_6$), δ ppm 0.68 (d, J=6.6 Hz, 3 H), 0.93 (m, 12 H), 0.88-0.97 (m, 1 H), 1.22-1.33 (m, 1H), 1.47-1.56 (m, 2H), 1.72-1.84 (m, 1H), 2.38-2.45 (m, 1H), 2.62-2.73 (m, 3H), 2.79-2.86 (m, 1H), 2.98-3.10 (m, 3H), 3.55-3.63 (m, 4H), 3.89-3.94 (m, 2H), 4.07-4.21 (m, 2H), 4.80 (s, 2H), 6.79 (d, J=9.56 Hz, 1 H), 6.93-7.20 (m, 10 H), 7.41 (d, J=4.41 Hz, 1 H), 7.48-7.53 (m, 1H), 7.57-7.62 (m, 1H), 7.75-7.80 (m, 1H), 7.87 (d, J=9.19 Hz, 1 H), 8.06 (d, J=8.45 Hz, 1 H), 8.30 (d, J=8.08 Hz, 1 H), 8.88 (d, J=4.41 Hz, 1 H).

EXAMPLE 135 methyl(1S)-1-({[(1S,3S,4S)-4({(2S)-2-[3-(2-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate

EXAMPLE 135A tert-butyl N-{2-[(2-fluorobenzyl)amino]ethyl}-3-methyl-L-valinate A solution of Example 6F (0.124 g, 0.538 mmol) and 2-fluorobenzaldehyde (56.7 µL, 0.565 mmol) in methanol (2.5 mL) and benzene (2.5 mL) was stirred at 50° C. for 16 h. The mixture was cooled to 25° C. and treated with sodium borohydride (40.7 mg, 1.076 mmol) for 2 h. The mixture was partitioned between sodium bicarbonate and ethyl acetate. The organic layer was separated, washed with brine, dried over MgSO$_4$, filtered and concentrated to give the title compound as a clear oil (183 mg, 100%).

EXAMPLE 135B tert-butyl(2S)-2-[3-(2-fluorobenzyl)-2-oxoimidazolidin-1-yl]-3,3-dimethylbutanoate A solution of Example 135A (183 mg, 0.54 mmol) and disuccinimidyl carbonate (0.165 g, 0.645 mmol) in dichloromethane (3 mL) was treated with triethylamine (90 uL, 0.645 mmol) at 25° C. for 16 h. The mixture was partitioned between 10% sodium carbonate and dichloromethane. The organic layer was separated, washed with brine, dried over MgSO$_4$, filtered and concentrated to give the crude title compound (199 mg, crude yield).

EXAMPLE 135C (2S)-2-[3-(2-fluorobenzyl)-2-oxoimidazolidin-1-yl]-3,3-dimethylbutanoic acid A solution of Example 135B (199 mg, 0.54 mmol) in dichloromethane (1.5 mL) was treated with trifluoroacetic acid (1.5 mL) at 25° C. for 16 h. The solvents were evaporated, and the crude residue was purified using reverse phase chromatography using 95% water (0.1% trifluoroacetic acid)/5% acetonitrile-100% acetonitrile to give the title compound (0.121 g, 73%).

EXAMPLE 135D methyl(1S)-1-({[(1S,3S,4S)-4-({(2S)-2-[3-(2-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate A solution of Example 135C (32 mg, 0.103 mmol) and Example 2C (50 mg, 0.094 mmol) in tetrahydrofuran (1 mL) was treated with DEPBT (42 mg, 0.14 mmol), and diisopropylethylamine (82 µL, 0.47 mmol) at 25° C. for 16 h. The crude residue was purified by silica gel chromatography using dichloromethane to 100% ethyl acetate to 95% ethyl acetate/5% methanol to give the title compound (47 mg, 61%). $^1$H NMR (300 MHz, DMSO-$d_6$) δ ppm 0.83(s, 9H), 0.88(s, 9H), 1.58-1.49(m, 2H), 2.35-2.27(m, 1H), 2.61-2.54(m, 1H), 2.67-2.65(d, J=6.99 Hz, 2H), 2.87-2.76(m, 2H), 3.03-2.94(q, J=8.70 Hz, 1H), 3.20-3.16(m, 1H), 3.50(s, 3H), 3.70-3.63(m, 1H), 3.86-3.83(d, J=9.93 Hz, 1H), 4.07(s, 1H), 4.23-4.10(m, 2H), 4.46-4.28(m, 2H), 4.55-4.52(d, J=7.35 Hz, 1H), 6.65-6.62(d, J=9.56 Hz, 1H), 7.09-6.99(m, 4H), 7.26-7.21(m, 4H), 7.40-7.28(m, 3H), 7.50-7.46(d, J=9.56 Hz, 1H), 7.91-7.82(m, 5H), 8.64-8.63(m, 1H).

EXAMPLE 136 methyl(1S)-1-({[(1S,3S,4S)-4-({(2S)-2-[3-(4-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate

EXAMPLE 136A tert-butyl N-{2-[(4-fluorobenzyl)amino]ethyl}-3-methyl-L-valinate A solution of Example 6F (0.124 g, 0.538 mmol) and 4-fluorobenzaldehyde (60.6 µL, 0.565 mmol) in methanol (2.5 mL) and benzene (2.5 mL) was stirred at 50° C. for 16 h. The mixture was cooled to 25° C. and treated with sodium borohydride (40.7 mg, 1.076 mmol) for 2 h. The mixture was partitioned between sodium bicarbonate and ethyl acetate. The organic layer was separated, washed with brine, dried over MgSO$_4$, filtered, and the solvents were evaporated to give the title compound as a crude residue which was used directly in the next step.

EXAMPLE 136 B tert-butyl(2S)-2-[3-(4-fluorobenzyl)-2-oxoimidazolidin-1-yl]-3,3-dimethylbutanoate A solution of Example 136A and disuccinimidyl carbonate (0.165 g, 0.645 mmol) in dichloromethane (3 mL) was treated with triethylamine (90 µL, 0.645 mmol) at 25° C. for 16 h. The mixture was partitioned between 10% sodium carbonate and dichloromethane. The organic layer was separated, washed with brine, dried over MgSO$_4$, filtered, and the solvents were evaporated to give the crude title compound.

EXAMPLE 136C (2S)-2-[3-(4-fluorobenzyl)-2-oxoimidazolidin-1-yl]-3,3-dimethylbutanoic acid A solution of Example 136B in dichloromethane (1.5 mL) was treated with trifluoroacetic acid (1.5 mL) at 25° C. for 16 h. The solvents were evaporated, and the crude residue was purified using reverse phase chromatography, eluting with a gradient of 95% water (0.1% trifluoroacetic acid)/5% acetonitrile to 100% acetonitrile to give the title compound (0.133 g, 80%).

EXAMPLE 136D methyl(1S)-1-({[(1S,3S,4S)-4-({(2S)-2-[3-(4-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate A solution of Example 136C (32 mg, 0.103 mmol) and Example 2C (50 mg, 0.094 mmol) in tetrahydrofuran (1 mL) was treated with DEPBT (42 mg, 0.14 mmol), and diisopropylethylamine (82 uL, 0.47 mmol) at 25° C. for 16 h. The crude residue was purified by silica gel chromatography eluting with a gradient of dichloromethane, 100% ethyl acetate, and 95% ethyl acetate/5% methanol to give the title compound (49 mg, 62%). $^1$H NMR (300 MHz, DMSO-$d_6$) δ ppm 0.83(s, 9H), 0.88(s, 9H), 1.58-1.49(m, 2H), 2.37-2.28(m, 1H), 2.61-2.54(m, 1H), 2.68-2.66(d, J=7.35 Hz, 2H), 2.90-2.75(m, 2H), 2.98-2.87(q, J=8.46 Hz, 1H), 3.20-3.16(m, 1H), 3.50(s, 3H), 3.70-3.63(m, 1H), 3.86-3.83(d, J=9.93 Hz, 1H), 4.08(s, 1H), 4.21-4.13(m, 2H), 4.30(s, 2H), 4.56-4.54(d, J=7.35 Hz, 1H), 6.65-6.62(d, J=9.56 Hz, 1H), 7.12-7.03(m, 4H), 7.24-7.18(m, 4H), 7.34-7.29(m, 3H), 7.49-7.46(d, J=9.56 Hz, 1H), 7.91-7.82(m, 5H), 8.64-8.63(m, 1H).

EXAMPLE 137 methyl(1S)-1-({[(1S,3S,4S)-4-({(2S)-2-[3-(3-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate

EXAMPLE 137A tert-butyl N-{2-[(3-fluorobenzyl)amino]ethyl}-3-methyl-L-valinate A solution of Example 6F (0.14 g, 0.61 mmol) and 3-fluorobenzaldehyde (60.6 µL, 0.565 mmol) in methanol (2.5 mL) and benzene (2.5 mL) was stirred at 50° C. for 16 h. The mixture was cooled to 25° C. and treated with sodium borohydride (46 mg, 1.2 mmol) for 2 h. The mixture was partitioned between sodium bicarbonate and ethyl acetate. The organic layer was separated, washed with brine, dried over $MgSO_4$, filtered and the solvents were evaporated to give the title compound as a crude residue (0.199 g, 0.588 mmol) which was used directly in the next step.

EXAMPLE 137B tert-butyl(2S)-2-[3-(3-fluorobenzyl)-2-oxoimidazolidin-1-yl]-3,3-dimethylbutanoate A solution of Example 137A (0.199 g, 0.588 mmol) and disuccinimidyl carbonate (0.181 g, 0.7 mmol) in dichloroethane (6 mL) was treated with triethylamine (98 µL, 0.71 mmol) at 25° C. for 16 h. The mixture was partitioned between 10% sodium carbonate and dichloromethane. The organic layer was separated, washed with brine, dried over $MgSO_4$, filtered and the solvents were evaporated to give the crude title compound.

EXAMPLE 137C (2S)-2-[3-(3-fluorobenzyl)-2-oxoimidazolidin-1-yl]-3,3-dimethylbutanoic acid A solution of Example 137B in dichloromethane (1.5 mL) was treated with trifluoroacetic acid (1.5 mL) at 25° C. for 16 h. The solvents were evaporated, and the crude residue was purified using reverse phase chromatography eluting with a gradient of 95% water (0.1% trifluoroacetic acid)/5% acetonitrile to 100% acetonitrile to give the title compound (0.14 g, 74%).

EXAMPLE 137D methyl(1S)-1-({[(1S,3S,4S)-4-({(2S)-2-[3-(3-fluorobenzyl)-2-oxoimidazolidin-1-yl]-3,3-dimethylbutanoyl}amino)-3-hydroxy-5-phenyl-1-(4-pyridin-2-ylbenzyl)pentyl]amino}carbonyl)-2,2-dimethylpropylcarbamate A solution of Example 137C (32 mg, 0.103 mmol) and Example 2C (50 mg, 0.094 mmol) in tetrahydrofuran (1 mL) was treated with DEPBT (42 mg, 0.14 mmol), and diisopropylethylamine (82 µL, 0.47 mmol) at 25° C. for 16 h. The crude residue was purified by silica gel chromatography eluting with a gradient of dichloromethane, 100% ethyl acetate, and 95% ethyl acetate/5% methanol to give the title compound (48 mg, 61%). $^1$H NMR (300 MHz, DMSO-$d_6$) δ ppm 0.83(s, 9H), 0.89(s, 9H), 1.58-1.49(m, 2H), 2.39-2.30(q, J=9.19 Hz, 1H), 2.62-2.54(m, 1H), 2.69-2.66(d, J=7.35 Hz, 2H), 2.90-2.77(m, 2H), 3.02-2.93(q, J=8.7 Hz, 1H), 3.27-3.18(m, 1H), 3.50(s, 3H), 3.70-3.63(m, 1H), 3.87-3.83(d, J=9.93 Hz, 1H), 4.09(s, 1H), 4.19-4.14(m, 2H), 4.39-4.27(m, 2H), 4.56-4.54(d, J=7.72 Hz, 1H), 6.65-6.62(d, J=9.56 Hz, 1H), 7.15-7.04(m, 8H), 7.24-7.21(d, J=8.46 Hz, 2H), 7.33-7.29(m, 1H), 7.46-7.39(m, 1H), 7.53-7.50(d, J=9.56 Hz, 1H), 7.91-7.82(m, 4H), 8.65-8.62(m, 1H).

EXAMPLE 138 methyl(1S)-1-({[(1S,3S,4S)-4-[((2S)-3,3-dimethyl-2-{2-oxo-3-[2-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate

EXAMPLE 138A tert-butyl 3-methyl-N-(2-{[2-(trifluoromethyl)benzyl]amino}ethyl)-L-valinate A solution of Example 6F (0.137 g, 0.595 mmol) and o-trifluoromethyl-benzaldehyde (82 µL, 0.62 mmol) in methanol (2.5 mL) and benzene (2.5 mL) was stirred at 50° C. for 16 h. The mixture was cooled to 25° C. and treated with sodium borohydride (45 mg, 1.2 mmol) for 2 h. The mixture was partitioned between sodium bicarbonate and ethyl acetate. The organic layer was separated, washed with brine, dried over $MgSO_4$, filtered, and the solvents were evaporated to give the title compound as a clear oil (225 mg, 100%).

EXAMPLE 138B tert-butyl(2S)-3,3-dimethyl-2-{2-oxo-3-[2-(trifluoromethyl)benzyl]imidazolidin-1-yl}butanoate A solution of Example 138A (225 mg, 0.595 mmol) and disuccinimidyl carbonate (0.183 g, 0.714 mmol) in dichloroethane (6 mL) was treated with triethylamine (99 µL, 0.714 mmol) at 25° C. for 16 h. The mixture was partitioned between 10% sodium carbonate and dichloromethane. The organic layer was separated, washed with brine, dried over $MgSO_4$, filtered, and the solvents were evaporated to give the crude title compound.

EXAMPLE 138C (2S)-3,3-dimethyl-2-{2-oxo-3-[2-(trifluoromethyl)benzyl]imidazolidin-1-yl}butanoic acid A solution of Example 138B in dichloromethane (1.5 mL) was treated with trifluoroacetic acid (1.5 mL) at 25° C. for 16 h. The solvents were evaporated, and the crude residue was purified using reverse phase chromatography eluting with a gradient of 95% water (0.1% trifluoroacetic acid)/5% acetonitrile to 100% acetonitrile to give the title compound (0.121 g, 73%).

EXAMPLE 138D methyl(1S)-1-({[(1S,3S,4S)-4-[((2S)-3,3-dimethyl-2-{2-oxo-3-[2-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate A solution of Example 137C (37 mg, 0.103 mmol) and Example 2C (50 mg, 0.094 mmol) in tetrahydrofuran (1 mL) was treated with DEPBT (42 mg, 0.14 mmol), and diisopropylethylamine (82 µL, 0.47 mmol) at 25° C. for 16 h. The crude residue was purified by silica gel chromatography eluting with a gradient of dichloromethane, 100% ethyl acetate, and 95% ethyl acetate/5% methanol to give the title compound (57 mg, 63%). $^1$H NMR (300 MHz, DMSO-$d_6$) δ ppm 0.83(s, 9H), 0.91(s, 9H), 1.59-1.52(m, 2H), 2.62-2.44(m, 2H), 2.71-2.68(d, J=6.99 Hz, 2H), 2.82-2.76(m, 1H), 2.92-2.85(m, 1H), 3.07-2.99(q, J=9.19 Hz, 1H), 3.26-3.23(m, 1H), 3.50(s, 3H), 3.71-3.62(m, 1H), 3.87-3.83(d, J=9.93 Hz, 1H), 4.10(s, 1H), 4.25-4.13(m, 2H), 4.55-4.41(m, 2H), 4.58-4.55 (d, J=7.72 Hz, 1H), 6.65-6.62(d, J=9.93 Hz, 1H), 7.07-7.05 (m, 3H), 7.15-7.12(m, 2H), 7.24-7.21(d, J=8.09 Hz, 2H), 7.33-7.29(m, 1H), 7.55-7.49(m, 3H), 7.78-7.70(dd, J=17.1, 7.91 Hz, 2H), 7.92-7.82(m, 4H), 8.64-8.63(m, 1H).

EXAMPLE 139 methyl(1S)-1-({[(1S,3S,4S)-4-[((2S)-3,3-dimethyl-2-{2-oxo-3-[4-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate

EXAMPLE 139A tert-butyl 3-methyl-N-(2-{[4-(trifluoromethyl)benzyl]amino}ethyl)-L-valinate A solution of Example 6F (0.124 g, 0.538 mmol) and p-trifluoromethyl-benzaldehyde (86.8 µL, 0.647 mmol) in methanol (2.5 mL) and benzene (2.5 mL) was stirred at 50° C. for 16 h. The mixture was cooled to 25° C. and treated with sodium borohydride (46.6 mg, 1.22 mmol) for 2 h. The mixture was partitioned between sodium bicarbonate and ethyl acetate. The organic layer was separated, washed with brine, dried over MgSO$_4$, filtered, and the solvents were evaporated to give the title compound as a crude residue which was used directly in the next step.

EXAMPLE 139B tert-butyl(2S)-3,3-dimethyl-2-{2-oxo-3-[4-(trifluoromethyl)benzyl]imidazolidin-1-yl}butanoate A solution of Example 139A and disuccinimidyl carbonate (0.19 g, 0.74 mmol) in dichloromethane (6 mL) was treated with triethylamine (103 µL, 0.74 mmol) at 25° C. for 16 h. The mixture was partitioned between 10% sodium carbonate and dichloromethane. The organic layer was separated, washed with brine, dried over MgSO$_4$, filtered, and the solvents were evaporated to give the crude title compound (0.262 g).

EXAMPLE 139C (2S)-3,3-dimethyl-2-{2-oxo-3-[4-(trifluoromethyl)benzyl]imidazolidin-1-yl}butanoic acid A solution of Example 139B (0.262 g) in dichloromethane (3 mL) was treated with trifluoroacetic acid (3 mL) at 25° C. for 16 h. The solvents were evaporated, and the crude residue was purified using reverse phase chromatography eluting with 95%water (0.1% trifluoroacetic acid)/5% acetonitrile to 100% acetonitrile to give the title compound (0.172 g, 78%).

EXAMPLE 139D methyl(1S)-1-({[(1S,3S,4S)-4-[((2S)-3,3-dimethyl-2-{2-oxo-3-[4-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate A solution of Example 139C (37 mg, 0.103 mmol) and Example 2C (50 mg, 0.094 mmol) in tetrahydrofuran (1 mL) was treated with DEPBT (42 mg, 0.14 mmol), and diisopropylethylamine (82 uL, 0.47 mmol) at 25° C. for 16 h. The crude residue was purified by silica gel chromatography using dichloromethane to 100% ethyl acetate to 95% ethyl acetate/5% methanol to give the title compound (42 mg, 51%). $^1$H NMR (300 MHz, DMSO-d$_6$) δ ppm 0.83(s, 9H), 0.90(s, 9H), 1.58-1.49(m, 2H), 2.44-2.35(q, J=9.07 Hz, 1H), 2.62-2.54(m, 1H), 2.69-2.67(d, J=6.99 Hz, 2H), 2.81-2.76(m, 1H), 2.90-2.84(m, 1H), 3.09-2.95(q, J=8.70, 1H), 3.27-3.18 (m, 1H), 3.50(s, 3H), 3.70-3.63(m, 1H), 3.87-3.83(d, J=9.93 Hz 1H), 4.09(s, 1H), 4.26-4.12(m, 2H), 4.41(s, 2H), 4.57-4.55(d, J=7.35 Hz, 1H), 6.66-6.62(d, J=10.30 Hz, 1H), 7.12-7.05(m, 5H), 7.24-7.21(d, J=8.09 Hz, 2H), 7.33-7.29(m, 1H), 7.51-7.49(d, J=7.72 Hz, 3H), 7.76-7.73(d, J=8.46 Hz, 2H), 7.91-7.82(m, 4H), 8.64-8.63(d, J=4.41 Hz, 1H).

EXAMPLE 140 methyl(1S)-1-({[(1S,3S,4S)-4-[((2S)-3,3-dimethyl-2-{2-oxo-3-[3-(trifluoromethyl)benzyl]imidazolidin-1-yl}butanoyl)amino]-3-hydroxy-5-phenyl-1-(4-pyridin-2-ylbenzyl)pentyl]amino}carbonyl)-2,2-dimethylpropylcarbamate

EXAMPLE 140A tert-butyl 3-methyl-N-(2-{[3-(trifluoromethyl)benzyl]amino}ethyl)-L-valinate A solution of Example 6F (0.143 g, 0.623 mmol) and m-trifluoromethyl-benzaldehyde (87.5 µL, 0.654 mmol) in methanol (2.5 mL) and benzene (2.5 mL) was stirred at 50° C. for 16 h. The mixture was cooled to 25° C. and treated with sodium borohydride (47 mg, 1.25 mmol) for 2 h. The mixture was partitioned between sodium bicarbonate and ethyl acetate. The organic layer was separated, washed with brine, dried over MgSO$_4$, filtered and the solvents were evaporated to give the title compound as a crude residue which was used directly in the next step.

EXAMPLE 140B tert-butyl(2S)-3,3-dimethyl-2-{2-oxo-3-[3-(trifluoromethyl)benzyl]imidazolidin-1-yl}butanoate A solution of Example 140A and disuccinimidyl carbonate (0.192 g, 0.75 mmol) in dichloromethane (6 mL) was treated with triethylamine (104 µL, 0.75 mmol) at 25° C. for 16 h. The mixture was partitioned between 10% sodium carbonate and dichloromethane. The organic layer was separated, washed with brine, dried over MgSO$_4$, filtered, and the solvents were evaporated to give the crude title compound (0.261 g, 100%).

EXAMPLE 140C (2S)-3,3-dimethyl-2-{2-oxo-3-[3-(trifluoromethyl)benzyl]imidazolidin-1-yl}butanoic acid A solution of Example 140B (0.261 g, 0.623 mmol) in dichloromethane (3 mL) was treated with trifluoroacetic acid (3 mL) at 25° C. for 16 h. The solvents were evaporated, and the crude residue was purified using reverse phase chromatography eluting with 95% water (0.1% trifluoroacetic acid)/5% acetonitrile to 100% acetonitrile to give the title compound (0.172 g 77%).

EXAMPLE 140D methyl(1S)-1-({[(1S,3S,4S)-4-[((2S)-3,3-dimethyl-2-
{2-oxo-3-[3-(trifluoromethyl)benzyl]imidazolidin-1-
yl}butanoyl)amino]-3-hydroxy-5-phenyl-1-(4-pyridin-2-ylbenzyl)pentyl]amino}carbonyl)-2,2-
dimethylpropylcarbamate A solution of Example 140C (37 mg, 0.103 mmol) and Example 2C (50 mg, 0.094 mmol) in tetrahydrofuran (1 mL) was treated with DEPBT (42 mg, 0.14 mmol), and diisopropylethylamine (82 µL, 0.47 mmol) at 25° C. for 16 h. The crude residue was purified by silica gel chromatography eluting with dichloromethane, 100% ethyl acetate, and 95% ethyl acetate/5% methanol to give the title compound (55 mg, 67%). $^1$H NMR (300 MHz, DMSO-$d_6$) δ ppm 0.83(s, 9H), 0.90(s, 9H), 1.58-1.49(m, 2H), 2.34-2.25(q, J=9.44 Hz, 1H), 2.62-2.54(m, 1H), 2.68-2.65(d, J=7.35 Hz, 2H), 2.81-2.76(m, 1H), 3.00-2.86(m, 2H), 3.22-3.16(m, 1H), 3.50(s, 3H), 3.70-3.63(m, 1H), 3.87-3.83(d, J=9.56 Hz 1H), 4.09(s, 1H), 4.26-4.12(m, 2H), 4.42(s, 2H), 4.55-4.53(d, J=7.35 Hz, 1H), 6.66-6.62(d, J=9.93 Hz, 1H), 7.10-7.01(m, 5H), 7.24-7.21(d, J=8.46 Hz, 2H), 7.33-7.29(m, 1H), 7.54-7.51(d, J=9.56 Hz, 1H), 7.68-7.58(m, 4H), 7.91-7.82(m, 4H), 8.64-8.63(d, J=4.41 Hz, 1H).

EXAMPLE 141 methyl(1S)-1-({[(1S,3S,4S)-4-({(2S)-2-[3-(2-amino-3-methylbenzyl)-2-oxoimidazolidin-1-yl]-3,3-
dimethylbutanoyl}amino)-3-hydroxy-5-phenyl-1-(4-pyridin-2-ylbenzyl)pentyl]amino}carbonyl)-2,2-
dimethylpropylcarbamate

EXAMPLE 141A 3-methyl-2-nitrobenzaldehyde

A solution of 3-methyl-2-nitrobenzyl alcohol (0.4 g, 2.4 mmol) in acetonitrile (8 mL) was treated with Dess-Martin reagent (1.11 g, 2.63 mmol) at 25° C. for 16 h. The mixture was quenched with sodium bicarbonate/sodium thiosulfate (1:1, 15 mL), and the mixture was extracted with dichloromethane, the organic layer separated, washed with brine, dried over sodium sulfate, filtered, and the solvents were evaporated to give the crude title compound (0.387 g, 98%).

EXAMPLE 141B tert-butyl 3-methyl-N-{2-[(3-methyl-2-nitrobenzyl)
amino]ethyl}-L-valinate A solution of Example 6F (0.148 g, 0.64 mmol) and 3-methyl-2-nitrobenzaldehyde (116.5 mg, 0.705 mmol) in methanol (2.5 mL) and benzene (2.5 mL) was stirred at 50° C. for 16 h. The mixture was cooled to 25° C. and treated with sodium borohydride (48 mg, 1.28 mmol) for 2 h. The mixture was partitioned between sodium bicarbonate and ethyl acetate. The organic layer was separated, washed with brine, dried over MgSO$_4$, filtered and the solvents were evaporated to give the title compound as a crude residue which was used directly in the next step.

EXAMPLE 141C tert-butyl(2S)-3,3-dimethyl-2-[3-(3-methyl-2-nitrobenzyl)-2-oxoimidazolidin-1-yl]butanoate A solution of Example 141B and disuccinimidyl carbonate (0.197 g, 0.77 mmol) in dichloromethane (6 mL) was treated with triethylamine (107 µL, 0.79 mmol) at 25° C. for 16 h. The mixture was partitioned between 10% sodium carbonate and dichloromethane. The organic layer was separated, washed with brine, dried over MgSO$_4$, filtered, and the solvents were evaporated to give the crude title compound.

EXAMPLE 141D (2S)-3,3-dimethyl-2-[3-(3-methyl-2-nitrobenzyl)-2-oxoimidazolidin-1-yl]butanoic acid A solution of Example 141 C in dichloromethane (3 mL) was treated with trifluoroacetic acid (3 mL) at 25° C. for 16 h. The solvents were evaporated, and the crude residue was purified using reverse phase chromatography eluting with 95% water (0.1% trifluoroacetic acid)/5% acetonitrile to 100% acetonitrile to give the title compound (0.172 g, 77%).

EXAMPLE 141E methyl(1S)-1-({[(1 S,3S,4S)-4-({(2S)-2-[3-(2-nitro-3-methylbenzyl)-2-oxoimidazolidin-1-yl]-3,3-
dimethylbutanoyl}amino)-3-hydroxy-5-phenyl-1-(4-pyridin-2-ylbenzyl)pentyl]amino}carbonyl)-2,2-
dimethylpropylcarbamate A solution of Example 141D (36 mg, 0.103 mmol) and Example 2C (50 mg, 0.094 mmol) in tetrahydrofuran (1 mL) was treated with DEPBT (42 mg, 0.14 mmol), and diisopropylethylamine (82 µL, 0.47 mmol) at 25° C. for 16 h. The crude residue was purified by silica gel chromatography eluting with a gradient of dichloromethane, 100% ethyl acetate, and 95% ethyl acetate/5% methanol to give the title compound (64 mg, 79%).

EXAMPLE 141F methyl(1S)-1-({[(1S,3S,4S)-4-({(2S)-2-[3-(2-amino-3-methylbenzyl)-2-oxoimidazolidin-1-yl]-3,3-
dimethylbutanoyl}amino)-3-hydroxy-5-phenyl-1-(4-pyridin-2-ylbenzyl)pentyl]amino}carbonyl)-2,2-
dimethylpropylcarbamate A solution of Example 141E (64 mg, 0.074 mmol) in ethanol (2 mL) was treated with 10% Pd/C (23.6 mg, 0.022 mmol) with a hydrogen balloon at 25° C. for 16 h. The catalyst was filtered through Celite®, rinsed with ethanol, and the solvents were evaporated. The crude residue was purified using reverse phase chromatography eluting with a gradient of 95% water (0.1% trifluoroacetic acid)/5% acetonitrile to 100% acetonitrile to give the title compound (0.051 g, 83%). $^1$H NMR (300 MHz, DMSO-$d_6$) δ ppm 0.83(s, 9H), 0.87(s, 9H), 1.58-1.49(m, 2H), 2.12(s, 3H), 2.23-2.12(m, 1H), 2.61-2.54(m, 1H), 2.66-2.64(d, J=7.35 Hz, 2H), 2.88-2.81(m, 2H), 3.02-2.93(q, J=8.58 Hz, 1H), 3.18-3.12(m, 1H), 3.48(s, 3H), 3.69-3.65(m, 1H), 3.86-3.82(d, J=9.93 Hz, 1H), 4.05(s, 1H), 4.33-4.13(m, 4H), 6.65-6.58(m, 2H), 6.99-6.90(m, 4H), 7.08-7.05(d, J=7.72 Hz, 2H), 7.28-7.25(d, J=8.46 Hz, 2H), 7.37-7.33(d, J=9.93 H, 1H), 7.46-7.42(m, 1H), 7.90-7.83(m, 2H), 8.03-7.90(m, 2H), 8.69-8.67(d, J=4.78 Hz, 1H).

EXAMPLE 142 methyl(1S,4S,5S,7S,10S)-4benzyl-10-tert-butyl-5-hydroxy-2,9,12-trioxo-7-(4-pyridin-2-ylbenzyl)-1-[(3R)-tetrahydrofuran-3-yl]-13-oxa-3,8,11-triazatetradec-1-ylcarbamate

EXAMPLE 142A $N^1$-[(1S,3S,4S)-4-({(2S)-2-azido-2-[(3R)-tetrahydrofuran-3-yl]ethanoyl}amino)-3-hydroxy-5-phenyl-1-(4-pyridin-2-ylbenzyl)pentyl]-$N^2$-(methoxycarbonyl)-3-methyl-L-valinamide A solution of the product of Example 2C (0.050 g, 0.094 mmol) in tetrahydrofuran (1.0 mL) was treated with 2(S)-azido 2-(3(R)-tetrahydrofuranyl)acetic acid (J. Med. Chem. 1993, 36, 2300-2310) (0.020 g, 0.117 mmol), DEPBT (0.045 g, 0.151 mmol), and N,N-diisopropylethylamine (0.080 mL, 0.459 mmol), stirred at 25° C. for 12 hours and partitioned between ethyl acetate and 10% $Na_2CO_3$ solution. The organic layer was washed with additional 10% $Na_2CO_3$ solution and brine, dried over $MgSO_4$, filtered and concentrated. The residue was chromatographed on silica gel eluting with a gradient starting with chloroform and ending with 5% methanol in ethyl acetate to give the title compound (0.041 g, 64% yield).

EXAMPLE 142B methyl(1S,4S,5S,7S,10S)-4benzyl-10-tert-butyl-5-hydroxy-2,9,12-trioxo-7-(4-pyridin-2-ylbenzyl)-1-[(3R)-tetrahydrofuran-3-yl]-13-oxa-3,8,11-triazatetradec-1-ylcarbamate To a solution of the product of Example 142A (0.038 g, 0.055 mmol) in a mixture of methanol (0.40 mL) and ethyl acetate (0.40 mL) was added 10% Pd on C (0.038 g), and the reaction was stirred under an atmosphere of hydrogen (balloon pressure) for 2 hours. The mixture was filtered through celite and the solvent was evaporated. The residue was dissolved in dichloromethane (0.40 mL) and pyridine (0.007 mL, 0.087 mmol) and methyl chloroformate (0.004 mL, 0.052 mmol) were added and the mixture was stirred at room temperature for 1 hour. The reaction was diluted with ethyl acetate and the organic layer was washed with dilute $NaHCO_3$, and brine, dried over $MgSO_4$, filtered and concentrated. The residue was chromatographed on silica gel eluting with a gradient starting with chloroform and ending with 5% methanol in ethyl acetate to give the title compound (0.017 g, 43% yield). $^1$H NMR (300 MHz, MeOH-$d_4$), δ ppm 0.87 (s, 9 H), 1.51-1.66 (m, 4 H), 2.31-2.43 (m, 1 H), 2.66 (dd, J=13.4, 9.0 Hz, 1 H), 2.83-2.96 (m, 3 H), 3.44 (dd, J=6.4, 9.0 Hz, 1 H), 3.52 (s, 3 H), 3.55-3.85 (m, 5 H), 3.65 (s, 3 H), 3.91 (d, J=9.6 Hz, 1 H), 4.24-4.30 (m, 1 H), 4.34-4.42 (m, 1 H), 7.11-7.35 (m, 8 H), 7.78-7.90 (m, 4 H), 8.57 (m, 1 H).

EXAMPLE 143 methyl(1S)-1-({[(1S,3S,4S)-3-hydroxy-4-({(2S)-2-[3-(3-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate

EXAMPLE 143A tert-butyl N-{2-[(3-hydroxybenzyl)amino]ethyl}-3-methyl-L-valinate A solution of Example 6F (0.052 g, 0.226 mmol) and m-hydroxybenzaldehyde (30.3 mg, 0.248 mmol) in methanol (1.25 mL) and benzene (1.25 mL) was stirred at 50° C. for 16 h. The mixture was cooled to 25° C. and treated with sodium borohydride (19 mg, 0.496 mmol) for 2 h. The mixture was partitioned between sodium bicarbonate and ethyl acetate. The organic layer was separated, washed with brine, dried over $MgSO_4$, filtered, and the solvents were evaporated to give the title compound as a crude residue (0.073 g, 96%) which was used directly in the next step.

EXAMPLE 143B tert-butyl(2S)-2-[3-(3-hydroxybenzyl)-2-oxoimidazolidin-1-yl]-3,3-dimethylbutanoate A solution of Example 143A (0.073 g, 0.23 mmol) and disuccinimidyl carbonate (0.069 g, 0.27 mmol) in dichloroethane (3 mL) was treated with triethylamine (38 µL, 0.27 mmol) at 25° C. for 16 h. The mixture was partitioned between 10% sodium carbonate and dichloromethane. The organic layer was separated, washed with brine, dried over $MgSO_4$, filtered, and the solvents were evaporated to give the crude title compound (0.026 g, 32%).

EXAMPLE 143C (2S)-2-[3-(3-hydroxybenzyl)-2-oxoimidazolidin-1-yl]-3,3-dimethylbutanoic acid A solution of Example 143B (0.026 g, 0.072 mmol) in dichloromethane (1.5 mL) was treated with trifluoroacetic acid (1.5 mL) at 25° C. for 16 h. The solvents were evaporated, and the crude residue was purified using reverse phase chromatography eluting with a gradient of 95% water (0.1% trifluoroacetic acid)/5% acetonitrile to 100% acetonitrile to give the title compound (0.022 g, 100%).

EXAMPLE 143D methyl(1S)-1-({[(1S,3S,4S)-3-hydroxy-4-({(2S)-2-[3-(3-hydroxybenzyl)-2oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate A solution of Example 143C (22 mg, 0.072 mmol) and Example 2C (25.4 mg, 0.048 mmol) in tetrahydrofuran (1 mL) was treated with DEPBT (21 mg, 0.072 mmol), and diisopropylethylamine (42 µL, 0.24 mmol) at 25° C. for 16 h. The crude residue was purified by silica gel chromatography eluting with a gradient of dichloromethane, 100% ethyl acetate, and 95% ethyl acetate/5% methanol to give the title compound (12 mg, 30%). $^1$H NMR (300 MHz, DMSO-$d_6$)

0.83(s, 9H), 0.89(s, 9H), 1.58-1.49(m, 2H), 2.35-2.26(m, 1H), 2.61-2.54(m, 1H), 2.68-2.66(d, J=6.99, 2H), 2.86-2.76 (m, 2H), 2.98-2.89(m, 1H), 3.19-3.13(m, 1H), 3.50(s, 3H), 3.70-3.63(m, 1H), 3.87-3.83(d, J=9.93 Hz, 1H), 4.08(s, 1H), 4.27-4.14(m, 4H), 4.56-4.54(d, J=7.35 Hz, 1H), 6.69-6.63(m, 3H), 7.17-7.04(m, 7H), 7.24-7.21(d, J=8.46 Hz, 2H), 7.33-7.29(m, 1H) 7.46-7.43(d, J=9.56 Hz, 1H), 7.91-7.82(m, 5H), 8.64(m, 1H), 9.39(s, 1H).

EXAMPLE 144 methyl(1S)-1-({[(1S,3S,4S)-3-hydroxy-4-({(2S)-2-[3-(4-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate

EXAMPLE 144A tert-butyl N-{2-[(4-hydroxybenzyl)amino]ethyl}-3-methyl-L-valinate A solution of Example 6F (0.075 g, 0.326 mmol) and p-hydroxybenzaldehyde (44 mg, 0.358 mmol) in methanol (1.6 mL) and benzene (1.6 mL) was stirred at 50° C. for 16 h. The mixture was cooled to 25° C. and treated with sodium borohydride (25 mg, 0.651 mmol) for 2 h. The mixture was partitioned between sodium bicarbonate and ethyl acetate. The organic layer was separated, washed with brine, dried over MgSO$_4$, filtered, and the solvents were evaporated to give the title compound as a crude residue (0.1 g, 100%) which was used directly in the next step.

EXAMPLE 144B tert-butyl(2S)-2-[3-(4-hydroxybenzyl)-2-oxoimidazolidin-1-yl]-3,3-dimethylbutanoate A solution of Example 144A (0.1 g, 0.32 mmol) and disuccinimidyl carbonate (0.1 g, 0.39 mmol) in dichloroethane (3 mL) was treated with triethylamine (91 μL, 0.65 mmol) at 25° C. for 16 h. The mixture was partitioned between 10% sodium carbonate and dichloromethane. The organic layer was separated, washed with brine, dried over MgSO$_4$, filtered, and the solvents were evaporated and the crude residue was purified using silica gel chromatography eluting with a gradient of 100% hexanes to 60% hexanes in ethyl acetate to give the title compound (0.046 g, 39%).

EXAMPLE 144C (2S)-2-[3-(4-hydroxybenzyl)-2-oxoimidazolidin-1-yl]-3,3-dimethylbutanoic acid A solution of Example 144B (0.04 g, 0.11 mmol) in dichloromethane (0.5 mL) was treated with trifluoroacetic acid (0.5 mL) at 25° C. for 16 h. The solvents were evaporated, and the crude residue was twice azeotroped with ethyl acetate to give the crude title compound (0.034 g, 100%).

EXAMPLE 144D methyl(1S)-1-({[(1S,3S,4S)-3-hydroxy-4-({(2S)-2-[3-(4-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate A solution of Example 144C (34 mg, 0.11 mmol) and Example 2C (53.2 mg, 0.1 mmol) in tetrahydrofuran (1 mL) was treated with DEPBT (45 mg, 0.15 mmol), and diisopropylethylamine (87 μL, 0.5 mmol) at 25° C. for 16 h. The crude residue was purified using reverse phase chromatography eluting with a gradient of 95% water(0.1% trifluoroacetic acid)/5% acetonitrile to 100% acetonitrile to give the title compound (10 mg, 12%). $^1$H NMR (300 MHz, DMSO-d$_6$) 0.83(s, 9H), 0.89(s, 9H), 1.58-1.51(m, 2H), 2.33-2.24(m, 1H), 2.61-2.54(m, 1H), 2.67-2.65(d, J=7.35, 2H), 2.81-2.77 (m, 2H), 2.94-2.85(m, 1H), 3.14(m, 1H), 3.50(s, 3H), 3.66(m, 1H), 3.86-3.83(d, J=9.93 Hz, 1H), 4.07(s, 1H), 4.24-4.13(m, 4H), 6.66-6.63(d, J=9.53 Hz, 1H), 6.75-6.72(d, J=8.46 Hz, 2H), 7.09-7.02(m, 7H), 7.24-7.21(d, J=8.09 Hz, 2H), 7.33-7.30(m, 1H), 7.46-7.43(d, J=9.93 Hz, 1H), 7.91-7.82(m, 5H), 8.65(m, 1H), 9.34(s, 1H).

EXAMPLE 145 methyl(1S)-1-({[(1S,3S,4S)-3-hydroxy-4-({(2S)-2-[3-(2-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate

EXAMPLE 145A tert-butyl N-{2-[(2-hydroxybenzyl)amino]ethyl}-3-methyl-L-valinate A solution of Example 6F (0.12 g, 0.521 mmol) and o-hydroxybenzaldehyde (60 μL, 0.573 mmol) in methanol (2.5 mL) and benzene (2.5 mL) was stirred at 50° C. for 16 h. The mixture was cooled to 25° C. and treated with sodium borohydride (40 mg, 1.04 mmol) for 2 h. The mixture was partitioned between sodium bicarbonate and ethyl acetate. The organic layer was separated, washed with brine, dried over MgSO$_4$, filtered, and the solvents were evaporated to give the title compound as a clear oil (180 mg, 100%).

EXAMPLE 145B tert-butyl(2S)-2-[3-(2-hydroxybenzyl)-2-oxoimidazolidin-1-yl]-3,3-dimethylbutanoate A solution of Example 145A (180 mg, 0.521 mmol) and disuccinimidyl carbonate (0.16 g, 0.625 mmol) in dichloroethane (5 mL) was treated with triethylamine (87 μL, 0.625 mmol) at 25° C. for 16 h. The mixture was partitioned between 10% sodium carbonate and dichloromethane. The organic layer was separated, washed with brine, dried over MgSO$_4$, filtered, and the solvents were evaporated to give the crude residue which was purified using silica gel chromatography eluting with a gradient of 100% hexanes to 60% hexanes in ethyl acetate to give the title compound (0.127 g, 67%).

EXAMPLE 145C (2S)-2-[3-(2-hydroxybenzyl)-2-oxoimidazolidin-1-yl]-3,3-dimethylbutanoic acid A solution of Example 145B (0.127 g, 0.35 mmol) in dichloromethane (1.75 mL) was treated with trifluoroacetic acid (1.75 mL) at 25° C. for 16 h. The solvents were evaporated, and the crude residue was azeotroped twice with ethyl acetate to give crude material which was used directly in the next step.

EXAMPLE 145D methyl(1S)-1-({[(1S,3S,4S)-3-hydroxy-4-({(2S)-2-[3-(2-hydroxybenzyl)-2-oxoimidazolidin-1-yl]-3,3-dimethylbutanoyl}amino)-5-phenyl-1-(4-pyridin-2-ylbenzyl)pentyl]amino}carbonyl)-2,2-dimethylpropylcarbamate A solution of Example 145C and Example 2C (58 mg, 0.12 mmol) in tetrahydrofuran (1.1 mL) was treated with DEPBT (49 mg, 0.163 mmol), and diisopropylethylamine (95 µL, 0.545 mmol) at 25° C. for 16 h. The crude residue was purified by silica gel chromatography eluting with a gradient of dichloromethane, 100% ethyl acetate to 95% ethyl acetate/5% methanol, to afford the title compound (45 mg, 50%). $^1$H NMR (300MHz, DMSO-$d_6$) δ ppm 0.83(s, 9H), 0.88(s, 9H), 1.62-1.48(m, 2H), 2.36-2.27(m, 1H), 2.61-2.54(m, 1H), 2.67-2.64(d, J=6.99, 2H), 2.81-2.79(m, 1H), 2.95-2.84(m, 1H), 3.07-2.95(m, 1H), 3.21-3.17(m, 1H), 3.50(s, 3H), 3.70-3.63 (m, 1H), 3.87-3.83(d, J=9.93 Hz, 1H), 4.07(s, 1H), 4.15(m, 2H), 4.34-4.4.24(m, 2H), 4.55-4.53(d, J=7.72 Hz, 1H), 6.66-6.63(d, J=9.93 Hz, 1H), 6.85-6.77(m, 2H), 7.02(m, 3H), 7.13-7.08(m, 4H), 7.24-7.21(d, J=8.09 Hz, 2H), 7.33-7.29(m, 1H), 7.48-7.45(d, J=9.93 Hz, 1H), 7.91-7.82(m, 5H), 8.64-8.63(d, J=4.78 Hz, 1H), 9.56(s, 1H).

EXAMPLE 146 methyl(1S,4S,5S,7S,10S)-4benzyl-1,10-di-tert-butyl-5-hydroxy-2,9,12-trioxo-7-[4-(1,3-thiazol-2-yl)benzyl]-13-oxa-3,8,11-triazatetradec-1-ylcarbamate

EXAMPLE 146A tert-butyl(1S,2S,4S)-4-amino-1-benzyl-2-{[tert-butyl (dimethyl)silyl]oxy}-5-[4-(1,3-thiazol-2-yl)phenyl] pentylcarbamate To a solution containing the product from Example 92D (0.050 g, 0.070 mmol) in N,N-dimethylformamide (1.8 mL) were added silver(I) oxide (0.016 g, 0.070 mmol), tetrakis (triphenylphosphine)palladium (0.004 g, 0.003 mmol), and 2-tributylstannylthiazole (0.126 g, 0.337 mmol), and the mixture was irradiated at 60 W in a microwave (internal temperature reached 100° C.) for 2 minutes. The mixture was then irradiated at 200 W in a microwave (internal temperature reached 100° C.) for 4 minutes The reaction was cooled, diluted with chloroform and washed with dilute NaHCO$_3$, and brine, dried over MgSO$_4$, filtered and concentrated. The residue was chromatographed on silica gel eluting with 30% methanol in chloroform containing 0.2% ammonium hydroxide to give the title compound (0.053 g).

EXAMPLE 146B

N$^1$-{(1S,3S,4S)-4-[(tert-butoxycarbonyl)amino]-3-{[tert-butyl(dimethyl)silyl]oxy}-5-phenyl-1-[4-(1,3-thiazol-2-yl)benzyl]pentyl}-N$^2$-(methoxycarbonyl)-3-methyl-L-valinamide To a solution containing the product from Example 146A (0.053 g) in tetrahydrofuran (0.70 mL) were added the product from Example 1F (0.015 g, 0.079 mmol), DEPBT (0.033 g, 0.110 mmol), and N,N-diisopropylethylamine (0.065 mL, 0.373 mmol) and the mixture was stirred at room temperature for 1 hour. The mixture was partitioned between ethyl acetate and 10% Na$_2$CO$_3$ solution. The organic was washed with additional 10% Na$_2$CO$_3$ solution and then brine, dried over MgSO$_4$, filtered and evaporated. The residue was chromatographed on silica gel eluting with a gradient starting with chloroform and ending with 80 % ethyl acetate in chloroform to give the product (0.042 g).

EXAMPLE 146C

N$^1$-{(1S,3S,4S)-4-amino-3-hydroxy-5-phenyl-1-[4-(1,3-thiazol-2-yl)benzyl]pentyl}-N$^2$-(methoxycarbonyl)-3-methyl-L-valinamide To the product from Example 146B (0.042 g, 0.056 mmol) was added tetrabutyl ammonium fluoride solution in tetrahydrofuran (0.28 mL, 1N) and the mixture was stirred at room temperature for 18 hours. The tetrahydrofuran was evaporated and the mixture was partitioned between ethyl acetate and water. The organic was washed with brine, dried over MgSO$_4$, filtered and evaporated. The residue was dissolved in dichloromethane (0.40 mL) and trifluoroacetic acid (0.20 mL) was added and the mixture was stirred at room temperature for 30 minutes. The solvent was evaporated and the residue was partitioned between chloroform and dilute NaHCO$_3$, and brine, dried over MgSO$_4$, filtered and concentrated to give the title compound (0.035 g), which was used without further purification.

EXAMPLE 146D methyl(1S,4S,5S,7S,10S)-4benzyl-1,10-di-tert-butyl-5-hydroxy-2,9,12-trioxo-7-[4-(1,3-thiazol-2-yl)benzyl]-13-oxa-3,8,11-triazatetradec-1-ylcarbamate To a solution containing the product from Example 146C (0.035 g, 0.065 mmol) in tetrahydrofuran (0.70 mL) were added the product from Example 1F (0.012 g, 0.063 mmol), DEPBT (0.029 g, 0.097 mmol), and N,N-diisopropylethylamine (0.056 mL, 0.321 mmol) and the mixture was stirred at room temperature for 3 hours. The mixture was partitioned between ethyl acetate and 10% Na$_2$CO$_3$ solution. The organic was washed with additional 10% Na$_2$CO$_3$ solution and then brine, dried over MgSO$_4$, filtered and evaporated. The residue was chromatographed on reverse phase HPLC on a C18 column, eluting with a gradient starting with water (containing 0.1% trifluoroacetic acid) and ending with acetonitrile to give the product (0.021 g, 46% yield). $^1$H NMR (300 MHz, MeOH-$d_6$), δ ppm 0.86 (s, 9 H), 0.88 (s, 9 H), 1.61-1.71 (m, 2 H), 2.58-2.65 (m, 1 H), 2.76-2.96 (m, 4 H), 3.57 (s, 3H), 3.65 (s, 3 H), 3.74-3.79 (m, 1 H), 3.81 (s, 1 H), 3.1 (s, 1 H), 4.19-4.28 (m, 1 H), 4.30-4.40 (m, 1 H), 7.10-7.28 (m, 7 H), 7.56 (d, J=3.3 Hz, 1 H), 7.78 (d, J=8.1 Hz, 2 H), 7.83 (d, J=3.3 Hz, 1 H).

EXAMPLE 147 methyl(1S,4S,5S,7S,10S)-4benzyl-10-tert-butyl-5-hydroxy-1-[(1S)-1-methylpropyl]-2,9,12-trioxo-7-(4-pyridin-2-ylbenzyl)-13-oxa-3,8,11-triazatetradec-1-ylcarbamate A solution of Example 5A (8.9 mg, 0.047 mmol) and Example 2C (25 mg, 0.047 mmol) in tetrahydrofuran (0.5 mL) was treated with DEPBT (21 mg, 0.07 mmol), and diisopropylethylamine (41 µL, 0.235 mmol) at 25° C. for 16 h. The crude residue was purified by silica gel chromatography eluting with a gradient of dichloromethane, 100% ethyl acetate to 95% ethyl acetate/5% methanol to give the title compound (23 mg, 69%). $^1$H NMR (300 MHz, DMSO-d$_6$) 0.66-0.64(d, J=6.62 Hz, 3H), 0.76-0.71(t, J=7.35 Hz, 3H), 0.80(s, 9H), 1.03-0.93(m, 1H), 1.29-1.23(m, 1H), 1.62-1.44(m, 2H), 2.56-2.51(m, 1H), 2.77-2.71(m, 3H), 3.49(s, 3H), 3.49(m, 1H), 3.54(s, 3H), 3.62(m, 1H), 3.79(m, 1H), 3.84-3.81(d, J=9.56 Hz, 1H), 4.15-4.06(m, 2H), 4.92-4.90(d, J=5.52 Hz, 1H), 6.64-6.61(d, J=9.56 Hz, 1H), 7.05-7.02(d, J=9.19 Hz, 1H), 7.21-7.10(m, 6H), 7.33-7.29(m, 1H), 7.45-7.42(d, J=9.19 Hz, 1H), 7.82-7.78(d, J=8.46 Hz, 1H), 7.90-7.83(m, 5H), 8.64(m, 1H).

EXAMPLE 148 methyl(1S,4S,5S,7S,10S)-4benzyl-1,10-di-tert-butyl-5-hydroxy-2,9,12-trioxo-7-(4-pyridin-3-ylbenzyl)-13-oxa-3,8,11-triazatetradec-1-ylcarbamate

EXAMPLE 148A tert-butyl(1S,2S,4S)-1-benzyl-4-{[(benzyloxy)carbonyl]amino}-2-{[tert-butyl(dimethyl)silyl]oxy}-5-(4-pyridin-3-ylphenyl)pentylcarbamate To a solution containing the product from Example 92D (0.50 g, 0.70 mmol) in N,N-dimethylformamide (7.0 mL) were added lithium chloride (0.30 g, 7.08 mmol), dichlorobis(triphenylphosphine)palladium(II) (0.150 g, 0.214 mmol), and 3-tributylstannylpyridine (0.776 g, 2.11 mmol), and the mixture was heated to 100° C. for 18 hours. The reaction was filtered, diluted with ethyl acetate and washed with water, and brine, dried over MgSO$_4$, filtered and concentrated. The residue was chromatographed on silica gel eluting with a gradient starting with chloroform and ending with 25% ethyl acetate in chloroform to give the title compound (0.365 g).

EXAMPLE 148B tert-butyl(1S,2S,4S)-1-benzyl-4-{[(benzyloxy)carbonyl]amino}-2-hydroxy-5-(4-pyridin-3-ylphenyl)pentylcarbamate To the product from Example 148A (0.365 g, 0.51 mmol) was added tetrabutyl ammonium fluoride solution in tetrahydrofuran (2.0 mL, 1N) and the mixture was stirred at room temperature for 18 hours. The tetrahydrofuran was evaporated and the mixture was partitioned between ethyl acetate and water. The organic was washed with brine, dried over MgSO$_4$, filtered and evaporated. The residue was chromatographed on silica gel eluting with a gradient starting with chloroform and ending with 80% ethyl acetate in chloroform to give the title compound (0.172 g, 41% over two steps).

EXAMPLE 148C tert-butyl(1S,2S,4S)-4-amino-1-benzyl-2-hydroxy-5-(4-pyridin-3-ylphenyl)pentylcarbamate The product from Example 148B (0.170 g, 0.29 mmol) was dissolved in a mixture of ethyl acetate (1.5 mL) and methanol (1.5 mL) and 20% Pd(OH)$_2$ on carbon (0.080 g) and a solution of HCl in dioxane (0.070 mL, 4 N) were added, and the reaction was stirred under an atmosphere of hydrogen (balloon pressure) for 18 hours. The mixture was filtered through celite® and the solvent was evaporated to give the title compound as the hydrochloride salt, which was used without further purification.

EXAMPLE 148D tert-butyl(1S,2S,4S)-1-benzyl-2-hydroxy-4-{[N-(methoxycarbonyl)-3-methyl-L-valyl]amino}-5-(4-pyridin-3-ylphenyl)pentylcarbamate To a solution containing the product from Example 148C (0.29 mmol) in tetrahydrofuran (3.0 mL) were added the product from Example 1F (0.060 g, 0.317 mmol), DEPBT (0.130 g, 0.435 mmol), and N,N-diisopropylethylamine (0.25 mL, 1.44 mmol) and the mixture was stirred at room temperature for 3 hours. The mixture was partitioned between ethyl acetate and 10% Na$_2$CO$_3$ solution. The organic was washed with additional 10% Na$_2$CO$_3$ solution and then brine, dried over MgSO$_4$, filtered and evaporated. The residue was chromatographed on silica gel eluting with a gradient starting with 50% ethyl acetate in chloroform and ending with 80% ethyl acetate in chloroform to give the product (0.108 g, 59% yield).

EXAMPLE 148E $N^1$-[(1S,3S,4S)-4-amino-3-hydroxy-5-phenyl-1-(4-pyridin-3-ylbenzyl)pentyl]-$N^2$-(methoxycarbonyl)-3-methyl-L-valinamide To a solution of the product of Example 148D (0.108 g, 0.17 mmol) in dichloromethane (2.0 mL) was added trifluoroacetic acid (0.5 mL), and the mixture was stirred at room temperature for 1 hour. The solvent was evaporated, and the reaction was partitioned between ethyl acetate and diluted NaHCO$_3$ solution. The organic layer was washed with brine, dried over MgSO$_4$, filtered and concentrated.

EXAMPLE 148F methyl(1S,4S,5S,7S,10S)-4benzyl-1,10-di-tert-butyl-5-hydroxy-2,9,12-trioxo-7-(4-pyridin-3-ylbenzyl)-13-oxa-3,8,11-triazatetradec-1-ylcarbamate To a solution containing the product from Example 148E (0.17 mmol) in tetrahydrofuran (1.7 mL) were added the product from Example 1F (0.036 g, 0.190 mmol), DEPBT (0.077 g, 0.258 mmol), and N,N-diisopropylethylamine (0.15 mL, 0.861 mmol) and the mixture was stirred at room temperature for 18 hours. The mixture was partitioned between ethyl acetate and 10% Na$_2$CO$_3$ solution. The organic was washed with additional 10% Na$_2$CO$_3$ solution and then brine, dried over MgSO$_4$, filtered and evaporated. The residue was chromatographed on reverse phase HPLC on C18 column eluting with a gradient starting with water and ending with methanol to give the product (0.044 g, 37% yield). $^1$H NMR (300 MHz, DMSO-d$_6$), δ ppm 0.80 (s, 9 H), 0.82 (s, 9 H), 1.42-1.59 (m, 2 H), 2.67-2.79 (m, 3 H), 3.47 (s, 3 H), 3.59-3.67 (m, 1 H), 3.81 (d, J=9.6 Hz, 1 H), 3.91 (d, J=9.6 Hz, 1 H), 4.02-4.21 (m, 2 H), 4.87 (d, J=5.2 Hz, 1 H), 6.65 (d, J=9.6 Hz, 1 H), 6.80 (d, J=9.9 Hz, 1 H), 7.12-7.23 (m, 8 H), 7.45-7.55 (m, 4 H), 7.80 (d, J=8.5 Hz, 1 H), 8.01 (d, J=8.1 Hz, 1 H), 8.54 (d, J=4.8 Hz, 1 H), 8.83 (d, J=1.8 Hz, 1 H).

EXAMPLE 149 methyl(1S)-1-({[(1S,3S,4S)-3-hydroxy-4-{[(2S)-2-methyl-3-(methylsulfonyl)propanoyl]amino}-5-phenyl-1-(4-pyridin-2-ylbenzyl)pentyl]amino}carbonyl)-2,2-dimethylpropylcarbamate

EXAMPLE 149A (2S)-2-methyl-3-(methylthio)propanoic acid

A solution of D-(−)-3-acetyl-b-mercaptoisobutyric acid (0.3 g, 1.85 mmol) in 5M KOH in methanol (0.74 mL, 3.7 mmol) at 0° C. was stirred for 25 minutes. The mixture was treated with dimethyl sulfate (0.233 g, 1.85 mmol) and allowed to warm to 25° C. for 1.5 h. The mixture was filtered through Celite® and rinsed with methanol. The solvents were evaporated, and the crude residue was partitioned between water and ethyl acetate. The aqueous layer was separated, acidified with 1N HCl, and extracted with ethyl acetate. The organic layer was dried over $MgSO_4$, filtered, and the solvents were evaporated to give the crude title compound (0.14 g, 56%).

EXAMPLE 149B (2S)-2-methyl-3-(methylsulfonyl)propanoic acid

A solution of Example 149A (0.085 g, 0.63 mmol) in acetone (1.2 mL) and water (0.25 mL) at 0° C. was treated with oxone (1.17 g, 1.9 mmol) and the mixture was stirred at 25° C. for 3 h. The mixture was filtered, rinsed with acetone, and the solvents were evaporated. The residue was dissolved in ethyl acetate, dried over $MgSO_4$, filtered and the solvents were evaporated to give the crude title compound (47 mg, 45%).

EXAMPLE 149C methyl(1S)-1-({[(1S,3S,4S)-3-hydroxy-4-{[(2S)-2-methyl-3-(methylsulfonyl)propanoyl]amino}-5-phenyl-1-(4-pyridin-2-ylbenzyl)pentyl]amino}carbonyl)-2,2-dimethylpropylcarbamate A solution of Example 149B (47 mg, 0.283 mmol) in N,N-dimethylformamide (1 mL) at 0° C. was treated with 1-hydroxybenzotriazole hydrate (57.3 mg, 0.42 mmol), 1-(3-dimethylaminopropyl)-3-ethylcarbodiimide hydrochloride (EDAC) (48.2 mg, 0.311 mmol), diisopropylethylamine (59 µL, 0.34 mmol) and Example 2C (0.15 mg, 0.28 mmol) for 3 h at 25° C., then for 16 h at 0° C. The mixture was partitioned between ethyl acetate and 5% potassium bisulfate, the organic layer was separated, washed with saturated sodium bicarbonate, brine, dried over $MgSO_4$, filtered, and the solvents were evaporated. The crude residue was purified by silica gel chromatography eluting with dichloromethane, 100% ethyl acetate, and 95% ethyl acetate/5% methanol to give the title compound (19 mg, 10%). $^1$H NMR (300 MHz, $CDCl_3$) δ ppm 0.93(s, 9H), 1.21-1.18(d, J=6.99 Hz, 3H), 1.71-1.57(m, 2H), 2.57(s, 3H), 2.88-2.76(m, 5H), 3.66-3.48 (m, 1H), 3.63(s, 3H), 3.79-3.70(m, 2H), 4.06-4.99(m, 2H), 4.27-4.20(m, 1H), 5.38-5.35(d, J=8.82 Hz, 1H), 6.22-6.20(d, J=6.99 Hz, 1H), 6.39-6.32(d, J=9.19 Hz, 1H), 7.27-7.14(m, 8H), 7.77-7.67(m, 2H), 7.89-7.86(d, J=8.46 Hz, 2H), 8.67-8.66(d, J=4.04 Hz, 1H).

EXAMPLE 150 methyl(1S,4S,5S,7S,10S)-4benzyl-1,10-di-tert-butyl-5-hydroxy-2,9,12-trioxo-7-(4-pyridin-4-ylbenzyl)-13-oxa-3,8,11-triazatetradec-1-ylcarbamate

EXAMPLE 150A tert-butyl(1S,2S,4S)-1-benzyl-4-{[(benzyloxy)carbonyl]amino}-2-{[tert-butyl(dimethyl)silyl]oxy}-5-(4-pyridin-4-ylphenyl)pentylcarbamate To a solution containing the product from Example 92D (0.50 g, 0.70 mmol) in N,N-dimethylformamide (7.0 mL) were added lithium chloride (0.30 g, 7.08 mmol), dichlorobis(triphenylphosphine)palladium(II) (0.150 g, 0.214 mmol), and 4-tributylstannylpyridine (0.776 g, 2.11 mmol), and the mixture was heated to 100° C. for 18 hours. The reaction was filtered, diluted with ethyl acetate and washed with water, and brine, dried over $MgSO_4$, filtered and concentrated. The residue was dissolved in acetonitrile and washed twice with hexanes, and the acetonitrile layer was evaporated to give the title compound (0.422 g).

EXAMPLE 150B tert-butyl(1S,2S,4S)-1-benzyl-4-{[(benzyloxy)carbonyl]amino}-2-hydroxy-5-(4-pyridin-4-ylphenyl)pentylcarbamate To the product from Example 150A (0.422 g, 0.60 mmol) was added tetrabutyl ammonium fluoride solution in tetrahydrofuran (2.3 mL, 1N) and the mixture was stirred at room temperature for 18 hours. The tetrahydrofuran was evaporated and the mixture was partitioned between ethyl acetate and water. The organic was washed with brined, dried over $MgSO_4$ filtered and evaporated. The residue was chromatographed on silica gel eluting with a gradient starting with chloroform and ending with 80% ethyl acetate in chloroform to give the title compound (0.242 g, 58% over two steps).

EXAMPLE 150C tert-butyl(1S,2S,4S)-4-amino-1-benzyl-2-hydroxy-5-(4-pyridin-4-ylphenyl)pentylcarbamate The product from Example 150B (0.242 g, 0.41 mmol) was dissolved in a mixture of ethyl acetate (2.0 mL) and methanol (2.0 mL) and 20% $Pd(OH)_2$ on carbon (0.10 g) and a solution of HCl in dioxane (0.10 mL, 4 N) were added, and the reaction was stirred under an atmosphere of hydrogen (balloon pressure) for 18 hours. The mixture was filtered through celite and the solvent was evaporated to give the title compound as the hydrochloride salt (0.273 g, which was used without further purification.

EXAMPLE 150D tert-butyl(1S,2S,4S)-1-benzyl-2-hydroxy-4-{[N-(methoxycarbonyl)-3-methyl-L-valyl]amino}-5-(4-pyridin-4-ylphenyl)pentylcarbamate To a solution containing the product from Example 150C (0.41 mmol) in tetrahydrofuran (4.0 mL) were added the product from Example 1F (0.085 g, 0.450 mmol), DEPBT (0.183 g, 0.612 mmol), and N,N-diisopropylethylamine (0.36 mL, 2.07 mmol) and the mixture was stirred at room temperature for 3 hours. The mixture was partitioned between ethyl acetate and 10% $Na_2CO_3$ solution. The organic was washed with additional 10% $Na_2CO_3$ solution and then brine, dried over $MgSO_4$, filtered and evaporated. The residue was chromatographed on silica gel eluting with a gradient starting with chloroform and ending with 80% ethyl acetate in chloroform to give the product (0.138 g, 53% yield).

EXAMPLE 150E $N^1$-[(1S,3S,4S)-4-amino-3-hydroxy-5-phenyl-1-(4-pyridin-4-ylbenzyl)pentyl]-$N^2$-(methoxycarbonyl)-3-methyl-L-valinamide To a solution of the product of Example 150D (0.138 g, 0.22 mmol) in dichloromethane (2.0 mL) was added trifluoroacetic acid (0.5 mL), and the mixture was stirred at room temperature for 1 hour. The solvent was evaporated, and the reaction was partitioned between ethyl acetate and diluted $NaHCO_3$ solution. The organic layer was washed with brine, dried over $MgSO_4$, filtered and concentrated.

EXAMPLE 150F methyl(1S,4S,5S,7S,10S)-4-benzyl-1,10-di-tert-butyl-5-hydroxy-2,9,12-trioxo-7-(4-pyridin-4-ylbenzyl)-13-oxa-3,8,11-triazatetradec-1-ylcarbamate To a solution containing the product from Example 150E (0.22 mmol) in tetrahydrofuran (2.5 mL) were added the product from Example 1F (0.046 g, 0.243 mmol), DEPBT (0.099 g, 0.331 mmol), and N,N-diisopropylethylamine (0.19 mL, 1.09 mmol) and the mixture was stirred at room temperature for 68 hours. The mixture was partitioned between ethyl acetate and 10% $Na_2CO_3$ solution. The organic was washed with additional 10% $Na_2CO_3$ solution and then brine, dried over $MgSO_4$, filtered and evaporated. The residue was chromatographed on reverse phase HPLC on a C18 column, eluting with a gradient starting with water and ending with methanol to give the title compound (0.108 g, 70% yield). $^1$H NMR (300 MHz, DMSO-$d_6$), δ ppm 0.79 (s, 9 H), 0.82 (s, 9 H), 1.42-1.59 (m, 2 H), 2.71-2.79 (m, 3 H), 3.48 (s, 3 H), 3.55 (s, 3 H), 3.61-3.67 (m, 1 H), 3.81 (d, J=9.9 Hz, 1 H), 3.91 (d, J=9.6 Hz, 1 H), 4.03-4.20 (m, 2 H), 4.87 (d, J=5.2 Hz, 1 H), 6.64 (d, J=9.6 Hz, 1 H), 6.80 (d, J=9.6 Hz, 1 H), 7.12-7.23 (m, 8 H), 7.50-7.60 (m, 4 H), 7.65 (d, J=5.9 Hz, 2 H), 7.80 (d, J=8.5 Hz, 1 H), 8.61 (d, J=5.9 Hz, 2 H).

EXAMPLE 151 methyl(1S)-1-({[(1S,3S,4S)-3-hydroxy-4-{[(2S)-2-hydroxy-3,3-dimethylbutanoyl]amino}-5-phenyl-1-(4-pyridin-2-ylbenzyl)pentyl]amino}carbonyl)-2,2-dimethylpropylcarbamate A solution of the product of Example 2C (0.020 g, 0.038 mmol) in tetrahydrofuran (0.40 mL) was treated with (s)-(−)-2-hydroxy-3,3-dimethylbutyric acid (0.006 g, 0.045 mmol), DEPBT (0.017 g, 0.057 mmol), and N,N-diisopropylethylamine (0.035 mL, 0.201 mmol), stirred at 25° C. for 2 hours and partitioned between ethyl acetate and 10% $Na_2CO_3$ solution. The organic layer was washed with additional 10% $Na_2CO_3$ solution and brine, dried over $MgSO_4$, filtered and concentrated. The residue was chromatographed on silica gel eluting with a gradient starting with dichloromethane and ending with ethyl acetate to give the title compound (0.005 g, 21% yield). $^1$H NMR (300 MHz, DMSO-$d_6$), δ ppm 0.70 (s, 9 H), 0.79 (s, 9 H), 1.42-1.54 (m, 2 H), 2.71-2.76 (m, 3 H), 3.42 (d, J=5.9 Hz, 1 H), 3.48 (s, 3 H), 3.61-3.67 (m, 1 H), 3.82 (d, J=9.9 Hz, 1 H), 4.10-4.21 (m, 2 H), 4.98 (d, J=5.5 Hz, 1 H), 5.33 (d, J=5.8 Hz, 1 H), 6.65 (d, J=9.6 Hz, 1 H), 7.09-7.24 (m, 9 H), 7.28-7.32 (m, 1 H), 7.80 (d, J=8.5 Hz, 1 H), 7.84-7.89 (m, 4 H), 8.62 (m, 1 H).

EXAMPLE 152 methyl(1S,4S,6S,7S,10S)-7-benzyl-1,10-di-tert-butyl-6-hydroxy-12,12-dioxido-2,9-dioxo-4-(4-pyridin-2-ylbenzyl)-12-thia-3,8,11-triazatridec-1-ylcarbamate

EXAMPLE 152A tert-butyl 3-methyl-N-(methylsulfonyl)-L-valinate

A solution of tert-butyl 3-methyl-L-valinate (50 mg, 0.223 mmol) in dichloromethane (1 mL) at 0° C. was treated with 4-(dimethylamino)pyridine (5.4 mg, 0.045 mmol), triethylamine (93.4 μL, 0.67 mmol), and methanesulfonyl chloride (34.5 L, 0.45 mmol), and the mixture was warmed to 25° C. for 1 h. The mixture was washed with 5% potassium bisulfate, saturated sodium bicarbonate, brine, and dried over $MgSO_4$, filtered, and the solvents were evaporated to give the crude title compound (59 mg, 100%).

EXAMPLE 152B 3-methyl-N-(methylsulfonyl)-L-valine

A solution of Example 152A (59 mg, 0.22 mmol) in 4N HCl in dioxane (1 mL) at 25° C. for 4 h, and the solvents were evaporated to give the crude title compound (49 mg, 100%).

EXAMPLE 152C methyl(1S,4S,6S,7S,10S)-7-benzyl-1,10-di-tert-butyl-6-hydroxy-12,12-dioxido-2,9-dioxo-4-(4-pyridin-2-ylbenzyl)-12-thia-3,8,11-triazatridec-1-ylcarbamate A solution of Example 152B (22.7 mg, 0.108 mmol) in N,N-dimethylformamide (0.2 mL) was treated with 1-hydroxybenzotriazole hydrate (HOBT) (21 mg, 0.153 mmol), 1-(3-dimethylaminopropyl)-3-ethylcarbodiimide hydrochloride (EDAC) (18.2 mg, 0.117 mmol), Example 2C (48 mg, 0.09 mmol), and diisopropylethylamine (79 μL, 0.45 mmol) at 0° C. After 1 h the mixture was warmed to 25° C. for 16 h. The solvents were evaporated, and the crude residue was purified using reverse phase chromatography eluting with a gradient of 95% water (0.1% trifluoroacetic acid)/5% acetonitrile to 100% acetonitrile to give the title compound (15 mg, 23%). $^1$H NMR (300 MHz, CDCl$_3$) δ ppm 0.92(s, 9H), 0.95 (s, 9H), 1.70-1.56(m, 2H), 2.47(bs, 3H), 2.91-2.77(m, 5H), 3.43-3.37(m, 1H), 3.64(s, 3H), 3.70(m, 1H), 4.29-4.12(m, 2H), 5.20(m, 1H), 5.31(m, 1H), 6.15-6.12(d, J=8.09 Hz, 1H), 6.21(m, 1H), 7.24-7.13(m, 8H), 7.79-7.68(m, 2H), 7.89-7.86 (d, J=8.09 Hz, 2H), 8.69-8.67(d, J=4.78 Hz, 1H).

EXAMPLE 153 methyl(1R,4S,5S,7S,10S)-4-benzyl-10-tert-butyl-5-hydroxy-1-[(methylthio)methyl]-2,9,12-trioxo-7-(4-pyridin-2-ylbenzyl)-13-oxa-3,8,11-triazatetradec-1-ylcarbamate

EXAMPLE 153A

N-(methoxycarbonyl)-S-methyl-L-cysteine

A solution of L-cysteine (50 mg, 0.413 mmol) in methanol (0.4 mL) was treated with 1N NaOH (0.45 mL, 0.45 mmol) and methyl iodide (28.3 µL, 0.45 mmol) at 0° C. The mixture was warmed to 25° C. over 16 h, recooled to 0° C., and treated with 3N NaOH (0.45 µL, 1.3 mmol) and methyl chloroformate (64 µL, 0.83 mmol) at 25° C. for 4 h. The mixture was acidified with 2N HCl, and partitioned between ethyl acetate and water. The organic layer was separated, washed with water, brine, and dried over MgSO$_4$ and filtered. The solvents were evaporated to give the crude title compound (60 mg, 75%).

EXAMPLE 153B methyl(1R,4S,5S,7S,10S)-4-benzyl-10-tert-butyl-5-hydroxy-1-[(methylthio)methyl]-2,9,12-trioxo-7-(4-pyridin-2-ylbenzyl)-13-oxa-3,8,11-triazatetradec-1-ylcarbamate A solution of Example 153A (25 mg, 0.129 mmol) in N,N-dimethylformamide (0.3 µL) was treated with 1-hydroxybenzotriazole hydrate (HOBT) (24.8 mg, 0.18 mmol), 1-(3-dimethylaminopropyl)-3-ethylcarbodiimide hydrochloride (EDAC) (21.7 mg, 0.14 mmol), Example 2C (57.4 mg, 0.107 mmol), and diisopropylethylamine (94 µL, 0.54 mmol) at 25° C. for 16 h. The solvents were evaporated and the crude residue was dissolved in ethyl acetate, washed with saturated sodium bicarbonate, brine, dried over MgSO$_4$ and filtered. The solvents were evaporated, and the crude residue was purified by silica gel chromatography eluting with a gradient of dichloromethane to 100% ethyl acetate to give the title compound (48 mg, 63%). $^1$H NMR (300 MHz, CDCl$_3$) δ ppm 0.93(s, 9H), 1.67-1.62(m, 2H), 2.05(s, 3H), 2.72-2.70(d, J=6.25 Hz, 2H), 2.80-2.76(m, 1H), 2.93-2.86(m, 3H), 3.62(s, 3H), 3.68(s, 3H), 3.78-3.75(m, 2H), 4.05-3.97(m, 1H), 4.22-4.15(m, 2H), 5.33-5.30(d, J=8.82 Hz, 1H), 5.58-5.55(d, J=6.25 Hz, 1H), 6.15-6.12(d, J=7.35 Hz, 1H), 6.63-6.60(d, J=8.82 Hz, 1H), 7.24-7.16(m, 8H), 7.77-7.68(m, 2H), 7.89-7.86(d, J=8.46 Hz, 2H), 8.68-8.66(m, 1H).

EXAMPLE 154 methyl(1R,4S,5S,7S,10S)-4-benzyl-10-tert-butyl-5-hydroxy-1-[(methylsulfonyl)methyl]-2,9,12-trioxo-7-(4-pyridin-2-ylbenzyl)-13-oxa-3,8,11-triazatetradec-1-ylcarbamate A solution of Example 153B (20 mg, 0.028 mmol) in methanol (0.28 mL) and water (0.28 mL) was treated with oxone (52 mg, 0.082 mmol) at 25° C. for 1 h. The solvents were evaporated, and the residue was partitioned between ethyl acetate/water, the organic layer was separated, washed with brine, dried over MgSO$_4$, filtered, and the solvents were evaporated. The crude residue was purified by silica gel chromatography eluting with a gradient of dichloromethane, 100% ethyl acetate, to 95% ethyl acetate/5% methanol to give the title compound (9 mg, 43%). $^1$H NMR (300 MHz, MeOH-D6) δ ppm 0.86(s, 9H), 1.69-1.60(m, 2H), 2.70-2.63(m, 1H), 2.89-2.82(m, 3H), 2.93(s, 3H), 3.3-3.23(m, 1H), 3.45-3.39 (m, 1H), 3.53(s, 3H), 3.67(s, 3H), 3.77-3.73(t, J=6.62 Hz, 1H), 3.81(s, 1H), 4.27-4.22(m, 1H), 4.33(m, 1H), 4.63-4.59 (dd, J=8.09, 4.78 Hz, 1H), 7.19-7.12(m, 1H), 7.24-7.23(d, J=4.41 Hz, 4H), 7.30-7.27(d, J=8.09 Hz, 2H), 7.35-7.30(m, 1H), 7.80-7.78(d, J=8.09 Hz, 2H), 7.82(m, 1H), 7.87-7.84 (dd, J=6.99, 1.84 Hz, 1H), 8.58-8.57(d, J=4.04 Hz, 1H).

EXAMPLE 155 methyl(1R)-1-{[(((1S,2S,4S)-4-{[4-(aminosulfonyl)benzoyl]amino}-1-benzyl-2-hydroxy-5-phenylpentyl)amino]carbonyl}-2,2-dimethylpropylcarbamate A solution of benzenesulfonamide-4-carboxylic acid (0.1 g, 0.49 mmol) and Example 23S (0.22 g, 0.48 mmol) in tetrahydrofuran (8 mL) was treated with DEPBT (0.22 g, 0.73 mmol) and diisopropylethylamine (0.32 g, 2.4 mmol) at 25° C. The mixture was stirred for 16 h and partitioned between 10% sodium carbonate and dichloromethane. The organic layer was separated, dried over sodium sulfate, and the solvents were evaporated. The crude residue was purified by chromatography on silica gel eluting with 30% ethyl acetate in dichloromethane to give the title compound (0.17 g, 55% yield). $^1$H NMR (300 MHz, CDCl$_3$) δ ppm 0.85-0.95 (m, 9 H), 2.74-3.08 (m, 5 H), 3.60 (s, 3 H), 3.65-3.71 (m, 1 H), 3.78 (s, 2 H), 4.07 (s, 2 H), 4.31 (s, 1 H), 5.27 (d, J=8.82 Hz, 1 H), 6.29 (d, J=8.82 Hz, 1 H), 6.81 (d, J=7.35 Hz, 1 H), 7.09 (s, 1 H), 7.11-7.25 (m, 10 H), 7.64 (d, J=8.46 Hz, 2 H), 7.80 (d, J=8.46 Hz, 2 H).

EXAMPLE 156 methyl(1S)-1-({[(1S,3S,4S)-3-hydroxy-4-{[(2R)-2-hydroxy-3-methyl-3-(methylsulfonyl)butanoyl]amino}-5-phenyl-1-(4-pyridin-2-ylbenzyl)pentyl]amino}carbonyl)-2,2-dimethylpropylcarbamate

EXAMPLE 156A

N-[(9H-fluoren-9-ylmethoxy)carbonyl]-3-(methylthio)-L-valine

To a solution of L-penicillamine (0.60 g, 4.02 mmol) in mixture of water (20 mL) and dioxane (20.0 mL) at room temperature were added potassium carbonate (11.04 g, 79.9 mmol) and methyl iodide (0.31 mL, 4.98 mmol), and the mixture was stirred for 1 hour. 9-fluorenylmethyl succinimidyl carbonate (5.39 g, 16.0 mmol) was added, and the reaction was stirred at room temperature for 12 hours. The reaction was evaporated, and the residue was partitioned between ether and water, and the mixture was adjusted to pH 3 with 2 N HCl. The organic was washed with brine and dried over MgSO$_4$, filtered and evaporated. The residue was chromatographed on silica gel eluting with a gradient starting with dichloromethane and ending with 10% methanol in dichloromethane to give the product (2.13 g).

EXAMPLE 156B

N-[(9H-fluoren-9-ylmethoxy)carbonyl]-3-(methyl-sulfonyl)-L-valine

To a solution of the product from Example 156A (2.13 g) in mixture of water (11 mL) and acetone (5.5 mL) at room temperature were added sodium bicarbonate (3.7 g, 44.0 mmol) and sodium hydroxide solution (6.6 mL, 1 N). To this mixture was added a solution of oxone in water (4.75 g in 15 mL) dropwise at room temperature and the reaction was stirred for 2 hours. Ethyl acetate was added and the solution was adjusted to pH 3 with concentrated HCl. The organic was washed with brine and dried over $MgSO_4$, filtered and evaporated. The residue was chromatographed on silica gel eluting with a gradient starting with dichloromethane and ending with 20% methanol in dichloromethane to give the product (0.70 g, 42% over 2 steps).

EXAMPLE 156C (2R)-2-hydroxy-3-methyl-3-(methylsulfonyl)butanoic acid

To a solution of the product from Example 156B (0.35 g, 0.838 mmol) in N,N-dimethylformamide (3.0 mL) was added piperidine (0.17 mL, 1.72 mmol), and this mixture was stirred at room temperature for 1 hour. The reaction mixture was partitioned between dichloromethane and water. The isolated organic layer was washed with brine and dried over $MgSO_4$, filtered and evaporated. The residue dissolved in water (1.0 mL) and concentrated sulfuric acid (0.10 mL) was added at room temperature, followed by heating to 50° C. A solution of sodium nitrite (0.25 g) in water (0.60 mL) was added dropwise at 50° C. and the reaction was stirred for 1 hour. The reaction was extracted with ethyl acetate and washed with water and brine. The organic was dried over $MgSO_4$, filtered and evaporated to give the crude product (0.041 g, 25% yield), which was used without further purification.

EXAMPLE 156D methyl(1S)-1-({[(1S,3S,4S)-3-hydroxy-4-{[(2R)-2-hydroxy-3-(methylsulfonyl)butanoyl]amino}-5-phenyl-1-(4-pyridin-2-ylbenzyl)pentyl]amino}carbonyl)-2,2-dimethylpropylcarbamate To a solution containing the product from Example 2C (0.020 g, 0.038 mmol) in tetrahydrofuran (0.40 mL) were added the product from Example 156C (0.008 g, 0.041 mmol), DEPBT (0.015 g, 0.050 mmol), and N,N-diisopropylethylamine (0.020 mL, 0.115 mmol) and the mixture was stirred at room temperature for 1 hour. The mixture was partitioned between ethyl acetate and 10% $Na_2CO_3$ solution. The organic was washed with additional 10% $Na_2CO_3$ solution and then brine, dried over $MgSO_4$, filtered and evaporated. The residue was chromatographed on silica gel eluting with a gradient starting with dichloromethane and ending with 50% acetone in dichloromethane to give the product (0.015 g, 56% yield). $^1$H NMR (300 MHz, DMSO-$d_6$), δ ppm 0.81 (s, 9 H), 0.97 (s, 3 H), 1.01 (s, 3 H), 1.49-1.53 (m, 2 H), 2.53-2.60 (m, 1 H), 2.76-2.81 (m, 3 H), 2.93 (s, 3 H), 3.49 (s, 3 H), 3.64-3.70 (m, 3 H), 3.83 (d, J=9.9 Hz, 1 H), 4.21 (d, J=6.3 Hz, 1 H), 4.17-4.30 (m, 2 H), 4.98 (d, J=5.5 Hz, 1 H), 6.28 (d, J=6.3 Hz, 1 H), 6.67 (d, J=9.92 Hz, 1 H), 7.12-7.33 (m, 9 H), 7.52 (d, J=9.6 Hz, 1 H), 7.80-7.91 (m, 5 H), 8.64 (d, J=4.8 Hz, 1 H).

EXAMPLE 157 methyl(1S)-1-({[(1R,3S,4S)-4-[(4-chloro-2-methyl-benzoyl)amino]-3-hydroxy-5-phenyl-1-(4-pyridin-2-ylbenzyl)pentyl]amino}carbonyl)-2,2-dimethylpropylcarbamate A solution of 4-chloro-o-toluic acid (8.4 mg, 0.47 mmol) in N,N-dimethylformamide (0.3 mL) was treated with Example 1H (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 μL, 0.09 mmol) at 25° C. for 16 h. The solvents were evaporated, and the crude residue purified by silica gel chromatography eluting with a gradient of dichloromethane, 100% ethyl acetate, and 95% ethyl acetate/5% methanol to give the title compound (24 mg, 75%). $^1$H NMR (300 MHz, CDCl$_3$) δ ppm 0.81(s, 9H), 1.45-1.38(m, 1H), 1.88-1.79(m, 1H), 2.18(s, 3H), 2.89-2.85(m, 2H), 2.98-2.96(m, 2H), 3.67(s, 3H), 3.74-3.60(m, 2H), 4.33-4.25(m, 1H), 4.47-4.36(m, 1H), 5.31-5.28(d, J=8.46 Hz, 1H), 5.96-5.93(d, J=8.82 Hz, 1H), 6.12-6.09(d, J=9.19 Hz, 1H), 7.02-6.94(m, 2H), 7.10(bs, 1H), 7.33-7.15(m, 8H), 7.71-7.68 (m, 1H), 7.86-7.81(m, 1H), 7.91-7.89(d, J=8.09 Hz, 2H), 8.76-8.74(d, J=4.04 Hz, 1H).

EXAMPLE 158 methyl(1S)-1-({[(1R,3S,4S)-3-hydroxy-4-[(4-methoxy-2-methylbenzoyl)amino]-5-phenyl-1-(4-pyridin-2-ylbenzyl)pentyl]amino}carbonyl)-2,2-dimethylpropylcarbamate A solution of 4-methoxy-2-methyl benzoic acid (8.2 mg, 0.49 mmol) in N,N-dimethylformamide (0.3 mL) was treated with Example 1H (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 μL, 0.09 mmol) at 25° C. for 16 h. The solvents were evaporated, and the crude residue purified by silica gel chromatography eluting with a gradient of dichloromethane, 100% ethyl acetate, and 95% ethyl acetate/5% methanol to give the title compound (25.8 mg, 80%). $^1$H NMR (300 MHz, CDCl$_3$) δ ppm 0.80(s, 9H), 1.46-1.38(m, 1H), 1.91-1.82(m, 1H), 2.27 (s, 3H), 2.91-2.77(m, 2H), 2.99-2.96(m, 2H), 3.74-3.59(m, 2H), 3.67(s, 3H), 3.73(s, 3H), 4.32-4.24(m, 1H), 4.44-4.37 (m, 1H), 4.50(m, 1H), 5.29-5.26(d, J=8.82 Hz, 1H), 5.96-5.93 (d, J=8.46 Hz, 1H), 6.13-6.10(d, J=9.19 Hz, 1H), 6.59-6.55 (dd, J=8.46, 2.57 Hz, 1H), 6.65(d, J=2.21 Hz, 1H), 7.08-7.06 (d, J=8.46 Hz, 1H), 7.25-7.14(m, 8H), 7.68-7.66(m, 1H), 7.77-7.72(m, 1H), 7.92-7.90(d, J=8.46 Hz, 2H), 8.70-8.68(d, J=4.04 Hz, 1H).

EXAMPLE 159 methyl(1S)-1-({[(1R,3S,4S)-3-hydroxy-4-[(2-methylbenzoyl)amino]-5-phenyl-1-(4-pyridin-2-ylbenzyl)pentyl]amino}carbonyl)-2,2-dimethylpropylcarbamate A solution of o-toluic acid (6.7 mg, 0.49 mmol) in N,N-dimethylformamide (0.3 mL) was treated with Example-1H (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 µL, 0.09 mmol) at 25° C. for 16 h. The solvents were evaporated, and the crude residue purified by silica gel chromatography eluting with a gradient of dichloromethane, 100% ethyl acetate, and 95% ethyl acetate/5% methanol to give the title compound (25 mg, 83%). $^1$H NMR (300MHz, CDCl$_3$) δ ppm 0.79(s, 9H), 1.47-1.39(m, 1H), 1.93-1.84(m, 1H), 2.25(s, 3H), 2.93-2.77(m, 2H), 3.00-2.97(dd, J=7.72, 2.94 Hz, 2H), 3.72-3.60(m, 2H), 3.66(s, 3H), 4.354.27(m, 1H), 4.45-4.39(m, 1H), 4.52(m, 1H), 5.28-5.26(d, J=8.46 Hz, 1H), 5.91-5.89(d, J=8.46 Hz, 1H), 6.16-6.13(d, J=9.56 Hz, 1H), 7.14-7.04(m, 3H), 7.25-7.18(m, 9H), 7.69-7.66(m, 1H), 7.78-7.72(m, 1H), 7.93-7.90 (d, J=8.09 Hz, 2H), 8.70-8.68(d, J=4.04 Hz, 1H).

EXAMPLE 160 methyl(1S)-1-({[(1R,3S,4S)-4-{[(2S)-3,3-dimethyl-2-(2-oxoimidazolidin-1-yl)butanoyl]amino}-3-hydroxy-5-phenyl-1-(4-pyridin-2-ylbenzyl)pentyl]amino}carbonyl)-2,2-dimethylpropylcarbamate

EXAMPLE 160A tert-butyl(2S)-3,3-dimethyl-2-(2-oxoimidazolidin-1-yl)butanoate To a solution containing the product from Example 6F (0.050 g, 0.22 mmol) in toluene (4.0 mL) was added bis(4-nitrophenyl)carbonate (0.080 g, 0.263 mmol), and the mixture was heated to 100° C. for 48 hours. The reaction was cooled, diluted with ethyl acetate, and washed three times with 10% Na$_2$CO$_3$. The organic was washed with brine and dried over MgSO$_4$, filtered and evaporated. The residue was chromatographed on silica gel eluting with a gradient starting with chloroform and ending with 50% ethyl acetate in chloroform to give the product (0.062 g).

EXAMPLE 160B (2S)-3,3-dimethyl-2-(2-oxoimidazolidin-1-yl)butanoic acid

To a solution containing the product from Example 160A (0.050 g, 0.195 mmol) in dichloromethane (1.0 mL) was added trifluoracetic acid (1.0 mL), and the mixture was stirred at room temperature for 2 hours. The solvent was evaporated and the residue was triturated with ether to give a white solid, which was collected by filtration and used without further purification.

EXAMPLE 160C methyl(1S)-1-({[(1R,3S,4S)-4-{[(2S)-3,3-dimethyl-2-(2-oxoimidazolidin-1-yl)butanoyl]amino}-3-hydroxy-5-phenyl-1-(4-pyridin-2-ylbenzyl)pentyl]amino}carbonyl)-2,2-dimethylpropylcarbamate A solution of the product of Example 1H (0.020 g, 0.038 mmol) in tetrahydrofuran (0.40 mL) was treated with the product from Example 160B (0.0075 g, 0.038 mmol), DEPBT (0.017 g, 0.057 mmol), and N,N-diisopropylethylamine (0.035 mL, 0.201 mmol), stirred at 25° C. for 12 hours and partitioned between ethyl acetate and 10% Na$_2$CO$_3$ solution. The organic layer was washed with additional 10% Na$_2$CO$_3$ solution and brine, dried over MgSO$_4$, filtered and concentrated. The residue was chromatographed on silica gel eluting with a gradient starting with dichloromethane and ending with 50% acetone in dichloromethane to give the title compound (0.020 g, 74% yield). $^1$H NMR (300 MHz, DMSO-d$_6$), δ ppm 0.80 (s, 9 H), 0.86 (s, 9 H), 1.33-1.56 (m, 2 H), 2.55-2.72 (m, 4 H), 2.82 (dd, J=5.9, 12.9 Hz, 1 H), 2.89-2.56 (m, 1 H), 3.08 (q, J=8.8 Hz, 1 H), 3.24-3.28 (m, 1 H), 3.50-3.57 (m, 4 H), 3.83 (d, J=9.6 Hz, 1 H), 3.87-3.94 (m, 1 H), 3.97 (s, 1 H), 4.14-4.20 (m, 1H), 4.42 (d, J=7.4 Hz, 1 H), 6.29 (s, 1 H), 6.88 (d, J=9.6 Hz, 1 H), 7.09-7.25 (m, 7 H), 7.30-7.34 (m, 1 H), 7.44 (d, J=9.6 Hz, 1 H), 7.83-7.97 (m, 5 H), 8.62 (m, 1 H).

EXAMPLE 161 methyl(1S)-1-({[(1R,3S,4S)-3-hydroxy-4-{[(2S,3S)-3-methyl-2-(2-oxoimidazolidin-1-yl)pentanoyl]amino}-5-phenyl-1-(4-pyridin-2-ylbenzyl)pentyl]amino}carbonyl)-2,2-dimethylpropylcarbamate

EXAMPLE 161A tert-butyl(2S,3S)-3-methyl-2-(2-oxoimidazolidin-1-yl)pentanoate To a solution containing the product from Example 3G (0.50 g, 2.08 mmol) in 1,2-dichloroethane (90.0 mL) was added bis(4nitrophenyl) carbonate (0.80 g, 2.63 mmol), and the mixture was heated to 70° C. for 12 hours. The reaction mixture was cooled and concentrated. The residue was dissolved in ethyl acetate, and washed with 10% Na$_2$CO$_3$ (3×), brine, dried over MgSO$_4$, filtered and concentrated. The residue was chromatographed on silica gel eluting with a gradient starting with dichloromethane and ending ethyl acetate to give the product (0.49 g, 88% yield).

EXAMPLE 161B (2S,3S)-3-methyl-2-(2-oxoimidazolidin-1-yl)pentanoic acid

To a solution containing the product from Example 161A (0.49 g, 1.91 mmol) in tetrahydrofuran (10.0 mL) was added aqueous HCl solution (5.0 mL, 4 N), and the mixture was stirred at 60° C. for 12 hours. The solvent was evaporated to give a white solid, which was used without further purification.

EXAMPLE 161C methyl(1S)-1-({[(1R,3S,4S)-3-hydroxy-4-{[(2S,3S)-3-methyl-2-(2-oxoimidazolidin-1-yl)pentanoyl]amino}-5-phenyl-1-(4-pyridin-2-ylbenzyl)pentyl]amino}carbonyl)-2,2-dimethylpropylcarbamate A solution of the product of Example 1H (0.020 g, 0.038 mmol) in tetrahydrofuran (0.40 mL) was treated with the product from Example 161B (0.0075 g, 0.038 mmol), DEPBT (0.017 g, 0.057 mmol), and N,N-diisopropylethylamine (0.035 mL, 0.201 mmol), stirred at 25° C. for 12 hours and partitioned between ethyl acetate and 10% Na$_2$CO$_3$ solution. The organic layer was washed with additional 10% Na$_2$CO$_3$ solution and brine, dried over MgSO$_4$, filtered and concentrated. The residue was chromatographed on silica gel eluting with a gradient starting with dichloromethane and ending with 50% acetone in dichloromethane to give the title compound (0.019 g, 71% yield). $^1$H NMR (300 MHz, DMSO-d$_6$), δ ppm 0.68 (d, J=6.6 Hz, 3 H), 0.75 (t, J=7.4 Hz, 3 H), 0.80 (s, 9 H), 0.85-0.96 (m, 1H), 1.24-1.35 (m, 2H), 1.48-1.56 (m, 1 H), 1.70-1.79 (m, 1 H), 2.54-2.72 (m, 3 H), 2.79-2.85 (m, 2H), 2.98-3.14 (m, 3H), 3.50-5.58 (m, 4 H), 3.77-3.91 (m, 3 H), 4.11-4.23 (m, 1H), 4.54 (d, J=7.4 Hz, 1 H), 6.31 (s, 1 H), 6.90 (d, J=9.6 Hz, 1 H), 7.09-7.26 (m, 8 H), 7.30-7.34 (m, 1 H), 7.80-7.97 (m, 5 H), 8.64 (m, 1 H).

EXAMPLE 162 methyl(1S)-1-{1[((1S,2S,4S)4-{[3-(aminosulfonyl)benzoyl]amino}-1-benzyl-2-hydroxy-5-phenylpentyl)amino]carbonyl}-2,2-dimethylpropylcarbamate A solution of benzenesulfonamide-3-carboxylic acid (0.05 g, 0.25 mmol) and Example 23S (0.11 g, 0.24 mmol) in tetrahydrofuran (4 mL) was treated with DEPBT (0.11 g, 0.37 mmol) and diisopropylethylamine (0.16 g, 1.2 mmol) at 25° C. The mixture was stirred for 16 h and partitioned between 10% sodium carbonate and dichloromethane. The organic layer was separated, dried over sodium sulfate, and the solvents were evaporated. The crude residue was purified by chromatography on silica gel eluting with 30% ethyl acetate in dichloromethane to give the title compound (0.09 g, 58% yield). $^1$H NMR (300 MHz, CDCl$_3$) δ ppm 1.68 (s, 9 H), 2.77-3.02 (m, 5 H), 3.54 (s, 3 H), 3.84 (d, J=8.82 Hz, 2 H), 4.00-4.17 (m, 2 H), 4.30-4.42 (m, 1 H), 5.30 (s, 1 H), 5.79 (s, 2 H), 6.57 (s, 1 H), 7.04 (s, 1 H), 7.09-7.23 (m, 10 H), 7.43 (t, J=7.72 Hz, 1 H), 7.73 (s, 1 H), 7.92 (d, J=7.35 Hz, 1 H), 8.19 (s, 1 H).

EXAMPLE 163 methyl(1S)-1-({[(1S,3S,4S)-4-[(3-chloro-2-methylbenzoyl)amino]-3-hydroxy-5-phenyl-1-(4-pyridin-2-ylbenzyl)pentyl]amino}carbonyl)-2,2-dimethylpropylcarbamate A solution of 3-chloro-2-methyl benzoic acid (8.4 mg, 0.49 mmol) in N,N-dimethylformamide (0.3 mL) was treated with Example 2C (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 uL, 0.09 mmol) at 25° C. for 16 h. The solvents were evaporated, and the crude residue purified by silica gel chromatography eluting with a gradient of dichloromethane, 100% ethyl acetate, and 95% ethyl acetate/5% methanol to give the title compound (17.7 mg, 55%). $^1$H NMR (300 MHz, CDCl$_3$) δ ppm 0.92(s, 9H), 1.89-1.72(m, 2H), 2.20(s, 3H), 2.98-2.80(m, 4H), 3.60(s, 3H), 3.79-3.74(m, 2H), 4.05(m, 1H), 4.28-4.20 (m, 2H), 5.29(m, 1H), 6.07-6.04(d, J=9.19 Hz, 1H), 6.22-6.20 (d, J=7.72 Hz, 1H), 6.88(m, 1H), 7.02-6.97(t, J=7.72 Hz, 1H), 7.32-7.16(m, 9H), 7.68-7.65(m, 1H), 7.77-7.71(m, 1H), 7.89-7.87(d, J=8.09 Hz, 2H), 8.68(m, 1H).

EXAMPLE 164 methyl(1S)-1-({[(1S,3S,4S)-3-hydroxy-4-[(3-hydroxy-2-methylbenzoyl)amino]-5-phenyl-1-(4-pyridin-2-ylbenzyl)pentyl]amino}carbonyl)-2,2-dimethylpropylcarbamate A solution of 3-hydroxy-2-methyl benzoic acid (7.5 mg, 0.49 mmol) in N,N-dimethylformamide (0.3 mL) was treated with Example 2C (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 μL, 0.09 mmol) at 25° C. for 16 h. The solvents were evaporated, and the crude residue purified by silica gel chromatography eluting with a gradient of dichloromethane, 100% ethyl acetate, and 95% ethyl acetate/5% methanol to give the title compound (24.8 mg, 79%). $^1$H NMR (300 MHz, CD$_3$OD) δ ppm 0.89(s, 9H), 1.86-1.77(m, 2H), 1.91(s, 3H), 2.77-2.70(m, 1H), 2.94-2.92(m, 3H), 3.53(s, 3H), 3.85(m, 2H), 4.53-4.48 (m, 2H), 6.48-6.45(d, J=6.62 Hz, 1H), 6.73-6.71(d, J=7.35 Hz, 1H), 6.90-6.85(t, J=7.72 Hz, 1H), 7.35-7.18(m, 8H), 7.80-7.75(m, 3H), 7.89-7.84(m, 1H), 8.57(m, 1H).

EXAMPLE 165 methyl(1S)-1-({[(1S,3S,4S)-3-hydroxy-4-{[(3-methylisoxazol-4-yl)carbonyl]amino}-5-phenyl-1-(4-pyridin-2-ylbenzyl)pentyl]amino}carbonyl)-2,2-dimethylpropylcarbamate A solution of 3-methyl-4-carboxyl isoxazole (6.3 mg, 0.49 mmol) in N,N-dimethylformamide (0.3 mL) was treated with Example 2C (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 μL, 0.09 mmol) at 25° C. for 16 h. The solvents were evaporated, and the crude residue purified by silica gel chromatography eluting with a gradient of dichloromethane, 100% ethyl acetate, and 95% ethyl acetate/5% methanol to give the title compound (24 mg, 80%). $^1$H NMR (300 MHz, CDCl$_3$-D6) δ ppm 0.89(s, 9H), 1.75-1.64(m, 2H), 2.39(s, 3H), 2.94-2.79(m, 4H), 3.60(s, 3H), 3.76-3.70(m, 2H), 4.21-4.07(m, 2H), 4.29 (d, J=4.78 Hz, 1H), 5.25-5.22(d, J=8.46 Hz, 1H), 6.16-6.13(d, J=7.72 Hz, 1H), 6.31-6.28(d, J=8.82 Hz, 1H), 7.25-7.15(m, 8H), 7.68-7.65(m, 1H), 7.78-7.73(m, 1H), 7.87-7.84(d, J=8.46 Hz, 2H), 8.60(s, 1H), 8.68-8.66(m, 1H).

EXAMPLE 166 methyl(1S)-1-({[(1S,3S,4S)-4-{[(3,5-dimethylisoxazol-4-yl)carbonyl]amino}-3-hydroxy-5-phenyl-1-(4-pyridin-2-ylbenzyl)pentyl]amino}carbonyl)-2,2-dimethylpropylcarbamate A solution of 3,5-dimethyl isoxazole 4-carboxylic acid (6.9 mg, 0.49 mmol) in N,N-dimethylformamide (0.3 mL) was treated with Example 2C (25 mg, 0.047 mmol), 1-hydroxybenzotriazole hydrate (HOBT) (7.6 mg, 0.056 mmol), 1-(3-dimethylaminopropyl)-3-ethylcarbodiimide hydrochloride (EDAC) (11 mg, 0.07 mmol), diisopropylethylamine (16.4 μL, 0.09 mmol) at 25° C. for 16 h. The solvents were evaporated, and the crude residue was purified by silica gel chromatography eluting with a gradient of dichloromethane, 100% ethyl acetate, and 95% ethyl acetate/5% methanol to give the title compound (13 mg, 42%). $^1$H NMR (300 MHz, CDCl$_3$) δ ppm 0.90(s, 9H), 1.77-1.63(m, 2H), 2.27(s, 3H), 2.45(s, 3H), 3.02-2.75(m, 4H), 3.60(s, 3H), 3.77-3.70(m, 2H), 4.20-4.11(m, 2H), 4.23-4.22(d, J=4.04 Hz, 1H), 5.25-5.22(d, J=8.82 Hz, 1H), 6.00-5.97(d, J=8.82 Hz, 1H), 6.13-6.11(d, J=6.99 Hz, 1H), 7.25-7.13(m, 8H), 7.68-7.66(m, 1H), 7.78-7.73(m, 1H), 7.87-7.84(d, J=8.09 Hz, 2H), 8.68(m, 1H).

EXAMPLE 167 methyl(1S,4S,5S,7S,10S)-4benzyl-10-tert-butyl-5-hydroxy-1-isobutyl-2,9,12-trioxo-7-(4-pyridin-2-ylbenzyl)-13-oxa-3,8,11-triazatetradec-1-ylcarbamate

EXAMPLE 167A $N^1$-[(1S,2S,4S)-1-benzyl-2-hydroxy-4-{[N-(methoxycarbonyl)-3-methyl-L-valyl]amino}-5-(4-pyridin-2-ylphenyl)pentyl]-$N^2$-[(benzyloxy)carbonyl]-L-leucinamide A solution of N-[(benzyloxy)carbonyl]-L-leucine (22 µL, 0.083 mmol) in N,N-dimethylformamide (0.4 mL) was treated with Example 2C (40 mg, 0.075 mmol), 1-hydroxybenzotriazole hydrate (HOBT) (12.2 mg, 0.09 mmol), 1-(3-dimethylaminopropyl)-3-ethylcarbodiimide hydrochloride (EDAC) (17.5 mg, 0.112 mmol), diisopropylethylamine (26 µL, 0.15 mmol) at 25° C. for 16 h. The solvents were evaporated, and the crude residue purified by silica gel chromatography eluting with a gradient starting with dichloromethane and ending with 100% ethyl acetate to give the title compound (45.6 mg, 78%).

EXAMPLE 167B $N^1$-[(1S,2S,4S)-1-benzyl-2-hydroxy-4-{[N-(methoxycarbonyl)-3-methyl-L-valyl]amino}-5-(4-pyridin-2-ylphenyl)pentyl]-L-leucinamide A solution of Example 167A (40 mg, 0.051 mmol) in ethyl acetate (0.25 mL) and methanol (0.25 mL) was treated with 1N HCl in dioxane, a hydrogen balloon, and 10% Pd/C (11 mg, 0.01 mmol) at 25° C. for 16h. The mixture was filtered, rinsed with methanol, and the solvents were evaporated to give the title compound (33 mg, 100%).

EXAMPLE 167C methyl(1S,4S,5S,7S,10S)-4benzyl-10-tert-butyl-5-hydroxy-1-isobutyl-2,9,12-trioxo-7-(4-pyridin-2-ylbenzyl)-13-oxa-3,8,11-triazatetradec-1-ylcarbamate A solution of Example 167B (11.2 mg, 0.017 mmol) in dichloromethane (0.25 mL) was treated with methyl chloroformate (2 µL, 0.026 mmol), and triethylamine (4.8 µL, 0.034 mmol) at 25° C. for 1 h. The solvents were evaporated, and the crude residue was purified by silica gel chromatography eluting with a gradient of dichloromethane, 100% ethyl acetate, and 95% ethyl acetate/7% methanol to give the title compound (7 mg, 57%). $^1$H NMR (300 MHz, $CDCl_3$) δ ppm 0.87-0.84(s, 15H), 1.34-1.29(m, 2H), 1.65-1.51(m, 3H), 2.67-2.60(m, 2H), 2.86-2.83(d, J=7.72 Hz, 2H), 2.95-2.87(m, 1H), 3.52(s, 3H), 3.65(s, 3H), 3.78-3.73(m, 1H), 3.81(s, 1H), 4.08-4.03(m, 1H), 4.24-4.19(m, 1H), 4.33(m, 1H), 7.17-7.12 (m, 1H), 7.26-7.20(m, H), 7.29-7.26(d, J=8.46 Hz, 2H), 7.35-7.30(m, 1H), 7.81-7.77(m, 3H), 7.90-7.84(m, 1H).

EXAMPLE 168 methyl(1S,4S,5S,7S,10S)-1-(2-amino-2-oxoethyl)-4-benzyl-10-tert-butyl-5-hydroxy-2,9,12-trioxo-7-(4-pyridin-2-ylbenzyl)-1 3-oxa-3,8,11-triazatetradec-1-ylcarbamate

EXAMPLE 168A $N^1$-[(1S,2S,4S)-1-benzyl-2-hydroxy-4-{[N-(methoxycarbonyl)-3-methyl-L-valyl]amino}-5-(4-pyridin-2-ylphenyl)pentyl]-$N^2$-[(9H-fluoren-9-ylmethoxy)carbonyl]-$N^4$-trityl-L-aspartamide A solution of $N^2$-[(9H-fluoren-9-ylmethoxy)carbonyl]-$N^4$-trityl-L-asparagine (47 µL, 0.079 mmol) in N,N-dimethylformamide (0.3 mL) was treated with Example 2C (40 mg, 0.075 mmol), 1-hydroxybenzotriazole hydrate (HOBT) (12.2 mg, 0.09 mmol), 1-(3-dimethylaminopropyl)-3-ethylcarbodiimide hydrochloride (EDAC) (17.5 mg, 0.112 mmol), diisopropylethylamine (26 µL, 0.15 mmol) at 25° C. for 16 h. The solvents were evaporated, and the crude residue purified by silica gel chromatography eluting with a gradient starting with dichloromethane and ending with 100% ethyl acetate to give the title compound (45 mg, 59%).

EXAMPLE 168B $N^1$-[(1S,2S,4S)-1-benzyl-2-hydroxy-4-{[N-(methoxycarbonyl)-3-methyl-L-valyl]amino}-5-(4-pyridin-2-ylphenyl)pentyl]-$N^4$-trityl-L-aspartamide A solution of Example 168A (45 mg, 0.04 mmol) in N,N-dimethylformamide (0.4 mL) was treated with piperidine (80 µL) at 25° C. for 16 h. The solvents were evaporated to give the crude title compound which was used directly in the next step.

EXAMPLE 168C $N^1$-[(1S,2S,4S)-1-benzyl-2-hydroxy-4-{[N-(methoxycarbonyl)-3-methyl-L-valyl]amino}-5-(4-pyridin-2-ylphenyl)pentyl]-$N^2$-(methoxycarbonyl)-$N^4$-trityl-L-aspartamide A solution of Example 168B (24 mg, 0.027 mmol) in dioxane (0.25 mL) was treated with methyl chloroformate (3.2 µL, 0.041 mmol) and triethylamine (7.5 µL, 0.054 mmol) at 25° C. for 0.5 h. The solvents were evaporated to give the crude title compound (27.7 mg, 100%).

EXAMPLE 168D methyl(1S,4S,5S,7S,10S)-1-(2-amino-2-oxoethyl)-4-benzyl-10-tert-butyl-5-hydroxy-2,9,12-trioxo-7-(4-pyridin-2-ylbenzyl)-13-oxa-3,8,11-triazatetradec-1-ylcarbamate A solution of Example 168C (27.7 mg, 0.027 mmol) in dichloromethane (0.5 mL) was treated with trifluoroacetic acid (0.25 mL) at 25° C. for 2 h. The solvents were evaporated, and the residue was dissolved in dichloromethane, washed with saturated sodium bicarbonate, dried over $MgSO_4$, filtered, and the solvents were evaporated. The crude residue was purified by silica gel chromatography eluting with a gradient of dichloromethane, 100% ethyl acetate, and 95% ethyl acetate/7% methanol to give the title compound (4 mg, 16%). ¹H NMR (300 MHz, DMSO-d₆) δ ppm 0.81(s, 9H), 1.53(m, 2H), 2.42-2.30(m, 2H), 2.64-2.60(m, 1H), 2.79-2.71(m, 4H), 3.50(s, 3H), 3.54(s, 3H), 3.61(m, 1H), 3.79(d, J=4.04 Hz, 1H), 4.03(m, 4.13(m, 1H), 4.27(m, 1H), 4.57(bs, 1H), 6.17(m, 1H), 6.84(m, 1H), 7.12(m, 1H), 7.21-7.19(m, 7H), 7.27(m, 1H), 7.48(d, J=7.81 Hz, 1H), 7.82(bs, 2H), 7.87-7.86(d, J=7.81 Hz, 2H), 8.62-8.61(d, J=4.39 Hz, 1H).

EXAMPLE 169 methyl 2-{[(1S,2S,4S)-1-benzyl-2-hydroxy-4-{[N-(methoxycarbonyl)-3-methyl-L-valyl]amino}-5-(4-pyridin-2-ylphenyl)pentyl]amino}-1-[(methoxycarbonyl)amino]-2-oxoethylcarbamate

EXAMPLE 169A bis[(methoxycarbonyl)amino]acetic acid

Methyl carbamate (1.0 g, 13.3 mmol) and glyoxylic acid monohydrate (0.63 g, 6.7 mmol) were combined in chloroform (7 mL). Naphthalene sulfonic acid (13 mg, 0.06 mmol) was added and the mixture was heated at reflux for 6 hours. The solution was then filtered and the white solid was collected and dried to yield 1.4 g, 51%:

EXAMPLE 169B methyl 2-{[(1S,2S,4S)-1-benzyl-2-hydroxy-4-{[N-(methoxycarbonyl)-3-methyl-L-valyl]amino}-5-(4-pyridin-2-ylphenyl)pentyl]amino}-1-[(methoxycarbonyl)amino]-2-oxoethylcarbamate The product from Example 169A (13.2 mg, 0.06 mmol) was dissolved in N,N-dimethylformamide (0.25 mL) and N-hydroxybenzotriazole (13 mg, 0.10 mmol) and 1-(3-dimethylaminopropyl)-3-ethylcarbodiimide (18.4 mg, 0.10 mmol) were added followed by the product from Example 2C (34.2 mg, 0.06 mmol). Triethylamine (9 uL, 0.06 mmol) was added and the mixture was stirred at ambient temperature for 18 hours. The solution was concentrated and the crude residue was purified on a 2 mm preparative silica gel TLC plate (5% CH₃OH/CHCl₃) to give an amorphous solid (38.4 mg, 83%). ¹H NMR (CDCl₁) δ 8.65 (d, 1H), 7.86 (d, 2H), 7.78-7.60 (m, 2H), 7.27-7.11 (m, 9H), 6.94-6.70 (br s, 1H), 6.36-6.24 (br s, 1H), 6.24-6.04 (br d, 1H), 6.02-5.84 (br d, 1H), 5.41-5.25 (m, 2H), 4.23-4.10 (m, 1H), 4.10-3.95 (q, 1H), 3.75 (d, 1H), 3.67 (s, 3H), 3.66 (s, 3H), 3.63 (s, 3H), 2.98-2.8 (m, 3H), 2.8-2.65 (m, 1H), 0.91 (s, 9H).

EXAMPLE 170 methyl(1S,4S,6S,7S,10S)-7-benzyl-1,10-di-tert-butyl-6-hydroxy-2,9,12,14-tetraoxo-4-(4-pyridin-2-ylbenzyl)-15-oxa-3,8,11,13-tetraazahexadec-1-ylcarbamate A solution of Example 58C (11.8 mg, 0.0183 mmol) in dioxane (0.2 mL) was treated with methyl isocyanoformate (2.2 μL, 0.027 mmol) and triethylamine (5.1 μL, 0.0365 mmol) at 25° C. for 1 h. The solvents were evaporated and the crude residue was purified by silica gel chromatography using dichloromethane to 100% ethyl acetate to 95% ethyl acetate/5% methanol to give the title compound (9 mg, 66%). ¹H NMR (300 MHz, CD₃OD) δ ppm 0.86(s, 9H), 0.92(s, 9H), 1.71-1.65(m, 2H), 2.67-2.60(m, 1H), 2.86-2.81(m, 2H), 2.98-2.92(m, 1H), 3.52(s, 3H), 3.76(s, 3H), 3.82-3.79(d, J=6.99 Hz, 2H), 4.08(m, 1H), 4.19(m, 1H), 4.33(m, 1H), 7.11-7.06 (m, 1H), 7.33-7.16(m, 6H), 7.73-7.70(d, J=9.19 Hz, 1H), 7.81-7.77(m, 3H), 7.90-7.84(m, 1H), 8.56(d, J=4.04 Hz, 1H).

EXAMPLE 171 methyl(1S,4S,6S,7S,10S)-7-benzyl-1,10-di-tert-butyl-6-hydroxy-14,14-dimethyl-2,9,12,15-tetraoxo-4-(4-pyridin-2-ylbenzyl)-13-oxa-3,8,11-triazahexadec-1-ylcarbamate A solution of Example 58C (11.2 mg, 0.0173 mmol) in dioxane (0.2 mL) was treated with 1-chlorocarbonyl-1-methyl ethyl acetate (3.8 μL, 0.0259 mmol) and triethylamine (4.8 uL, 0.0345 mmol) at 25° C. for 1 h. The solvents were evaporated, and the crude residue was purified by silica gel chromatography using dichloromethane to 100% ethyl acetate to 95% ethyl acetate/5% methanol to give the title compound (11 mg, 82%). ¹H NMR (300 MHz, CDCl₃) δ ppm 0.90(s, 9H), 0.92(s, 9H), 1.61(s, 3H), 1.67(s, 3H), 1.67-1.61 (m, 2H), 2.10(s, 3H), 2.96-2.77(m, 4H), 3.62(s, 3H), 3.60(m, 1H), 3.74(m, 2H), 4.02(m, 1H), 4.06-4.03(d, J=8.46 Hz, 1H), 4.24-4.17(m, 1H), 5.36-5.33(d, J=9.19 Hz, 1H), 6.16-6.14(d, J=7.72 Hz, 1H), 6.25-6.22(d, J=8.82 Hz, 1H), 6.43-6.41(d, J=8.09 Hz, 1H), 7.23-7.13(m, 8H), 7.77-7.68(m, 2H), 7.88-7.85(d, J=8.09 Hz, 2H), 8.68-8.66(d, J=4.78 Hz, 1H).

EXAMPLE 172

(4S,7S,8S,10S,13S)-7-benzyl-4,13-di-tert-butyl-8-hydroxy-2,5,12,15-tetraoxo-10-(4-pyridin-2-ylbenzyl)-16-oxa-3,6,11,14-tetraazaheptadec-1-yl acetate A solution of Example 58C (34 mg, 0.0526 mmol) in dioxane (0.2 mL) was treated with acetoxy acetyl chloride (8.5 μL, 0.079 mmol) and triethylamine (14.6 μL, 0.105 mmol) at 25° C. for 1 h. The solvents were evaporated, and the crude residue was purified by silica gel chromatography using dichloromethane to 100% ethyl acetate to 95% ethyl acetate/5% methanol to give the title compound (30 mg, 77%). ¹H NMR (300 MHz, CDCl₃) δ ppm 0.92(s, 18H), 1.66-1.61(m, 2H), 2.16(m, 1H), 2.17(s, 3H), 2.88-2.77(m, 4H), 3.62(s, 3H), 3.70-3.66(m, 1H), 3.78-3.75(d, J=8.82 Hz, 1H), 4.06-3.97(m, 1H), 4.22-4.19(m, 2H), 4.62-4.47(m, 2H), 5.43-5.40(d, J=9.19 Hz, 1H), 6.21-6.18(d, J=7.72 Hz, 1H), 6.40-6.37(d, J=9.19 Hz, 1H), 6.71-6.68(d, J=9.19 Hz, 1H), 7.24-7.13(m, 8H), 7.79-7.67(m, 2H), 7.86-7.83(m, 2H), 8.70 (m, 1H).

EXAMPLE 173 methyl(1S)-1-({[(1S,3S,4S)-4-{[(2S)-2-(glycoloylamino)-3,3-dimethylbutanoyl]amino}-3-hydroxy-5-phenyl-1-(4-pyridin-2-ylbenzyl)pentyl]amino}carbonyl)-2,2-dimethylpropylcarbamate A solution of Example 58C (22 mg, 0.029 mmol) in methanol (0.15 mL) and tetrahydrofuran (0.15 mL) was treated with potassium carbonate (12.2 mg, 0.082 mmol) at 25° C. for 1 h. The solvents were evaporated, and the crude residue was purified by silica gel chromatography eluting with a gradient of dichloromethane, 100% ethyl acetate, and 95% ethyl acetate/7% methanol to give the title compound (16 mg, 78%). ¹H NMR (300 MHz, CDCl₃) δ ppm 0.88(s, 9H), 0.93 (s, 9H), 1.56(m, 2H), 2.97-2.74(m, 4H), 3.58(m, 1H), 3.67(s, 3H), 3.94-3.78(m, 4H), 4.08(m, 1H), 4.22-4.19(d, J=9.56 Hz, 1H), 4.55-4.53(d, J=6.25 Hz, 1H), 5.44-5.41(d, J=9.19 Hz, 1H), 6.82-6.80(d, J=6.25 Hz, 1H), 7.30-7.11(m, 11H), 7.70-7.63(m, 3H), 7.81-7.75(m, 1H), 8.65-8.64(d, J=4.05 Hz, 1H).

EXAMPLE 174

(3S,6S,7S,9S,12S)-6-benzyl-3[(tert-butoxycarbonyl)amino]-12-tert-butyl-7-hydroxy-2,2-dimethyl-4,11,14trioxo-9-(4pyridin-2-ylbenzyl)-15-oxa-5,10,13-triazahexadec-1-yl acetate

EXAMPLE 174A (3R)-4,4dimethyl-2-oxotetrahydrofuran-3-yl trifluoromethanesulfonate To a solution containing R-(−)-pantolactone (12.0 g, 92.31 mmol) in dichloromethane (125.0 mL) was added pyridine (9.2 mL, 118.92 mmol), and the mixture was cooled to −78° C. and triflic anhydride (17.0 mL, 101.05 mmol) was added dropwise. The mixture was stirred at −78° C. for 30 minutes and then at room temperature for 1 hour. The reaction was evaporated and the residue was dissolved in ether, and washed with 5% KHSO$_4$. The organic was washed with brine and dried over MgSO$_4$, filtered and evaporated to give the crude product (23.71 g), which was used without further purification.

EXAMPLE 174B (3S)-3-azido-4,4-dimethyldihydrofuran-2(3H)-one

To a solution containing the product from Example 174A (4.6 g, 17.56 mmol) in toluene (80.0 mL) was added tetra-n-butylammonium azide (5.0 g, 17.57 mmol) at room temperature, and the mixture was stirred for 5 hours. The reaction was diluted with ether and washed with water, dilute NaHCO$_3$, 10% citric acid and brine. The organic layer was dried over MgSO$_4$, filtered and concentrated to give the crude product, which was used without further purification (2.79 g).

EXAMPLE 174C

Add Name

To a solution of the product of Example 174B (4.58 g, 29.55 mmol) in methanol (100.0 mL) was added 10% Pd on carbon (1.5 g), and the reaction was stirred under an atmosphere of hydrogen (balloon pressure) for 12 hours. The mixture was filtered through celite and the solvent was evaporated. The residue was dissolved in tetrahydrofuran (150.0 mL) and triethylamine (12.0 mL, 86.10 mmol) and di-tert-butyl dicarbonate (7.0 g, 32.07 mmol) were added and the mixture was stirred at room temperature for 12 hours. The solvent was evaporated and the residue was dissolved in ethyl acetate and the organic layer was washed with 10% citric acid, dilute NaHCO$_3$, and brine, dried over MgSO$_4$, filtered and concentrated. The residue was chromatographed on silica gel eluting with a gradient starting with dichloromethane and ending with 10% ethyl acetate in dichloromethane to give the title compound (4.2 g, 62% yield).

EXAMPLE 174D benzyl N-(tert-butoxycarbonyl)-4-hydroxy-3-methyl-L-valinate

To a solution of the product of Example 174C (0.20 g, 0.872 mmol) in dioxane (1.5 mL) was added a solution of potassium hydroxide (0.050 g, 0.891 mmol) in water (1.5 ml) at room temperature, and the mixture was stirred for 60 hours. The solvent was evaporated and toluene was added and evaporated twice to give a white solid. The solid was dissolved in N,N-dimethylformamide (4.0 mL) and benzyl bromide (0.10 mL, 0.841 mmol) was added and the mixture was stirred at room temperature for 12 hours. The reaction was extracted with ethyl acetate and the organic layer was washed with water and brine, dried over MgSO$_4$, filtered and concentrated. The residue was chromatographed on silica gel eluting with a gradient starting with hexanes and ending with 40% ethyl acetate in hexanes to give the title compound (0.196 g, 67% yield).

EXAMPLE 174E 4-(acetyloxy)-N-(tert-butoxycarbonyl)-3-methyl-L-valine

To a solution of the product of Example 174D (0.175 g, 0.519 mmol) in dichloromethane (5.0 mL) were added 4-(dimethylamino)pyridine (0.070 g, 0.573 mmol) and acetic anhydride (0.054 mL, 0.571 mmol) and the mixture was stirred at room temperature for 30 minutes. The reaction was extracted with ethyl acetate and the organic layer was washed with 10% citric acid, dilute NaHCO$_3$, and brine, dried over MgSO$_4$, filtered and concentrated. The residue was dissolved in a mixture of ethyl acetate (4.0 mL) and methanol (1.0 mL) and 20% Pd(OH)$_2$ on carbon (0.10 g) was added, and the reaction was stirred under an atmosphere of hydrogen (balloon pressure) for 1 hour. The mixture was filtered through celite and the solvent was evaporated to give the title compound (0.15 g), which was used without further purification.

EXAMPLE 174F (3S,6S,7S,9S,12S)-6-benzyl-3-[(tert-butoxycarbonyl)amino]-12-tert-butyl-7-hydroxy-2,2-dimethyl-4,11,14-trioxo-9-(4-pyridin-2-ylbenzyl)-15-oxa-5,10,13-triazahexadec-1-yl acetate To a solution of the product of Example 2C (0.275 g, 0.517 mmol) in tetrahydrofuran (0.40 mL) were added the product from Example 174E (0.15 g, 0.519 mmol), DEPBT (0.233 g, 0.779 mmol), and N,N-diisopropylethylamine (0.45 mL, 2.58 mmol), and the mixture was stirred at room temperature for 2 hours. The reaction was partitioned between ethyl acetate and 10% Na$_2$CO$_3$ solution. The organic layer was washed with additional 10% Na$_2$CO$_3$ solution and brine, dried over MgSO$_4$, filtered and concentrated. The residue was chromatographed on silica gel eluting with a gradient starting with dichloromethane and ending with ethyl acetate to give the title compound (0.214 g, 50% yield). $^1$H NMR (300 MHz, DMSO-d$_6$), δ ppm 0.80 (m, 15 H), 1.39 (s, 9 H), 1.47-1.56 (m, 2 H), 1.99 (s, 3 H), 2.72-2.79 (m, 3 H), 3.49 (s, 3 H), 3.62-3.65 (m, 2 H), 3.80-3.84 (m, 2 H), 4.05 (d, J=9.9 Hz, 1 H), 4.10-4.24 (m, 2 H), 4.94 (d, J=4.8 Hz, 1 H), 6.60-6.65 (m, 2 H), 7.10-7.21 (m, 8 H), 7.29-7.31 (m, 1 H), 7.52 (d, J=8.8 Hz, 1 H), 7.77 (d, J=8.5 Hz, 1 H), 7.82-7.89 (m, 4 H), 8.64 (m, 1 H).

EXAMPLE 175 methyl(1S,4S,5S,7S,10S)-4benzyl-10-tert-butyl-5-hydroxy-1-(2-hydroxy-1,1-dimethylethyl)-2,9,12-trioxo-7-(4-pyridin-2-ylbenzyl)-13-oxa-3,8,11-triazatetradec-1-ylcarbamate

EXAMPLE 175A $N^1$-[(1S,3S,4S)-4-({(2S)-2-[(tert-butoxycarbonyl)amino]-4-hydroxy-3,3-dimethylbutanoyl}amino)-3-hydroxy-5-phenyl-1-(4-pyridin-2-ylbenzyl)pentyl]-$N^2$-(methoxycarbonyl)-3-methyl-L-valinamide A solution of the product of Example 174F (0.020 g, 0.025 mmol) in a mixture of dioxane (0.250 mL) and water (0.100 mL) was added an aqueous solution of lithium hydroxide (0.028 mL, 1 N), and the mixture was stirred at room temperature for 1 hour. The reaction was diluted with ethyl acetate and washed with brine, dried over MgSO₄, filtered and concentrated to give the title compound, which was used without further purification.

EXAMPLE 175B methyl(1S,4S,5S,7S,10S)-4benzyl-10-tert-butyl-5-hydroxy-1-(2-hydroxy-1,1-dimethylethyl)-2,9,12-trioxo-7-(4-pyridin-2-ylbenzyl)-13-oxa-3,8,11-triazatetradec-1-ylcarbamate To a solution of the product of Example 175A (0.025 mmol) in dichloromethane (1.0 mL) was added trifluoroacetic acid (1.0 mL), and the mixture was stirred at room temperature for 1 hour. The solvent was evaporated, and the reaction mixture was partitioned between ethyl acetate and dilute NaHCO₃ solution. The organic layer was washed with brine, dried over MgSO₄, filtered and concentrated. The residue was dissolved in tetrahydrofuran (0.25 mL) and diisopropylethylamine (0.015 mL, 0.086 mmol) and methyl chloroformate (0.002 mL, 0.026 mmol) were added at room temperature. After 2 hours water was added and the reaction was extracted with ethyl acetate. The organic layer was washed with brine, dried over MgSO₄, filtered and concentrated. The residue was chromatographed on silica gel eluting with a gradient starting with dichloromethane and ending with ethyl acetate to give the title compound (0.006 g, 34% yield). $^1$H NMR (300 MHz, DMSO-$d_6$), δ ppm 0.76 (2s, 6 H), 0.79 (s, 9 H), 1.45-1.56 (m, 2 H), 2.71-2.80 (m, 3 H), 3.08 (dd, J=5.4, 10.9 Hz, 1 H), 3.18 (dd, J=5.4, 10.9 Hz, 1 H), 3.49 (s, 3 H), 3.55 (s, 3 H), 3.59-3.67 (m, 1 H), 3.81 (d, J=9.6 Hz, 1 H), 4.02 (d, J=9.2 Hz, 1 H), 4.04-4.21 (m, 2 H), 4.62 (m, 1 H), 4.90 (d, J=5.5 Hz, 1 H), 6.61 (d, J=9.6 Hz, 1 H), 6.92 (d, J=9.2 Hz, 1 H), 7.10-7.21 (m, 7 H), 7.29-7.31 (m, 1 H), 7.47 (d, J=8.8 Hz, 1 H), 7.78 (d, J=8.8 Hz, 1 H), 7.82-7.89 (m, 4 H), 8.64 (m, 1 H).

EXAMPLE 176 methyl(1S,4S,5S,7S,10)-1-{[(aminocarbonyl)amino]methyl}-4-benzyl-10-tert-butyl-5-hydroxy-2,9,12-trioxo-7-(4-pyridin-2-ylbenzyl)-13-oxa-3,8,11-triazatetradec-1-ylcarbamate

EXAMPLE 176A

3-[(aminocarbonyl)amino]-N-(methoxycarbonyl)-L-alanine

A solution of 2-amino-3-ureido-propionic acid (0.147 g, 1.0 mmol) in 1,4-dioxane (1.0 mL) and 1 N NaOH (3.6 mL) was treated with methyl chloroformate (0.153 mL, 2.0 mmol), stirred at 60° C. for 7 hours, and extracted with dichloromethane. The aqueous phase was acidified to pH 7 with 1 N HCl and evaporated to dryness. The resulting solid was trituated with 3:1 dichloromethane/isopropanol, filtered, and the filtrate was concentrated to yield a white solid (0.11 g, 53.6%) which was used for the next step without further purification.

EXAMPLE 176B methyl(1S,4S,5S,7S,10S)-1-{[(aminocarbonyl)amino]methyl}-4-benzyl-10-tert-butyl-5-hydroxy-2,9,12-trioxo-7-(4-pyridin-2-ylbenzyl)-13-oxa-3,8,11-triazatetradec-1-ylcarbamate A solution containing the product from Example 2C (0.025 g, 0.047 mmol) in tetrahydrofuran (0.5 mL) was treated with the product from Example 176A (0.014 g, 0.07 mmol), DEPBT (0.028 g, 0.094 mmol), and triethylamine (0.016 mL, 0.117 mmol), stirred at 25° C. for 7 hours, and partitioned between ethyl acetate and 10% NaHCO₃ solution. The organic phase was washed with additional 10% NaHCO₃ solution and brine, dried over MgSO₄, filtered and concentrated. The product was purified by chromatography on silica gel eluting with 7% methanol/dichloromethane to give the title compound (0.019 g, 55% yield). $^1$H NMR (300 MHz, DMSO-$d_6$) δ ppm 0.79 (s, 9H), 1.33-1.60 (m, 2H), 2.63-2.86 (m, 4H), 2.99-3.28 (m, 2H), 3.49 (s, 3H), 3.55 (s, 3H), 3.81 (d, J=9.56 Hz, 1H), 3.89-4.22 (m, 3H), 4.89 (d, J=6.62 Hz, 1H), 5.63 (s, 2H), 5.97 (s, 1H), 6.61 (d, 1H), 7.09-7.37 (m, 9H), 7.49 (d, J=9.19 Hz, 1H), 7.69-7.96 (m, 5H), 8.63 (d, J=4.41 Hz, 1H).

EXAMPLE 177 methyl(1S,4S,5S,7S,10S)-4benzyl-10-tert-butyl-5-hydroxy-2,9,12-trioxo-7-(4-pyridin-2-ylbenzyl)-1-(pyridin-2-ylmethyl)-13-oxa-3,8,11-triazatetradec-1-ylcarbamate

EXAMPLE 177A

N-(methoxycarbonyl)-3-pyridin-2-yl-L-alanine

A solution of 2-amino-3-pyridin-2-yl-propionic acid (0.168 g, 1.0 mmol) in 1,4-dioxane (1.0 mL) and 1 N NaOH (3.6 mL) was treated with methyl chloroformate (0.153 mL, 2.0 mmol), stirred at 60° C. for 7 hours, and extracted with dichloromethane. The aqueous phase was acidified to pH 7 with 1 N HCl and evaporated to dryness. The resulting solid was trituated with 3:1 dichloromethane/isopropanol, filtered, and the filtrate was concentrated to yield a yellow solid (0.146 g, 65%) which was used for the next step without further purification.

EXAMPLE 177B methyl(1S,4S,5S,7S,10S)-4benzyl-10-tert-butyl-5-hydroxy-2,9,12-trioxo-7-(4-pyridin-2-ylbenzyl)-1-(pyridin-2-ylmethyl)-13-oxa-3,8,11-triazatetradec-1-ylcarbamate A solution containing the product from Example 2C (0.025 g, 0.047 mmol) in tetrahydrofuran (0.5 mL) was treated with the product from Example 177B (0.016 g, 0.07 mmol), DEPBT (0.028 g, 0.094 mmol), and triethylamine (0.016 mL, 0.1 17 mmol), stirred at 25° C. for 7 hours, and partitioned between ethyl acetate and 10% NaHCO$_3$ solution. The organic phase was washed with additional 10% NaHCO$_3$ solution and brine, dried over MgSO$_4$, filtered and concentrated. The product was purified by chromatography on silica gel eluting with 7% methanol/dichloromethane to give the title compound (0.02 g, 58% yield). $^1$H NMR (300 MHz, DMSO-d$_6$) δ ppm 0.79 (s, 9H), 1.35-1.56 (m, 2H), 2.52-2.66 (m, 2H), 2.66-2.88 (m, 4H), 3.43 (s, 3H), 3.48 (s, 3H), 3.59-3.70 (m, 1H), 3.82 (d, J=9.93 Hz, 1H), 3.99-4.29 (m, 3H), 4.95 (d, J=5.52 Hz, 1H), 6.65 (d, J=10.66 Hz, 1H), 7.09-7.38 (m, 10H), 7.59 (d, J=7.72 Hz, 1H), 7.69 (d, J=9.19 Hz, 1H), 7.76-7.87 (m, 4H), 7.89 (d, J=8.46 Hz, 2H), 8.37 (d, J=4.78 Hz, 1H), 8.41 (s, 1H), 8.61 (d, J=4.78 Hz, 1H).

EXAMPLE 178 methyl(1S,4S,5S,7S,10S)-4benzyl-10-tert-butyl-5-hydroxy-2,9,12-trioxo-7-(4-pyridin-2-ylbenzyl)-1-(1,3-thiazol-4-ylmethyl)-13-oxa-3,8,11-triazatetradec-1-ylcarbamate

EXAMPLE 178A

N-(methoxycarbonyl)-3-(1,3-thiazol-4-yl)-L-alanine

A solution of 2-amino-3-thiazol-2-yl-propionic acid (0.172 g, 1.0 mmol) in 1,4dioxane (1.0 mL) and 1 N NaOH (3.6 mL) was treated with methyl chloroformate (0.153 mL, 2.0 mmol), stirred at 60° C. for 7 hours, and extracted with dichloromethane. The aqueous phase was acidified to pH 7 with 1 N HCl and evaporated to dryness. The resulting solid was triturated with 3:1 dichloromethane/isopropanol, filtered, and the filtrate was concentrated to yield a white solid (0.155 g, 67%) which was used for the next step without further purification.

EXAMPLE 178B methyl(1S,4S,5S,7S,10S)-4benzyl-10-tert-butyl-5-hydroxy-2,9,12-trioxo-7-(4-pyridin-2-ylbenzyl)-1-(1,3-thiazol-4-ylmethyl)-1 3-oxa-3,8,11-triazatetradec-1-ylcarbamate A solution containing the product from Example 2C (0.025 g, 0.047 mmol) in tetrahydrofuran (0.5 mL) was treated with the product from Example 178B (0.016 g, 0.07 mmol), DEPBT (0.028 g, 0.094 mmol), and triethylamine (0.016 mL, 0.117 mmol), stirred at 25° C. for 7 hours, and partitioned between ethyl acetate and 10% NaHCO$_3$ solution. The organic phase was washed with additional 10% NaHCO$_3$ solution and brine, dried over MgSO$_4$, filtered and concentrated. The product was purified by chromatography on silica gel eluting with 7% methanol/dichloromethane to give the title compound (0.019 g, 54% yield). $^1$H NMR (300 MHz, DMSO-d$_6$) δ ppm 0.79 (s, 9H), 1.32-1.56 (m, 2H), 2.64-2.77 (m, 3H), 2.78-3.04 (m, 2H), 3.49 (s, 6H,) 3.56-3.67 (m, 1H), 3.82 (d, J=10.30 Hz, 1H), 4.01-4.17 (m, 2H), 4.29-4.43 (m, 1H), 4.91 (d, J=5.52 Hz, 1H,) 6.65 (d, 1H), 7.07-7.41 (m, 11H), 7.55 (d, 1H), 7.73-7.94 (m, 6H), 8.62 (d, J=4.41 Hz, 1H), 8.99 (d, J=1.84 Hz, 1H).

EXAMPLE 179

(3S,6S,7S,9S,12S)-6-benzyl-12-tert-butyl-7-hydroxy-3-[(methoxycarbonyl)amino]-2,2-dimethyl-4,11,14-trioxo-9-(4-pyridin-2-ylbenzyl)-15-oxa-5,10,13-triazahexadec-1-yl acetate To a solution of the product of Example 174F (0.030 g, 0.037 mmol) in dioxane (0.50 mL) at 0° C. was added a solution of HCl in dioxane (3.0 mL, 4 N), and the mixture was stirred at room temperature for 1 hour. The solvent was evaporated, and the residue was dissolved in tetrahydrofuran (0.40 mL) and diisopropylethylamine (0.030 mL, 0.172 mmol) and methyl chloroformate (0.0032 mL, 0.041 mmol) were added at room temperature. After 1 hour water was added and the reaction was extracted with ethyl acetate. The organic layer was washed with brine, dried over MgSO$_4$, filtered and concentrated. The residue was chromatographed on silica gel eluting with a gradient starting with dichloromethane and ending with 50% acetone in dichloromethane to give the title compound (0.019 g, 67% yield). $^1$H NMR (300 MHz, DMSO-d$_6$), δ ppm 0.80-0.82 (m, 15 H), 1.41-1.58 (m, 2 H), 2.00 (s, 3 H), 2.54-2.57 (m, 1 H), 2.71-2.79 (m, 3 H), 3.49 (s, 3 H), 3.55 (s, 3 H), 3.61-3.73 (m, 2 H), 3.78-3.84 (m, 1 H), 4.03-4.24 (m, 3 H), 4.90 (d, J=5.5 Hz, 1 H), 6.62 (d, J=9.6 Hz, 1 H), 7.09 (d, J=9.6 Hz, 1 H), 7.10-7.21 (m, 7 H), 7.29-7.31 (m, 1 H), 7.57 (d, J=8.8 Hz, 1 H), 7.80 (d, J=9.9 Hz, 1 H), 7.85-7.89 (m, 4 H), 8.64 (m, 1 H).

EXAMPLE 180 methyl(1S,4R,6S,7S,10S)-7-benzyl-1,10-di-tert-butyl-6-hydroxy-15,15-dioxido-2,9-dioxido-4-(4-pyridin-2-ylbenzyl)-15-thia-3,8,11,14-tetraazahexadec-1-ylcarbamate

EXAMPLE 180A tert-butyl N-(2-{[(benzyloxy)carbonyl]amino}ethyl)-3-methyl-L-valinate To a solution containing the product from Example 6F (0.20 g, 0.870 mmol) in tetrahydrofuran (9.0 mL) were added triethylamine (0.120 mL, 0.861 mmol) and N-(benzyloxycarbonyloxy)succinimide (0.217 g, 0.871 mmol), and the mixture was stirred at room temperature for 12 hours. The reaction was diluted with ethyl acetate, and washed three times with 10% Na$_2$CO$_3$. The organic was washed with brine and dried over MgSO$_4$ filtered and evaporated to give the crude product, which was used without further purification.

EXAMPLE 180B

N-(2-{[(benzyloxy)carbonyl]amino}ethyl)-3-methyl-L-valine

The product from Example 180A (0.870 mmol) was dissolved in an HCl solution in dioxane (5.0 mL, 4 N), and the mixture was stirred at room temperature for 12 hours. The solvent was evaporated to afford the title compound as the hydrochloride salt. The residue was used without further purification.

EXAMPLE 180C

N¹-[(1R,3S,4S)-4-({(2S)-2-[(2-(benzyloxy)carbonylaminoethyl)amino]-3,3-dimethylbanoyl}amino)-3-hydroxy-5-phenyl-1-(4-pyridin-2-ylbenzyl)pentyl]-N²-(methoxycarbonyl)-3-methyl-L-valinamide A solution of the product of Example 1H (0.230 g, 0.432 mmol) in tetrahydrofuran (4.0 mL) was treated with the product from Example 180B (0.435 mmol), DEPBT (0.20 g, 0.669 mmol), and N,N-diisopropylethylamine (0.75 mL, 4.31 mmol), stirred at 25° C. for 12 hours and partitioned between ethyl acetate and 10% $Na_2CO_3$ solution. The organic layer was washed with additional 10% $Na_2CO_3$ solution and brine, dried over $MgSO_4$, filtered and concentrated. The residue was chromatographed on silica gel eluting with a gradient starting with dichloromethane and ending with ethyl acetate to give the title compound (0.203 g, 56% yield).

EXAMPLE 180D

N¹-[(1R,3S,4S)-4-({(2S)-2-[(2-aminoethyl)amino]-3,3-dimethylbanoyl}amino)-3-hydroxy-5-phenyl-1-(4-pyridin-2-ylbenzyl)pentyl]-N²-(methoxycarbonyl)-3-methyl-L-valinamide The product from Example 180C (0.200 g, 0.243 mmol) was dissolved in methanol (2.5 mL) and 20% $Pd(OH)_2$ on carbon (0.040 g) was added, and the reaction was stirred under an atmosphere of hydrogen (balloon pressure) for 1.5 hours. The mixture was filtered through celite and the solvent was evaporated to give the title compound, which was used without further purification.

EXAMPLE 180E methyl(1S,4R,6S,7S,10S)-7-benzyl-1,10-di-tert-butyl-6-hydroxy-15,15-dioxido-2,9-4-(4-pyridin-2-ylbenzyl)-15-thia-3,8,11,14-tetraazahexadec-1-ylcarbamate To a solution of the product of Example 180D (0.015 g, 0.022 mmol) in dichloromethane (0.20 mL) at room temperature were added diisopropylethylamine (0.011 mL, 0.063 mmol) and methanesulfonyl chloride (0.0019 mL, 0.025 mmol) at room temperature. After 2 hours water was added and the reaction was extracted with ethyl acetate. The organic layer was washed with brine, dried over $MgSO_4$, filtered and concentrated. The residue was chromatographed on silica gel eluting first with a gradient starting with dichloromethane and ending with ethyl acetate and then with 5% methanol in ethyl acetate to give the title compound (0.011 g, 66% yield). ¹H NMR (300 MHz, DMSO-$d_6$), δ ppm 0.76 (s, 9 H), 0.77 (s, 9 H), 1.17-1.38 (m, 2 H), 1.52-1.60 (m, 1 H), 2.04-2.16 (m, 1 H), 2.57-2.70 (m, 3 H), 2.75-2.88 (m, 7 H), 3.52-3.61 (m, 4), 3.81 (d, J=9.6 Hz, 1 H), 3.95-4.03 (m, 1 H), 4.11-4.21 (m, 1H), 4.93 (d, J=4.8 Hz, 1 H), 6.76 (t, J=5.9 Hz, 1 H), 6.87 (d, J=9.6 Hz, 1 H), 7.10-7.25 (m, 7 H), 7.30-7.34 (m, 1 H), 7.56 (d, J=9.2 Hz, 1 H), 7.83-7.96 (m, 5 H), 8.64 (m, 1 H).

EXAMPLE 181 methyl(1S,4R,6S,7S,10S)-7-benzyl-1,10-di-tert-butyl-6-hydroxy-2,9,15-trioxo-4-(4-pyridin-2-ylbenzyl)-16-oxa-3,8,11,14-tetraazaheptadec-1-ylcarbamate To a solution of the product of Example 180D (0.015 g, 0.022 mmol) in dichloromethane (0.20 mL) at room temperature were added diisopropylethylamine (0.011 mL, 0.063 mmol) and methyl chloroformate (0.002 mL, 0.026 mmol) at room temperature. After 2 hours water was added and the reaction was extracted with ethyl acetate. The organic layer was washed with brine, dried over $MgSO_4$, filtered and concentrated. The residue was chromatographed on silica gel eluting first with a gradient starting with dichloromethane and ending with ethyl acetate and then with 5% methanol in ethyl acetate to give the title compound (0.012 g, 74% yield). ¹H NMR (300 MHz, DMSO-$d_6$), δ ppm 0.75 (s, 18 H), 1.13-1.38 (m, 3 H), 1.52-1.62 (m, 1 H), 1.63-1.75 (m, 1 H), 1.96-2.14 (m, 1 H), 2.53-2.92 (m, 8 H), 3.51 (s, 3 H), 3.51-3.58 (m, 1 H), 3.56 (s, 3 H), 3.82 (d, J=9.9 Hz, 1 H), 3.94-4.02 (m, 1 H), 4.11-4.19 (m, 1H), 4.92 (d, J=4.8 Hz, 1 H), 6.63-6.89 (m, 2H), 7.08-7.24 (m, 8 H), 7.30-7.34 (m, 1 H), 7.54 (d, J=9.2 Hz, 1 H), 7.83-7.96 (m, 5 H), 8.64 (m, 1 H).

EXAMPLE 182 methyl(1S)-1-({[(1R,3S,4S)-4-{[(2S)-2-(1,1-dioxido-1,2,5-thiadiazolidin-2-yl)-3,3-dimethylbutanoyl]amino}-3-hydroxy-5-phenyl-1-(4-pyridin-2-ylbenzyl)pentyl]amino}carbonyl-2,2-dimethylpropylcarbamate To a solution of the product of Example 180D (0.112 g, 0.163 mmol) in dichloromethane (1.60 mL) at 0° C. were added diisopropylethylamine (0.14 mL, 0.80 mmol) and a solution of sulfuryl chloride in dichloromethane (0.20 mL, 1 N), and the solution was allowed to warm to room temperature. After 1 hour water was added and the reaction was extracted with ethyl acetate. The organic layer was washed with brine, dried over $MgSO_4$, filtered and concentrated. The residue was chromatographed on silica gel eluting with a gradient starting with dichloromethane and ending with ethyl acetate to give the title compound (0.0093 g, 7.6% yield).

¹H NMR (300 MHz, DMSO-$d_6$), δ ppm 0.74 (s, 9 H), 0.93 (s, 9 H), 1.13-1.33 (m, 3 H), 1.52-1.64 (m, 1 H), 2.58-2.69 (m, 2 H), 2.73-2.81 (m, 2 H), 2.87-2.97 (m, 1 H), 3.14-3.24 (m, 1 H), 3.37-3.42 (m, 1 H), 3.57 (s, 3 H), 3.67 (s, 1 H), 3.79 (d, J=9.6 Hz, 1 H), 3.843.92 (m, 1 H), 4.09-4.20 (m, 1H), 4.66 (d, J=6.6 Hz, 1 H), 6.85 (d, J=9.6 Hz, 1 H), 7.00 (t, J=6.6 Hz, 1 H), 7.11-7.26 (m, 7 H), 7.30-7.34 (m, 1 H), 7.52 (d, J=9.6 Hz, 1 H), 7.74 (d, J=8.5 Hz, 1 H), 7.83-7.96 (m, 4 H), 8.64 (m, 1 H).

EXAMPLE 183 methyl(5S,8S,10S,11S,14S)-1-benzyl-5-tert-butyl-10-hydroxy-14-[(methoxycarbonyl)amino]-15-methyl-3,6,13-trioxo-8-(4-pyridin-2-ylbenzyl)-2-oxa-4,7,12-triazahexadecan-16-oate

EXAMPLE 183A 1-tert-butyl 4-methyl N-[(9H-fluoren-9-ylmethoxy)carbonyl]-L-aspartate 1-tert-butyl 4-methyl N-[(9H-fluoren-9-ylmethoxy)carbonyl]-L-aspartate (516 mg, 1.25 mmol) was dissolved in tetrahydrofuran (5 mL). The solution was cooled to 0° C. and (trimethylsilyl)-diazomethane (0.75 mL, 2M) was added. Methanol (550 µL, 13 mmol) was added dropwise and the solution was allowed to warm to ambient temperature over 1 hour. The solution was concentrated and placed under vacuum to afford the title compound as a colorless oil.

EXAMPLE 183B 1-tert-butyl 4-methyl N-(9-phenyl-9H-fluoren-9-yl)-L-aspartate

Example 183A (1.25 mmol) was dissolved in acetonitrile (8 mL) and diethylamine (0.39 mL, 3.8 mmol) was added and the solution was stirred at ambient temperature for 3 hours. The solution was concentrated and purified by column chromatography on silica gel (20-100% ethyl acetate/hexane) to give a colorless oil (176 mg, 69%). To all of this material (176 mg, 0.9 mmol) was added dichloromethane (2 mL) and the solution was treated with triethylamine (253 uL, 1.8 mmol) and stirred at ambient temperature for 15 minutes. Lead nitrate (192 mg, 0.6 mmol) was added, followed by a solution of 9-bromo-9-phenylfluorene (362 mg, 1.1 mmol) in dichloromethane (3 mL) and stirring was continued at ambient temperature for 4 hours. Methanol (8 mL) was added and stirring was continued for 30 minutes. The solution was filtered and the filtrate was concentrated to give a crude residue which was taken up in 1:1 5% citric acid/ether (10 mL). The aqueous layer was extracted with ether (3 times 5 mL), the organic extracts combined, washed with saturated brine solution (10 mL) and dried ($Na_2SO_4$). The solution was filtered and the filtrate concentrated to give a crude residue which was purified by column chromatography on silica gel (10% ethyl acetate/hexane) to yield a colorless oil (308 mg, 80%):

EXAMPLE 183C 1-tert-butyl 4-methyl 3-methyl-N-(9-phenyl-9H-fluoren-9-yl)-L-aspartate Potassium bis(trimethylsilyl)amide in toluene (1.6 mL, 0.5M) was added to tetrahydrofuran (3 mL) and cooled to −78° C. A solution of Example 183B (300 mg, 0.66 mmol) in tetrahydrofuran (2 mL) was added dropwise and stirring was continued at −78° C. for 20 minutes. Methyl iodide (102 uL, 1.64 mmol) was added and the solution was stirred at −78° C. for 3 hours. Potassium bis(trimethylsilyl)amide in toluene (1.6 mL, 0.5M) was added and the solution stirred for another 20 minutes at −78° C. Methyl iodide (102 uL, 1.64 mmol) was added and the solution was warmed to ambient temperature and stirred for 72 hours. To this solution was added 10 mL of saturated $NH_4Cl$ and 10 mL of $H_2O$. The resulting solution was extracted with ethyl acetate (3 times 20 mL), the organic extracts were combined, washed with saturated brine solution (20 mL) and dried ($Na_2SO_4$). The solution was filtered and the filtrate concentrated to yield a crude residue which was purified by column chromatography on silica gel (3% ethyl acetate/hexane) to give the title compound (79 mg, 25%).

EXAMPLE 183D methyl(5S,8S,10S,11S,14S)-11-benzyl-5-tert-butyl-10-hydroxy-14-[(methoxycarbonyl)amino]-15-methyl-3,6,13-trioxo-8-(4-pyridin-2-ylbenzyl)-2-oxa-4,7,12-triazahexadecan-16-oate Example 183C (50 mg, 0.11 mmol) was dissolved in dichloromethane (1 mL) and cooled to 0° C. Trifluoroacetic acid (1 mL) was added and the solution was stirred at 0° C. for 1 hour. The ice bath was removed and the solution was allowed to warm to ambient temperature over 3 hours. The solution was concentrated, toluene (5 mL) was added and the solution concentrated again. The residue was placed under vacuum for 2 hours, dissolved in dioxane (1 mL). To this solution was added sodium hydroxide (120 μL, 3N) and methyl chloroformate (17 μL, 0.22 mmol) and the solution was stirred and heated at 60° C. for 18 hours. The solution was cooled to ambient temperature and 4N HCl was added until the pH was acidic, then $H_2O$ (5 mL) was added and the solution was extracted with ethyl acetate (3 times 5 mL) and the extracts combined and dried ($Na_2SO_4$), filtered and the filtrate concentrated to yield a crude residue which was purified by column chromatography on silica gel (10% methanol/chloroform) to give a tan solid (25 mg, 100%). To this solid (25 mg, 0.11 mmol) was added N,N-dimethylformamide (1 mL) followed by N-hydroxybenzotriazole (23 mg, 0.17 mmol), 1-(3-dimethylaminopropyl)-3-ethylcarbodiimide (33 mg, 0.17 mmol), triethylamine (16 uL, 0.11 mmol) and the product from Example 2C (61 mg, 0.11 mmol). The solution was stirred at ambient temperature for 18 hours then $H_2O$ (5 mL) was added and the solution extracted with ether (3 times 5 mL). The organic extracts were combined and washed with saturated brine (5 mL), dried ($Na_2SO_4$), filtered and the filtrate concentrated to yield a crude product which was purified by column chromatography on silica gel (2% $CH_3OH$/$CHCl_3$) to yield a white solid (11 mg, 13%): $^1H$ NMR δ 8.73-8.61 (d, 1H), 7.89, 7.86 (d, 2H), 7.82-7.63 (m, 2H), 7.26-7.00 (m, 8H), 6.73, 6.70 (d, 1H), 6.18-5.99 (m, 1H), 5.88, 5.85 (d, 1H), 5.39-5.13 (br s, 1H), 4.43-4.29 (m, 1H), 4.21-4.01 (m, 1H), 3.94-3.81 (m, 1H), 3.81-3.71 (m, 1H), 3.69 (s, 3H), 3.66 (s, 3H), 3.62 (s, 3H), 3.37-3.19 (m, 1H), 3.00-2.63 (m, 3H), 1.26-1.17 (m, 3H), 0.92 (s, 9H).

EXAMPLE 184 methyl(5S,8S,10S,11S,14S)-11-benzyl-5-tert-butyl-10-hydroxy-14-[(methoxycarbonyl)amino]-15,15-dimethyl-3,6,13-trioxo-8-(4-pyridin-2-ylbenzyl)-2-oxa-4,7,12-triazahexadecan-16-oate

EXAMPLE 184A 1-tert-butyl 4-methyl 3,3-dimethyl-N-(9-phenyl-9H-fluoren-9-yl)-L-aspartate Potassium bis(trimethylsilyl)amide in toluene (1.6 mL, 0.5M) was added to tetrahydrofuran (3 mL) and cooled to −78° C. A solution of Example 183B (300 mg, 0.66 mmol) in tetrahydrofuran (2 mL) was added dropwise and stirring was continued at −78° C. for 20 minutes. Methyl iodide (102 uL, 1.64 mmol) was added and the solution was stirred at −78° C. for 3 hours. Potassium bis(trimethylsilyl)amide in toluene (1.6 mL, 0.5M) was added and the solution stirred for another 20 minutes at −78° C. Methyl iodide (102 uL, 1.64 mmol) was added and the solution was warmed to ambient temperature and stirred for 72 hours. To this solution was added 10 mL of saturated $NH_4Cl$ and 10 mL of $H_2O$. The resulting solution was extracted with ethyl acetate (3 times 20 mL), the organic extracts were combined, washed with saturated brine solution (20 mL) and dried ($Na_2SO_4$). The solution was filtered and the filtrate concentrated to yield a crude residue which was purified by column chromatography on silica gel (3% ethyl acetate/hexane) to give the title compound (125 mg, 39% yield):

EXAMPLE 184B methyl(5S,8S,10S,11S,14S)-11-benzyl-5-tert-butyl-10-hydroxy-14-[(methoxycarbonyl)amino]-15,15-dimethyl-3,6,13-trioxo-8-(4-pyridin-2-ylbenzyl)-2-oxa-4,7,12-triazahexadecan-16-oate Example 184A (50 mg, 0.11 mmol) was dissolved in dichloromethane (1 mL) and cooled to 0° C. Trifluoroacetic acid (1 mL) was added and the solution was stirred at 0° C. for 1 hour. The ice bath was removed and the solution was allowed to warm to ambient temperature over 3 hours. The solution was concentrated, toluene (5 mL) was added and the solution concentrated again. The residue was placed under vacuum for 2 hours, dissolved in dioxane (1 mL) and 10% sodium bicarbonate (0.25 mL). With stirring, di-tert-butyl dicarbonate (47 mg, 0.22 mmol) was added and the solution was stirred for 18 hours, the solution was concentrated and the residue distributed between ether (5 mL) and $H_2O$ (5 mL). Hydrochloric acid (0.25 mL, 0.5 M) was added and the aqueous layer was extracted with ether (3 times 5 mL), the organic extracts combined and washed with $H_2O$ (10 mL), dried ($Na_2SO_4$), filtered and the filtrate concentrated. The residue was purified by column chromatography on silica gel (10% $CH_3OH/CHCl_3$) to yield a tan solid (21 mg, 72%) which was dissolved in N,N-dimethylformamide (0.5 mL) and N-hydroxybenzotriazole (16 mg, 0.11 mmol), 1-(3-dimethylaminopropyl)-3-ethylcarbodiimide (22 mg, 0.11 mmol), triethylamine (11 uL, 0.08 mmol) and the product from Example 2C (41 mg, 0.08 mmol) were added. The solution was stirred at ambient temperature for 18 hours, $H_2O$ (5 mL) was added, and the solution extracted with ether (3 times 5 mL), the organic extracts combined, dried ($Na_2SO_4$), filtered and concentrated. The residue was purified by column chromatography on silica gel (2% $CH_3OH/CHCl_3$) to yield a white solid (21 mg, 35%) which was dissolved in tetrahydrofuiran (1 mL) and hydrochloric acid (1 mL, 4M). The solution was stirred at 60° C. for 3 hours, cooled to ambient temperature and concentrated. Dioxane (1 mL) was added followed by sodium hydroxide (29 uL, 3N) and methyl chloroformate (4 uL, 0.05 mmol) and the solution was stirred at 60° C. for 18 hours. The solution was cooled to ambient temperature and poured into 1:1 ethyl acetate/HCl (1 N) (5 mL) and extracted with ethyl acetate (3 times 5 mL), the organic extracts combined, dried ($Na_2SO_4$), filtered and the filtrate concentrated to yield a crude product which was purified by column chromatography on silica gel (2% $CH_3OH/CHCl_3$) to yield a white solid (10 mg, 50%): $^1H$ NMR δ 8.74-8.62 (d, 1H), 7.94-7.81 (d, 2H), 7.80-7.63 (m, 2H), 7.29-7.08 (m, 8H), 6.44-6.30 (d, 1H), 6.13-5.97 (d, 1H), 5.94-5.83 (d, 1H), 5.35-5.12 (br s, 1H), 4.28, 4.25 (d, 1H), 4.23-4.09 (m, 1H), 4.03-3.90 (m, 1H), 3.80-3.68 (m, 1H), 3.71 (s, 3H), 3.69 (s, 3H), 3.63 (s, 3H), 2.90-2.72 (m, 3H), 1.22 (s, 3H), 1.13 (s, 3H), 0.92 (s, 3H).

EXAMPLE 185 methyl(1S)-1-[({(1S,2S,4S)-1-benzyl-2-hydroxy-5-phenyl-4-[(thien-2-ylcarbonyl)amino]pentyl}amino)carbonyl]-2,2-dimethylpropylcarbamate A Smith Process Vial (2-5 mL) was charged with a stir bar and PS-Carbodiimide resin (108 mg, 0.12 mmol.). To the vessel were added thiophene-2-carboxylic acid (5.6 mg, 0.044 mmol.) d in 0.2 mL dimethyl acetamide, 1-hydroxybenzotriazole hydrate (5.4 mg, 0.04 mmol.) in 0.5 mL acetonitrile (acetonitrile), diisopropylethylamine (16.7 mg, 0.12 mmol.) in 0.5 mL acetonitrile and the product of Example 23S (19.6 mg, 0.04 mmol.) in 0.7 mL acetonitrile. The reaction vessel was sealed and heated to 100° C. for 300 seconds in an Ermys Optimizer. After cooling the reaction mixture was transferred to a pre-packed 1 g column of Si-Carbonate (>4 eq. of functionalized reagent), which had been previously conditioned with methanol. The reaction products were collected, and the solvents were evaporated. The crude residue was dissolved in 1:1 dimethyl sulfoxide/methanol and purified by reverse phase HPLC to give 8.7 mg (35%) of the title compound. $^1H$ NMR (500 MHz, DMSO-$d_6$) δ ppm 0.83 (s, 9 H), 1.55-1.76 (m, 2 H), 2.64-2.83 (m, 4 H), 3.55 (s, 3 H), 3.60 (t, J=6.26 Hz, 1 H), 3.88 (s, 1 H), 4.18 (d, J=7.63 Hz, 1 H), 4.29 (s, 1 H), 7.01-7.25 (m, 12 H), 7.54 (d, J=8.85 Hz, 1 H), 7.60 (d, J=3.66 Hz, 1 H), 7.66-7.68 (m, 1 H), 8.18 (d, J=8.85 Hz, 1 H).

EXAMPLE 186 methyl(1S)-1-[({(1S,2S,4S)-1-benzyl-2-hydroxy-5-phenyl-4-[(thien-3-ylcarbonyl)amino]pentyl}amino)carbonyl]-2,2-dimethylpropylcarbamate Using the same procedure as in Example 185, substituting thiophene-3-carboxylic acid in place of thiophene-2-carboxylic acid, gave 29% of the title compound. $^1H$ NMR (500 MHz, DMSO-$d_6$) δ ppm 0.83 (s, 9 H), 1.52-1.71 (m, 2 H), 2.64-2.83 (m, 4 H), 3.55 (s, 3 H), 3.60 (t, J=6.26 Hz, 1 H), 3.88 (s, 1 H), 4.19 (d, J=7.93 Hz, 1 H), 4.28 (s, 1 H), 7.06-7.24 (m, 12 H), 7.37 (dd, J=4.88, 1.22 Hz, 1 H), 7.51 (dd, J=5.03, 2.90 Hz, 1 H), 7.52-7.56 (m, 1 H), 7.94 (dd, J=3.05, 1.22 Hz, 1 H).

EXAMPLE 187 methyl(1S)-1-{[((1S,2S,4S)-1-benzyl-2-hydroxy-4-{[(3-methylthien-2-yl)carbonyl]amino}-5-phenyl-pentyl)amino]carbonyl}-2,2-dimethylpropylcarbamate Using the same procedure as in Example 185, substituting 3-methylthiophene-2-carboxylic acid in place of thiophene-2-carboxylic acid, gave 32% of the title compound. $^1H$ NMR (500 MHz, DMSO-$d_6$) δ ppm 0.84 (s, 9 H), 1.52-1.75 (m, 2 H), 2.18 (s, 3 H), 2.65-2.85 (m, 4 H), 3.56 (s, 3 H), 3.63 (t, J=6.10 Hz, 1 H), 3.88 (s, 1 H), 4.19 (s, 1 H), 4.30 (s, 1 H), 6.88 (d, J=4.88 Hz, 1 H), 7.08-7.27 (m, 11 H), 7.46 (d, J=4.88 Hz, 1 H), 7.56 (d, J=9.15 Hz, 1 H), 7.64 (d, J=8.54 Hz, 1 H).

EXAMPLE 188 methyl(1S)-1-{[((1S,2S,4S)-1-benzyl-2-hydroxy-4-{[(5-methylthien-2-yl)carbonyl]amino}-5-phenyl-pentyl)amino]carbonyl}-2,2-dimethylpropylcarbamate Using the same procedure as in Example 185, substituting 5-methylthiophene-2-carboxylic acid in place of thiophene-2-carboxylic acid, gave 32% of the title compound. $^1H$ NMR (500 MHz, DMSO-$d_6$) δ ppm 0.83 (s, 9 H), 1.52-1.73 (m, 2 H), 2.43 (s, 3 H), 2.62-2.85 (m, 4 H), 3.55 (s, 3 H), 3.60 (t, J=6.26 Hz, 1 H), 3.87 (s, 1 H), 4.18 (s, 1 H), 4.24 (s, 1 H), 6.78 (d, J=2.44 Hz, 1 H), 7.06-7.25 (m, 12 H), 7.40 (d, J=3.66 Hz, 1 H), 7.53 (d, J=8.85 Hz, 1 H).

EXAMPLE 189 methyl(1S)-1-{[(((1S,2S,4S)-1-benzyl-2-hydroxy-4-{[(1-methyl-1H-pyrrol-2-yl)carbonyl]amino}-5-phenylpentyl)amino]carbonyl}-2,2-dimethylpropylcarbamate Using the same procedure as in Example 185, substituting N-1-methylpyrrole-2-carboxylic acid in place of thiophene-2-carboxylic acid, gave 30% of the title compound. $^1$H NMR (500 MHz, DMSO-$d_6$) δ ppm 0.84 (s, 9 H), 1.52-1.72 (m, 2 H), 2.65-2.87 (m, 4 H), 3.55 (s, 3 H), 3.57-3.63 (m, 1 H), 3.70 (s, 3 H), 3.88 (s, 1 H), 4.14-4.32 (m, 2 H), 5.96 (dd, J=3.81, 2.59 Hz, 1 H), 6.57 (dd, J=3.97, 1.83 Hz, 1 H), 6.81 (t, J=1.98 Hz, 1 H), 7.03-7.26 (m, 12 H), 7.53 (d, J=9.15 Hz, 1 H).

EXAMPLE 190 methyl(1S)-1-{[(((1S,2S,4S)-1-benzyl-4-{[(3,5-dimethylisoxazol-4-yl)carbonyl]amino}-2-hydroxy-5-phenylpentyl)amino]carbonyl}-2,2-dimethylpropylcarbamate Using the same procedure as in Example 185, substituting 3,5-dimethylisoxazole-4-carboxylic acid in place of thiophene-2-carboxylic acid, gave 37% of the title compound. $^1$H NMR (500 MHz, DMSO-$d_6$) δ ppm 0.85 (s, 9 H), 1.54-1.75 (m, 2 H), 1.99 (s, 3 H), 2.17 (s, 3 H), 2.57-2.64 (m, 1 H), 2.68-2.90 (m, 3 H), 3.56 (s, 3 H), 3.59-3.67 (m, 1 H), 3.90 (s, 1 H), 4.19 (d, J=7.02 Hz, 1 H), 4.34 (s, 1 H), 7.12 (t, J=7.02 Hz, 1 H), 7.14-7.30 (m, 10 H), 7.57 (d, J=9.15 Hz, 1 H), 7.80 (d, J=8.85 Hz, 1 H).

EXAMPLE 191 methyl(1S)-1-({[(1S,3S,4S)-4-{[(2S)-2-(3-benzyl-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate

EXAMPLE 191A dibenzyl(1S,3S)-1-((1S)-1-{[(2S)-2-(3-benzyl-2-oxoimidazolidin-1-yl)-3,3-dimethylbutanoyl]amino}-2-phenylethyl)-3-{[N-(methoxycarbonyl)-3-methyl-L-valyl]amino}-4-(4-pyridin-2-ylphenyl)butyl phosphate A solution of the compound of Example 111 (0.100 g, 0.124 mmol), dibenzyl diethylphosphoramidite (0.088 mL, 294 mmol), and 1H-tetrazole (0.045 g, 0.642 mmol) in tetrahydrofuran (1.2 mL) was stirred at room temperature for 12 hours. Dichloromethane (1.2 mL) was added and the mixture was cooled to −45° C., followed by addition of m-chloroperbenzoic acid (0.075 g, 0.434 mmol). After stirring for 30 minutes at −45° C., the reaction was diluted with ethyl acetate and washed twice with 10% Na$_2$CO$_3$ and then with brine. The organic phase was dried over MgSO$_4$, filtered and evaporated. The residue was purified by chromatography on silica gel, eluting with a gradient starting with dichloromethane and ending with ethyl acetate, to give the title compound (0.104 g, 80% yield).

EXAMPLE 191B methyl(1S)-1-({[(1S,3S,4S)-4-{[(2S)-2-(3-benzyl-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate To a solution of the product from Example 191A (0.100 g, 0.094 mmol) in a mixture of ethyl acetate (1.0 mL) and methanol (1.0 mL) were added a solution of HCl in dioxane (0.006 mL, 4 N) and Pd(OH)$_2$ on carbon (0.027 g, 20% by wt. Pd), and the mixture was stirred under an atmosphere of hydrogen (balloon pressure) for 30 minutes. The reaction was filtered through celite and the solvent was evaporated. Methanol and water were added and the pH was adjusted to 9 by addition of NaHCO$_3$ (0.030 g), and purified by chromatography using a C18 column, eluting with a gradient starting with water and ending with methanol, to give the title compound as a disodium salt (0.066 g, 76% yield). $^1$H NMR (300 MHz, MeOH-$d_4$), δ ppm 0.79 (s, 9 H), 1.01 (s, 9 H), 2.76-3.01 (m, 6 H), 3.13-3.19 (m, 1 H), 3.60 (s, 3 H), 3.99 (s, 1 H), 4.09 (s, 1 H), 4.29-4.47 (m, 2 H), 4.34 (s, 3 H), 6.94-7.01 (m, 3 H), 7.13-7.15 (m, 2 H), 7.27-7.39 (m, 8 H), 7.78-7.89, (m, 4 H), 8.55-8.57 (m, 1 H).

EXAMPLE 192 methyl(1S)-1-({[(1R,3S,4S)-4-{[(2S)-2-(3-{[6-(1-hydroxy-1-methylethyl)pyridin-2-yl]-methyl}-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate

EXAMPLE 192A dibenzyl(1S,3R)-1-((1S)-1-{[(2S)-2-(3-{[6-(1-hydroxy-1-methylethyl)pyridin-2-yl]methyl}-2-oxoimidazolidin-1-yl)-3,3-dimethylbutanoyl]amino}-2-phenylethyl)-3-{[N-(methoxycarbonyl)-3-methyl-L-valyl]amino}-4-(4-pyridin-2-ylphenyl)butyl phosphate A solution of the compound of Example 50 (0.100 g, 0.116 mmol), dibenzyl diethylphosphoramidite (0.080 mL, 267 mmol), and 1H-tetrazole (0.040 g, 0.571 mmol) in tetrahydrofuran (1.0 mL) was stirred at room temperature for 12 hours. Dichloromethane (1.0 mL) was added and the mixture was cooled to −45° C., followed by addition of m-chloroperbenzoic acid (0.072 g, 0.417 mmol). After stirring for 30 minutes at −45° C., the reaction was diluted with ethyl acetate and washed twice with 10% Na$_2$CO$_3$ and then with brine. The organic phase was dried over MgSO$_4$, filtered and evaporated. The residue was purified by chromatography on silica gel, eluting with a gradient starting with dichloromethane and ending with ethyl acetate, to give the title compound (0.104 g, 80% yield).

EXAMPLE 192B methyl(1S)-1-({[(1R,3S,4S)-4-{[(2S)-2-(3-{[6-(1-hydroxy-1-methylethyl)pyridin-2-yl]methyl}-2-oxoimidazolidin-1-yl)-3,3-dimethylbutanoyl]amino}-5-phenyl-3-(phosphonooxy)-1-(4-pyridin-2-ylbenzyl)pentyl]amino}carbonyl)-2,2-dimethylpropylcarbamate To a solution of the product from Example 192A (0.104 g, 0.093 mmol) in a mixture of ethyl acetate (0.5 mL) and methanol (0.5 mL) were added a solution of HCl in dioxane (0.046 mL, 4 N) and Pd(OH)$_2$ on carbon (0.020 g, 20% by wt. Pd), and the mixture was stirred under an atmosphere of hydrogen (balloon pressure) for 30 minutes. The reaction was filtered through celite and the solvent was evaporated. Methanol and water were added and the pH was adjusted to 9 by addition of NaHCO$_3$ (0.045 g), and purified by chromatography using a C18 column, eluting with a gradient starting with water and ending with methanol, to give the title compound as the disodium salt (0.059 g, 65% yield). $^1$H NMR (300 MHz, MeOH-d$_4$), δ ppm 0.88 (s, 9 H), 0.89 (s, 9 H), 1.52 (s, 3 H), 1.53 (s, 3 H), 1.65-1.74 (m, 1 H), 2.03-2.06 (m, 1 H), 2.31 (q, J=9.3 Hz, 1 H), 2.91-3.04 (m, 5 H), 3.18 (q, J=9.8 Hz, 1 H), 3.26-3.28 (m, 1 H), 3.64 (s, 3 H), 3.97 (s, 1 H), 4.06-4.08 (m, 1 H), 4.14 (s, 1 H), 4.39 (d, J=15.6 Hz, 1 H), 4.43-4.49 (m, 2 H), 4.57 (d, J=15.6 Hz, 1 H), 6.97-7.05 (m, 3 H), 7.16-7.21 (m, 3 H), 7.30-7.32 (m, 1 H), 7.37 (d, J=7.8 Hz, 2 H), 7.52 (d, J=7.3 Hz, 1 H), 7.75-7.88 (m, 5 H), 8.57 (m, 1 H).

EXAMPLE 193

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl) butyl (2S)-2-aminopropanoate

EXAMPLE 193A (1S,3S)-1-((1S)-1-{[(2S)-2-(3-benzyl-2-oxoimidazolidin-1-yl)-3,3-dimethylbutanoyl]amino}-2-phenylethyl)-3-{[N-(methoxycarbonyl)-3-methyl-L-valyl] amino}-4-(4-pyridin-2-ylphenyl)butyl N-(tert-butoxycarbonyl)-L-alaninate To a solution containing the compound of Example 111 (0.100 g, 0.124 mmol), N-(tert-butoxycarbonyl) L-alanine (0.028 g, 0.147 mmol)), and 4(dimethylamino)pyridine (0.018 g, 0.147 mmol) in N,N-dimethylformamide (1.0 mL) was added 1-(3-dimethylaminopropyl)-3-ethylcarbodiimide hydrochloride (EDAC) (0.029 g, 0.151 mmol) and the mixture was stirred at room temperature for 2 hours. Two subsequent additions of N-(tert-butoxycarbonyl) L-alanine (0.028 g) and 1-(3-dimethylaminopropyl)-3-ethylcarbodiimide hydrochloride (EDAC) (0.029 g) were made at two hour intervals. The solvent was evaporated and the reaction mixture was partitioned between ethyl acetate and aqueous NaHCO$_3$. The organic layer was washed with brine, dried over MgSO$_4$, filtered and evaporated. The residue was purified by chromatography on silica gel, eluting with a gradient starting with chloroform and ending with 66% ethyl acetate in chloroform, to give the title compound (0.100 g, 82%).

EXAMPLE 193B (1S,3 S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl) butyl (2S)-2-aminopropanoate To a solution of the product of Example 193A (0.098 g, 0.037 mmol) in dichloromethane (1.0 mL) at room temperature was added a solution of HCl in dioxane (0.13 mL, 4 N), and the mixture was stirred at room temperature for 3 hours. The solvent was evaporated to give the title compound as the bis hydrochloride salt (0.089 g). $^1$H NMR (300 MHz, DMSO-d$_6$), δ ppm 0.88 (s, 9 H), 0.91 (s, 9 H), 1.57 (d, J=7.4 Hz, 1 H), 1.69-1.74 (m, 2 H), 2.27 (q, J=9.6 Hz, 1 H), 2.53-2.56 (m, 2 H), 2.72-2.85 (m, 3 H), 2.94 (q, J=8.8 Hz, 1 H), 3.17-3.24 (m, 1 H), 3.46 (s, 3 ), 3.87 (d, J=9.9 Hz, 1 H), 4.14 (s, 1 H), 4.19-4.37 (m, 4 H), 4.31 (s, 2 H), 4.60-4.70 (m, 1 H), 5.14 (t, J=7.4 Hz, 1 H), 6.66 (d, J=9.6 Hz, 1 H), 7.00-7.08 (m, 3 H), 7.08-7.16 (m, 2 H), 7.26-7.47 (m, 8 H), 7.90-7.99 (m, 6 H), 8.46-8.57 (m, 3 H), 8.67-8.68 (m, 1 H).

EXAMPLE 194 methyl(1S)-1-({[(1R,3S,4S)-4)-{(2S)-3,3-dimethyl-2-[3-({6-[1-methyl-1-(phosphonooxy)ethyl]pyridin-2-yl}methyl)-2-oxoimidazolidin-1-yl] butanoyl}amino)-3-hydroxy-5-phenyl-1-(4-pyridin-2-ylbenzyl)pentyl]amino}carbonyl)-2,2-dimethylpropylcarbamate

EXAMPLE 194A tert-butyl(1S,3R)-1-((1S)-1-{[(2S)-2-(3-{[6-(1-hydroxy-1-methylethyl)pyridin-2-yl]methyl}-2-oxoimidazolidin-1-yl)-3,3-dimethylbutanoyl]amino}-2-phenylethyl)-3-{[N-(methoxycarbonyl)-3-methyl-L-valyl]amino}-4-(4-pyridin-2-ylphenyl)butyl carbonate To a solution of the product from Example 50 (1.0 g, 1.16 mmol) in tetrahydrofuran (11.0 mL) were added 4-(dimethylamino)pyridine, (0.155 g, 1.27 mmol) and di-tert-butyl dicarbonate (0.33 g, 1.51 mmol), and the mixture was stirred at room temperature for 12 hours. Ethyl acetate was added and the organic layer was washed with dilute NaHCO$_3$, and brine, dried over MgSO$_4$ filtered and concentrated to give the crude product, which was used without further purification.

EXAMPLE 194B (1S,3R)-1-((1S)-1-{[(2S)-2-(3-{[6-(1-{[bis(benzyloxy)phosphoryl]oxy}-1methylethyl)pyridin-2-yl] methyl}-2-oxoimidazolidin-1-yl)-3,3-dimethylbutanoyl]amino}-2-phenylethyl)-3-{[N-(methoxycarbonyl)-3-methyl-L-valyl]amino}-4-(4-pyridin-2-ylphenyl)butyl tert-butyl carbonate A solution of the compound of Example 194A (1.16 mmol), dibenzyl diethylphosphoramidite (1.25 mL, 4.17 mmol), and 1H-tetrazole (0.40 g, 5.71 mmol) in tetrahydrofuran (11.0 mL) was stirred at room temperature for 12 hours. Dichloromethane (11.0 mL) was added and the mixture was cooled to −45° C., followed by addition of m-chloroperbenzoic acid (1.15 g, 6.66 mmol). After stirring for 1 hour at −45° C., the reaction was diluted with ethyl acetate and washed twice with 10% Na$_2$CO$_3$ and then with brine. The organic phase was dried over MgSO$_4$, filtered and evaporated. The residue was purified by chromatography on silica gel, eluting with a gradient starting with dichloromethane and ending with 75% ethyl acetate in dichloromethane, to give the title compound (0.684 g, 48% yield over two steps).

EXAMPLE 194C methyl(1S)-1-({[(1R,3S,4S)-4-({(2S)-3,3-dimethyl-2-[3-({6-[1-methyl-1-(phosphonooxy)ethyl]pyridin-2-yl}methyl)-2-oxoimidazolidin-1-yl] butanoyl}amino)-3-hydroxy-5-phenyl-1-(4-pyridin-2-ylbenzyl)pentyl]amino}carbonyl)-2,2-dimethylpropylcarbamate To a solution of the product from Example 194B (0.684 g, 0.559 mmol) in dichloromethane (10.0 mL) was added trif luoroacetic acid (10.0 mL), and the mixture was stirred at room temperature for 4 hours, and the solvent was evaporated. Methanol and water were added and the pH was adjusted to 8 by addition of NaHCO$_3$, and the mixture was purified by chromatography using a C18 column, eluting with a gradient starting with water and ending with methanol, to give the title compound as the disodium salt (0.342 g, 62% yield). $^1$H NMR (300 MHz, MeOH-d$_4$), δ ppm 0.86 (s, 9 H), 0.90 (s, 9 H), 1.43-1.53 (m, 1 H), 1.66-1.75 (m, 1 H), 1.78 (s, 3 H), 1.81 (s, 3 H), 2.28-2.36 (m, 1 H), 2.68-3.06 (m, 5 H), 3.19 3.27 (m, 2 H), 3.66 (s, 3 H), 3.77 (d, J=10.3 Hz, 1 H), 3.88 (s, 1 H), 4.00 (s, 1 H), 4.04-4.08 (m, 1 H), 4.36 (d, J=15.4 Hz, 1 H), 4.41-4.51 (m, 1 H), 4.58 (d, J=15.4 Hz, 1 H), 7.07-7.16 (m, 6 H), 7.32-7.36 (m, 3 H), 7.69-7.91 (m, 5 H), 8.58 (m, 1 H).

EXAMPLE 195

(3S,5S,8S)-3-((1S)-1-{[(2S)-2-(3-benzyl-2-oxoimi-dazolidin-1-yl)-3,3-dimethylbutanoyl]-amino}-2-phenylethyl)-8-tert-butyl-7,10-dioxo-5-(4-pyridin-2-ylbenzyl)-2,11-dioxa-6,9-diazadodec-1-yl-(dimethylamino)acetate

EXAMPLE 195A

N$^1$-[(1S,3S,4S)-4-{[(2S)-2-(3-benzyl-2-oxoimidazolidin-1-yl)-3,3-dimethylbutanoyl]amino}-3-[(methylthio)methoxy]-5-phenyl-1-(4-pyridin-2-ylbenzyl)pentyl]-N$^2$-(methoxycarbonyl)-3-methyl-L-valinamide To a solution of the compound of Example 111 (1.4 g, 1.74 mmol) and methyl sulfide (3.2 mL, 43.3 mmol) in acetonitrile (18 mL) at 0° C. was added benzoyl peroxide (1.7 g), and the mixture was warmed to room temperature and stirred for 30 minutes. The reaction was cooled to 0° C. and benzoyl peroxide (1.7 g) was added, and the mixture was warmed to room temperature and stirred for 30 minutes. Water was added and the reaction was diluted with ethyl acetate and washed with 10% Na$_2$CO$_3$ and brine. The organic was dried over MgSO$_4$, filtered and evaporated. The residue was chromatographed on silica gel eluting with a gradient starting with dichloromethane and ending with ethyl acetate to give the title compound (1.24 g, 83% yield).

EXAMPLE 195B (3S,5S,8S)-3-((1S)-1-{[(2S)-2-(3-benzyl-2-oxoimidazolidin-1-yl)-3,3-dimethylbutanoyl]amino}-2-phenylethyl)-8-tert-butyl-7,10-dioxo-5-(4-pyridin-2-ylbenzyl)-2,11-dioxa-6,9-diazadodec-1-yl (dimethylamino)acetate To a solution of the product from Example 195A (0.045 g, 0.052 mmol) in 1,2-dichloromethane (1.5 mL) were added molecular sieves (4 Å, 0.24 g), N,N-dimethylglycine hydrochloride (0.075 g, 0.537 mmol), followed by N-iodosuccinimide (0.013 g, 0.058 mmol), and the mixture was stirred at room temperature for 2 hours. The reaction was filtered through celite. The filtrate was diluted with ethyl acetate and was washed with a mixture of dilute NaHCO$_3$ and Na$_2$S$_2$O$_3$, dried over MgSO$_4$, filtered and evaporated. The residue was dissolved in ether and 2 equivalents of 4 N HCl in dioxane were added. The crude product was purified by chromatography on silica gel eluting with a gradient starting with dichloromethane and ending with methanol to give the title compound as the bis hydrochloride salt (0.037 g, 77% yield). $^1$H NMR (300 MHz, DMSO-d$_6$), δ ppm 0.87 (s, 9 H), 0.88 (s, 9 H), 1.60-1.73 (m, 2 H), 2.22 (s, 6 H), 2.29 (q, J=9.6 Hz, 1 H), 2.54-2.84 (m, 6 H), 2.93 (q, J=8.8 Hz, 1 H), 3.08-3.24 (m, 4 H), 3.53 (s, 3 H), 3.72-3.76 (m, 1 H), 3.87 (d, J=9.6 Hz, 1 H), 4.11-4.35 (m, 5 H), 5.26 (d, J=6.6 Hz, 1 H), 5.37 (d, J=6.6 Hz, 1 H), 6.78 (d, J=9.6 Hz, 1 H), 6.94-7.15 (m, 5 H), 7.22-7.40 (m, 8 H), 7.82-7.95 (m, 6 H), 8.63 (m, 1 H).

EXAMPLE 196

(1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl(phosphonooxy)methyl carbonate

EXAMPLE 196A (1S,3S)-1-((1S)-1-{[(2S)-2-(3-benzyl-2-oxoimidazolidin-1-yl)-3,3-dimethylbutanoyl]amino}-2-phenylethyl) -3-{[N-(methoxycarbonyl)-3-methyl-L-valyl]amino}-4-(4-pyridin-2-ylphenyl)butyl chloromethyl carbonate To a solution of the product from Example 111 (0.050 g, 0.062 mmol) in pyridine (0.60 mL) at room temperature was added chloromethyl chloroformate (0.007 mL, 0.079 mmol), and the mixture was stirred for 30 minutes. Additional chloromethyl chloroformate (0.007 mL) was added and the reaction was stirred for 30 minutes. The reaction was diluted with ethyl acetate and washed with dilute NaHCO$_3$ and brine. The organic was dried over MgSO$_4$, filtered and evaporated to give the title compound (0.047 g, 84% yield), which was used without further purification.

EXAMPLE 196B (1S,3S)-1-((1S)-1-{[(2S)-2-(3-benzyl-2-oxoimidazolidin-1-yl)-3,3-dimethylbutanoyl]-amino}-2-phenylethyl) -3-{[N-(methoxycarbonyl)-3-methyl-L-valyl]amino}-4-(4-pyridin-2-ylphenyl)butyl{[bis(benzyloxy)phosphoryl]oxy}methyl carbonate To a solution of dibenzyl phosphate (0.175 g, 0.62 mmol) in methanol (6.0 mL) was added a solution of tetramethylammonium hydroxide in methanol (0.23 mL, 25%), and the solvent was evaporated. To this salt was added a solution of the product from Example 196A (0.047 g, 0.052 mmol) in N,N-dimethylformamide (0.60 mL) and the reaction was stirred at 50° C. for 5 hours. The reaction was diluted with ethyl acetate and washed with dilute NaHCO$_3$ and brine. The organic was dried over MgSO$_4$, filtered and evaporated. The compound was purified by chromatography on silica gel eluting with a gradient starting with chloroform and ending with 66% ethyl acetate in chloroform to give the title compound (0.022 g, 37% yield).

EXAMPLE 196C (1S,3S)-1-((1S)-1-{[(2S)-2-(3-benzyl-2-oxoimidazolidin-1-yl)-3,3-dimethylbutanoyl]amino}-2-phenylethyl)-3-({(2S)-2-[(methoxycarbonyl)amino]-3,3-dimethylbutanoyl}amino)-4-(4-pyridin-2-ylphenyl)butyl (phosphonooxy)methyl carbonate To a solution of the product from Example 196B (0.125 g, 0.110 mmol) in a mixture of ethyl acetate (1.0 mL) and methanol (1.0 mL) was added Pd(OH)$_2$ on carbon (0.10 g, 20% by wt. Pd), and the mixture was stirred under an atmosphere of hydrogen (balloon pressure) for 1 hour. The reaction was filtered through celite and the solvent was evaporated. The compound was purified by chromatography on silica gel, eluting with a gradient starting with 20% methanol in ethyl acetate and ending with 50% methanol in ethyl acetate, to give the title compound (0.078 g, 74% yield). $^1$H NMR (300 MHz, DMSO-d$_6$), δ ppm 0.86 (s, 9 H), 0.87 (s, 9 H), 1.73-1.78 (m, 2 H), 2.17 (q, J=9.2 Hz, 1 H), 2.58-2.83 (m, 5 H), 2.91 (q, J=8.8 Hz, 1 H), 3.09-3.17 (m, 2 H), 3.48 (s, 3 H), 3.86 (d, J=9.9 Hz, 1 H), 4.18 (s, 1 H), 4.20-4.31 (m, 1 H), 4.31 (s, 2 H), 4.46-4.55 (m, 1 H), 4.94 (t, J=7.0 Hz, 1 H), 5.49-5.59 (m, 2 H), 6.72 (d, J=9.9 Hz, 1 H), 6.97-7.06 (m, 3 H), 7.11-7.17 (m, 2 H), 7.23-7.40 (m, 9 H), 7.81-7.92 (m, 4 H), 8.01 (d, J=8.5 Hz, 1 H), 8.17 (d, J=9.6 Hz, 1 H), 8.63 (m, 1 H).

EXAMPLE 197

(5S,7S,10S)-5-((1S)-1-{[(2S)-2-(3-benzyl-2-oxoimidazolidin-1-yl)-3,3-dimethylbutanoyl]amino}-2-phenylethyl)-10-tert-butyl-3,9,12-trioxo-7-(4-pyridin-2-ylbenzyl)-2,4,13-trioxa-8,11-diazatetradec-1-yl(dimethylamino)acetate To a solution of the product from Example 196A (0.202 g, 0.22 mmol) in N,N-dimethylformamide (1.0 mL) were added N,N-dimethylglycine hydrochloride (0.156 g, 1.12 mmol), and N,N-diisopropylethylamine (0.58 mL, 3.33 mmol), and the reaction was stirred at room temperature for 68 hours. The reaction was diluted with ethyl acetate and washed with dilute NaHCO$_3$ and brine. The organic was dried over MgSO$_4$, filtered and evaporated. The compound was purified by chromatography on silica gel eluting with a gradient starting with 5% methanol in chloroform and ending with 50% methanol in chloroform to give the title compound (0.085 g, 40% yield). $^1$H NMR (300 MHz, DMSO-d$_6$), δ ppm 0.86 (s, 9 H), 0.89 (s, 9 H), 1.75-1.85 (m, 2 H), 2.24 (q, J=9.2 Hz, 1 H), 2.57-2.84 (m, 5 H), 2.93 (q, J=8.9 Hz, 1 H), 3.13-3.23 (m, 1 H), 3.18 (s, 3 H), 3.19 (s, 3 H), 3.49 (s, 3 H), 3.86 (d, J=9.6 Hz, 1 H), 4.17 (s, 1 ), 4.17-4.26 (m, 1 H), 4.31 (s, 2 H), 4.48-4.56 (m, 1 H), 4.94 (t, J=6.6 Hz, 1 H), 5.68 (s, 2 H), 6.71 (d, J=9.6 Hz, 1 H), 7.01-7.06 (m, 3 H), 7.14-7.17 (m, 2 H), 7.24-7.41 (m, 8 H), 7.82-7.93 (m, 4 H), 8.03 (d, J=8.5 Hz, 1 H), 8.17 (d, J=9.2 Hz, 1 H), 8.63 (m, 1 H).

EXAMPLE 198

(5S,8S,10S)-10-((1S)-1-{[(2S)-2-(3-benzyl-2-oxoimidazolidin-1-yl)-3,3-dimethylbutanoyl]amino}-2-phenylethyl)-5-tert-butyl-3,6,12-trioxo-8-(4-pyridin-2-ylbenzyl)-2,11-dioxa-4,7-diazapentadecan-15-oic acid A solution of Example 111 (60 mg, 0.074 mmol) in tetrahydrofuran (0.25 mL) and diethyl ether (0.5 mL) was treated with succinic anhydride (8.2 mg, 0.082 mmol) and dicyclohexylamine (16.3 μL, 0.082 mmol) at 25° C. for 6 h. Over the next 2 days more succinic anhydride (16.4 mg, 0.16 mmol) was added in portions. The mixture was partitioned between dichloromethane and 10% citric acid. The organic layer was separated, washed with brine, dried over MgSO$_4$, and the solvents were evaporated to give the title compound (66 mg, 98%). $^1$H NMR (300 MHz, DMSO-d$_6$) δ ppm 0.86(s, 9H), 0.89(s, 9H), 1.25(m, 1H), 1.66(m, 1H), 2.34-2.24(m, 1H), 2.83-2.55(m, 9H), 2.98-2.89(m, 1H), 3.22-2.12(m, 1H), 3.46(s, 3H), 3.86-3.83(d, J=9.93 Hz, 1H), 4.48-1.09(m, 6H), 5.15-5.10(m, 1H), 6.61-6.58(d, J=9.56 Hz, 1H), 7.05-7.00(m, 3H), 7.13-7.11(m, 2H), 7.31-7.25(m, 4H), 7.44-7.36(m, 3H), 7.92-7.87(m, 3H), 7.96(m, 2H), 8.06-8.02(d, J=9.56 Hz, 1H), 8.68-8.66(m, 1H).

EXAMPLE 199

(1S,3S)-1-((1S)-1-{[(2S)-2-(3-benzyl-2-oxoimidazolidin-1-yl)-3,3-dimethylbutanoyl]-amino}-2-phenylethyl)-3-({(2S)-2-[(methoxycarbonyl)amino]-3,3-dimethylbutanoyl}amino)-4-(4-pyridin-2-ylphenyl)butyl{[ethoxy(hydroxy)phosphoryl]oxy}methyl carbonate To a solution of ethyl phosphate (0.170 g, 1.35 mmol) in methanol (6.0 mL) was added a solution of tetramethylammonium hydroxide in methanol (0.50 mL, 25%), and the solvent was evaporated. To this salt was added a solution of the product from Example 196A (0.150 g, 0.167 mmol) in N,N-dimethylformamide (2.0 mL) and the reaction was stirred at 50° C. for 20 hours and then at 70° C. for 8 hours. The reaction was diluted with ethyl acetate and washed with water and brine. The organic was dried over MgSO$_4$, filtered and evaporated. Methanol and water were added and the pH was adjusted to 8 by addition of NaHCO$_3$, and the mixture was purified by chromatography using a C18 column, eluting with a gradient starting with water and ending with methanol, to give the title compound as a monosodium salt (0.035 g, 20% yield). $^1$H NMR (300 MHz, DMSO-d$_6$), δ ppm 0.85 (s, 9 H), 0.87 (s, 9 H), 1.10 (t, J=7.0 Hz, 3 H), 1.67-1.84 (m, 2 H), 2.24 (q, J=9.2 Hz, 1 H), 2.54-2.96 (m, 6 H), 3.11-3.19 (m, 1 H), 3.48 (s, 3 H), 3.69 (m, 2 H), 3.86 (d, J=9.6 Hz, 1 H), 4.20 (s, 1 H), 4.27 4.36 (s, 3 H), 4.44-4.51 (m, 1 H), 4.80-4.85 (m, 1 H), 5.37-5.51 (m, 2 H), 6.89 (d, J=9.9 Hz, 1 H), 7.00-7.02 (m, 3 H), 7.12-7.15 (m, 2 H), 7.23-7.40 (m, 8 H), 7.81-7.92 (m, 4 H), 8.13 (d, J=9.2 Hz, 1 H), 8.33 (d, J=9.2 Hz, 1 H), 8.63 (m, 1 H).

EXAMPLE 200 methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10-hydroxy-10-oxido-2-oxo-4-(4-pyridin-2-ylbenzyl)-7,9,11-trioxa-3-aza-10-phosphatridec-1-ylcarbamate To a solution of the product from Example 195A (0.050 g, 0.058 mmol) in 1,2-dichloromethane (1.0 mL) at 0° C. were added molecular sieves (4 Å, 0.200 g), ethyl phosphate (0.100 g, 0.794 mmol), followed by N-iodosuccinimide (0.016 g, 0.071 mmol), and the mixture was stirred at room temperature for 30 minutes. The reaction was filtered through celite. The filtrate was diluted with ethyl acetate and was washed with a mixture of dilute NaHCO$_3$ and Na$_2$S$_2$O$_3$, dried over MgSO$_4$, filtered and evaporated. Methanol and water were added and the pH was adjusted to 8 by addition of NaHCO$_3$, and the mixture was purified by chromatography using a C18 column, eluting with a gradient starting with water and ending with methanol, to give the title compound as the monosodium salt (0.040 g, 74% yield). $^1$H NMR (300 MHz, DMSO-d$_6$), δ ppm $^1$H NMR (300 MHz, DMSO-d$_6$), δ ppm 0.67 (s, 9 H), 0.92 (s, 9 H), 1.11 (t, J=7.0 Hz, 3 H), 1.47-1.60 (m, 1 H), 1.81-1.92 (m, 1 H), 2.26 (q, J=9.2 Hz, 1 H), 2.54-2.93 (m, 6 H), 3.07-3.13 (m, 1 H), 3.52 (s, 3 H), 3.67-3.76 (m, 1 H), 3.92-4.11 (m, 5 H), 4.28 (s, 2 H), 4.94-5.04 (m, 2 H), 6.98-

7.04 (m, 5 H), 7.23-7.38 (m, 8 H), 7.63 (d, J=9.2 Hz, 1 H), 7.81-7.92 (m, 4 H), 8.63 (m, 1 H).

EXAMPLE 201 methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10,10-dihydroxy-10-oxido-2-oxo-4-(4-pyridin-2-ylbenzyl)-7,9-dioxa-3-aza-10-phosphadec-1-ylcarbamate To a solution of the product from Example 195A (1.24 g, 1.43 mmol) in tetrahydrofuran (7.0 mL) at room temperature were added molecular sieves (4 Å, 3.5 g), a solution of phosphoric acid in N,N-dimethylformamide (14.0 mL, 0.5 M), and N-iodosuccinimide (0.650 g, 2.89 mmol), and the mixture was stirred at room temperature for 45 minutes. The reaction was diluted with methanol (250 mL) and filtered through celite. The filtrate was treated with $Na_2S_2O_3$ (saturated) and the pH was adjusted to 9 with 10% $Na_2CO_3$. The methanol was evaporated and the mixture was purified by chromatography using a C18 column, eluting with a gradient starting with water and ending with methanol, to give the title compound as the disodium salt (0.76 g, 55% yield). $^1$H NMR (300 MHz, MeOH-$d_4$), δ ppm 0.86 (s, 9 H), 0.95 (s, 9 H), 1.69-1.77 (m, 1H), 2.02-2.20 (m, 2 H), 3.73-3.02 (m, 6 H), 3.17-3.23 (m, 1 H), 3.56 (s, 3 H), 3.81-3.86 (m, 1 H), 3.96 (s, 1 H), 4.07 (s, 1 H), 4.35 (s, 2 H), 4.41-4.50 (m, 1 H), 5.06 (dd, J=9.0, 5.3 Hz, 1 H), 5.20 (dd, J=8.8, 5.5 Hz, 1 H), 6.95-7.03 (m, 3 H), 7.14-7.17 (m, 2 H), 7.27-7.39 (m, 8 H), 7.79-7.89, (m, 4 H), 8.56 (m, 1 H).

EXAMPLE 202 methyl(1S,4S,5S,7S,10S)-4-benzyl-1,10-bis(tert-butyl)-2,9,12-trioxo-5-(phosphonooxy)-7-(4-pyridin-2-ylbenzyl)-13-oxa-3,8,11-triazatetradec-1-ylcarbamate

EXAMPLE 202A methyl(1S,4S,5S,7S,10S)-4benzyl-1,10-bis(tert-butyl)-2,9,12-trioxo-5-{[bis(benzyloxy)phosphoryl]oxy}-7-(4-pyridin-2-ylbenzyl)-13-oxa-3,8,11-triazatetradec-1-ylcarbamate A solution of Example 2D (98.7 mg, 0.14 mmol) in tetrahydrofuran (1.4 mL) was treated with diethyl dibenyzlphosphoramidite (99 uL, 0.28 mmol) and tetrazole (49 mg, 0.7 mmol) at 25° C. for 16 h. The mixture was cooled to −45° C. and treated with m-chloroperbenzoic acid (70%, 87 mg, 0.35 mmol) and stirred for 1 h. The mixture was quenched with 10% sodium carbonate, warmed to 25° C., and the organic layer was separated, dried over $MgSO_4$, and the solvents were evaporated. The crude residue was purified by silica gel chromatography using dichloromethane to 100% ethyl acetate to give the title compound (110 mg, 81%).

EXAMPLE 202B methyl(1S,4S,5S,7S,10S)-4-benzyl-1,10-bis(tert-butyl)-2,9,12-trioxo-5-(phosphonooxy)-7-(4-pyridin-2-ylbenzyl)-13-oxa-3,8,11-triazatetradec-1-ylcarbamate A solution of Example 202A (105 mg, 0.109 mmol) in ethyl acetate (2 mL) and methanol (2 mL) was treated with a hydrogen balloon, 20% $Pd(OH)_2$ (8 mg, 0.011 mmol), and 4N HCl in dioxane (27 uL, 0.109 mmol) at 25° C. for 1 h. The mixture was filtered through Celite, rinsed with methanol, combined with water (1 mL) and treated with sodium bicarbonate (71 mg, 0.84 mmol). This mixture was purified using reverse phase chromatography on C18 column using 0-100% methanol/water to give the title compound as the disodium salt (80 mg, 89%). $^1$H NMR (300 MHz, $CD_3OD$) δ ppm 0.69(s, 9H), 0.99(s, 9H), 1.69(m, 1H), 2.10(m, 1H), 2.88-2.76 (m, 3H), 3.06-2.98(m, 1H), 3.62(s, 3H), 3.63(s, 3H), 3.90(s, 1H), 3.99(s, 1H), 4.32-4.19(m, 3H), 7.13-7.01(m, 3H), 7.21-7.19(m, 2H), 7.32-7.29(m, 3H), 7.88-7.76(m, 4H), 8.57(m, 1H).

849122 EXAMPLE 203 DAVID DEGOEY methyl(1S,4S,5S,7S,10S)-7-benzyl-1,10-bis(tert-butyl)-2,9,12-trioxo-5-[(phosphonooxy)methoxy]-4-(4-pyridin-2-ylbenzyl)-13-oxa-3,8,11-triazatetradec-1-ylcarbamate

EXAMPLE 203A methyl(1S)-1-({[(1S,3S,4S)-1-benzyl-4-{[N-(methoxycarbonyl)-3-methyl-L-valyl]amino}-3-[(methylthio)methoxy]-5-(4-pyridin-2-ylphenyl)pentyl]amino}carbonyl)-2,2-dimethylpropylcarbamate To a solution of the compound of Example 25 (0.125 g, 0.178 mmol) and methyl sulfide (0.405 mL, 5.48 mmol) in acetonitrile (0.75 mL) at 0° C. was added benzoyl peroxide (0.63 g, 2.60 mmol), and the mixture was stirred at 0° C. for 1 hour. The reaction was diluted with ethyl acetate and washed with 10% $Na_2CO_3$ and brine. The organic was dried over $MgSO_4$, filtered and evaporated. The residue was chromatographed on silica gel eluting with a gradient starting with dichloromethane and ending with ethyl acetate to give the title compound (0.104 g, 77% yield).

EXAMPLE 203B methyl(1S,4S,5S,7S,10S)-7-benzyl-1,10-bis(tert-butyl)-2,9,12-trioxo-5-[(phosphonooxy)methoxy]-4-(4-pyridin-2-ylbenzyl)-13-oxa-3,8,11-triazatetradec-1-ylcarbamate To a solution of the product from Example 203A (0.104 g, 0.136 mmol) in tetrahydrofuran (2.0 mL) at room temperature were added molecular sieves (4 Å, 0.40 g) and phosphoric acid (0.125 g, 1.28 mmol), and the reaction was cooled to 0° C., followed by addition of N-iodosuccinimide (0.060 g, 0.267 mmol), and the mixture was stirred at room temperature for 30 minutes. The reaction was diluted with methanol and filtered through celite. The filtrate was treated with $Na_2S_2O_3$ (saturated) and the pH was adjusted to 9 with 10% $Na_2CO_3$. The methanol was evaporated and the mixture was purified by chromatography using a C18 column, eluting with a gradient starting with water and ending with methanol, to give the title compound as the disodium salt (0.060 g, 52% yield). $^1$H NMR (300 MHz, MeOH-$d_6$), δ ppm 0.83 (s, 9 H), 0.85 (s, 9 H), 1.65-1.74 (m, 1H), 1.97-2.06 (m, 1 H), 2.62-2.79 (m, 2 H), 2.87-3.05 (m, 2 H), 3.49 (s, 3 H), 3.67 (s, 3 H), 3.71-3.75 (m, 1 H), 3.92 (s, 1 H), 3.95 (s, 1 H), 4.17-4.27 (m, 1 H), 4.37-4.42 (m, 1 H), 5.05 (dd, J=8.5, 5.5 Hz, 1 H), 5.15 (dd, J=92, 5.5 Hz,

EXAMPLE 204 methyl(1S,4S,5S,7S,10S)-4benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate

EXAMPLE 204A methyl(1S)-1-({[(1S,2S,4S)-1-benzyl-4-{[N-(methoxycarbonyl)-3-methyl-L-valyl]amino}-2-[(methylthio)methoxy]-5-(4-pyridin-2-ylphenyl)pentyl]amino}carbonyl)-2,2-dimethylpropylcarbamate A slurry of Example 2D (2.5 g, 3.55 mmol) in acetonitrile (70.0 mL) was treated with dimethyl sulfide (6.6 mL, 89.2 mmol) at 25° C. followed by benzoyl peroxide (3.4 g, 14.0 mmol), and the mixture was stirred at 25° C. for 15 minutes. The mixture was treated with additional benzoyl peroxide (3.4 g, 14.0 mmol), and stirred for 1 hour at 25° C. Water was added and the mixture was partitioned between ethyl acetate and 10% $Na_2CO_3$. The organic phase was washed with brine, dried over $MgSO_4$, filtered, and the solvents were evaporated. The crude residue was purified by silica gel chromatography eluting with a gradient starting with dichloromethane and ending with 100% ethyl acetate to give the title compound (2.46 g, 91%).

EXAMPLE 204B methyl(1S,4S,5S,7S,10S)-4-benzyl-1,10-bis(tert-butyl)-2,9,12-trioxo-5-[(phosphonooxy)methoxy]-7-(4-pyridin-2-ylbenzyl)-13-oxa-3,8,11-triazatetradec-1-ylcarbamate A solution of Example 204A (2.46 mg, 3.2 mmol) in tetrahydrofuran (16.0 mL) was treated with 4 Å molecular sieves (8.0 g), a solution of phosphoric acid (32.0 mL, 0.5 M in DMF), and N-iodosuccinimide (1.45 g, 6.4 mmol) at 25° C. for 45 minutes. The mixture was poured into cold 10% sodium carbonate, diluted with methanol, filtered and through celite. The filtrate was decolorized with saturated sodium thiosulfate and concentrated. The resulting concentrate was dissolved in methanol, filtered and concentrated. Methanol and water were added to the resulting concentrate and the pH was adjusted to 9 by addition of 10% $Na_2CO_3$, and the mixture was purified by reverse phase HPLC using a C18 column, eluting with a gradient starting with water and ending with methanol, to give the title compound as a disodium salt (1.53 g, 56% yield). $^1$H NMR (300 MHz, MeOH-$d_4$), δ ppm 0.80 (s, 9 H), 0.88 (s, 9 H), 1.67-1.76 (m, 1H), 2.00-2.10 (m, 1 H), 2.68-2.99 (m, 4 H), 3.54 (s, 3 H), 3.65 (s, 3 H), 3.70-3.74 (m, 1 H), 3.93 (s, 1 H), 3.94 (s, 1 H), 4.22-4.32 (m, 1 H), 4.34-4.38 (m, 1 H), 5.02 (dd, J=8.8, 5.5 Hz, 1 H), 5.15 (dd, J=8.8, 5.2 Hz, 1 H), 7.05-7.33 (m, 8 H), 7.77-7.89 (m, 4 H), 8.56 (m, 1 H).

EXAMPLE 205 methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10,10-dihydroxy-8-methyl-10-oxido-2-oxo-4-(4-pyridin-2-ylbenzyl)-7,9-dioxa-3-aza-10-phosphadec-1-ylcarbamate

EXAMPLE 205A $N^1$-[(1S,3S,4S)-4-{[(2S)-2-(3-benzyl-2-oxoimidazolidin-1-yl)-3,3-dimethylbutanoyl]amino}-3-[1-(ethylthio)ethoxy]-5-phenyl-1-(4-pyridin-2-ylbenzyl)pentyl]-$N^2$-(methoxycarbonyl)-3-methyl-L-valinamide To a solution of the compound of Example 111 (0.200 g, 0.248 mmol) and ethyl sulfide (0.70 mL, 6.48 mmol) in acetonitrile (2.0 mL) at 0° C. was added benzoyl peroxide (0.38 g, 1.57 mmol) in three portions over 2 hours. The reaction was diluted with ethyl acetate and washed with 10% $Na_2CO_3$ and brine. The organic was dried over $MgSO_4$, filtered and evaporated. The residue was chromatographed on silica gel eluting with a gradient starting with dichloromethane and ending with ethyl acetate to give the title compound (0.210 g, 95% yield).

EXAMPLE 205B methyl(1S,4S,6S)-6-((1S)-1-{[(2S)-2-(3-benzyl-2-oxoimidazolidin-1-yl)-3,3-dimethylbutanoyl]amino}-2-phenylethyl)-1-tert-butyl-10,10-dihydroxy-8-methyl-10-oxido-2-oxo-4-(4-pyridin-2-ylbenzyl)-7,9-dioxa-3-aza-10-phosphadec-1-ylcarbamate To a solution of the product from Example 205A (0.285 g, 0.319 mmol) in N,N-dimethylformamide (6.0 mL) at room temperature was added molecular sieves (4 Å, 1.20 g), and the reaction was cooled to 0° C. A solution of phosphoric acid (0.100 g, 1.02 mmol) in N,N-dimethylformamide (5.0 mL) was added, followed by addition of N-iodosuccinimide (0.145 g, 0.644 mmol), and the mixture was stirred at room temperature for 1 hour. The reaction was diluted with methanol and filtered through celite. The filtrate was treated with $Na_2S_2O_3$ (saturated) and the pH was adjusted to 9 with 10% $Na_2CO_3$. The methanol was evaporated and the mixture was purified by chromatography using a C18 column, eluting with a gradient starting with water and ending with methanol, to give the title compound as the disodium salt (0.069 g, 22% yield). $^1$H NMR (300 MHz, MeOH-$d_4$), δ ppm 0.79 (s, 9 H), 0.97, 1.01 (2s, 9 H), 1.49 (d, J=5.2 Hz, 1.5 H), 1.51 (d, J=5.2 Hz, 1.5 H), 1.54-1.77 (m, 1H), 1.92-2.31 (m, 2 H), 2.63-3.02 (m, 6 H), 3.12-3.21 (m, 1 H), 3.57, 3.59 (2s, 3 H), 3.99-4.03 (m, 2.5 H), 4.17-4.21 (m, 0.5 H), 4.29-4.47 (m, 4 H), 5.39-5.46 (m, 0.5 H), 5.46-5.53 (m, 0.5 H), 6.95-6.99 (m, 3 H), 7.06-7.12 (m, 2 H), 7.27-7.39 (m, 8 H), 7.79-7.89, (m, 4 H), 8.56 (m, 1 H).

EXAMPLE 206 methyl(1S,4S,5S)-4benzyl-1-tert-butyl-5-{(2S)-2-
[((2S)-3,3-dimethyl-2-{3-[(6-methylpyridin-2-yl)
methyl]-2-oxoimidazolidin-1-yl}butanoyl)amino]-3-
phenylpropyl}-9,9-dihydroxy-9-oxido-2-oxo-6,8-
dioxa-3-aza-9-phosphanon-1-ylcarbamate

EXAMPLE 206A $N^1$-{(1S,2S,4S)-1-benzyl-4-[((2S)-3,3-dimethyl-2-
{3-[(6-methylpyridin-2-yl)methyl]-2-oxoimidazoli-
din-1-yl}butanoyl)amino]-2-[(methylthio)methoxy]-
5-phenylpentyl}-$N^2$-(methoxycarbonyl)-3-methyl-L-
valinamide A solution containing the product of Example 10E (1.71 g, 2.3 mmol) in DMSO (3.3 g, 42.3 mmol) was treated with acetic acid (4.1 g, 69 mmol) and acetic anhydride (2.35 g, 23 mmol) at 25° C. for 3 days. Excess ice was added to the mixture which was then made alkaline with 10% sodium carbonate. The mixture was extracted with ethyl acetate, the organic layer was separated, washed with 10% sodium carbonate, water (3×), brine, and dried over sodium sulfate. The solvents were evaporated, and the product was purified by chromatography on silica gel eluting with 30-100% ethyl acetate/dichloromethane to give the title compound (1.1 g, 60% yield).

EXAMPLE 206B methyl(1S,4S,5S)-4-benzyl-1-tert-butyl-5-{(2S)-2-
[((2S)-3,3-dimethyl-2-{3-[((6-methylpyridin-2-yl)
methyl]-2-oxoimidazolidin-1-yl}butanoyl)amino]-3-
phenylpropyl}-9,9-dihydroxy-9-oxido-2-oxo-6,8-
dioxa-3-aza-9-phosphanon-1-ylcarbamate A mixture of Example 206A, phosphoric acid (0.85 g, 8.6 mmol), and molecular sieves (4A, 6 g) in N,N-dimethylformamide (28 mL) at 0° C. was treated with NIS (0.41 g, 1.78 mmol) for 3 h. The mixture was filtered, the solids washed with methanol, and the resultant filtrant was treated with sodium sulfite until colorless and made alkaline with 10% sodium carbonate to pH 9. The mixture was refiltered, and the solvents were evaporated. The residue was triturated with methanol, filtered, and the solvents were evaporated. The crude residue was purified by chromatography on silica gel eluting with (reverse phase) 100% water-100% methanol to give the title compound as the disodium salt (0.68 g, 55% yield). $^1$H NMR (300 MHz, MeOD-$d_4$) δ ppm 0.84-0.93 (m, 9 H), 0.95 (s, 9 H), 1.61-1.87 (m, 1 H), 1.97-2.14 (m, 1 H), 2.39-2.49 (m, 2 H), 2.54 (s, 3 H), 2.75 (s, 1 H), 2.77-2.82 (m, 1 H), 2.86 (d, J=5.15 Hz, 1 H), 2.90-2.98 (m, 1 H), 2.98-3.08 (m, 1 H), 3.13 (q, J=8.82 Hz, 1 H), 3.34-3.36 (m, 2 H), 3.66 (s, 3 H), 3.70 (s, 1 H), 3.98 (s, 1 H), 4.10 (s, 1 H), 4.38 (s, 1 H), 4.44 (d, J=5.15 Hz, 2 H), 4.56 (s, 1 H), 5.03 (dd, J=9.38, 5.33 Hz, 1 H), 5.18 (dd, J=8.82, 5.52 Hz, 1 H), 6.98-7.31 (m, 12 H), 7.72 (t, J=7.72 Hz, 1 H).

EXAMPLE 207 methyl(1S,4S,5S,7S,10S)-4benzyl-1,10-bis(tert-bu-
tyl)-2,9,12-trioxo-5-[1-(phosphonooxy)ethoxy]-7-(4-
pyridin-2-ylbenzyl)-13-oxa-3,8,11-triazatetradec-1-
ylcarbamate

EXAMPLE 207A methyl(1S)-1-({[(1S,2S,4S)-1-benzyl-2-[1-(eth-
ylthio)ethoxy]-4-{[N-(methoxycarbonyl)-3-methyl-
L-valyl]amino}-5-(4-pyridin-2-ylphenyl)pentyl]
amino}carbonyl)-2,2-dimethylpropylcarbamate To a slurry of the compound of Example 2D (2.00 g, 2.84 mmol) and ethyl sulfide (8.0 mL, 74.06 mmol) in acetonitrile (28.0 mL) at room temperature was added benzoyl peroxide (4.95 g, 20.45 mmol) in three portions over 2 hours. The reaction was diluted with ethyl acetate and washed with 10% $Na_2CO_3$ and brine. The organic was dried over $MgSO_4$, filtered and evaporated. The residue was chromatographed on silica gel eluting with a gradient starting with dichloromethane and ending with ethyl acetate to give the title compound (2.35 g, 84% yield).

EXAMPLE 207B methyl(1S,4S,5S,7S,10S)-4-benzyl-1,10-bis(tert-
butyl)-2,9,12-trioxo-5-[1-(phosphonooxy)ethoxy]-7-
(4-pyridin-2-ylbenzyl)-13-oxa-3,8,11-triazatetradec-
1-ylcarbamate To a slurry of the product from Example 207A (1.10 g, 1.39 mmol) and molecular sieves (4 Å, 3.5 g), in N,N-dimethylformamide (7.0 mL) at 0° C. were added a solution of phosphoric acid in N,N-dimethylformamide (13.0 mL, 0.5 M) and N-iodosuccinimide (0.626 g, 2.78 mmol), and the mixture was stirred at 0° C. for 4 hours. The reaction was treated with $Na_2S_2O_3$ (saturated) and the pH was adjusted to 9 with 10% $Na_2CO_3$. The mixture was diluted with methanol and filtered through celite The methanol was evaporated and the mixture was purified by chromatography using a C18 column, eluting with a gradient starting with water and ending with methanol, to give the title compound as the disodium salt (0.70 g, 58% yield). $^1$H NMR (300 MHz, MeOH-$d_4$), δ ppm 0.69 (s, 9 H), 0.93, 1.00 (2s, 9 H), 1.44 (d, J=5.2 Hz, 1.5 H), 1.47 (d, J=4.8 Hz, 1.5 H), 1.52-1.76 (m, 1H), 1.95-2.05 (m, 0.5 H), 2.30-2.40 (m, 0.5 H), 2.76-2.91 (m, 4 H), 3.58, 3.60 (2s, 3 H), 3.64 (s, 3 H), 3.84, 3.87 (2s, 1 H), 3.89-3.97 (m, 0.5 H), 4.03, 4.06 (2s, 1 H), 4.14-4.37 (m, 2.5 H), 5.34-5.41 (m, 0.5 H), 5.43-5.50 (m, 0.5 H), 7.02-7.19 (m, 5 H), 7.28-7.37 (m, 3 H), 7.77-7.89, (m, 4 H), 8.57 (m, 1 H).

EXAMPLE 208 methyl(1S)-3-amino-1-({[(1S,2S,4S)-1-benzyl-2-hydroxy-4-{[N-(methoxycarbonyl)-3-methyl-L-valyl]amino}-5-(4-pyridin-2-ylphenyl)pentyl]amino}carbonyl)-2,2-dimethyl-3-oxopropylcarbamate

EXAMPLE 208A methyl(3S)-3-[(tert-butoxycarbonyl)amino]-3-carboxy-2,2-dimethylpropanoate Example 184A (100 mg, 0.21 mmol) was dissolved in dichloromethane (2 mL) and cooled to 0° C. Trifluoroacetic acid (2 mL) was added and the solution was stirred at 0° C. for 1 hour. The ice bath was removed and the solution was allowed to warm to ambient temperature over 3 hours. The solution was concentrated, toluene (5 mL) was added and the solution concentrated again. The residue was placed under vacuum for 2 hours, dissolved in dioxane (4 mL) and 10% sodium bicarbonate (1 mL). With stirring, di-tert-butyl dicarbonate (93 mg, 0.42 mmol) was added and the solution was stirred for 18 hours, the solution was concentrated and the residue distributed between ether (10 mL) and $H_2O$ (10 mL). Hydrochloric acid (1 mL, 0.5 M) was added and the aqueous layer was extracted with ether (3 times 10 mL), the organic extracts combined and washed with $H_2O$ (10 mL), dried ($Na_2SO_4$), filtered and the filtrate concentrated. The residue was purified by column chromatography on silica gel (10% methanol/chloroform) to yield a tan solid.

EXAMPLE 208B methyl $N^1$-[(1S,2S,4S)-1-benzyl-2-hydroxy-4-{[N-(methoxycarbonyl)-3-methyl-L-valyl]amino}-5-(4-pyridin-2-ylphenyl)pentyl]-$N^2$-(tert-butoxycarbonyl)-3,3-dimethyl-L-asparaginate Example 208A (0.21 mmol) was dissolved in tetrahydrofuran (1 mL) and the product from Example 2C (114 mg, 0.21 mmol), diisopropylethylamine (111 uL, 0.64 mmol) and 3-(diethoxyphosphoryloxy)-1,2,3-benzotriazin-4(3H)-one (127 mg, 0.42 mmol) were added. The solution was stirred at ambient temperature for 3 hours. 10% $Na_2CO_3$ (5 mL) was added and stirring was continued for 20 minutes. $H_2O$ (5 mL) was added and the solution extracted with ethyl acetate (3 times 10 mL), the organic extracts combined, washed with 10% $Na_2CO_3$ (10 mL) and saturated brine solution (10 mL), dried ($Na_2SO_4$), filtered and concentrated. The residue was purified by column chromatography on silica gel (5% $CH_3OH/CHCl_3$) to yield a white solid (138 mg, 82%).

EXAMPLE 208C methyl(1S)-3-amino-1-({[(1S,2S,4S)-1-benzyl-2-hydroxy-4-{[N-(methoxycarbonyl)-3-methyl-L-valyl]amino}-5-(4-pyridin-2-ylphenyl)pentyl]amino}carbonyl)-2,2-dimethyl-3-oxopropylcarbamate To Example 208B (56 mg, 0.07 mmol) were added dioxane (1 mL) and LiOH (0.28 mL, 0.5 M in $H_2O$) and the mixture was stirred for 1 hour at ambient temperature and followed by the addition of HCl (0.5 mL, 1.0 N) and $H_2O$ (3 mL). The mixture was extract with ethyl acetate (3 times 5 mL) and the combined ethyl acetate extracts were dried ($Na_2SO_4$), filtered and concentrated. The crude residue (19 mg, 0.024 mmol) was dissolved in dioxane (1 mL) and to this solution was added ammonia (61 µL, 2M in methanol) followed by N-hydroxybenzotriazole (5 mg, 0.037 mmol) and 1-(3-dimethylaminopropyl)-3-ethylcarbodiimide (7 mg, 0.0.037 mmol) and stirring was continued at ambient temperature for 4 hours. The solution was concentrated and the crude residue was dissolved in dichloromethane (1 mL) and trifluoroacetic acid (1 mL) was added. The resulting mixture was stirred at ambient temperature for 1 hour. The solution was concentrated and toluene (5 mL) was added and the solution concentrated again. The residue was placed under vacuum for 2 hours then dissolved in dioxane (1 mL) and to this solution was added sodium hydroxide (27 µL, 3N) and methyl chloroformate (5 µL, 0.037 mmol). The mixture was stirred at 60° C. for 18 hours, cooled to ambient temperature and concentrated. The crude residue was purified on a preparative TLC plate (silica gel, 20×20 cm, 5% methanol/chloroform) to give a solid white product (7 mg, 39%); $^1$H NMR ($d_6$-DMSO) δ 8.64 (d, 1H), 7.97-7.30 (m, 6H), 7.35-6.82 (m, 6H), 6.71-6.57 (t, 1H), 4.85-4.75 (m, 1H), 4.23-4.05 (m, 2H), 3.87-3.76 (d, 1H), 3.50 (s, 3H), 3.31 (s, 3H), 2.85-2.63 (m, 4H), 1.70-1.36 (m, 4H), 1.23 (s, 3H), 1.04 (s, 3H), 0.80 (s, 9H).

The following additional compounds of the present invention can be prepared by one skilled in the art using known synthetic methodology or by using synthetic methodology described in the Schemes and Examples contained herein. The additional compounds encompassed by the following tables can be described by taking one core from Table 1, one $R^1$ substituent from Table 2, one $R^2$ substituent from Table 3, one $R^3$ substituent from Table 4, one $R^6$ substituent from Table 5, one $R^7$ substituent from Table 6, and one $R^8$ substituent from Table 7, one $R^9$ substituent from Table 8, or one $R^{11}$ substituent from Table 9; wherein $X_1$ in the tables of substituents represents the Core Ring Structure.

TABLE 1

Examples of Core Ring Structures

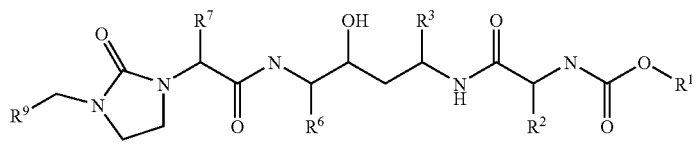

TABLE 1-continued

Examples of Core Ring Structures

2

2

4

5

6

TABLE 2

Examples of R¹ Substituents

| X₁—CH₃ | X₁ | X₁ | X₁ |
|---|---|---|---|
| 1 | 2 | 3 | 4 |
| X₁ | X₁ | X₁ | X₁ |
| 5 | 6 | 7 | 8 |

TABLE 3

Examples of R² Substituents

| X₁—H | X₁—CH₃ | X₁ | X₁ |
|---|---|---|---|
| 1 | 2 | 3 | 4 |
| X₁ | X₁ | X₁ | X₁ |
| 5 | 6 | 7 | 8 |
| X₁ | X₁ | X₁ | X₁ |
| 9 | 10 | 11 | 12 |

TABLE 3-continued

Examples of R² Substituents 13, 14, 15, 16, 17, 18, 19, 20

TABLE 4

Examples of R³ Substituents 1, 2, 3, 4, 5, 6, 7

TABLE 4-continued

Examples of R³ Substituents 8, 9, 10, 11, 12, 13, 14, 15, 16, 17, 18, 19, 20

TABLE 5
Examples of $R^6$ Substituents
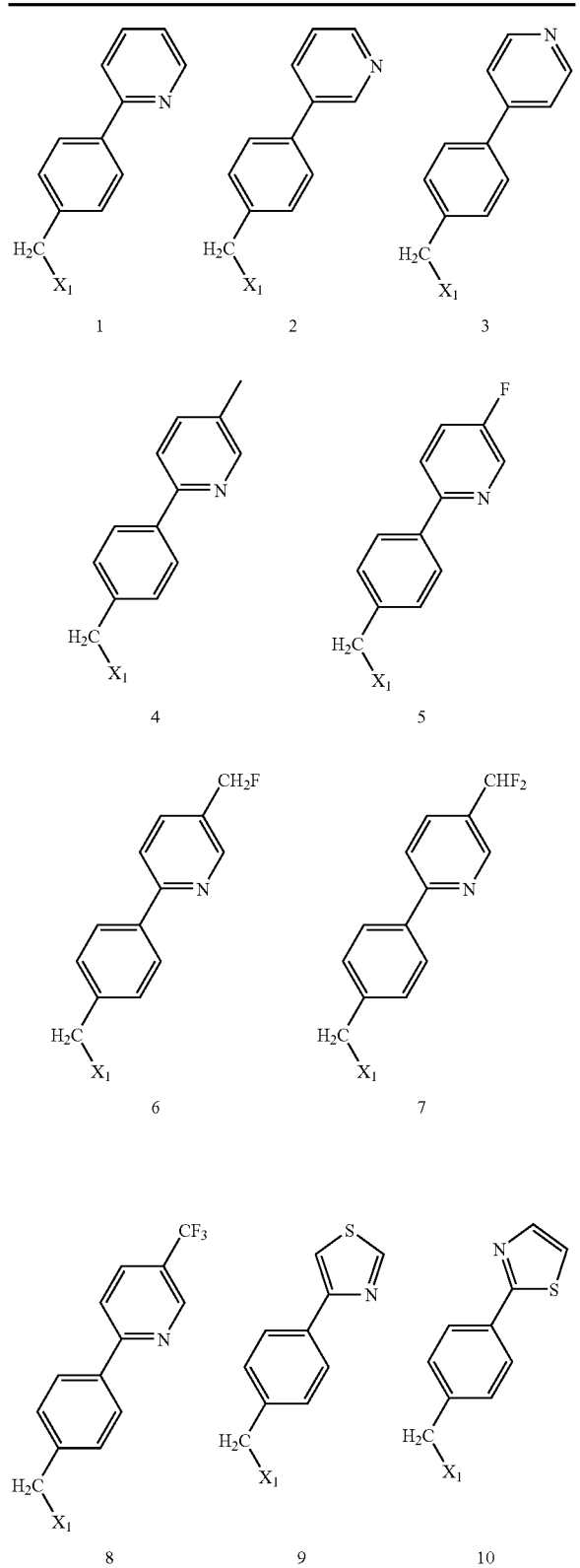
TABLE 5-continued
Examples of $R^6$ Substituents
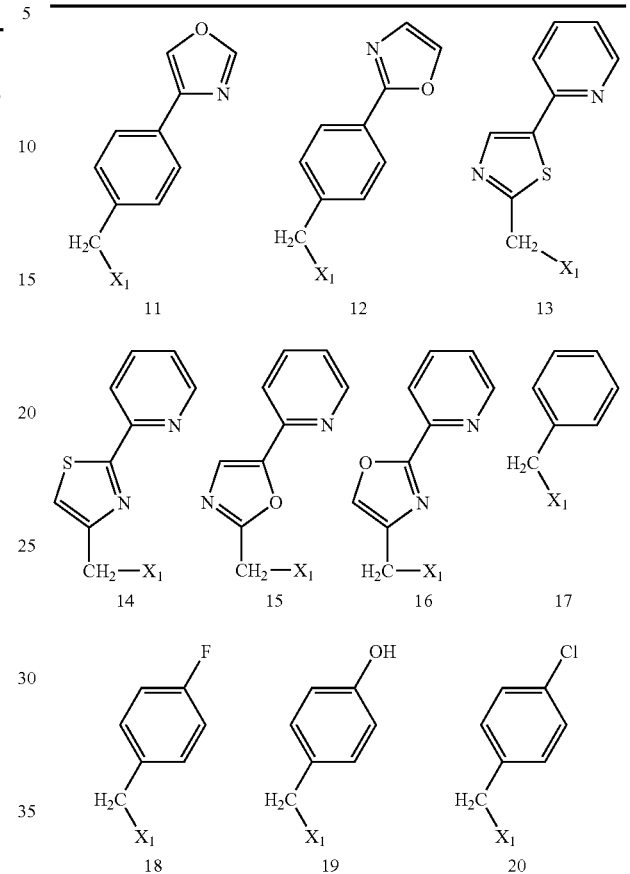
TABLE 6
Examples of $R^7$ Substituents
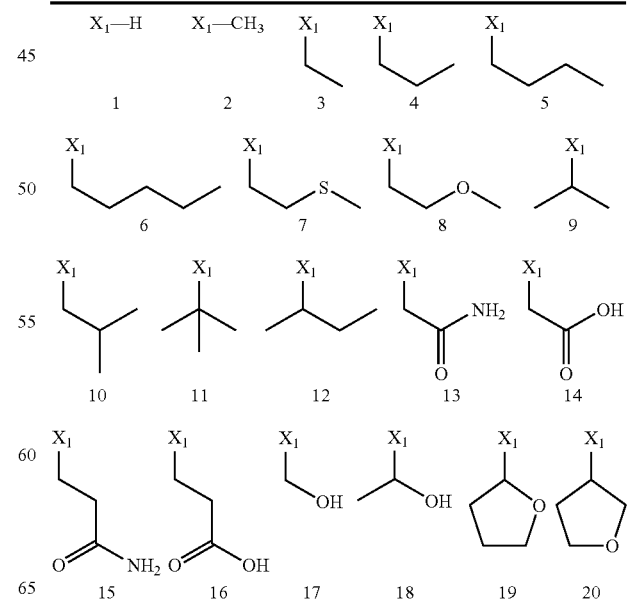

TABLE 7
Examples of R⁸ Substituents
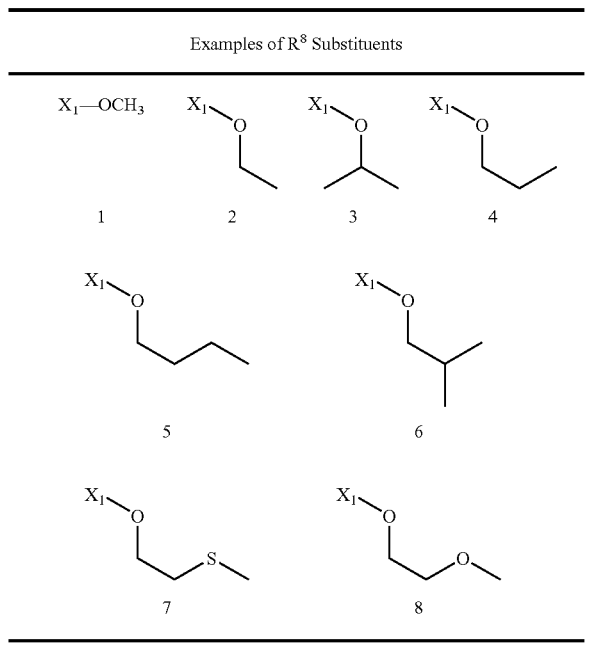
TABLE 8
Examples of R⁹ Substituents
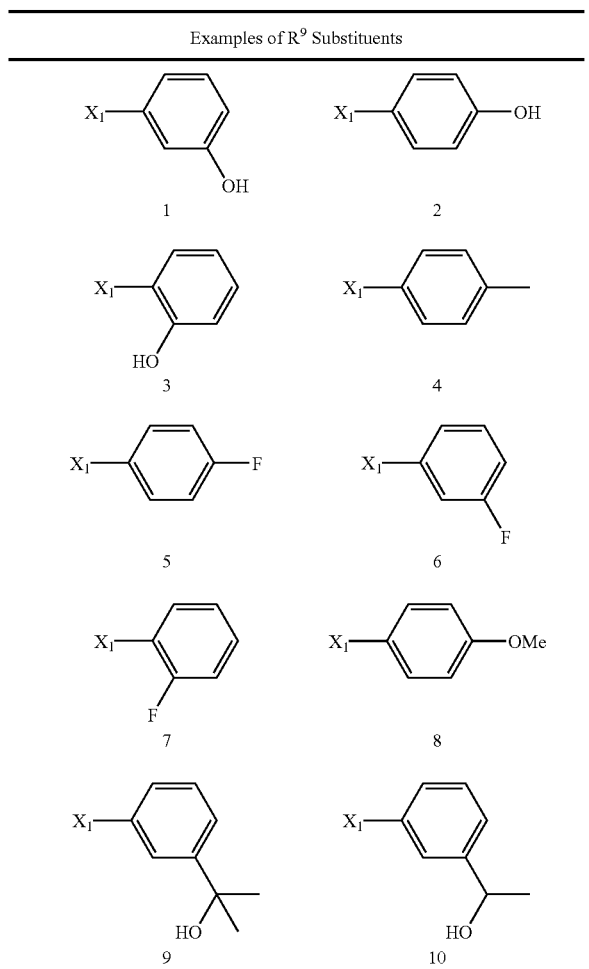
TABLE 8-continued
Examples of R⁹ Substituents
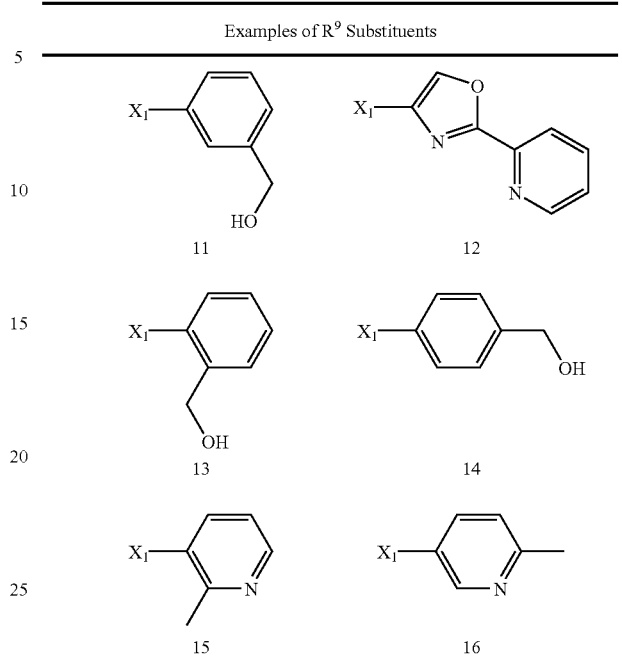
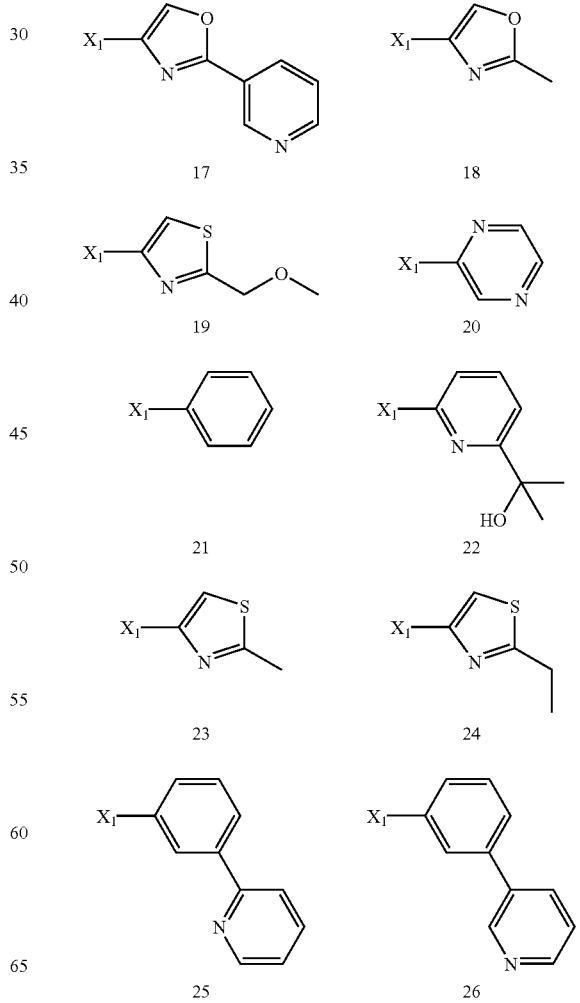

TABLE 8-continued

Examples of $R^9$ Substituents

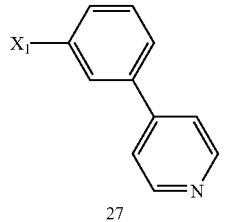
27

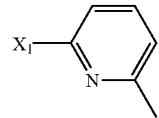
28

TABLE 9

Examples of $R^{11}$ Substituents

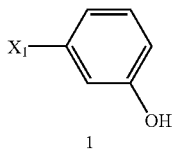
1

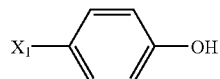
2

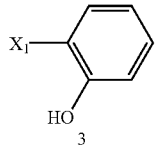
3

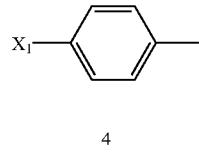
4

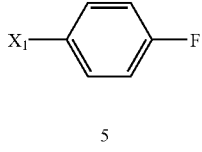
5

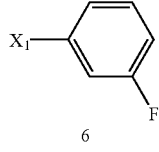
6

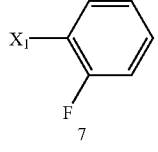
7

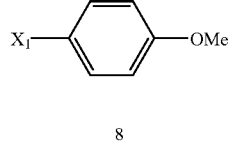
8

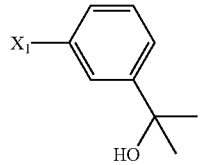
9

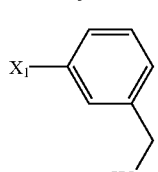
10

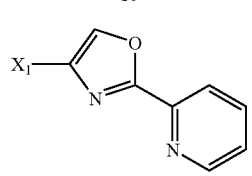
11

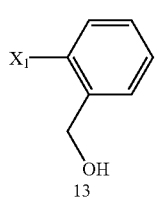
12

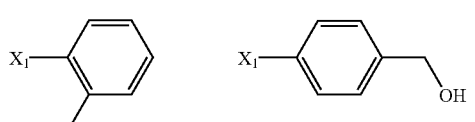
13 14

TABLE 9-continued

Examples of $R^{11}$ Substituents

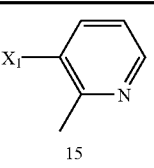
15

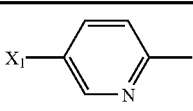
16

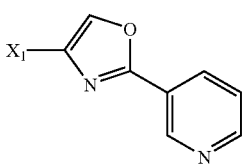
17

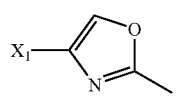
18

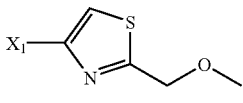
19

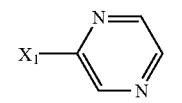
20

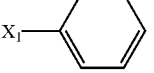
21

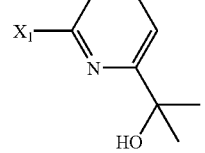
22

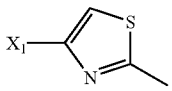
23

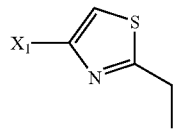
24

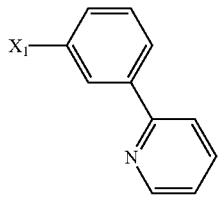
25

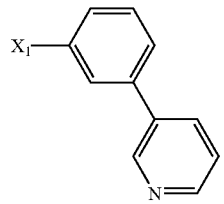
26

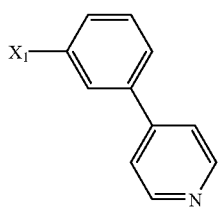
27

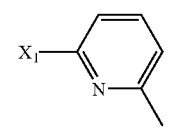
28

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound having formula (III)

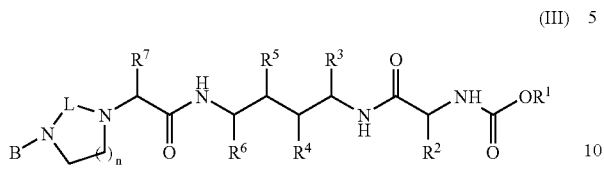

or a pharmaceutically acceptable salt form or a stereoisomer thereof, wherein:

B is H or —CH$_2$R$^9$;

L is —C(=O), —C(=S), —C(=NH) or —S(O)$_2$;

R$^1$ is alkyl, alkenyl, alkynyl, cycloalkyl, cycloalkenyl, heterocycle, aryl or heteroaryl; wherein each R$^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and R$^{1a}$;

R$^{1a}$ is cycloalkyl, cycloalkenyl, heterocycle, aryl or heteroaryl; wherein each R$^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^2$ is alkyl, alkenyl, alkynyl, cycloalkyl, cycloalkenyl, heterocycle, aryl or heteroaryl; wherein each R$^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$ —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{2a}$;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^3$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^4$ is H and R$^5$ is OR$^{16}$;

R$^6$ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN (H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R$^7$ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R$^9$ is alkyl, alkenyl, alkynyl, cycloalkyl, cycloalkenyl, aryl, heteroaryl or heterocycle; wherein each R$^9$ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$;

R$^{9a}$ is cycloalkyl, cycloalkenyl, heterocycle, aryl or heteroaryl; wherein each R$^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^{16}$ is hydrogen or R$^{15}$;

R$^{15}$ is

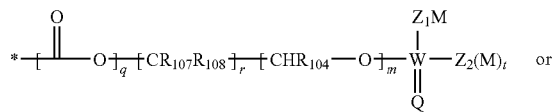

(XVI)

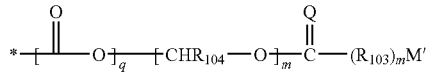

(XVII)

R$_{103}$ is C(R$_{105}$)$_2$, O or —N(R$_{105}$);

R$_{104}$ is hydrogen, alkyl, haloalkyl, alkoxycarbonyl, aminocarbonyl, alkylaminocarbonyl or dialkylaminocarbonyl, each M is independently selected from the group consisting of H, —N(R$_{105}$)$_2$, alkyl, alkenyl, and R$_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$, NO$_2$ and phenyl; provided that when M is —N(R$_{105}$)$_2$, Z$_1$ and Z$_2$ are —CH$_2$;

Z$_1$ is CH$_2$, O, S, —N(R$_{105}$), or, when M is absent, H;

Z$_2$ is CH$_2$, O, S or —N(R$_{105}$);

Q is O or S;

W is P or S; wherein when W is S, Z$_1$ and Z$_2$ are not S;

M' is H, alkyl, alkenyl or R$_{106}$; wherein 1 to 4 —CH$_2$ radicals of the alkyl or alkenyl is optionally replaced by a heteroatom group selected from O, S, S(O), SO$_2$, or N(R$_{105}$); and wherein any hydrogen in said alkyl, alkenyl or R$_{106}$ is optionally replaced with a substituent selected from the group consisting of oxo, —OR$_{105}$, —R$_{105}$, —N(R$_{105}$)$_2$, —CN, —C(O)OR$_{105}$, —C(O)N(R$_{105}$)$_2$, —SO$_2$N(R$_{105}$), —N(R$_{105}$)C(O)R$_{105}$, —C(O)R$_{105}$, —SR$_{105}$, —S(O)R$_{105}$, —SO$_2$R$_{105}$, —OCF$_3$, —SR$_{106}$, —SOR$_{106}$, —SO$_2$R$_{106}$, —N(R$_{105}$)SO$_2$R$_{105}$, halo, —CF$_3$ and NO$_2$;

R$_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and N(R$_{105}$); and wherein any of said ring system is substituted with 0, 1, 2, 3, 4, 5 or 6 substituents selected from the group consisting of hydroxy, alkyl, alkoxy, and —OC(O)alkyl;

each R$_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and N(R$_{105}$); and wherein any one of said ring systems is substituted with 0, 1, 2, 3 or 4 substituents selected from the group consisting of oxo, —OR$_{105}$, —R$_{105}$, —N(R$_{105}$)$_2$, —N(R$_{105}$)C(O)R$_{105}$, —CN, —C(O)OR$_{105}$, —C(O)N(R$_{105}$)$_2$, halo and —CF$_3$;

each R$_{107}$ and R$_{108}$ are independently selected from the group consisting of hydrogen and alkyl;

q is 0 or 1;
m is 0 or 1;
m' is 0 or 1;
m" is 0 or 1;
r is 0, 1, 2, 3 or 4;
t is 0 or 1;

R$_a$ and R$_b$ at each occurrence are independently selected from the group consisting of hydrogen, alkyl, alkenyl, alkynyl, cycloalkyl, aryl, heteroaryl and heterocycle; wherein each R$_a$ and R$_b$, at each occurrence, is independently substituted with 0, 1, 2 or 3 substituents independently selected from the group consisting of cyano, nitro, halo, oxo, hydroxy, alkoxy, alkyl, alkenyl, alkynyl, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

alternatively, R$_a$ and R$_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$_c$;

R$_c$ is aryl, heteroaryl or heterocycle; wherein each R$_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

2. A compound having formula (III)

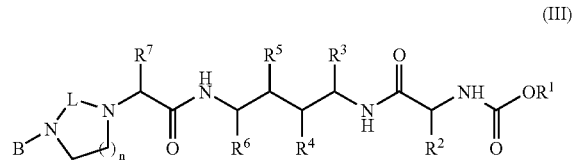

(III)

or a pharmaceutically acceptable salt form or a stereoisomer thereof, wherein:

B is H or —CH$_2$R$^9$;

L is —C(=O), —C(=S), —C(=NH) or —S(O)$_2$;

R$^1$ is alkyl, alkenyl, alkynyl, cycloalkyl, cycloalkenyl, heterocycle, aryl or heteroaryl; wherein each R$^1$ is substituted with 0, 1 or 2 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$, and R$^{1a}$;

R$^{1a}$ is cycloalkyl, cycloalkenyl, heterocycle, aryl or heteroaryl; wherein each R$^{1a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

R$^2$ is alkyl, alkenyl, alkynyl, cycloalkyl, cycloalkenyl, heterocycle, aryl or heteroaryl; wherein each R$^2$ is substituted with 0, 1 or 2 substituents independently selected from the group consisting of halo, —OR$_a$, —SR$_a$, —SOR$_a$, —SO$_2$R$_a$, —NR$_a$R$_b$, —NR$_b$C(O)R$_a$ —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{2a}$;

R$^{2a}$ is cycloalkyl, cycloalkenyl, heterocycle, aryl or heteroaryl; wherein each R$^{2a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkyl-C(O)N(alkyl)$_2$;

R³ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{3a}$;

R$^{3a}$ is cycloalkyl, cycloalkenyl, heterocycle, aryl or heteroaryl; wherein each R$^{3a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R⁵ is H and R⁴ is OR$^{16}$;

R⁶ is alkyl, alkenyl, alkynyl, haloalkyl, haloalkenyl, -alkylOR$_a$, -alkylSR$_a$, -alkylSOR$_a$, -alkylSO$_2$R$_a$, -alkylNR$_a$R$_b$, -alkylN(R$_b$)C(O)R$_a$, -alkylN(R$_b$)C(O)OR$_a$, -alkylN(R$_a$)C(=N)NR$_a$R$_b$, -alkylN(R$_a$)C(O)NR$_a$R$_b$, -alkylC(O)NR$_a$R$_b$, -alkylC(O)OR$_a$, cycloalkyl, cycloalkylalkyl, cycloalkenyl, cycloalkenylalkyl, heterocycle, heterocyclealkyl, aryl, arylalkyl, heteroaryl or heteroarylalkyl; wherein the cycloalkyl, cycloalkenyl, heterocycle, aryl, heteroaryl, cycloalkyl moiety of the cycloalkylalkyl, cycloalkenyl moiety of the cycloalkenylalkyl, heterocycle moiety of the heterocyclealkyl, heteroaryl moiety of the heteroarylalkyl and the aryl moiety of the arylalkyl are independently substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and R$^{6a}$;

R$^{6a}$ is cycloalkyl, cycloalkenyl, heterocycle, aryl or heteroaryl; wherein each R$^{6a}$ is substituted with 0, 1, 2, 3 or 4 substituents independently selected from the group consisting of cyano, halo, oxo, alkyl, alkenyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), and -alkylC(O)N(alkyl)$_2$;

R⁷ is —N(R$_b$)C(O)OR$_a$, alkyl, alkenyl, alkynyl, cycloalkyl, cycloalkenyl, heterocycle, aryl or heteroaryl; wherein the alkyl, alkenyl, alkynyl, cycloalkyl, cycloalkenyl, heterocycle, aryl and heteroaryl are independently substituted with 0, 1 or 2 substituents independently selected from the group consisting of halo, —OR$_a$, —OC(O)R$_a$, —SR$_a$, —SOR$_a$, —SO$_2$R$_a$, —NR$_a$R$_b$, —N(R$_b$)C(O)R$_a$, —N(R$_b$)C(O)OR$_a$, —N(R$_a$)C(=N)NR$_a$R$_b$, —N(R$_a$)C(O)NR$_a$R$_b$, —C(O)NR$_a$R$_b$, —C(O)OR$_a$ and R$^{7a}$;

R$^{7a}$ is cycloalkyl, cycloalkenyl, heterocycle, aryl or heteroaryl; wherein each R$^{7a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)0alkyl, -alkylC(O)NH$_2$, -alkylC(O)N(H)(alkyl) and -alkyl-C(O)N(alkyl)$_2$;

R⁹ is alkyl, alkenyl, alkynyl, cycloalkyl, cycloalkenyl, aryl, heteroaryl or heterocycle; wherein each R⁹ is substituted with 0, 1, 2 or 3 substituents independently selected from the group consisting of alkyl, alkenyl, alkynyl, cyano, formyl, halo, nitro, oxo, —OR$_a$, —SR$_a$, —SOR$_a$, —SO$_2$R$_a$, —SO$_2$NR$_a$, —SO$_2$OR$_a$, —NR$_a$R$_b$, —N(R$_b$)C(O)R$_a$, —N(R$_b$)SO$_2$R$_a$, —N(R$_b$)SO$_2$NR$_a$R$_b$, —N(R$_b$)C(O)NR$_a$R$_b$, —N(R$_b$)C(O)OR$_a$, —C(O)R$_a$, —C(O)NR$_a$R$_b$, —C(O)OR$_a$, haloalkyl, nitroalkyl, cynaoalkyl, formylalkyl, -alkylOR$_a$, -alkyl-O—P(O)(OR$_a$)(OR$_a$), -alkylNR$_a$R$_b$, -alkylN(R$_b$)C(O)OR$_a$, -alkylN(R$_b$)SO$_2$NR$_a$R$_b$, -alkylN(R$_b$)C(O)R$_a$, -alkylN(R$_b$)C(O)NR$_a$R$_b$, -alkylN(R$_b$)SO$_2$R$_a$, -alkylC(O)OR$_a$, -alkylC(O)R$_a$, -alkylC(O)NR$_a$R$_b$ and R$^{9a}$;

R$^{9a}$ is cycloalkyl, cycloalkenyl, heterocycle, aryl or heteroaryl; wherein each R$^{9a}$ is substituted with 0, 1, 2, 3 or 4 substituents independently selected from the group consisting of cyano, halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, haloalkyl, hydroxyalkyl, alkoxyalkyl, -alkylNH$_2$, -alkylN(H)

(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl) and -alkylC(O)N(alkyl)$_2$;

$R^{16}$ is hydrogen or $R^{15}$;

$R^{15}$ is

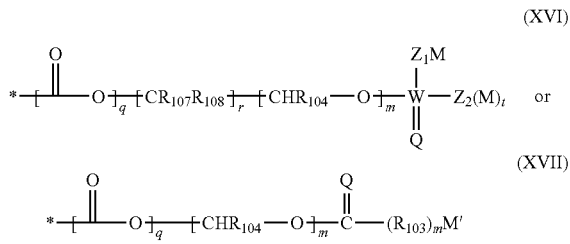

(XVI)

(XVII)

$R_{103}$ is $C(R_{105})_2$, O or —$N(R_{105})$;

$R_{104}$ is hydrogen, alkyl, haloalkyl, alkoxycarbonyl, aminocarbonyl, alkylaminocarbonyl or dialkylaminocarbonyl, each M is independently selected from the group consisting of H, —$N(R_{105})_2$, alkyl, alkenyl, and $R_{106}$; wherein 1 to 4 —CH$_2$ radicals of the alkyl or alkenyl, other than the —CH$_2$ radical that is bound to Z, is optionally replaced by a heteroatom group selected from the group consisting of O, S, S(O), SO$_2$ and $N(R_{105})$; and wherein any hydrogen in said alkyl, alkenyl or $R_{106}$ is optionally replaced with a substituent selected from the group consisting of oxo, —$OR_{105}$, —$R_{105}$, —$N(R_{105})_2$, —CN, —$C(O)OR_{105}$, —$C(O)N(R_{105})_2$, —$SO_2N(R_{105})$, —$N(R_{105})C(O)R_{105}$, —$C(O)R_{105}$, —$SR_{105}$, —$S(O)R_{105}$, —$SO_2R_{105}$, —$OCF_3$, —$SR_{106}$, —$SOR_{106}$, —$SO_2R_{106}$, —$N(R_{105})SO_2R_{105}$, halo, —$CF_3$, $NO_2$ and phenyl; provided that when M is —$N(R_{105})_2$, $Z_1$ and $Z_2$ are —CH$_2$;

$Z_1$ is CH$_2$, O, S, —$N(R_{105})$, or, when M is absent, H;

$Z_2$ is CH$_2$, O, S or —$N(R_{105})$;

Q is O or S;

W is P or S; wherein when W is S, $Z_1$ and $Z_2$ are not S;

M' is H, alkyl, alkenyl or $R_{106}$; wherein 1 to 4 —CH$_2$ radicals of the alkyl or alkenyl is optionally replaced by a heteroatom group selected from O, S, S(O), SO$_2$, or $N(R_{105})$; and wherein any hydrogen in said alkyl, alkenyl or $R_{106}$ is optionally replaced with a substituent selected from the group consisting of oxo, —$OR_{105}$, —$R_{105}$, —$N(R_{105})_2$, —CN, —$C(O)OR_{105}$, —$C(O)N(R_{105})_2$, —$SO_2N(R_{105})$, —$N(R_{105})C(O)R_{105}$, —$C(O)R_{105}$, —$SR_{105}$, —$S(O)R_{105}$, —$SO_2R_{105}$, —$OCF_3$, —$SR_{106}$, —$SOR_{106}$, —$SO_2R_{106}$, —$N(R_{105})SO_2R_{105}$, halo, —$CF_3$ and $NO_2$;

$R_{106}$ is a monocyclic or bicyclic ring system selected from the group consisting of aryl, cycloalkyl, cycloalkenyl heteroaryl and heterocycle; wherein any of said heteroaryl and heterocycle ring systems contains one or more heteroatoms selected from the group consisting of O, N, S, SO, SO$_2$ and $N(R_{105})$; and wherein any of said ring system is substituted with 0, 1, 2, 3, 4, 5 or 6 substituents selected from the group consisting of hydroxy, alkyl, alkoxy, and —OC(O)alkyl;

each $R_{105}$ is independently selected from the group consisting of H or alkyl; wherein said alkyl is optionally substituted with a ring system selected from the group consisting of aryl, cycloalkyl, cycloalkenyl, heteroaryl and heterocycle; wherein any of said heteroaryl and heterocycle ring systems contains one or more heteroatoms selected from the group consisting of O, N, S, SO, SO$_2$, and $N(R_{105})$; and wherein any one of said ring systems is substituted with 0, 1, 2, 3 or 4 substituents selected from the group consisting of oxo, —$OR_{105}$, —$R_{105}$, —$N(R_{105})_2$, —$N(R_{105})C(O)R_{105}$, —CN, —$C(O)OR_{105}$, —$C(O)N(R_{105})_2$, halo and —$CF_3$;

each $R_{107}$ and $R_{108}$ are independently selected from the group consisting of hydrogen and alkyl;

q is 0 or 1;

m is 0 or 1;

m' is 0 or 1;

m" is 0 or 1;

r is 0, 1, 2, 3 or 4;

t is 0 or 1;

$R_a$ and $R_b$ at each occurrence are independently selected from the group consisting of hydrogen, alkyl, alkenyl, alkynyl, cycloalkyl, aryl, heteroaryl and heterocycle; wherein each $R_a$ and $R_b$, at each occurrence, is independently substituted with 0, 1, 2 or 3 substituents independently selected from the group consisting of cyano, nitro, halo, oxo, hydroxy, alkoxy, alkyl, alkenyl, alkynyl, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

alternatively, $R_a$ and $R_b$, together with the nitrogen atom to which they are attached, form a ring selected from the group consisting of heteroaryl and heterocycle; wherein each of the heteroaryl and heterocycle is independently substituted with 0, 1, 2 or 3 substituents independently selected from the group consisting of alkyl, alkenyl, alkynyl, cyano, formyl, nitro, halo, oxo, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, cyanoalkyl, formylalkyl, nitroalkyl, haloalkyl, hydroxyalkyl, alkoxyalkyl, -alkylNH$_2$, -alkylN(H)(alkyl), -alkylN(alkyl)$_2$, -alkylN(H)C(O)NH$_2$, -alkylN(H)C(O)N(H)(alkyl), -alkylN(H)C(O)N(alkyl)$_2$, -alkylC(O)OH, -alkylC(O)Oalkyl, -alkylC(O)NH$_2$, -alkylC(O)N(H)(alkyl), -alkylC(O)N(alkyl)$_2$ and $R_c$;

$R_c$ is aryl, heteroaryl or heterocycle; wherein each $R_c$ is independently substituted with 0, 1, 2, 3 or 4 substituents independently selected from the group consisting of halo, nitro, oxo, alkyl, alkenyl, alkynyl, hydroxy, alkoxy, —NH$_2$, —N(H)(alkyl), —N(alkyl)$_2$, —SH, —S(alkyl), —SO$_2$(alkyl), —N(H)C(O)alkyl, —N(alkyl)C(O)alkyl, —N(H)C(O)NH$_2$, —N(H)C(O)N(H)(alkyl), —N(H)C(O)N(alkyl)$_2$, —C(O)OH, —C(O)Oalkyl, —C(O)NH$_2$, —C(O)N(H)(alkyl), —C(O)N(alkyl)$_2$, haloalkyl, hydroxyalkyl, alkoxyalkyl, -alkyl-NH$_2$, -alkyl-N(H)(alkyl), -alkyl-N(alkyl)$_2$, -alkyl-N(H)C(O)NH$_2$, -alkyl-N(H)C(O)N(H)(alkyl), -alkyl-N(H)C(O)N(alkyl)$_2$, -alkyl-C(O)OH, -alkyl-C(O)Oalkyl, -alkyl-C(O)NH$_2$, -alkyl-C(O)N(H)(alkyl) and -alkyl-C(O)N(alkyl)$_2$; and n is 1 or 2.

3. The compound of claim 1 wherein, L is —C(=O) or —C(=S) and $R^2$ is alkyl.

4. The compound of claim 2 wherein, L is —C(=O) or —C(=S) and $R^2$ is alkyl.

5. The compound of claim 1 wherein L is —C(=O) or —C(=S), $R^2$ is alkyl, $R^3$ is arylalkyl wherein the aryl moiety of the arylalkyl is substituted with 0 or one $R^{3a}$, and $R^{3a}$ is aryl or heteroaryl.

6. The compound of claim 2 wherein L is —C(=O) or —C(=S), $R^2$ is alkyl, $R^3$ is arylalkyl wherein the aryl moiety of the arylalkyl is substituted with 0 or one $R^{3a}$, and $R^{3a}$ is aryl or heteroaryl.

7. The compound of claim 1 wherein L is —C(=O) or —C(=S), $R^2$ is alkyl, $R^3$ is arylalkyl wherein the aryl moiety of the arylalkyl is substituted with 0 or one $R^{3a}$ wherein $R^{3a}$ is aryl or heteroaryl and $R^9$ is aryl or heteroaryl.

8. The compound of claim 2 wherein L is —C(=O) or —C(=S), $R^2$ is alkyl, $R^3$ is arylalkyl wherein the aryl moiety of the arylalkyl is substituted with 0 or one $R^{3a}$ wherein $R^{3a}$ is aryl or heteroaryl and $R^9$ is aryl or heteroaryl.

9. A pharmaceutical composition comprising a therapeutically effective amount of a compound or combination of compounds, or a pharmaceutically acceptable salt form or stereoisomer thereof, and a pharmaceutically acceptable carrier, wherein the compound, or at least one of said compounds, is selected from the group consisting of
methyl(1S)-1-[({(1R,3S,4S)-3-hydroxy-4-{[(2S)-2-(3-{[6-(1-hydroxy-1-methylethyl)-2-pyridinyl]methyl}-2-oxo-1-imidazolidinyl)-3,3-dimethylbutanoyl]amino}-5-phenyl-1[4-(2-pyridinyl) benzyl]pentyl}amino)carbonyl]-2,2-dimethylpropylcarbamate, and
methyl(1S )-1-[({(1S,3S,4S)-4-{[(2S)-2-(3-benzyl-2-oxo-1-imidazolidinyl)-3,3-dimethylbutanoyl] amino }-3-hydroxy-5-phenyl-1-[4-(2-pyridinyl) benzyl]pentyl}amino)carbonyl]-2,2-dimethylpropylcarbamate.

* * * * *